US011672800B2

(12) United States Patent
Campbell et al.

(10) Patent No.: US 11,672,800 B2
(45) Date of Patent: Jun. 13, 2023

(54) COMBINATION THERAPIES WITH EHMT2 INHIBITORS

(71) Applicant: Epizyme, Inc., Cambridge, MA (US)

(72) Inventors: John Emmerson Campbell, Cambridge, MA (US); Kenneth William Duncan, Westwood, MA (US); Maria Alejandra Raimondi, Jamaica Plain, MA (US); Christine Klaus, Waban, MA (US); Elayne Penebre, Auburndale, MA (US)

(73) Assignee: Epizyme, Inc., Cambridge, MA (US)

( * ) Notice: Subject to any disclaimer, the term of this patent is extended or adjusted under 35 U.S.C. 154(b) by 299 days.

(21) Appl. No.: 16/606,833

(22) PCT Filed: Apr. 20, 2018

(86) PCT No.: PCT/US2018/028609
§ 371 (c)(1),
(2) Date: Oct. 21, 2019

(87) PCT Pub. No.: WO2018/195450
PCT Pub. Date: Oct. 25, 2018

(65) Prior Publication Data
US 2020/0054635 A1    Feb. 20, 2020

Related U.S. Application Data

(60) Provisional application No. 62/574,147, filed on Oct. 18, 2017, provisional application No. 62/488,679, filed on Apr. 21, 2017.

(51) Int. Cl.
*A61K 31/505* (2006.01)
*A61K 31/506* (2006.01)
(Continued)

(52) U.S. Cl.
CPC .......... *A61K 31/506* (2013.01); *A61K 31/203* (2013.01); *A61K 31/4375* (2013.01);
(Continued)

(58) Field of Classification Search
CPC ..... A61K 31/505; A61K 45/06; A61K 31/404
See application file for complete search history.

(56) References Cited

U.S. PATENT DOCUMENTS 2,443,305 A    6/1948  Curd et al.
4,522,811 A    6/1985  Eppstein et al.
(Continued)

FOREIGN PATENT DOCUMENTS

CN    104230911 A    12/2011
CN    103172637 A    6/2013
(Continued)

OTHER PUBLICATIONS

Sato et al, Cancer Res; 77(2) Jan. 15, 2017, First Published Online Nov. 22, 2016.pp. 470-481. (Year: 2016).*
(Continued)

*Primary Examiner* — Craig D Ricci
*Assistant Examiner* — Janet L Coppins
(74) *Attorney, Agent, or Firm* — Cooley LLP; Heidi A. Erlacher; Christine E. Dunne

(57) ABSTRACT

The present disclosure relates to a method of preventing or treating a cancer via administering an EHMT2 inhibitor or a combination comprising an EHMT2 inhibitor compound and one or more additional therapeutic agent disclosed herein or a pharmaceutical composition thereof to subjects in need thereof. The present disclosure also relates to the use of such compounds or combinations for research or other non-therapeutic purposes.

20 Claims, 19 Drawing Sheets

G9a AML Combinations: Cell Line Panel

| CELL LINES | Clinical data | Cpd 205 IC50 (μM) Killing 14 days LTP | Cell Killing (LTP) | FAB class | Fusion | Mutations/Amplifications |
|---|---|---|---|---|---|---|
| AP-1060 | 45 y/o male at 4th relapse resistant to ATRA | 0.13 | Y | M3 | PML-RARA | |
| OCI-AML-2 | 65 y/o man with AML at diagnosis | 0.21 | | M4 | | DNMT3A R635W; FLT3 T227M (homo); TP53 P33R (homo); TET2 I1762V (het); IDH1 V178I (het); FLT3 A680V (het) |
| EOL-1 | 33 y/o male with AML after hypereosinophilic syndrome | 0.31 | | Eosinophilic Leukemia | MLL-PTD FIP1L1/PDGFRA | FLT3 T227M (het); TP53 P33R (het); TET2 I1762V (low); ABL1 S991L (het); |
| OCI-AML-3 | 57 y/o man with AML at diagnosis | 0.4 | | M4 | | NPM1 gene mutation (type A) DNMT3A R882C; FLT3 T227M (het); TP53 P33R (homo); TET2 I1762V (het); NRAW Q61L (homo); DNMT3A R822C (het); NPM1 W288C (low) |
| Molm-13 | 20 y/o male MDS (RAEB) | 0.9 | | M5a | MLL-AF9 | FLT3-ITD (DOT1L Dependent), CBL deltaExon8 mutation; FLT3 T227M (het); TP53 P33R (het); TET2 I1762V (het); FLT3 Y599F (low); |
| HL-60 | 36 y/o woman with APL | 0.9 | | M3--> M2 | | MYC amp |
| ML-2 | 28 y/o male T-NHL-T-ALL | 1.1 | Y | M4 | MLL-AF6 | TP53 P33R (het); IDH1 V178I (het); TET2 Y867H (het); TET2 P1723S (het); TET2 H1778R (het); KRAS A146T (het); |
| Kasumi-1 | 7 y/o Japanese male at 2nd relapse | 1.2 | Y | M2 | RUNX1/AML1/CBFA2 T1(ETO) | |
| Molm-16 | 77 y/o Japanese female at relapse resistant | 1.4 | | M0 | | |
| SKM-1 | 76 y/o Japanese male with AML after MDS (RAEBT) refractory | 1.5 | | M5 | | FLT3 T227M (homo); TP53 R209Q (het); FBXW7 E489D (het); KRAS K117N (homo); ASXL1 Y590* (het); |
| AML-193 | 13 y/o male at relapse | 2.1 | Y | M5 | | |
| NOMO-1 | 31 y/o female at 2nd relapse | 3.3 | | M5a | MLL-AF9 | FLT3 T227M (homo); ABL1 D579N (het); KRAS G13D (het); DOT1L G1386S (het) |

Panel of Second Agent

| Rationale | Modality | Drug name |
|---|---|---|
| AML SOC | Antimetabolite | Ara-C |
| | Topoisomerase II inhibitor | Daunorubicin |
| Epigenetic drugs | DNA Hypomethylating agent | Azacitidine |
| | | Decitabine |
| | HDAC inhibitors | Pracinostat |
| | | Panobinostat |
| | EZH2 inhibitor | Tazemetostat |
| | DOT1L inhibitor | Pinometostat |
| Targeted Therapies | Differentiation agent | ATRA |
| | FLT3 inhibitors | Gilteritinib |
| | | Midostaurin |
| | BCL2 inhibitor | Venetoclax |

(51) Int. Cl.

| | |
|---|---|
| *A61P 35/00* | (2006.01) |
| *A61K 31/203* | (2006.01) |
| *A61K 31/4375* | (2006.01) |
| *A61K 31/44* | (2006.01) |
| *A61K 31/496* | (2006.01) |
| *A61K 31/517* | (2006.01) |
| *A61K 31/519* | (2006.01) |
| *A61K 31/706* | (2006.01) |

(52) U.S. Cl.
CPC ............ *A61K 31/44* (2013.01); *A61K 31/496* (2013.01); *A61K 31/517* (2013.01); *A61K 31/519* (2013.01); *A61K 31/706* (2013.01); *A61P 35/00* (2018.01)

(56) References Cited

U.S. PATENT DOCUMENTS

| | | | |
|---|---|---|---|
| 5,106,862 | A | 4/1992 | Briving et al. |
| 5,247,083 | A | 9/1993 | Knox et al. |
| 5,763,263 | A | 6/1998 | Dehlinger |
| 6,025,379 | A | 2/2000 | Iyengar et al. |
| 6,235,746 | B1 | 5/2001 | Davis et al. |
| 6,924,290 | B2 | 8/2005 | Nagarathnam et al. |
| 7,479,495 | B2 | 1/2009 | Moriarty et al. |
| 7,517,886 | B2 | 4/2009 | Singh et al. |
| 7,935,710 | B2 | 5/2011 | Van Roey et al. |
| 8,026,248 | B2 | 9/2011 | Andries et al. |
| 8,575,165 | B2 | 11/2013 | Guruaja et al. |
| 8,604,042 | B2 | 12/2013 | Noronha et al. |
| 8,680,113 | B2 | 3/2014 | Moon et al. |
| 8,785,444 | B2 | 7/2014 | Mortimore et al. |
| 8,986,994 | B2 | 3/2015 | Mihovilovic et al. |
| 9,018,209 | B2 | 4/2015 | Jorgensen et al. |
| 9,056,837 | B2 | 6/2015 | Li |
| 9,284,272 | B2 | 3/2016 | Pluishchev et al. |
| 9,487,504 | B2 | 11/2016 | Lim et al. |
| 2002/0143176 | A1 | 10/2002 | Liu et al. |
| 2004/0082627 | A1 | 4/2004 | Darrow et al. |
| 2004/0204386 | A1 | 10/2004 | Bhatt et al. |
| 2005/0014753 | A1 | 1/2005 | Ding et al. |
| 2006/0058525 | A1 | 3/2006 | Singh et al. |
| 2007/0021446 | A1 | 1/2007 | Elhert et al. |
| 2007/0191405 | A1 | 8/2007 | Noronha et al. |
| 2010/0317706 | A1 | 12/2010 | Levine et al. |
| 2011/0046108 | A1 | 2/2011 | Kettle et al. |
| 2011/0230478 | A1 | 9/2011 | Greul et al. |
| 2011/0275157 | A1 | 11/2011 | You et al. |
| 2012/0071418 | A1 | 3/2012 | Copeland et al. |
| 2012/0189670 | A1 | 7/2012 | Kirkpatrick et al. |
| 2012/0197013 | A1 | 8/2012 | Nunes et al. |
| 2013/0023532 | A1 | 1/2013 | Casillas et al. |
| 2013/0310379 | A1 | 11/2013 | Albrecht et al. |
| 2013/0317018 | A1 | 11/2013 | Philpot et al. |
| 2014/0128391 | A1 | 5/2014 | van Duzer et al. |
| 2015/0087673 | A1 | 3/2015 | Hitoshi et al. |
| 2015/0174132 | A1 | 6/2015 | Foley et al. |
| 2015/0250824 | A1 | 9/2015 | Ma |
| 2015/0274660 | A1* | 10/2015 | Pluishchev .......... C07D 209/96 514/210.21 |
| 2017/0121316 | A1 | 5/2017 | Aguirre Ena et al. |
| 2017/0209444 | A1 | 7/2017 | Classon et al. |
| 2017/0355712 | A1 | 12/2017 | Campbell et al. |
| 2020/0039961 | A1 | 2/2020 | Campbell et al. |
| 2020/0039998 | A1 | 2/2020 | Campbell et al. |
| 2020/0113901 | A1 | 4/2020 | Campbell et al. |
| 2020/0247790 | A1 | 8/2020 | Campbell et al. |
| 2020/0317642 | A1 | 10/2020 | Campbell et al. |
| 2021/0198277 | A1 | 7/2021 | Campbell et al. |
| 2021/0213014 | A1 | 7/2021 | Cosmopoulos et al. |
| 2021/0260040 | A1 | 8/2021 | Penebre et al. |
| 2022/0235065 | A1 | 7/2022 | Campbell et al. |
| 2022/0274961 | A1 | 9/2022 | Campbell et al. |
| 2022/0324851 | A1 | 10/2022 | Campbell et al. |

FOREIGN PATENT DOCUMENTS

| | | |
|---|---|---|
| EP | 0 356 234 B1 | 5/1994 |
| EP | 3381916 A1 | 10/2018 |
| KR | 1452235 B1 | 10/2014 |
| WO | WO-9405648 A1 | 3/1994 |
| WO | WO 2000/25780 A1 | 5/2000 |
| WO | WO-0066555 A1 | 11/2000 |
| WO | WO-0066556 A1 | 11/2000 |
| WO | WO 2001/55119 A2 | 8/2001 |
| WO | WO 2002/059088 A1 | 8/2002 |
| WO | WO 2002/068417 A2 | 9/2002 |
| WO | WO 2003/002542 A1 | 1/2003 |
| WO | WO 2003/032994 A2 | 4/2003 |
| WO | WO 2003/040141 A1 | 5/2003 |
| WO | WO 2003/053939 A1 | 7/2003 |
| WO | WO 2005/013996 A2 | 2/2005 |
| WO | WO-2005026130 A1 | 3/2005 |
| WO | WO 2005/037273 A1 | 4/2005 |
| WO | WO 2005/113548 A1 | 12/2005 |
| WO | WO 2006/000420 A1 | 1/2006 |
| WO | WO 2007/009524 A1 | 1/2007 |
| WO | WO 2007/053452 A1 | 5/2007 |
| WO | WO 2007/088277 A1 | 8/2007 |
| WO | WO-2007085833 A2 | 8/2007 |
| WO | WO 2008/092049 A1 | 7/2008 |
| WO | WO-2008131547 A1 | 11/2008 |
| WO | WO 2009/012421 A1 | 1/2009 |
| WO | WO 2009/103652 A1 | 8/2009 |
| WO | WO 2009/126537 A1 | 10/2009 |
| WO | WO 2010/007116 A2 | 1/2010 |
| WO | WO 2010/017122 A2 | 2/2010 |
| WO | WO 2010/085684 A1 | 7/2010 |
| WO | WO-2010090875 A1 | 8/2010 |
| WO | WO 2010/129802 A1 | 11/2010 |
| WO | WO 2011/016472 A1 | 2/2011 |
| WO | WO 2012/023285 A1 | 2/2012 |
| WO | WO 2012/038417 A1 | 3/2012 |
| WO | WO 2012/044936 A1 | 4/2012 |
| WO | WO 2012/115479 A2 | 8/2012 |
| WO | WO 2013/040215 A1 | 3/2013 |
| WO | WO 2013/070852 A2 | 5/2013 |
| WO | WO 2013/078468 A1 | 5/2013 |
| WO | WO 2013/140148 A1 | 9/2013 |
| WO | WO 2013/179033 A1 | 12/2013 |
| WO | WO 2014/058921 A2 | 4/2014 |
| WO | WO 2014/089112 A1 | 6/2014 |
| WO | WO-2014124230 A2 | 8/2014 |
| WO | WO 2014/151900 A1 | 9/2014 |
| WO | WO-2015095679 A1 | 6/2015 |
| WO | WO 2015/192981 A1 | 12/2015 |
| WO | WO 2015/200329 A1 | 12/2015 |
| WO | WO 2016/073956 A1 | 5/2016 |
| WO | WO 2017/061957 A1 | 4/2017 |
| WO | WO-2017085053 A1 | 5/2017 |
| WO | WO-2017102677 A1 | 6/2017 |
| WO | WO 2017/142947 A1 | 8/2017 |
| WO | WO 2017/177955 A1 | 10/2017 |
| WO | WO 2017/178416 A1 | 10/2017 |
| WO | WO 2017/178582 A1 | 10/2017 |
| WO | WO 2017/181117 A1 | 10/2017 |
| WO | WO 2017/181177 A1 | 10/2017 |
| WO | WO 2017/210540 A1 | 12/2017 |
| WO | WO 2017/212010 A1 | 12/2017 |
| WO | WO 2017/212012 A1 | 12/2017 |
| WO | WO 2017/214395 A1 | 12/2017 |
| WO | WO 2018/060323 A1 | 4/2018 |
| WO | WO 2018/064557 A1 | 4/2018 |
| WO | WO 2018/118842 A1 | 6/2018 |
| WO | WO 2018/119208 A1 | 6/2018 |
| WO | WO 2018/119263 A1 | 6/2018 |
| WO | WO-2018183923 A1 | 10/2018 |
| WO | WO 2019/036377 A1 | 2/2019 |
| WO | WO 2019/079485 A1 | 4/2019 |
| WO | WO 2019/079540 A1 | 4/2019 |

(56) References Cited

FOREIGN PATENT DOCUMENTS

| WO | WO-2019079596 A1 | 4/2019 |
|---|---|---|
| WO | WO-2019079607 A9 | 5/2020 |

OTHER PUBLICATIONS

Dermer, Bio/Technology 1994, vol. 12, p. 320. (Year: 1994).*
Anderson Chemistry & Biology 2003, vol. 10, 787-797. (Year: 2003).*
Thiel, Nature Biotechnology 2004 vol. 22 (5), p. 513-519. (Year: 2004).*
Lopez Lopez et al., J Computer-Aided Molecular Design 2020, vol. 34, pp. 659-669. (Year: 2020).*
Sato et al, Cancer Research, vol. 77(2), 2016, pp. 470-481 (Year: 2016).*
Akinsheye, I. et al. (Jul. 7, 2011) "Fetal hemoglobin in sickle cell anemia" Blood, 118(1):19-27.
Anderson, A.C. et al. (2003) "The Process of Structure-Based Drug Design" Chem & Biol, 10:787-797.
Anderson, E.M. et al. (2018) "Overexpression of the Histone Dimethyltransferase G9a in Nucleus Accumbens Shell Increases Cocaine Self-Administration, Stress-Induced Reinstatement, and Anxiety" J Neurosci, 38(4):803-813.
Antignano, F. et al. (2014) "Methyltransferase G9A regulates T cell differentiation during murine intestinal inflammation" J Clinical Investigation, 124(5):1945-1955.
Bradner, J.E. et al. (Jul. 13, 2010) "Chemical genetic strategy identifies histone deacetylase 1 (HDAC1) and HDAC2 as therapeutic targets in sickle cell disease" Proc Natl Acad Sci USA, 107(28):12617-12622.
Broccatelli, F. et al. (2018) "Why Decreasing Lipophilicity Alone Is Often Not a Reliable Strategy for Extending IV Half-life" ACS Med Chem Lett, 9:522-527.
Buchanan, J.L. et al. (2011) "Discovery of 2,4-bis-arylamino-1,3-pyrimidines as insulin-growth factor-1 receptor (IGF-1R) inhibitors," Bioorganic & Medicinal Chemistry Letters, 21:2394-2399.
Cahn, R.S. (1964) "An Introduction to the Sequence Rule: A system for the specification of absolute configuration," J. Chem. Educ., 41(3):116-125.
Cahn, R.S. et al. (1951) "Specification of Configuration about Quadricovalent Asymmetric Atoms," J. Chem. Soc., pp. 612-622.
Cahn, R.S. et al. (1956) "The Specification of Asymmetric Configuration in Organic Chemistry," Experientia, vol. 12, pp. 81-94.
Cahn, R.S. et al. (1966) "Specification of Molecular Chirality," Agnew. Chem. Inter. Edit., vol. 5, No. 4, pp. 385-415, with Errata, p. 511.
Campbell, J.E. et al. (2015) "EPZ011989, A Potent, Orally-Available EZH2 Inhibitor with Robust in Vivo Activity" ACS Med Chem Lett, 6:491-495.
Cebrian, A. et al. (2006) "Genetic variants in epigenetic genes and breast cancer risk" Carcinogenesis, 27(8):1661-1669.
Chan, R. and L.Z. Benet (May 8, 2018) "Evaluation of the relevance of DILI predictive hypotheses in early drug development: review of in vitro methodologies vs. BDDCS classification" Toxicol Res, 7(3):358-370.
Chen, P. et al. (2015) "Effect of BIX-01294 on H3K9me2 levels and the imprinted gene Snrpn in mouse embryonic fibroblast cells" Biosci Rep, 35:e00257, doi:10.1042/BSR20150064, 9 pages.
Cheng, C.-C. et al. (Aug. 7, 2017) "YM155 as an inhibitor of cancer sternness simultaneously inhibits autophosphorylation of epidermal growth factor receptor and G9a-mediated sternness in lung cancer cells" PLoS ONE, 12(8):e0182149, 15 pages.
Cho, H-S. et al. (2011) "Enhanced Expression of EHMT2 is Involved in the Proliferation of Cancer Cells through Negative Regulation of SIAH1", Neoplasia, 13:676-684.
Copeland, R.A. (Dec. 2013) "Molecular pathways: protein methyltransferases in cancer" Clin Cancer Res, 19(23):6344-6350.

Cui, J. et al., "EHMT2 inhibitor BIX-01294 induces apoptosis through PMAIP1-USP9X-MC1 axis in human bladder cancer cells," Cancer Cell International (2015), vol. 15, No. 4, 9 pages.
Curry, E. et al. (2015) "Dual EZH2 and EHMT2 histone methyltransferase inhibition increases biological efficacy in breast cancer cells" Clin Epigenet, 7:84, doi: 10.1186/s13148-015-0118-9; 12 pages.
Daigle, S.R. et al. (Jul. 12, 2011) "Selective Killing of Mixed Lineage Leukemia Cells by a Potent Small-Molecule DOT1L Inhibitor" Cancer Cell, 20:53-65.
Das, P. et al. (2008) "Dithiocarbamate and CuO promoted one-pot synthesis of 2-(N-substituted)-aminobenzimidazoles and related heterocycles" Tetrahedron Letters, 49(6):992-995.
Database Pubchem SID: 162351176 (May 21, 2013) "1H-Benzimidazol-2-amine, 2,3-dihydro-" [online]. U.S. National Library of Medicine; National Center for Biotechnology Information. Retrieved from: https://pubchem.ncbi.nlm.nih.gov/substance/162351176; retrieved on Nov. 15, 2018, 5 printed pages.
Database Registry RN 1508841-66-4 (Jan. 1, 2014) "2,4-Pyrimidinediamine, N2-(3,4-dimethoxyphenyl)-6-methyl-" [online]. Retrieved from STN, 1 page.
Database Registry RN 1510052-80-8 (Jan. 3, 2014), supplied by Aurora Fine Chemicals [online]. Retrieved from STN, 1 page.
Database Registry RN 1515183-33-1 (Jan. 9, 2014) and RN 1538052-23-1 (Feb. 6, 2014) [online]. Retrieved from STN, 2 pages.
Database Registry RN 872510-72-0 (Jan. 24, 2006) [online]. Retrieved from STN, 1 page.
Database Registry Nos. RN 1774002-60-6 (Jun. 5, 2015), 1771477-54-3 (Jun. 2, 2015), 1516153-59-5 (Jan. 10, 2014), 1508841-66-4 (Jan. 1, 2014), and 1216044-93-7 (Apr. 4, 2010); retrieved from STN on Nov. 2021, 2 pages.
Devkota, K. et al., "Analogues of the Natural Product Sinefungin as Inhibitors of EHMT1 and EHMT2," ACS Medicinal Chemistry Letters (2014), vol. 5, pp. 293-297.
Eggerman, T. et al. (2015) "Congenital imprinting disorders: EUCID. net—a network to decipher their aetiology and to improve the diagnostic and clinical care" Clin Epigenetics, 7:123; DOI 10.1186/s13148-015-0050-z, 10 pages.
Feldman, N. et al. (Feb. 2006) "G9a-mediated irreversible epigenetic inactivation of Oct-3/4 during early embryogenesis" Nat Cell Biol, 8(2):188-194, with Supplementary Information, 3 pages.
Giarratana, M.-C. et al., "Proof of principle for transfusion of in vitro-generated blood cells," Blood (2011), vol. 118, No. 19, pp. 5071-5079.
Ginjala, V. et al. (2017) "Protein-lysine methyltransferases G9a and GLP1 promote responses to DNA damage" Sci Reports, 7:16613, DOI:10.1038/s41598-017-16480-5, 28 pages.
Graham, J.M. et al. (May 2016) "KCNK9 Imprinting Syndrome—Further Delineation of a Possible Treatable Disorder" Am J Med Genet Pt A, 170(10):2632-2637.
Harris, C.M. et al. (2010) "2,4-Diaminopyrimidine MK2 inhibitors. Part II: Structure-based inhibitor optimization" Bioorg Med Chem Lett, 20(1):334-337.
He, Y. et al., "Targeting protein lysine methylation and demethylation in cancers," Acta Biochem. Biophys. Sin. (2012), vol. 44, Issue 1, pp. 70-79.
Huang, W. et al. (Nov. 1, 2007) "N4-Phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease" Bioorg Med Chem Lett, 17(21):5783-5789.
Kaniskan, H. et al. (Mar. 2017) "Inhibitors of Protein Methyltransferases and Demethylases" Chem Rev, 118:989-1068; DOI: 10.1021/acs.chemrev.6b00801.
Katayama, K. et al. (Aug. 2020) "Discovery of novel histone lysine methyltransferase G9a/GLP (EHMT2/1) inhibitors: Design, synthesis, and structure-activity relationships of 2,4-diamino-6-methylpyrimidines" Bioorg & Med Chem Lett, 30(20):127475, doi: 10.1016/j.bmcl.2020.127475.
Kato, G.J. et al. (Mar. 15, 2018) "Sickle cell disease" Nat Rev Dis Primers, 4:18010, doi: 10.1038/nrdp.2010.10, 22 pages.
Keilhack, H. et al. (2015) "Small Molecule Inhibitors of EZH2: the Emerging Translational Landscape" Epigenomics, 7:337-341.

(56) References Cited

OTHER PUBLICATIONS

Kim, Y. et al. (Feb. 2017; Epub Dec. 26, 2016) "Targeting the histone methyltransferase G9a activates imprinted genes and improves survival of a mouse model of Prader-Willi syndrome" Nat Med, Advance Online Publication, doi: 10.1038/nm.4257, plus Supplemental Information, 31 total pages. Final publication in Nat Med, 23(2):213-222.

Knutson, S.K. et al. (Apr. 2014) "Selective Inhibition of EZH2 by EPZ-6438 Leads to Potent Antitumor Activity in EZH2-Mutant Non-HodgkinLymphoma" Mol Cancer Ther, 13(4):842-854.

Knutson, S.K. et al. (May 7, 2013) "Durable tumor regression in genetically altered malignant rhabdoid tumors by inhibition of methyltransferase EZH2" Proc Natl Acad Sci USA, 110(19):7922-7927.

Kondengaden, S.M. et al. (Oct. 2016) "Discovery of novel small molecule inhibitors of lysine methyltransferase G9a and their mechanism in leukemia cell lines" Eur J Med Chem, 122:382-393.

Krivega, I. et al. (2015) "Inhibition of G9a methyltransferase stimulates fetal hemoglobin production by facilitating LCR/γ-globin looping," Blood, 126(5):665-672.

Kubicek, S. et al. (Feb. 9, 2007) "Reversal of H3K9me2 by a small-molecule inhibitor for the G9a histone methyltransferase" Mol Cell, 25(3):473-481.

Laumet, G. et al. (Dec. 2015) "G9a is essential for epigenetic silencing of K+ channel genes in acute-to-chronic pain transition" Nature Neuroscience, 18(12):1746-1758.

Lavelle, D. et al. (Feb. 2, 2012) "Effects of tetrahydrouridine on pharmacokinetics and pharmacodynamics of oral decitabine" Blood, 119(5):1240-1247.

Lehnertz, B. et al. (2014) "The methyltransferase G9a regulates HoxA9-dependent transcription in AML" Genes Dev, 28:317-327.

Liu, F. et al. (2009) "Discovery of a 2,4-Diamino-7-aminoalkoxyquinazoline as a Potent and Selective Inhibitor of Histone Lysine Methyltransferase G9a" J Med Chem, 52:7950-7953.

Liu, F. et al. (Aug. 2010) "Protein Lysine Methyltransferase G9a Inhibitors: Design, Synthesis, and Structure Activity Relationships of 2,4-Diamino-7-aminoaloxy-quinazolines" J Med Chem, 53(15):5844-5557 [online], Retrieved from: pubs.acs.org/jmc, DOI: 10.1021/jm10478y, 14 pages.

Liu, F. et al. (Jan. 2011) "Optimization of Cellular Activity of G9a Inhibitors 7-Aminoalkoxy-quinazolines" J Med Chem, 54(17):6139-6150. NIH Public Access Author Manuscript; retrieved from https://www.ncbi.nlm.nih.gov/pmc/articles/PMC3171737/pdf/nihms-317339.pdf; 29 pages.

Liu, F. et al. (Oct. 31, 2013) "Discovery of an in Vivo Chemical Probe of the Lysine Methyltransferases G9a and GLP" J Med Chem, 56(21):8931-8942.

Lopez-Lopez, E. et al. (2020) "Towards the understanding of the activity of G9a inhibitors: an activity landscape and molecular modeling approach" J Computer-Aided Mol Des, 34:659-669.

Ma, Q. et al. (Dec. 2007) "Fetal hemoglobin in sickle cell anemia: genetic determinants of response to hydroxyurea" Pharmacogenomics J, 7(6):386-394.

McElroy, W.T. et al. (2015) "Discovery and hit-to-lead optimization of 2,6-diaminopyrimidine inhibitors of interleukin-1 receptor-associated kinase 4" Bioorg Med Chem Lett, 25(9):1836-1841.

Mesirca, P. et al. (Aug. 2013) "The G-protein-gated K+ channel, IKACh, is required for regulation of pacemaker activity and recovery of resting heart rate after sympathetic stimulation" J Gen Physiol, 142(2):113-126.

Miura, S. et al. (Mar. 2014) "Immunohistochemistry for Histone H3 Lysine 9 Methyltransferase and Demethylase Proteins in Human Melanomas" Am J Dermatopathol, 36(3):211-216.

Molokie, R. et al. (Sep. 2017) "Oral tetrahydrouridine and decitabine for non-cytotoxic epigenetic gene regulation in sickle cell disease: A randomized phase 1 study" PLoS Med, 14(9):e1002382, 28 pages.

Murshudov, G.N. et al. (1997) "Refinement of Macromolecular Structures by the Maximum-Likelihood Method" Acta Cryst Section D, 53(3):240-255.

Neel, J.V. (Jul. 15, 1949) "The Inheritance of Sickle Cell Anemia" Science, 110(2846):64-66.

Nevitt, S.J. (2017) "Hydroxyurea (hydroxycarbamide) for sickle cell disease (Review)" Cochrane Database Syst Rev, 4:CD002202, DOI: 10.1002/14651858.CD002202.pub2, pp. i-iv, 1-120.

Niihara, Y. et al. (Nov. 8, 2018) "A Phase 3 Trial of 1-Glutamine in Sickle Cell Disease" N Engl J Med, 379(19):1879-1880.

Noguchi, C.T. et al. (1988) "Levels of fetal hemoglobin necessary for treatment of sickle cell disease" N Engl J Med, 318(2):96-99.

Otwinoski, Z. and W. Minor (1997) "Processing of X-ray Diffraction Data Collected in Oscillation Mode" Methods in Enzymology, 276:307-326.

Pappano, W.N. et al. (Jul. 6, 2015) "The Histone Methyltransferase Inhibitor A-366 Uncovers a Role for G9a/GLP in the Epigenetics of Leukemia" PLoS One, 10(7):e0131716, doi:10.1371/journal.pone.0131716, 13 pages plus S1 Table, 1 page.

Patani, G.A. et al., "Bioisosterism: A Rational Approach in Drug Design," Chem. Rev. (1996), vol. 96, No. 8, pp. 3147-3176.

Pitts, W.J. et al. (Jan. 1, 2002) "Rapid Synthesis of Triazine Inhibitors of Inosine Monophosphate Dehydrogenase" Bioorg Med Chem Lett, 12(16):2137-2140.

Platt, O.S. et al. (1994) "Mortality in sickle cell disease. Life expectancy and risk factors for early death" N Engl J Med, 330(23):1639-1644.

Powars, D. (Apr. 1984) "Is there a threshold level of fetal hemoglobin that ameliorates morbidity in sickle cell anemia?" Blood, 63(4):921-926.

Powell, N.A. et al. (2013) "Highly selective 2,4-diaminopyrimidine-5-carboxamide inhibitors of Sky kinase" Bioorg Med Chem Lett, 23(4):1046-1050.

Qian, G. et al. (2014) "Hypervalent Iodine(III) Promoted Direct Synthesis of Imidazo[1,2-alpha]pyrimidines" Eur J Org Chem, 2014(22):4837-4843.

Rabal, O. et al. (Jun. 28, 2018) "Discovery of reversible DNA methyltransferase and lysine methyltransferase G9a inhibitors with antitumoral in vivo efficacy" Just Accepted Manuscript, J Med Chem, DOI: 10.1021/acs.jmedchem.7b01926 [online]. Retrieved from: http://pubs.acs.org; retrieved on Jun. 29, 2018, 103 pages.

Renneville, A. et al. (2015) "EHMT1 and EHMT2 inhibition induces fetal hemoglobin expression," Blood, 126(16):1930-1939.

Rivers, A. et al. (2016) "The LSD1 inhibitor RN-1 recapitulates the fetal pattern of hemoglobin synthesis in baboons (P. anubis)" Haematologica; 101(6):688-697.

Rivers, A. et al. (Nov. 2018) "Oral administration of the LSD1 inhibitor ORY-3001 increases fetal hemoglobin in sickle cell mice and baboons" Exp Hematol, 67:60-64.

Sankaran, V.G. and S.H. Orkin (Jan. 1, 2013) "The switch from fetal to adult hemoglobin" Cold Spring Harb Perspect Med,3(1):a011643, doi: 10.1101/cshperspect.a011643, 14 pages.

Savickiene, J. et al., "Euchromatic histone Methyltransferase 2 inhibitor, BIX-01294, sensitizes human promyelocytic leukemia HL-60 and NB4 cells to growth inhibition and differentiation," Leukemia Research 2014, vol. 38, No. 7, pp. 822-829.

Schüttelkopf, A.W. and D.M.F. van Aalten (2004) "PRODRG: a tool for high-throughput crystallography of protein-ligand complexes" Acta Crystallographica Section D, D60(8):1355-1363.

Shankar, S.R. et al. (2013) "G9a, a multipotent regulator of gene expression" Epigenetics, 8(1):16-22.

Shinkai, Y. and M. Tachibana (2011) "H3K9 methyltransferase G9a and the related molecule GLP" Genes Dev, 25(8):781-788.

Sim et al. Abstract for WO 2012/115479 (2012) Chemical Abstracts, 157 Abstract 410317, 3 pages.

Sweis, R.F. et al. (2014) "Discovery and Development of Potent and Selective Inhibitors of Histone Methyltransferase G9a" ACS Med Chem Letters, 5:205-209.

Tachibana, M. et al. (2002) "G9a histone methyltransferase plays a dominant role in euchromatic histone H3 lysine 9 methylation and is essential for early embryogenesis" Genes Dev, 16:1779-1791.

(56) References Cited

OTHER PUBLICATIONS

Tachibana, M. et al. (2005) "Histone methyltransferases G9a and GLP form heteromeric complexes and are both crucial for methylation of euchromatin at H3-K9" Genes Dev, 19(7):815-826.
Thiel (May 5, 2004) "Structure-aided drug design's next generation" Nat Biotechnol, 22(5):513-519.
Toxnet, Hazardous Substances Data Bank (HSDB), "N-Methylaniline". U.S. National Library of Medicine; Reviewed by SRP Sep. 14, 1995 [online]. Retrieved from: https://toxnet.nlm.nih.gov/> on Jan. 28, 2019, 22 pages.
U.S. Federal Register, 76(27), Feb. 9, 2011, pp. 7162-7175.
Van Putten, L.M. (Aug. 1958) "The life span of red cells in the rat and the mouse as determined by labeling with DFP32 in vivo" Blood, 13(8):789-794.
Vedadi, M. et al. (2011) "A chemical probe selectively inhibits G9a and GLP methyltransferase activity in cells" Nat Chem Biol, 7(8):566-574. NIH Public Access Author Manuscript; available in PMC Aug. 1, 2012, 21 pages.
Verbaro, D.J. et al. (Jun. 15, 2018, Epub May 2, 2018) "Cutting Edge: The Histone Methyltransferase G9a Is Required for Silencing of Helper T Lineage-Associated Genes in Proliferating CD8 T Cells" Advance Online Publication, doi: 10.4049/jimmunol. 1701700, 7 pages. Final publication in J Immunol, 200(12):3891-3896.
Wolenski, F.S. et al. (2017) "Fasiglifam (TAK-875) alters bile acid homeostasis in rats and dogs: a potential cause of drug induced liver injury" Toxicol Sci, 157:50-61.
Wu, H. et al. (Jan. 2010) "Structural Biology of Human H3K9 Methyltransferases" PLoS ONE, 5(1):e8570, 10 pages.
Xiao, X. et al. (Jun. 21, 2016) "The Costimulatory Receptor 0X40 Inhibits Interleukin-17 Expression through Activation of Repressive Chromatin Remodeling Pathways" Immunity, 44:1-13 [online]. Retrieved from: http://dx.doi.org/10.1016/j.immuni.2016.05.013.
Xin, Z. et al. (Apr. 25, 2003) "Role of Histone Methyltransferase G9a in CpG Methylation of the Prader-Willi Syndrome Imprinting Center" J Biol Chem, 278(17):14996-15000.
Xiong, Y. et al. (2017) "Discovery of Potent and Selective Inhibitors for G9a-Like Protein (GLP) Lysine Methyltransferase" J Med Chem, 60(5):1876-1891.
Xiong, Y. et al. (2017) "Structure-activity relationship studies of G9a-like protein (GLP) inhibitors" Bioorg Med Chem Lett, 25:4414-4423.
Yokoyama, M. et al. (2017) "Histone lysine methyltransferase G9a is a novel epigenetic target for the treatment of hepatocellular carcinoma" Oncotarget, 8(13):21315-21326.
Yuan, Y. et al. (2012) "A Small-Molecule Probe of the Histone Methyltransferase G9a Induces Cellular Senescence in Pancreatic Adenocarcinoma" ACS Chem Biol, 7:1152-1157.
Yuan, Y. et al. (2013) "Gossypol and an HMT G9a inhibitor act in synergy to induce cell death in pancreatic cancer cells" Cell Death and Disease, 4:e690, doi:10.1038/cddis.2013.191, 8 pages.
Zhang, T. et al. (Apr. 5, 2016) "G9a/GLP Complex Maintains Imprinted DNA Methylation in Embryonic Stem Cells" Cell Reports, 15:77-85.
Zhu, X. et al. (2017) "Hydroxyurea differentially modulates activator and repressors of γ-globin gene in erythroblasts of responsive and non-responsive patients with sickle cell disease in correlation with Index of Hydroxyurea Responsiveness" Haematologica, 102(12):1995-2004.
Ali, O.M. (2007) Synthesis of N2-Arylisocytidines and N2-Aryl-2'-deoxyisocytidines. Monatschefte fur Chemie, 138:917-922.
Bolden, J.E. et al. (2013). HDAC inhibitors induce tumor-cell-selective pro-apoptotic transcriptional responses. Cell Death & Disease. 4(2):e519, 15 pages. https://doi.org/10.1038/cddis.2013.9.
Database Registry RN 1516531-77-3 (Jan. 10, 2014) "2,4-Pyrimidinediamine, N2-(3,4-dimethoxyphenyl)-" [online]. Retrieved from STN, 1 page.
Database Registry RN 400752-03-6 (Mar. 1., 2002) "2,4-Pyridinediamine, N4-phenyl-" [online]. Retrieved from STN, 1 page.
Database Registry RN 848468-54-2 (Apr. 14, 2005) "Phenol, 4-chloro-2-[[2-[[4-methoxy-3-[3-(1-pyrrolidinyl)propoxy]phenyl]amino]-4-pyrimidinyl]amino]-" [online], Retrieved from STN, 1 page.
Database Registry RN 861299-13-0 (Aug. 23, 2005) "2-Pyridinamine, N-(2-methoxyphenyl)-N-methyl-" [online]. Retrieved from STN, 2 pages.
Database Registry RN 871888-74-3 (Jan. 13, 2006) "Phenol, 2-(methyl-2-pyridinylamino)-" [online]. Retrieved from STN, 1 page.
Forest, M.C. et al. (1992) A novel class of cardiotonic agents: synthesis and biological evaluation of 5-substituted 3,6-dihydrothiadiazin-2-ones with cyclic AMP phosphodiesterase inhibiting and myofibrillar calcium sensitizing properties. J Med Chem. 35(1):163-172. https://doi.org/10.1021/jm00079a022.
Gao, J. et al. (Mar. 1, 2015) "Discovery of novel 5-fluoro-N2,N4-diphenylpyrimidine-2,4-diamines as potent inhibitors against CDK2 and CDK9." Medchemcomm 6(3):444-454. doi: 10.1039/C4MD00412D.
Golubeva, G. A. et al. (1985) "Electrophilic substitution reactions of alkylated 2-aminoindole derivatives". Chemistry of Heterocyclic Compounds 21(7):786-791.
Guagnano, V. et al. (Oct. 27, 2011) "Discovery of 3-(2,6-dichloro-3,5-dimethoxy-phenyl)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase." J Med Chem 54(20):7066-7083. doi: 10.1021/jm2006222. Epub Sep. 21, 2011.
Hitchings, G.H. and P.B. Russell (1949) The Preparation and Reactions of 4-Amino-2-(caroboxymethylthio)pyrimidines. J Chem Soc, 1949:2454-2456.
Kashyab, S. et al. "Using 'biased-privileged' scaffolds to identify lysine methyltransferase inhibitors" Bioorganic & Medicinal Chemistry 22 (2014) 2253-2260.
Köhrer, S. et al. (Jun. 2016) "Pre-BCR signaling in precursor B-cell acute lymphoblastic leukemia regulates PI3K/AKT, FOXO1 and MYC, and can be targeted by SYK inhibition." Leukemia 30(6):1246-1354. doi: 10.1038/leu.2016.9. Epub Feb. 5, 2016.
Li, F. et al. (2014). Molecular-targeted agents combination therapy for cancer: developments and potentials. International Journal of Cancer, 134(6):1257-1269. https://doi.org/10.1002/ijc.28261.
Li, S. et al. (2015). Autophagy regulators as potential cancer therapeutic agents: a review. Current Topics in Medicinal Chemistry, 15(8):720-744. https://doi.org/10.2174/1568026615666150302105343.
Li, Y. et al. (2016) "AutoT&T v.2: An Efficient and Versatile Tool for Lead Structure Generation and Optimization." J Chem Inf Model 56(2):435-453. doi: 10.1021/acs.jcim.5b00691. Epub Feb. 3, 2016.
Naderi et al. (2013) "Lymphoplasmacytic Lymphoma and Waldenstrom Macroglobulinemia" Archives of Pathology & Laboratory Medicine, 137:580-585.
NYU Langone Hospitals (Jul. 2015) "Medication for Inflammatory Bowel Disease in Adults" [online]. Retrieved from: https://nyulangone.org/conditions/inflammatory-bowel-disease-in-adults; 11 printed pages.
Parente-Ribes, A. et al. (Feb. 1, 2016) "Spleen tyrosine kinase inhibitors reduce CD40L-induced proliferation of chronic lymphocytic leukemia cells but not normal B cells." Haematologica 101(2):e59-e62. DOI: 10.3324/haematol 2015.135590.
Park, S. E. et al. (2016). Inhibition of EHMT2/G9a epigenetically increases the transcription of Beclin-1 via an increase in ROS and activation of NF-KB. Oncotarget, 7(26):39796-39808. https://doi.org/10.18632/oncotarget.9290; with Correction, in Oncotarget, 2019, 10(42):4348-4349.
Scheer, S. et al. (2017) "The lysine methyltransferase G9a in immune cell differentiation and function". Frontiers in Immunology 8(429): 1-11.
Song, J. et al. (Sep. 24, 2015) Structure-Activity Relationship of Indole-Tethered Pyrimidine Derivatives that Concurrently Inhibit Epidermal Growth Factor Receptor and Other Angiokinases. PLoS One 10(9):e0138823. doi: 10.1371/journal.pone.0138823.
Steinberg et al. (Feb. 1, 1997) "Fetal Hemoglobin in Sickle Cell Anemia: Determinants of Response to Hydroxyurea" Blood, 89(3):1078-1088.

(56) References Cited

OTHER PUBLICATIONS

Wang, W. et al. (2014). New benzimidazole-2-urea derivates as tubulin inhibitors. Bioorganic & Medicinal Chemistry Letters. 24(17):4250-4253. https://doi.org/10.1016/j.bmcl.2014.07.035.

* cited by examiner

G9a AML Combinations: Cell Line Panel

| CELL LINES | Clinical data | Cpd 205 IC$_{50}$ (µM) 14 days LTP | Cell Killing (LTP) | FAB class | Fusion | Mutations/Amplifications |
|---|---|---|---|---|---|---|
| AP-1060 | 45 y/o male at 4th relapse resistant to ATRA | 0.13 | Y | M3 | PML-RARA | |
| OCI-AML-2 | 65 y/o man with AML at diagnosis | 0.21 | | M4 | | DNMT3A R635W; FLT3 T227M (homo); TP53 P33R (homo); TET2 I1762V (het); IDH1 V178I (het); FLT3 A680V (het) |
| EOL-1 | 33 y/o male with AML after hypereosinophilic syndrome | 0.31 | | Eosinophilic Leukemia | MLL-PTD FIP1L1/PDGFRA | FLT3 T227M (het); TP53 P33R (het); TET2 I1762V (low); ABL1 S991L (het); |
| OCI-AML-3 | 57 y/o man with AML at diagnosis | 0.4 | | M4 | | NPM1 gene mutation (type A) DNMT3A R882C; FLT3 T227M (het); TP53 P33R (homo); TET2 I1762V (het); NRAW Q61L (homo); DNMT3A R822C (het); NPM1 V288C (low) |
| Molm-13 | 20 y/o male MDS (RAEB) | 0.9 | | M5a | MLL-AF9 | FLT3-ITD (DOT1L Dependent), CBL deltaExon8 mutation; FLT3 T227M (het); TP53 P33R (het); TET2 I1762V (het); FLT3 Y599F (low); |
| HL-60 | 36 y/o woman with APL | 0.9 | | M3--> M2 | | MYC amp |
| ML-2 | 26 y/o male T-NHL-T-ALL | 1.1 | Y | M4 | MLL-AF6 | TP53 P33R (het); IDH1 V178I (het); TET2 Y867H (het); KRAS A146T (het); TET2 H1778R (het); KRAS A146T (het); |
| Kasumi-1 | 7 y/o Japanese male at 2nd relapse | 1.2 | Y | M2 | RUNX1(AML1)CBFA2 T1(ETO) | |
| Molm-16 | 77 y/o Japanese female at relapse resistant | 1.4 | | M0 | | |
| SKM-1 | 76 y/o Japanese male with AML after MDS (RAEBT) refractory | 1.5 | | M5 | | FLT3 T227M (homo); TP53 R209Q (het); FBXW7 E489D (het); KRAS K117N (homo); ASXL1 Y590* (het); |
| AML-193 | 13 y/o male at relapse | 2.1 | Y | M5 | | |
| NOMO-1 | 31 y/o female at 2nd relapse | 3.3 | | M5a | MLL-AF9 | FLT3 T227M (homo); ABL1 D579N (het); KRAS G13D (het); DOT1L G1386S (het) |

Figure 1

Panel of Second Agent

| Rationale | Modality | Drug name |
|---|---|---|
| AML SOC | Antimetabolite | Ara-C |
| | Topoisomerase II inhibitor | Daunorubicin |
| Epigenetic drugs | DNA Hypomethylating agent | Azacitidine |
| | | Decitabine |
| | HDAC inhibitors | Pracinostat |
| | | Panobinostat |
| | EZH2 inhibitor | Tazemetostat |
| | DOT1L inhibitor | Pinometostat |
| Targeted Therapies | Differentiation agent | ATRA |
| | FLT3 inhibitors | Gilteritinib |
| | | Midostaurin |
| | BCL2 inhibitor | Venetoclax |

Figure 1 (continued)

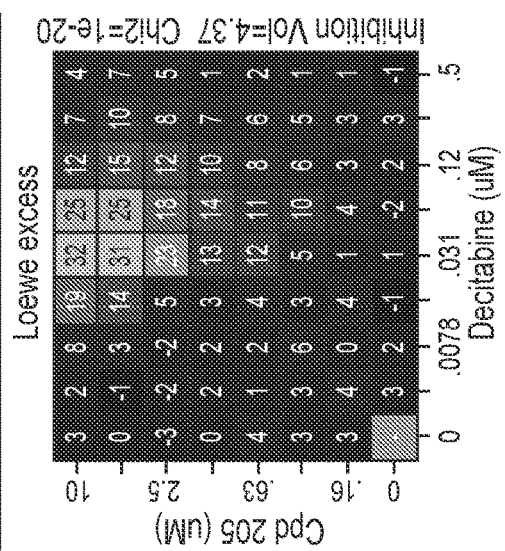
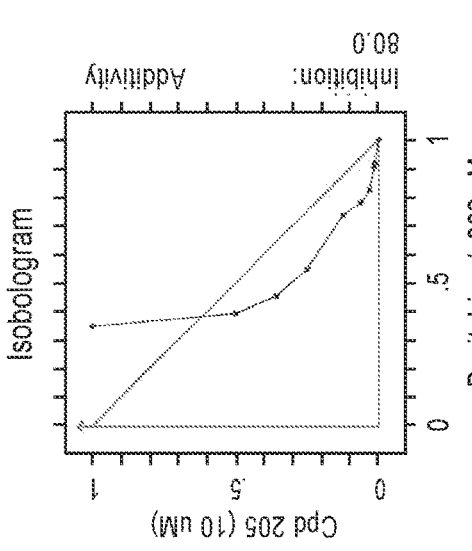
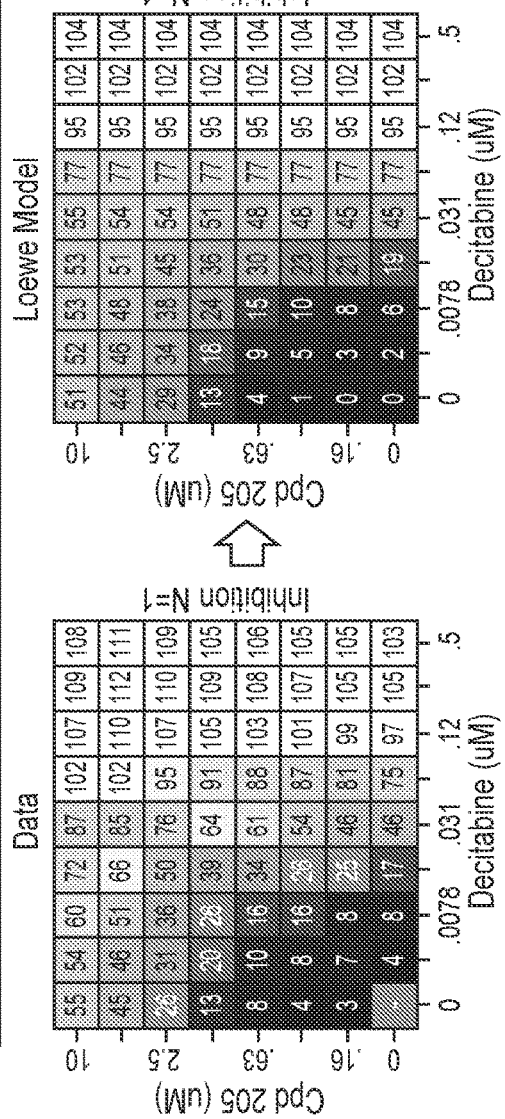
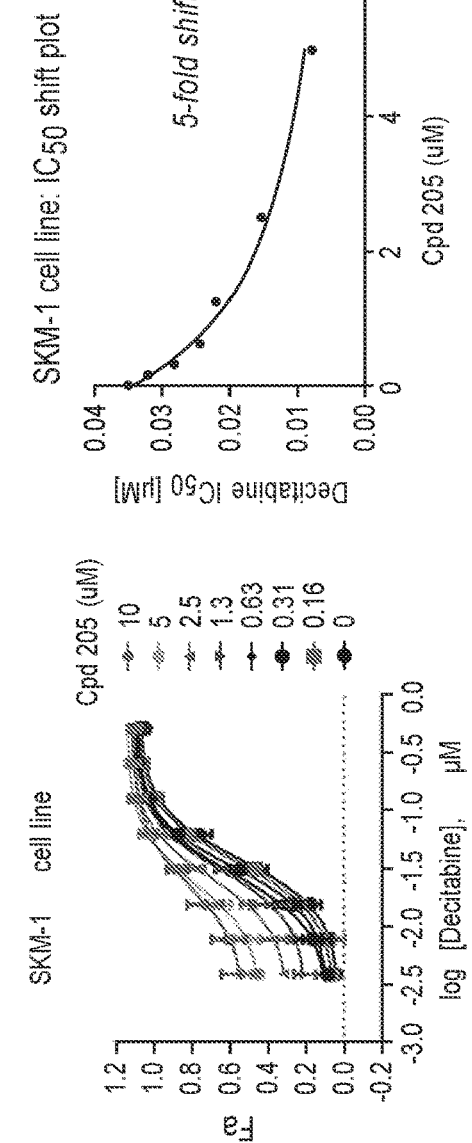
Figure 1 (continued)

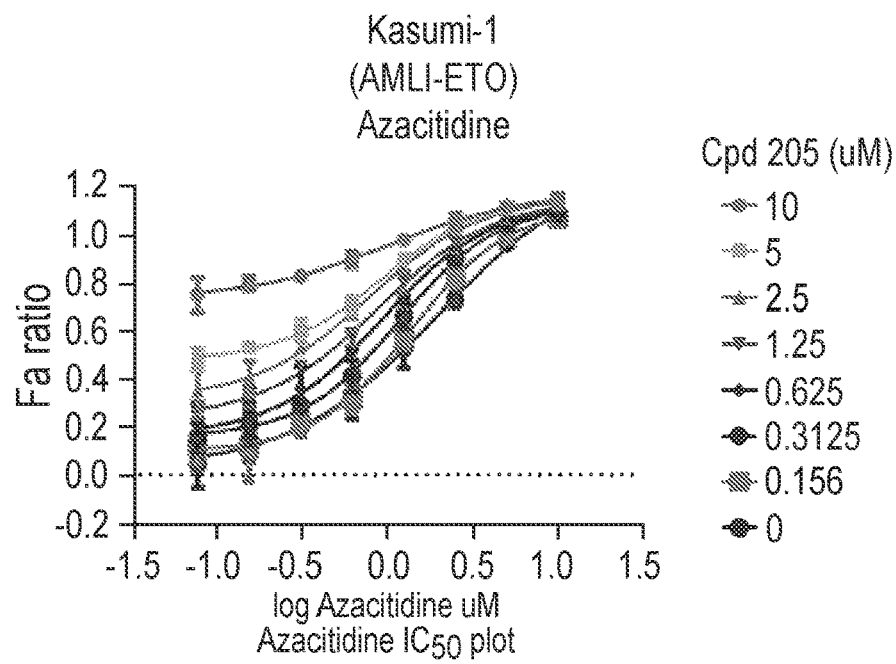
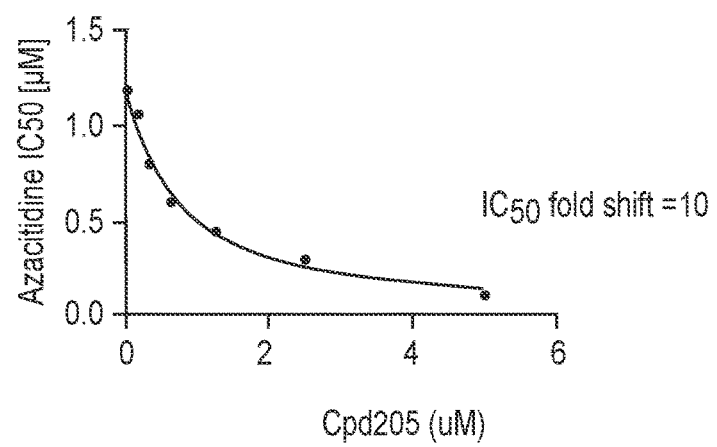
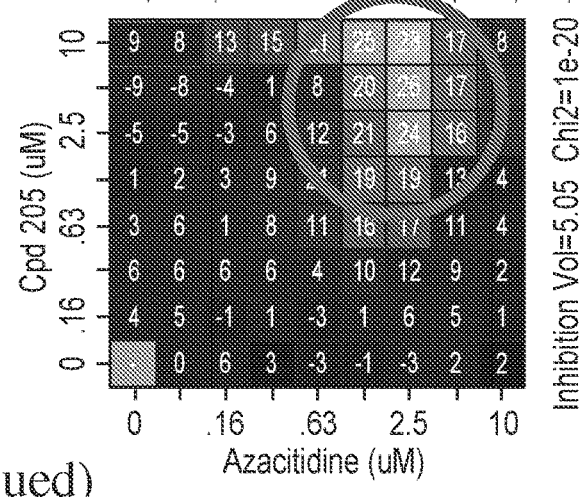
Figure 1 (continued)

Figure 1 (continued)
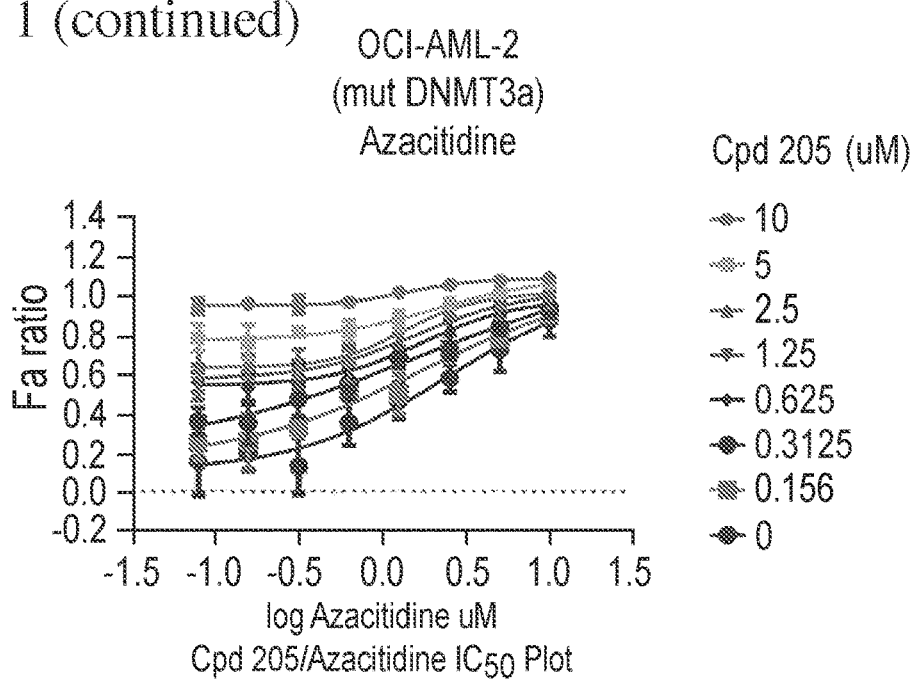
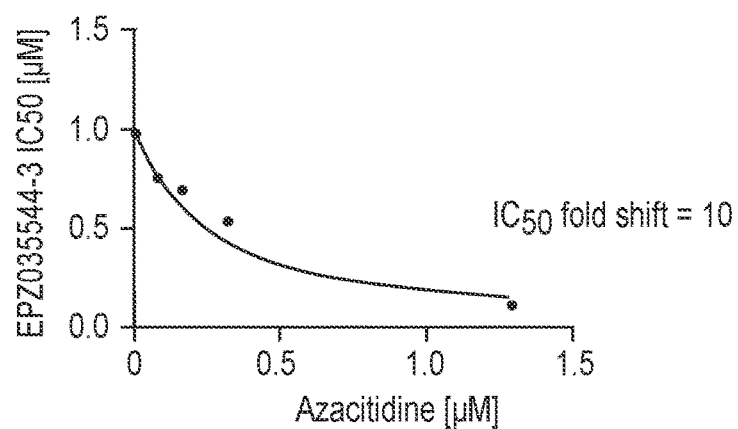
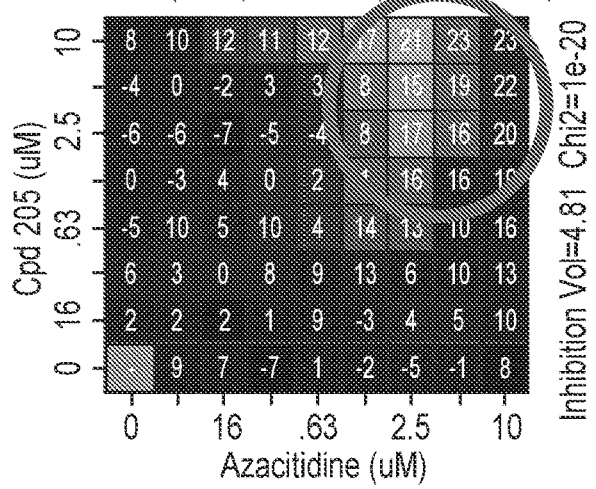

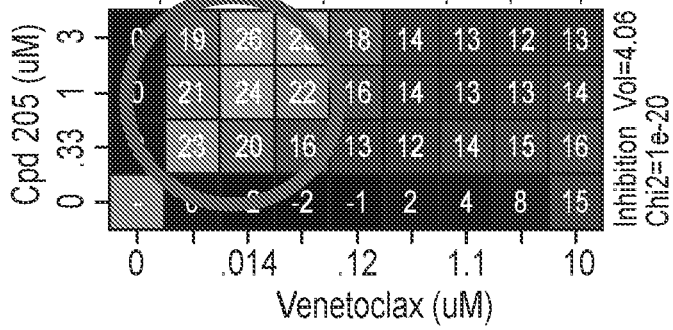
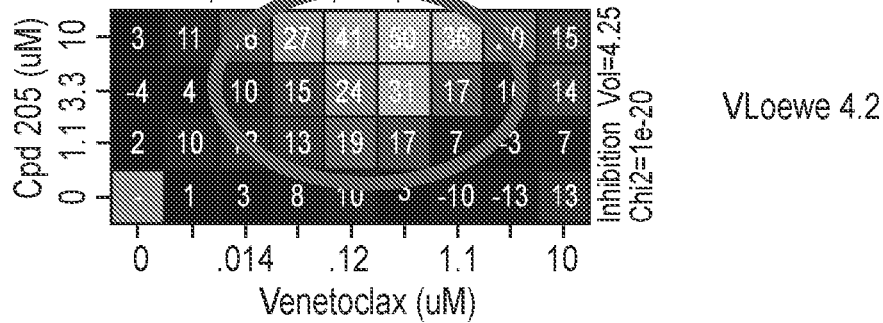
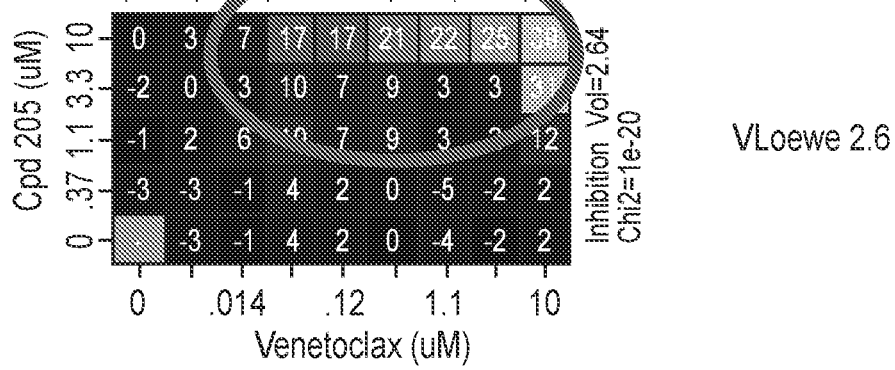
Figure 1 (continued)

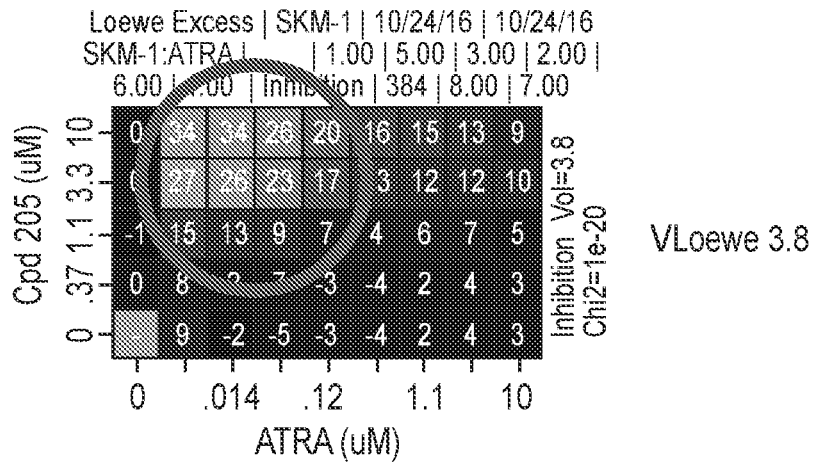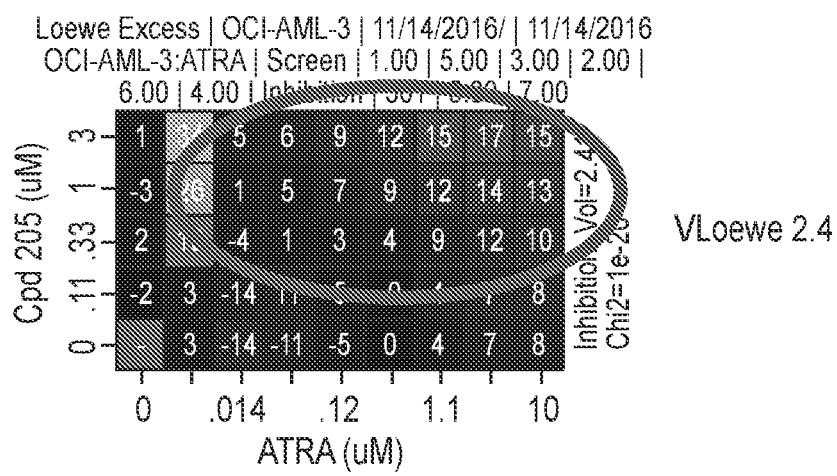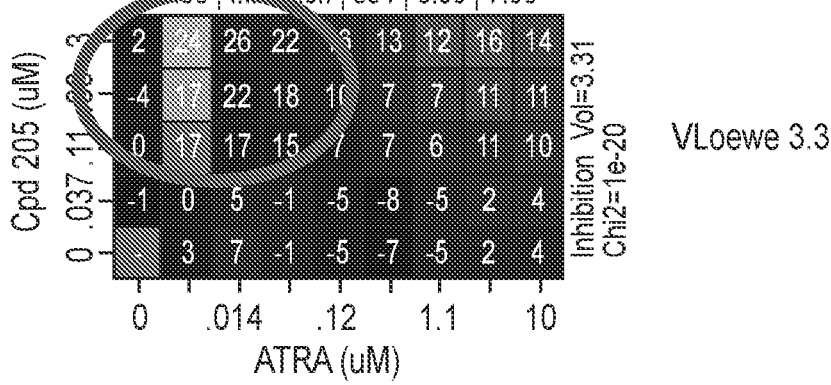
Figure 1 (continued)

Figure 3

| CELL LINE | TISSUE | TYPE | SPECIFIC TISSUE/TUMOR TYPE | Cell Line | Cell Count IC50 (microM) |
|---|---|---|---|---|---|
| SCC-9 | Head and Neck | Head and Neck | Squamous cell carcinoma (tongue) | SCC-9 | 4.07E-03 |
| SCC-25 | Head and Neck | Head and Neck | Squamous cell carcinoma (tongue) | SCC-25 | 6.29E-03 |
| BFTC-905 | Bladder | Bladder | | BFTC-905 | 1.17E-02 |
| A204 | Soft & Connective Tissue | Sarcoma | | A204 | 1.27E-02 |
| Hs 729 | Soft & Connective Tissue | Sarcoma | Rhabdomyosarcoma | Hs 729 | 1.87E-02 |
| DB | Hematopoietic | Lymphoma | B-cell lymphoma | DB | 6.97E-02 |
| WM-266-4 | Skin | Melanoma | | WM-266-4 | 1.25E-01 |
| MT-3 | Colon | Colon | | MT-3 | 1.41E-01 |
| LNCaP | Prostate | Prostate | | LNCaP | 1.91E-01 |
| CHP-212 | Central Nervous System | Neuroblastoma | | CHP-212 | 2.15E-01 |
| Ca Ski | Female GU | Cervix | Epidermoid carcinoma | Ca Ski | 2.35E-01 |
| SW684 | Soft & Connective Tissue | Sarcoma | Fibrosarcoma | SW684 | 2.65E-01 |
| BC-1 | Hematopoietic | Lymphoma | B-cell lymphoma | BC-1 | 3.34E-01 |
| SW1463 | Colon | Colon | Rectum | SW1463 | 4.58E-01 |
| MV-4-11 | Hematopoietic | Leukemia | Biphenotypic B myelomonocytic leukemia | MV-4-11 | 4.97E-01 |
| RPMI 6666 | Hematopoietic | Lymphoma | Hodgkin's lymphoma | RPMI 6666 | 5.24E-01 |
| TCCSUP | Bladder | Bladder | | TCCSUP | 5.57E-01 |
| DMS53 | Lung | SCLC | | DMS53 | 5.81E-01 |
| NCI-H69 | Lung | SCLC | | NCI-H69 | 6.09E-01 |
| U-118 MG | Central Nervous System | Glioma | Glioblastoma | U-118 MG | 6.34E-01 |
| SaOS2 | Bone | Osteosarcoma | | SaOS2 | 6.38E-01 |
| HOS | Bone | Osteosarcoma | | HOS | 6.71E-01 |
| SU-DHL-4 | Hematopoietic | Lymphoma | B-cell non-Hodgkin lymphoma | SU-DHL-4 | 6.94E-01 |
| OCUG-1 | Liver | Liver | Gall bladder | OCUG-1 | 7.84E-01 |
| NCI-H661 | Lung | NSCLC | | NCI-H661 | 9.43E-01 |
| TE 125.T | Soft & Connective Tissue | Sarcoma | Rhabdomyosarcoma | TE 125.T | 9.43E-01 |
| COR-L105 | Lung | NSCLC | | COR-L105 | 1.12E+00 |
| CAMA-1 | Breast | Breast | | CAMA-1 | 1.14E+00 |
| NAMALWA | Hematopoietic | Lymphoma | Burkitt's lymphoma | NAMALWA | 1.27E+00 |

Figure 3 (continued)

| | | | | | |
|---|---|---|---|---|---|
| SJSA1 | Bone | Osteosarcoma | | SJSA1 | 1.30E+00 |
| MeWo | Skin | Melanoma | | MeWo | 1.37E+00 |
| ACHN | Kidney | Kidney | | ACHN | 1.53E+00 |
| Hs 445 | Hematopoietic | Lymphoma | Hodgkin's lymphoma | Hs 445 | 1.53E+00 |
| MG-63 | Bone | Osteosarcoma | | MG-63 | 1.57E+00 |
| ARH-77 | Hematopoietic | Myeloma | B-cell leukemia/plasma cell leukemia | ARH-77 | 1.59E+00 |
| TF-1 | Hematopoietic | Luekemia | Erythroleukemia | TF-1 | 1.62E+00 |
| RS4;11 | Hematopoietic | Leukemia | Acute lymphoblastic leukemia | RS4;11 | 1.65E+00 |
| SR | Hematopoietic | Lymphoma | Large cell immunoblastic lymphoma | SR | 1.68E+00 |
| NALM-6 | Hematopoietic | Leukemia | B-cell precursor leukemia (ALL) | NALM-6 | 1.77E+00 |
| DMS114 | Lung | SCLC | | DMS114 | 1.84E+00 |
| MOLT-16 | Hematopoietic | Luekemia | Acute lymphoblastic leukemia | MOLT-16 | 1.93E+00 |
| MDA MB 468 | Breast | Breast | | MDA MB 468 | 1.98E+00 |
| SUP-T1 | Hematopoietic | Lymphoma | T-cell lymphoblastic lymphoma | SUP-T1 | 1.98E+00 |
| SU-DHL-10 | Hematopoietic | Lymphoma | Large cell lymphoma | SU-DHL-10 | 2.02E+00 |
| HUH-6 Clone 5 | Liver | Liver | | HUH-6 Clone 5 | 2.05E+00 |
| KATO III | Stomach | Stomach | | KATO III | 2.25E+00 |
| HPAF-II | Pancreas | Pancreas | | HPAF-II | 2.30E+00 |
| Jurkat | Hematopoietic | Luekemia | Acute lymphoblastic leukemia | Jurkat | 2.32E+00 |
| SK-BR-3 | Breast | Breast | | SK-BR-3 | 2.67E+00 |
| RPMI 8226 | Hematopoietic | Myeloma | B-cell myeloma (plasmacytoma) | RPMI 8226 | 2.71E+00 |
| SKO-007 | Hematopoietic | Myeloma | B-cell myeloma | SKO-007 | 2.76E+00 |
| Daudi | Hematopoietic | Lymphoma | Burkitt's lymphoma | Daudi | 3.00E+00 |
| AsPC-1 | Pancreas | Pancreas | | AsPC-1 | 3.02E+00 |
| SK-MEL-28 | Skin | Melanoma | | SK-MEL-28 | 3.17E+00 |
| COLO 829 | Skin | Melanoma | | COLO 829 | 3.21E+00 |
| BV-173 | Hematopoietic | Leukemia | B-cell precursor leukemia (CML) | BV-173 | 3.26E+00 |
| SJRH30 | Soft & Connective Tissue | Sarcoma | Rhabdomyosarcoma | SJRH30 | 3.28E+00 |
| Thp1 | Hematopoietic | Leukemia | Acute monocytic leukemia | Thp1 | 3.34E+00 |
| HT | Hematopoietic | Lymphoma | B-cell diffuse mixed lymphoma | HT | 3.45E+00 |
| SNU-423 | Liver | Liver | | SNU-423 | 3.46E+00 |
| JeKo-1 | Hematopoietic | Lymphoma | Mantle cell lymphoma | JeKo-1 | 3.56E+00 |
| Hs 611.T | Hematopoietic | Lymphoma | Hodgkin's lymphoma | Hs 611.T | 3.58E+00 |
| 22Rv1 | Prostate | Prostate | | 22Rv1 | 3.58E+00 |
| A2058 | Skin | Melanoma | | A2058 | 3.64E+00 |

Figure 3 (contiued)

| | | | | | |
|---|---|---|---|---|---|
| SNU-5 | Stomach | Stomach | | SNU-5 | 3.66E+00 |
| MOLT-3 | Hematopoietic | Luekemia | Acute lymphoblastic leukemia | MOLT-3 | 3.67E+00 |
| SU-DHL-8 | Hematopoietic | Lymphoma | Large cell lymphoma | SU-DHL-8 | 3.75E+00 |
| SK-PN-DW | Soft & Connective Tissue | Sarcoma | Neuroectodermal tumor (retroperitoneal) | SK-PN-DW | 3.75E+00 |
| C32TG | Skin | Melanoma | | C32TG | 3.76E+00 |
| MES-SA | Soft & Connective Tissue | Sarcoma | Uterine sarcoma | MES-SA | 3.79E+00 |
| Caki-1 | Kidney | Kidney | | Caki-1 | 3.80E+00 |
| G-402 | Kidney | Kidney | | G-402 | 3.81E+00 |
| A388 | Skin | Head and Neck | Epidermoid carcinoma | A388 | 3.82E+00 |
| EM-2 | Hematopoietic | Leukemia | Chronic myelogenous leukemia | EM-2 | 3.82E+00 |
| DOHH-2 | Hematopoietic | Lymphoma | B-cell lymphoma | DOHH-2 | 3.94E+00 |
| SNU-16 | Stomach | Stomach | | SNU-16 | 3.95E+00 |
| G-361 | Skin | Melanoma | | G-361 | 3.99E+00 |
| CML-T1 | Hematopoietic | Luekemia | T-cell leukemia (CML) | CML-T1 | 4.01E+00 |
| A-704 | Kidney | Kidney | | A-704 | 4.02E+00 |
| RD | Soft & Connective Tissue | Sarcoma | Rhabdomyosarcoma | RD | 4.23E+00 |
| MDA MB 453 | Breast | Breast | | MDA MB 453 | 4.26E+00 |
| 769-P | Kidney | Kidney | | 769-P | 4.30E+00 |
| CA46 | Hematopoietic | Lymphoma | Burkitt's lymphoma | CA46 | 4.34E+00 |
| A427 | Lung | NSCLC | | A427 | 4.36E+00 |
| SK-MEL-3 | Skin | Melanoma | | SK-MEL-3 | 4.38E+00 |
| MHH-PREB-1 | Hematopoietic | Leukemia | B-cell lymphoblastic non-Hodgkin lymphoma | MHH-PREB-1 | 4.39E+00 |
| U266B1 | Hematopoietic | Myeloma | B-cell myeloma | U266B1 | 4.42E+00 |
| TE 381.T | Soft & Connective Tissue | Sarcoma | Rhabdomyosarcoma | TE 381.T | 4.44E+00 |
| KHOS-240S | Bone | Osteosarcoma | | KHOS-240S | 4.45E+00 |
| HT-1197 | Bladder | Bladder | | HT-1197 | 4.49E+00 |
| SH-4 | Skin | Melanoma | | SH-4 | 4.54E+00 |
| C32 | Skin | h | | C32 | 4.57E+00 |
| BT474 | Breast | Breast | | BT474 | 4.68E+00 |
| TUR | Hematopoietic | Lymphoma | Histiocytic lymphoma | TUR | 4.76E+00 |
| ST486 | Hematopoietic | Lymphoma | Burkitt's lymphoma | ST486 | 4.80E+00 |
| PSN-1 | Pancreas | Pancreas | | PSN-1 | 4.82E+00 |
| AU565 | Breast | Breast | | AU565 | 4.94E+00 |

Figure 3 (contiued)

| | | | | | |
|---|---|---|---|---|---|
| Hs 936.T(C1) | Skin | Melanoma | | Hs 936.T(C1) | 5.06E+00 |
| Hs 695T | Skin | Melanoma | | Hs 695T | 5.09E+00 |
| Hs 821.T | Soft & Connective Tissue | Sarcoma | Giant cell sarcoma | Hs 821.T | 5.10E+00 |
| A498 | Kidney | Kidney | | A498 | 5.37E+00 |
| RPMI-7951 | Skin | Melanoma | | RPMI-7951 | 5.39E+00 |
| HuCCT1 | Liver | Liver | Cholangiocarcinoma (bile duct) | HuCCT1 | 5.41E+00 |
| MEG01 | Hematopoietic | Leukemia | Chronic myelogenous leukemia | MEG01 | 5.47E+00 |
| AGS | Stomach | Stomach | | AGS | 5.49E+00 |
| HuP-T4 | Pancreas | Pancreas | | HuP-T4 | 5.51E+00 |
| Hs 294T | Skin | Melanoma | | Hs 294T | 5.64E+00 |
| SCaBER | Bladder | Bladder | Squamous cell carcinoma | SCaBER | 5.77E+00 |
| A101D | Skin | Melanoma | | A101D | 5.97E+00 |
| Hs 688(A).T | Skin | Melanoma | | Hs 688(A).T | 6.26E+00 |
| HLF | Liver | Liver | | HLF | 6.41E+00 |
| SW872 | Soft & Connective Tissue | Sarcoma | Liposarcoma | SW872 | 6.77E+00 |
| MDA MB 231 | Breast | Breast | | MDA MB 231 | 7.12E+00 |
| Ramos (RA 1) | Hematopoietic | Lymphoma | Burkitt's lymphoma | Ramos (RA 1) | 7.13E+00 |
| U2OS | Bone | Osteosarcoma | | U2OS | 7.35E+00 |
| EB2 | Hematopoietic | Lymphoma | Burkitt's lymphoma | EB2 | 7.43E+00 |
| Caki-2 | Kidney | Kidney | | Caki-2 | 7.80E+00 |
| K562 | Hematopoietic | Leukemia | Chronic myelogenous leukemia | K562 | 7.82E+00 |
| PANC-1 | Pancreas | Pancreas | | PANC-1 | 7.95E+00 |
| NCIH446 | Lung | SCLC | | NCIH446 | 8.08E+00 |
| SKMES1 | Lung | NSCLC | Squamous cell carcinoma | SKMES1 | 8.33E+00 |
| 647-V | Bladder | Bladder | | 647-V | 8.35E+00 |
| SK-MEL-1 | Skin | Melanoma | | SK-MEL-1 | 8.36E+00 |
| SW900 | Lung | SCLC | Squamous cell carcinoma | SW900 | 8.96E+00 |
| A375 | Skin | Melanoma | | A375 | 9.06E+00 |
| NTERA-2 cl.D1 | Testis | Testis | | NTERA-2 cl.D1 | 9.26E+00 |
| J82 | Bladder | Bladder | | J82 | 9.35E+00 |
| COR-L23 | Lung | NSCLC | Large cell carcinoma | COR-L23 | 9.40E+00 |
| BxPC-3 | Pancreas | Pancreas | | BxPC-3 | 9.40E+00 |
| Mia PaCa-2 | Pancreas | Pancreas | | Mia PaCa-2 | 9.41E+00 |
| A431 | Skin | Head and Neck | Epidermoid carcinoma | A431 | 9.82E+00 |
| UM-UC-3 | Bladder | Bladder | | UM-UC-3 | 9.93e+00 |

| Drug | AML-193 | AP-1060 | EOL-1 | HL-60 | Kasumi-1 | ML-2 | MOLM-13 | MOLM-16 | NOMO-1 | OCI-AML-2 | OCI-AML-3 | SKM-1 |
|---|---|---|---|---|---|---|---|---|---|---|---|---|
| | | PML-RARA | MLL-PTD | MYCamp | AML1-ETO | MLL-AF6TP53 | MLL-AF9 FLT3-ITD | | MLL-AF9KRAS | DNMT3 | DNMT3A NPM1 | ASXL1 |
| Cytarabine | SYN | ADD | SYN | ADD | SYN | ADD | ADD | ANT | ANT | ADD | ADD | ADD |
| Daunorubicin | ADD | ADD | ADD | ADD | ADD | SYN | ADD | ADD | ANT | ADD | ADD | ADD |
| ATRA | ADD | ADD | ADD | SYN | SYN | SYN | ADD | ANT | ADD | SYN | SYN | SYN |
| Azacitidine | SYN | ADD | ADD | ADD | SYN | ADD | ADD | ADD | SYN | SYN | ADD | ADD |
| Decitabine | SYN | ADD | SYN | SYN | SYN | SYN | SYN | ANT | SYN | SYN | ADD | ADD |
| Pinometostat | ADD | SYN | SYN | NE | ADD | NE | NE | NE | NE | SYN | NE | ADD |
| Tazemetostat | ADD | SYN | SYN | NE | SYN | NE | NE | NE | NE | SYN | NE | ADD |
| Gilteritinib | ADD | SYN | SYN | SYN | SYN | SYN | SYN | ADD | SYN | SYN | ADD | ADD |
| Midostaurin | ADD | SYN | SYN | ADD | SYN | ADD | SYN | ANT | ANT | SYN | ADD | ADD |
| Panobinostat | ADD | SYN | SYN | SYN | SYN | SYN | ADD | SYN | ADD | SYN | SYN | SYN |
| Pracinostat | ADD | SYN | SYN | SYN | SYN | ADD | ADD | ADD | ADD | SYN | SYN | ADD |
| Venetoclax | ANT | SYN | SYN | SYN | SYN | ANT | SYN | ADD | ADD | ADD | ADD | ADD |
| Schedule | 7+7 | 7+7 | 7+3 | 7+3 | 7+7 | 7+3 | 7+3 | 7+3 | 7+3 | 7+3 | 7+3 | 7+3 |

| | |
|---|---|
| SYN | Synergy | Loewe volume >1 |
| ADD | Additivity | Loewe volume between -1 and 1 |
| ANT | Antagonism | Loewe volume <1 |
| NE | No effect | Neither agent or combination of the two reached 50% inhibitory concentration |

Figure 4

| Drug | AML-193 | AP-1060 | EOL-1 | HL-60 | Kasumi-1 | ML-2 | MOLM-16 | OCI-AML2 | OCI-AML-3 | SKM-1 |
|---|---|---|---|---|---|---|---|---|---|---|
| Azacitidine | SYN | ADD | ADD | SYN | SYN | SYN | ADD | SYN | ADD | SYN |
| Decitabine | SYN | SYN | SYN | SYN | SYN | SYN | ANT | SYN | ADD | SYN |
| EPZ-5676 | NE | SYN | SYN | NE | SYN | SYN | ADD | SYN | ADD | SYN |
| EPZ-6438 | NE | SYN | SYN | NE | SYN | ANT | ADD | ADD | ANT | ADD |
| Ara-C | | | SYN | | SYN | | | SYN | ADD | |
| Atra | | | SYN | | ADD | | | SYN | SYN | |
| Pracinostat | | | | | | | | SYN | ADD | |
| Venetoclax | | | SYN | | SYN | | | SYN | ADD | |

| | |
|---|---|
| SYN | Synergy | Loewe volume >1 |
| ADD | Additivity | Loewe volume between -1 and 1 |
| ANT | Antagonism | Loewe volume <1 |
| Ne | No effect | Neither agent or combination of the two reached 50% inhibitory concentration |
| | Not tested |

Figure 5

COMBINATION THERAPIES WITH EHMT2 INHIBITORS

RELATED APPLICATION

This application is a U.S. National Phase application, filed under 35 U.S.C. § 371, of International Application No. PCT/US2018/028609, filed Apr. 20, 2018, which claims priority to U.S. Application Nos. 62/574,147, filed Oct. 18, 2017, and 62/488,679, filed Apr. 21, 2017, the entire contents of each of which are incorporated herein by reference.

BACKGROUND

Methylation of protein lysine residues is an important signaling mechanism in eukaryotic cells, and the methylation state of histone lysines encodes signals that are recognized by a multitude of proteins and protein complexes in the context of epigenetic gene regulation.

Histone methylation is catalyzed by histone methyltransferases (HMTs), and HMTs have been implicated in various human diseases. HMTs can play a role in either activating or repressing gene expression, and certain HMTs (e.g., euchromatic histone-lysine N-methyltransferase 2 or EHMT2, also called G9a) may methylate many nonhistone proteins, such as tumor suppressor proteins (see, e.g., Liu et al., *Journal of Medicinal Chemistry* 56:8931-8942, 2013 and Krivega et al., *Blood* 126(5):665-672, 2015).

Two related HMTs, EHMT1 and EHMT2, are overexpressed or play a role in diseases and disorders such as sickle cell anemia (see, e.g., Renneville et al., *Blood* 126(16):1930-1939, 2015) and proliferative disorders (e.g., cancers), and other blood disorders.

SUMMARY

In one aspect, the present disclosure features a method of preventing or treating a cancer, the method comprising administering to a subject in need thereof a therapeutically effective amount of an EHMT2 inhibitor. In some embodiments, the method further comprises administering one or more additional therapeutic agent in a therapeutically effective amount. In some embodiments, the EHMT2 inhibitor is a compound disclosed herein. In some embodiments, the EHMT2 inhibitor is not 2-cyclohexyl-6-methoxy-N-[1-(1-methylethyl)-4-piperidinyl]-7-[3-(1-pyrrolidinyl)propoxy]-4-quinazolinamine; N-(1-isopropylpiperidin-4-yl)-6-methoxy-2-(4-methyl-1,4-diazepan-1-yl)-7-(3-(piperidin-1-yl)propoxy)quinazolin-4-amine; 2-(4,4-difluoropiperidin-1-yl)-N-(1-isopropylpiperidin-4-yl)-6-methoxy-7-(3-(pyrrol-idin-1-yl)propoxy)quinazolin-4-amine; or 2-(4-isopropyl-1,4-diazepan-1-yl)-N-(1-isopropylpiperidin-4-yl)-6-methoxy-7-(3-(piperidin-1-yl)propoxy)quinazolin-4-amine.

In another aspect, the disclosure also provides a method of inhibiting or decreasing growth, viability, survival, or proliferation of a cancer cell comprising (1) contacting the cell with (a) an effective amount of EHMT2 inhibitor, and (b) one or more additional therapeutic agent.

In certain embodiments, the effective amount of the EHMT2 inhibitor is an amount sufficient to inhibit or decrease growth, viability, survival, or proliferation of the cancer cell by at least 50%, at least 70%, or at least 90%.

In certain embodiments, the contacting is in vitro or ex vivo. In some embodiments, the contacting is in vivo by administering the EHMT2 inhibitor and the one or more additional therapeutic agent to a subject harboring the cancer cell.

In certain embodiments, the cancer is a hematological cancer, leukemia, hepatocellular carcinoma, lung cancer, brain and central nervous system (CNS) cancer, head and neck cancer, kidney cancer, ovarian cancer, pancreatic cancer, lymphoma, myeloma, sarcoma, breast cancer, prostate cancer, adrenal cancer, adrenal gland cancer, bladder cancer, breast cancer, cervix cancer, colon cancer, eye cancer, duodenum cancer, glioma, liver cancer, medulloblastoma, melanoma, myeloma, neuroblastoma, small cell lung cancer (SCLC), non-small cell lung cancer (NSCLC), osteosarcoma, placenta cancer, stomach cancer, testicular cancer, thyroid cancer, uterine cancer, vulvar cancer, oligodendroglioma, ovarian clear cell adenocarcinoma, ovarian endometrioid adenocarcinoma, ovarian serous adenocarcinoma, pancreatic ductal adenocarcinoma, pancreatic endocrine tumor, malignant rhabdoid tumor, astrocytoma, atypical teratoid/rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epithelioid sarcoma, renal medullary carcinoma, diffuse large B-cell lymphoma, follicular lymphoma, or not otherwise specified (NOS) sarcoma.

In certain embodiments, the cancer is a hematological cancer, leukemia, hepatocellular carcinoma, lung cancer, brain and central nervous system (CNS) cancer, head and neck cancer, kidney cancer, ovarian cancer, pancreatic cancer, lymphoma, myeloma, sarcoma, breast cancer, prostate cancer, adrenal cancer, adrenal gland cancer, bladder cancer, breast cancer, cervix cancer, colon cancer, eye cancer, duodenum cancer, glioma, liver cancer, medulloblastoma, melanoma, myeloma, neuroblastoma, small cell lung cancer (SCLC), non-small cell lung cancer (NSCLC), osteosarcoma, placenta cancer, stomach cancer, testicular cancer, thyroid cancer, uterine cancer, or vulvar cancer.

In certain embodiments, the cancer is brain and central nervous system (CNS) cancer, head and neck cancer, kidney cancer, ovarian cancer, pancreatic cancer, leukemia, lung cancer, lymphoma, myeloma, sarcoma, breast cancer, prostate cancer, or skin cancer.

In certain embodiments, the EHMT2 inhibitor is a compound of any one of Formulae (I), (I'), (I''), (II''), (III''), (I'''), (II'''), and (III'''):

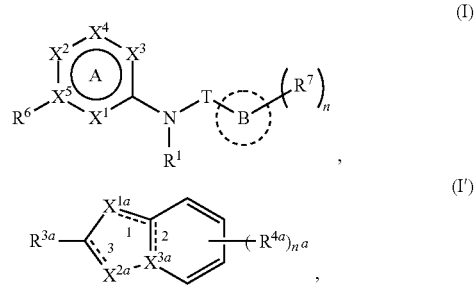

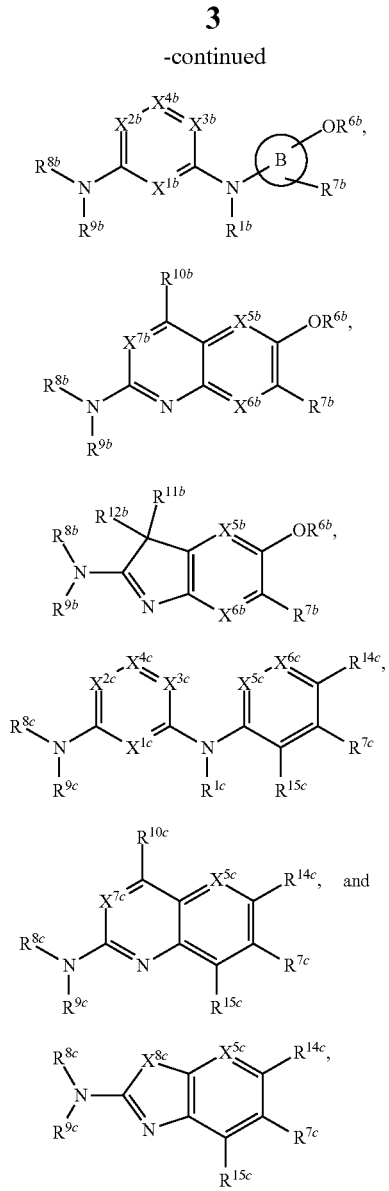

and a tautomer thereof, a pharmaceutically acceptable salt of the compound, or a pharmaceutically acceptable salt of the tautomer, wherein the variables are as defined herein.

In certain embodiments, the one or more additional therapeutic agent comprises a standard-of-care treatment modality for treating AML, a standard-of-care treatment modality for treating melanoma, an epigenetic drug, a targeted therapy, or a combination thereof.

In certain embodiments, the one or more additional therapeutic agent comprises an antimetabolite, a topoisomerase II inhibitor, DNA hypomethylating agent, a DNA methyltransferase (DNMT) inhibitor, an HDAC inhibitor, an EZH2 inhibitor, a DOT1L inhibitor, a differentiation agent, a FLT3 inhibitor, a BCL2 inhibitor, a glucocorticoid receptor agonist (GRag), a BCR inhibitor, a corticosteroid, or a combination thereof.

In certain embodiments, the one or more additional therapeutic agent comprises Ara-C, CHOP, Daunorubicin, Azacitidine, Decitabine, Pracinostat, Panobinostat, Tazemetostat, Pinometostat. All trans retinoic acid (ATRA), Gilteritinib, Midostaurin, Venetoclax, AG-120, AG-221, Cytarabine, Midostaurin, pembrolizumab, ipilimumab, dacarbazine, temozolomide, interleukin-2, nivolumab, vemurafenib, dabrafenib, trametinib, carmustine, cisplatin, interferon alfa-2b, cobimetinib, Dexamethasone, Prednisolone, Pomalidomide, Lenalidomide, Thalidomide, Ixazomib. Bortezomib, Carfilzomib, Melphalan, Vincristine, Mafosfamide, Etoposide, Doxorubicin, Bendamustine, Trametinib, Idelalisib, Ibrutinib, Tamatinib, Alisertib, Enzastaurin, Ipatasertib, doxorubicin, cytarabine, vincristine, everolimus, alisertib, topotecan, etoposide, carboplatin, entinostat, panobinostat, romidepsin, palbociclib, abemaciclib, selumetinib, trametinib, MK-2206. Vorinostat, Navitoclax, Rituximab, Obatoclax, atezolizumab, ABT-199. Velcade, Dasatinib, GSK1070916, GSK690693, Sorafenib, Omipalisib, Ruxolitinib, Fedratinib, JQ1, Methotrexate, Tofacitinib, OG-L002, GSK J4, Ribociclib, or a combination thereof.

In certain embodiments, the cancer is leukemia and the one or more additional therapeutic agent comprises Ara-C, Daunorubicin, Azacitidine, Decitabine, Pracinostat, Panobinostat, Tazemetostat, Pinometostat, All trans retinoic acid (ATRA), Gilteritinib, Midostaurin, Venetoclax, AG-120, AG-221, Cytarabine, Midostaurin, or a combination thereof.

In certain embodiments, the cancer is melanoma and the one or more additional therapeutic agent comprises pembrolizumab, ipilimumab, atezolizumab, dacarbazine, temozolomide, interleukin-2, nivolumab, vemurafenib, dabrafenib, trametinib, carmustine, cisplatin, interferon alfa-2b, cobimetinib, or a combination thereof.

In certain embodiments, the EHMT2 inhibitor and the one or more additional therapeutic agent are administered simultaneously.

In certain embodiments, the EHMT2 inhibitor and the one or more additional therapeutic agent are administered sequentially.

In certain embodiments, the EHMT2 inhibitor and the one or more additional therapeutic agent are administered in alternation.

In certain embodiments, the one or more additional therapeutic agent is administered prior to the EHMT2 inhibitor.

In certain embodiments, the EHMT2 inhibitor is administered prior to the one or more additional therapeutic agent.

In certain embodiments, the therapeutically effective amount of the EHMT2 inhibitor is an amount sufficient to sensitize the subject to a treatment by administration of the one or more additional therapeutic agent, e.g., simultaneously with, subsequent to, or prior to the administration of the EHMT2 inhibitor.

In certain embodiments, the therapeutically effective amount of the EHMT2 inhibitor is an amount sufficient to sensitize the subject to a subsequent treatment by administration of the one or more additional therapeutic agent.

In certain embodiments, the amount of the one or more additional therapeutic agent that is therapeutically effective is smaller than the amount of the same agent that is therapeutically effective in a subject not administered with the EHMT2 inhibitor.

In yet another aspect, the disclosure relates to a method of treating cancer by administering to a subject in need thereof an EHMT2 inhibitor in an amount sufficient to sensitize the subject to a treatment with one or more cancer treatment modalities.

In some embodiments, sensitizing a subject includes inducing sensitivity to treatment with a standard of care treatment, or another agents, or a combination of agents in a subject having a cancer that is resistant or refractory to treatment with said standard of care treatment or another agents, or combination of agents. In some embodiments, sensitizing a subject includes increasing the efficacy of a standard of care treatment, or another agents, or a combination of agents. In some embodiments, sensitizing may be achieved by administering the standard of care treatment, other agents, or combination of agents in combination with an EHMT2 inhibitor. In some embodiments sensitizing may be achieved by administering an EHMT2 inhibitor prior to the treatment with standard of care treatment, or another agents, or a combination of agents, or, sensitizing may be achieved by administering an EHMT2 inhibitor concurrently with the treatment with standard of care treatment, or another agents, or a combination of agents. In some embodiments, sensitizing a subject may include that a lower dose of a standard of care treatment, or another agents, or a combination of agents could be administered when used in combination with an EHMT2 inhibitor. In some embodiments, sensitizing may include that inhibition of proliferation of diseased cells is increased. In some embodiments inhibition of proliferation may be increased by 5%, 10% 15%, 20%, 25%, 30%, 50%, 75%, 90% or more as compared to the standard of care treatment, or treatment with agents, or treatment with a combination of agents without administration of an EHMT2 inhibitor. In further embodiments, sensitizing may result in an improvement in the clinical response of a patient to the combination treatment, e.g., in a complete response (CR) in a patient who showed only partial response (PR), stable disease (SD), or progressive disease (PD), in response to standard of care treatment, or treatment with agents, or treatment with a combination of agents without administration of an EHMT2 inhibitor. In further embodiments, sensitizing may result in an improvement in the clinical response of a patient to the combination treatment, e.g., in a complete response (CR) or a partial response (PR) in a patient who showed only stable disease (SD), or progressive disease (PD) in response to standard of care treatment, or treatment with agents, or treatment with a combination of agents without administration of an EHMT2 inhibitor. In further embodiments sensitizing may result in an improvement in the clinical response of a patient to the combination treatment, e.g., in a complete response (CR), partial response (PR), or stable disease (SD), in a patient who showed progressive disease (PD) in response to standard of care treatment, or treatment with agents, or treatment with a combination of agents without administration of an EHMT2 inhibitor. The terms complete response (CR), partial response (PR), stable disease (SD), and progressive disease (PD) are well known in the art (see, e.g., Eisenhauer et al. New response evaluation criteria in solid tumors: Revised RECIST guideline (version 1.1), EUROPEAN JOURNAL OF CANCER 45 (2009) 228-247, at page 232 and 233, section 4.3—"response criteria", the entire contents of which are incorporated herein by reference), and one or ordinary skill in the art will be aware of how to classify clinical responses according to these criteria.

In certain embodiments, the EHMT2 inhibitor is administered prior to the administration of a combination of the EHMT2 inhibitor and the one or more additional therapeutic agent.

In certain embodiments, the EHMT2 inhibitor is administered after the administration of a combination of the EHMT2 inhibitor and the one or more additional therapeutic agent.

In certain embodiments, the one or more additional therapeutic agent comprises an antimetabolite, a topoisomerase II inhibitor, a DNA hypomethylating agent, an HDAC inhibitor, an EZH2 inhibitor, a DOT1L inhibitor, a differentiation agent, an FLT3 inhibitor, or a BCL2 inhibitor.

In certain embodiments, the one or more additional therapeutic agent comprises cytarabine (Ara-C), daunorubicin, azacitidine, decitabine, pracinostat, panobinostat, tazemetostat, pinometostat, all-trans retinoic acid (ATRA), gilteritinib, midostaurin, venetoclax, pembrolizumab, ipilimumab, dacarbazine, temozolomide, interleukin-2, nivolumab, vemurafenib, dabrafenib, trametinib, carmustine, cisplatin, interferon alfa-2b, or cobimetinib.

In certain embodiments, the compounds of any of Formulae (I), (I'), (I''), (II''), (III''), (I'''), (II'''), and (III''') inhibit a kinase with an enzyme inhibition $IC_{50}$ value of about 100 nM or greater, 1 μM or greater, 10 μM or greater, 100 μM or greater, or 1000 μM or greater.

In certain embodiments, the compounds of any of Formulae (I), (I'), (I''), (II''), (III''), (I'''), (II'''), and (III''') inhibit a kinase with an enzyme inhibition $IC_{50}$ value of about 1 mM or greater.

In certain embodiments, the compounds of any of Formulae (I), (I'), (I''), (II''), (III''), (I'''), (II'''), and (III''') inhibit a kinase with an enzyme inhibition $IC_{50}$ value of 1 μM or greater, 2 μM or greater, 5 μM or greater, or 10 μM or greater, wherein the kinase is one or more of the following: AbI, AurA, CHK1, MAP4K, IRAK4, JAK3, EphA2, FGFR3, KDR, Lck, MARK1, MNK2, PKCb2, SIK, and Src.

Also provided herein are pharmaceutical compositions comprising one or more pharmaceutically acceptable carriers and a combination comprising one or more compounds of any of the Formulae (I), (I'), (I''), (II''), (III''), (I'''), (II'''), and (III''') described herein and one or more additional therapeutic agent.

In one aspect, the present disclosure provides an EHMT2 inhibitor disclosed herein (e.g., a compound of any of the Formulae (I), (I'), (I''), (II''), (III''), (I'''), (II'''), and (III''') disclosed herein) for use in the prevention or treatment of a cancer, wherein the prevention or treatment further comprises administering to a subject in need thereof a therapeutically effective amount of one or more additional therapeutic agent disclosed herein.

In one aspect, the present disclosure provides one or more additional therapeutic agent disclosed herein for use in the prevention or treatment of a cancer, wherein the prevention or treatment further comprises administering to a subject in need thereof a therapeutically effective amount of an EHMT2 inhibitor disclosed herein (e.g., a compound of any of the Formulae (I), (I'), (I''), (II''), (III''), (I'''), (II'''), and (III''') disclosed herein).

In one aspect, the present disclosure provides a combination of an EHMT2 inhibitor disclosed herein (e.g., a compound of any of the Formulae (I), (I'), (I''), (II''), (III''), (I'''), (II'''), and (III''') disclosed herein) and one or more additional therapeutic agent disclosed herein in for use in the prevention or treatment of a cancer.

In one aspect, the present disclosure provides use of an EHMT2 inhibitor disclosed herein (e.g., a compound of any of the Formulae (I), (I'), (I''), (II''), (III''), (I'''), (II'''), and (III''') disclosed herein) in the manufacture of a medicament for the prevention or treatment of a cancer, wherein the prevention or treatment further comprises administering to a subject in need thereof a therapeutically effective amount of one or more additional therapeutic agent disclosed herein.

In one aspect, the present disclosure provides use of one or more additional therapeutic agent disclosed herein in the manufacture of a medicament for the prevention or treatment of a cancer, wherein the prevention or treatment further comprises administering to a subject in need thereof a therapeutically effective amount of an EHMT2 inhibitor disclosed herein (e.g., a compound of any of the Formulae (I), (I'), (I''), (II''), (III''), (I'''), (II'''), and (III''') disclosed herein).

In one aspect, the present disclosure provides use of a combination of an EHMT2 inhibitor disclosed herein (e.g., a compound of any of the Formulae (I), (I'), (I''), (II''), (III''), (I'''), (II'''), and (III''') disclosed herein) and one or more additional therapeutic agent disclosed herein in the manufacture of a medicament for the prevention or treatment of a cancer.

Another aspect of this disclosure is a method of preventing or treating an EHMT-mediated disorder. The method includes administering to a subject in need thereof a therapeutically effective amount of a compound of any of Formulae (I), (I'), (I''), (II''), (III''), (I'''), (II'''), and (III'''), or a tautomer thereof, or a pharmaceutically acceptable salt of the compound or the tautomer, and a therapeutically effective amount of one or more additional therapeutic agent. The EHMT-mediated disorder is a disease, disorder, or condition that is mediated at least in part by the activity of EHMT1 or EHMT2 or both. In some embodiments, the EHMT-mediated disorder is a blood disease or disorder. In certain embodiments, the EHMT-mediated disorder is selected from proliferative disorders (e.g. Cancers such as leukemia, hepatocellular carcinoma, prostate carcinoma, lung cancer, and melanoma), addiction (e.g., cocaine addiction), and mental retardation.

In one aspect, the present disclosure provides an EHMT2 inhibitor disclosed herein (e.g., a compound of any of the Formulae (I), (I'), (I''), (II''), (III''), (I'''), (II'''), and (III''') disclosed herein) for use in the prevention or treatment of an EHMT-mediated disorder, wherein the prevention or treatment further comprises administering to a subject in need thereof a therapeutically effective amount of one or more additional therapeutic agent disclosed herein.

In one aspect, the present disclosure provides one or more additional therapeutic agent disclosed herein for use in the prevention or treatment of an EHMT-mediated disorder, wherein the prevention or treatment further comprises administering to a subject in need thereof a therapeutically effective amount of an EHMT2 inhibitor disclosed herein (e.g., a compound of any of the Formulae (I), (I'), (I''), (II''), (III''), (I'''), (II'''), and (III''') disclosed herein).

In one aspect, the present disclosure provides a combination of an EHMT2 inhibitor disclosed herein (e.g., a compound of any of the Formulae (I), (I'), (I''), (II''), (III''), (I'''), (II'''), and (III''') disclosed herein) and one or more additional therapeutic agent disclosed herein in for use in the prevention or treatment of an EHMT-mediated disorder.

In one aspect, the present disclosure provides use of an EHMT2 inhibitor disclosed herein (e.g., a compound of any of the Formulae (I), (I'), (I''), (II''), (III''), (I'''), (II'''), and (III''') disclosed herein) in the manufacture of a medicament for the prevention or treatment of an EHMT-mediated disorder, wherein the prevention or treatment further comprises administering to a subject in need thereof a therapeutically effective amount of one or more additional therapeutic agent disclosed herein.

In one aspect, the present disclosure provides use of one or more additional therapeutic agent disclosed herein in the manufacture of a medicament for the prevention or treatment of an EHMT-mediated disorder, wherein the prevention or treatment further comprises administering to a subject in need thereof a therapeutically effective amount of an EHMT2 inhibitor disclosed herein (e.g., a compound of any of the Formulae (I), (I'), (I''), (II''), (III''), (I'''), (II'''), and (III''') disclosed herein).

In one aspect, the present disclosure provides use of a combination of an EHMT2 inhibitor disclosed herein (e.g., a compound of any of the Formulae (I), (I'), (I''), (II''), (III''), (I'''), (II'''), and (III''') disclosed herein) and one or more additional therapeutic agent disclosed herein in the manufacture of a medicament for the prevention or treatment of an EHMT-mediated disorder.

Compounds that are suitable for the methods of the disclosure include subsets of the compounds of Formulae (I), (I'), (I''), (II''), (III''), (I'''), (II''') and specific examples that are described in U.S. Application Nos. 62/323,602, 62/348,837, 62/402,997, 62/402,863, 62/509,620, 62/436,139, 62/517,840, 62/573,442, and 62/573,917, and PCT Application Nos. PCT/US/027918, PCT/US2017/054468, and PCT/US2017/067192, the contents of each of which are incorporated herein by reference in their entireties.

In some embodiments, the one or more additional therapeutic agent consists of a single additional therapeutic agent. In some embodiments, the one or more additional therapeutic agent comprises a therapeutic agent provided herein. In some embodiments, the one or more additional therapeutic agent comprises a plurality of therapeutic agents, e.g., 2, 3, 4, 5, 6, 7, 8, 9, or 10 additional therapeutic agents. In some embodiments, the one or more additional therapeutic agent comprises more than 10 additional therapeutic agents.

Unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models. Methods described herein may be used to identify suitable candidates for treating or preventing EHMT-mediated disorders. In some embodiments, the disclosure also provides methods of identifying an inhibitor of EHMT1 or EHMT2 or both.

In some embodiments, the EHMT-mediated disease or disorder comprises a disorder that is associated with gene silencing by EHMT1 or EHMT2, e.g., cancer associated with gene silencing by EHMT2.

In some embodiments, the cancer is a hematological cancer or skin cancer.

In some embodiments, the hematological cancer is acute myeloid leukemia (AML) or chronic lymphocytic leukemia (CLL).

In some embodiments, the skin cancer is melanoma.

In some embodiments, the method further comprises the steps of performing an assay to detect the degree of histone methylation by EHMT1 or EHMT2 in a sample comprising blood cells from a subject in need thereof.

In some embodiments, performing the assay to detect methylation of H3-K9 in the histone substrate comprises measuring incorporation of labeled methyl groups.

In some embodiments, the labeled methyl groups are isotopically labeled methyl groups.

In some embodiments, performing the assay to detect methylation of H3-K9 in the histone substrate comprises contacting the histone substrate with an antibody that binds specifically to dimethylated H3-K9.

Still another aspect of the disclosure is a method of inhibiting conversion of H3-K9 to dimethylated H3-K9. The method comprises the step of contacting a mutant EHMT, the wild-type EHMT, or both, with a histone substrate comprising H3-K9 and an effective amount of an EHMT2 inhibitor disclosed herein and an effective amount of one or more additional therapeutic agent, wherein the combination of the EHMT2 inhibitor and the one or more additional therapeutic agent inhibits histone methyltransferase activity of EHMT, thereby inhibiting conversion of H3-K9 to dimethylated H3-K9.

Further, the compounds or methods described herein can be used for research (e.g., studying epigenetic enzymes) and other non-therapeutic purposes.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following figures, detailed description and claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

The above and further features will be more clearly appreciated from the following detailed description when taken in conjunction with the accompanying drawings.

FIG. 3 is a table of indications which are suitable for treatment via EHMT2 inhibition via a single agent, e.g., an EHMT2 inhibitor.

FIG. 4 shows examples of synergy of Compound 205 with various second therapeutic agents in AML cell lines in a pre-treatment assay.

FIG. 5 shows examples of synergy of Compound 205 with various second therapeutic agents in AML cell lines in a co-treatment assay.

DETAILED DESCRIPTION

Figure 1:
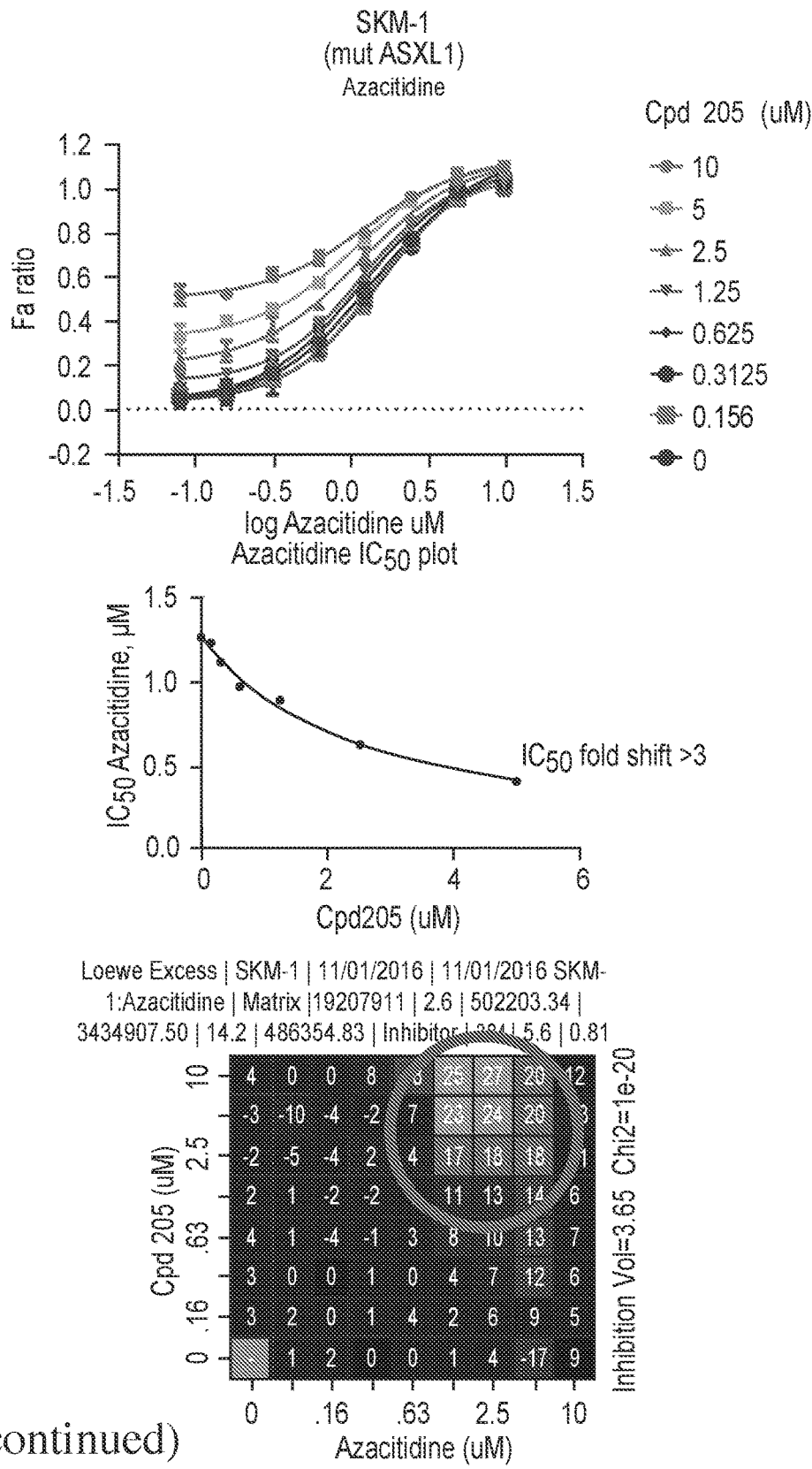
FIG. 1 is a series of tables and graphs illustrates the in vitro or in vivo studies of combining Compound 205 (an EHMT2 or G9a inhibitor) with various second agents.
Figure 1:
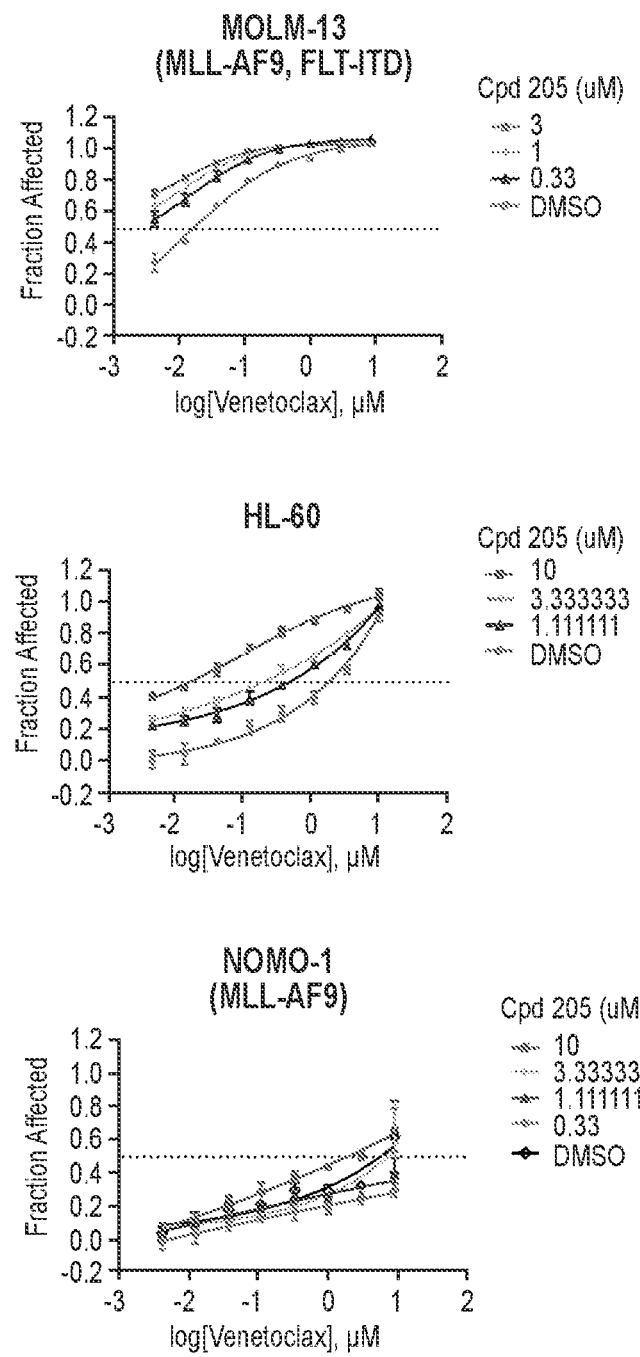
Figure 1:
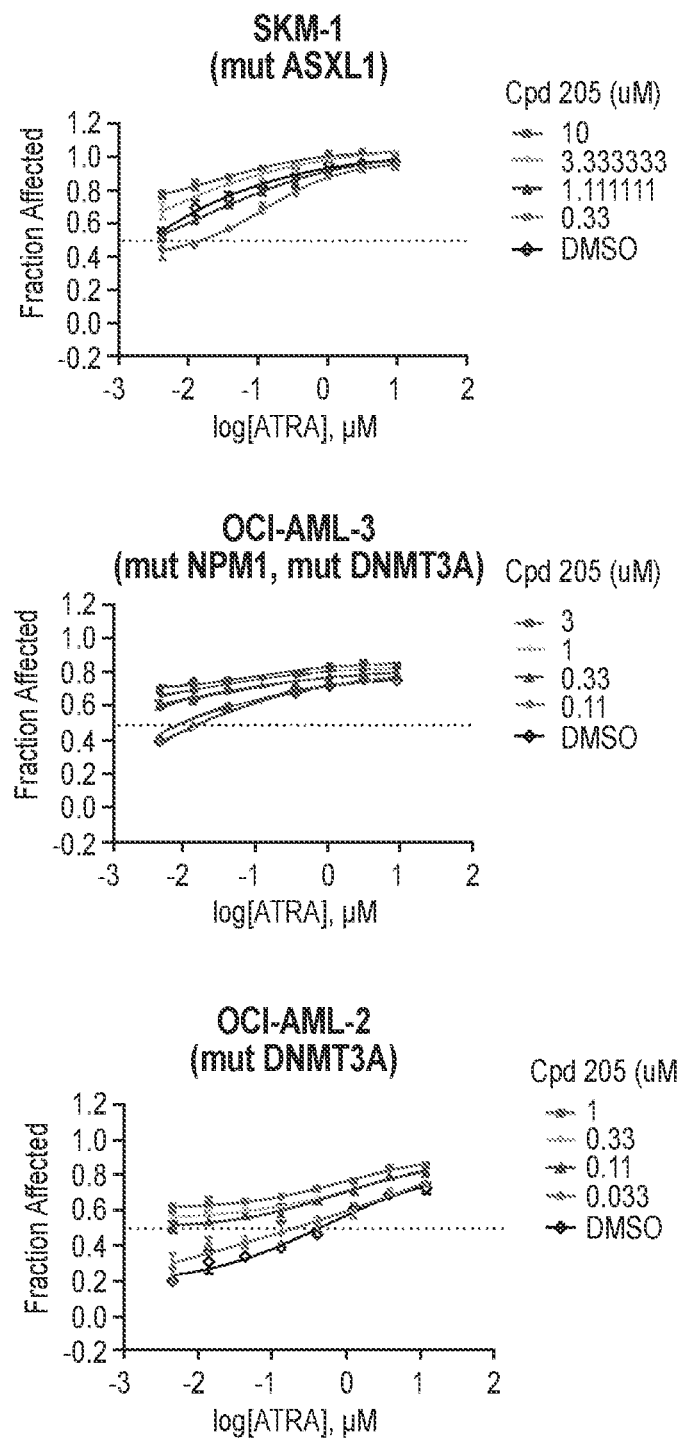

The present disclosure provides a method of preventing or treating a cancer, the method comprising administering to a subject in need thereof a therapeutically effective amount of an EHMT2 inhibitor. The method may further comprise administering a therapeutically effective amount of one or more additional therapeutic agent. In some embodiments, the EHMT2 inhibitor is a compound disclosed herein. In some embodiments, the EHMT2 inhibitor is not 2-cyclohexyl-6-methoxy-N-[1-(1-methylethyl)-4-piperidinyl]-7-[3-(1-pyrrolidinyl)propoxy]-4-quinazolinamine; N-(1-isopropylpiperidin-4-yl)-6-methoxy-2-(4-methyl-1,4-diazepan-1-yl)-7-(3-(piperidin-1-yl)propoxy)quinazolin-4-amine; 2-(4,4-difluoropiperidin-1-yl)-N-(1-isopropylpiperidin-4-yl)-6-methoxy-7-(3-(pyrrolidin-1-yl)propoxy)quinazolin-4-amine; or 2-(4-isopropyl-1,4-diazepan-1-yl)-N-(1-isopropylpiperidin-4-yl)-6-methoxy-7-(3-(piperidin-1-yl) propoxy)quinazolin-4-amine.

In certain embodiments, the one or more additional therapeutic agent comprises a standard-of-care treatment modality for treating AML, a standard-of-care treatment modality for treating melanoma, an epigenetic drug, a targeted therapy, or a combination thereof.

In certain embodiments, the one or more additional therapeutic agent comprises an antimetabolite, a topoisomerase II inhibitor, DNA hypomethylating agent, a DNA methyltransferase (DNMT) inhibitor, an HDAC inhibitor, an EZH2 inhibitor, a DOT1L inhibitor, a differentiation agent, a FLT3 inhibitor, a BCL2 inhibitor, a glucocorticoid receptor agonist (GRag), a BCR inhibitor, a corticosteroid, or a combination thereof.

In certain embodiments, the one or more additional therapeutic agent comprises Ara-C, CHOP, Daunorubicin, Azacitidine, Decitabine, Pracinostat, Panobinostat, Tazemetostat, Pinometostat, All trans retinoic acid (ATRA), Gilteritinib, Midostaurin, Venetoclax, AG-120, AG-221, Cytarabine, Midostaurin, pembrolizumab, ipilimumab, dacarbazine, temozolomide, interleukin-2, nivolumab, vemurafenib, dabrafenib, trametinib, carmustine, cisplatin, interferon alfa-2b, cobimetinib, Dexamethasone, Prednisolone, Pomalidomide, Lenalidomide, Thalidomide, Ixazomib, Bortezomib, Carfilzomib, Melphalan, Vincristine, Mafosfamide, Etoposide, Doxorubicin, Bendamustine, Trametinib, Idelalisib, Ibrutinib, Tamatinib, Alisertib, Enzastaurin, Ipatasertib, doxorubicin, cytarabine, vincristine, everolimus, alisertib, topotecan, etoposide, carboplatin, entinostat, panobinostat, romidepsin, palbociclib, abemaciclib, selumetinib, trametinib, MK-2206, Vorinostat, Navitoclax, Rituximab, Obatoclax, atezolizumab, ABT-199, Velcade, Dasatinib, GSK1070916, GSK690693, Sorafenib, Omipalisib, Ruxolitinib, Fedratinib, JQ1, Methotrexate, Tofacitinib, OG-L002, GSK J4, Ribociclib, or a combination thereof.

In some embodiments, the one or more additional therapeutic agent comprises an antimetabolite, a topoisomerase II inhibitor, a DNA hypomethylating agent, an HDAC inhibitor, an EZH2 inhibitor, a DOT1L inhibitor, a differentiation agent, an FLT3 inhibitor, or a BCL2 inhibitor.

In some embodiments, the one or more additional therapeutic agent comprises cytarabine (Ara-C), daunorubicin, azacitidine, decitabine, pracinostat, panobinostat, tazemetostat, pinometostat, all-trans retinoic acid (ATRA), gilteritinib, midostaurin, venetoclax, pembrolizumab, ipilimumab, dacarbazine, temozolomide, interleukin-2, nivolumab, vemurafenib, dabrafenib, trametinib, carmustine, cisplatin, interferon alfa-2b, or cobimetinib.

In certain embodiments, for the methods disclosed herein, the cancer is a hematological cancer, leukemia, hepatocellular carcinoma, lung cancer, brain and central nervous system (CNS) cancer, head and neck cancer, kidney cancer, ovarian cancer, pancreatic cancer, lymphoma, myeloma, sarcoma, breast cancer, prostate cancer, adrenal cancer, adrenal gland cancer, bladder cancer, breast cancer, cervix cancer, colon cancer, eye cancer, duodenum cancer, glioma, liver cancer, medulloblastoma, melanoma, myeloma, neuroblastoma, small cell lung cancer (SCLC), non-small cell lung cancer (NSCLC), osteosarcoma, placenta cancer, stomach cancer, testicular cancer, thyroid cancer, uterine cancer, vulvar cancer, oligodendroglioma, ovarian clear cell adenocarcinoma, ovarian endometrioid adenocarcinoma, ovarian serous adenocarcinoma, pancreatic ductal adenocarcinoma, pancreatic endocrine tumor, malignant rhabdoid tumor, astrocytoma, atypical teratoid/rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epithelioid sarcoma, renal medullary carcinoma, diffuse large B-cell lymphoma, follicular lymphoma, or not otherwise specified (NOS) sarcoma.

In certain embodiments, for the methods disclosed herein, the cancer is a hematological cancer, leukemia, hepatocellular carcinoma, lung cancer, brain and central nervous system (CNS) cancer, head and neck cancer, kidney cancer, ovarian cancer, pancreatic cancer, lymphoma, myeloma, sarcoma, breast cancer, prostate cancer, adrenal cancer, adrenal gland cancer, bladder cancer, breast cancer, cervix cancer, colon cancer, eye cancer, duodenum cancer, glioma, liver cancer, medulloblastoma, melanoma, myeloma, neuroblastoma, small cell lung cancer (SCLC), non-small cell lung cancer (NSCLC), osteosarcoma, placenta cancer, stomach cancer, testicular cancer, thyroid cancer, uterine cancer, or vulvar cancer.

In certain embodiments, for the methods disclosed herein, the cancer is brain and/or central nervous system (CNS) cancer, head and/or neck cancer, kidney cancer, ovarian cancer, pancreatic cancer, leukemia, lung cancer, lymphoma, myeloma, sarcoma, breast cancer, prostate cancer, or skin cancer.

In certain embodiments, for the methods disclosed herein, the cancer is leukemia and the one or more additional therapeutic agent comprises Ara-C, Daunorubicin, Azacitidine, Decitabine, Pracinostat, Panobinostat, Tazemetostat. Pinometostat, All trans retinoic acid (ATRA), Gilteritinib. Midostaurin, Venetoclax, AG-120, AG-221, Cytarabine, Midostaurin, or a combination thereof.

In certain embodiments, for the methods disclosed herein, the cancer is melanoma and the one or more additional therapeutic agent comprises pembrolizumab, ipilimumab, atezolizumab, dacarbazine, temozolomide, interleukin-2, nivolumab, vemurafenib, dabrafenib, trametinib, carmustine, cisplatin, interferon alfa-2b, cobimetinib, or a combination thereof.

More examples of EZH2 inhibitors, DOT1L inhibitors, and one or more additional therapeutic agents are described in US 2012/0264734, WO 2013/155464. WO 2015/085325, WO 2016/172199, WO 2016/043874, WO 2016/201328, WO 2014/026198, and WO 2016/025635, the contents of each of which are incorporated herein by reference in their entireties.

In certain embodiments, for the methods disclosed herein, the EHMT2 inhibitor is a compound of Formula (I) below:

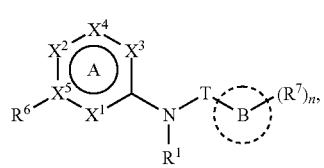

(I)

or a tautomer thereof, or a pharmaceutically acceptable salt of the compound or the tautomer, wherein ring A is phenyl or a 5- or 6-membered heteroaryl:

$X^1$ is N, $CR^2$, or $NR^{2'}$ as valency permits;

$X^2$ is N, $CR^3$, or $NR^{3'}$ as valency permits;

$X^3$ is N, $CR^4$, or $NR^{4'}$ as valency permits;

$X^4$ is N or $CR^5$, or $X^4$ is absent such that ring A is a 5-membered heteroaryl containing at least one N atom;

$X^5$ is C or N as valency permits;

B is absent or a ring structure selected from the group consisting of $C_6$-$C_{10}$ aryl, $C_3$-$C_{10}$ cycloalkyl, 5- to 10-membered heteroaryl, and 4- to 12-membered heterocycloalkyl containing 1-4 heteroatoms selected from N, O, and S;

T is a bond or $C_1$-$C_6$ alkylene. $C_2$-$C_6$ alkenylene, or $C_2$-$C_6$ alkynylene linker optionally substituted with one or more of halo, cyano, hydroxyl, oxo; or $C_1$-$C_6$ alkoxy when B is present; or T is H and n is 0 when B is absent; or T is $C_1$-$C_6$ alkyl optionally substituted with $(R^7)_n$ when B is absent; or when B is absent, T and $R^1$ together with the atoms to which they are attached optionally form a 4-7 membered heterocycloalkyl or 5-6 membered heteroaryl, each of which is optionally substituted with $(R^7)_n$;

$R^1$ is H or $C_1$-$C_4$ alkyl;

each of $R^2$, $R^3$, and $R^4$, independently is selected from the group consisting of H, halo, cyano, $C_1$-$C_6$ alkoxyl, $C_6$-$C_{10}$ aryl, $NR^aR^b$, $C(O)NR^aR^b$, $NR^aC(O)R^b$, $C_3$-$C_8$ cycloalkyl, 4- to 7-membered heterocycloalkyl, 5- to 6-membered heteroaryl, and $C_1$-$C_6$ alkyl, wherein $C_1$-$C_6$ alkoxyl and $C_1$-$C_6$ alkyl are optionally substituted with one or more of halo, $OR^a$, or $NR^aR^b$, in which each of $R^a$ and $R^b$ independently is H or $C_1$-$C_6$ alkyl, or $R^3$ is -$Q^1$-$T^1$, in which $Q^1$ is a bond or $C_1$-$C_6$ alkylene, $C_2$-$C_6$ alkenylene, or $C_2$-$C_6$ alkynylene linker optionally substituted with one or more of halo, cyano, hydroxyl, oxo, or $C_1$-$C_6$ alkoxyl, and $T^1$ is H, halo, cyano, $NR^8R^9$, $C(O)NR^8R^9$, $OR^5$, $OR^9$, or $R^{S1}$, in which $R^{S1}$ is $C_3$-$C_8$ cycloalkyl, phenyl, 4- to 12-membered heterocycloalkyl containing 1-4 heteroatoms selected from N, O, and S, or a 5- or 6-membered heteroaryl and $R^{S1}$ is optionally substituted with one or more of halo, $C_1$-$C_6$ alkyl, hydroxyl, oxo, —$C(O)R^9$, —$SO_2R^8$, —$SO_2N(R^8)_2$, —$NR^8C(O)R^9$, amino, mono- or di-alkylamino, or $C_1$-$C_6$ alkoxyl; or when ring A is a 5-membered heteroaryl containing at least one N atom, $R^4$ is a spiro-fused 4- to 12-membered heterocycloalkyl containing 1-4 heteroatoms selected from N, O, and S;

each of $R^{2'}$, $R^{3'}$ and $R^{4'}$ independently is H or $C_1$-$C_3$ alkyl;

$R^5$ is selected from the group consisting of H, F. Br, cyano, $C_1$-$C_6$ alkoxyl, $C_6$-$C_{10}$ aryl, $NR^aR^b$, $C(O)NR^aR^b$, $NR^aC(O)R^b$, $C_3$-$C_8$ cycloalkyl, 4- to 12-membered heterocycloalkyl containing 1-4 heteroatoms selected from N, O, and S, $C_1$-$C_6$ alkyl optionally substituted with one or more of halo, $OR^a$ or $NR^aR^b$, and $C_2$-$C_6$ alkynyl optionally substituted with 4- to 12-membered heterocycloalkyl; wherein said $C_3$-$C_8$ cycloalkyl or 4- to 12-membered heterocycloalkyl are optionally substituted with one or more of halo, $C(O)R^a$, $OR^a$, $NR^aR^b$, 4- to 7-membered heterocycloalkyl, —$C_1$-$C_6$ alkylene-4- to 7-membered heterocycloalkyl, or $C_1$-$C_4$ alkyl optionally substituted with one or more of halo, $OR^a$ or $NR^aR^b$, in which each of $R^a$ and $R^b$ independently is H or $C_1$-$C_6$ alkyl; or $R^5$ and one of $R^3$ or $R^4$ together with the atoms to which they are attached form phenyl or a 5- or 6-membered heteroaryl; or $R^5$ and one of $R^{3'}$ or $R^{4'}$ together with the atoms to which they are attached form a 5- or 6-membered heteroaryl, in which the phenyl or 5- or 6-membered heteroaryl as formed is optionally substituted with one or more of halo, $C_1$-$C_3$ alkyl, hydroxyl or $C_1$-$C_3$ alkoxyl;

$R^6$ is absent when $X^5$ is N and ring A is a 6-membered heteroaryl; or $R^6$ is $-Q^1-T^1$, in which $Q^1$ is a bond or $C_1-C_6$ alkylene, $C_2-C_6$ alkenylene, or $C_2-C_6$ alkynylene linker optionally substituted with one or more of halo, cyano, hydroxyl, oxo, or $C_1-C_6$ alkoxyl, and $T^1$ is H, halo, cyano, $NR^8R^9$, $C(O)NR^8R^9$, $C(O)R^9$, $OR^8$, $OR^9$, or $R^{S1}$, in which $R^{S1}$ is $C_3-C_8$ cycloalkyl, phenyl, 4- to 12-membered heterocycloalkyl containing 1-4 heteroatoms selected from N, O, and S, or a 5- or 6-membered heteroaryl and $R^{S1}$ is optionally substituted with one or more of halo, $C_1-C_6$ alkyl, hydroxyl, oxo, $-C(O)R^9$, $-SO_2R^8$, $-SO_2N(R^8)_2$, $-NR^8C(O)R^9$, $NR^8R^9$, or $C_1-C_6$ alkoxyl; and $R^6$ is not $NR^8C(O)NR^{12}R^{13}$; or $R^6$ and one of $R^2$ or $R^3$ together with the atoms to which they are attached form phenyl or a 5- or 6-membered heteroaryl; or $R^6$ and one of $R^{2'}$ or $R^{3'}$ together with the atoms to which they are attached form a 5- or 6-membered heteroaryl, in which the phenyl or 5- or 6-membered heteroaryl as formed is optionally substituted with one or more of halo, $C_1-C_3$ alkyl, hydroxyl, oxo (=O), $C_1-C_3$ alkoxyl, or $-Q^1-T^1$;

each $R^7$ is independently oxo (=O) or $-Q^2-T^2$, in which each $Q^2$ independently is a bond or $C_1-C_6$ alkylene, $C_2-C_6$ alkenylene, or $C_2-C_6$ alkynylene linker optionally substituted with one or more of halo, cyano, hydroxyl, amino, mono- or di-alkylamino, or $C_1-C_6$ alkoxyl, and each $T^2$ independently is H, halo, cyano, $OR^{10}$, $OR^{11}$, $C(O)R^{11}$, $NR^{10}R^{11}$, $C(O)NR^{10}R^{11}$, $NR^{10}C(O)R^{11}$, 5- to 10-membered heteroaryl, $C_3-C_8$ cycloalkyl, or 4- to 12-membered heterocycloalkyl containing 1-4 heteroatoms selected from N, O, and S, and wherein the 5- to 10-membered heteroaryl, $C_3-C_8$ cycloalkyl or 4- to 12-membered heterocycloalkyl is optionally substituted with one or more of halo, $C_1-C_6$ alkyl optionally substituted with $NR^xR^y$, hydroxyl, oxo, $N(R^8)_2$, cyano, $C_1-C_6$ haloalkyl, $-SO_2R^8$, or $C_1-C_6$ alkoxyl, each of $R^x$ and $R^y$ independently being H or $C_1-C_6$ alkyl; and $R^7$ is not H or $C(O)OR^g$;

each $R^8$ independently is H or $C_1-C_6$ alkyl;

each $R^9$ is independently $-Q^3-T^3$, in which $Q^3$ is a bond or $C_1-C_6$ alkylene, $C_2-C_6$ alkenylene, or $C_2-C_6$ alkynylene linker optionally substituted with one or more of halo, cyano, hydroxyl, or $C_1-C_6$ alkoxyl, and $T^3$ is H, halo, $OR^{12}$, $OR^{13}$, $NR^{12}R^{13}$, $NR^{12}C(O)R^{13}$, $C(O)NR^{12}R^{13}$, $C(O)R^{13}$, $S(O)_2R^{13}$, $S(O)_2NR^{12}R^{13}$, or $R^{S2}$, in which $R^{S2}$ is $C_3-C_8$ cycloalkyl, $C_6-C_{10}$ aryl, 4- to 12-membered heterocycloalkyl containing 1-4 heteroatoms selected from N, O, and S, or a 5- to 10-membered heteroaryl, and $R^{S2}$ is optionally substituted with one or more $-Q^4-T^4$, wherein each $Q^4$ independently is a bond or $C_1-C_3$ alkylene, $C_2-C_3$ alkenylene, or $C_2-C_3$ alkynylene linker each optionally substituted with one or more of halo, cyano, hydroxyl, or $C_1-C_6$ alkoxy, and each $T^4$ independently is selected from the group consisting of H, halo, cyano, $C_1-C_6$ alkyl, $C_3-C_8$ cycloalkyl, $C_6-C_{10}$ aryl, 4- to 7-membered heterocycloalkyl containing 1-4 heteroatoms selected from N, O, and S, 5- to 6-membered heteroaryl, $OR^c$, $C(O)R^c$, $S(O)_2R^c$, $NR^cR^d$, $C(O)NR^cR^d$, and $NR^cC(O)R^d$, each of $R^c$ and $R^d$ independently being H or $C_1-C_6$ alkyl; or $-Q^4-T^4$ is oxo; or $R^8$ and $R^9$ taken together with the nitrogen atom to which they are attached form a 4- to 12-membered heterocycloalkyl containing 1-4 heteroatoms selected from N, O and S, which is optionally substituted with one or more of $-Q^5-T^5$, wherein each $Q^5$ independently is a bond or $C_1-C_3$ alkylene, $C_2-C_3$ alkenylene, or $C_2-C_3$ alkynylene linker each optionally substituted with one or more of halo, cyano, hydroxyl, or $C_1-C_6$ alkoxy, and each $T^5$ independently is selected from the group consisting of H, halo, cyano, $C_1-C_6$ alkyl, $C_3-C_8$ cycloalkyl, $C_6-C_{10}$ aryl, 4- to 7-membered heterocycloalkyl containing 1-4 heteroatoms selected from N, O, and S, 5- to 6-membered heteroaryl, $OR^e$, $C(O)R^e$, $S(O)_2R^e$, $S(O)_2NR^e$ $R^f$, $NR^eR^f$, $C(O)NR^eR^f$, and $NR^eC(O)R^f$, each of $R^e$ and $R^f$ independently being H or $C_1-C_6$ alkyl; or $-Q^5-T^5$ is oxo;

$R^{10}$ is selected from the group consisting of H and $C_1-C_6$ alkyl;

$R^{11}$ is $-Q^6-T^6$, in which $Q^6$ is a bond or $C_1-C_6$ alkylene, $C_2-C_6$ alkenylene, or $C_2-C_6$ alkynylene linker optionally substituted with one or more of halo, cyano, hydroxyl, oxo, or $C_1-C_6$ alkoxyl, and $T^6$ is H, halo, $OR^g$, $NR^gR^h$, $NR^gC(O)R^h$, $C(O)NR^gR^h$, $C(O)R^g$, $S(O)_2R^g$, or $R^{S3}$, in which each of $R^g$ and $R^h$ independently is H, phenyl, $C_3-C_8$ cycloalkyl, or $C_1-C_6$ alkyl optionally substituted with $C_3-C_8$ cycloalkyl, or $R^g$ and $R^h$ together with the nitrogen atom to which they are attached form a 4- to 12-membered heterocycloalkyl containing 1-4 heteroatoms selected from N, O, and S, and $R^{S3}$ is $C_3-C_8$ cycloalkyl, $C_6-C_{10}$ aryl, 4- to 12-membered heterocycloalkyl containing 1-4 heteroatoms selected from N, O and S, or a 5- to 10-membered heteroaryl, and $R^{S3}$ is optionally substituted with one or more $-Q^7-T^7$, wherein each $Q^7$ independently is a bond or $C_1-C_3$ alkylene, $C_2-C_3$ alkenylene, or $C_2-C_3$ alkynylene linker each optionally substituted with one or more of halo, cyano, hydroxyl, or $C_1-C_6$ alkoxy, and each $T^7$ independently is selected from the group consisting of H, halo, cyano, $C_1-C_6$ alkyl, $C_3-C_8$ cycloalkyl, $C_6-C_{10}$ aryl, 4- to 7-membered heterocycloalkyl containing 1-4 heteroatoms selected from N, O, and S, 5- to 6-membered heteroaryl, $OR^j$, $C(O)R^j$, $NR^jR^k$, $C(O)NR^jR^k$, $S(O)_2R^j$, and $NR^jC(O)R^k$, each of $R^j$ and $R^k$ independently being H or $C_1-C_6$ alkyl optionally substituted with one or more halo; or $-Q^7-T^7$ is oxo; or $R^{10}$ and $R^{11}$ taken together with the nitrogen atom to which they are attached form a 4- to 12-membered heterocycloalkyl containing 1-4 heteroatoms selected from N, O, and S, which is optionally substituted with one or more of halo, $C_1-C_6$ alkyl, hydroxyl, or $C_1-C_6$ alkoxyl:

$R^{12}$ is H or $C_1-C_6$ alkyl;

$R^{13}$ is $C_1-C_6$ alkyl, $C_3-C_8$ cycloalkyl, $C_6-C_{10}$ aryl, 4- to 12-membered heterocycloalkyl containing 1-4 heteroatoms selected from N, O, and S, or a 5- to 10-membered heteroaryl, each of which is optionally substituted with one or more $-Q^8-T^8$, wherein each $Q^8$ independently is a bond or $C_1-C_3$ alkylene, $C_2-C_3$ alkenylene, or $C_2-C_3$ alkynylene linker each optionally substituted with one or more of halo, cyano, hydroxyl, or $C_1-C_6$ alkoxy, and each $T^8$ independently is selected from the group consisting of H, halo, cyano, $C_1-C_6$ alkyl, $C_3-C_8$ cycloalkyl, $C_6-C_{10}$ aryl, 4- to 7-membered heterocycloalkyl containing 1-4 heteroatoms selected from N, O, and S, and 5- to 6-membered heteroaryl; or $-Q^8-T^8$ is oxo; and n is 0, 1, 2, 3, or 4, provided that the compound of Formula (I) is not 2-cyclohexyl-6-methoxy-N-[1-(1-methylethyl)-4-piperidinyl]-7-[3-(1-pyrrolidinyl)propoxy]-4-quinazolinamine;

N-(1-isopropylpiperidin-4-yl)-6-methoxy-2-(4-methyl-1,4-diazepan-1-yl)-7-(3-(piperidin-1-yl)propoxy)quinazolin-4-amine;

2-(4,4-difluoropiperidin-1-yl)-N-(1-isopropylpiperidin-4-yl)-6-methoxy-7-(3-(pyrrolidin-1-yl)propoxy)quinazolin-4-amine; or 2-(4-isopropyl-1,4-diazepan-1-yl)-N-(1-isopropylpiperidin-4-yl)-6-methoxy-7-(3-(piperidin-1-yl)propoxy)quinazolin-4-amine.

The compounds of Formula (I) may have one or more of the following features when applicable.

In some embodiments, the EHMT2-inhibitor is not a compound selected from the group consisting of:
4-(((2-((1-acetylindolin-6-yl)amino)-6-(trifluoromethyl)pyrimidin-4-yl)amino)methyl)benzenesulfonamide;
5-bromo-$N^4$-(4-fluorophenyl)-$N^2$-(4-methoxy-3-(2-(pyrrolidin-1-yl)ethoxy)phenyl)pyrimidine-2,4-diamine;
$N^2$-(4-methoxy-3-(2-(pyrrolidin-1-yl)ethoxy)phenyl)-$N^4$-(5-(tert-pentyl)-1H-pyrazol-3-yl)pyrimidine-2,4-diamine;
4-((2,4-dichloro-5-methoxyphenyl)amino)-2-((3-(2-(pyrrolidin-1-yl)ethoxy)phenyl)amino)pyrimidine-5-carbonitrile;
N-(naphthalen-2-yl)-2-(piperidin-1-ylmethoxy)pyrimidin-4-amine;
N-(3,5-difluorobenzyl)-2-(3-(pyrrolidin-1-yl)propyl)pyrimidin-4-amine;
N-(((4-(3-(piperidin-1-yl)propyl)pyrimidin-2-yl)amino)methyl)benzamide;
N-(2-((2-(3-(dimethylamino)propyl)pyrimidin-4-yl)amino)ethyl)benzamide; and
2-(hexahydro-4-methyl-1H-1,4-diazepin-1-yl)-6,7-dimethoxy-N-[1-(phenylmethyl)-4-piperidinyl]-4-quinazolinamine:

In some embodiments, when T is a bond, B is substituted phenyl, and $R^6$ is $NR^8R^9$, in which $R^9$ is $-Q^3-R^{S2}$, and $R^{S2}$ is optionally substituted 4- to 7-membered heterocycloalkyl or a 5- to 6-membered heteroaryl, then B is substituted with at least one substituent selected from (i) $-Q^2-OR^{11}$ in which $R^{11}$ is $-Q^6-R^{S3}$ and $Q^6$ is optionally substituted $C_2-C_6$ alkylene, $C_2-C_6$ alkenylene, or $C_2-C_6$ alkynylene linker and (ii) $-Q^2-NR^{10}R^{11}$ in which $R^{11}$ is $-Q^6-R^{S3}$;

In some embodiments, when T is a bond and B is optionally substituted phenyl, then $R^6$ is not $OR^9$ or $NR^8R^9$ in which $R^9$ is optionally substituted naphthyl;

In some embodiments, when T is a bond and B is optionally substituted phenyl, naphthyl, indanyl or 1,2,3,4-tetrahydronaphthyl, then $R^6$ is not $NR^8R^9$ in which $R^9$ is optionally substituted phenyl, naphthyl, indanyl or 1,2,3,4-tetrahydronaphthyl;

In some embodiments, when T is a bond and B is optionally substituted phenyl or thiazolyl, then $R^6$ is not optionally substituted imidazolyl, pyrazolyl, pyridyl, pyrimidyl, or $NR^8R^9$ in which $R^9$ is optionally substituted imidazolyl or 6- to 10-membered heteroaryl; or In some embodiments, when T is a $C_1-C_6$ alkylene linker and B is absent or optionally substituted $C_6-C_{10}$ aryl or 4- to 12-membered heterocycloalkyl; or when T is a bond and B is optionally substituted $C_3-C_{10}$ cycloalkyl or 4- to 12-membered heterocycloalkyl, then $R^6$ is not $NR^8C(O)R^{13}$;

In some embodiments, when $X^1$ and $X^3$ are N, $X^2$ is $CR^3$, $X^4$ is $CR^5$, $X^5$ is C, $R^5$ is 4- to 12-membered heterocycloalkyl substituted with one or more $C_1-C_6$ alkyl, and $R^6$ and $R^3$ together with the atoms to which they are attached form phenyl which is substituted with one or more of optionally substituted $C_1-C_3$ alkoxyl, then B is absent, $C_6-C_{10}$ aryl, $C_3-C_{10}$ cycloalkyl, or 5- to 10-membered heteroaryl, or In some embodiments, when $X^2$ and $X^3$ are N, $X^1$ is $CR^2$, $X^4$ is $CR^5$, $X^5$ is C, $R^5$ is $C_3-C_8$ cycloalkyl or 4- to 12-membered heterocycloalkyl, each optionally substituted with one or more $C_1-C_6$ alkyl, and $R^6$ and $R^2$ together with the atoms to which they are attached form phenyl which is substituted with one or more of optionally substituted $C_1-C_3$ alkoxyl, then B is absent, $C_6-C_{10}$ aryl, $C_3-C_{10}$ cycloalkyl, or 5- to 10-membered heteroaryl.

In some embodiments, ring A is a 6-membered heteroaryl, at least one of $X^1$, $X^2$, $X^3$ and $X^4$ is N and $X^5$ is C.

In some embodiments, ring A is a 6-membered heteroaryl, two of $X^1$, $X^2$, $X^3$ and $X^4$ are N and $X^5$ is C.

In some embodiments, $R^6$ and one of $R^2$ or $R^3$ together with the ring A to which they are attached form a 6,5-fused bicyclic heteroaryl; or $R^6$ and one of $R^{2'}$ or $R^{3'}$ together the ring A to which they are attached form a 6,5-fused bicyclic heteroaryl.

In some embodiments, at least one of $R^6$, $R^2$, $R^3$, and $R^4$ is not H.

In some embodiments, when one or more of $R^{2'}$, $R^{3'}$, and $R^{4'}$ are present, at least one of $R^6$, $R^{2'}$, $R^{3'}$, and $R^{4'}$ is not H.

In some embodiments, the EHMT2 inhibitor is a compound of Formula (II):

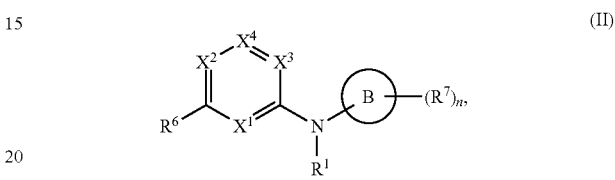

wherein ring B is phenyl or pyridyl, one or both of $X^1$ and $X^2$ are N while $X^3$ is $CR^4$ and $X^4$ is $CR^5$ or one or both of $X^1$ and $X^3$ are N while $X^2$ is $CR^3$ and $X^4$ is $CR^5$; and n is 1, 2, or 3.

In some embodiments, the EHMT2 inhibitor is a compound of Formula (IIa1), (IIa2), (IIa3), (IIa4), or (IIa5):

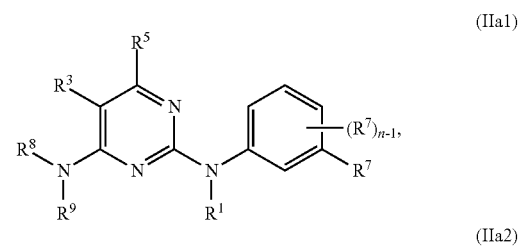

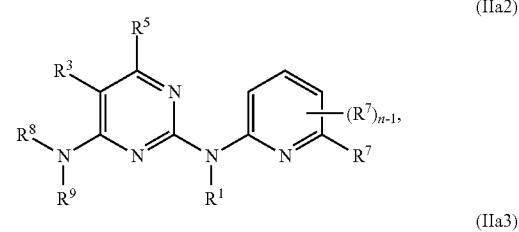

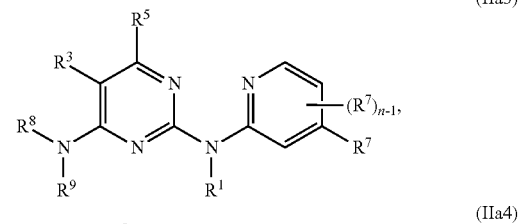

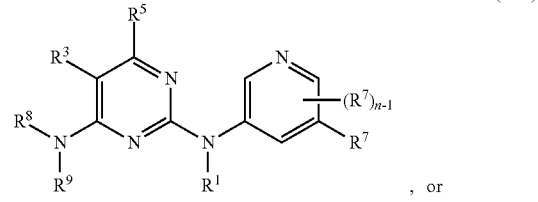

, or (IIa5)

In some embodiments, at most one of R³ and R⁵ is not H.

In some embodiments, the EHMT2 inhibitor is a compound of Formula (IIb1), (IIb2), (IIb3), (IIb4), or (IIb5):

(IIb1)

(IIb2)

(IIb3)

(IIb4)

, or (IIb5)

In some embodiments, at most one of R³, R⁴ and R⁵ is not H.

In some embodiments, the EHMT2 inhibitor is a compound of Formula (IIc1), (IIc2), (IIc3), (IIc4), or (IIc5):

(IIc1)

(IIc2)

(IIc3)

(IIc4)  or (IIc5)

In some embodiments, at most one of R⁴ and R⁵ is not H.

In some embodiments, the EHMT2 inhibitor is a compound of Formula (IId1), (IId2), (IId3), (IId4), or (IId5):

(IId1)

(IId2)

-continued (IId3)

(IId4)

(IId5)

In some embodiments, at most one of $R^2$, $R^4$, and $R^5$ is not H.

In some embodiments, ring A is a 5-membered heteroaryl.

In some embodiments, the EHMT2 inhibitor is a compound of Formula (III):

(III)

wherein
ring B is phenyl or pyridyl,
at least one of $X^2$ and $X^3$ is N; and
n is 1 or 2.

In some embodiments, the EHMT2 inhibitor is a compound of Formula (IIIa):

(IIIa)

In some embodiments, at most one of $R^{4'}$ and $R^2$ is not H.

In some embodiments, the optionally substituted 6,5-fused bicyclic heteroaryl contains 1-4 N atoms.

In some embodiments, T is a bond and ring B is phenyl or pyridyl.

In some embodiments, n is 1 or 2.

In some embodiments, the EHMT2 inhibitor is a compound of Formula (IV):

(IV)

wherein
ring B is $C_3$-$C_6$ cycloalkyl;
each of $R^{20}$, $R^{21}$, $R^{22}$ and $R^{23}$ independently is H, halo, $C_1$-$C_3$ alkyl, hydroxyl, or $C_1$-$C_3$ alkoxyl; and
n is 1 or 2.

In some embodiments, ring B is cyclohexyl.

In some embodiments, $R^1$ is H or $CH_3$.

In some embodiments, n is 1 or 2, and at least one of $R^7$ is -$Q^2$-$OR^{11}$ in which $R^{11}$ is -$Q^6$-$R^{S3}$ and $Q^6$ is optionally substituted $C_2$-$C_6$ alkylene, $C_2$-$C_6$ alkenylene, or $C_2$-$C_6$ alkynylene linker.

In some embodiments, n is 1 or 2, and at least one of $R^1$ is -$Q^2$-$NR^{10}R^{11}$ in which $R^{11}$ is -$Q^6$-$R^{S3}$.

In some embodiments, $Q^6$ is $C_2$-$C_6$ alkylene, $C_2$-$C_6$ alkenylene, or $C_2$-$C_6$ alkynylene linker optionally substituted with a hydroxyl and $R^{S3}$ is 4- to 7-membered heterocycloalkyl optionally substituted with one or more -$Q^7$-$T^7$.

In some embodiments, $Q^6$ is $C_1$-$C_6$ alkylene, $C_2$-$C_6$ alkenylene, or $C_2$-$C_6$ alkynylene linker optionally substituted with a hydroxyl and $R^{S3}$ is $C_3$-$C_6$ cycloalkyl optionally substituted with one or more -$Q^7$-$T^7$.

In some embodiments, each $Q^7$ is independently a bond or a $C_1$-$C_3$ alkylene, $C_2$-$C_3$ alkenylene, or $C_2$-$C_3$ alkynylene linker and each $T^7$ is independently H, halo, $C_1$-$C_6$ alkyl, or phenyl.

In some embodiments, $Q^2$ is a bond or a $C_1$-$C_4$ alkylene, $C_2$-$C_4$ alkenylene, or $C_2$-$C_4$ alkynylene linker.

In some embodiments, at least one of $R^7$ is

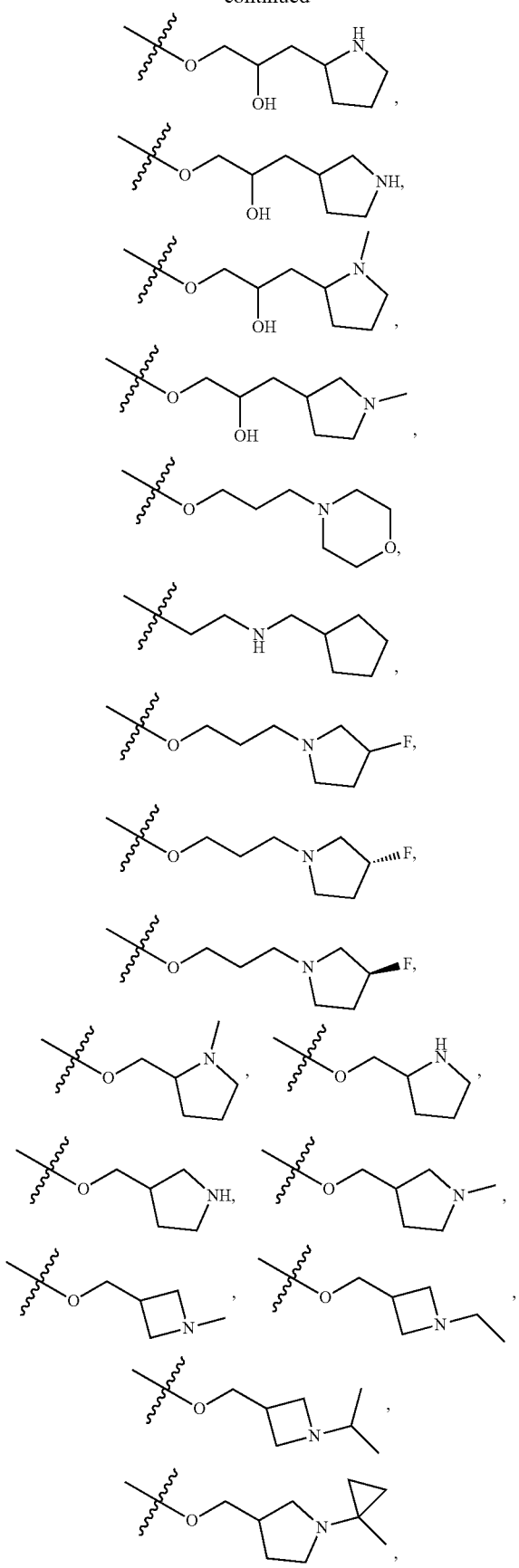
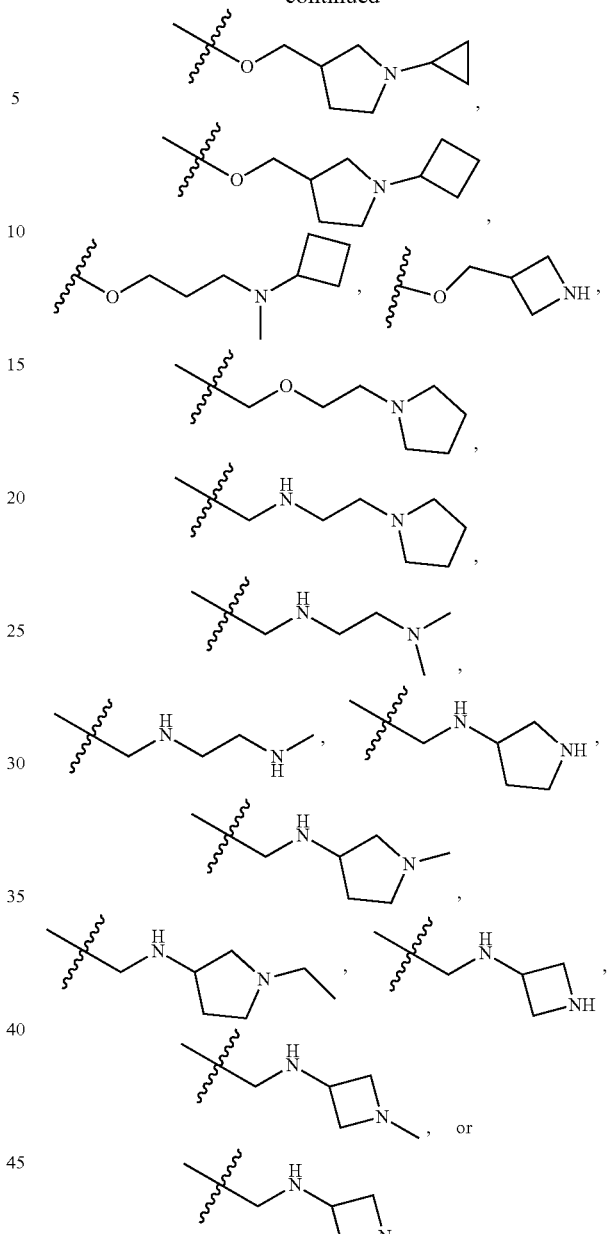

In some embodiments, n is 2 and the compound further comprises another $R^7$ selected from halo and methoxy.

In some embodiments, ring B is selected from phenyl, pyridyl, and cyclohexyl, and the halo or methoxy is at the para-position to $NR^1$.

In some embodiments, $R^6$ is $NR^8R^9$.

In some embodiments, $R^9$ is -$Q^3$-$T^3$, in which $T^3$ is $OR^{12}$, $NR^{12}C(O)R^3$, $C(O)R^{13}$, $C(O)NR^{12}R^{13}$, $S(O)_2NR^{12}R^{13}$, or $R^{S2}$.

In some embodiments, $Q^3$ is $C_1$-$C_6$ alkylene, $C_2$-$C_6$ alkenylene, or $C_2$-$C_6$ alkynylene linker optionally substituted with a hydroxyl.

In some embodiments, $R^{S2}$ is $C_3$-$C_6$ cycloalkyl, phenyl, 4- to 12-membered heterocycloalkyl, or a 5- to 10-membered heteroaryl, and $R^{S2}$ is optionally substituted with one or more -$Q^4$-$T^4$.

In some embodiments, each $Q^4$ is independently a bond or $C_1$-$C_3$ alkylene, $C_2$-$C_3$ alkenylene, or $C_2$-$C_3$ alkynylene linker optionally substituted with one or more of hydroxyl and halo, and each $T^4$ is independently H, halo, $C_1$-$C_6$ alkyl, or phenyl; or $-Q^4-T^4$ is oxo.
In some embodiments, $R^6$ or $NR^8R^9$ is selected from the group consisting of:
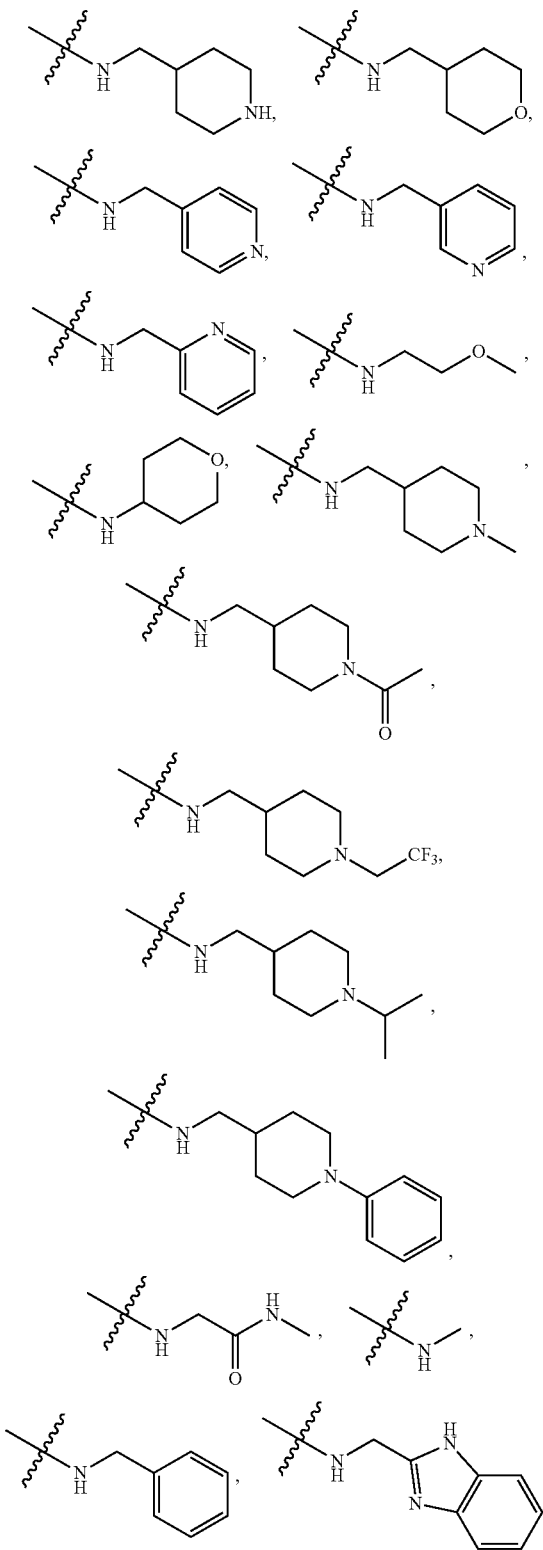
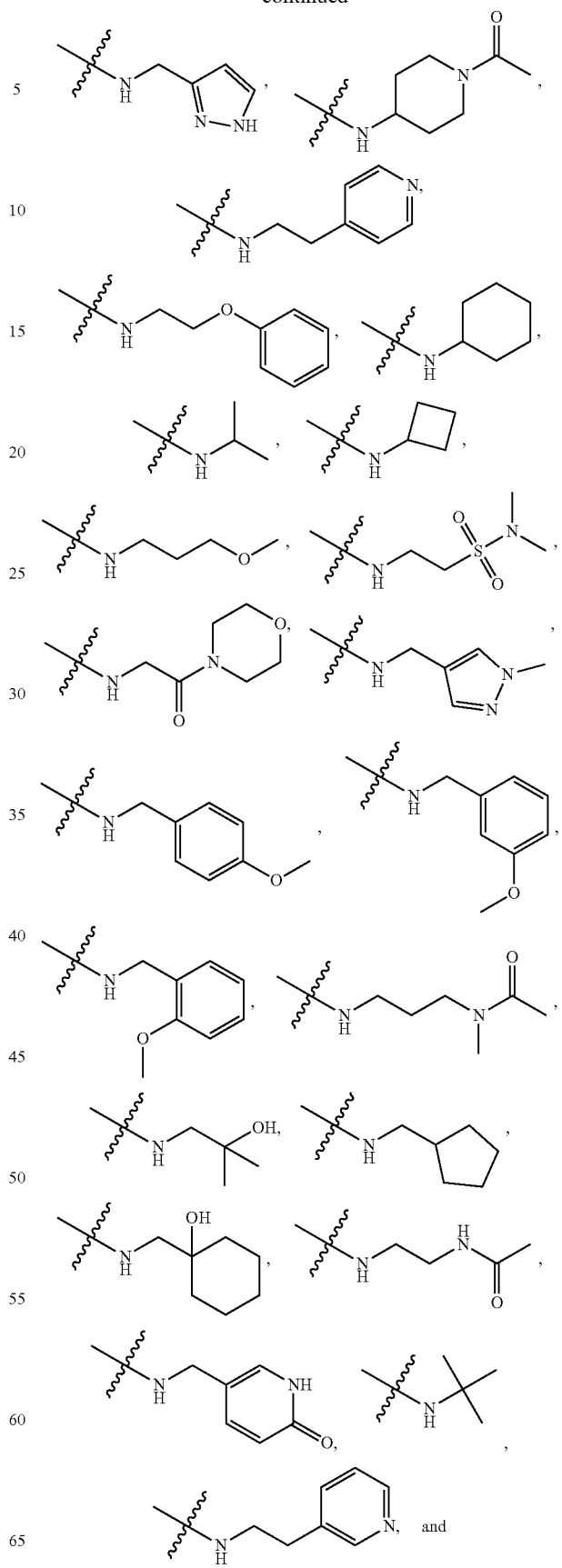

-continued

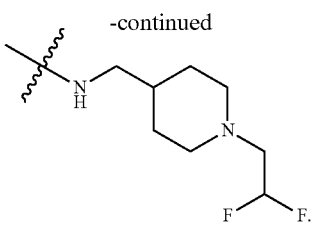

In some embodiments, B is absent and T is unsubstituted $C_1$-$C_6$ alkyl or T is $C_1$-$C_6$ alkyl substituted with at least one $R^7$.

In some embodiments, B is 4- to 12-membered heterocycloalkyl and T is unsubstituted $C_1$-$C_6$ alkyl.

In some embodiments, the EHMT2 inhibitor is a compound of Formula (V):

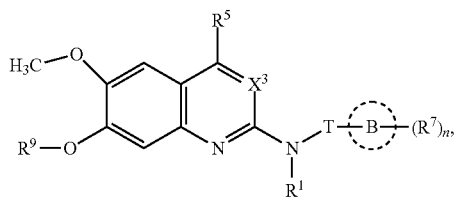

wherein
ring B is absent or $C_3$-$C_6$ cycloalkyl
$X^1$ is N or $CR^4$ in which $R^4$ is H or $C_1$-$C_4$ alkyl;
$R^1$ is H or $C_1$-$C_4$ alkyl;
or when B is absent, T and $R^1$ together with the atoms to which they are attached optionally form a 4-7 membered heterocycloalkyl or 5-6 membered heteroaryl, each of which is optionally substituted with $(R^7)_n$; or when B is absent, T is H and n is 0;
each $R^7$ is independently oxo (=O) or $-Q^2$-$T^2$, in which each $Q^2$ independently is a bond or $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, or $C_1$-$C_6$ alkoxyl, and each $T^2$ independently is H, halo, $OR^{10}$, $OR^{11}$, $C(O)R^{11}$, $NR^{10}R^{11}$, $C(O)NR^{10}R^{11}$, $NR^{10}C(O)R^{11}$, $C_3$-$C_8$ cycloalkyl, or 4- to 12-membered heterocycloalkyl containing 1-4 heteroatoms selected from N, O, and S, and wherein the $C_3$-$C_8$ cycloalkyl or 4- to 12-membered heterocycloalkyl is optionally substituted with one or more of halo, $C_1$-$C_6$ alkyl optionally substituted with $NR^xR^y$, hydroxyl, oxo, $N(R^8)_2$, cyano, $C_1$-$C_6$ haloalkyl, $-SO_2R^8$, or $C_1$-$C_6$ alkoxyl, each of $R^x$ and $R^y$ independently being H or $C_1$-$C_6$ alkyl; and $R^7$ is not H or $C(O)OR^g$;
$R^5$ is selected from the group consisting of $C_1$-$C_6$ alkyl, $C_3$-$C_8$ cycloalkyl and 4- to 12-membered heterocycloalkyl containing 1-4 heteroatoms selected from N, O and S, wherein the $C_3$-$C_8$ cycloalkyl and 4- to 12-membered heterocycloalkyl is optionally substituted with one or more of 4- to 7-membered heterocycloalkyl, $-C_1$-$C_6$ alkylene-4- to 7-membered heterocycloalkyl, $-C(O)C_1$-$C_6$ alkyl or $C_1$-$C_6$ alkyl optionally substituted with one or more of halo or $OR^a$;
$R^9$ is $-Q^3$-$T^3$, in which $Q^3$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^3$ is 4- to 12-membered heterocycloalkyl containing 1-4 heteroatoms selected from N, O, and S, optionally substituted with one or more $-Q^4$-$T^4$, wherein each $Q^4$ independently is a bond or $C_1$-$C_3$ alkylene, $C_2$-$C_3$ alkenylene, or $C_2$-$C_3$ alkynylene linker each optionally substituted with one or more of halo, cyano, hydroxyl, or $C_1$-$C_6$ alkoxy, and each $T^4$ independently is selected from the group consisting of H, halo, cyano, $C_1$-$C_6$ alkyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, $OR^c$, $C(O)R^c$, $S(O)_2R^c$, $NR^cR^d$, $C(O)NR^cR^d$, and $NR^cC(O)R^d$, each of $R^c$ and $R^d$ independently being H or $C_1$-$C_6$ alkyl; or $Q^4$-$T^4$ is oxo; and
n is 0, 1 or 2.

In some embodiments, the EHMT2 inhibitor is a compound of Formula (VI):

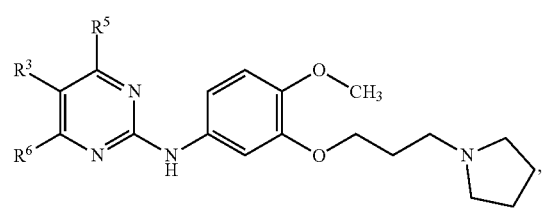

wherein
$R^5$ and $R^6$ are independently selected from the group consisting of $C_1$-$C_6$ alkyl and $NR^8R^9$, or $R^6$ and $R^3$ together with the atoms to which they are attached form phenyl or a 5- or 6-membered heteroaryl.

In some embodiments, $R^6$ is methyl.

In some embodiments, the EHMT2 inhibitor is a compound of Formula (VII):

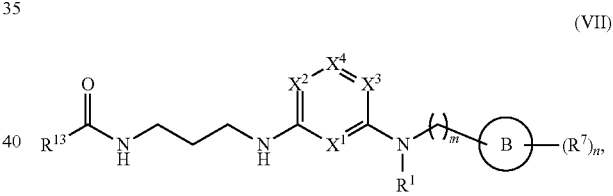

wherein m is 1 or 2 and n is 0, 1, or 2.

In some embodiments, both of $X^1$ and $X^3$ are N while $X^2$ is $CR^3$ and $X^4$ is $CR^5$.

In some embodiments, the EHMT2 inhibitor is a compound of Formula (VIIIa):

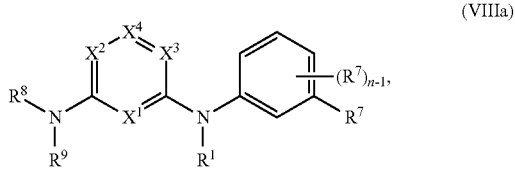

wherein
$X^1$ is N or $CR^2$;
$X^2$ is N or $CR^3$;
$X^3$ is N or $CR^4$;
$X^4$ is N or $CR^5$;
$R^2$ is selected from the group consisting of H, $C_3$-$C_8$ cycloalkyl, and $C_1$-$C_6$ alkyl optionally substituted with one or more of halo, $OR^a$, or $NR^aR^b$;
each of $R^3$ and $R^4$ is H; and $R^5$ are independently selected from the group consisting of H, $C_3$-$C_8$ cycloalkyl, and $C_1$-$C_6$ alkyl optionally substituted with one or more of halo or $OR^a$; or $R^5$ and one of $R^3$ or $R^4$ together with the atoms to which they are attached form phenyl or a 5- or 6-membered heteroaryl; or $R^5$ and one of $R^{3\prime}$ or $R^{4\prime}$ together with the atoms to which they are attached form a 5- or 6-membered heteroaryl, in which the phenyl or 5- or 6-membered heteroaryl as formed is optionally substituted with one or more of halo, $C_1$-$C_3$ alkyl, hydroxyl or $C_1$-$C_3$ alkoxyl; and wherein at least one of $R_2$ or $R_5$ are not H.

In some embodiments, the EHMT2 inhibitor is a compound of Formula (VIIIb):

(VIIIb)

wherein $X^1$ is N or $CR^2$;
$X^2$ is N or $CR^3$;
$X^3$ is N or $CR^4$:
$X^4$ is N or $CR^5$;
$R^2$ is selected from the group consisting of H, $C_3$-$C_8$ cycloalkyl, and $C_1$-$C_6$ alkyl
each of $R^3$ and $R^4$ is H; and
$R^5$ is selected from the group consisting of H, $C_3$-$C_8$ cycloalkyl, and $C_1$-$C_6$ alkyl; or
$R^5$ and one of $R^3$ or $R^4$ together with the atoms to which they are attached form phenyl or a 5- or 6-membered heteroaryl; or $R^5$ and one of $R^{3\prime}$ or $R^{4\prime}$ together with the atoms to which they are attached form a 5- or 6-membered heteroaryl, in which the phenyl or 5- or 6-membered heteroaryl as formed is optionally substituted with one or more of halo, $C_1$-$C_3$ alkyl, hydroxyl or $C_1$-$C_3$ alkoxyl; and
wherein at least one of $R_2$ or $R_5$ are not H.

In some embodiments, the EHMT2 inhibitor is a compound of Formula (VIIIc):

(VIIIc)

wherein $X^1$ is N or $CR^2$;
$X^2$ is N or $CR^3$;
$X^3$ is N or $CR^4$;
$X^4$ is N or $CR^5$;
$R^2$ is selected from the group consisting of H, $C_3$-$C_8$ cycloalkyl, and $C_1$-$C_6$ alkyl
each of $R^3$ and $R^4$ is H; and
$R^5$ is selected from the group consisting of H, $C_3$-$C_8$ cycloalkyl, and $C_1$-$C_6$ alkyl; or
$R^5$ and one of $R^3$ or $R^4$ together with the atoms to which they are attached form phenyl or a 5- or 6-membered heteroaryl; or $R^5$ and one of $R^{3\prime}$ or $R^{4\prime}$ together with the atoms to which they are attached form a 5- or 6-membered heteroaryl, in which the phenyl or 5- or 6-membered heteroaryl as formed is optionally substituted with one or more of halo, $C_1$-$C_3$ alkyl, hydroxyl or $C_1$-$C_3$ alkoxyl; and wherein at least one of $R_2$ or $R_5$ are not H.

In some embodiments, the EHMT2 inhibitor is a compound of (IX):

(IX)

or a tautomer thereof, or a pharmaceutically acceptable salt of the compound or the tautomer, wherein $X^6$ is N or CH;
$X^7$ is N or CH;
$X^3$ is N or $CR^4$;
$R^4$, independently is selected from the group consisting of H, halo, cyano, $C_1$-$C_6$ alkoxyl, $C_6$-$C_{10}$ aryl. $NR^aR^b$, $C(O)NR^aR^b$, $NR^aC(O)R^b$, $C_3$-$C_8$ cycloalkyl, 4- to 7-membered heterocycloalkyl, 5- to 6-membered heteroaryl, and $C_1$-$C_6$ alkyl, wherein $C_1$-$C_6$ alkoxyl and $C_1$-$C_6$ alkyl are optionally substituted with one or more of halo, $OR^a$, or $NR^aR^b$, in which each of $R^a$ and $R^b$ independently is H or $C_1$-$C_6$ alkyl;
each $R^9$ is independently -$Q^3$-$T^3$, in which $Q^3$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^3$ is H, halo, $OR^{12}$, $OR^{13}$, $NR^{12}R^{13}$, $NR^{12}C(O)R^{13}$, $C(O)NR^{12}R^{13}$, $C(O)R^{13}$, $S(O)_2R^{13}$, $S(O)_2NR^{12}R^{13}$, or $R^{S2}$, in which $R^{S2}$ is $C_3$-$C_8$ cycloalkyl, $C_6$-$C_{10}$ aryl, 4- to 12-membered heterocycloalkyl containing 1-4 heteroatoms selected from N, O, and S, or a 5- to 10-membered heteroaryl, and $R^{S2}$ is optionally substituted with one or more -$Q^4$-$T^4$, wherein each $Q^4$ independently is a bond or $C_1$-$C_3$ alkylene, $C_2$-$C_3$ alkenylene, or $C_2$-$C_3$ alkynylene linker each optionally substituted with one or more of halo, cyano, hydroxyl, or $C_1$-$C_6$ alkoxy, and each $T^4$ independently is selected from the group consisting of H, halo, cyano, $C_1$-$C_6$ alkyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, $OR^c$, $C(O)R^c$, $S(O)_2R^c$, $NR^cR^d$, $C(O)NR^cR^d$, and $NR^cC(O)R^d$, each of $R^c$ and $R^d$ independently being H or $C_1$-$C_6$ alkyl; or -$Q^4$-$T^4$ is oxo; or
$R^{12}$ is H or $C_1$-$C_6$ alkyl;
$R^{13}$ is $C_1$-$C_6$ alkyl, $C_3$-$C_8$ cycloalkyl, $C_6$-$C_{10}$ aryl, 4- to 12-membered heterocycloalkyl containing 1-4 heteroatoms selected from N, O, and S, or a 5- to 10-membered heteroaryl, each of which is optionally substituted with one or more -$Q^8$-$T^8$, wherein each $Q^8$ independently is a bond or $C_1$-$C_3$ alkylene, $C_2$-$C_3$ alkenylene, or $C_2$-$C_3$ alkynylene linker each optionally substituted with one or more of halo, cyano, hydroxyl, or $C_1$-$C_6$ alkoxy, and each $T^8$ independently is selected from the group consisting of H, halo, cyano, $C_1$-$C_6$ alkyl, $C_3$-$C_8$ cycloalkyl, $C_6$-$C_{10}$ aryl, 4- to 7-membered heterocycloalkyl containing 1-4 heteroatoms selected from N, O, and S, and 5- to 6-membered heteroaryl or -$Q^8$-$T^8$ is oxo;
$R^{15}$ is $C_1$-$C_6$ alkyl, $NHR^{17}$, $C_3$-$C_8$ cycloalkyl, $C_6$-$C_{10}$ aryl, 4- to 12-membered heterocycloalkyl containing 1-4 heteroatoms selected from N, O, and S, or 5- to 10-membered heteroaryl, wherein each of said $C_1$-$C_6$ alkyl, $C_3$-$C_8$ cycloalkyl, $C_6$-$C_{10}$ aryl, 4- to 12-membered heterocycloalkyl, and 5- to 10-membered heteroaryl is optionally substituted with one or more -$Q^9$-$T^9$, wherein each $Q^9$ independently is a bond or $C_1$-$C_3$ alkylene, $C_2$-$C_3$; alkenylene, or $C_2$-$C_3$ alkynylene linker each optionally substituted with one or more of halo, cyano, hydroxyl, or $C_1$-$C_6$ alkoxy, and each $T^9$ independently is selected from the group consisting of H, halo, cyano, $C_1$-$C_6$ alkyl, $C_3$-$C_8$ cycloalkyl, $C_6$-$C_{10}$ aryl, 4- to 7-membered heterocycloalkyl containing 1-4 heteroatoms selected from N, O, and S, and 5- to 6-membered heteroaryl; or -$Q^9$-$T^9$ is oxo;

$R^{16}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 12-membered heterocycloalkyl containing 1-4 heteroatoms selected from N, O, and S, or a 5- to 10-membered heteroaryl, each of which is optionally substituted with one or more -$Q^{10}$-$T^{10}$, wherein each $Q^{10}$ independently is a bond or $C_1$-$C_3$ alkylene, $C_2$-$C_3$ alkenylene, or $C_2$-$C_3$ alkynylene linker each optionally substituted with one or more of halo, cyano, hydroxyl, or $C_1$-$C_6$ alkoxy, and each $T^{10}$ independently is selected from the group consisting of H, halo, cyano, $C_1$-$C_6$ alkyl, $C_3$-$C_8$ cycloalkyl, $C_6$-$C_{10}$ aryl, 4- to 7-membered heterocycloalkyl containing 1-4 heteroatoms selected from N, O, and S, and 5- to 6-membered heteroaryl; or -$Q^{10}$-$T^{10}$ is oxo;

$R^{17}$ is H or $C_1$-$C_6$ alkyl; and v is 0, 1, or 2.

In some embodiments, each $T^3$ independently is $OR^{12}$ or $OR^{13}$.

In some embodiments, each $Q^3$ independently is a bond or $C_1$-$C_6$ alkylene. $C_2$-$C_6$ alkenylene, or $C_2$-$C_6$ alkynylene linker optionally substituted with a hydroxyl.

In some embodiments, $R^{15}$ is $C_1$-$C_6$ alkyl, $NHR^{17}$, or 4- to 12-membered heterocycloalkyl.

In some embodiments, $R^{16}$ is $C_1$-$C_6$ alkyl or 4- to 12-membered heterocycloalkyl, each optionally substituted with one or more -$Q^{10}$-$T^{10}$.

In some embodiments, each $T^{10}$ independently is selected from the group consisting of H, halo, cyano, $C_1$-$C_6$ alkyl, and 4- to 7-membered heterocycloalkyl.

In some embodiments, each $Q^{10}$ independently is a bond or $C_1$-$C_3$ alkylene. $C_2$-$C_3$ alkenylene, or $C_2$-$C_3$ alkynylene linker optionally substituted with a hydroxyl.

In some embodiments, the EHMT2 inhibitor is a compound of Formula (X):

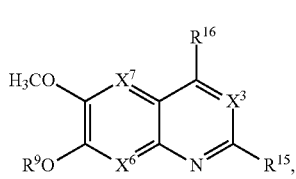

(X)

wherein $X^3$ is N or $CR^4$, wherein $R^4$ is selected from the group consisting of H, halo, and cyano.

In some embodiments, the EHMT2 inhibitor is a compound of Formula (Xa), (Xb), (Xc), (Xd), (Xe), (Xf), or (Xg):

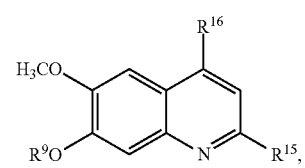

(Xa)

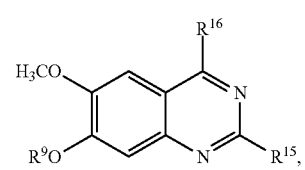

(Xb)

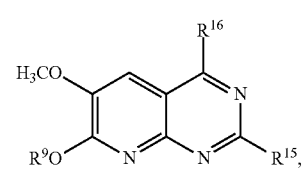

(Xc)

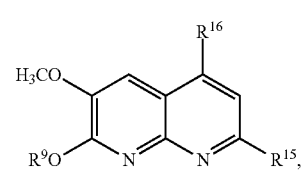

(Xd)

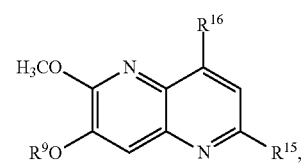

(Xe)

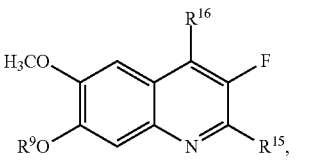

(Xf)

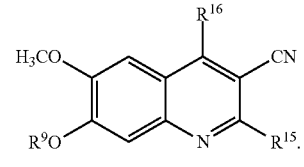

(Xg)

In some embodiments, at least one of $X^1$, $X^2$, $X^3$ and $X^4$ is N.

In some embodiments, $X^1$ and $X^3$ is CH, and $X^1$ and $X^4$ is N.

In some embodiments, $X^1$ and $X^3$ is N, $X^1$ is $CR^2$, and $X^4$ is $CR^5$.

In some embodiments, $R^6$ is $NR^8R^9$ and $R^5$ is $C_{1-6}$ alkyl or $R^5$ and $R^3$ together with the atoms to which they are attached form phenyl or a 5- to 6-membered heteroaryl ring.

In certain embodiments, for the methods disclosed herein, the EHMT2 inhibitor is a compound of Formula (I'):

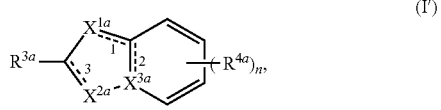
(I′)

or a tautomer thereof, or a pharmaceutically acceptable salt of the compound or the tautomer, wherein $X^{1a}$ is O, S, $CR^{1a}R^{11a}$, or $NR^{1a'}$ when ―1― is a single bond, or $X^{1a}$ is N when ―1― is a double bond;

$X^{2a}$ is N or $CR^{2a}$ when ―3― is a double bond, or $X^{2a}$ is $NR^{2a'}$ when ―3― is a single bond;

$X^{3a}$ is N or C; when $X^{3a}$ is N, ―1― is a double bond and ―2― is a single bond, and when $X^{3a}$ is C, ―1― is a single bond and ―2― is a double bond;

each of $R^{1a}$, $R^{2a}$ and $R^{11a}$, independently, is -$Q^{1a}$-$T^{1a}$, in which each $Q^{1a}$ independently is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and each $T^{1a}$ independently is H, halo, cyano, $NR^{5a}R^{6a}$, $C(O)NR^{5a}R^{6a}$, —$OC(O)NR^{5a}R^{6a}$, $C(O)OR^{5a}$, —$OC(O)R^{5a}$, $C(O)R^{5a}$, —$NR^{5a}C(O)R^{6a}$, —$NR^{5a}C(O)OR^{6a}$, $OR^{5a}$, or $R^{S1a}$, in which $R^{S1a}$ is $C_3$-$C_{12}$ cycloalkyl, phenyl, 4- to 12-membered heterocycloalkyl containing 1-4 heteroatoms selected from N, O, and S, or a 5- or 6-membered heteroaryl and $R^{S1a}$ is optionally substituted with one or more of halo, $C_1$-$C_6$ alkyl, hydroxyl, oxo, —$C(O)R^{6a}$, —$SO_2R^{5a}$, —$SO_2N(R^{5a})_2$, —$NR^{5a}C(O)R^{6a}$, amino, mono- or di-alkylamino, or $C_1$-$C_6$ alkoxyl; or $R^{1a}$ and $R^{11a}$ together with the carbon atom to which they are attached form a $C_3$-$C_{12}$ cycloalkyl or 4- to 12-membered heterocycloalkyl containing 1-4 heteroatoms selected from N, O, and S, wherein the $C_3$-$C_{12}$ cycloalkyl or 4- to 12-membered heterocycloalkyl is optionally substituted with one or more of halo, $C_1$-$C_6$ alkyl, hydroxyl, oxo, amino, mono- or di-alkylamino, or $C_1$-$C_6$ alkoxyl;

each of $R^{1a'}$ and $R^{2a'}$, independently, is -$Q^{2a}$-$T^{2a}$, in which $Q^{2a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{2a}$ is H, halo, cyano, or $R^{S2a}$, in which $R^{S2a}$ is $C_3$-$C_{12}$ cycloalkyl, phenyl, 4- to 12-membered heterocycloalkyl containing 1-4 heteroatoms selected from N, O, and S, or a 5- or 6-membered heteroaryl and $R^{S2a}$ is optionally substituted with one or more of halo, $C_1$-$C_6$ alkyl, hydroxyl, oxo, —$C(O)R^{6a}$, —$SO_2R^{5a}$, —$SO_2N(R^{5a})_2$, —$NR^{5a}C(O)R^{6a}$, amino, mono- or di-alkylamino, or $C_1$-$C_6$ alkoxyl;

$R^{3a}$ is H, $NR^{aa}R^{ba}$, $OR^{aa}$, or $R^{S4a}$, in which $R^{S4a}$ is $C_1$-$C_6$ alkyl, $C_2$-$C_6$ alkenyl, $C_2$-$C_6$ alkynyl, $C_3$-$C_{12}$ cycloalkyl, phenyl, 5- or 6-membered heteroaryl, or 4- to 12-membered heterocycloalkyl containing 1-4 heteroatoms selected from N, O, and S, wherein each of $R^{aa}$ and $R^{ba}$ independently is H or $R^{S5a}$, or $R^{aa}$ and $R^{ba}$ together with the nitrogen atom to which they are attached form a 4- to 12-membered heterocycloalkyl containing 1-4 heteroatoms selected from N, O, and S; in which $R^{S5a}$ is $C_1$-$C_6$ alkyl, phenyl, 5- or 6-membered heteroaryl, or 4- to 12-membered heterocycloalkyl containing 1-4 heteroatoms selected from N, O, and S, and each of $R^{S4a}$, $R^{S5a}$, and the heterocycloalkyl formed by $R^{aa}$ and $R^{ba}$ is independently optionally substituted with one or more of halo, hydroxyl, oxo, CN, amino, mono- or di-alkylamino, $C_1$-$C_6$ alkyl, $C_1$-$C_6$ alkoxyl, $C_3$-$C_{12}$ cycloalkyl, phenyl, 5- or 6-membered heteroaryl, or 4- to 12-membered heterocycloalkyl containing 1-4 heteroatoms selected from N, O, and S, or alternatively;

$R^{3a}$ and one of $R^{1a'}$, $R^{2a'}$, $R^{1a}$, $R^{2a}$ and $R^{11a}$, together with the atoms to which they are attached, form a 5- or 6-membered heteroaryl that is optionally substituted with one or more of halo, $C_1$-$C_3$ alkyl, hydroxyl or $C_1$—C alkoxyl; or $R^{3a}$ is oxo and ―3― is a single bond;

each $R^{4a}$ independently is -$Q^{3a}$-$T^{3a}$, in which each $Q^{3a}$ independently is a bond or $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, or $C_1$-$C_6$ alkoxyl, and each $T^{3a}$ independently is H, halo, cyano, $OR^{4a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$;

each of $R^{5a}$, $R^{6a}$, and $R^{7a}$, independently, is H or $C_1$-$C_6$ alkyl optionally substituted with one or more of halo, cyano, hydroxyl, amino, mono- or di-alkylamino, or $C_1$-$C_6$ alkoxyl;

$R^{8a}$ is -$Q^{4a}$-$T^{4a}$, in which $Q^{4a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{4a}$ is H, halo, or $R^{S3a}$, in which $R^{S3a}$ is $C_3$-$C_{12}$ cycloalkyl, $C_6$-$C_{10}$ aryl, 4- to 12-membered heterocycloalkyl containing 1-4 heteroatoms selected from N, O and S, or a 5- to 10-membered heteroaryl, and $R^{S3a}$ is optionally substituted with one or more -$Q^{5a}$-$T^{5a}$, wherein each $Q^{5a}$ independently is a bond or $C_1$-$C_3$ alkylene, $C_2$-$C_3$ alkenylene, or $C_2$-$C_3$ alkynylene linker each optionally substituted with one or more of halo, cyano, hydroxyl, or $C_1$-$C_6$ alkoxy, and each $T^{5a}$ independently is selected from the group consisting of H, halo, cyano, $C_1$-$C_6$ alkyl, $C_3$-$C_{12}$ cycloalkyl, $C_6$-$C_{10}$ aryl, 4- to 7-membered heterocycloalkyl containing 1-4 heteroatoms selected from N, O, and S, 5- to 6-membered heteroaryl, $OR^{ca}$, $C(O)R^{ca}$, $NR^{ca}R^{da}$, $C(O)NR^{ca}R^{da}$, $S(O)_2R^{ca}$, and $NR^{ca}C(O)R^{da}$, each of $R^{ca}$ and $R^{da}$ independently being H or $C_1$-$C_6$ alkyl optionally substituted with one or more halo; or -$Q^{5a}$-$T^{5a}$ is oxo; and n is 1, 2, 3, or 4.

In some embodiments, the compound is not

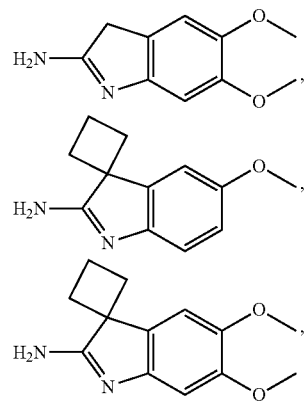

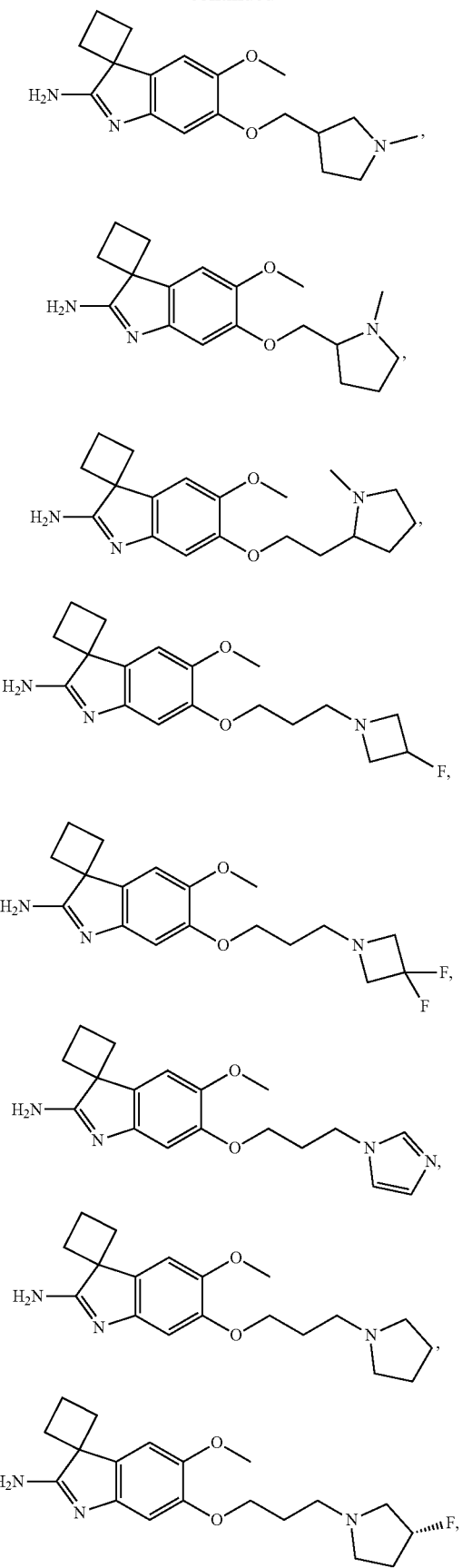
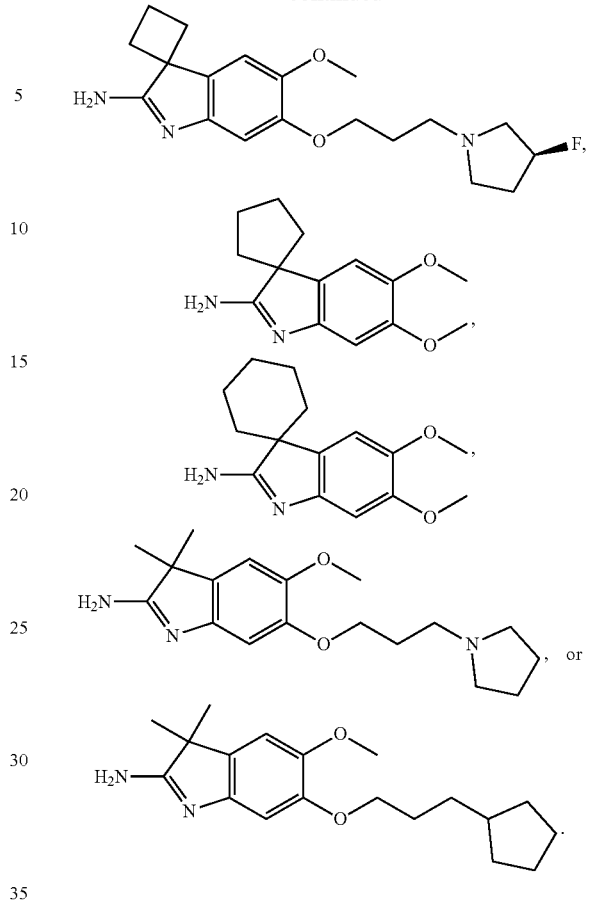

In some embodiments, when n is 2, $X^{1a}$ is $CR^{1a}R^{11a}$, $X^{2a}$ is N, $X^{3a}$ is C, $R^{3a}$ is $NH_2$, and at least one $R^{4a}$ is $OR^{7a}$, then one of (1)-(4) below applies:

(1) at least one of $R^{1a}$ and $R^{11a}$ is $-Q^{1a}-T^{1a}$, in which $Q^{1a}$ is a $C_1$-$C_6$ alkylene linker optionally substituted with one or more of halo, cyano, hydroxyl, or $C_1$-$C_6$ alkoxyl, and $T^{1a}$ is cyano, $NR^{5a}R^{6a}$, $C(O)NR^{5a}R^{6a}$, —$OC(O)NR^{5a}R^{6a}$, $C(O)OR^{5a}$, —$OC(O)R^{5a}$, $C(O)R^{5a}$, —$NR^{5a}C(O)R^{6a}$, —$NR^{5a}C(O)OR^{6a}$, $OR^{5a}$, or $R^{S1a}$, in which $R^{S1a}$ is $C_3$-$C_{12}$ cycloalkyl, phenyl, 4- to 12-membered heterocycloalkyl containing 1-4 heteroatoms selected from N, O, and S, or a 5- or 6-membered heteroaryl and $R^{S1a}$ is optionally substituted with one or more of halo, $C_1$-$C_6$ alkyl, hydroxyl, oxo. —$C(O)R^{6a}$, —$SO_2R^{5a}$, —$SO_2N(R^{5a})_2$, —$NR^{5a}C(O)R^{6a}$, amino, mono- or di-alkylamino, or $C_1$-$C_6$ alkoxyl; or (2) at least one of $R^{1a}$ and $R^{11a}$ is $-Q^{1a}-T^{1a}$, in which $Q^{1a}$ is a $C_2$-$C_6$ alkenylene or $C_2$-$C_6$ alkynylene linker optionally substituted with one or more of halo, cyano, hydroxyl, or $C_1$-$C_6$ alkoxyl, and $T^{1a}$ is H, halo, cyano, $NR^{5a}R^{6a}$, $C(O)NR^{5a}R^{6a}$, —$OC(O)NR^{5a}R^{6a}$, $C(O)OR^{5a}$, —$OC(O)R^{5a}$, $C(O)R^{5a}$, —$NR^{5a}C(O)R^{6a}$, —$NR^{5a}C(O)OR^{6a}$, $OR^{5a}$, or $R^{S1a}$, in which $R^{S1a}$ is $C_3$-$C_{12}$ cycloalkyl, phenyl, 4- to 12-membered heterocycloalkyl containing 1-4 heteroatoms selected from N, O, and S, or a 5- or 6-membered heteroaryl and $R^{S1a}$ is optionally substituted with one or more of halo, $C_1$-$C_6$ alkyl, hydroxyl, oxo, —$C(O)R^{6a}$, —$SO_2R^{5a}$, —$SO_2N(R^{5a})_2$, —$NR^{5a}C(O)R^{6a}$, amino, mono- or di-alkylamino, or $C_1$-$C_6$ alkoxyl; or (3) at least one of $R^{1a}$ and $R^{11a}$ is $-Q^{1a}-T^{1a}$, in which $Q^{1a}$ is a bond, and $T^{1a}$ is halo, cyano, $NR^{5a}R^{6a}$, $C(O)NR^{5a}R^{6a}$, —$OC(O)NR^{5a}R^{6a}$, $C(O)OR^{5a}$, —$OC(O)R^{5a}$, $C(O)R^{5a}$, —NR$^{5a}$C(O)R$^{6a}$, —NR$^{5a}$C(O)OR$^{6a}$, OR$^{5a}$, or R$^{S1a}$, in which R$^{S1a}$ is C$_3$-C$_{12}$ cycloalkyl, phenyl, 4- to 12-membered heterocycloalkyl containing 1-4 heteroatoms selected from N, O, and S, or a 5- or 6-membered heteroaryl and R$^{S1a}$ is optionally substituted with one or more of halo, C$_1$-C$_6$ alkyl, hydroxyl, oxo, —C(O)R$^{6a}$, —SO$_2$R$^{5a}$, —SO$_2$N(R$^{5a}$)$_2$, —NR$^{5a}$C(O)R$^{6a}$, amino, mono- or di-alkylamino, or C$_1$-C$_6$ alkoxyl; or (4) R$^{1a}$ and R$^{11a}$ together with the carbon atom to which they are attached form a C$_7$-C$_{12}$ cycloalkyl or 4- to 12-membered heterocycloalkyl containing 1-4 heteroatoms selected from N, O, and S, wherein the C$_7$-C$_{12}$ cycloalkyl or 4- to 12-membered heterocycloalkyl is optionally substituted with one or more of halo, C$_1$-C$_6$ alkyl, hydroxyl, oxo, amino, mono- or di-alkylamino, or C$_1$-C$_6$ alkoxyl.

In some embodiments, at least one of X$^{2a}$ and X$^{3a}$ is N.

In some embodiments, at least two of X$^{1a}$, X$^{2a}$, and X$^{3a}$ comprise N.

In some embodiments, at least one of ═1═, ═2═ and ═3═ is a double bond.

In some embodiments, ═3═ is a double bond.

In some embodiments, ═3═ is a single bond.

In some embodiments, X$^{2a}$ is NR$^{2a'}$ and R$^{3a}$ is oxo.

In some embodiments, X$^{2a}$ is N and X$^{3a}$ is C.

In some embodiments, X$^{2a}$ is CR$^{2a}$ and X$^{3a}$ is N.

In some embodiments, X$^{1a}$ is S.

In some embodiments, X$^{1a}$ is NR$^{1a'}$.

In some embodiments, X$^{1a}$ is CR$^{1a}$R$^{11a}$.

In some embodiments, R$^{1a}$ and R$^{11a}$ together with the carbon atom to which they are attached form a 4- to 7-membered heterocycloalkyl containing 1-4 heteroatoms selected from N, O, and S, wherein the 4- to 7-membered heterocycloalkyl is optionally substituted with one or more of halo, C$_1$-C$_6$ alkyl, hydroxyl, oxo, amino, mono- or di-alkylamino, or C$_1$-C$_6$ alkoxyl.

In some embodiments, n is 1 or 2.

In some embodiments, n is 2.

In some embodiments, the compound is of Formula (Ia'), (IIb'), (IIc'), (IId'), (IIe'), (IIIa'), (IIIv'), (IIIc'), (IIId'), (IIIe'), (IIIf'), (IVa'), or (IVb'):

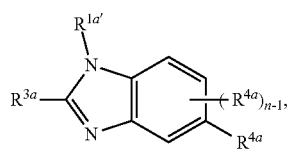

(IIa')

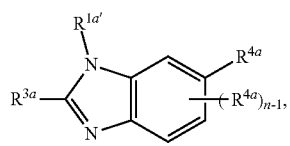

(IIb')

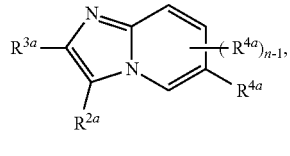

(IIc')

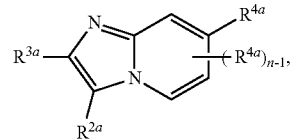

(IId')

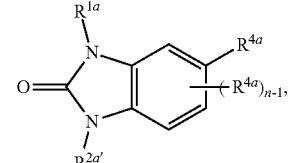

(IIe')

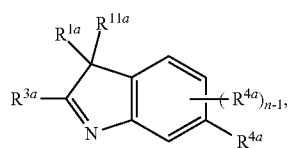

(IIIa')

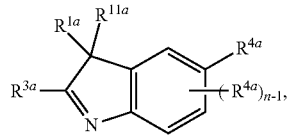

(IIIb')

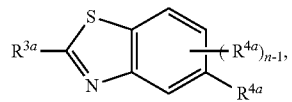

(IIIc')

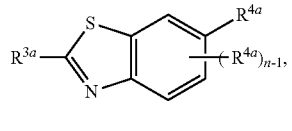

(IIId')

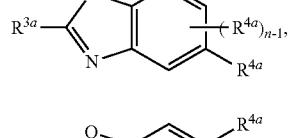

(IIIe')

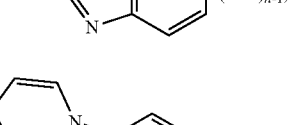

(IIIf')

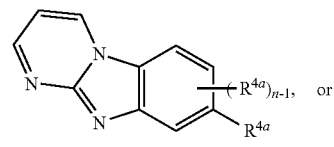

(IVa')

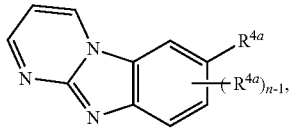

(IVb')

a tautomer thereof, or a pharmaceutically acceptable salt of the compound or the tautomer.

In some embodiments, the compound is of Formula (IIf'), (IIg'), (IIh'), (IIIi'), (IIIj'), (IIIk'), or (IIII'):

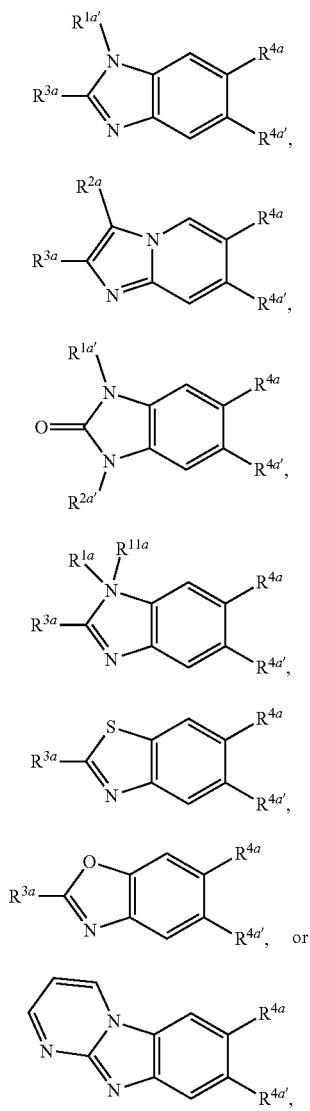

a tautomer thereof, or a pharmaceutically acceptable salt of the compound or the tautomer, wherein $R^{3a}$ is H, $NR^{aa}R^{ba}$, $OR^{aa}$, or $R^{S4a}$, in which $R^{S4a}$ is $C_1$-$C_6$ alkyl, $C_2$-$C_6$ alkenyl, $C_2$-$C_6$ alkynyl, $C_3$-$C_{12}$ cycloalkyl, phenyl, 5- or 6-membered heteroaryl, or 4- to 12-membered heterocycloalkyl containing 1-4 heteroatoms selected from N, O, and S, wherein each of $R^{aa}$ and $R^{ba}$ independently is H or $R^{S5a}$, or $R^{aa}$ and $R^{ba}$ together with the nitrogen atom to which they are attached form a 4- to 12-membered heterocycloalkyl containing 1-4 heteroatoms selected from N, O, and S; in which $R^{S5a}$ is $C_1$-$C_6$ alkyl, phenyl, 5- or 6-membered heteroaryl, or 4- to 12-membered heterocycloalkyl containing 1-4 heteroatoms selected from N, O, and S, and each of $R^{S4a}$, $R^{S5a}$, and the heterocycloalkyl formed by $R^{aa}$ and $R^{ba}$ is independently optionally substituted with one or more of halo, hydroxyl, oxo, CN, amino, mono- or di-alkylamino, $C_1$-$C_6$ alkyl, $C_1$-$C_6$ alkoxyl, $C_3$-$C_{12}$ cycloalkyl, phenyl, 5- or 6-membered heteroaryl, or 4- to 12-membered heterocycloalkyl containing 1-4 heteroatoms selected from N, O, and S;

each of $R^{4a}$ and $R^{4a'}$ independently is -$Q^{3a}$-$T^{3a}$, in which each $Q^{3a}$ independently is a bond or $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, or $C_1$-$C_6$ alkoxyl, and each $T^{3a}$ independently is H, halo, cyano, $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$;

each of $R^{5a}$, $R^{6a}$, and $R^{7a}$, independently, is H or $C_1$-$C_6$ alkyl optionally substituted with one or more of halo, cyano, hydroxyl, amino, mono- or di-alkylamino, or $C_1$-$C_6$ alkoxyl;

$R^{8a}$ is -$Q^{4a}$-$T^{4a}$, in which $Q^{4a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{4a}$ is H, halo, or $R^{S3a}$, in which $R^{S3a}$ is $C_3$-$C_{12}$ cycloalkyl, $C_6$-$C_{10}$ aryl, 4- to 12-membered heterocycloalkyl containing 1-4 heteroatoms selected from N, O and S, or a 5- to 10-membered heteroaryl, and $R^{S3a}$ is optionally substituted with one or more -$Q^{5a}$-$T^{5a}$, wherein each $Q^{5a}$ independently is a bond or $C_1$-$C_3$ alkylene, $C_2$-$C_3$ alkenylene, or $C_2$-$C_3$ alkynylene linker each optionally substituted with one or more of halo, cyano, hydroxyl, or $C_1$-$C_6$ alkoxy, and each $T^{5a}$ independently is selected from the group consisting of H, halo, cyano, $C_1$-$C_6$ alkyl, $C_3$-$C_{12}$ cycloalkyl, $C_6$-$C_{10}$ aryl, 4- to 7-membered heterocycloalkyl containing 1-4 heteroatoms selected from N, O, and S, 5- to 6-membered heteroaryl, $OR^{ca}$, $C(O)R^{ca}$, $NR^{ca}R^{da}$, $C(O)NR^{ca}R^{da}$, $S(O)_2R^{ca}$, and $NR^{ca}C(O)R^{da}$, each of $R^{ca}$ and $R^{da}$ independently being H or $C_1$-$C_6$ alkyl optionally substituted with one or more halo; or -$Q^{5a}$-$T^{5a}$ is oxo.

In some embodiments, the compound is not one of those described in EP 0356234; U.S. Pat. Nos. 5,106,862; 6,025,379; 9,284,272; WO2002/059088; and/or WO2015/200329.

In some embodiments, when n is 2, $X^{1a}$ is $CR^{1a}R^{11a}$, $X^{2a}$ is N, $X^{3a}$ is C, $R^{3a}$ is $NH_2$, and at least one $R^{4a}$ is $OR^{7a}$, then at least one of $R^{1a}$ and $R^{11a}$ is -$Q^{1a}$-$T^{1a}$, in which $Q^{1a}$ is a $C_1$-$C_6$ alkylene linker optionally substituted with one or more of halo, cyano, hydroxyl, or $C_1$-$C_6$ alkoxyl, and $T^{1a}$ is cyano, $NR^{5a}R^{6a}$, $C(O)NR^{5a}R^{6a}$, —$OC(O)NR^{5a}R^{6a}$, $C(O)OR^{5a}$, —$OC(O)R^{5a}$, $C(O)R^{5a}$, —$NR^{5a}C(O)R^{6a}$, —$NR^{5a}C(O)OR^{6a}$, $OR^{5a}$, or $R^{S1a}$, in which $R^{S1a}$ is $C_3$-$C_{12}$ cycloalkyl, phenyl, 4- to 12-membered heterocycloalkyl (e.g., 4- to 7-membered heterocycloalkyl) containing 1-4 heteroatoms selected from N, O, and S, or a 5- or 6-membered heteroaryl and $R^{S1a}$ is optionally substituted with one or more of halo, $C_1$-$C_6$ alkyl, hydroxyl, oxo, —$C(O)R^{6a}$, —$SO_2R^{5a}$, —$SO_2N(R^{5a})_2$, —$NR^{5a}C(O)R^{6a}$, amino, mono- or di-alkylamino, or $C_1$-$C_6$ alkoxyl.

In some embodiments, when n is 2, $X^{1a}$ is $CR^{1a}R^{11a}$, $X^{2a}$ is N, $X^{3a}$ is C, $R^{3a}$ is $NH_2$, and at least one $R^{aa}$ is $OR^{7a}$, then at least one of $R^{1a}$ and $R^{11a}$ is -$Q^{1a}$-$T^{1a}$, in which $Q^{1a}$ is a $C_2$-$C_6$ alkenylene or $C_2$-$C_6$ alkynylene linker optionally substituted with one or more of halo, cyano, hydroxyl, or $C_1$-$C_6$ alkoxyl, and $T^{1a}$ is H, halo, cyano. $NR^{5a}R^{6a}$, $C(O)NR^{5a}R^{6a}$, —$OC(O)NR^{5a}R^{6a}$, $C(O)OR^{5a}$, —$OC(O)R^{5a}$, $C(O)R^{5a}$, —$NR^{5a}C(O)R^{6a}$, —$NR^{5a}C(O)OR^{6a}$, $OR^{5a}$, or $R^{S1a}$, in which $R^{S1a}$ is $C_3$-$C_{12}$ cycloalkyl, phenyl, 4- to 12-membered heterocycloalkyl (e.g., 4- to 7-membered heterocycloalkyl) containing 1-4 heteroatoms selected from N, O, and S, or a 5- or 6-membered heteroaryl and $R_{S1a}$ is optionally substituted with one or more of halo, $C_1$-$C_6$ alkyl, hydroxyl, oxo, —C(O)$R^{6a}$, —SO$_2$$R^{5a}$, —SO$_2$N($R^{5a}$)$_2$, —N$R^{5a}$C(O)$R^{6a}$, amino, mono- or di-alkylamino, or $C_1$-$C_6$ alkoxyl.

In some embodiments, when n is 2, $X^{1a}$ is CR$^{1a}$R$^{11a}$, $X^{2a}$ is N, $X^{3a}$ is C, $R^{3a}$ is NH$_2$, and at least one $R^{4a}$ is OR$^{7a}$, then at least one of $R^{1a}$ and $R^{11a}$ is -$Q^{1a}$-$T^{1a}$, in which $Q^{1a}$ is a bond, and $T^{1a}$ is halo, cyano, NR$^{5a}$R$^{6a}$, C(O)NR$^{5a}$R$^{6a}$, —OC(O)NR$^{5a}$R$^{6a}$, C(O)OR$^{5a}$, —OC(O)R$^{5a}$, C(O)R$^{5a}$, —NR$^{5a}$C(O)R$^{6a}$, —NR$^{5a}$C(O)OR$^{6a}$, OR$^{5a}$, or R$^{S1a}$, in which R$^{S1a}$ is $C_3$-$C_{12}$ cycloalkyl, phenyl, 4- to 12-membered heterocycloalkyl (e.g., 4- to 7-membered heterocycloalkyl) containing 1-4 heteroatoms selected from N, O, and S, or a 5- or 6-membered heteroaryl and R$^{S1a}$ is optionally substituted with one or more of halo, $C_1$-$C_6$ alkyl, hydroxyl, oxo, —C(O)R$^{6a}$, —SO$_2$R$^{5a}$, —SO$_2$N(R$^{5a}$)$_2$, —NR$^{5a}$C(O)R$^{6a}$, amino, mono- or di-alkylamino, or $C_1$-$C_6$ alkoxyl.

In some embodiments, when n is 2, $X^{1a}$ is CR$^{1a}$R$^{11a}$, $X^{2a}$ is N, $X^{3a}$ is C, $R^{3a}$ is NH$_2$, and at least one $R^{4a}$ is OR$^{7a}$, then $R^{1a}$ and $R^{11a}$ together with the carbon atom to which they are attached form a $C_7$-$C_{12}$ cycloalkyl or 4- to 12-membered heterocycloalkyl (e.g., 4- to 7-membered heterocycloalkyl) containing 1-4 heteroatoms selected from N, O, and S, wherein the $C_7$-$C_{12}$ cycloalkyl or 4- to 12-membered heterocycloalkyl (e.g., 4- to 7-membered heterocycloalkyl) is optionally substituted with one or more of halo, $C_1$-$C_6$ alkyl, hydroxyl, oxo, amino, mono- or di-alkylamino, or $C_1$-$C_6$ alkoxyl.

In some embodiments, $R^{2a}$ is -$Q^{1a}$-$T^{1a}$, in which $Q^{1a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{1a}$ is H, halo, cyano, or R$^{S1a}$, in which R$^{S1a}$ is $C_3$-$C_{12}$ cycloalkyl (e.g., $C_3$-$C_8$ cycloalkyl), phenyl, 4- to 12-membered heterocycloalkyl (e.g., 4- to 7-membered heterocycloalkyl) containing 1-4 heteroatoms selected from N, O, and S, or a 5- or 6-membered heteroaryl and R$^{S1a}$ is optionally substituted with one or more of halo, $C_1$-$C_6$ alkyl, hydroxyl, oxo, amino, mono- or di-alkylamino, or $C_1$-$C_6$ alkoxyl.

In some embodiments, $R^{2a}$ is $C_1$-$C_6$ alkyl optionally substituted with one or more of halo, cyano, hydroxyl, or $C_1$-$C_6$ alkoxyl. In some embodiments, $R^{2a}$ is unsubstituted $C_1$-$C_6$ alkyl.

In some embodiments, $Q^{1a}$ is a bond or $C_1$-$C_6$ alkylene linker optionally substituted with one or more of halo, cyano, hydroxyl, or $C_1$-$C_6$ alkoxyl, and $T^{1a}$ is H, halo, cyano, or R$^{S1a}$, in which R$^{S1a}$ is $C_3$-$C_{12}$ cycloalkyl (e.g., $C_3$-$C_8$ cycloalkyl), phenyl, 4- to 12-membered heterocycloalkyl (e.g., 4- to 7-membered heterocycloalkyl) containing 1-4 heteroatoms selected from N, O, and S, or a 5- or 6-membered heteroaryl and R$^{S1a}$ is optionally substituted with one or more of halo, $C_1$-$C_6$ alkyl, hydroxyl, oxo, amino, mono- or di-alkylamino, or $C_1$-$C_6$ alkoxyl.

In some embodiments, $Q^{1a}$ is a $C_2$-$C_6$ alkenylene or $C_2$-$C_6$ alkynylene linker optionally substituted with one or more of halo, cyano, hydroxyl, or $C_1$-$C_6$ alkoxyl, and $T^{1a}$ is H, halo, cyano, or R$^{S1a}$, in which R$^{S1a}$ is $C_3$-$C_{12}$ cycloalkyl (e.g., $C_3$-$C_8$ cycloalkyl), phenyl, 4- to 12-membered heterocycloalkyl (e.g., 4- to 7-membered heterocycloalkyl) containing 1-4 heteroatoms selected from N, O, and S, or a 5- or 6-membered heteroaryl and R$^{S1a}$ is optionally substituted with one or more of halo. $C_1$-$C_6$ alkyl, hydroxyl, oxo, amino, mono- or di-alkylamino, or $C_1$-$C_6$ alkoxyl.

In some embodiments, $R^{1a'}$ is -$Q^{2a}$-$T^{2a}$, in which $Q^{2a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{2a}$ is H, halo, cyano, or R$^{S2a}$, in which R$^{S2a}$ is $C_3$-$C_{12}$ cycloalkyl (e.g., $C_3$-$C_8$ cycloalkyl), phenyl, 4- to 12-membered heterocycloalkyl (e.g., 4- to 7-membered heterocycloalkyl) containing 1-4 heteroatoms selected from N, O, and S, or a 5- or 6-membered heteroaryl and R$^{S2a}$ is optionally substituted with one or more of halo, $C_1$-$C_6$ alkyl, hydroxyl, oxo, amino, mono- or di-alkylamino, or $C_1$-$C_6$ alkoxyl.

In some embodiments, $R^{2a'}$ is -$Q^{2a}$-$T^{2a}$, in which $Q^{2a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{2a}$ is H, halo, cyano, or R$^{S2a}$, in which R$^{S2a}$ is $C_3$-$C_{12}$ cycloalkyl (e.g., $C_3$-$C_8$ cycloalkyl), phenyl, 4- to 12-membered heterocycloalkyl (e.g., 4- to 7-membered heterocycloalkyl) containing 1-4 heteroatoms selected from N, O, and S, or a 5- or 6-membered heteroaryl and R$^{S2a}$ is optionally substituted with one or more of halo, $C_1$-$C_6$ alkyl, hydroxyl, oxo, amino, mono- or di-alkylamino, or $C_1$-$C_6$ alkoxyl.

In some embodiments, each $Q^{2a}$ independently is a bond or $C_1$-$C_6$ alkylene linker optionally substituted with one or more of halo and each $T^{2a}$ independently is H, halo, $C_3$-$C_{12}$ cycloalkyl (e.g., $C_3$-$C_8$ cycloalkyl), or a 4- to 7-membered heterocycloalkyl.

In some embodiments, each $Q^{2a}$ independently is $C_2$-$C_6$ alkenylene or $C_2$-$C_6$ alkynylene linker optionally substituted with one or more of halo, cyano, hydroxyl, or $C_1$-$C_6$ alkoxyl.

In some embodiments, $R^{2a'}$ is H or $C_1$-$C_6$ alkyl.

In some embodiments, $R^{3a}$ is H.

In some embodiments, $R^{3a}$ is NR$^{aa}$R$^{ba}$ or OR$^{aa}$, wherein each of R$^{aa}$ and R$^{ba}$ independently is H or $C_1$-$C_6$ alkyl optionally substituted with one or more of halo, hydroxyl, CN, amino, mono- or di-alkylamino, or $C_1$-$C_6$ alkoxyl.

In some embodiments, $R^{3a}$ is NR$^{aa}$R$^{ba}$ or OR$^{aa}$, wherein each of R$^{aa}$ and R$^{ba}$ independently is H or $C_1$-$C_6$ alkyl optionally substituted with one or more of halo, hydroxyl, amino, mono- or di-alkylamino, $C_1$-$C_6$ alkoxyl, $C_3$-$C_{12}$ cycloalkyl, phenyl, 5- or 6-membered heteroaryl, or 4- to 12-membered heterocycloalkyl (e.g., 4- to 7-membered heterocycloalkyl) containing 1-4 heteroatoms selected from N, O, and S.

In some embodiments, $R^{3a}$ is NR$^{aa}$R$^{ba}$.

In some embodiments, each of R$^{aa}$ and R$^{ba}$ independently is H or R$^{S5a}$.

In some embodiments, one of R$^{aa}$ and R$^{ba}$ is H and the other is R$^{S5a}$.

In some embodiments, R$^{aa}$ and R$^{ba}$ together with the nitrogen atom to which they are attached form a 4- to 12-membered heterocycloalkyl (e.g., 4- to 7-membered heterocycloalkyl), which is optionally substituted with one or more of halo, hydroxyl, oxo, CN, amino, mono- or di-alkylamino, $C_1$-$C_6$ alkyl, $C_1$-$C_6$ alkoxyl, $C_3$-$C_{12}$ cycloalkyl, phenyl, 5- or 6-membered heteroaryl, or 4- to 12-membered heterocycloalkyl (e.g., 4- to 7-membered heterocycloalkyl).

In some embodiments, R$^{aa}$ and R$^{ba}$ together with the nitrogen atom to which they are attached form a 4- to 12-membered heterocycloalkyl (e.g., 4- to 7-membered heterocycloalkyl), which is optionally substituted with one or more of halo, hydroxyl, oxo, CN, amino, mono- or di-alkylamino, $C_1$-$C_6$ alkyl, or $C_1$-$C_6$ alkoxyl.

In some embodiments, R$^{S5a}$ is $C_1$-$C_6$ alkyl, and R$^{S5a}$ is optionally substituted with one or more of halo, hydroxyl, CN, amino, mono- or di-alkylamino, $C_1$-$C_6$ alkoxyl, $C_3$-$C_{12}$ cycloalkyl, phenyl, 5- or 6-membered heteroaryl, or 4- to 12-membered heterocycloalkyl (e.g., 4- to 7-membered heterocycloalkyl).

In some embodiments, R$^{S5a}$ is phenyl, 5- or 6-membered heteroaryl, or 4- to 12-membered heterocycloalkyl (e.g., 4- to 7-membered heterocycloalkyl), and R$^{S5a}$ is optionally substituted with one or more of halo, hydroxyl, oxo, CN, amino, mono- or di-alkylamino, $C_1$-$C_6$ alkyl, $C_1$-$C_6$ alkoxyl, $C_3$-$C_{12}$ cycloalkyl, phenyl, 5- or 6-membered heteroaryl, or 4- to 12-membered heterocycloalkyl (e.g., 4- to 7-membered heterocycloalkyl).

In some embodiments, the compound is of Formulae (Va'), (Vb'), (Vc'), (Vd'), (Ve'), or (Vf'):

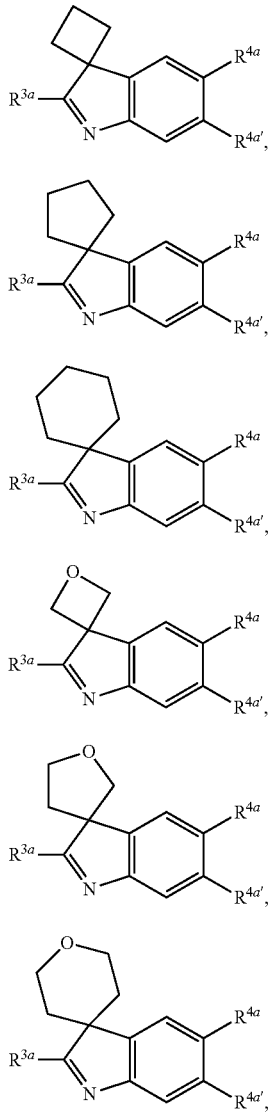

a tautomer thereof, or a pharmaceutically acceptable salt of the compound or the tautomer, wherein $R^{3a}$ is H, $NR^{aa}R^{ba}$, $OR^{aa}$, or $R^{S4a}$, in which $R^{S4a}$ is $C_1$-$C_6$ alkyl, $C_2$-$C_6$ alkenyl, $C_2$-$C_6$ alkynyl, $C_3$-$C_{12}$ cycloalkyl, phenyl, 5- or 6-membered heteroaryl, or 4- to 12-membered heterocycloalkyl containing 1-4 heteroatoms selected from N, O, and S, wherein each of $R^{aa}$ and $R^{ba}$ independently is H or $R^{S5a}$, or $R^{aa}$ and $R^{ba}$ together with the nitrogen atom to which they are attached form a 4- to 12-membered heterocycloalkyl containing 1-4 heteroatoms selected from N, O, and S; in which $R^{S5a}$ is $C_1$-$C_6$ alkyl, phenyl, 5- or 6-membered heteroaryl, or 4- to 12-membered heterocycloalkyl containing 1-4 heteroatoms selected from N, O, and S, and each of $R^{S4a}$, $R^{S5a}$, and the heterocycloalkyl formed by $R^{aa}$ and $R^{ba}$ is independently optionally substituted with one or more of halo, hydroxyl, oxo, CN, amino, mono- or di-alkylamino, $C_1$-$C_6$ alkyl, $C_1$-$C_6$ alkoxyl, $C_3$-$C_{12}$ cycloalkyl, phenyl, 5- or 6-membered heteroaryl, or 4- to 12-membered heterocycloalkyl containing 1-4 heteroatoms selected from N, O, and S;

each of $R^{4a}$ and $R^{4a'}$ independently is -$Q^{3a}$-$T^{3a}$, in which each $Q^{3a}$ independently is a bond or $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, or $C_1$-$C_6$ alkoxyl, and each $T^{3a}$ independently is H, halo, cyano, $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$;

each of $R^{5a}$, $R^{6a}$, and $R^{7a}$, independently, is H or $C_1$-$C_6$ alkyl optionally substituted with one or more of halo, cyano, hydroxyl, amino, mono- or di-alkylamino, or $C_1$-$C_6$ alkoxyl; and $R^{8a}$ is -$Q^{4a}$-$T^{4a}$, in which $Q^{4a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{4a}$ is H, halo, or $R^{S3a}$, in which $R^{S3a}$ is $C_3$-$C_{12}$ cycloalkyl, $C_6$-$C_{10}$ aryl, 4- to 12-membered heterocycloalkyl containing 1-4 heteroatoms selected from N, O and S, or a 5- to 10-membered heteroaryl, and $R^{S3a}$ is optionally substituted with one or more -$Q^{5a}$-$T^{5a}$, wherein each $Q^{5a}$ independently is a bond or $C_1$-$C_3$ alkylene, $C_2$-$C_3$ alkenylene, or $C_2$-$C_3$ alkynylene linker each optionally substituted with one or more of halo, cyano, hydroxyl, or $C_1$-$C_6$ alkoxy, and each $T^{5a}$ independently is selected from the group consisting of H, halo, cyano, $C_1$-$C_6$ alkyl, $C_3$-$C_{12}$ cycloalkyl, $C_6$-$C_{10}$ aryl, 4- to 7-membered heterocycloalkyl containing 1-4 heteroatoms selected from N, O, and S, 5- to 6-membered heteroaryl, $OR^{ca}$, $C(O)R^{ca}$, $NR^{ca}R^{da}$, $C(O)NR^{ca}R^{da}$, $S(O)_2R^{ca}$, and $NR^{ca}C(O)R^{da}$, each of $R^{ca}$ and $R^{da}$ independently being H or $C_1$-$C_6$ alkyl optionally substituted with one or more halo; or -$Q^{5a}$-$T^{5a}$ is oxo.

In some embodiments, when $R^{3a}$ is —$NH_2$, then $R^{4a}$ is not —$OCH_3$.

In some embodiments, when $R^{3a}$ is —$NH_2$, and $R^{4a}$ is not —$OCH_3$, then $R^{4a'}$ is not $OR^{8a}$.

In some embodiments, $R^{3a}$ is $C_1$-$C_6$ alkyl, $C_2$-$C_6$ alkenyl, or $C_2$-$C_6$ alkynyl, each of which is optionally substituted with one or more of halo, hydroxyl, oxo, CN, amino, mono- or di-alkylamino, $C_1$-$C_6$ alkoxyl, $C_3$-$C_{12}$ cycloalkyl, phenyl, 5- or 6-membered heteroaryl, or 4- to 12-membered heterocycloalkyl (e.g., 4- to 7-membered heterocycloalkyl) containing 1-4 heteroatoms selected from N, O, and S; in which each of the $C_3$-$C_{12}$ cycloalkyl, phenyl, 5- or 6-membered heteroaryl, and 4- to 12-membered heterocycloalkyl (e.g., 4- to 7-membered heterocycloalkyl) is independently optionally substituted with one or more of halo, hydroxyl, oxo, CN, amino, mono- or di-alkylamino, $C_1$-$C_6$ alkyl, or $C_1$-$C_6$ alkoxyl.

In some embodiments, $R^{3a}$ is $C_3$-$C_{12}$ cycloalkyl or 4- to 12-membered heterocycloalkyl (e.g., 4- to 7-membered heterocycloalkyl) containing 1-4 heteroatoms selected from N, O, and S, wherein each of the $C_3$-$C_{12}$ cycloalkyl and 4- to 12-membered heterocycloalkyl (e.g., 4- to 7-membered heterocycloalkyl) is independently optionally substituted with one or more of halo, hydroxyl, oxo, CN, amino, mono- or di-alkylamino, $C_1$-$C_6$ alkyl, or $C_1$-$C_6$ alkoxyl.

In some embodiments, $R^{3a}$ is

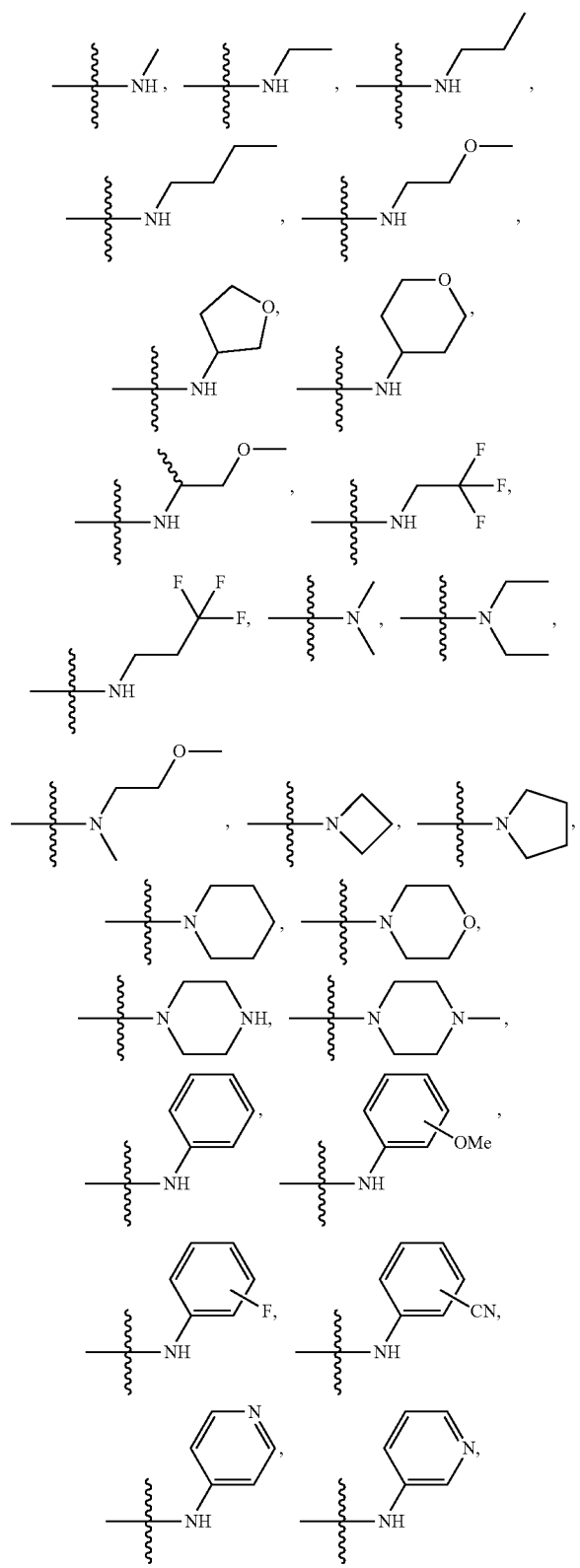

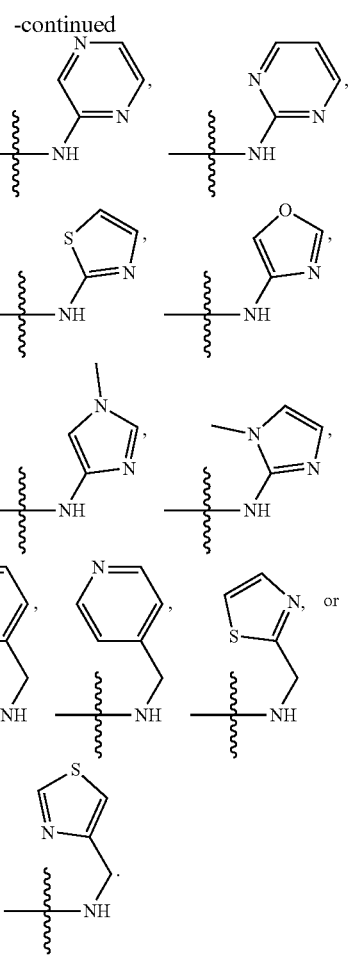

In some embodiments, $R^{3a}$ is $NH_2$.

In some embodiments, $R^{3a}$ is $NR^{aa}R^{ba}$, in which one of $R^{aa}$ and $R^{ba}$ is H and the other is $C_1$-$C_6$ alkyl optionally substituted with one or more of halo or $C_1$-$C_6$ alkoxyl.

In some embodiments, $R^{3a}$ is oxo and ⋰⋰⋰ is a single bond.

In some embodiments, $R^{3a}$ is OH.

In some embodiments, $R^{3a}$ is $C_1$-$C_6$ alkoxyl.

In some embodiments, $R^{3a}$ and one of $R^{1a'}$, $R^{2a'}$, $R^{1a}$, $R^{2a}$ and $R^{11a}$, together with the atoms to which they are attached, form a 6-membered heteroaryl that is optionally substituted with one or more of halo, $C_1$-$C_3$ alkyl, hydroxyl or $C_1$-$C_6$ alkoxyl.

In some embodiments, $R^{3a}$ and one of $R^{1a'}$, $R^{2a'}$, $R^{1a}$, $R^{2a}$ and $R^{11a}$, together with the atoms to which they are attached, form a 5-membered heteroaryl that is optionally substituted with one or more of halo, $C_1$-$C_3$ alkyl, hydroxyl or $C_1$-$C_3$ alkoxyl.

In some embodiments, the compound is of Formulae (VIa'), (VIb'), (VIc'), (VId'), (VIe'), or (VIf'):

(VIa')

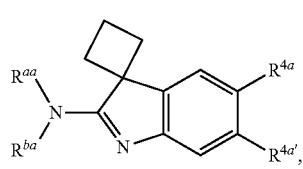

-continued (VIb')

(VIc')

(VId')

(VIe')

(VIf')

a tautomer thereof, or a pharmaceutically acceptable salt of the compound or the tautomer, wherein each of $R^{aa}$ and $R^{ba}$ independently is H or $R^{S5a}$, or $R^{aa}$ and $R^{ba}$ together with the nitrogen atom to which they are attached form a 4- to 12-membered heterocycloalkyl containing 1-4 heteroatoms selected from N, O, and S; in which $R^{S5a}$ is $C_1$-$C_6$ alkyl, phenyl, 5- or 6-membered heteroaryl, or 4- to 12-membered heterocycloalkyl containing 1-4 heteroatoms selected from N, O, and S, and each of $R^{S4a}$, $R^{S5a}$, and the heterocycloalkyl formed by $R^{aa}$ and $R^{ba}$ is independently optionally substituted with one or more of halo, hydroxyl, oxo, CN, amino, mono- or di-alkylamino, $C_1$-$C_6$ alkyl, $C_1$-$C_6$ alkoxyl, $C_3$-$C_{12}$ cycloalkyl, phenyl, 5- or 6-membered heteroaryl, or 4- to 12-membered heterocycloalkyl containing 1-4 heteroatoms selected from N, O, and S, or alternatively; and each of $R^{4a}$ and $R^{4a'}$ independently is -$Q^{3a}$-$T^{3a}$, in which each $Q^{3a}$ independently is a bond or $C_1$-$C_6$ alkylene. $C_2$-$C_6$ alkenylene, or $C_2$-$C_6$ alkynylene linker optionally substituted with one or more of halo, cyano, hydroxyl, amino, mono- or di-alkylamino, or $C_1$-$C_6$ alkoxyl, and each $T^{3a}$ independently is H, halo, cyano, $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$;

each of $R^{5a}$, $R^{6a}$, and $R^{7a}$, independently, is H or $C_1$-$C_6$ alkyl optionally substituted with one or more of halo, cyano, hydroxyl, amino, mono- or di-alkylamino, or $C_1$-$C_6$ alkoxyl; and $R^{8a}$ is -$Q^{4a}$-$T^{4a}$, in which $Q^{4a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{4a}$ is H, halo, or $R^{S3a}$, in which $R^{S3a}$ is $C_3$-$C_{12}$ cycloalkyl, $C_6$-$C_{10}$ aryl, 4- to 12-membered heterocycloalkyl containing 1-4 heteroatoms selected from N, O and S, or a 5- to 10-membered heteroaryl, and $R^{S3a}$ is optionally substituted with one or more -$Q^{5a}$-$T^{5a}$, wherein each Q independently is a bond or $C_1$-$C_3$ alkylene, $C_2$-$C_3$ alkenylene, or $C_2$-$C_3$ alkynylene linker each optionally substituted with one or more of halo, cyano, hydroxyl, or $C_1$-$C_6$ alkoxy, and each $T^{5a}$ independently is selected from the group consisting of H, halo, cyano, $C_1$-$C_6$ alkyl, $C_3$-$C_{12}$ cycloalkyl, $C_6$-$C_{10}$ aryl, 4- to 7-membered heterocycloalkyl selected from N, O, and S, 5- to 6-membered heteroaryl, $OR^{ca}$, $C(O)R^{ca}$, $NR^{ca}R^{da}$, $C(O)NR^{ca}R^{da}$, $S(O)_2R^{ca}$, and $NR^{ca}C(O)R^{da}$, each of $R^{ca}$ and $R^{da}$ independently being H or $C_1$-$C_6$ alkyl optionally substituted with one or more halo; or -$Q^{5a}$-$T^{5a}$ is oxo.

In some embodiments, at least one of $R^{aa}$ and $R^{ba}$ is $R^{S5a}$.

In some embodiments, when both of $R^{aa}$ and $R^{ba}$ are H, then $R^{4a}$ is not —$OCH_3$.

In some embodiments, when both of $R^{aa}$ and $R^{ba}$ are H, and $R^{4a}$ is —$OCH_3$, then $R^{4a'}$ is not $OR^{8a}$.

In some embodiments, each of $R^{4a}$ and $R^{4a'}$ is independently -$Q^{3a}$-$T^{3a}$, in which each $Q^{3a}$ independently is a bond or $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, or $C_1$-$C_6$ alkoxyl, and each $T^{3a}$ independently is H, halo, $OR^{7a}$, $OR^{8a}$, $NR^{7a}R^{8a}$, $C_6$-$C_{10}$ aryl, 5- to 10-membered heteroaryl, $C_3$-$C_{12}$ cycloalkyl, or 4- to 12-membered heterocycloalkyl.

In some embodiments, $R^{4a}$ is -$Q^{3a}$-$T^{3a}$, in which $Q^{3a}$ is a bond or $C_1$-$C_6$ alkylene linker, and $T^{3a}$ is H, halo, $OR^{7a}$, $C_6$-$C_{10}$ aryl, or 5- to 10-membered heteroaryl.

In some embodiments, $R^{4a'}$ is -$Q^{3a}$-$T^{3a}$, in which $Q^{3a}$ independently is a bond or $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, or $C_1$-$C_6$ alkoxyl, and each $T^{3a}$ independently is H, $OR^{7a}$, $OR^{8a}$, $NR^{7a}R^{8a}$, $C_3$-$C_{12}$ cycloalkyl, or 4- to 12-membered heterocycloalkyl.

In some embodiments, at least one of $R^{4a}$ and $R^{4a'}$ is $C_1$-$C_6$ alkyl. In some embodiments, $R^{4a}$ is $C_1$-$C_6$ alkyl.

In some embodiments, at least one of $R^{4a}$ and $R^{4a'}$ is $CH_3$. In some embodiments, $R^{4a}$ is $CH_3$.

In some embodiments, at least one of $R^{4a}$ and $R^{4a'}$ is halo. In some embodiments, $R^{4a}$ is halo.

In some embodiments, at least one of $R^{48}$ and $R^{4a'}$ is F or Cl. In some embodiments, $R^{4a}$ is F or Cl.

In some embodiments, at least one of $R^{4a}$ and $R^{4a'}$ is $C_6$-$C_{10}$ aryl. In some embodiments, $R^{4a}$ is $C_6$-$C_{10}$ aryl.

In some embodiments, at least one of $R^{4a}$ and $R^{4a'}$ is

In some embodiments, $R^{4a}$ is

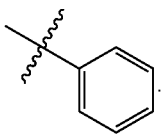 [SMILES: *c1ccccc1]

In some embodiments, at least one of $R^{4a}$ and $R^{4a'}$ is 5- to 10-membered heteroaryl. In some embodiments, $R^{4a}$ is 5- to 10-membered heteroaryl.

In some embodiments, at least one of $R^{4a}$ and $R^{4a'}$ is, or

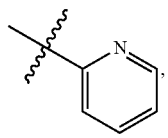 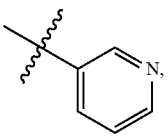 or 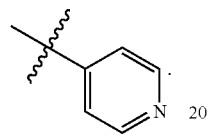

In some embodiments, $R^{4a}$ is

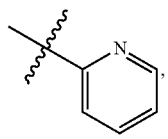 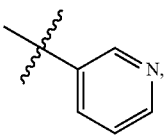 or 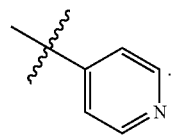

In some embodiments, at least one of $R^{4a}$ and $R^{4a'}$ is

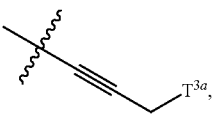

wherein $T^{3a}$ is H, halo, cyano, $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$.

In some embodiments, $R^{4a'}$ is

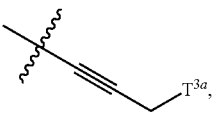

wherein $T^{3a}$ is H, halo, cyano, $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$.

In some embodiments, at least one of $R^{4a}$ and $R^{4a'}$ is

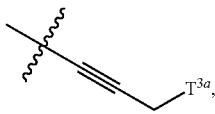

wherein $T^{3a}$ is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl.

In some embodiments, $R^{4a'}$ is

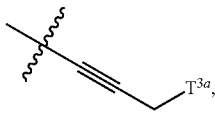

wherein $T^{3a}$ is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl.

In some embodiments, at least one of $R^{4a}$ and $R^{4a'}$ is

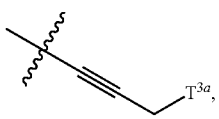

wherein $T^{3a}$ is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl and the other of $R^{4a}$ and $R^{4a'}$ halo, $C_1$-$C_6$ alkyl, or $OR^{7a}$. In some embodiments, $R^{7a}$ is H or $C_1$-$C_6$ alkyl optionally substituted with one or more of hydroxyl, amino or mono- or di-alkylamino.

In some embodiments, at least one of $R^{4a}$ and $R^{4a'}$ is —$OCH_3$, —$OCH_2CH_3$, or —$OCH(CH_3)_2$. In some embodiments, at least one of $R^{4a}$ and $R_{4'}$ is

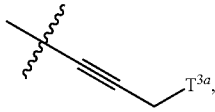

wherein $T^{3a}$ is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl and the other of $R^{4a}$ and $R^{4a'}$ is $OCH_3$. —$OCH_2CH_3$, or —$OCH(CH_3)_2$.

In some embodiments, at least one of $R^{4a}$ and $R^{4a'}$ is —$OCH_3$.

In some embodiments, at least one of $R^{4a}$ and $R^{4a'}$ is

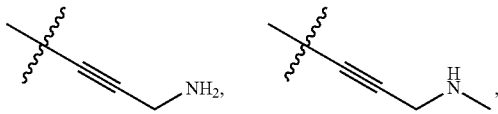

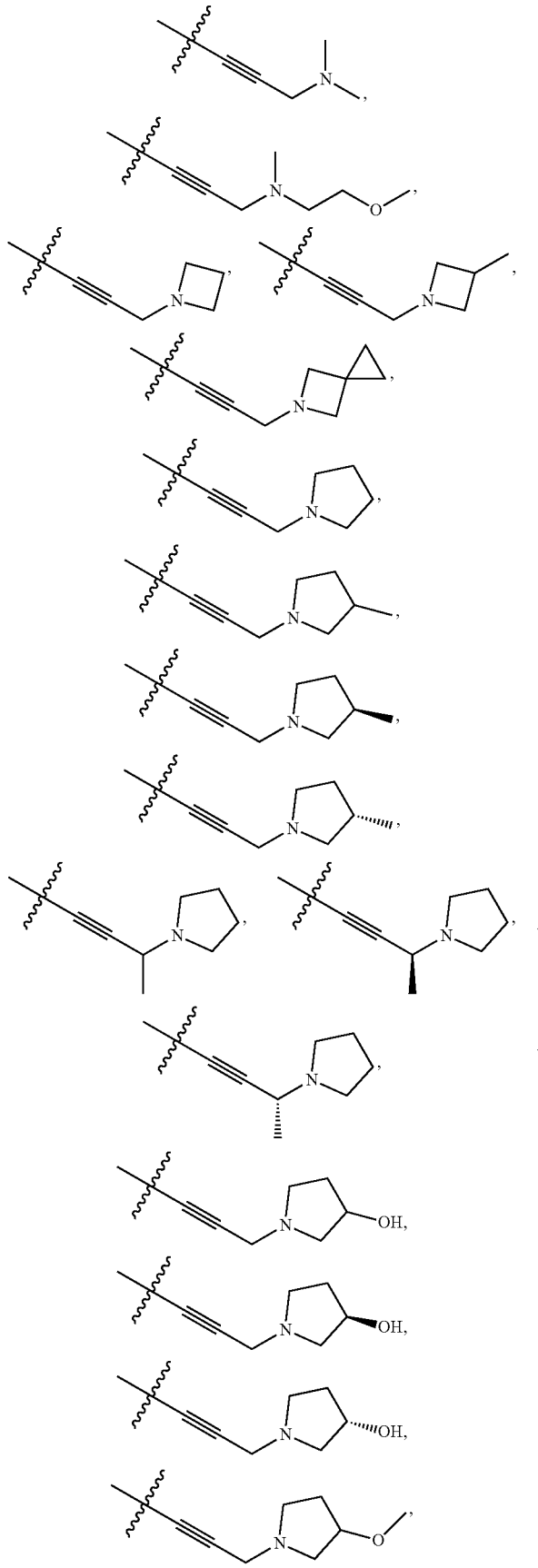
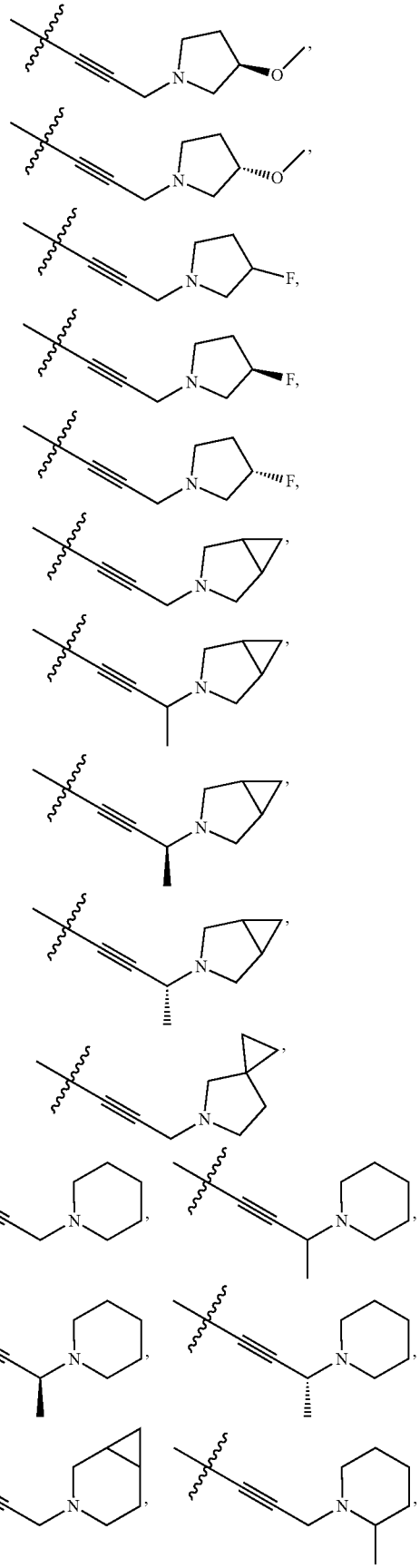

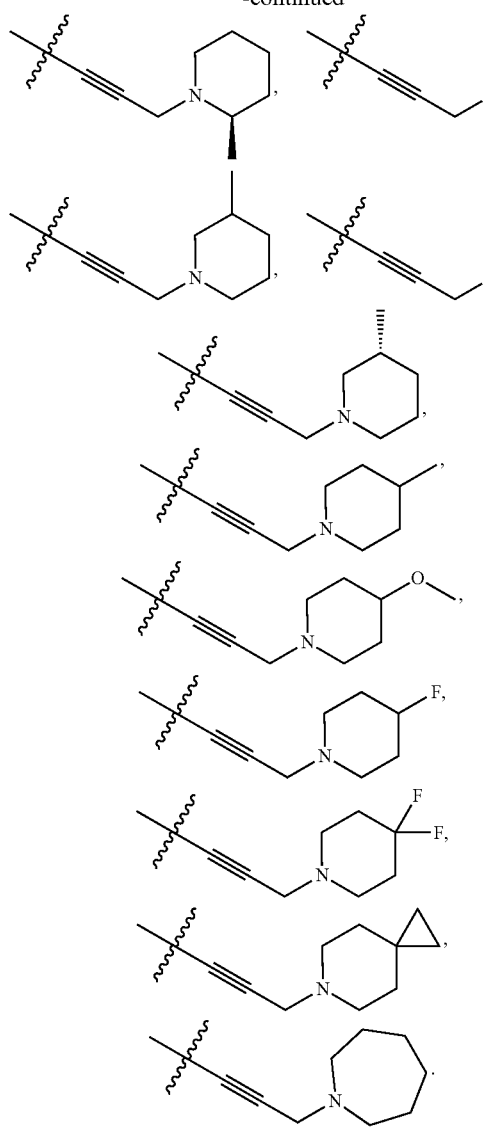
In some embodiments, $R^{4a'}$ is
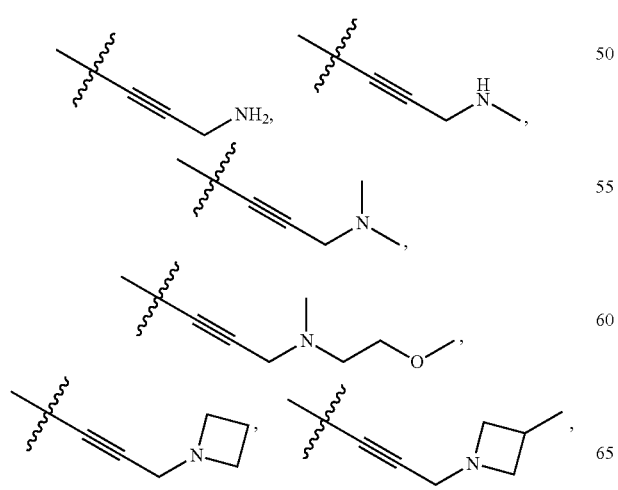
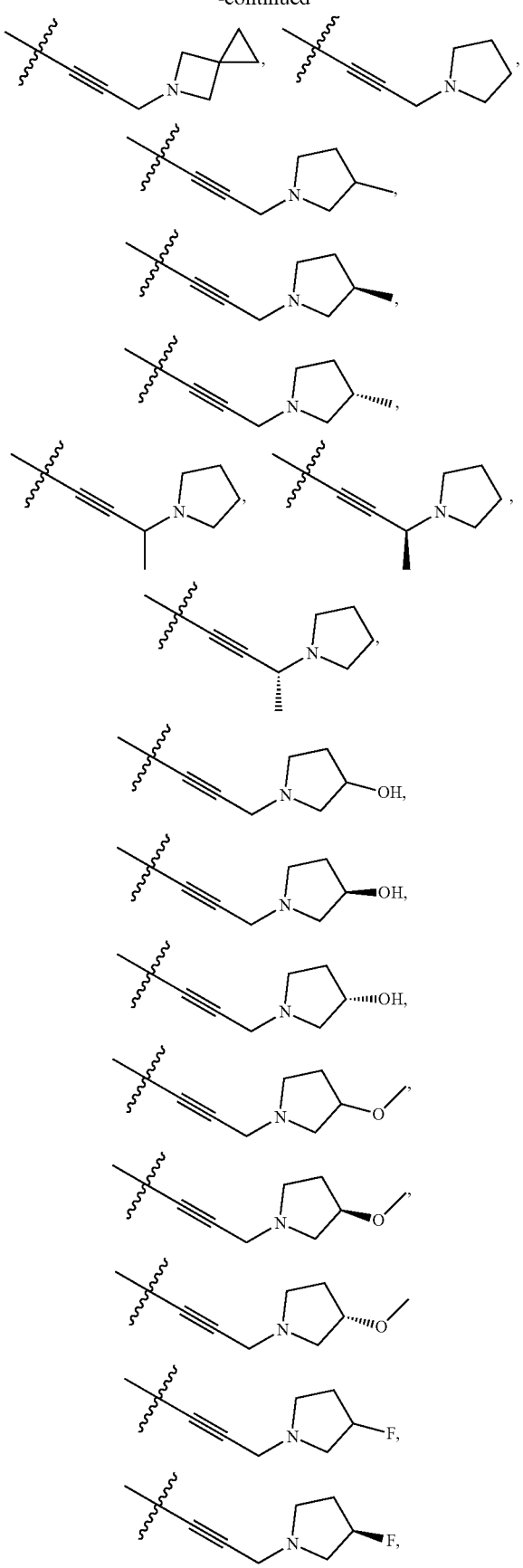

-continued

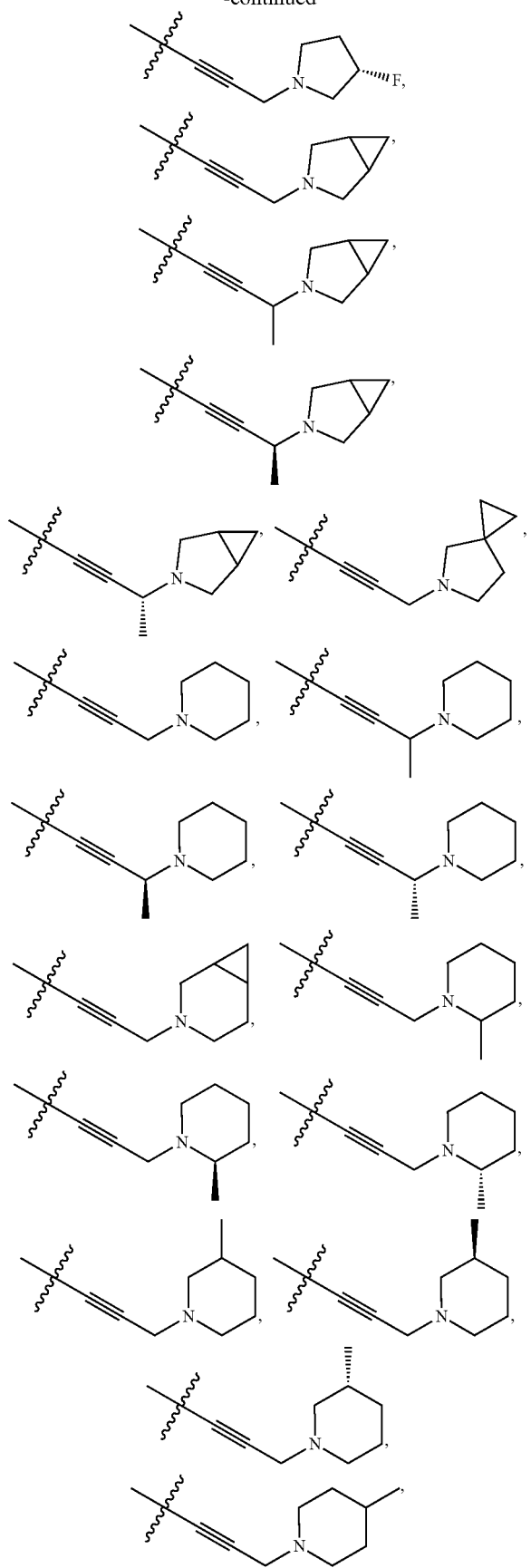

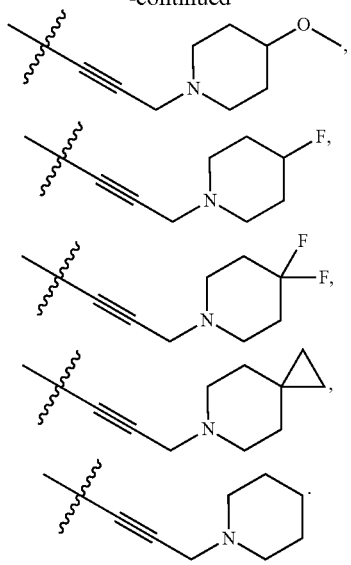

In some embodiments, at least one of $R^{4a}$ and $R^{4a'}$ is $OR^{7a}$. In some embodiments, $R^{4a}$ is $OR^{7a}$. In some embodiments, $R^{4a'}$ is $OR^{7a}$ In some embodiments, at least one of $R^{4a}$ and $R^{4a'}$ is $OR^{8a}$. In some embodiments, $R^{4a'}$ is $OR^{8a}$.

In some embodiments, at least one of $R^{4a}$ and $R^{4a'}$ is —$CH_2$-$T^{3a}$, wherein $T^{3a}$ is H, halo, cyano, $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$.

In some embodiments, $R^{4a'}$ is —$CH_2$-$T^{3a}$, wherein $T^{3a}$ is H, halo, cyano, $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$.

In some embodiments, at least one of $R^{4a}$ and $R^{4a'}$ is —$CH_2$—$OR_8$. In some embodiments, $R^{4a'}$ is —$CH_2$—$OR_8$.

In some embodiments, at least one of $R^{4a}$ and $R^{4a'}$ is —$CH_2$—$NR_7R_8$. In some embodiments, $R^{4a'}$ is —$CH_2$—$NR_7R_8$.

In some embodiments, at least one of $R^{4a}$ and $R^{4a'}$ is halo, $C_1$-$C_6$ alkyl, or $OR^{7a}$. In some embodiments, $R^{4a}$ is halo. $C_1$-$C_6$ alkyl, or $OR^{7a}$.

In some embodiments, at least one of $R^{4a}$ and $R^{4a'}$ is $C_1$-$C_6$ alkoxyl. In some embodiments, $R^{4a}$ is $C_1$-$C_6$ alkoxyl.

In some embodiments, at least one of $R^{4a}$ and $R^{4a'}$ is —$OCH_3$, —$OCH_2CH_3$, or —$OCH(CH_3)_2$. In some embodiments, $R^{4a}$ is —$OCH_3$, —$OCH_2CH_3$, or —$OCH(CH_3)_2$.

In some embodiments, at least one of $R^{4a}$ and $R^{4a'}$ is —$OCH_3$. In some embodiments, $R^{4a}$ is —$OCH_3$.

In some embodiments, $R^{7a}$ is H or $C_1$-$C_6$ alkyl optionally substituted with one or more of hydroxyl, amino or mono- or di-alkylamino.

In some embodiments, $R^{8a}$ is -$Q^{4a}$-$T^{4a}$, in which $Q^{4a}$ is a $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{4a}$ is $C_3$-$C_{12}$ cycloalkyl, $C_6$-$C_{10}$ aryl, or 4- to 12-membered heterocycloalkyl (e.g., 4- to 7-membered heterocycloalkyl) containing 1-4 heteroatoms selected from N, O and S which is optionally substituted with one or more -$Q^{5a}$-$T^{5a}$.

In some embodiments, each 4- to 12-membered heterocycloalkyl described herein include, e.g., a 4 to 7-membered monocyclic heterocycloalkyl or 7 to 12-membered bicyclic heterocycloalkyl such as azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, morpholinyl, 3-azabicyclo[3.1.0]hexan-3-yl, 3-azabicyclo[3.1.0]hexanyl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like.

In some embodiments, $R^{8a}$ is -$Q^{4a}$-$R^{S3a}$, in which $Q^{4a}$ is a bond or a $C_1$-$C_6$ alkylene linker (e.g., $C_2$-$C_6$ alkylene linker) optionally substituted with a hydroxyl and $R^{S3a}$ is 4- to 12-membered heterocycloalkyl (e.g., a 4 to 7-membered monocyclic heterocycloalkyl or 7 to 12-membered bicyclic heterocycloalkyl such as azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, morpholinyl, 3-azabicyclo[3.1.0]hexan-3-yl, 3-azabicyclo[3.1.0]hexanyl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like), which is optionally substituted with one or more -$Q^{5a}$-$T^{5a}$.

In some embodiments, $Q^{4a}$ is $C_1$-$C_6$ alkylene linker optionally substituted with a hydroxyl and $R^{S3a}$ is $C_3$-$C_6$ cycloalkyl optionally substituted with one or more -$Q^{5a}$-$T^{5a}$.

In some embodiments, $Q^{4a}$ is an optionally substituted $C_2$-$C_6$ alkenylene or $C_2$-$C_6$ alkynylene linker and $R^{S3a}$ is 4- to 12-membered heterocycloalkyl (e.g., a 4 to 7-membered monocyclic heterocycloalkyl or 7 to 12-membered bicyclic heterocycloalkyl such as azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, morpholinyl, 3-azabicyclo[3.1.0]hexan-3-yl, 3-azabicyclo[3.1.0]hexanyl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like), which is optionally substituted with one or more -$Q^{5a}$-$T^{5a}$.

In some embodiments, $Q^{4a}$ is an optionally substituted $C_2$-$C_6$ alkenylene or $C_2$-$C_6$ alkynylene linker and $R^{S3a}$ is $C_3$-$C_6$ cycloalkyl optionally substituted with one or more -$Q^{5a}$-$T^{aa}$.

In some embodiments, each $Q^{5a}$ independently is a bond or $C_1$-$C_3$ alkylene linker each optionally substituted with one or more of halo, cyano, hydroxyl, or $C_1$-$C_6$ alkoxy, and each $T^{5a}$ independently is selected from the group consisting of H, halo, cyano, $C_1$-$C_6$ alkyl, $C_3$-$C_{12}$ cycloalkyl (e.g., $C_3$-$C_8$ cycloalkyl), or 4- to 7-membered heterocycloalkyl containing 1-4 heteroatoms selected from N, O, and S.

In some embodiments, each $Q^1$ independently is a $C_2$-$C_3$ alkenylene, or $C_2$-$C_3$ alkynylene linker each optionally substituted with one or more of halo, cyano, hydroxyl, or $C_1$-$C_6$ alkoxy, and each $T^{5a}$ independently is selected from the group consisting of H, halo, cyano, $C_1$-$C_6$ alkyl, $C_3$-$C_{12}$ cycloalkyl (e.g., $C_3$-$C_8$ cycloalkyl), or 4- to 7-membered heterocycloalkyl containing 1-4 heteroatoms selected from N, O, and S.

In some embodiments, -$Q^{5a}$-$T^{5a}$ is oxo.

In some embodiments, at least one of $R^{4a}$ and $R^{4a'}$ is

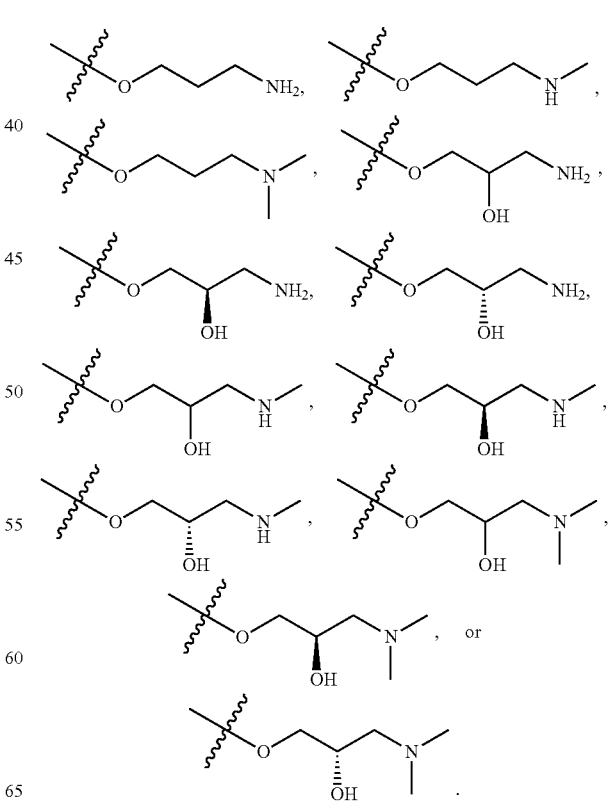

In some embodiments, $R^{4a'}$ is
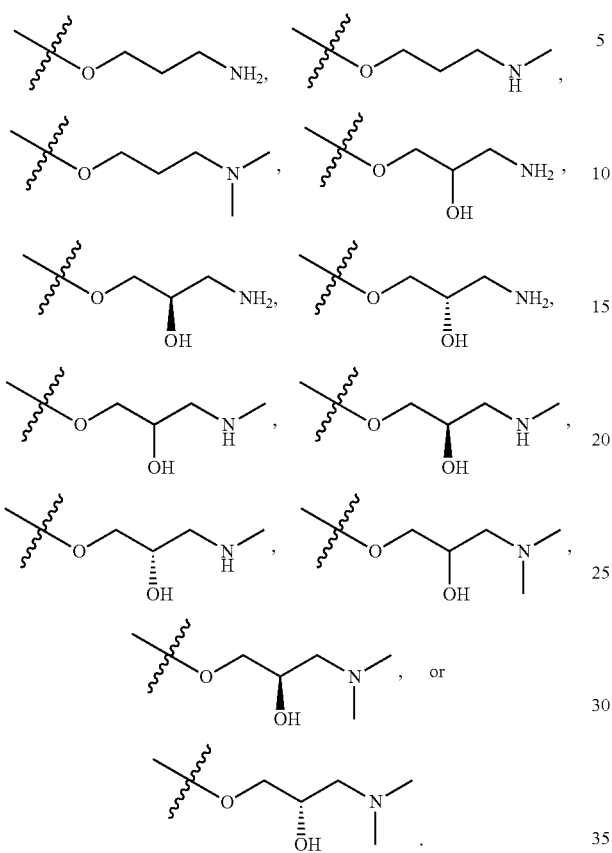
In some embodiments, at least one of $R^{4a}$ and $R^{4a'}$ is
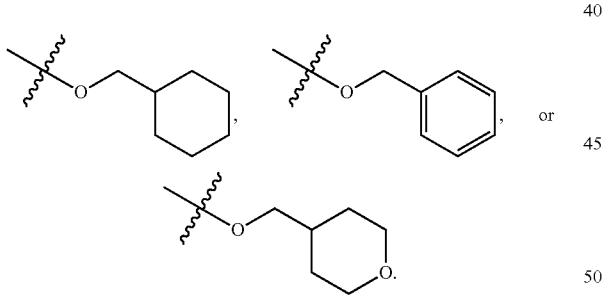
In some embodiments, $R^{4a'}$ is
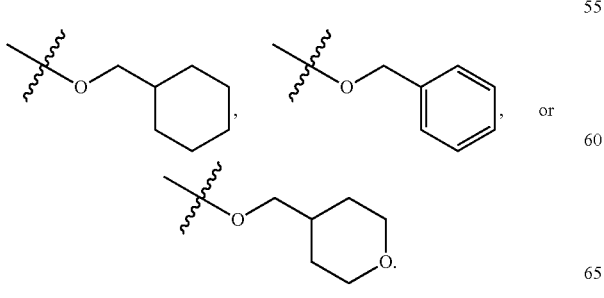
In some embodiments, at least one of $R^{4a}$ and $R^{4a'}$ is
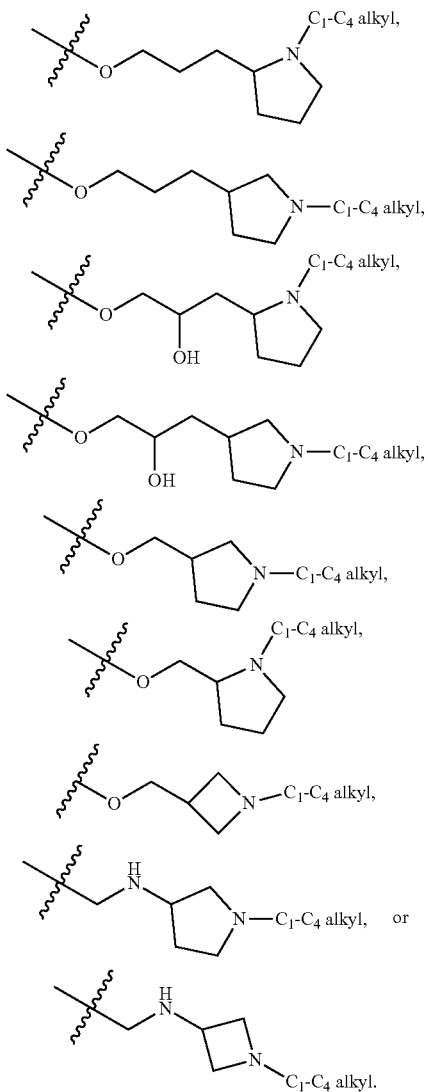
In some embodiments, $R^{4a'}$ is
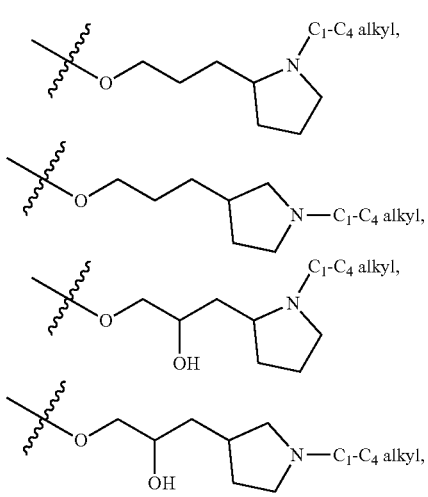

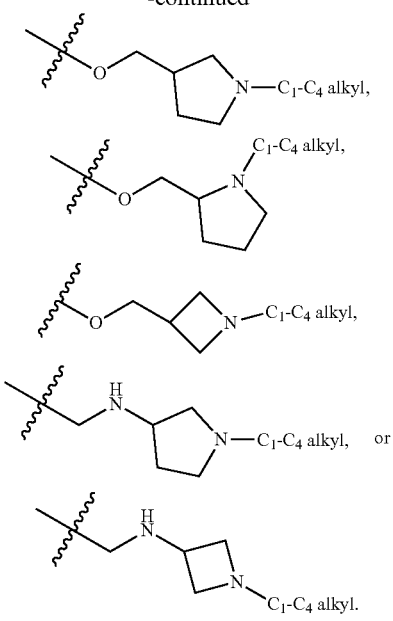
In some embodiments, at least one of $R^{4a}$ and $R^{4a'}$ is
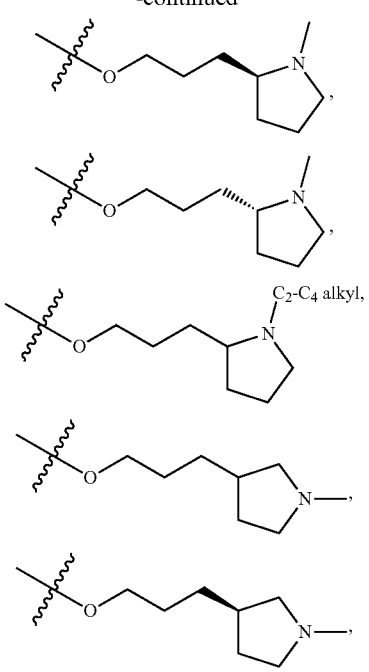
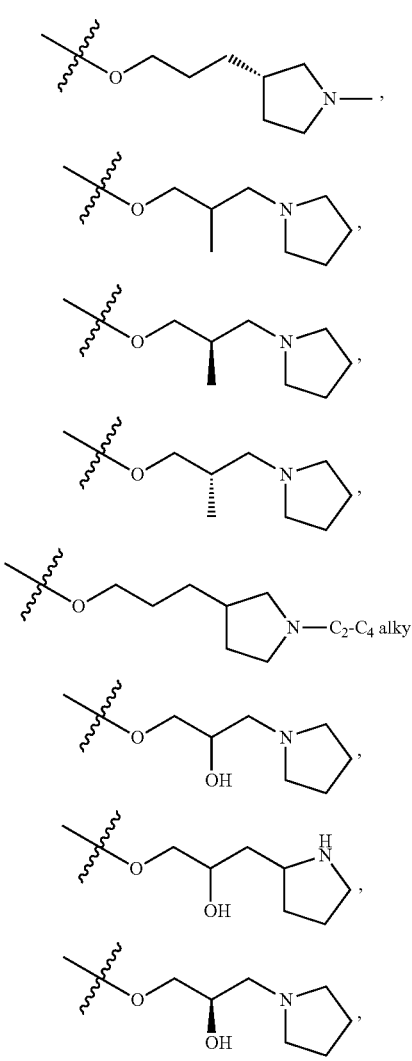

-continued
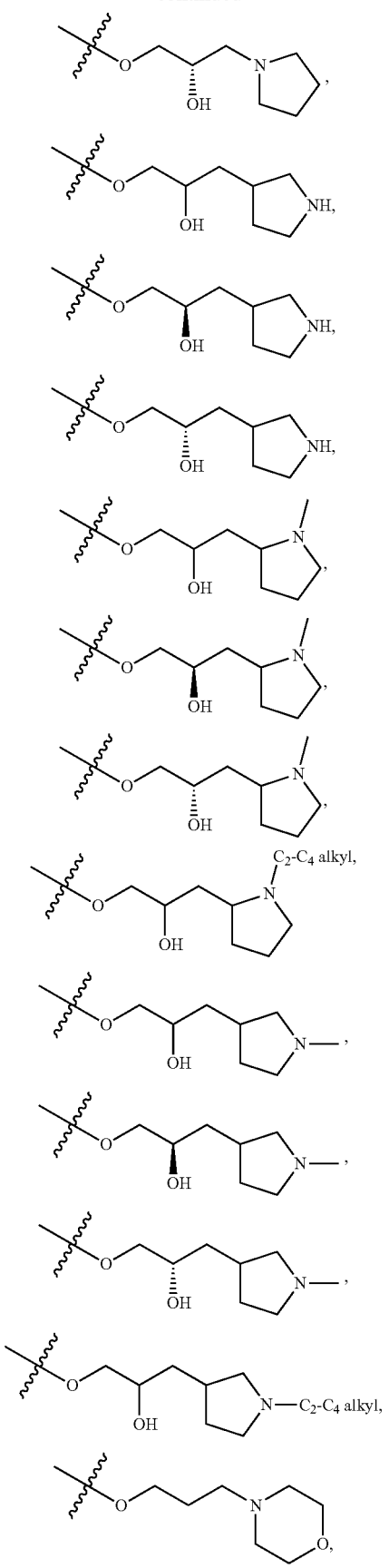
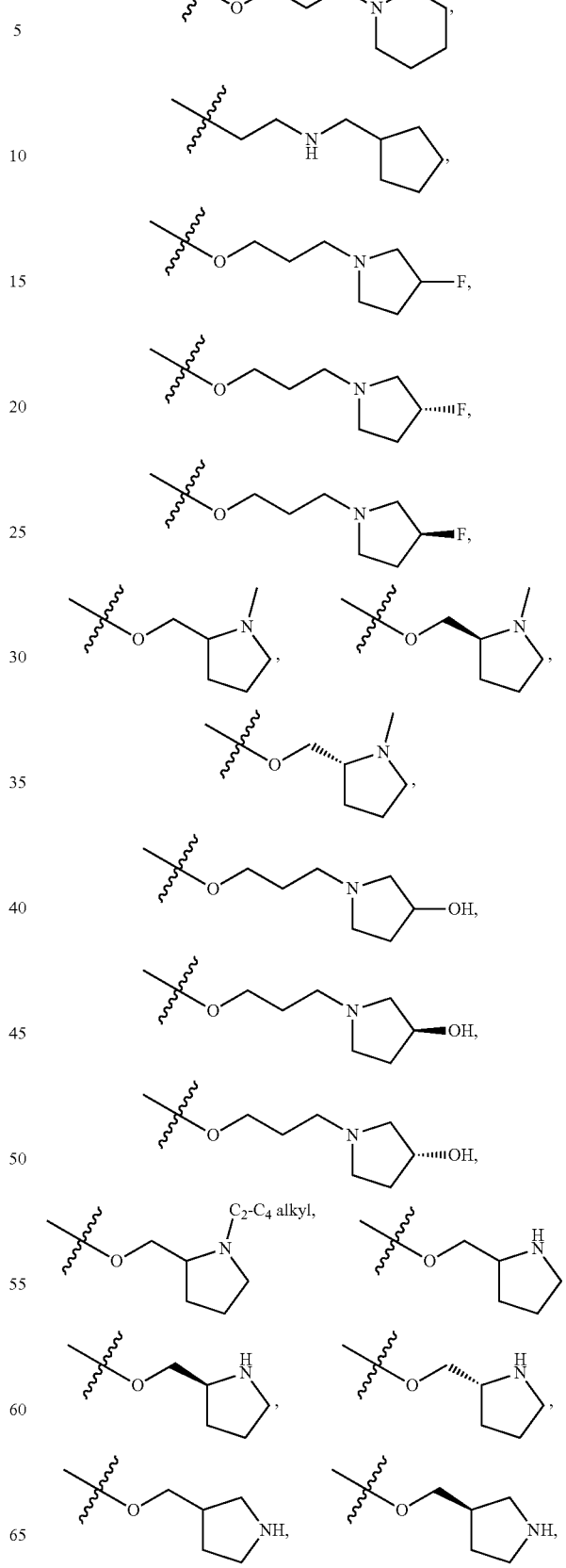

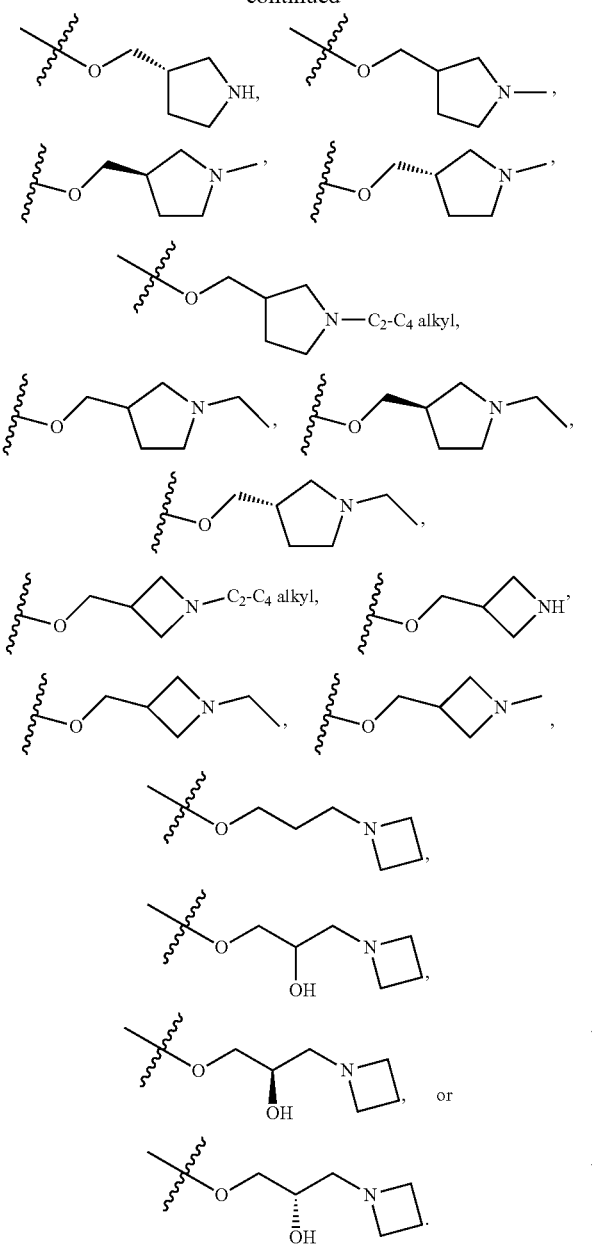
In some embodiments, $R^{4a'}$ is
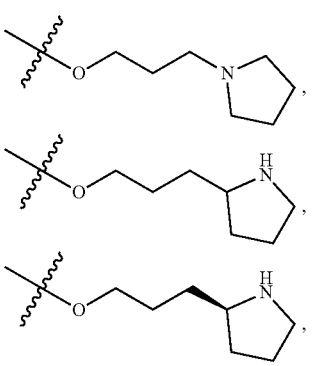
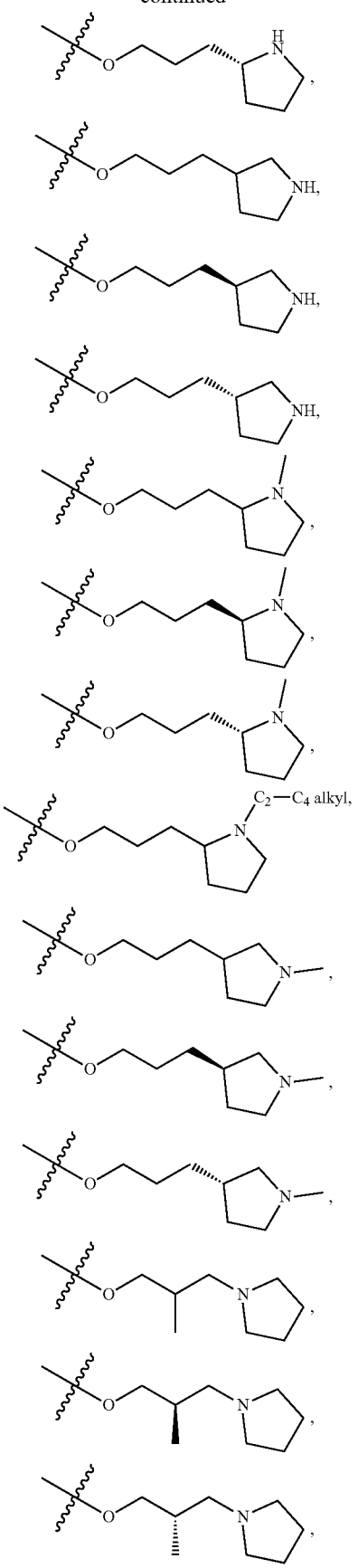

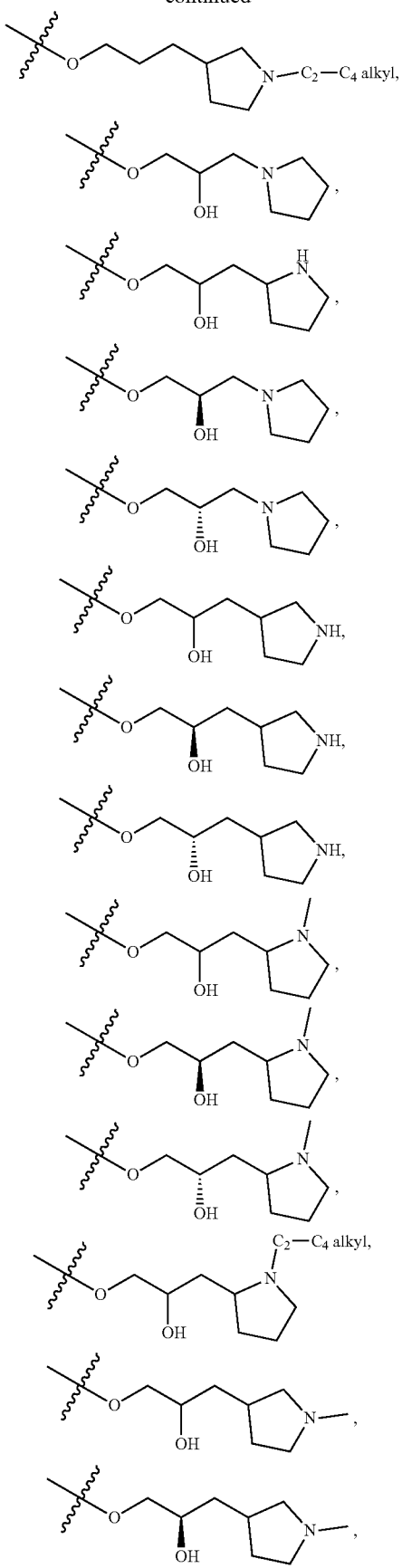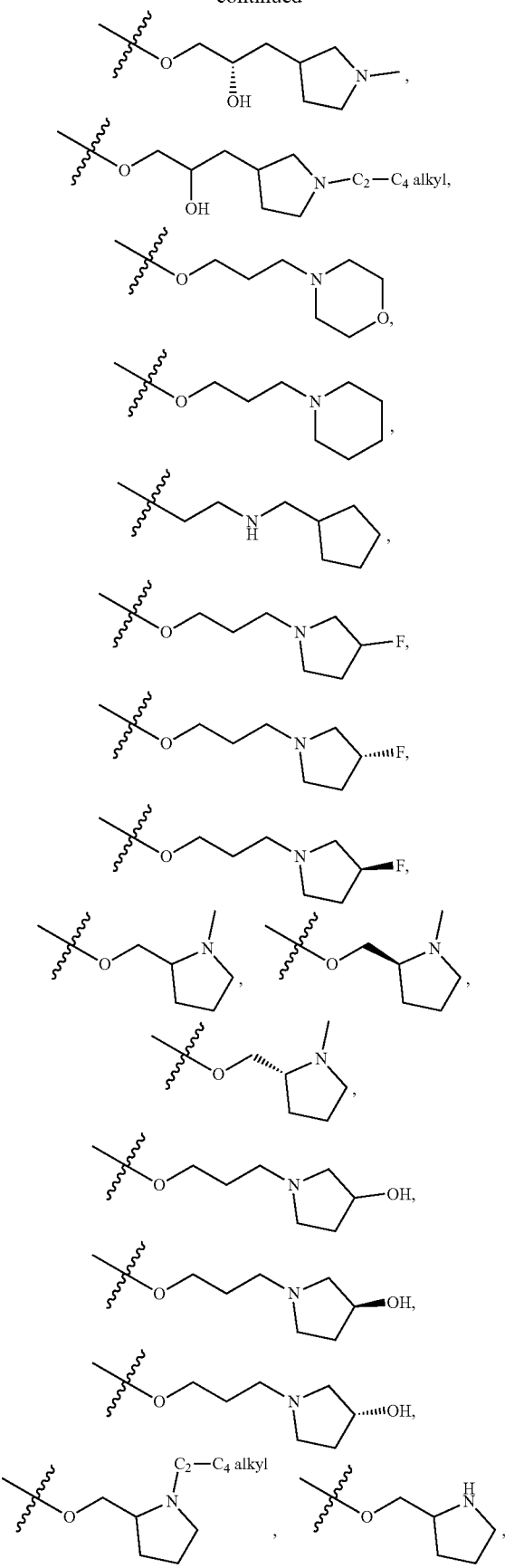

In some embodiments, wherein at least one of $R^{4a}$ and $R^{4a'}$ is a pyrrolidinylpropoxy group.

In some embodiments, $R^{4a'}$ is a pyrrolidinylpropoxy group.

In some embodiments, wherein at least one of $R^{4a}$ and $R^{4a'}$ is one of the depicted amine-linked pyrrolidine or azetidine groups.

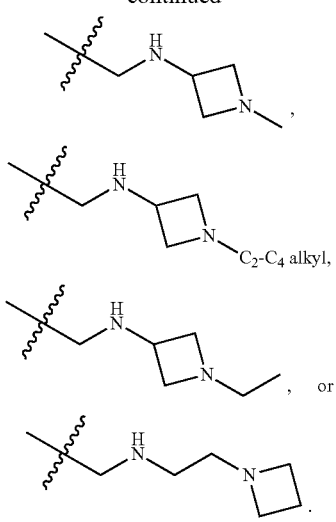

In some embodiments, R[4a'] is

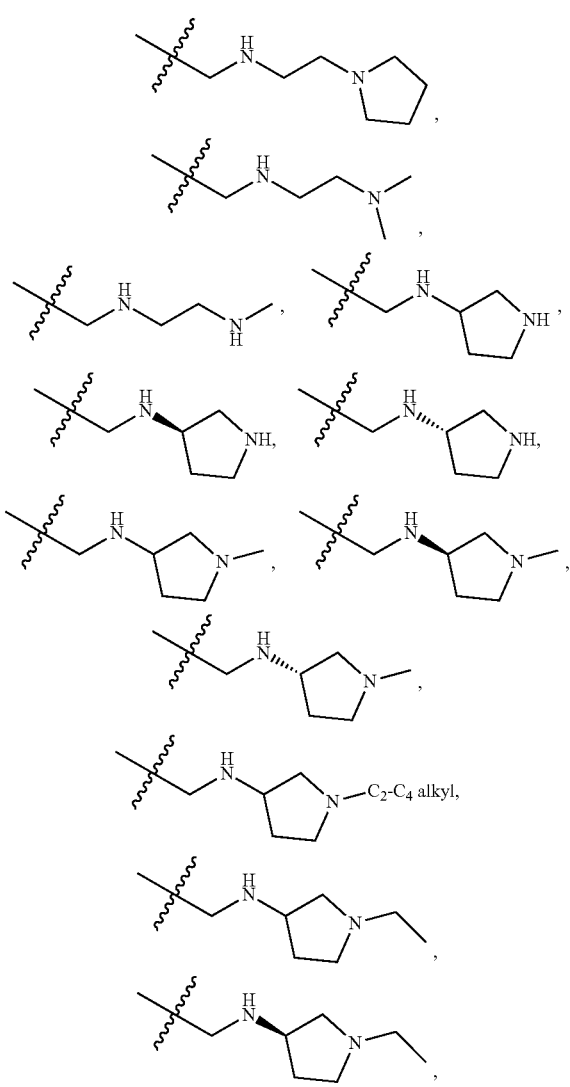

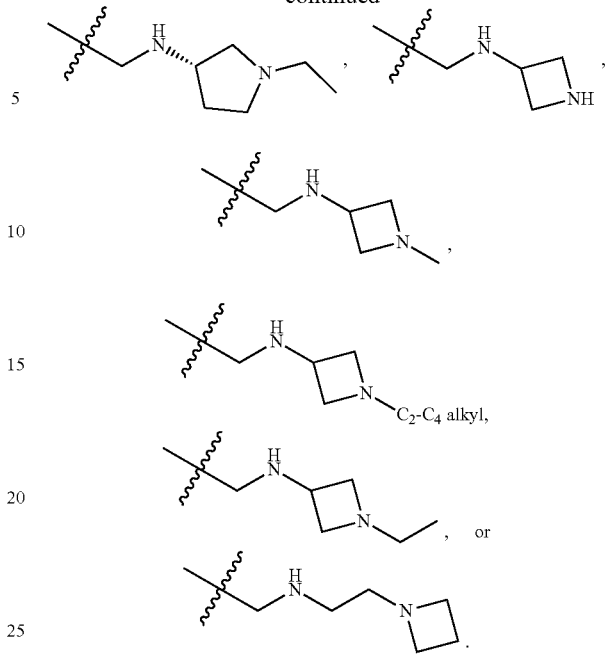

In some embodiments, one of R[4a] and R[4a'] is halo, $C_1$-$C_6$ alkyl, or OR[7a], and the other is

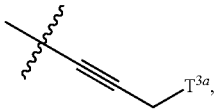

wherein T[3a] is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl.

In some embodiments, R[4a] is halo, $C_1$-$C_6$ alkyl, or OR[7a], and R[4a'] is

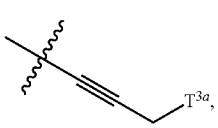

wherein T[3a] is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl.

In some embodiments, one of R[4a] and R[4a'] is $C_1$-$C_6$ alkoxyl and the other is

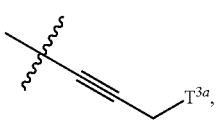

wherein T[3a] is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl.

In some embodiments, $R^{4a}$ is $C_1$-$C_6$ alkoxyl, and $R^{4a'}$ is

wherein $T^{3a}$ is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl.

In some embodiments, one of $R^{4a}$ and $R^{4a'}$ is —OCH$_3$, and the other is

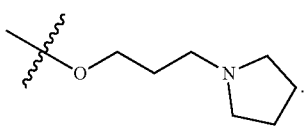 [SMILES: *OCCCN1CCCC1]

In some embodiments, $R^{4a}$ is —OCH$_3$, and $R^{4a'}$ is

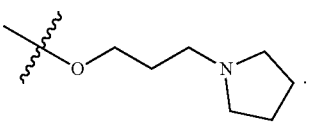 [SMILES: *OCCCN1CCCC1]

In some embodiments, and one of $R^{4a}$ and $R^{4a'}$ is —OCH$_3$, and the other is

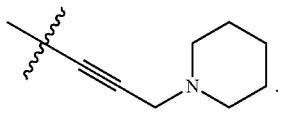

In some embodiments, $R^{4a}$ is —OCH$_3$, and $R^{4a'}$ is

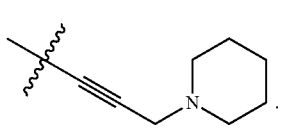 [SMILES: *C#CCN1CCCCC1]

In some embodiments, the compound is of Formula (VIIa'), (VIIb'), (VIIc'), (VIId'), (VIIe'), or (VIIf'):

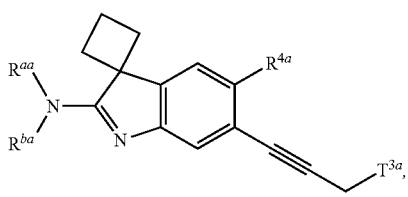
(VIIa')

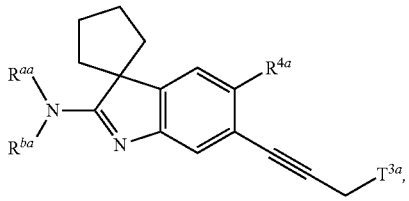
(VIIb')

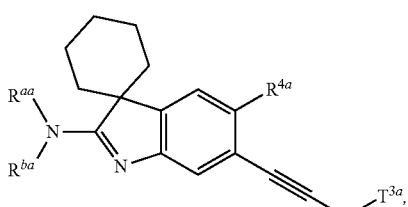
(VIIc')

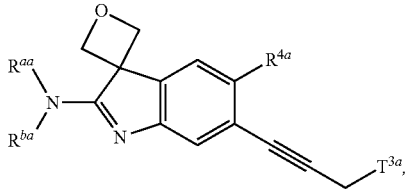
(VIId')

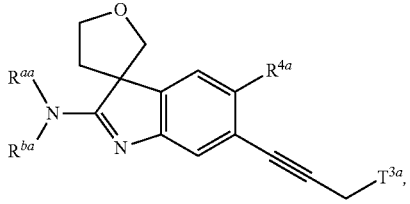
(VIIe')

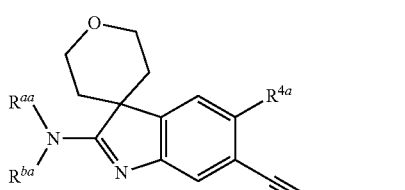
(VIIf')

a tautomer thereof, or a pharmaceutically acceptable salt of the compound or the tautomer, wherein each of $R^{aa}$ and $R^{ba}$ independently is H or $R^{S5a}$, or $R^{aa}$ and $R^{ba}$ together with the nitrogen atom to which they are attached form a 4- to 12-membered heterocycloalkyl containing 1-4 heteroatoms selected from N, O, and S; in which $R^{S5a}$ is $C_1$-$C_6$ alkyl, phenyl, 5- or 6-membered heteroaryl, or 4- to 12-membered heterocycloalkyl containing 1-4 heteroatoms selected from N, O, and S, and each of $R^{S4a}$, $R^{S5a}$, and the heterocycloalkyl formed by $R^{aa}$ and $R^{ba}$ is independently optionally substituted with one or more of halo, hydroxyl, oxo, CN, amino, mono- or di-alkylamino. $C_1$-$C_6$ alkyl, $C_1$-$C_6$ alkoxyl, $C_3$-$C_{12}$ cycloalkyl, phenyl, 5- or 6-membered heteroaryl, or 4- to 12-membered heterocycloalkyl containing 1-4 heteroatoms selected from N, O, and S, or alternatively; and $R^{4a}$ is halo, $C_1$-$C_6$ alkyl, or $OR^{7a}$;

$T^{3a}$ is H, halo, cyano, $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ Cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$;

each of $R^{5a}$, $R^{6a}$, and $R^{7a}$, independently, is H or $C_1$-$C_6$ alkyl optionally substituted with one or more of halo, cyano, hydroxyl, amino, mono- or di-alkylamino, or $C_1$-$C_6$ alkoxyl; and each $R^{8a}$ independently is -$Q^{4a}$-$T^{4a}$, in which $Q^{4a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{4a}$ is H, halo, or $R^{S3a}$, in which $R^{S3a}$ is $C_3$-$C_{12}$ cycloalkyl, $C_6$-$C_{10}$ aryl, 4- to 12-membered heterocycloalkyl containing 1-4 heteroatoms selected from N, O and S, or a 5- to 10-membered heteroaryl, and $R^{S3a}$ is optionally substituted with one or more -$Q^{5a}$-$T^{5a}$, wherein each $Q^{5a}$ independently is a bond or $C_1$-$C_3$ alkylene, $C_2$-$C_3$ alkenylene, or $C_2$-$C_3$ alkynylene linker each optionally substituted with one or more of halo, cyano, hydroxyl, or $C_1$-$C_6$ alkoxy, and each $T^{5a}$ independently is selected from the group consisting of H, halo, cyano, $C_1$-$C_6$ alkyl, $C_3$-$C_{12}$ cycloalkyl, $C_6$-$C_{10}$ aryl, 4- to 7-membered heterocycloalkyl containing 1-4 heteroatoms selected from N, O, and S, 5- to 6-membered heteroaryl, $OR^{ca}$, $C(O)R^{ca}$, $NR^{ca}R^{da}$, $C(O)NR^{ca}R^{da}$, $S(O)_2R^{ca}$, and $NR^{ca}C(O)R^{da}$, each of $R^{ca}$ and $R^{da}$ independently being H or $C_1$-$C_6$ alkyl optionally substituted with one or more halo; or -$Q^{5a}$-$T^{5a}$ is oxo.

In some embodiments, $R^{4a}$ is —$OCH_3$.

In some embodiments, $T^{3a}$ is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl.

In some embodiments, the compound is of Formula (VIIIa'), (VIIIb'), (VIIIc'), (VIIId'), (VIIIe'), or (VIIIf'):

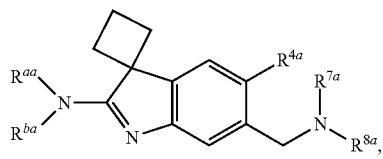
(VIIIa')

(VIIIb')

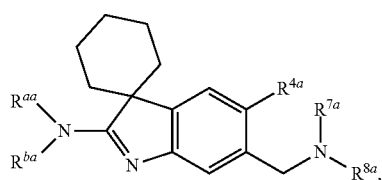
(VIIIc')

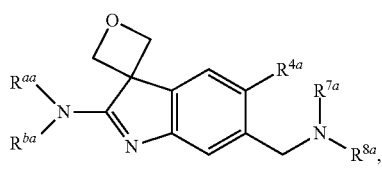
(VIIId')

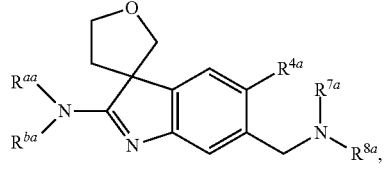
(VIIIe')

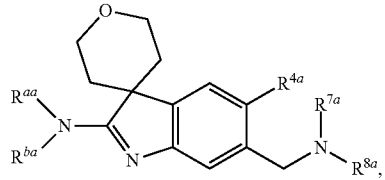
(VIIIf')

a tautomer thereof, or a pharmaceutically acceptable salt of the compound or the tautomer, wherein each of $R^{aa}$ and $R^{ba}$ independently is H or $R^{S5a}$, or $R^{aa}$ and $R^{ba}$ together with the nitrogen atom to which they are attached form a 4- to 12-membered heterocycloalkyl containing 1-4 heteroatoms selected from N, O, and S; in which $R^{S5a}$ is $C_1$-$C_6$ alkyl, phenyl, 5- or 6-membered heteroaryl, or 4- to 12-membered heterocycloalkyl containing 1-4 heteroatoms selected from N, O, and S, and each of $R^{S4a}$, $R^{S5a}$, and the heterocycloalkyl formed by $R^{aa}$ and $R^{ba}$ is independently optionally substituted with one or more of halo, hydroxyl, oxo, CN, amino, mono- or di-alkylamino, $C_1$-$C_6$ alkyl, $C_1$-$C_6$ alkoxyl, $C_3$-$C_{12}$ cycloalkyl, phenyl, 5- or 6-membered heteroaryl, or 4- to 12-membered heterocycloalkyl containing 1-4 heteroatoms selected from N, O, and S, or alternatively; and $R^{4a}$ is -$Q^{3a}$-$T^{3a}$, in which $Q^{3a}$ is a bond or $C_1$-$C_6$ alkylene. $C_2$-$C_6$ alkenylene, or $C_2$-$C_6$ alkynylene linker optionally substituted with one or more of halo, cyano, hydroxyl, amino, mono- or di-alkylamino, or $C_1$-$C_6$ alkoxyl, and $T^{3a}$ is H, halo, cyano. $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$;

each of $R^{5a}$, $R^{6a}$, and $R^{7a}$, independently, is H or $C_1$-$C_6$ alkyl optionally substituted with one or more of halo, cyano, hydroxyl, amino, mono- or di-alkylamino, or $C_1$-$C_6$ alkoxyl; and each $R^{8a}$ independently is -$Q^{4a}$-$T^{4a}$, in which $Q^{4a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{4a}$ is H, halo, or $R^{S3a}$, in which $R^{S3a}$ is $C_3$-$C_{12}$ cycloalkyl, $C_6$-$C_{10}$ aryl, 4- to 12-membered heterocycloalkyl containing 1-4 heteroatoms selected from N, O and S, or a 5- to 10-membered heteroaryl, and $R^{S3a}$ is optionally substituted with one or more -$Q^{5a}$-$T^{5a}$, wherein each $Q^{5a}$ independently is a bond or $C_1$-$C_3$ alkylene. $C_2$-$C_3$ alkenylene, or $C_2$-$C_3$ alkynylene linker each optionally substituted with one or more of halo, cyano, hydroxyl, or $C_1$-$C_6$ alkoxy, and each $T^{5a}$ independently is selected from the group consisting of H, halo, cyano, $C_1$-$C_6$ alkyl, $C_3$-$C_{12}$ cycloalkyl, $C_6$-$C_{10}$ aryl, 4- to 7-membered heterocycloalkyl containing 1-4 heteroatoms selected from N, O, and S, 5- to 6-membered heteroaryl, OR$^{ca}$, C(O)R$^{ca}$, NR$^{ca}$R$^{da}$, C(O)NR$^{ca}$R$^{da}$, S(O)$_2$R$^{ca}$, and NR$^{ca}$C(O)R$^{da}$, each of R$^{ca}$ and R$^{da}$ independently being H or C$_1$-C$_6$ alkyl optionally substituted with one or more halo; or -Q$^{5a}$-T$^{5a}$ is oxo.

In some embodiments, R$^{4a}$ is halo, C$_1$-C$_6$ alkyl, or OR$^{7a}$. In some embodiments, R$^{4a}$ is C$_1$-C$_6$ alkoxyl. In some embodiments, R$^{4'}$ is —OCH$_3$.

In some embodiments, the compound is of Formulae (IXa'), (IXb'), (IXc'), (IXd'), (IXe'), or (IXf'):

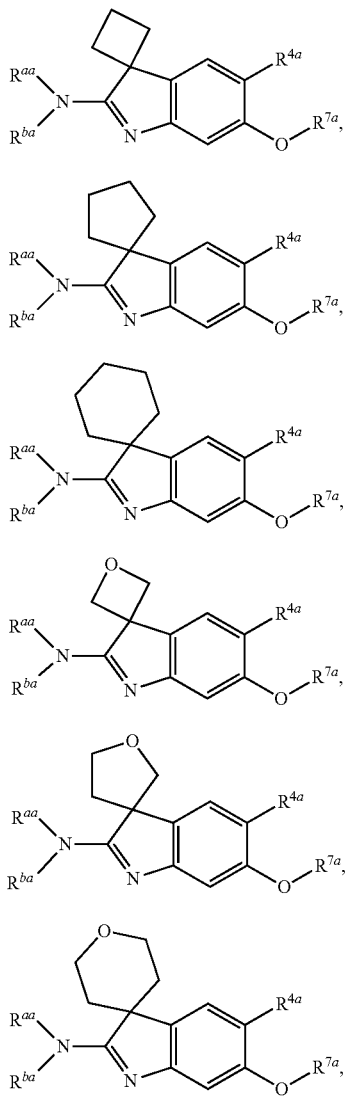

a tautomer thereof, or a pharmaceutically acceptable salt of the compound or the tautomer, wherein each of R$^{aa}$ and R$^{ba}$ independently is H or R$^{S5a}$, or R$^{aa}$ and R$^{ba}$ together with the nitrogen atom to which they are attached form a 4- to 12-membered heterocycloalkyl containing 1-4 heteroatoms selected from N, O, and S, in which R$^{S5a}$ is C$_1$-C$_6$ alkyl, phenyl, 5- or 6-membered heteroaryl, or 4- to 12-membered heterocycloalkyl containing 1-4 heteroatoms selected from N, O, and S, and each of R$^{S4a}$, R$^{S5a}$, and the heterocycloalkyl formed by R$^{aa}$ and R$^{ba}$ is independently optionally substituted with one or more of halo, hydroxyl, oxo, CN, amino, mono- or di-alkylamino, C$_1$-C$_6$ alkyl, C$_1$-C$_6$ alkoxyl, C$_3$-C$_{12}$ cycloalkyl, phenyl, 5- or 6-membered heteroaryl, or 4- to 12-membered heterocycloalkyl containing 1-4 heteroatoms selected from N, O, and S, or alternatively; and R$^{4a}$ is -Q$^{3a}$-T$^{3a}$, in which Q$^{3a}$ is a bond or C$_1$-C$_6$ alkylene, C$_2$-C$_6$ alkenylene, or C$_2$-C$_6$ alkynylene linker optionally substituted with one or more of halo, cyano, hydroxyl, amino, mono- or di-alkylamino, or C$_1$-C$_6$ alkoxyl, and T$^{3a}$ is H, halo, cyano, OR$^{7a}$, OR$^{8a}$, C(O)R$^{8a}$, NR$^{7a}$R$^{8a}$, C(O)NR$^{7a}$R$^{8a}$, NR$^{7a}$C(O)R$^{8a}$, C$_6$-C$_{10}$ aryl, 5- to 10-membered heteroaryl, C$_3$-C$_{12}$ cycloalkyl, or 4- to 12-membered heterocycloalkyl containing 1-4 heteroatoms selected from N, O, and S, and wherein the C$_6$-C$_{10}$ aryl, 5- to 10-membered heteroaryl, C$_3$-C$_{12}$ cycloalkyl or 4- to 12-membered heterocycloalkyl is optionally substituted with one or more of halo, hydroxyl, cyano, C$_1$-C$_6$ haloalkyl, —SO$_2$R$^{5a}$, C$_1$-C$_6$ alkoxyl or C$_1$-C$_6$ alkyl optionally substituted with one or more of NR$^{5a}$R$^{6a}$;

each of R$^{5a}$, R$^{6a}$, and R$^{7a}$, independently, is H or C$_1$-C$_6$ alkyl optionally substituted with one or more of halo, cyano, hydroxyl, amino, mono- or di-alkylamino, or C$_1$-C$_6$ alkoxyl; and each R$^{8a}$ independently is -Q$^{4a}$-T$^{4a}$ in which Q$^{4a}$ is a bond or C$_1$-C$_6$ alkylene, C$_2$-C$_6$ alkenylene, or C$_2$-C$_6$ alkynylene linker optionally substituted with one or more of halo, cyano, hydroxyl, or C$_1$-C$_6$ alkoxyl, and T$^{4a}$ is H, halo, or R$^{S3a}$, in which R$^{S3a}$ is C$_3$-C$_{12}$ cycloalkyl, C$_6$-C$_{10}$ aryl, 4- to 12-membered heterocycloalkyl containing 1-4 heteroatoms selected from N, O and S, or a 5- to 10-membered heteroaryl, and R$^{S3a}$ is optionally substituted with one or more -Q$^{5a}$-T$^{5a}$, wherein each Q$^1$ independently is a bond or C$_1$-C$_3$ alkylene, C$_2$-C$_3$ alkenylene, or C$_2$-C$_3$ alkynylene linker each optionally substituted with one or more of halo, cyano, hydroxyl, or C$_1$-C$_6$ alkoxy, and each T$^{5a}$ independently is selected from the group consisting of H, halo, cyano, C$_1$-C$_6$ alkyl, C$_3$-C$_{12}$ cycloalkyl, C$_6$-C$_{10}$ aryl, 4- to 7-membered heterocycloalkyl containing 1-4 heteroatoms selected from N, O, and S, 5- to 6-membered heteroaryl, OR$^{Q}$, C(O)R$^{ca}$, NR$^{ca}$R$^{da}$, C(O)NR$^{ca}$R$^{da}$, S(O)$_2$R$^{ca}$, and NR$^{ca}$C(O)R$^{da}$, each of R$^{ca}$ and R$^{da}$ independently being H or C$_1$-C$_6$ alkyl optionally substituted with one or more halo; or -Q$^{5a}$-T$^{5a}$ is oxo.

In some embodiments, R$^{4a}$ is halo, C$_1$-C$_6$ alkyl, or OR$^{7a}$. In some embodiments, R$^{4a}$ is C$_1$-C$_6$ alkoxyl. In some embodiments, R$^{4a}$ is —OCH$_3$.

In some embodiments, the compound is of Formula (Xa'), (Xb'), (Xc'), (Xd'), (Xe'), or (Xf'):

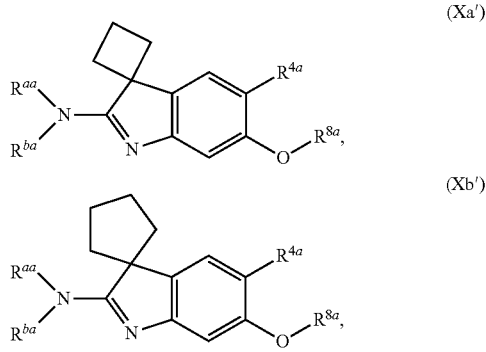

-continued

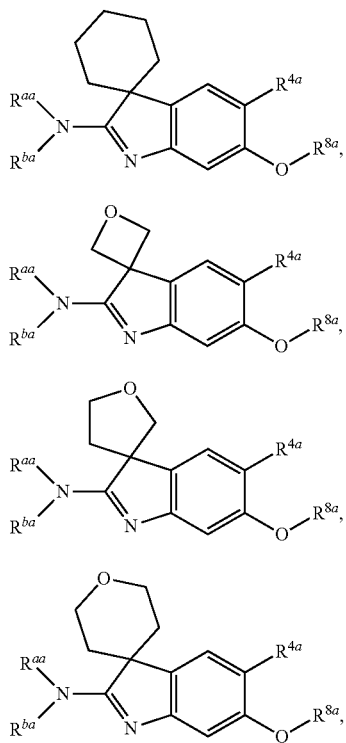

a tautomer thereof, or a pharmaceutically acceptable salt of the compound or the tautomer, wherein each of $R^{aa}$ and $R^{ba}$ independently is H or $R^{S5a}$, or $R^{aa}$ and $R^{ba}$ together with the nitrogen atom to which they are attached form a 4- to 12-membered heterocycloalkyl containing 1-4 heteroatoms selected from N, O, and S; in which $R^{S5a}$ is $C_1$-$C_6$ alkyl, phenyl, 5- or 6-membered heteroaryl, or 4- to 12-membered heterocycloalkyl containing 1-4 heteroatoms selected from N, O, and S, and each of $R^{S4a}$, $R^{S5a}$, and the heterocycloalkyl formed by $R^{aa}$ and $R^{ba}$ is independently optionally substituted with one or more of halo, hydroxyl, oxo, CN, amino, mono- or di-alkylamino, $C_1$-$C_6$ alkyl, $C_1$-$C_6$ alkoxyl, $C_3$-$C_{12}$ cycloalkyl, phenyl, 5- or 6-membered heteroaryl, or 4- to 12-membered heterocycloalkyl containing 1-4 heteroatoms selected from N, O, and S, or alternatively, and $R^{4a}$ is -$Q^{3a}$-$T^{3a}$, in which $Q^{3a}$ is a bond or $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, or $C_1$-$C_6$ alkoxyl, and $T^{3a}$ is H, halo, cyano, $OR^{7a}$, $OR^{8a}$, $C(O)R^{8a}$, $NR^{7a}R^{8a}$, $C(O)NR^{7a}R^{8a}$, $NR^{7a}C(O)R^{8a}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{5a}$, $C_1$-$C_6$ alkoxyl or $C_1$-$C_6$ alkyl optionally substituted with one or more of $NR^{5a}R^{6a}$;

each of $R^{5a}$, $R^{6a}$, and $R^{7a}$, independently, is H or $C_1$-$C_6$ alkyl optionally substituted with one or more of halo, cyano, hydroxyl, amino, mono- or di-alkylamino, or $C_1$-$C_6$ alkoxyl; and each $R^{8a}$ independently is -$Q^{4a}$-$T^{4a}$, in which $Q^{4a}$ is a bond or $C_1$-$C_6$ alkylene, $C_2$-$C_6$ alkenylene, or $C_2$-$C_6$ alkynylene linker optionally substituted with one or more of halo, cyano, hydroxyl, or $C_1$-$C_6$ alkoxyl, and $T^{4a}$ is H, halo, or $R^{S3a}$, in which $R^{S3a}$ is $C_3$-$C_{12}$ cycloalkyl, $C_6$-$C_{10}$ aryl, 4- to 12-membered heterocycloalkyl containing 1-4 heteroatoms selected from N, O and S, or a 5- to 10-membered heteroaryl, and $R^{S3a}$ is optionally substituted with one or more -$Q^{5a}$-$T^{5a}$, wherein each $Q^{5a}$ independently is a bond or $C_1$-$C_3$ alkylene. $C_2$-$C_3$ alkenylene, or $C_2$-$C_3$ alkynylene linker each optionally substituted with one or more of halo, cyano, hydroxyl, or $C_1$-$C_6$ alkoxy, and each $T^{5a}$ independently is selected from the group consisting of H, halo, cyano, $C_1$-$C_6$ alkyl, $C_3$-$C_{12}$ cycloalkyl, $C_6$-$C_0$ aryl, 4- to 7-membered heterocycloalkyl containing 1-4 heteroatoms selected from N, O, and S, 5- to 6-membered heteroaryl, $OR^{ca}$, $C(O)R^{ca}$, $NR^{ca}R^{da}$, $C(O)NR^{ca}R^{6a}$, $S(O)_2R^a$, and $NR^aC(O)R^{da}$, each of $R^{ca}$ and $R^{da}$ independently being H or $C_1$-$C_6$ alkyl optionally substituted with one or more halo; or -$Q^{5a}$-$T^{5a}$ is oxo.

In some embodiments, $R^{4a}$ is halo, $C_1$-$C_6$ alkyl, or $OR^{7a}$. In some embodiments, $R^4$ is $C_1$-$C_6$ alkoxyl. In some embodiments, $R^{4a}$ is —$OCH_3$.

In certain embodiments, for the methods disclosed herein, the EHMT2 inhibitor is a compound of Formula (I″), (II″), or (III″):

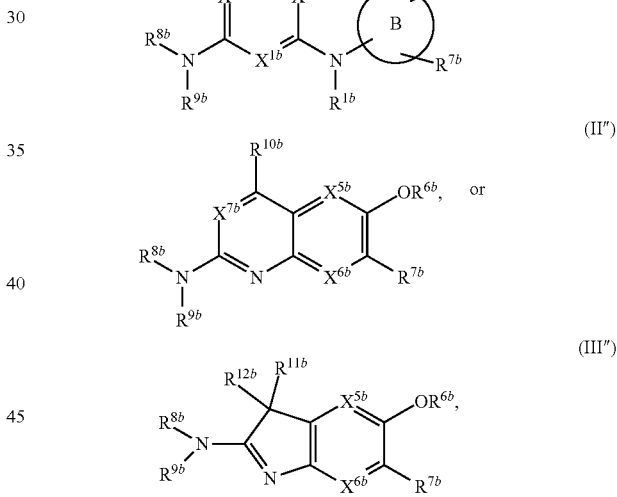

or a tautomer thereof, or a pharmaceutically acceptable salt of the compound or the tautomer, wherein $X^{1b}$ is N or $CR^{2b}$;
$X^{2b}$ is N or $CR^{3b}$;
$X^{3b}$ is N or $CR^{4b}$;
$X^{4b}$ is N or $CR^{5b}$;
each of $X^{5b}$, $X^{6b}$ and $X^{7b}$ is independently N or CH;
B is $C_6$-$C_{10}$ aryl or 5- to 10-membered heteroaryl;
$R^{1b}$ is H or $C_1$-$C_4$ alkyl;
each of $R^{2b}$, $R^{3b}$, $R^{4b}$, and $R^{5b}$, independently is selected from the group consisting of H, halo, cyano, $C_1$-$C_6$ alkoxyl, $C_6$-$C_{10}$ aryl, OH, $NR^{ab}R^{bb}$, $C(O)NR^{ab}R^{bb}$, $NR^{ab}C(O)R^{bb}$, $C(O)OR^{ab}$, $OC(O)R^{ab}$, $OC(O)NR^{ab}R^{bb}$, $NR^{ab}C(O)OR^{bb}$, $C_3$-$C_8$ cycloalkyl, 4- to 7-membered heterocycloalkyl, 5- to 6-membered heteroaryl, $C_1$-$C_6$ alkyl, $C_2$-$C_6$ alkenyl, and $C_2$-$C_6$ alkynyl, wherein the $C_6$-$C_{10}$ aryl, $C_3$-$C_8$ cycloalkyl, 4- to 7-membered heterocycloalkyl, 5- to 6-membered heteroaryl, $C_1$-$C_6$ alkoxyl, $C_1$-$C_6$ alkyl, $C_2$-$C_6$ alkenyl, and $C_2$-$C_6$ alkynyl, are each optionally substituted with one or more of halo, $OR^{ab}$, or $NR^{ab}R^{bb}$, in which each of $R^{ab}$ and $R^{bb}$ independently is H or $C_1$-$C_6$ alkyl;

$R^{6b}$ is -$Q^{1b}$-$T^{1b}$, in which $Q^{1b}$ is a bond, or $C_1$-$C_6$ alkylene, $C_2$-$C_6$ alkenylene, or $C_2$-$C_6$ alkynylene linker each optionally substituted with one or more of halo, cyano, hydroxyl, oxo, or $C_1$-$C_6$ alkoxyl, and $T^{1b}$ is H, halo, cyano, or $R^{S1b}$, in which $R^{S1b}$ is $C_3$-$C_8$ cycloalkyl, phenyl, 4- to 12-membered heterocycloalkyl containing 1-4 heteroatoms selected from N, O, and S, or a 5- or 6-membered heteroaryl and $R^{S1b}$ is optionally substituted with one or more of halo, $C_1$-$C_6$ alkyl, $C_2$-$C_6$ alkenyl, $C_2$-$C_6$ alkynyl, hydroxyl, oxo, —C(O)$R^{cb}$, —C(O)O$R^{cb}$, —$SO_2R^{cb}$, —$SO_2$N($R^{cb}$)$_2$, —$NR^{cb}$C(O)$R^{db}$, —C(O)$NR^{cb}R^{db}$, —$NR^{cb}$C(O)O$R^{db}$, —OC(O)$NR^{cb}R^{db}$, $NR^{cb}R^{db}$, or $C_1$-$C_6$ alkoxyl, in which each of $R^{cb}$ and $R^{db}$ independently is H or $C_1$-$C_6$ alkyl;

$R^{7b}$ is -$Q^{2b}$-$T^{2b}$, in which $Q^{2b}$ is a bond, C(O)$NR^{cb}$, or $NR^{eb}$C(O), $R^{eb}$ being H or $C_1$-$C_6$ alkyl and $T^{2b}$ is 5- to 10-membered heteroaryl or 4- to 12-membered heterocycloalkyl, and wherein the 5- to 10-membered heteroaryl or 4- to 12-membered heterocycloalkyl is optionally substituted with one or more -$Q^{3b}$-$T^{3b}$, wherein each $Q^{3b}$ independently is a bond or $C_1$-$C_3$ alkylene linker each optionally substituted with one or more of halo, cyano, hydroxyl, or $C_1$-$C_6$ alkoxy, and each $T^{3b}$ independently is selected from the group consisting of H, halo, cyano, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, $OR^{fb}$, C(O)$R^{fb}$, C(O)O$R^{fb}$, OC(O)$R^{fb}$, S(O)$_2R^{fb}$, $NR^{fb}R^{gb}$, OC(O)$NR^{fb}R^{gb}$, $NR^{fb}$C(O)O$R^{gb}$, C(O)$NR^{fb}R^{gb}$, and $NR^{fb}$C(O)$R^{gb}$, each of $R^{fb}$ and $R^{gb}$ independently being H or $C_1$-$C_6$ alkyl, in which the $C_3$-$C_8$ cycloalkyl, $C_6$-$C_{10}$ aryl, 4- to 7-membered heterocycloalkyl or 5- to 6-membered heteroaryl is optionally substituted with one or more halo, cyano, hydroxyl, $C_1$-$C_6$ alkyl, $C_2$-$C_6$ alkenyl, $C_2$-$C_6$ alkynyl, or $C_1$-$C_6$ alkoxy; or -$Q^{3b}$-$T^{3b}$ is oxo;

$R^{8b}$ is H or $C_1$-$C_6$ alkyl;

$R^{9b}$ is -$Q^{4b}$-$T^{4b}$, in which $Q^{4b}$ is a bond or $C_1$-$C_6$ alkylene, $C_2$-$C_6$ alkenylene, or $C_2$-$C_6$ alkynylene linker each optionally substituted with one or more of halo, cyano, hydroxyl, or $C_1$-$C_6$ alkoxyl, and $T^{4b}$ is H, halo, $OR^{hb}$, $NR^{hb}R^{ib}$, $NR^{hb}$C(O)$R^{ib}$, C(O)$NR^{hb}R^{ib}$, C(O)$R^{hb}$, C(O)O$R^{hb}$, $NR^{hb}$C(O)O$R^{ib}$, OC(O)$NR^{hb}R^{ib}$, S(O)$_2R^{hb}$, S(O)$_2NR^{hb}R^{ib}$, or $R^{S2b}$, in which each of $R^{hb}$ and $R^{ib}$ independently is H or $C_1$-$C_6$ alkyl, and $R^{S2b}$ is $C_3$-$C_8$ cycloalkyl, $C_6$-$C_{10}$ aryl, 4- to 12-membered heterocycloalkyl containing 1-4 heteroatoms selected from N, O, and S, or a 5- to 10-membered heteroaryl, and $R^{S2b}$ is optionally substituted with one or more -$Q^{5b}$-$T^{5b}$, wherein each $Q^{5b}$ independently is a bond or $C_1$-$C_3$ alkylene linker each optionally substituted with one or more of halo, cyano, hydroxyl, or $C_1$-$C_6$ alkoxy, and each $T^{5b}$ independently is selected from the group consisting of H, halo, cyano, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, $OR^{jb}$, C(O)$R^{jb}$, C(O)O$R^{jb}$, OC(O)$R^{jb}$, S(O)$_2R^{jb}$, $NR^{jb}R^{kb}$, OC(O)$NR^{jb}R^{kb}$, $NR^{jb}$C(O)O$R^{kb}$, C(O)$NR^{jb}R^{kb}$, and $NR^{jb}$C(O)$R^{kb}$, each of $R^{jb}$ and $R^{kb}$ independently being H or $C_1$-$C_6$ alkyl; or -$Q^{5b}$-$T^{5b}$ is oxo;

$R^{10b}$ is 4- to 12-membered heterocycloalkyl containing 1-4 heteroatoms selected from N, O, and S, which is optionally substituted with one or more halo, cyano, hydroxyl, oxo, amino, mono- or di-alkylamino, $C_1$-$C_6$ alkyl, $C_2$-$C_6$ alkenyl, $C_2$-$C_6$ alkynyl, or $C_1$-$C_6$ alkoxy; and $R^{11b}$ and $R^{12b}$ together with the carbon atom to which they are attached form a $C_3$-$C_{12}$ cycloalkyl or 4- to 12-membered heterocycloalkyl containing 1-4 heteroatoms selected from N, O, and S, wherein the $C_3$-$C_{12}$ cycloalkyl or 4- to 12-membered heterocycloalkyl is optionally substituted with one or more of halo, $C_1$-$C_6$ alkyl, $C_2$-$C_6$ alkenyl, $C_2$-$C_6$ alkynyl, hydroxyl, oxo, amino, mono- or di-alkylamino, or $C_1$-$C_6$ alkoxyl.

The compounds of Formulae (I")-(III") may have one or more of the following features when applicable.

In some embodiments, the EHMT2 inhibitor is a compound is of Formula (I").

In some embodiments, at least one of $X^{1b}$, $X^{2b}$, $X^{3b}$ and $X^{4b}$ is N.

In some embodiments, $X^{4b}$ and $X^{3b}$ are N.

In some embodiments, $X^{1b}$ and $X^{3b}$ are N, $X^{2b}$ is $CR^{3b}$ and $X^{4b}$ is $CR^{5b}$.

In some embodiments,

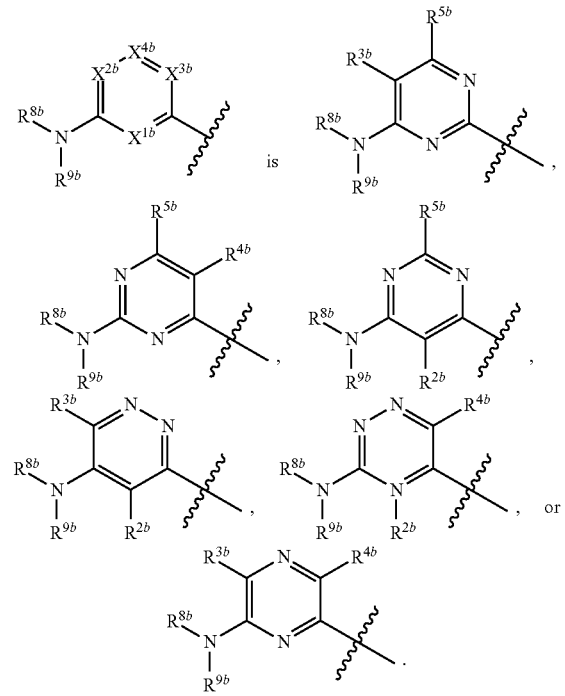

In some embodiments,

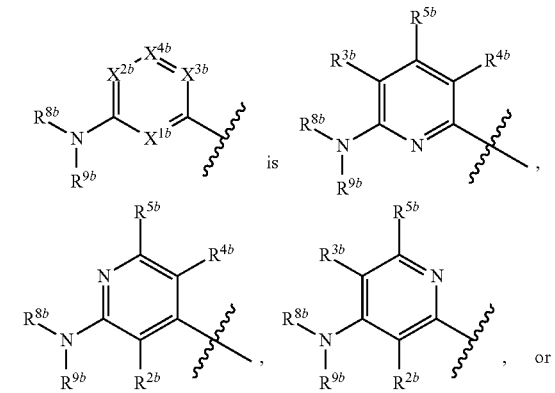

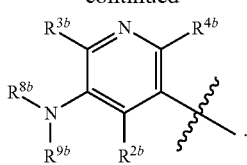

In some embodiments, ring B is phenyl or 6-membered heteroaryl.

In some embodiments,

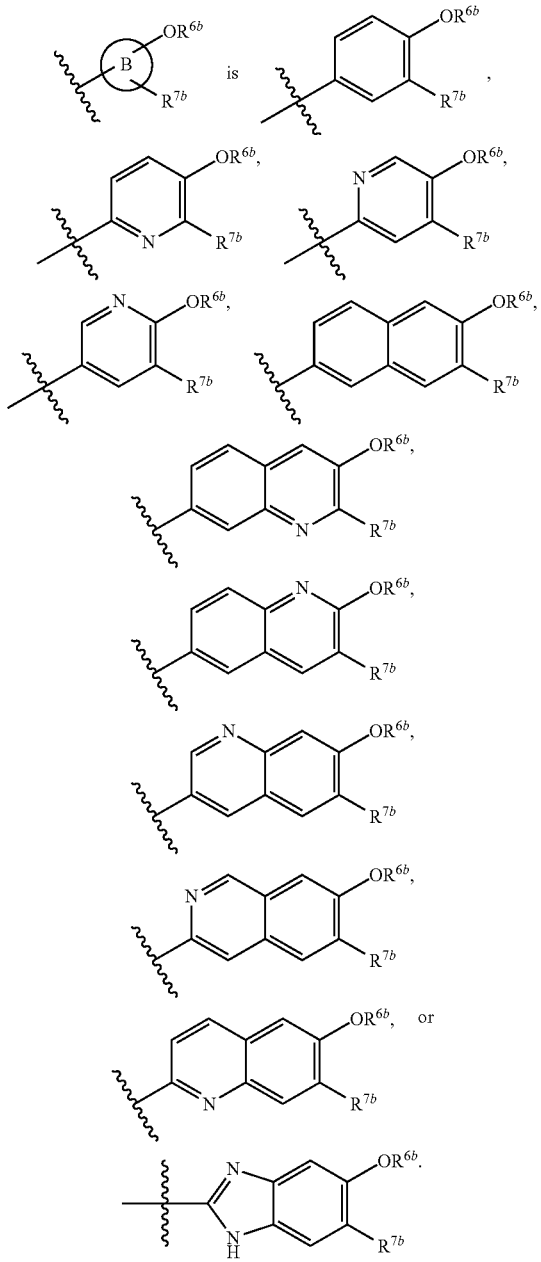

In some embodiments, ring B is phenyl or pyridyl.

In some embodiments, the EHMT2 inhibitor is a compound of Formula (Ia″), (Ib″), (Ic″), or (Id″):

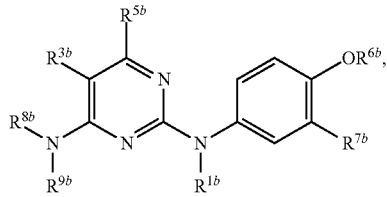

(Ia″)

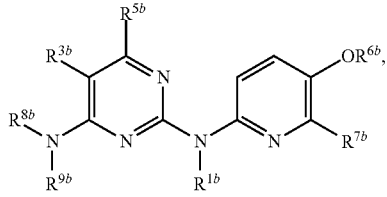

(Ib″)

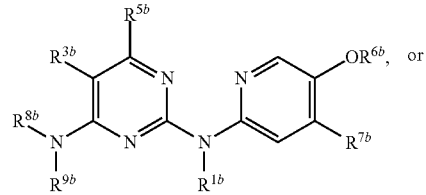

(Ic″)

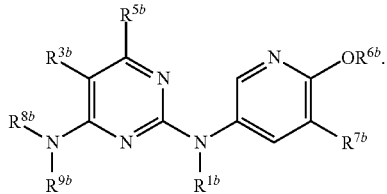

(Id″)

In some embodiments, at most one of $R^{3b}$ and $R^{5b}$ is not H.

In some embodiments, at least one of $R^{3b}$ and $R^{5b}$ is not H.

In some embodiments, $R^{3b}$ is H or halo.

In some embodiments, the EHMT2 inhibitor is a compound of Formula (Ie″), (If″), (Ig″), or (Ih″):

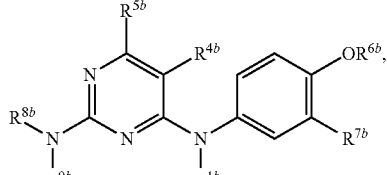

(Ie″)

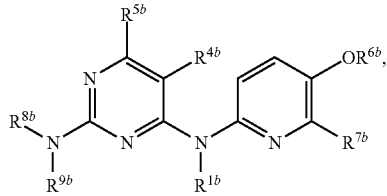

(If″)

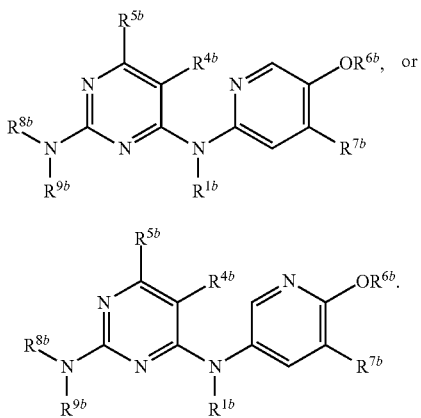

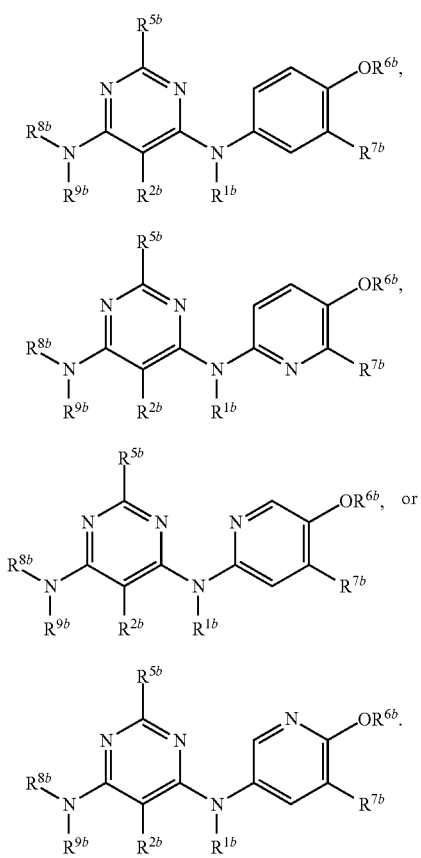

In some embodiments, at most one of $R^{2b}$ and $R^{5b}$ is not H.

In some embodiments, at least one of $R^{2b}$ and $R^{5b}$ is not H.

In some embodiments, $R^{2b}$ is H, $C_1$-$C_6$ alkyl, or halo.

In some embodiments, $R^{5b}$ is $C_1$-$C_6$ alkyl.

In some embodiments, the EHMT2 inhibitor is a compound is of Formula (II″).

In some embodiments, each of $X^{5b}$, $X^{6b}$ and $X^{7b}$ is CH.

In some embodiments, at least one of $X^{5b}$, $X^{6b}$ and $X^{7b}$ is N.

In some embodiments, at most one of $X^{5b}$, $X^{6b}$ and $X^{7b}$ is N.

In some embodiments, $R^{10b}$ is optionally substituted 4- to 7-membered heterocycloalkyl containing 1-4 heteroatoms selected from N, O, and S.

In some embodiments, $R^{10b}$ is connected to the bicyclic group of Formula (II″) via a carbon-carbon bond.

In some embodiments, $R^{10b}$ is connected to the bicyclic group of Formula (II″) via a carbon-nitrogen bond.

In some embodiments, the compound is of Formula (III″).

In some embodiments, $R^{11b}$ and $R^{12b}$ together with the carbon atom to which they are attached form a 4- to 7-membered heterocycloalkyl containing 1-4 heteroatoms selected from N, O, and S, wherein the 4- to 7-membered heterocycloalkyl is optionally substituted with one or more of halo, $C_1$-$C_6$ alkyl, hydroxyl, oxo, amino, mono- or di-alkylamino, or $C_1$-$C_6$ alkoxyl.

In some embodiments, $R^{11b}$ and $R^{12b}$ together with the carbon atom to which they are attached form a $C_4$-$C_8$ cycloalkyl which is optionally substituted with one or more of halo, $C_1$-$C_6$ alkyl, hydroxyl, oxo, amino, mono- or di-alkylamino, or $C_1$-$C_6$ alkoxyl.

In some embodiments, each of $X^{5b}$ and $X^{6b}$ is CH.

In some embodiments, each of $X^{5b}$ and $X^{6b}$ is N.

In some embodiments, one of $X^{5b}$ and $X^{6b}$ is CH and the other is CH.

In some embodiments, $R^{6b}$ is -$Q^{1b}$-$T^{1b}$, in which $Q^{1b}$ is a bond or $C_1$-$C_6$ alkylene linker optionally substituted with one or more of halo, and $T^b$ is H, halo, cyano, or $R^{S1b}$, in which $R^{S1b}$ is $C_3$-$C_8$ cycloalkyl, phenyl, 4- to 12-membered heterocycloalkyl containing 1-4 heteroatoms selected from N, O, and S, or a 5- or 6-membered heteroaryl and $R^{S1b}$ is optionally substituted with one or more of halo, $C_1$-$C_6$ alkyl, hydroxyl, oxo, $NR^{cb}R^{db}$, or $C_1$-$C_6$ alkoxyl.

In some embodiments, $R^{6b}$ is $C_1$-$C_6$ alkyl optionally substituted with one or more of halo, cyano, hydroxyl, or $C_1$-$C_6$ alkoxyl.

In some embodiments, $R^{6b}$ is unsubstituted $C_1$-$C_6$ alkyl.

In some embodiments, $R^{7b}$ is -$Q^{2b}$-$T^{2b}$, in which $Q^{2b}$ is a bond or $C(O)NR^{eb}$, and $T^{2b}$ is 5- to 10-membered heteroaryl or 4- to 12-membered heterocycloalkyl, wherein the 5- to 10-membered heteroaryl or 4- to 12-membered heterocycloalkyl is optionally substituted with one or more -$Q^{3b}$-$T^{3b}$.

In some embodiments, $Q^{2b}$ is a bond.

In some embodiments, $T^{2b}$ is 4- to 12-membered heterocycloalkyl containing 1-4 heteroatoms selected from N, O, and S, which is optionally substituted with one or more -$Q^{3b}$-$T^{3b}$.

In some embodiments, $T^{2b}$ is 8- to 12-membered bicyclic heterocycloalkyl that comprises a 5- or 6-membered aryl or heteroaryl ring fused with a non-aromatic ring.

In some embodiments, $T^{2b}$ is 8- to 12-membered bicyclic heterocycloalkyl that comprises a 5- or 6-membered aryl or heteroaryl ring fused with a non-aromatic ring, in which the 5- or 6-membered aryl or heteroaryl ring is connected to $Q^{2b}$.

In some embodiments, $T^{2b}$ is 5- to 10-membered heteroaryl.

In some embodiments, $T^{2b}$ is selected from

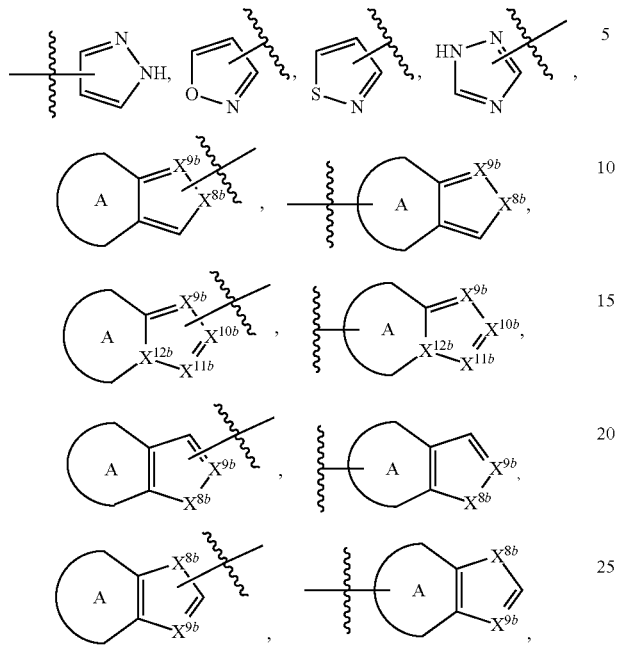

and tautomers thereof, each of which is optionally substituted with one or more $-Q^{3b}-T^{3b}$, wherein $X^{8b}$ is NH, O, or S, each of $X^{9b}$, $X^{10b}$, $X^{11b}$, and $X^{12b}$ is independently CH or N, and at least one of $X^{9b}$, $X^{10b}$, $X^{11b}$, and $X^{12b}$ is N, and ring A is a $C_5$-$C_8$ cycloalkyl, phenyl, 6-membered heteroaryl, or 4- to 8-membered heterocycloalkyl containing 1-4 heteroatoms selected from N, O, and S.

In some embodiments, $T^{2b}$ is selected from

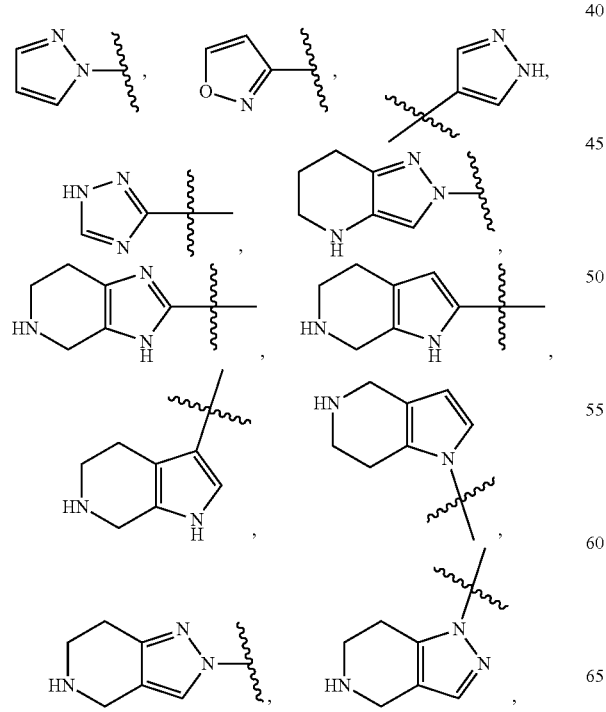

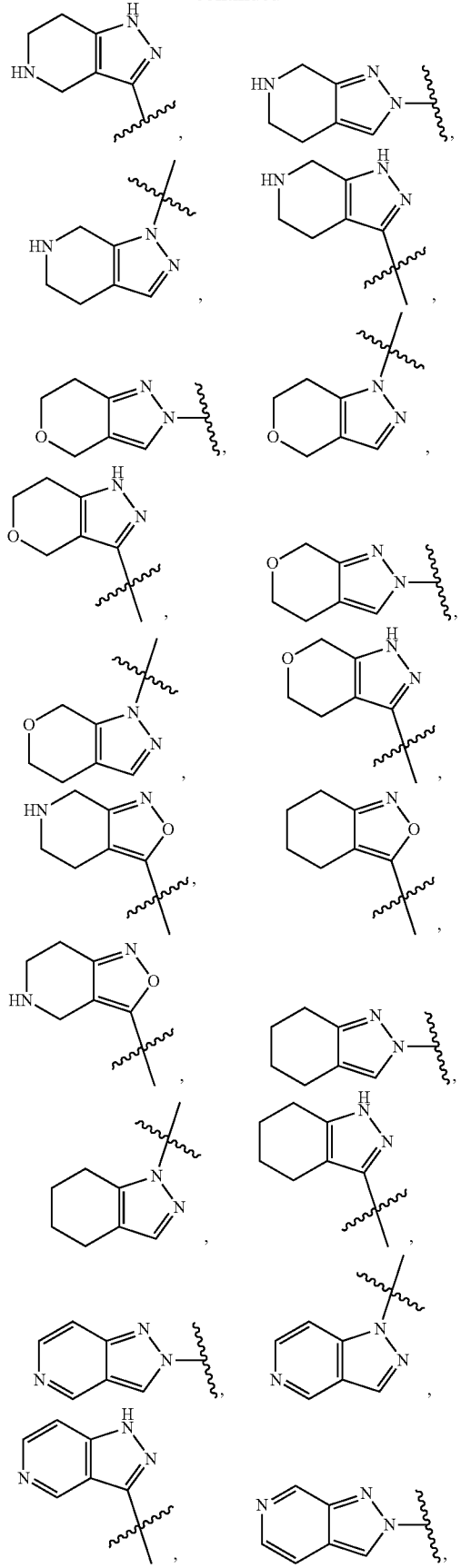

-continued

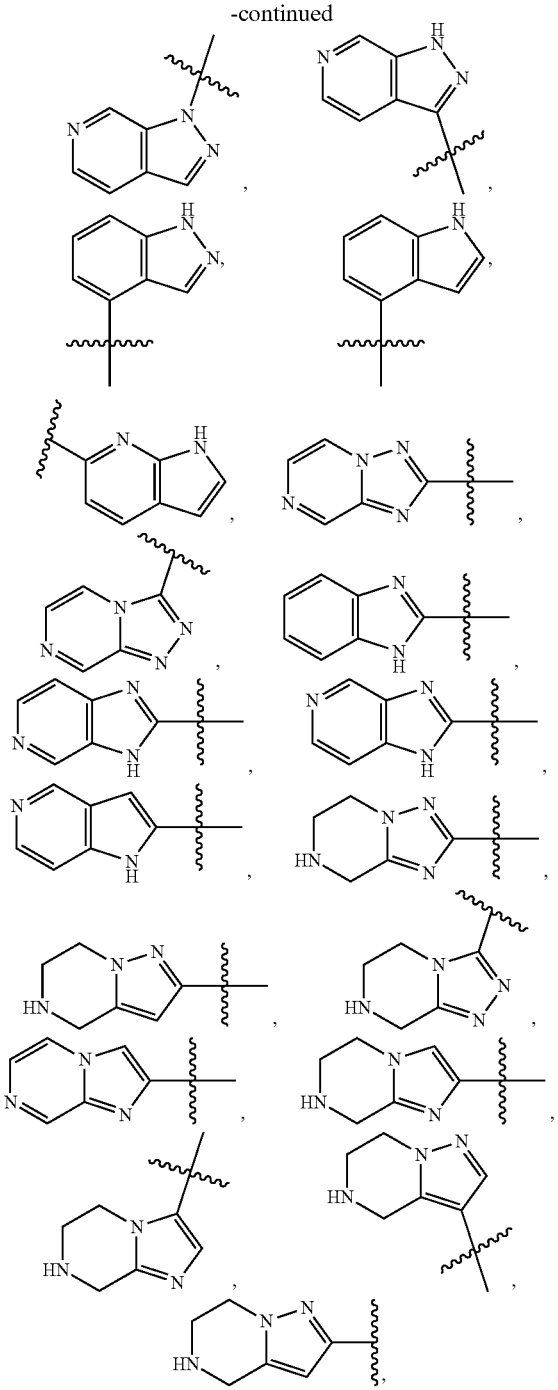

and tautomers thereof, each of which is optionally substituted with one or more -Q$^{3b}$-T$^{3b}$.

In some embodiments, each Q$^{3b}$ independently is a bond or C$_1$-C$_3$ alkylene linker each optionally substituted with one or more of halo, cyano, hydroxyl, or C$_1$-C$_6$ alkoxy, and each T$^{3b}$ independently is selected from the group consisting of H, C$_1$-C$_6$ alkyl, C$_3$-C$_8$ cycloalkyl, 4- to 7-membered heterocycloalkyl, OR$^{fb}$, C(O)R$^{fb}$, C(O)OR$^{fb}$, NR$^{fb}$R$^{gb}$, C(O)NR$^{fb}$R$^{gb}$, and NR$^{fb}$C(O)R$^{gb}$, in which the C$_3$-C$_8$ cycloalkyl or 4- to 7-membered heterocycloalkyl is optionally substituted with one or more halo, cyano, hydroxyl, C$_1$-C$_6$ alkyl or C$_1$-C$_6$ alkoxy.

In some embodiments, at least one of R$^{8b}$ and R$^{9b}$ is H.
In some embodiments, each of R$^{8b}$ and R$^{9b}$ is H.
In some embodiments, R$^{8b}$ is H.
In some embodiments, R$^{9b}$ is -Q$^{4b}$-T$^{4b}$, in which Q$^{4b}$ is a bond or C$_1$-C$_6$ alkylene linker optionally substituted with one or more of halo, cyano, hydroxyl, or C$_1$-C$_6$ alkoxyl, and T$^{4b}$ is H, halo, OR$^{hb}$, NR$^{hb}$R$^{ib}$, NR$^{hb}$C(O)R$^{ib}$, C(O)NR$^{hb}$R$^{ib}$, C(O)R$^{hb}$, C(O)OR$^{hb}$, or R$^{S2b}$, in which R$^{S2b}$ is C$_3$-C$_8$ cycloalkyl or 4- to 7-membered heterocycloalkyl, and R$^{S2b}$ is optionally substituted with one or more -Q$^{5b}$-T$^{5b}$.

In some embodiments, each Q$^{5b}$ independently is a bond or C$_1$-C$_3$ alkylene linker.

In some embodiments, each T$^{5b}$ independently is selected from the group consisting of H, halo, cyano, C$_1$-C$_6$ alkyl, OR$^{jb}$, C(O)R$^{jb}$, C(O)OR$^{jb}$, NR$^{jb}$R$^{kb}$, C(O)NR$^{jb}$R$^{kb}$, and NR$^{jb}$C(O)R$^{kb}$.

In some embodiments, R$^{9b}$ is C$_1$-C$_3$ alkyl.

In some embodiments, for the methods disclosed herein, the EHMT2 inhibitor is of Formula (I'''), (II'''), or (III'''):

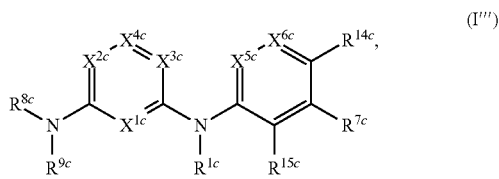

(I''')

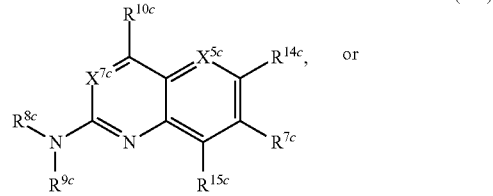

(II''')

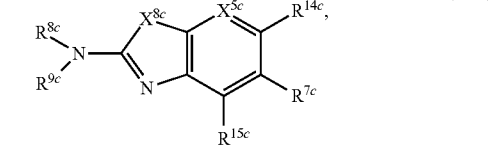

(III''')

a tautomer thereof, or a pharmaceutically acceptable salt of the compound or the tautomer, wherein
X$^{1c}$ is N or CR$^{2c}$;
X$^{2c}$ is N or CR$^{3c}$;
X$^{3c}$ is N or CR$^{4c}$;
X$^{4c}$ is N or CR$^{5c}$;
each of X$^{5c}$, X$^{6c}$ and X$^{7c}$ is independently N or CH;
X$^{8c}$ is NR$^{13c}$ or CR$^{11c}$CR$^{12c}$;
R$^{1c}$ is H or C$_1$-C$_4$ alkyl;
each of R$^{2c}$, R$^{3c}$, R$^{4c}$, and R$^{5c}$, independently is selected from the group consisting of H, halo, cyano, C$_1$-C$_6$ alkoxyl, C$_6$-C$_{10}$ aryl, OH, NR$^{ac}$R$^{bc}$, C(O)NR$^{ac}$R$^{bc}$, NR$^{ac}$C(O)R$^{bc}$, C(O)OR$^{ac}$, OC(O)R$^{ac}$, OC(O)NR$^{ac}$R$^{bc}$, NR$^{ac}$C(O)OR$^{bc}$, C$_3$-C$_8$ cycloalkyl, 4- to 7-membered heterocycloalkyl, 5- to 6-membered heteroaryl, C$_1$-C$_6$ alkyl, C$_2$-C$_6$ alkenyl, and C$_2$-C$_6$ alkynyl, wherein the C$_6$-C$_{10}$ aryl, C$_3$-C$_8$ cycloalkyl, 4- to 7-membered heterocycloalkyl, 5- to 6-membered heteroaryl, C$_1$-C$_6$ alkoxyl, C$_1$-C$_6$ alkyl, C$_2$-C$_6$ alkenyl, and C$_2$-C$_6$ alkynyl, are each optionally substituted with one or more of halo, OR$^{ac}$, or NR$^{ac}$R$^{bc}$, in which each of R$^{ac}$ and R$^{bc}$ independently is H or C$_1$-C$_6$ alkyl;
R$^{6c}$ is -Q$^{1c}$-T$^{1c}$, in which Q$^{1c}$ is a bond, or C$_1$-C$_6$ alkylene, C$_2$-C$_6$ alkenylene, or C$_2$-C$_6$ alkynylene linker each optionally substituted with one or more of halo, cyano, hydroxyl, oxo, or $C_1$-$C_6$ alkoxyl, and $T^{1c}$ is H, halo, cyano, or $R^{S1c}$, in which $R^{S1c}$ is $C_3$-$C_8$ cycloalkyl, phenyl, 4- to 12-membered heterocycloalkyl containing 1-4 heteroatoms selected from N, O, and S, or a 5- or 6-membered heteroaryl and $R^{S1c}$ is optionally substituted with one or more of halo, $C_1$-$C_6$ alkyl, $C_2$-$C_6$ alkenyl, $C_2$-$C_6$ alkynyl, hydroxyl, oxo, —C(O)$R^{cc}$, —C(O)O$R^{cc}$, —SO$_2$$R^{cc}$, —SO$_2$N($R^{cc}$)$_2$, —N$R^{cc}$C(O)$R^{dc}$, —C(O)N$R^{cc}R^{dc}$, —N$R^{cc}$C(O)O$R^{dc}$, —OC(O)N$R^{cc}R^{dc}$, N$R^{cc}R^{dc}$, or $C_1$-$C_6$ alkoxyl, in which each of $R^{cc}$ and $R^{dc}$ independently is H or $C_1$-$C_6$ alkyl;

$R^{7c}$ is -$Q^{2c}$-$T^{2c}$, in which $Q^{2c}$ is a bond, $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, and $T^{2c}$ is H, halo, cyano, O$R^{ec}$, O$R^{fc}$, C(O)$R^{fc}$, N$R^{ec}R^{fc}$, C(O)N$R^{ec}R^{fc}$, N$R^{ec}$C(O)$R^{fc}$, $C_6$-$C_{10}$ aryl, 5- to 10-membered heteroaryl, $C_3$-$C_{12}$ cycloalkyl, or 4- to 12-membered heterocycloalkyl, and wherein the $C_6$-$C_{10}$ aryl, 5- to 10-membered heteroaryl, $C_3$-$C_{12}$ cycloalkyl, or 4- to 12-membered heterocycloalkyl is optionally substituted with one or more -$Q^{3c}$-$T^{3c}$, wherein each $Q^3$ independently is a bond or $C_1$-$C_3$ alkylene linker each optionally substituted with one or more of halo, cyano, hydroxyl, or $C_1$-$C_6$ alkoxy, and each $T^3c$ independently is selected from the group consisting of H, halo, cyano, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, O$R^{ec}$, O$R^{fc}$, C(O)$R^{fc}$, C(O)O$R^{fc}$, OC(O)$R^{fc}$, S(O)$_2R^{fc}$, N$R^{fc}R^{gc}$, OC(O)N$R^{fc}R^{gc}$, N$R^{fc}$(O)O$R^{gc}$, C(O)N$R^{fc}R^{gc}$, and N$R^{fc}$C(O)$R^{gc}$; or -$Q^{3c}$-$T^{3c}$ is oxo;

each $R^{ec}$ independently is H or $C_1$-$C_6$ alkyl optionally substituted with one or more of halo, cyano, hydroxyl, amino, mono- or di-alkylamino, or $C_1$-$C_6$ alkoxyl;

each of $R^{fc}$ and $R^{gc}$, independently, is -$Q^{6c}$-$T^{6c}$, in which $Q^{6c}$ is a bond or $C_1$-$C_6$ alkylene, $C_2$-$C_6$ alkenylene, or $C_2$-$C_6$ alkynylene linker each optionally substituted with one or more of halo, cyano, hydroxyl, or $C_1$-$C_6$ alkoxyl, and $T^{6c}$ is H, halo, O$R^{m1c}$, N$R^{m1c}R^{m2c}$, N$R^{m1c}$C(O)$R^{m2c}$, C(O)N$R^{m1c}R^{m2c}$, C(O)$R^{m1c}$, C(O)O$R^{m1c}$, N$R^{m1c}$C(O)O$R^{m2c}$, OC(O)N$R^{m1c}R^{m2c}$, S(O)$_2R^{m1c}$, S(O)$_2$N$R^{m1c}R^{m2c}$, or $R^{S3c}$, in which each of $R^{m1c}$ and $R^{m2c}$ independently is H or $C_1$-$C_6$ alkyl, and $R^{S3c}$ is $C_3$-$C_8$ cycloalkyl, $C_6$-$C_{10}$ aryl, 4- to 12-membered heterocycloalkyl containing 1-4 heteroatoms selected from N, O, and S, or a 5- to 10-membered heteroaryl, and $R^{S3c}$ is optionally substituted with one or more -$Q^{7c}$-$T^{7c}$, wherein each $Q^{7c}$ independently is a bond or $C_1$-$C_3$ alkylene linker each optionally substituted with one or more of halo, cyano, hydroxyl, or $C_1$-$C_6$ alkoxy, and each $T^{7c}$ independently is selected from the group consisting of H, halo, cyano, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, O$R^{n1c}$, C(O)$R^{n1c}$, C(O)O$R^{n1c}$, OC(O)$R^{n1c}$, S(O)$_2R^{n1c}$, N$R^{n1c}R^{n2c}$, OC(O)N$R^{n1c}R^{n2c}$, N$R^{n1c}$C(O)O$R^{n2c}$, C(O)N$R^{n1c}R^{n2c}$, and N$R^{n1c}$C(O)$R^{n2c}$, each of $R^{n1c}$ and $R^{n2c}$ independently being H or $C_1$-$C_6$ alkyl; or -$Q^{7c}$-$T^{7c}$ is oxo;

$R^{8c}$ is H or $C_1$-$C_6$ alkyl;

$R^{9c}$ is -$Q^{4c}$-$T^{4c}$, in which $Q^{4c}$ is a bond or $C_1$-$C_6$ alkylene, $C_2$-$C_6$ alkenylene, or $C_2$-$C_6$ alkynylene linker each optionally substituted with one or more of halo, cyano, hydroxyl, or $C_1$-$C_6$ alkoxyl, and $T^{4c}$ is H, halo, O$R^{hc}$, N$R^{hc}R^{ic}$, N$R^{hc}$C(O)$R^{ic}$, C(O)N$R^{hc}R^{ic}$, C(O)$R^{hc}$, C(O)O$R^{hc}$, N$R^{hc}$C(O)O$R^{ic}$, OC(O)N$R^{hc}R^{ic}$, S(O)$_2R^{hc}$, S(O)$_2$N$R^{hc}R^{ic}$, or $R^{S2c}$, in which each of $R^{hc}$ and $R^{ic}$ independently is H or $C_1$-$C_6$ alkyl, and $R^{S2c}$ is $C_3$-$C_8$ cycloalkyl, $C_6$-$C_{10}$ aryl, 4- to 12-membered heterocycloalkyl containing 1-4 heteroatoms selected from N, O, and S, or a 5- to 10-membered heteroaryl, and $R^{S2c}$ is optionally substituted with one or more -$Q^{5c}$-$T^{5c}$, wherein each $Q^{5c}$ independently is a bond or $C_1$-$C_3$ alkylene linker each optionally substituted with one or more of halo, cyano, hydroxyl, or $C_1$-$C_6$ alkoxy, and each $T^5$ independently is selected from the group consisting of H, halo, cyano, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, O$R^{jc}$, C(O)$R^{jc}$, C(O)O$R^{jc}$, OC(O)$R^{jc}$, S(O)$_2R^{jc}$, N$R^{jc}R^{kc}$, OC(O)N$R^{jc}R^{kc}$, N$R^{jc}$C(O)O$R^{kc}$, C(O)N$R^{jc}R^{kc}$, and N$R^{jc}$C(O)$R^{kc}$, each of $R^{jc}$ and $R^{kc}$ independently being H or $C_1$-$C_6$ alkyl; or -$Q^{5c}$-$T^{5c}$ is oxo;

$R^{10c}$ is halo, $C_1$-$C_6$ alkyl, $C_2$-$C_6$ alkenyl, $C_2$-$C_6$ alkynyl, $C_3$-$C_8$ cycloalkyl, or 4- to 12-membered heterocycloalkyl containing 1-4 heteroatoms selected from N, O, and S, wherein each of the $C_1$-$C_6$ alkyl, $C_2$-$C_6$ alkenyl, $C_2$-$C_6$ alkynyl, $C_3$-$C_8$ cycloalkyl, and 4- to 12-membered heterocycloalkyl is optionally substituted with one or more halo, cyano, hydroxyl, oxo, amino, mono- or di-alkylamino, $C_1$-$C_6$ alkyl, $C_2$-$C_6$ alkenyl, $C_2$-$C_6$ alkynyl, $C_1$-$C_6$ alkoxy, C(O)N$R^{jc}R^{kc}$, or N$R^{jc}$C(O)$R^{kc}$;

$R^{11c}$ and $R^{12c}$ together with the carbon atom to which they are attached form a $C_3$-$C_{12}$ cycloalkyl or 4- to 12-membered heterocycloalkyl containing 1-4 heteroatoms selected from N, O, and S, wherein the $C_3$-$C_{12}$ cycloalkyl or 4- to 12-membered heterocycloalkyl is optionally substituted with one or more of halo, $C_1$-$C_6$ alkyl, $C_2$-$C_6$ alkenyl, $C_2$-$C_6$ alkynyl, hydroxyl, oxo, amino, mono- or di-alkylamino, or $C_1$-$C_6$ alkoxyl;

$R^{13c}$ is H, $C_1$-$C_6$ alkyl, $C_2$-$C_6$ alkenyl, $C_2$-$C_6$ alkynyl, $C_3$-$C_{12}$ cycloalkyl, or 4- to 12-membered heterocycloalkyl containing 1-4 heteroatoms selected from N, O, and S, and each of $R^{14c}$ and $R^{15c}$, independently, is H, halo, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —O$R^{6c}$.

In some embodiments, the compound is of Formula (I'''), a tautomer thereof, or a pharmaceutically acceptable salt of the compound or the tautomer.

In some embodiments, when $X^{1c}$ is N, $X^{2c}$ is CH, $X^{3c}$ is N, $X^{4c}$ is CCH$_3$, $X^{5c}$ is CH, $X^{6c}$ is CH, $R^{1c}$ is H, $R^{7c}$ is

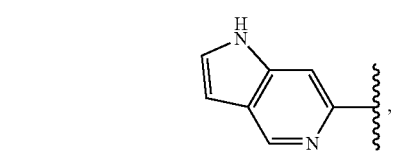 [SMILES: *c1cc2[nH]ccc2cn1]

one of $R^{8c}$ and $R^{9c}$ is H and the other one is CH$_3$, and $R^{14c}$ is OCH$_3$, then $R^{15c}$ is H, halo, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —O$R^6$.

In some embodiments, when $X^{1c}$ is N, $X^{2c}$ is CH, $X^{3c}$ is N, $X^{4c}$ is CCH$_3$, $X^{5c}$ is CH, $X^{6c}$ is CH, $R^{1c}$ is H, $R^{7c}$ is

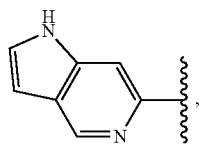 [SMILES: *c1cc2[nH]ccc2cn1]

one of $R^{8c}$ and $R^{9c}$ is H and the other one is $CH_3$, and $R^{14c}$ is $OCH_3$, then $R^{15c}$ is H, Cl, Br, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —$OR^6$.

In some embodiments, wherein when $X^{1c}$ is N, $X^{2c}$ is CH, $X^{3c}$ is N, $X^{4c}$ is $CCH_3$, $X^{5c}$ is CH, $X^{6c}$ is CH, $R^{1c}$ is H, $R^{7c}$ is selected from the group consisting of

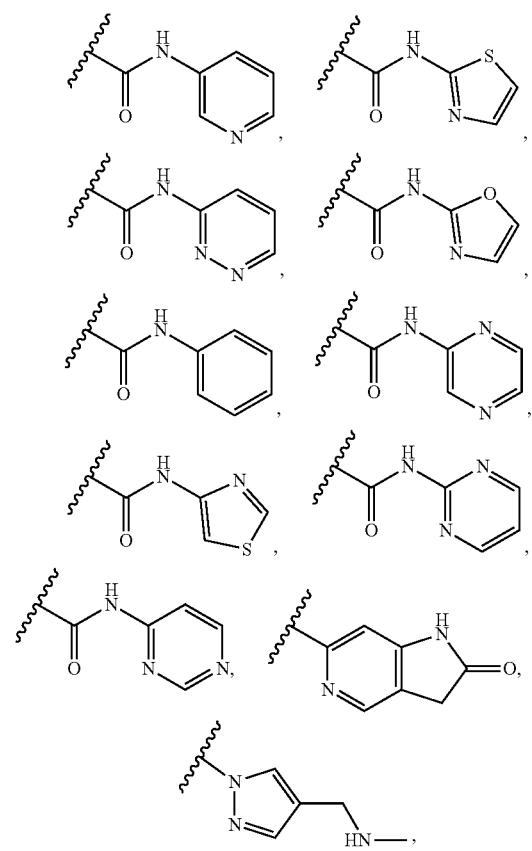

one of $R^{8c}$ and $R^{9c}$ is H and the other one is $CH_3$, and $R^{14c}$ is Cl, then $R^{15c}$ is H, halo, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —$OR^{6c}$.

In some embodiments, wherein when $X^{1c}$ is N, X is CH, $X^{3c}$ is N, $X^{4c}$ is $CCH_3$, $X^{5c}$ is CH, $X^{6c}$ is CH, $R^{1c}$ is H, $R^{7c}$ is selected from the group consisting of

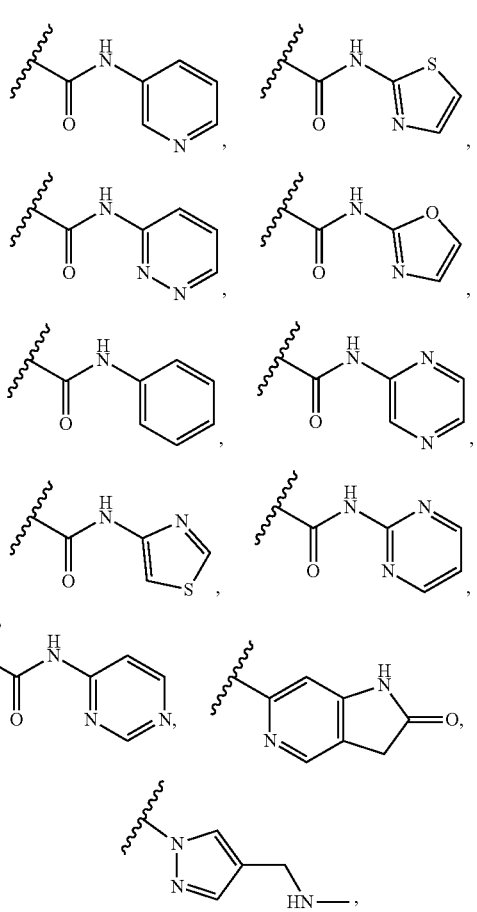

one of $R^{8c}$ and $R^{9c}$ is H and the other one is $CH_3$, and $R^{14c}$ is Cl, then $R^{15c}$ is halo, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —$OR^{6c}$.

In some embodiments, the compound is not one of the following compounds:

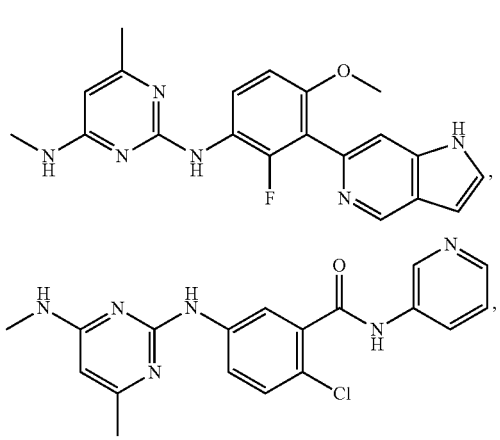

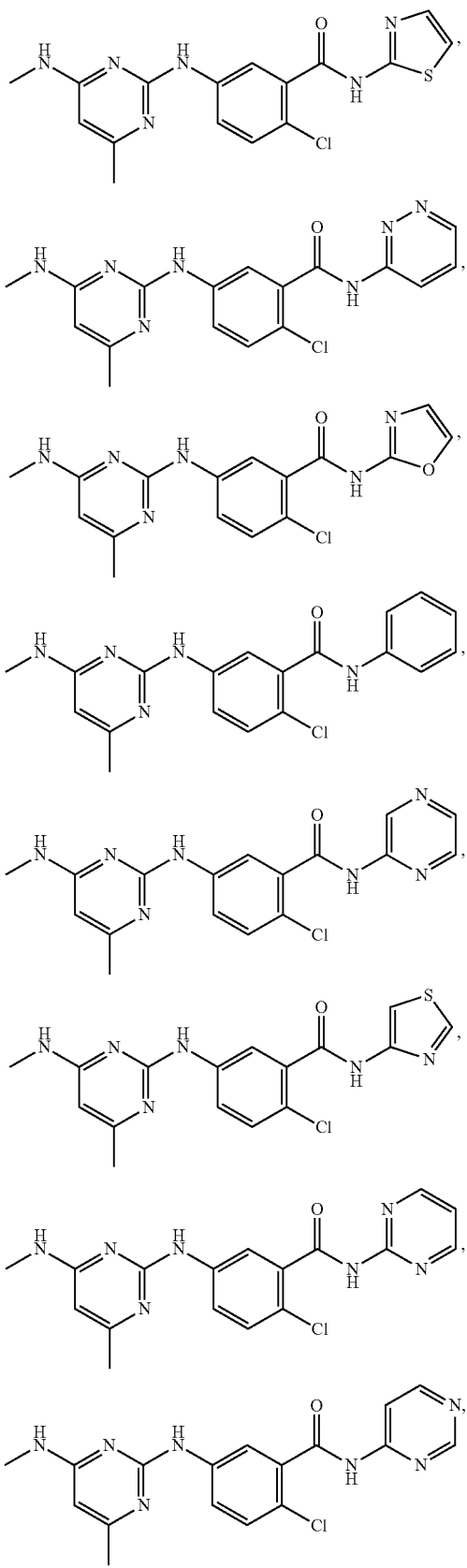

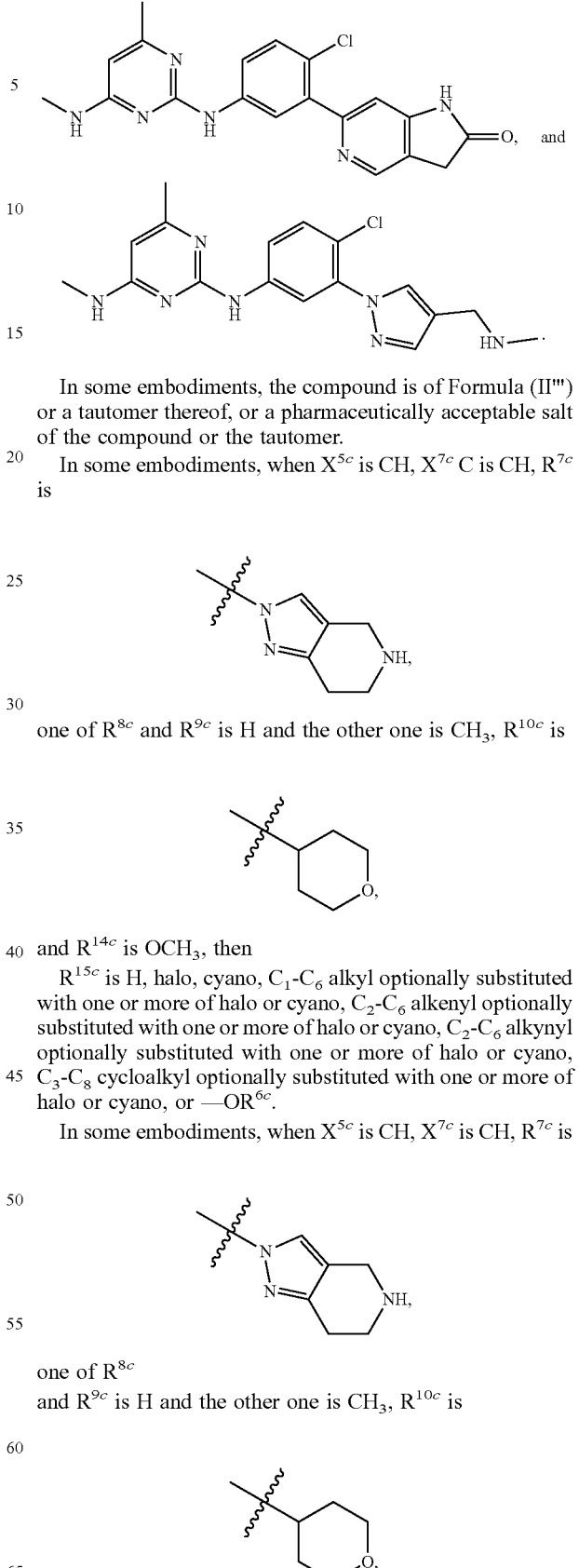

In some embodiments, the compound is of Formula (II'") or a tautomer thereof, or a pharmaceutically acceptable salt of the compound or the tautomer.

In some embodiments, when $X^{5c}$ is CH, $X^{7c}$ C is CH, $R^{7c}$ is one of $R^{8c}$ and $R^{9c}$ is H and the other one is $CH_3$, $R^{10c}$ is and $R^{14c}$ is $OCH_3$, then $R^{15c}$ is H, halo, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —$OR^{6c}$.

In some embodiments, when $X^{5c}$ is CH, $X^{7c}$ is CH, $R^{7c}$ is one of $R^{8c}$ and $R^{9c}$ is H and the other one is $CH_3$, $R^{10c}$ is and $R^{14c}$ is $OCH_3$, then $R^{15c}$ is H, Cl, Br, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —$OR^{6c}$.

In some embodiments, the compound is not

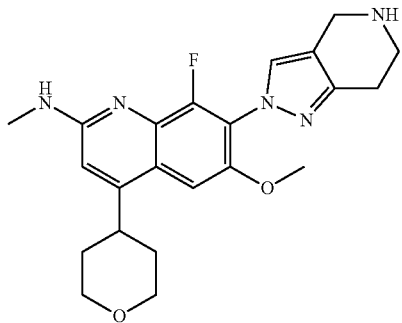
,

In some embodiments, the of Formula (III'") or a tautomer thereof, or a pharmaceutically acceptable salt of the compound or the tautomer.

In some embodiments, when $X^{5c}$ is CH, $X^{8c}$ is $CR^{11c}R^{12c}$, in which $R^{11c}$ and $R^{12c}$ together with the carbon atom to which they are attached form a cyclobutyl, $R^{7c}$ is

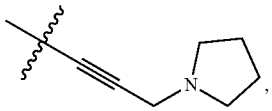 [SMILES: *C#CCN1CCCC1], one of $R^{8c}$ and $R^{9c}$ is H and the other one is $CH_3$, and $R^{14c}$ is $OCH_3$, then $R^{15c}$ is H, halo, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —$OR^{6c}$.

In some embodiments, when $X^{5c}$ is CH, $X^{8c}$ is $CR^{11c}R^{12c}$, in which $R^{11c}$ and $R^{12c}$ together with the carbon atom to which they are attached form a cyclobutyl, $R^{7c}$ is

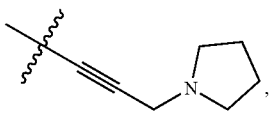, one of $R^{8c}$ and $R^{9c}$ is H and the other one is $CH_3$, and $R^{14c}$ is $OCH_3$, then $R^{15c}$ is H, Cl, Br, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —$OR^{6c}$.

In some embodiments, the compound is not

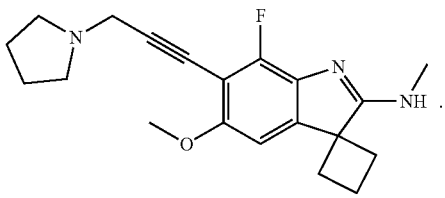 [SMILES: CNC1=Nc2c(cc(OC)c(C#CCN3CCCC3)c2F)C12CCC2]

In some embodiments, at least one of $R^{14c}$ and $R^{15c}$ is halo. In some embodiments, at least one of $R^{14c}$ and $R^{15c}$ is F. In some embodiments, at least one of $R^{14c}$ and $R^{15c}$ is Cl. In some embodiments, at least one of $R^{14c}$ and $R^{15c}$ is Br. In some embodiments, one of $R^{14c}$ and $R^{15c}$ is halo. In some embodiments, one of $R^{14c}$ and $R^{15c}$ is F. In some embodiments, one of $R^{14c}$ and $R^{15c}$ is Cl. In some embodiments, one of $R^{14c}$ and $R^{15c}$ is Br. In some embodiments, $R^{14c}$ is halo. In some embodiments, $R^{14c}$ is F. In some embodiments, $R^{14c}$ is Cl. In some embodiments, $R^{14c}$ is Br. In some embodiments, $R^{15c}$ is halo. In some embodiments, $R^{15c}$ is F. In some embodiments, $R^{15c}$ is Cl. In some embodiments, $R^{15c}$ is Br. In some embodiments, both of $R^{14c}$ and $R^{15c}$ are halo. In some embodiments, both of $R^{14c}$ and $R^{15c}$ are F. In some embodiments, both of $R^{14c}$ and $R^{15c}$ are Cl. In some embodiments, both of $R^{14c}$ and $R^{15c}$ are Br.

In some embodiments, one of $R^{14c}$ and $R^{15c}$ is halo, and the other one is H, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —$OR^{6c}$.

In some embodiments, one of $R^{14c}$ and $R^{15c}$ is halo, and the other one is H, $C_1$-$C_6$ alkyl optionally substituted with one or more of halo or cyano, $C_3$-$C_8$ cycloalkyl optionally substituted with one or more of halo or cyano, or —$OR^{6c}$, in which $R^{11}$ is $C_1$-$C_6$ alkyl optionally substituted with one or more of halo or cyano.

In some embodiments, one of $R^{14c}$ and $R^{15c}$ is halo, and the other one is H, $C_1$-$C_6$ alkyl, $C_3$-$C_8$ cycloalkyl, or —$OR^b$, in which $R^{6c}$ is $C_1$-$C_6$ alkyl. In some embodiments, $R^{14c}$ is halo, and $R^{15c}$ is H, $C_1$-$C_6$ alkyl, $C_3$-$C_8$ cycloalkyl, or —$OR^{6c}$, in which $R^{6c}$ is $C_1$-$C_6$ alkyl. In some embodiments, $R^{14c}$ halo, and $R^{15c}$ is H. In some embodiments, $R^{14c}$ is halo, and $R^{15c}$ is $C_1$-$C_6$ alkyl. In some embodiments, $R^{14c}$ is halo, and $R^{15c}$ is $C_3$-$C_8$ cycloalkyl. In some embodiments, $R^{14c}$ is halo, and $R^{15c}$ is —$OR^{6c}$, in which $R^{6c}$ is $C_1$-$C_6$ alkyl. In some embodiments, $R^{15c}$ is halo, and $R^{14c}$ is H, $C_1$-$C_6$ alkyl, $C_3$-$C_8$ cycloalkyl, or —$OR^{6c}$, in which $R^{6c}$ is $C_1$-$C_6$ alkyl. In some embodiments, $R^{15c}$ is halo, and $R^{14c}$ is H. In some embodiments, $R^{15c}$ is halo, and $R^{14c}$ is $C_1$-$C_6$ alkyl. In some embodiments, $R^{15c}$ is halo, and $R^{14c}$ is $C_3$-$C_8$ cycloalkyl. In some embodiments, $R^{15c}$ is halo, and $R^{14c}$ is —OR, in which $R^{6c}$ is $C_1$-$C_6$ alkyl. In some embodiments, one of $R^{14c}$ and $R^{15c}$ is halo, and the other one is H, —$CH_3$, cyclopropyl, or —$OCH_3$. In some embodiments, one of $R^{14}$ and $R^{15c}$ is halo, and the other one is H or —$OCH_3$.

In some embodiments, $R^{14c}$ is halo, and $R^{15c}$ is H or —$OCH_3$. In some embodiments, $R^{14c}$ is F, and $R^{15c}$ is H. In some embodiments, $R^{14c}$ is Cl, and $R^{15c}$ is H. In some embodiments. $R^{14c}$ is Br, and $R^{15c}$ is H. In some embodiments, $R^{14c}$ is F, and $R^{15c}$ is —$OCH_3$. In some embodiments, $R^{14c}$ is Cl, and $R^{15c}$ is —$OCH_3$. In some embodiments, $R^{14c}$ is Br, and $R^{15c}$ is —$OCH_3$.

In some embodiments, $R^{15c}$ is halo, and $R^{14c}$ is H or —OCH. In some embodiments, $R^{15c}$ is F, and $R^{14c}$ is H. In some embodiments, $R^{15c}$ is Cl, and $R^{14c}$ is H. In some embodiments, $R^{15c}$ is Br, and $R^{14c}$ is H. In some embodiments, $R^{15c}$ is F, and $R^{14c}$ is —OCH$_3$. In some embodiments, $R^{15c}$ is C$_1$, and $R^{14c}$ is —OCH$_3$. In some embodiments, $R^{15c}$ is Br, and $R^{14c}$ is —OCH$_3$.

In some embodiments, $R^{15c}$ is H, and $R^{14c}$ is halo, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, $C_3$-$C_8$ cycloalkyl optionally substituted with one or more of halo or cyano, or —OR$^{6c}$.

In some embodiments, $R^{15c}$ is H, and $R^{14c}$ is halo or —OR.

In some embodiments, $R^{15c}$ is H, and $R^{14c}$ is F, Cl, or Br.

In some embodiments, $R^{15c}$ is H, and $R^{14c}$ is —OCH.

In some embodiments, the compound is of any one of Formula (I'''-1), (I'''-2), (II'''-1), (II'''-2), (III'''-1), or (III'''-2):

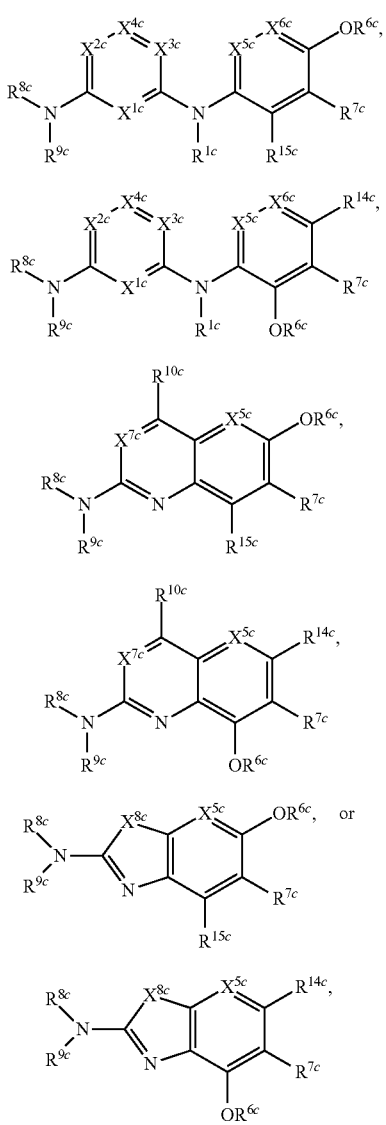

a tautomer thereof, or a pharmaceutically acceptable salt of the compound or the tautomer, wherein $X^{1c}$ is N or $CR^{2c}$;
$X^{2c}$ is N or $CR^{3c}$;
$X^{3c}$ is N or $CR^{4c}$;
$X^{4c}$ is N or $CR^{5c}$;
each of $X^{5c}$, $X^{6c}$ and $X^{7c}$ is independently N or CH;
$R^{1c}$ is H or $C_1$-$C_4$ alkyl;
each of $R^{2c}$, $R^{3c}$, $R^{4c}$, and $R^{5C}$, independently is selected from the group consisting of H, halo, cyano, $C_1$-$C_6$ alkoxyl, $C_6$-$C_{10}$ aryl, OH, $NR^{ac}R^{bc}$, $C(O)NR^{ac}R^{bc}$, $NR^{ac}C(O)R^{bc}$, $C(O)OR^{ac}$, $OC(O)R^{ac}$, $OC(O)NR^{ac}R^{bc}$, $NR^{ac}C(O)OR^{bc}$, $C_3$-$C_8$ cycloalkyl, 4- to 7-membered heterocycloalkyl, 5- to 6-membered heteroaryl, $C_1$-$C_6$ alkyl, $C_2$-$C_6$ alkenyl, and $C_2$-$C_6$ alkynyl, wherein the $C_6$-$C_{10}$ aryl, $C_3$-$C_8$ cycloalkyl, 4- to 7-membered heterocycloalkyl, 5- to 6-membered heteroaryl, $C_1$-$C_6$ alkoxyl, $C_1$-$C_6$ alkyl, $C_2$-$C_6$ alkenyl, and $C_2$-$C_6$ alkynyl, are each optionally substituted with one or more of halo, $OR^{ac}$, or $NR^{ac}R^{bc}$, in which each of $R^{ac}$ and $R^{bc}$ independently is H or $C_1$-$C_6$ alkyl;

$R^{6c}$ is -$Q^{1c}$-$T^{1c}$, in which $Q^{1c}$ is a bond, or $C_1$-$C_6$ alkylene, $C_2$-$C_6$ alkenylene, or $C_2$-$C_6$ alkynylene linker each optionally substituted with one or more of halo, cyano, hydroxyl, oxo, or $C_1$-$C_6$ alkoxyl, and $T^{1c}$ is H, halo, cyano, or $R^{S1c}$, in which $R^{S1c}$ is $C_3$-$C_8$ cycloalkyl, phenyl, 4- to 12-membered heterocycloalkyl containing 1-4 heteroatoms selected from N, O, and S, or a 5- or 6-membered heteroaryl and $R^{S1c}$ is optionally substituted with one or more of halo, $C_1$-$C_6$ alkyl, $C_2$-$C_6$ alkenyl, $C_2$-$C_6$ alkynyl, hydroxyl, oxo, —C(O)R$^{cc}$, —C(O)OR$^{cc}$, —SO$_2$R$^{cc}$, —SO$_2$N(R$^{cc}$)$_2$, —NR$^{cc}$C(O)R$^{dc}$, —C(O)NR$^{cc}$R$^{dc}$, —NR$^{cc}$C(O)OR$^{dc}$, —OC(O)NR$^{cc}$R$^{dc}$, NR$^{cc}$R$^{dc}$, or $C_1$-$C_6$ alkoxyl, in which each of R$^{cc}$ and R$^{dc}$ independently is H or $C_1$-$C_6$ alkyl;

$R^{7c}$ is -$Q^{2c}$-$T^{2c}$, in which $Q^{2c}$ is a bond, $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, and $T^{2c}$ is H, halo, cyano, OR$^{ec}$, OR$^{fc}$, C(O)R$^{fc}$, NR$^{ec}$R$^{fc}$, C(O)NR$^{ec}$R$^{fc}$, NR$^{ec}$C(O)R$^{fc}$, $C_6$-$C_{10}$ aryl, 5- to 10-membered heteroaryl, $C_3$-$C_{12}$ cycloalkyl, or 4- to 12-membered heterocycloalkyl, and wherein the $C_6$-$C_{10}$ aryl, 5- to 10-membered heteroaryl, $C_3$-$C_{12}$ cycloalkyl, or 4- to 12-membered heterocycloalkyl is optionally substituted with one or more -$Q^{3c}$-$T^{3c}$, wherein each $Q^3$ independently is a bond or $C_1$-$C_3$ alkylene linker each optionally substituted with one or more of halo, cyano, hydroxyl, or $C_1$-$C_6$ alkoxy, and each T$^3$c independently is selected from the group consisting of H, halo, cyano, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, OR$^{ec}$, OR$^{fc}$, C(O)R$^{fc}$, C(O)OR$^{fc}$, OC(O) R$^{fc}$, S(O)$_2$R$^{fc}$, NR$^{fc}$R$^{gc}$, OC(O)NR$^{fc}$R$^{gc}$, NR$^{fc}$(O)OR$^{gc}$, C(O)NR$^{fc}$R$^{gc}$, and NR$^{fc}$C(O)R$^{gc}$; or -$Q^{3c}$-$T^{3c}$ is oxo;

each R$^{ec}$ independently is H or $C_1$-$C_6$ alkyl optionally substituted with one or more of halo, cyano, hydroxyl, amino, mono- or di-alkylamino, or $C_1$-$C_6$ alkoxyl;

each of R$^{fc}$ and R$^{gc}$, independently, is -$Q^{6c}$-$T^{6c}$, in which $Q^{6c}$ is a bond or $C_1$-$C_6$ alkylene, $C_2$-$C_6$ alkenylene, or $C_2$-$C_6$ alkynylene linker each optionally substituted with one or more of halo, cyano, hydroxyl, or $C_1$-$C_6$ alkoxyl, and $T^{6c}$ is H, halo, OR$^{m1c}$, NR$^{m1c}$R$^{m2c}$, NR$^{m1c}$C(O)R$^{m2c}$, C(O) NR$^{m1c}$R$^{m2c}$, C(O)R$^{m1c}$, C(O)OR$^{m1c}$, NR$^{m1c}$C(O)OR$^{m2c}$, OC(O)NR$^{m1c}$R$^{m2c}$, S(O)$_2$R$^{m1c}$, S(O)$_2$NR$^{m1c}$R$^{m2c}$, or R$^{S3c}$, in which each of R$^{m1c}$ and R$^{m2c}$ independently is H or $C_1$-$C_6$ alkyl, and R$^{S3c}$ is $C_3$-$C_8$ cycloalkyl, $C_6$-$C_{10}$ aryl, 4- to 12-membered heterocycloalkyl containing 1-4 heteroatoms selected from N, O, and S, or a 5- to 10-membered heteroaryl, and R$^{S3c}$ is optionally substituted with one or more -$Q^{7c}$-$T^{7c}$, wherein each $Q^{7c}$ independently is a bond or $C_1$-$C_3$ alkylene linker each optionally substituted with one or more of halo, cyano, hydroxyl, or $C_1$-$C_6$ alkoxy, and each $T^{7c}$ independently is selected from the group consisting of H, halo, cyano, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, $OR^{n1c}$, $C(O)R^{n1c}$, $C(O)OR^{n1c}$, $OC(O)R^{n1c}$, $S(O)_2R^{n1c}$, $NR^{n1c}R^{n2c}$, $OC(O)NR^{n1c}R^{n2c}$, $NR^{n1c}C(O)OR^{n2c}$, $C(O)NR^{n1c}R^{n2c}$, and $NR^{n1c}C(O)R^{n2c}$, each of $R^{n1c}$ and $R^{n2c}$ independently being H or $C_1$-$C_6$ alkyl; or -$Q^{7c}$-$T^{7c}$ is oxo; $R^{8c}$ is H or $C_1$-$C_6$ alkyl;

$R^{9c}$ is -$Q^{4c}$-$T^{4c}$, in which $Q^{4c}$ is a bond or $C_1$-$C_6$ alkylene, $C_2$-$C_6$ alkenylene, or $C_2$-$C_6$ alkynylene linker each optionally substituted with one or more of halo, cyano, hydroxyl, or $C_1$-$C_6$ alkoxyl, and $T^{4c}$ is H, halo, $OR^{hc}$, $NR^{hc}R^{ic}$, $NR^{hc}C(O)R^{ic}$, $C(O)NR^{hc}R^{ic}$, $C(O)R^{hc}$, $C(O)OR^{hc}$, $NR^{hc}C(O)OR^{ic}$, $OC(O)NR^{hc}R^{ic}$, $S(O)_2R^{hc}$, $S(O)_2NR^{hc}R^{ic}$, or $R^{S2c}$, in which each of $R^{hc}$ and $R^{ic}$ independently is H or $C_1$-$C_6$ alkyl, and $R^{S2c}$ is $C_3$-$C_8$ cycloalkyl, $C_6$-$C_{10}$ aryl, 4- to 12-membered heterocycloalkyl containing 1-4 heteroatoms selected from N, O, and S, or a 5- to 10-membered heteroaryl, and $R^{S2c}$ is optionally substituted with one or more -$Q^{5c}$-$T^{5c}$, wherein each $Q^{5c}$ independently is a bond or $C_1$-$C_3$ alkylene linker each optionally substituted with one or more of halo, cyano, hydroxyl, or $C_1$-$C_6$ alkoxy, and each $T^5$ independently is selected from the group consisting of H, halo, cyano, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, $OR^{jc}$, $C(O)R^{jc}$, $C(O)OR^{jc}$, $OC(O)R^{jc}$, $S(O)_2R^{jc}$, $NR^{jc}R^{kc}$, $OC(O)NR^{jc}R^{kc}$, $NR^{jc}C(O)OR^{kc}$, $C(O)NR^{jc}R^{kc}$, and $NR^{jc}C(O)R^{kc}$, each of $R^{jc}$ and $R^{kc}$ independently being H or $C_1$-$C_6$ alkyl; or -$Q^{5c}$-$T^{5c}$ is oxo;

$R^{10}$ is halo, $C_1$-$C_6$ alkyl, $C_2$-$C_6$ alkenyl, $C_2$-$C_6$ alkynyl, $C_3$-$C_8$ cycloalkyl, or 4- to 12-membered heterocycloalkyl containing 1-4 heteroatoms selected from N, O, and S, wherein each of the $C_1$-$C_6$ alkyl, $C_2$-$C_6$ alkenyl, $C_2$-$C_6$ alkynyl, $C_3$-$C_8$ cycloalkyl, and 4- to 12-membered heterocycloalkyl is optionally substituted with one or more halo, cyano, hydroxyl, oxo, amino, mono- or di-alkylamino, $C_1$-$C_6$ alkyl, $C_2$-$C_6$ alkenyl, $C_2$-$C_6$ alkynyl, $C_1$-$C_6$ alkoxy, $C(O)NR^{jc}R^{kc}$, or $NR^{jc}C(O)R^{kc}$; and $R^{11c}$ and $R^{12c}$ together with the carbon atom to which they are attached form a $C_3$-$C_{12}$ cycloalkyl or 4- to 12-membered heterocycloalkyl containing 1-4 heteroatoms selected from N, O, and S, wherein the $C_3$-$C_{12}$ cycloalkyl or 4- to 12-membered heterocycloalkyl is optionally substituted with one or more of halo, $C_1$-$C_6$ alkyl, $C_2$-$C_6$ alkenyl, $C_2$-$C_6$ alkynyl, hydroxyl, oxo, amino, mono- or di-alkylamino, or $C_1$-$C_6$ alkoxyl;

each of $R^{14c}$ and $R^{15c}$, independently, is H, halo, cyano, $C_1$-$C_6$ alkyl optionally substituted with one or more of halo or cyano, $C_2$-$C_6$ alkenyl optionally substituted with one or more of halo or cyano, $C_2$-$C_6$ alkynyl optionally substituted with one or more of halo or cyano, or $C_3$-$C_8$ cycloalkyl optionally substituted with one or more of halo or cyano.

In some embodiments, the compound is of Formula (I'''-1) or (I'''-2), a tautomer thereof, or a pharmaceutically acceptable salt of the compound or the tautomer.

In some embodiments, at least one of $X^{1c}$, $X^{2c}$, $X^{3c}$ and $X^{4c}$ is N. In some embodiments, $X^{1c}$ and $X^{3c}$ are N. In some embodiments, $X^{1c}$ and $X^{3c}$ are N, $X^{2c}$ is $CR^{3c}$ and $X^{4c}$ is $CR^{5c}$.

In some embodiments,

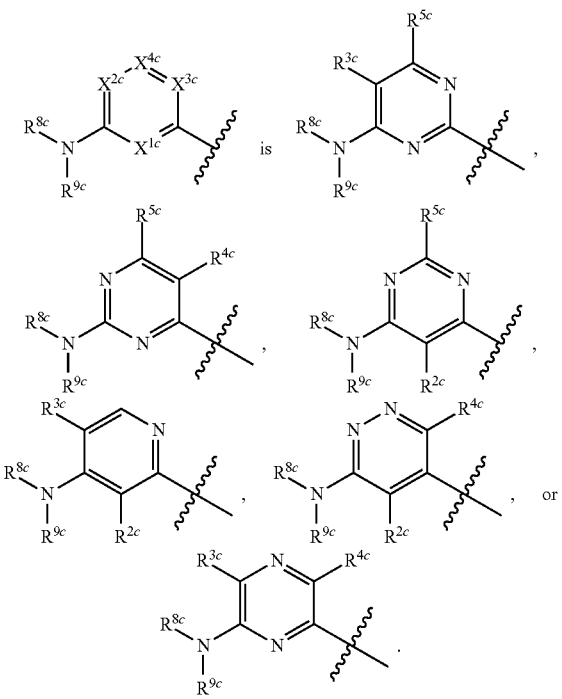

In some embodiments,

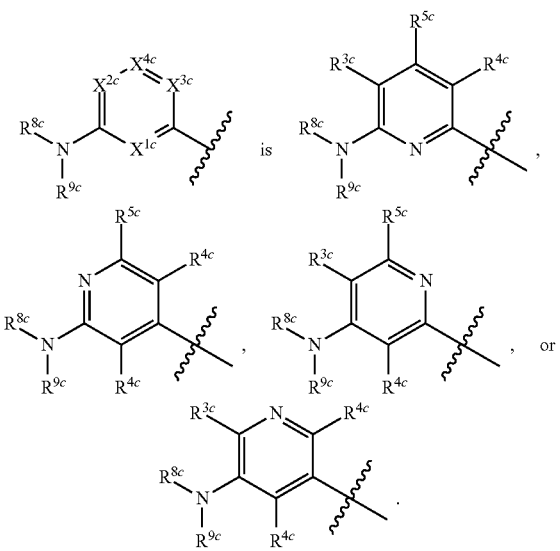

In some embodiments, the compound is of Formula (I'''-1a), (I'''-2a), (I'''-1b), (I'''-2b), (I'''-1c), or (I'''-2c):

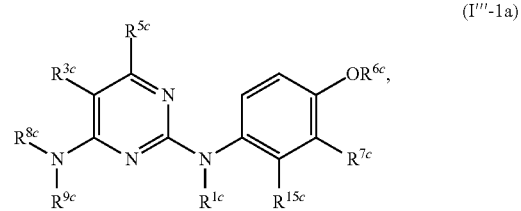

(I'''-1a)

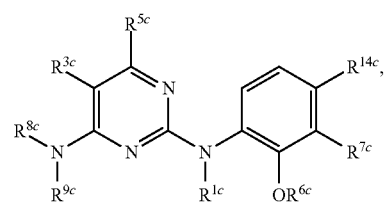 (I′′′-2a)

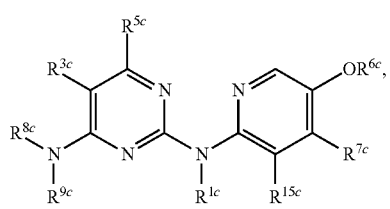 (I′′′-1b)

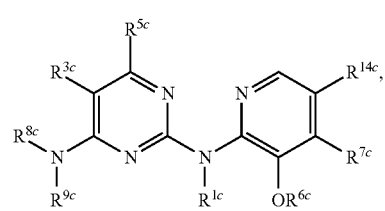 (I′′′-2b)

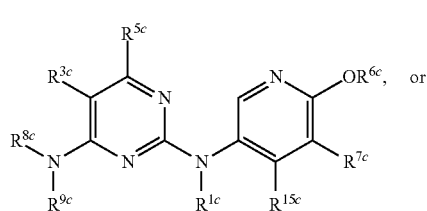 (I′′′-1c)

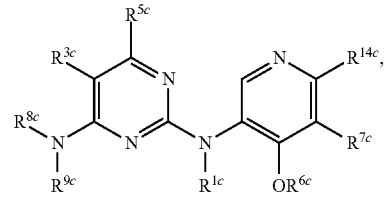 (I′′′-2c)

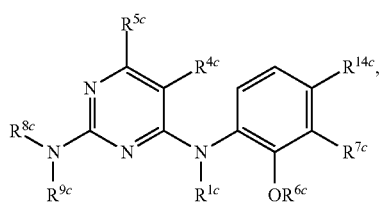 (I′′′-2d)

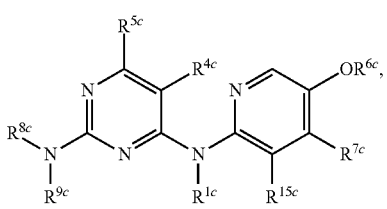 (I′′′-1e)

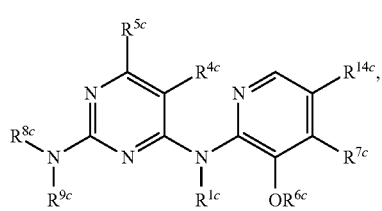 (I′′′-2e)

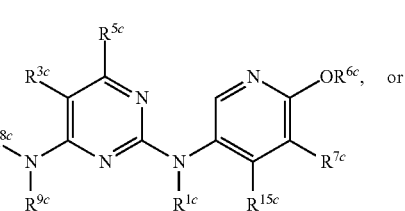 (I′′′-1f)

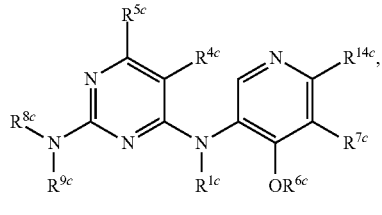 (I′′′-2f)

a tautomer thereof, or a pharmaceutically acceptable salt of the compound or the tautomer.

In some embodiments, at most one of $R^{3c}$ and $R^{5c}$ is not H. In some embodiments, at least one of $R^{3c}$ and $R^{5c}$ is not H. In some embodiments, $R^{3c}$ is H or halo.

In some embodiments, the compound is of Formula (I′′′-1d), (I′′′-2d), (I′′′-1e), (I′′′-2e), (I′′′-1f), or (I′′′-2f):

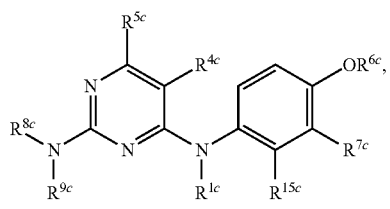 (I′′′-1d)

a tautomer thereof, or a pharmaceutically acceptable salt of the compound or the tautomer.

In some embodiments, at most one of $R^{4c}$ and $R^{5c}$ is not H. In some embodiments, at least one of $R^{4c}$ and $R^{5c}$ is not H. In some embodiments, $R^{4c}$ is H, $C_1$-$C_6$ alkyl, or halo.

In some embodiments, the compound of Formula (I′′′-1g), (I′′′-2g), (I′′′-1h), (I′′′-2h), (I′′′-1i), (I′′′-2i),

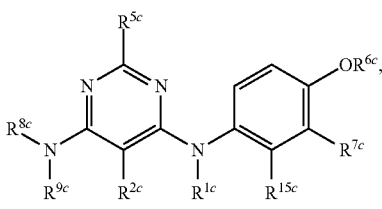 (I′′′-1g)

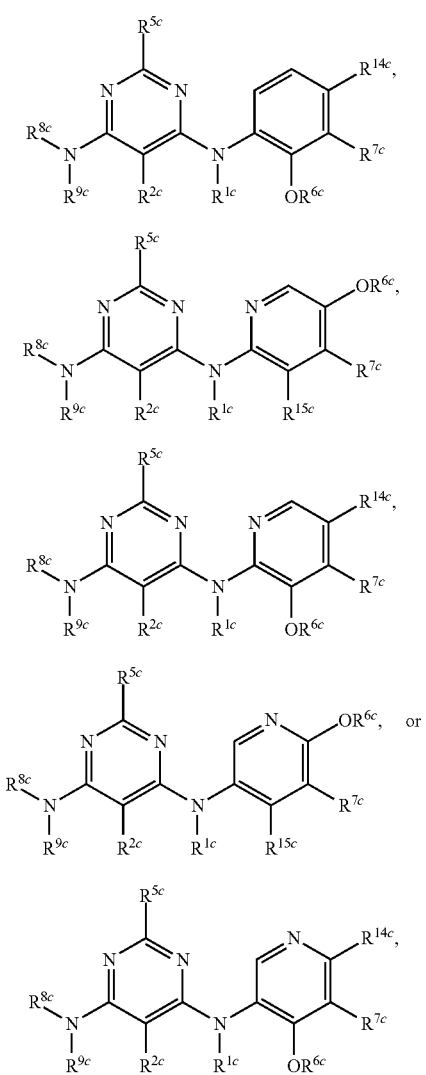

a tautomer thereof, or a pharmaceutically acceptable salt of the compound or the tautomer.

In some embodiments, at most one of $R^{3c}$ and $R^{5c}$ is not H. In some embodiments, at least one of $R^{2c}$ and $R^{5c}$ is not H. In some embodiments, $R^{2c}$ is H, $C_1$-$C_6$ alkyl, or halo. In some embodiments, $R^{5c}$ is $C_1$-$C_6$ alkyl.

In some embodiments, the compound is of Formula (II'''-1) of (II'''-2), a tautomer thereof, or a pharmaceutically acceptable salt of the compound or the tautomer.

In some embodiments, each of $X^{5c}$, $X^{6c}$ and $X^{7c}$ is CH. In some embodiments, at least one of $X^{5c}$, $X^{6c}$ and $X^{7c}$ is N. In some embodiments, at most one of $X^{5c}$, $X^{6c}$ and $X^{7c}$ is N.

In some embodiments, $R^{10}$ is optionally substituted 4- to 7-membered heterocycloalkyl containing 1-4 heteroatoms selected from N, O, and S. In some embodiments, $R^{10}$ is connected to the bicyclic group of Formula (II'''-1) or (II''-2) via a carbon-carbon bond. In some embodiments, $R^{10}$ is connected to the bicyclic group of Formula (II'''-1) or (II''-2) via a carbon-nitrogen bond.

In some embodiments, the compound is of Formula (III'''-1) or (III'''-2), a tautomer thereof, or a pharmaceutically acceptable salt of the compound or the tautomer.

In some embodiments, $R^{11c}$ and $R^{12c}$ together with the carbon atom to which they are attached form a 4- to 7-membered heterocycloalkyl containing 1-4 heteroatoms selected from N, O, and S, wherein the 4- to 7-membered heterocycloalkyl is optionally substituted with one or more of halo, $C_1$-$C_6$ alkyl, hydroxyl, oxo, amino, mono- or di-alkylamino, or $C_1$-$C_6$ alkoxyl.

In some embodiments, $R^{11c}$ and $R^{12c}$ together with the carbon atom to which they are attached form azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, or morpholinyl.

In some embodiments, $R^{11c}$ and $R^{12c}$ together with the carbon atom to which they are attached form tetrahyrofuranyl.

In some embodiments, $R^{11c}$ and $R^{12c}$ together with the carbon atom to which they are attached form a $C_4$-$C_8$ cycloalkyl which is optionally substituted with one or more of halo. $C_1$-$C_6$ alkyl, hydroxyl, oxo, amino, mono- or di-alkylamino, or $C_1$-$C_6$ alkoxyl.

In some embodiments, $R^{11c}$ and $R^{12c}$ together with the carbon atom to which they are attached form a $C_4$-$C_8$ cycloalkyl (e.g., cyclobutyl, cyclopentyl, or cyclohexyl).

In some embodiments, $R^{11c}$ and $R^{12c}$ together with the carbon atom to which they are attached form cyclobutyl.

In some embodiments, $R^{11c}$ and $R^{12c}$ together with the carbon atom to which they are attached form cyclopentyl.

In some embodiments, $R^{11c}$ and $R^{12c}$ together with the carbon atom to which they are attached form cyclohexyl.

In some embodiments, each of $X^{5C}$ and $X^{6c}$ is CH. In some embodiments, each of $X^{5c}$ and $X^{6c}$ is N. In some embodiments, one of $X^{5c}$ and $X^{6c}$ is CH and the other is CH.

In some embodiments, $R^{6c}$ is -$Q^{1c}$-$T^{1c}$, in which $Q^{1c}$ is a bond or $C_1$-$C_6$ alkylene linker optionally substituted with one or more of halo, and $T^{1c}$ is H, halo, cyano, or $R^{S1c}$, in which $R^{S1c}$ is $C_3$-$C_8$ cycloalkyl, phenyl, 4- to 12-membered heterocycloalkyl containing 1-4 heteroatoms selected from N, O, and S, or a 5- or 6-membered heteroaryl and $R^{S1c}$ is optionally substituted with one or more of halo, $C_1$-$C_6$ alkyl, hydroxyl, oxo, $NR^{cc}R^{dc}$, or $C_1$-$C_6$ alkoxyl.

In some embodiments, wherein $R^{6c}$ is $C_1$-$C_6$ alkyl optionally substituted with one or more of halo, cyano, hydroxyl, or $C_1$-$C_6$ alkoxyl. In some embodiments, $R^{6c}$ is $C_1$-$C_6$ alkyl. In some embodiments, $R^{6c}$ is —$CH_3$.

In some embodiments, $R^{7c}$ is -$Q^{2c}$-$T^{2c}$, in which $Q^{2c}$ is a bond or $C_1$-$C_6$ alkylene, $C_2$-$C_6$ alkenylene, or $C_2$-$C_6$ alkynylene linker optionally substituted with one or more of halo, cyano, hydroxyl, amino, mono- or di-alkylamino, and $T^{2c}$ is $C(O)NR^{ec}R^{fc}$.

In some embodiments, $Q^{2c}$ is a bond. In some embodiments, $R^{ec}$ is H. In some embodiments. $R^{fc}$ is -$Q^{6c}$-$T^{6c}$, in which $Q^{6c}$ is a bond or $C_1$-$C_6$ alkylene, $C_2$-$C_6$ alkenylene, or $C_2$-$C_6$ alkynylene linker each optionally substituted with one or more of halo, cyano, hydroxyl, or $C_1$-$C_6$ alkoxyl, and $T^{6c}$ is H, $NR^{m1c}R^{m2c}$, or $R^{S3c}$, in which each of $R^{m1c}$ and $R^{m2c}$ independently is H or $C_1$-$C_6$ alkyl, and $R^{S3c}$ is $C_3$-$C_8$ cycloalkyl, $C_6$-$C_{10}$ aryl, 4- to 12-membered heterocycloalkyl containing 1-4 heteroatoms selected from N, O, and S, or a 5- to 10-membered heteroaryl, and $R^{S3c}$ is optionally substituted with one or more -$Q^{7c}$-$T^{7c}$.

In some embodiments, $T^{6c}$ is 8- to 12-membered bicyclic heterocycloalkyl that comprises a 5- or 6-membered aryl or heteroaryl ring fused with a non-aromatic ring. In some embodiments, $T^{6c}$ is 8- to 12-membered bicyclic heterocycloalkyl that comprises a 5- or 6-membered aryl or heteroaryl ring fused with a non-aromatic ring, in which the 5- or 6-membered aryl or heteroaryl ring is connected to $Q^{2c}$. In some embodiments, $T^{6c}$ is 5- to 10-membered heteroaryl.

In some embodiments, $T^6$ is selected from

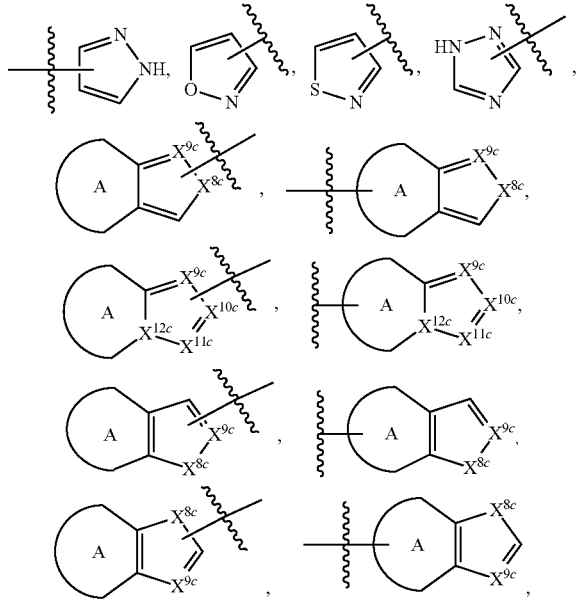

and tautomers thereof, each of which is optionally substituted with one or more $-Q^{7c}-T^{7c}$, wherein $X^{8c}$ is NH, O, or S, each of $X^{9c}$, $X^{10}$, $X^{11c}$, and $X^{12c}$ is independently CH or N, and at least one of $X^{9c}$, $X^{10}$, $X^{11c}$, and $X^{12c}$ is N, and ring A is a $C_5$-$C_8$ cycloalkyl, phenyl, 6-membered heteroaryl, or 4- to 8-membered heterocycloalkyl containing 1-4 heteroatoms selected from N, O, and S.

In some embodiments, $T^{6c}$ is selected from

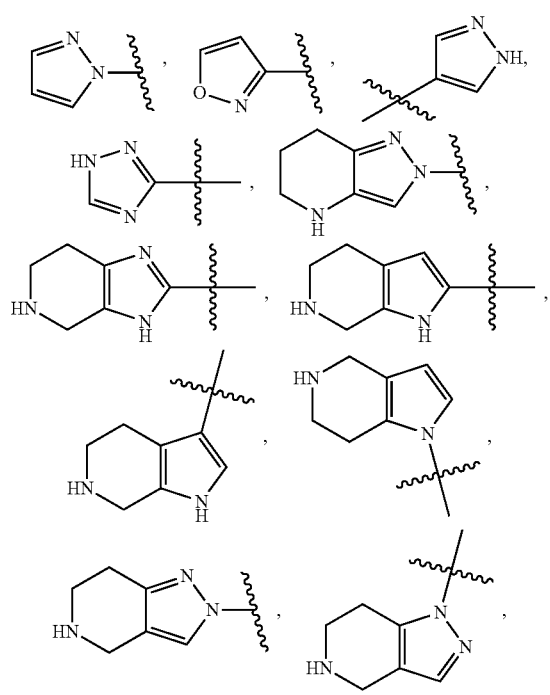

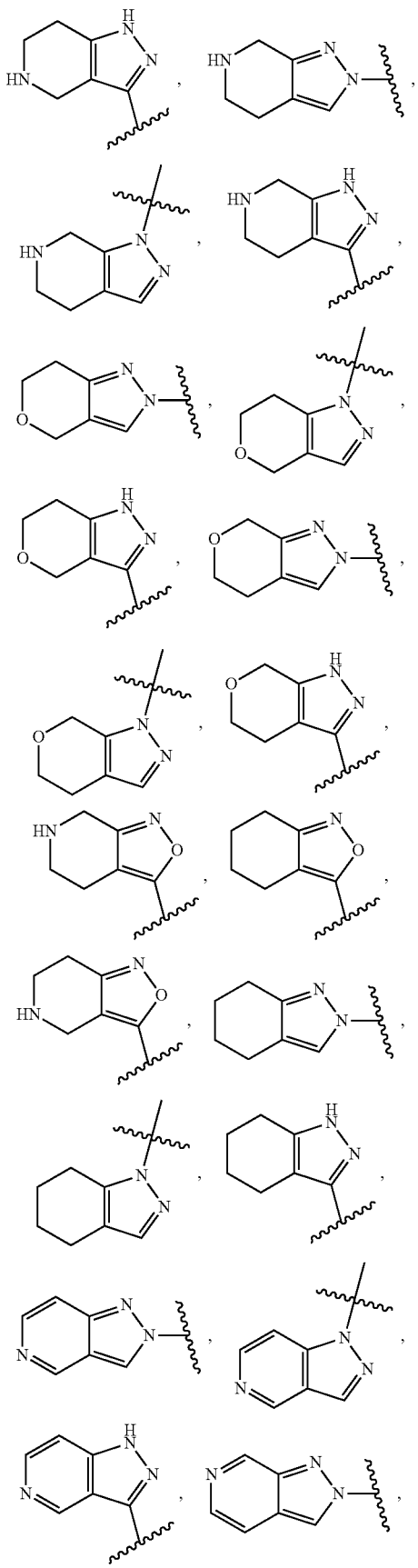

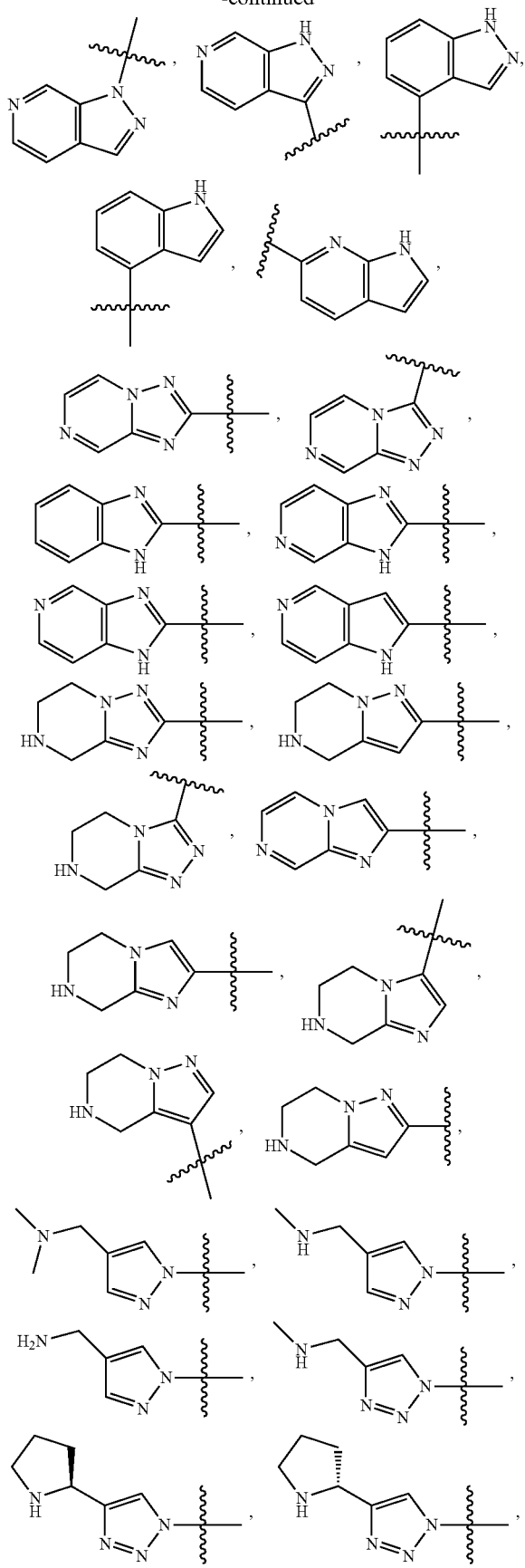

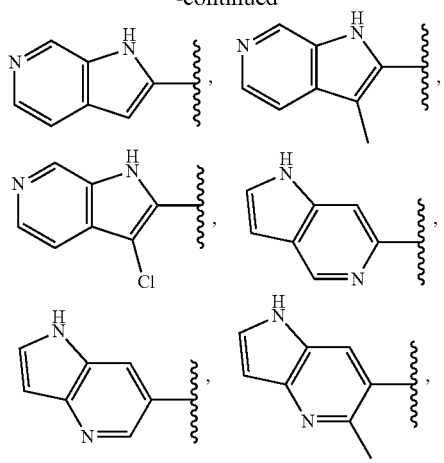

and tautomers thereof, each of which is optionally substituted with one or more $-Q^{7c}-T^{7c}$.

In some embodiments, each $Q^{7c}$ independently is a bond or $C_1$-$C_3$ alkylene linker each optionally substituted with one or more of halo, cyano, hydroxyl, or $C_1$-$C_6$ alkoxy, and each $T^{7c}$ independently is selected the group consisting of H, halo, cyano, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4- to 7-membered heterocycloalkyl containing 1-4 heteroatoms selected from N, O, and S, 5- to 6-membered heteroaryl, $OR^{n1c}$, $C(O)R^{n1c}$, $C(O)OR^{a1c}$, $OC(O)R^{n1c}$, $S(O)_2R^{n1c}$, $NR^{n1c}R^{n2c}$, $OC(O)NR^{n1c}R^{n2c}$, $NR^{n1c}C(O)OR^{n2c}$, $C(O)NR^{n1c}R^{n2c}$, and $NR^{n1c}C(O)R^{n2c}$, each of $R^{n1c}$ and $R^{n2c}$ independently being H or $C_1$-$C_6$ alkyl; or $-Q^{7c}-T^{7c}$ is oxo.

In some embodiments, each $Q^{7c}$ independently is a bond or $C_1$-$C_3$ alkylene linker each optionally substituted with one or more of halo, cyano, hydroxyl, or $C_1$-$C_6$ alkoxy, and each $T^{7c}$ independently is selected from the group consisting of H, halo, cyano, $C_1$-$C_6$ alkyl, and $NR^{n1c}R^{n2c}$, each of $R^{n1c}$ and $R^{n2c}$ independently being H or $C_1$-$C_6$ alkyl.

In some embodiments, $R^{7c}$ is

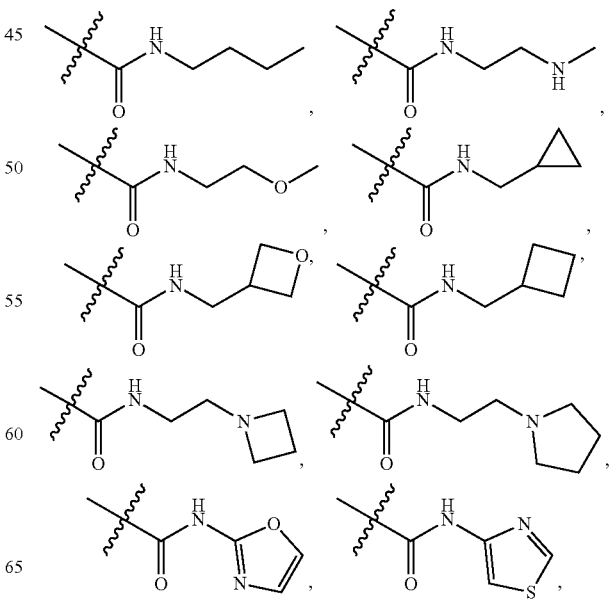

-continued

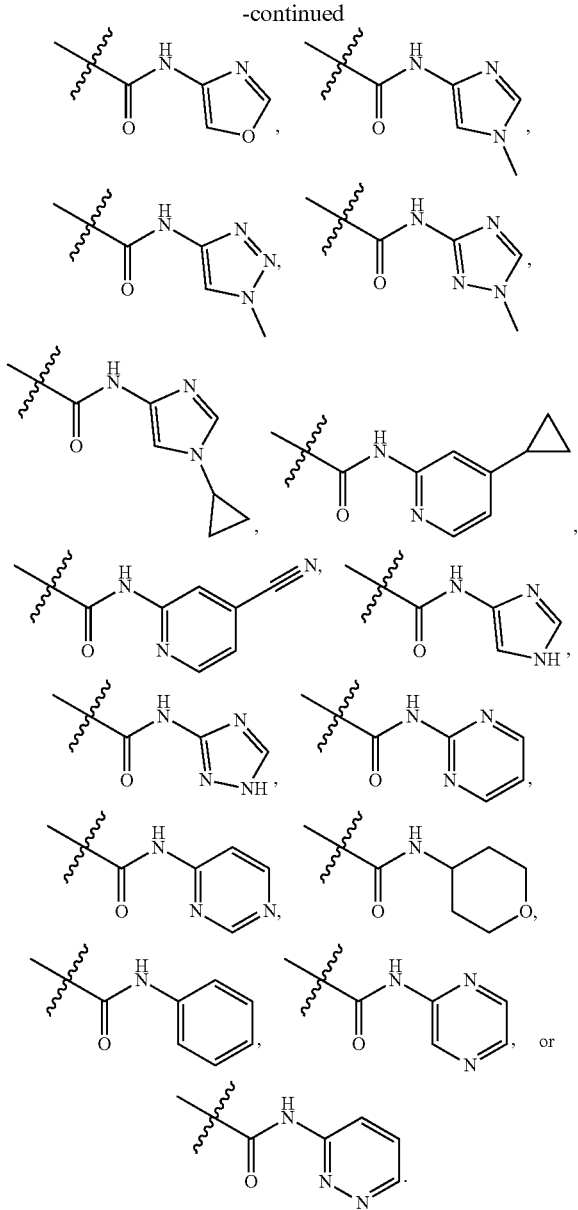

In some embodiments, $R^{7c}$ is

wherein $T^{2c}$ is H, halo, cyano, $OR^{ec}$, $OR^{fc}$, $C(O)R^{fc}$, $NR^{ec}R^{fc}$, $C(O)NR^{ec}R^{fc}$, $NR^{ec}C(O)R^{fc}$, $C_6$-$C_{10}$ aryl, 5- to 10-membered heteroaryl, $C_3$-$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{cc}$, $C_1$-$C_6$ alkoxyl or $C_1$-$C_6$ alkyl optionally substituted with one or more of $NR^{cc}R^{de}$.

In some embodiments, $R^{7c}$ is

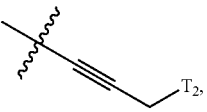

wherein $T^{2c}$ is 5- to 10-membered heteroaryl or 4- to 12-membered heterocycloalkyl optionally substituted with one or more of halo, hydroxyl, $C_1$-$C_6$ alkoxyl or $C_1$-$C_6$ alkyl.

In some embodiments, $R^{7c}$ is

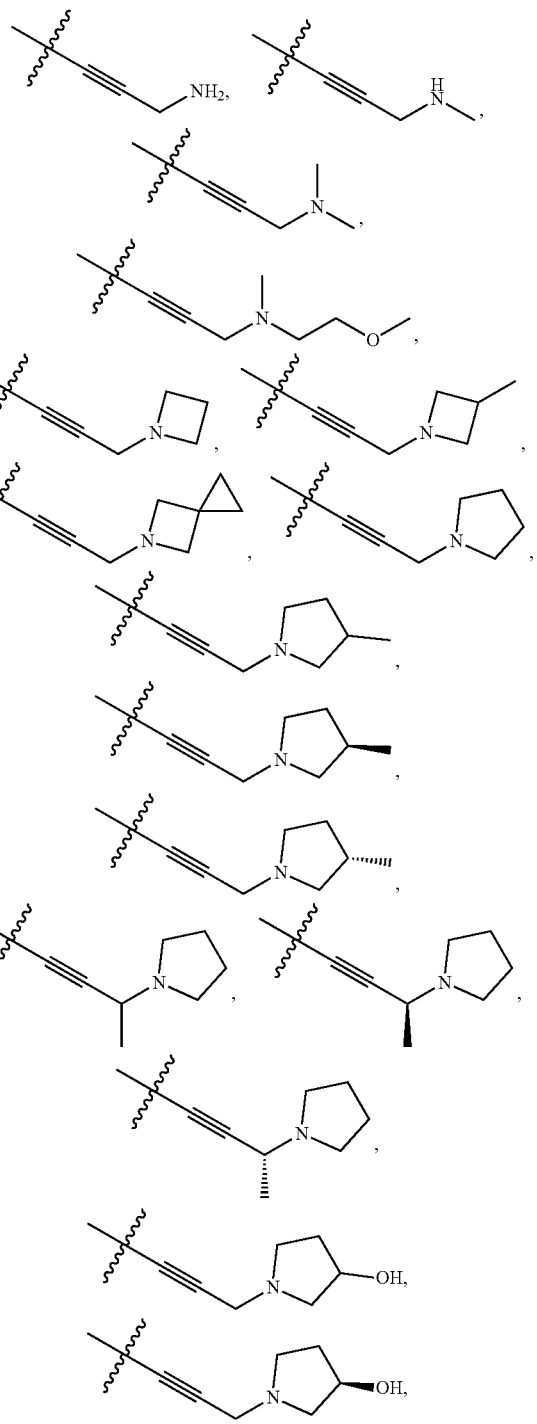

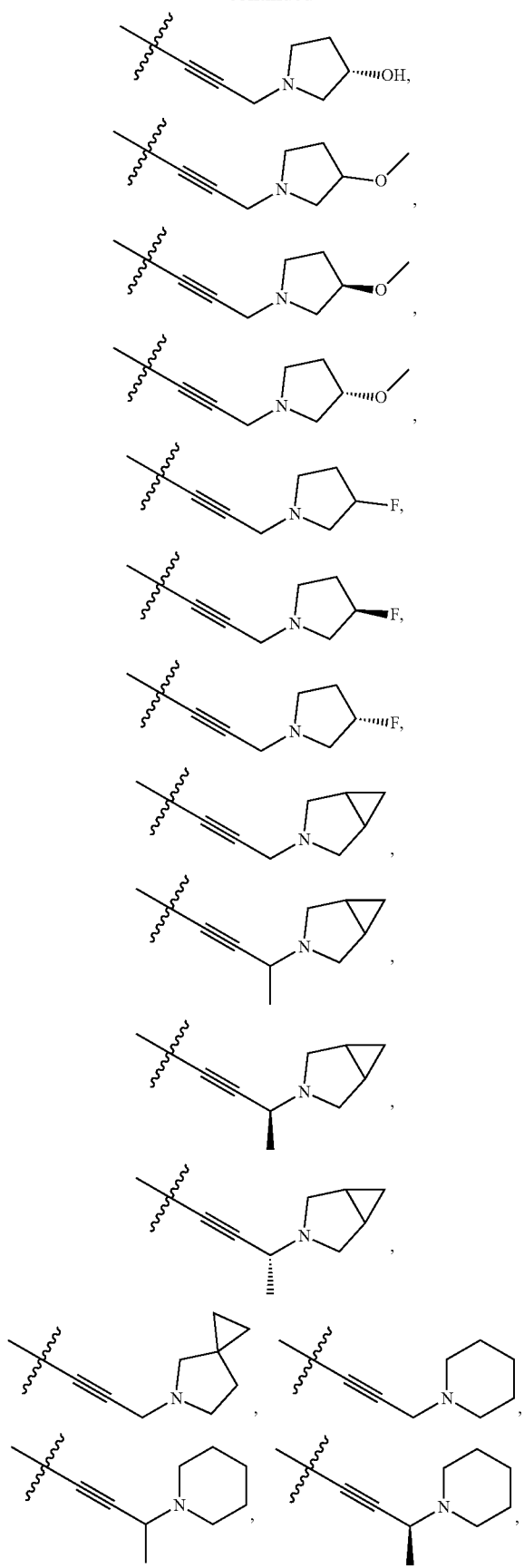
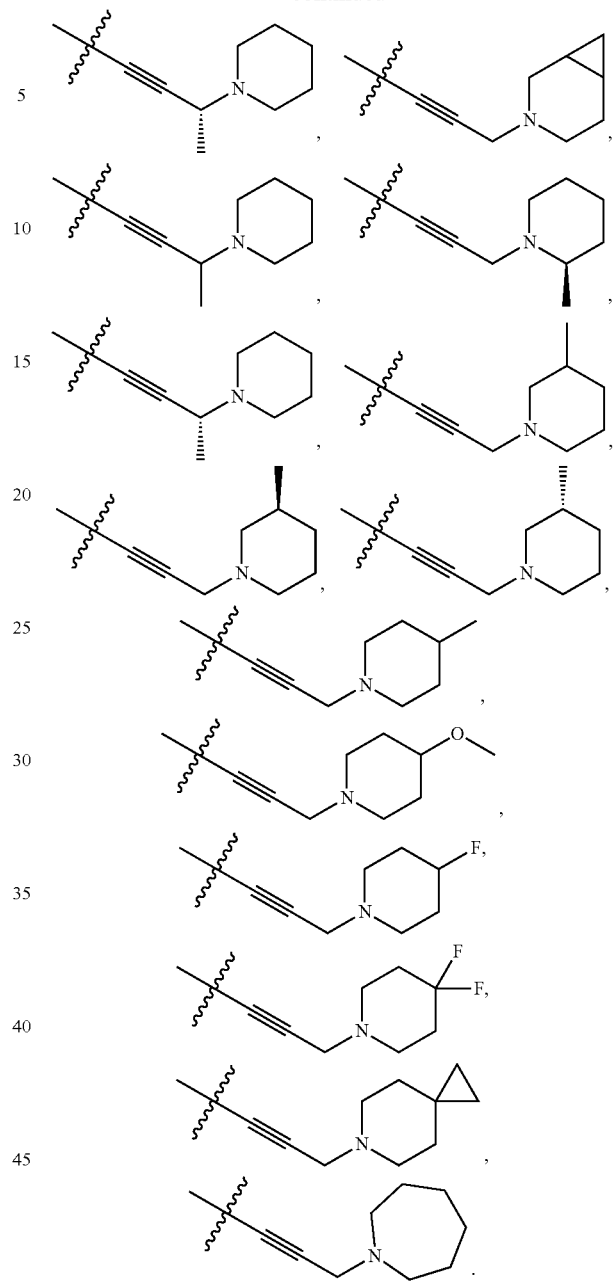

In some embodiments, $R^{7c}$ is $OR^{ec}$.

In some embodiments, $R^{7c}$ is $OR^{fc}$.

In some embodiments, $R^{7c}$ is —$CH_2$-$T^{2c}$, wherein $T^{2c}$ is H, halo, cyano, $OR^{ec}$, $OR^{fc}$ $C(O)R^{fc}$, $NR^{7c}R^{fc}$, $C(O)NR^{ec}R^{fc}$, $NR^{ec}C(O)R^{fc}$, $C_6$-$C_{10}$ aryl, 5- to 10-membered heteroaryl, $C_3$—$C_{12}$ cycloalkyl, or 4- to 12-membered heterocycloalkyl containing 1-4 heteroatoms selected from N, O, and S, and wherein the $C_6$-$C_{10}$ aryl, 5- to 10-membered heteroaryl, $C_3$-$C_{12}$ cycloalkyl or 4- to 12-membered heterocycloalkyl is optionally substituted with one or more of halo, hydroxyl, cyano, $C_1$-$C_6$ haloalkyl, —$SO_2R^{cc}$, $C_1$-$C_6$ alkoxyl or $C_1$-$C_6$ alkyl optionally substituted with one or more of $NR^{cc}R^{dc}$.

In some embodiments, $R^{7c}$ is —$CH_2$—$OR_8$.

In some embodiments, $R^{7c}$ is —$CH_2$—$NR_7R_8$.

In some embodiments, $R^{7c}$ is
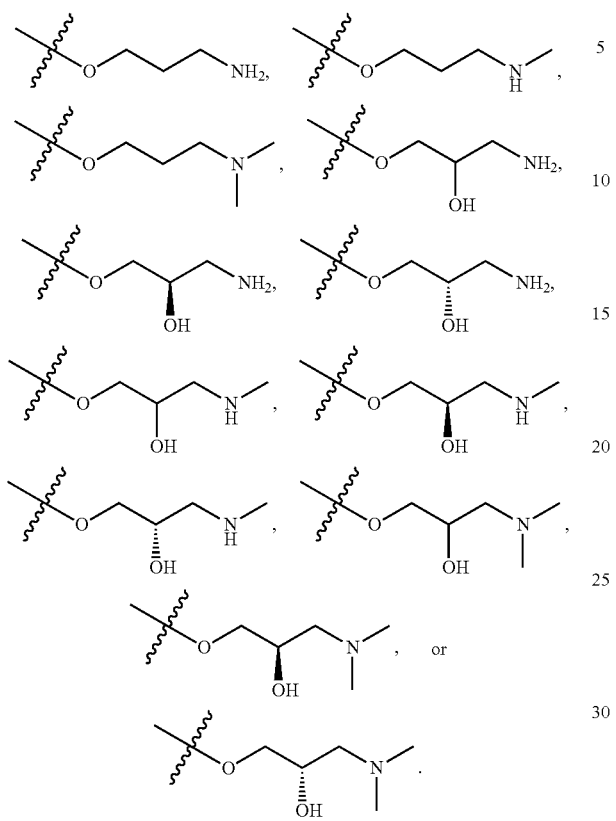
In some embodiments, $R^{7c}$ is
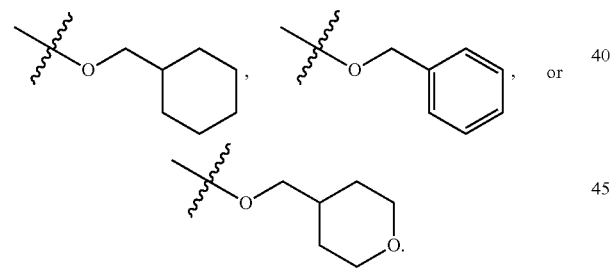
In some embodiments, $R^{7c}$ is
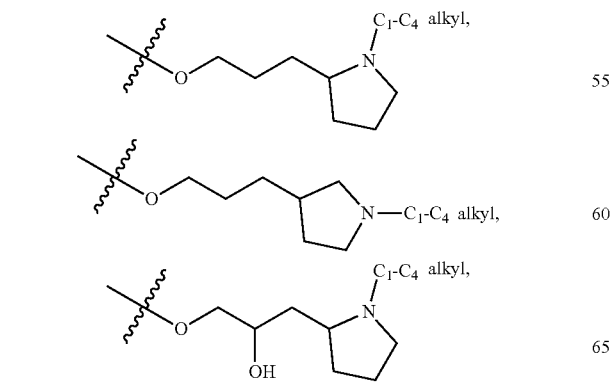
-continued
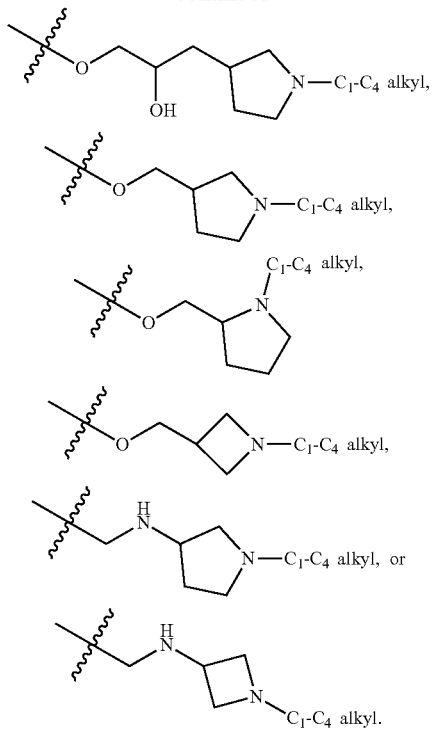
In some embodiments, $R^{7c}$ is
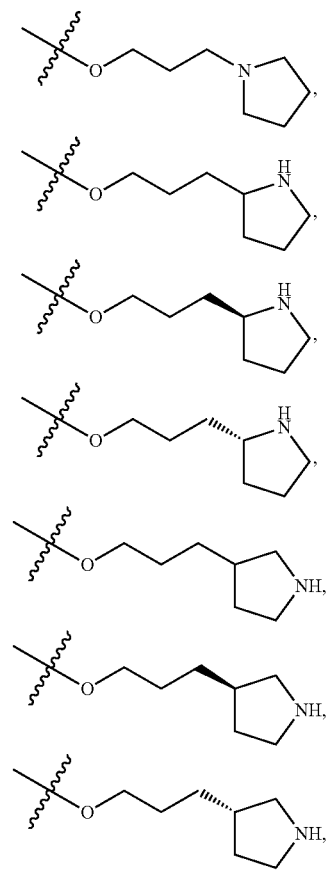

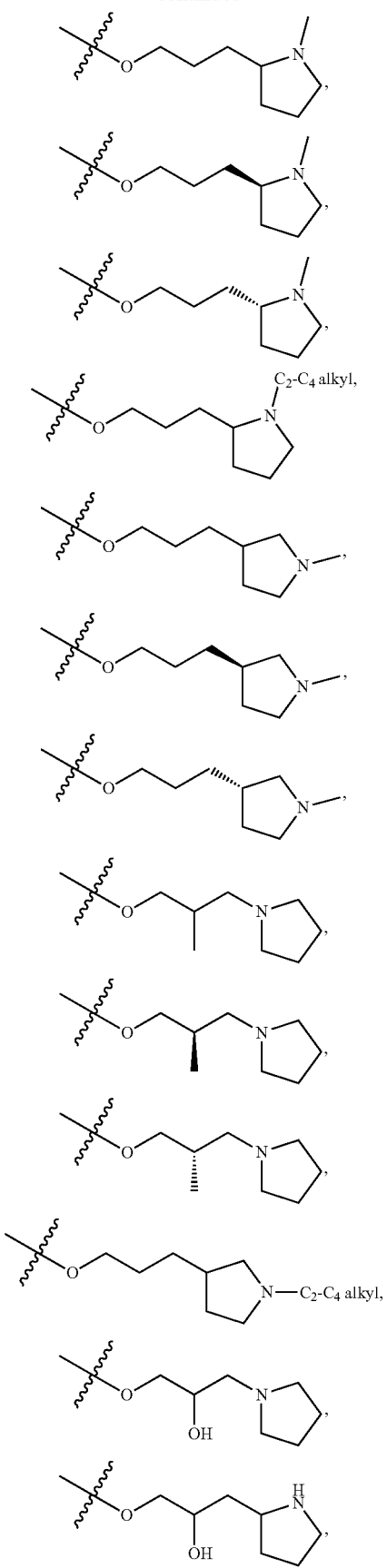
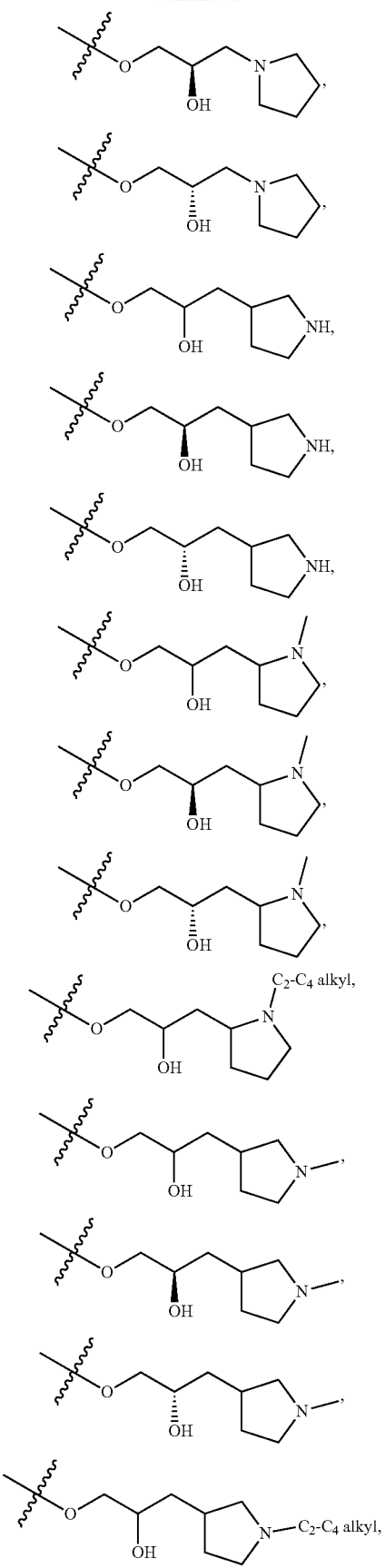

-continued
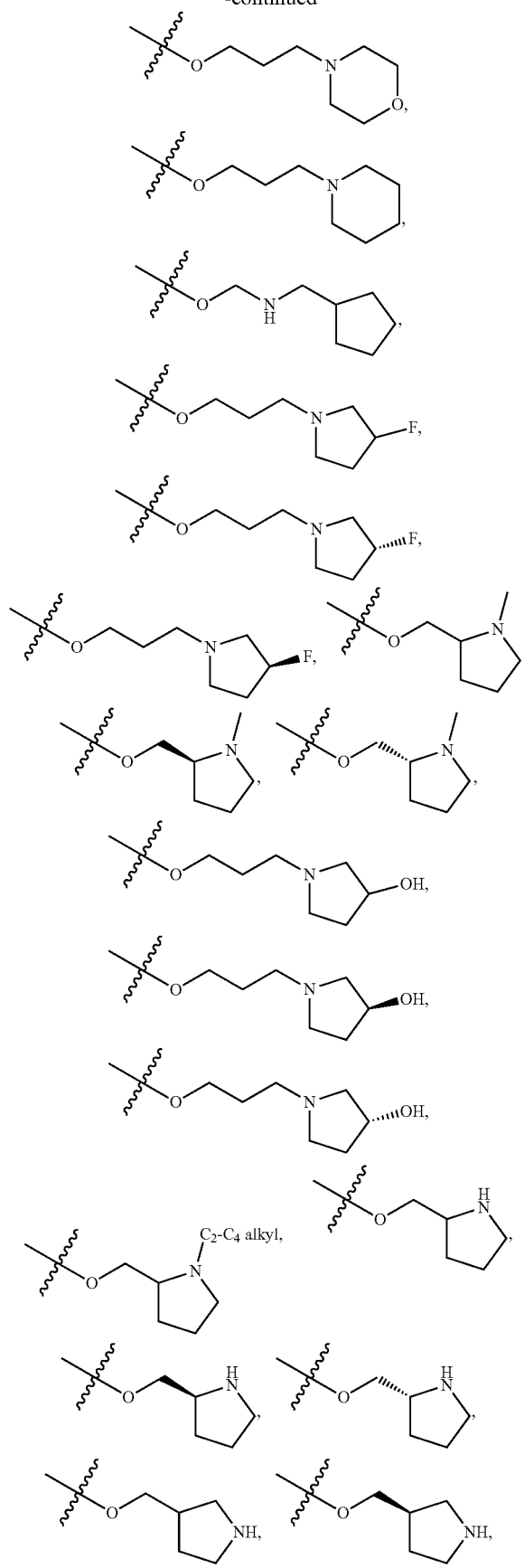
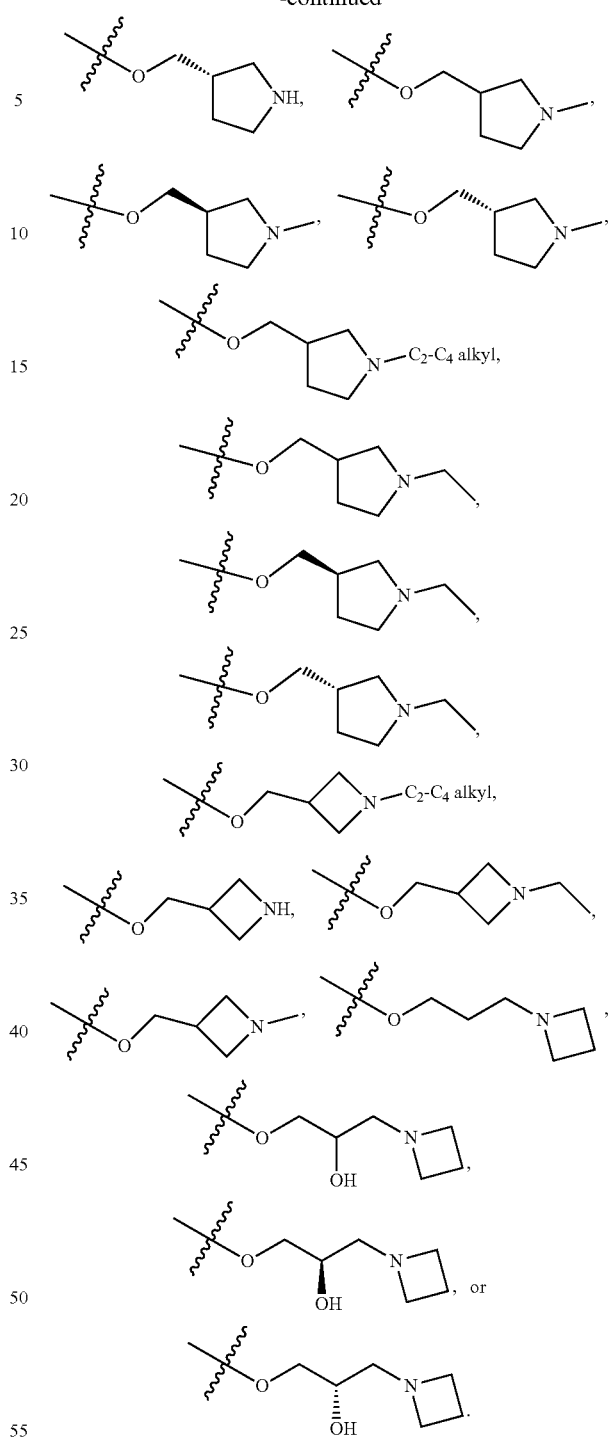
In some embodiments, $R^{7c}$ is
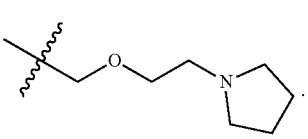 [SMILES: *COCCN1CCCC1]

In some embodiments, $R^{7c}$ is

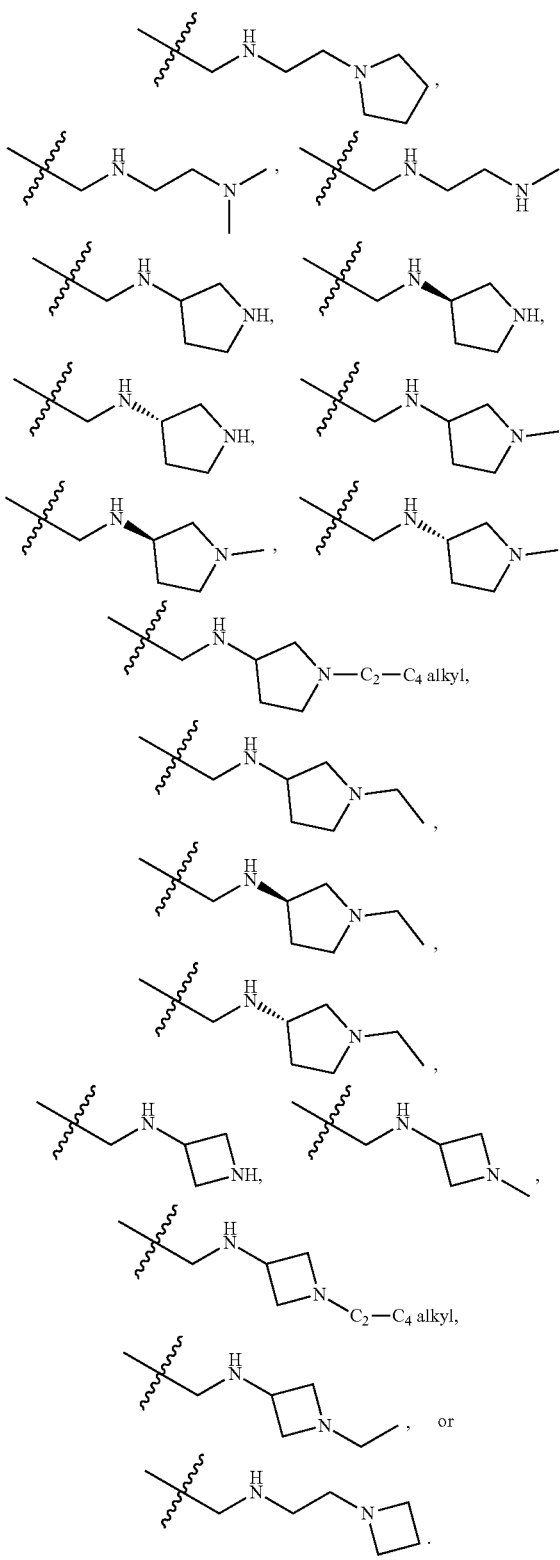

In some embodiments, $R^{7c}$ is $-Q^{2c}-T^{2c}$, in which $Q^{2c}$ is a bond or $C_1-C_6$ alkylene linker optionally substituted with one or more of halo, cyano, hydroxyl, amino, mono- or di-alkylamino, and $T^{2c}$ is 5- to 10-membered heteroaryl optionally substituted with one or more $-Q^{3c}-T^{3c}$.

In some embodiments, $R^{7c}$ is $-Q^{2c}-T^{2c}$, in which $Q^{2c}$ is a bond and $T^{2c}$ is 5- to 10-membered heteroaryl optionally substituted with one or more $-Q^{3c}-T^{3c}$.

In some embodiments, $T^{2c}$ is selected from N—,

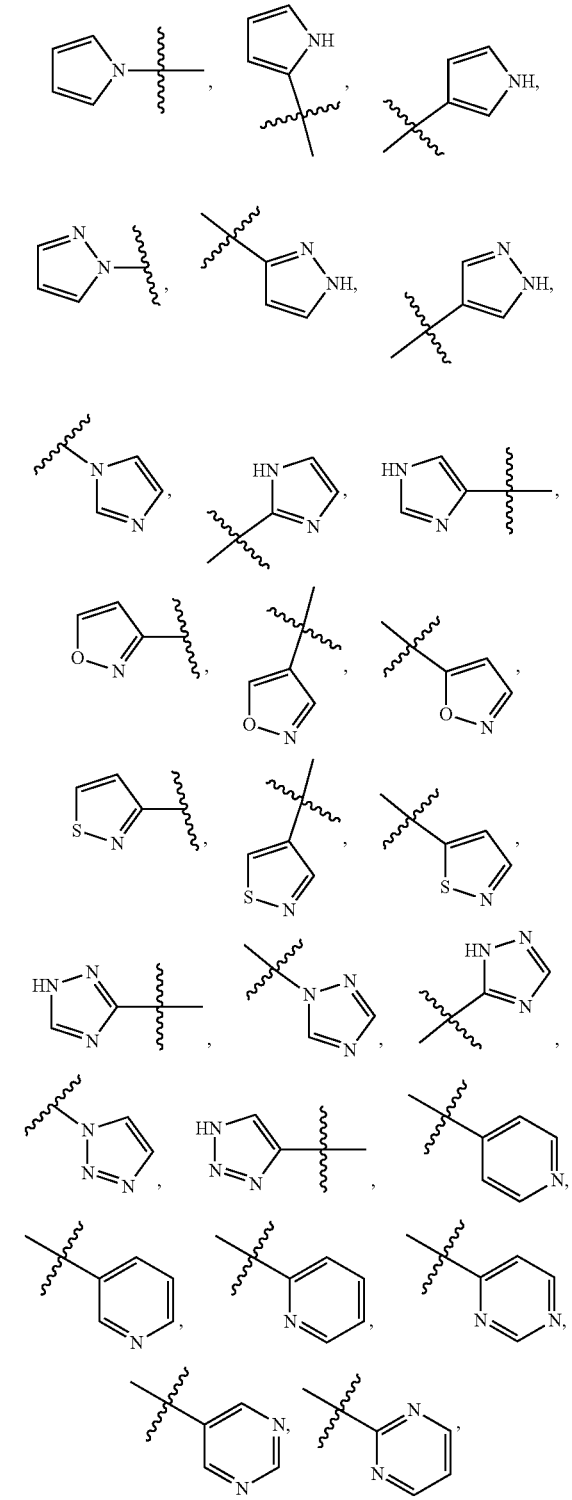

and tautomers thereof, each of which is optionally substituted with one or more $-Q^{3c}-T^{3}c$.

In some embodiments, $T^{2c}$ is selected from

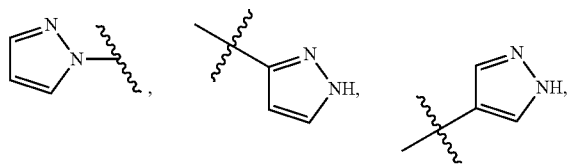 [SMILES: *n1cccn1 ; *c1cc[nH]n1 ; *c1cn[nH]c1]

and tautomers thereof, each of which is optionally substituted with one or more $-Q^{3c}-T^3c$.

In some embodiments, $T^{2c}$ is

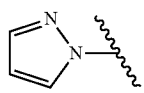

optionally substituted with one or more $-Q^{3c}-T^{3c}$.

In some embodiments, $T^{2c}$ is

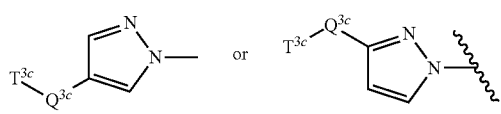

In some embodiments, $T^{2c}$ is

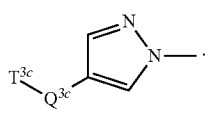

In some embodiments, $T^{2c}$ is

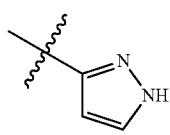 [SMILES: *c1cc[nH]n1]

optionally substituted with one or more $-Q^3-T^3$.

In some embodiments, $T^2$ is

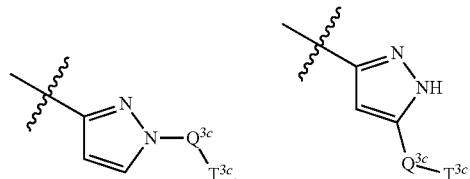

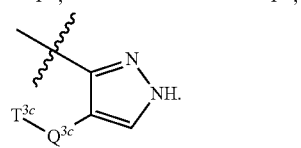

In some embodiments, $T^2$ is

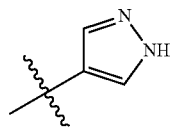 [SMILES: *c1cn[nH]c1]

optionally substituted with one or more $-Q^3-T^3$.

In some embodiments, $T^2$ is

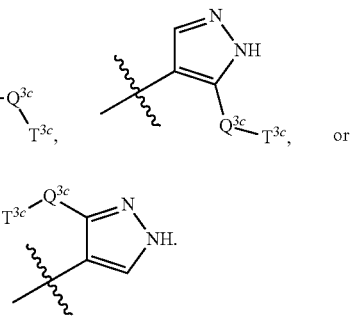

In some embodiments, each $Q^{3c}$ independently is a bond or $C_1$-$C_3$ alkylene linker each optionally substituted with one or more of halo, cyano, hydroxyl, or $C_1$-$C_6$ alkoxy, and each $T^{3c}$ independently is selected from the group consisting of H, $C_6$-$C_{10}$ aryl, 4- to 7-membered heterocycloalkyl containing 1-4 heteroatoms selected from N, O, and S, 5- to 6-membered heteroaryl, and $NR^{fc}R^{gc}$.

In some embodiments, each $Q^{3c}$ independently is a $C_1$-$C_3$ alkylene linker, and each $T^{3c}$ independently is $NR^{fc}R^{gc}$, each of $R^{fc}$ and $R^{gc}$ independently being H or $C_1$-$C_6$ alkyl.

In some embodiments, each $Q^{3c}$ independently is a $C_1$-$C_3$ alkylene linker, and each $T^{3c}$ independently is $NR^{fc}R^{gc}$, each of $R^{fc}$ and $R^{gc}$ independently being H or methyl.

In some embodiments, each $Q^{3c}$ independently is a $C_1$-$C_3$ alkylene linker, and each $T^{3c}$ independently is $NH_2$.

In some embodiments, each $Q^{3c}$ independently is methylene, and each $T^{3c}$ independently is $NH_2$.

In some embodiments, each $Q^{3c}$ independently is a $C_1$-$C_3$ alkylene linker, and each $T^{3c}$ independently is $NHCH_3$.

In some embodiments, each $Q^{3c}$ independently is methylene, and each $T^{3c}$ independently is $NHCH_3$.

In some embodiments, $R^{7c}$ is

In some embodiments, $R^{7c}$ is

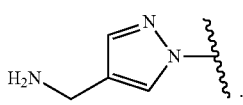

In some embodiments, $R^{7c}$ is

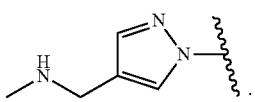

In some embodiments, each $Q^{3c}$ independently is a bond, and each $T^{3c}$ independently is selected from the group consisting of 4- to 7-membered heterocycloalkyl containing 1-4 heteroatoms selected from N, O, and S.

In some embodiments, each $Q^{3c}$ independently is a bond, and each $T^{3c}$ independently is 5-membered heterocycloalkyl containing 1-4 heteroatoms selected from N, O, and S.

In some embodiments, each $Q^{3c}$ independently is a bond, and each $T^{3c}$ independently is selected from

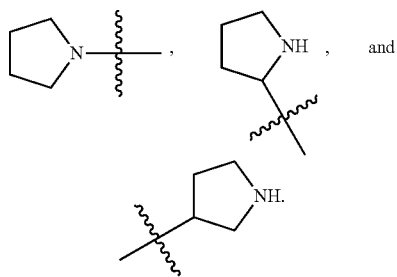

In some embodiments, each $Q^{3c}$ independently is a bond, and each $T^{3c}$ independently is selected from

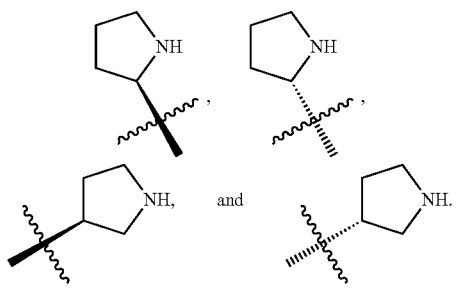

In some embodiments, each $Q^{3c}$ independently is a bond, and each $T^{3c}$ independently is

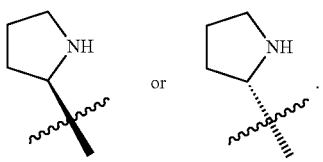

In some embodiments, each $Q^{3c}$ independently is a bond, and each $T^{3c}$ independently is

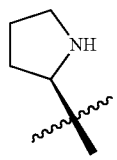

In some embodiments, each $Q^{3c}$ independently is a bond, and each $T^{3c}$ independently is

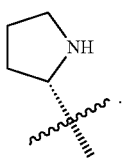

In some embodiments, each $Q^{3c}$ independently is a bond, and each $T^{3c}$ independently is

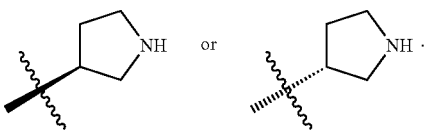

In some embodiments, each $Q^{3c}$ independently is a bond, and each $T^{3c}$ independently is

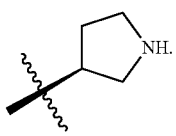

In some embodiments, each $Q^{3c}$ independently is a bond, and each $T^3c$ independently is

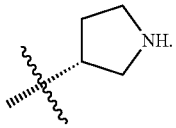

In some embodiments, $R^{7c}$ is

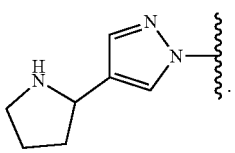 [SMILES: *n1cc([C@@H]2CCCN2)cn1]

In some embodiments, $R^{7c}$ is

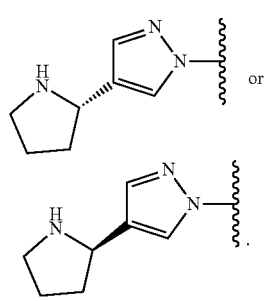

In some embodiments, $R^{7c}$ is

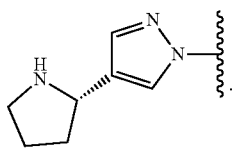

In some embodiments, $R^{7c}$ is

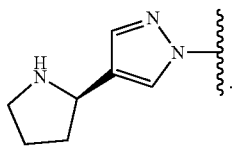 [SMILES: *n1cc([C@H]2CCCN2)cn1]

In some embodiments, $R^{7c}$ is. In

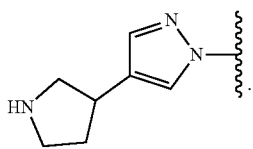

In some embodiments, $R^{7c}$ is

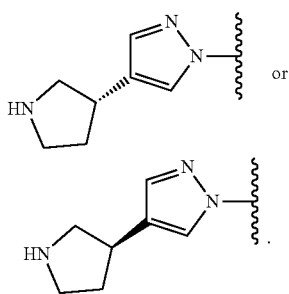 or

In some embodiments, $R^{7c}$ is

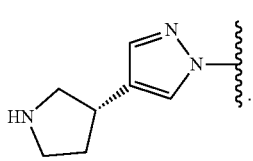

In some embodiments, $R^{7c}$ is

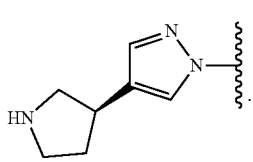

In some embodiments, at least one of $R^{8c}$ and $R^{9c}$ is H. In some embodiments, each of $R^{8c}$ and $R^{9c}$ is H. In some embodiments, $R^{8c}$ is H.

In some embodiments, $R^{9c}$ is $-Q^{4c}-T^{4c}$, in which $Q^{4c}$ is a bond or $C_1$-$C_6$ alkylene linker optionally substituted with one or more of halo, cyano, hydroxyl, or $C_1$-$C_6$ alkoxyl, and $T^{4c}$ is H, halo, $OR^{hc}$, $NR^{hc}R^{ic}$, $NR^{hc}C(O)R^{ic}$, $C(O)NR^{hc}R^{ic}$, $C(O)R^{hc}$, $C(O)OR^{hc}$, or $R^{S2c}$, in which $R^{S2c}$ is $C_3$-$C_8$ cycloalkyl or 4- to 7-membered heterocycloalkyl, and $R^{S2c}$ is optionally substituted with one or more $-Q^{5c}-T^{5c}$.

In some embodiments, each $Q^{5c}$ independently is a bond or $C_1$-$C_3$ alkylene linker.

In some embodiments, each $T^{5c}$ independently is selected from the group consisting of H, halo, cyano, $C_1$-$C_6$ alkyl, $OR^{jc}$, $C(O)R^{jc}$, $C(O)OR^{jc}$, $NR^{jc}R^{kc}$, $C(O)NR^{jc}R^{kc}$, and $NR^{jc}C(O)R^{kc}$.

In some embodiments, $R^{9c}$ is $C_1$-$C_3$ alkyl.

In some embodiments, $R^{14c}$ is H, halo, or $C_1$-$C_6$ alkyl.

In some embodiments, the compound is selected from those in Tables 1-6, 6A, and 7, tautomers thereof, and pharmaceutically acceptable salts of the compounds and tautomers.

In some embodiments, the compound is selected from those in Table 1, tautomers thereof, and pharmaceutically acceptable salts of the compounds and tautomers.

In some embodiments, the compound is selected from those in Table 2, tautomers thereof, and pharmaceutically acceptable salts of the compounds and tautomers.

In some embodiments, the compound is selected from those in Table 3, tautomers thereof, and pharmaceutically acceptable salts of the compounds and tautomers.

In some embodiments, the compound is selected from those in Table 4, tautomers thereof, and pharmaceutically acceptable salts of the compounds and tautomers.

In some embodiments, the compound is selected from those in Table 5, tautomers thereof, and pharmaceutically acceptable salts of the compounds and tautomers.

In some embodiments, the compound is selected from those in Table 6, tautomers thereof, and pharmaceutically acceptable salts of the compounds and tautomers.

In some embodiments, the compound is selected from those in Table 6A, tautomers thereof, and pharmaceutically acceptable salts of the compounds and tautomers.

In some embodiments, the compound is selected from those in Table 7, tautomers thereof, and pharmaceutically acceptable salts of the compounds and tautomers.

In some embodiments, the compound of is a selective inhibitor of EHMT2.

The present disclosure also provides a method of preventing or treating a cancer via inhibition of a methyltransferase enzyme selected from EHMT1 and EHMT2, the method comprising administering to a subject in need thereof a therapeutically effective amount of a compound of the present disclosure, and a therapeutically effective amount of one or more additional therapeutic agent.

In some embodiments, the compound of the present disclosure (e.g., the EHMT2 inhibitor) and the one or more additional therapeutic agent are administered simultaneously, sequentially, or alternately.

In some embodiments, the compound of the present disclosure (e.g., the EHMT2 inhibitor) and the one or more additional therapeutic agent are administered simultaneously. In some embodiments, the compound of the present disclosure (e.g., the EHMT2 inhibitor) and the one or more additional therapeutic agent are administered sequentially. In some embodiments, the compound of the present disclosure (e.g., the EHMT2 inhibitor) and the one or more additional therapeutic agent are administered alternately.

In some embodiments, the compound of the present disclosure (e.g., the EHMT2 inhibitor) is administered prior to the administration of the one or more additional therapeutic agent is administered prior to the administration of the compound of the present disclosure (e.g., the EHMT2 inhibitor).

In some embodiments, the compound of the present disclosure (e.g., the EHMT2 inhibitor) and the one or more additional therapeutic agent are administered in temporal proximity.

In some embodiments, the compound of the present disclosure (e.g., the EHMT2 inhibitor) and the one or more additional therapeutic agent are administered in a co-formulation.

In some embodiments, the compound of the present disclosure (e.g., the EHMT2 inhibitor) and the one or more additional therapeutic agent are administered in separate formulations.

In some embodiments, the compound of the present disclosure (e.g., the EHMT2 inhibitor) is administered with one or more drug holidays. In some embodiments, the compound of the present disclosure (e.g., the EHMT2 inhibitor) is administered without any drug holiday.

In some embodiments, the one or more additional therapeutic agent is administered with one or more drug holidays. In some embodiments, the one or more additional therapeutic agent is administered without any drug holiday.

In some embodiments, the one or more additional therapeutic agent comprises:

9CDHRA (9-cis-13,14-dihydro-retinoic acid),
A769662 (4-hydroxy-3-[4-(2-hydroxyphenyl)phenyl]-6-oxo-7H-thieno[2,3-b]pyridine-5-carbonitrile),
ABT263 (4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide),
AC-261066 (4-[4-(2-butoxyethoxy)-5-methyl-1,3-thiazol-2-yl]-2-fluorobenzoic acid),
AC-55649 (4-(4-octylphenyl)benzoic acid),
acitretin ((2E,4E,6E,8E)-9-(4-methoxy-2,3,6-trimethylphenyl)-3,7-dimethylnona-2,4,6,8-tetraenoic acid),
adapalene (6-[3-(1-adamantyl)-4-methoxyphenyl]naphthalene-2-carboxylic acid),
aldesleukin (proleukin).
alitretinoin (9-cis-retinoic acid),
all-trans retinoic acid (ARTA; 2E,4E,6E,8E)-3,7-Dimethyl-9-(2,6,6-trimethylcyclohexen-1-yl)nona-2,4,6,8-tetraenoic acid),
AM-580 (4-[(5,5,8,8-tetramethyl-6,7-dihydronaphthalene-2-carbonyl)amino]benzoic acid),
ara-C (cytarbine; 4-amino-1-[(2R,3S,4R,5R)-3,4-dihydroxy-5-(hydroxymethyl)oxolan-2-yl]pyrimidin-2-one)),
arotinoid acid (4-[(E)-2-(5,5,8,8-tetramethyl-6,7-dihydronaphthalen-2-yl)prop-1-enyl]benzoic acid).
arsenic trioxide,
AS252424 ((5Z)-5-[[5-(4-fluoro-2-hydroxyphenyl)furan-2-yl]methylidene]-1,3-thiazolidine-2,4-dione),
azacitidine (4-Amino-1-(β-D-ribofuranosyl)-1,3,5-triazin-2 (1H)-one),
AZD7762 (3-(carbamoylamino)-5-(3-fluorophenyl)-N-[(3S)-piperidin-3-yl]thiophene-2-carboxamide),
barasertib (AZD1152; 2-[ethyl-[3-[4-[[5-[2-(3-fluoroanilino)-2-oxoethyl]-1H-pyrazol-3-yl]amino]quinazolin-7-yl]oxypropyl]amino]ethyl dihydrogen phosphate),
bevacizumab (avastin; CAS No. 216974-75-3),
bexarotene (4-[1-(3,5,5,8,8-pentamethyl-6,7-dihydronaphthalen-2-yl)ethenyl]benzoic acid),
BI-78D3 (4-(2,3-dihydro-1,4-benzodioxin-6-yl)-3-[(5-nitro-1,3-thiazol-2-yl)sulfanyl]-1H-1,2,4-thiazol-5-one),
BI-D1870 (2-(3,5-difluoro-4-hydroxyanilino)-5,7-dimethyl-8-(3-methylbutyl)-7H-pteridin-6-one),
binimetinib (6-(4-bromo-2-fluoroanilino)-7-fluoro-N-(2-hydroxyethoxy)-3-methylbenzimidazole-5-carboxamide),
bivanib (BI2536; 4-[[(7R)-8-cyclopentyl-7-ethyl-5-methyl-6-oxo-7H-pteridin-2-yl]amino]-3-methoxy-N-(1-methylpiperidin-4-yl)benzamide),
bleomycin ((3-{[(2'-{(5S,8S,9S,10R,13S)-15-{6-amino-2-[(1 S)-3-amino-1-{[(2S)-2,3-diamino-3-oxopropyl] amino}-3-oxopropyl]-5-methylpyrimidin-4-yl}-13-[{ [(2R,3S,4S,5S,6S)-3-{[(2R,3S,4S,5R,6R)-4-(carbamoyloxy)-3,5-dihydroxy-6-(hydroxymethyl) tetrahydro-2H-pyran-2-yl]oxy}-4,5-dihydroxy-6-(hydroxymethyl)tetrahydro-2H-pyran-2-yl]oxy} (1H-imidazol-5-yl)methyl]-9-hydroxy-5-[(1R)-1-hydroxyethyl]-8,10-dimethyl-4,7,12,15-tetraoxo-3,6,11, 14-tetraazapentadec-1-yl}-2,4'-bi-1,3-thiazol-4-yl) carbonyl]amino}propyl)(dimethyl)sulfonium),
BMS-493 (4-[(E)-2-[5,5-dimethyl-8-(2-phenylethynyl)-6H-naphthalen-2-yl]ethenyl]benzoic acid),
BMS-536924 ((3Z)-4-[[(2S)-2-(3-chlorophenyl)-2-hydroxyethyl]amino]-3-(4-methyl-6-morpholin-4-yl-1,3-dihydrobenzimidazol-2-ylidene)pyridin-2-one)
BMS-753 (4-[(1,1,3,3-tetramethyl-2-oxoindene-5-carbonyl) amino]benzoic acid),
BMS-93559,
BMS-961 (3-fluoro-4-[[(2S)-2-hydroxy-2-(5,5,8,8-tetramethyl-6,7-dihydronaphthalen-2-yl)acetyl]amino]benzoic acid).
bortezomib ([(1R)-3-methyl-1-[[(2S)-3-phenyl-2-(pyrazine-2-carbonylamino)propanoyl]-amino]butyl]boronic acid),
buparlisib (BKM120; 5-(2,6-dimorpholin-4-ylpyrimidin-4-yl)-4-(trifluoromethyl)pyridin-2-amine),
C75 ((2R,3S)-4-methylidene-2-octyl-5-oxooxolane-3-carboxylic acid),
carboplatin (cis-diammine(cyclobutane-1,1-dicarboxylate-O,O')platinum(II)),
CD-1530 (4-[7-(1-adamantyl)-6-hydroxynaphthalen-2-yl] benzoic acid),
CD-2314 (5-(5,5,8,8-tetramethyl-6,7-dihydroanthracen-2-yl)thiophene-3-carboxylic acid),
CD-437 (6-[3-(1-adamantyl)-4-hydroxyphenyl]naphthalene-2-carboxylic acid),
cediranib (AZD-2171; 4-[(4-fluoro-2-methyl-1H-indol-5-yl)oxy]-6-methoxy-7-(3-pyrrolidin-1-ylpropoxy)quinazoline)
Ch-55 (4-[(E)-3-(3,5-ditert-butylphenyl)-3-oxoprop-1-enyl] benzoic acid),
CHIR265 (1-methyl-5-[2-[5-(trifluoromethyl)-1H-imidazol-2-yl]pyridin-4-yl]oxy-N-[4-(trifluoromethyl)phenyl] benzinmidazol-2-amine),
cisplatin ((SP-4-2)-diamminedichloroplatinum(II)),
cladribine (5-(6-Amino-2-chloro-purin-9-yl)-2-(hydroxymethyl)oxolan-3-ol),
clofarabine (5-(6-amino-2-chloro-purin-9-yl)-4-fluoro-2-(hydroxymethyl)oxolan-3-ol),
cobimetinib ([3,4-difluoro-2-(2-fluoro-4-iodoanilino)phenyl]-[3-hydroxy-3-[(2S)-piperidin-2-yl]azetidin-1-yl] methanone),
cobimetinib (cotellic; [3,4-difluoro-2-(2-fluoro-4-iodoanilino)phenyl]-[3-hydroxy-3-[(2S)-piperidin-2-yl]azetidin-1-yl]methanone),
crizotinib (PF2341066; 3-[(1R)-1-(2,6-dichloro-3-fluorophenyl)ethoxy]-5-(1-piperidin-4-ylpyrazol-4-yl)pyridin-2-amine),
cytarabine (4-amino-1-[(2R,3S,4S,5R)-3,4-dihydroxy-5-(hydroxymethyl)oxolan-2-yl]pyrimidin-2-one).

dabrafenib (tafinlar; N-[3-[5-(2-aminopyrimidin-4-yl)-2-tert-butyl-1,3-thiazol-4-yl]-2-fluorophenyl]-2,6-difluorobenzenesulfonamide), dacarbazine (5-(3,3-Dimethyl-1-triazenyl)imidazole-4-carboxamide), dactolisib (NVP-BEZ235; 2-methyl-2-[4-(3-methyl-2-oxo-8-quinolin-3-ylimidazo[4,5-c]quinolin-1-yl)phenyl]propanenitrile), daporinad (FK866; (E)-N-[4-(1-benzoylpiperidin-4-yl)butyl]-3-pyridin-3-ylprop-2-enamide).

darinaparsin ((2S)-2-amino-5-[[(2R)-1-(carboxymethylamino)-3-dimethylarsanylsulfanyl-1-oxopropan-2-yl]amino]-5-oxopentanoic acid), dasatanib (N-(2-chloro-6-methylphenyl)-2-[[6-[4-(2-hydroxyethyl)piperazin-1-yl]-2-methylpyrimidin-4-yl]amino]-1,3-thiazole-5-carboxamide), daunorubicin ((8S,10S)-8-acetyl-10-[(2S,4S,5S,6S)-4-amino-5-hydroxy-6-methyl-oxan-2-yl]oxy-6,8,11-trihydroxy-1-methoxy-9,10-dihydro-7H-tetracene-5,12-dione), decitabine (4-Amino-1-(2-deoxy-β-D-erythro-pentofuranosyl)-1,3,5-triazin-2(1H)-one), dinaciclib (2-[(2S)-1-[3-ethyl-7-[(1-oxidopyridin-1-ium-3-yl)methylamino]pyrazolo[1,5-a]pyrimidin-5-yl]piperidin-2-yl]ethanol), diphtheria toxin-Interleukin-2 fusion protein (denileukin diftitox; CAS No. 173146-27-5), disulfiram (diethylcarbamothioylsulfanyl N,N-diethylcarbamodithioate), docetaxel (1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}), dorsomorphin (6-[4-(2-piperidin-1-ylethoxy)phenyl]-3-pyridin-4-ylpyrazolo[1,5-a]pyrimidine), dovitinib (CHIR-258; (3Z)-4-amino-5-fluoro-3-[5-(4-methylpiperazin-1-yl)-1,3-dihydrobenzimidazol-2-ylidene]quinolin-2-one).

DS-8273a,

EC 23 (4-[2-(5,6,7,8-tetrahydro-5,5,8,8-tetramethyl-2-naphthalenyl)ethynyl]-benzoic acid).

elesciomol (STA-4783; 1-N',3-N'-bis(benzenecarbonothioyl)-1-N',3-N'-dimethylpropanedihydrazide), embelin (2,5-dihydroxy-3-undecylcyclohexa-2,5-diene-1,4-dione), enasidenib (AG-221; 2-methyl-1-[[4-[6-(trifluoromethyl)pyridin-2-yl]-6-[[2-(trifluoromethyl)pyridin-4-yl]amino]-1,3,5-triazin-2-yl]amino]propan-2-ol), encorafenib (methyl N-[1-[[4-[3-[5-chloro-2-fluoro-3-(methanesulfonamido)phenyl]-1-propan-2-ylpyrazol-4-yl]pyrimidin-2-yl]amino]propan-2-yl]carbamate).

ENMD-2076 (6-(4-methylpiperazin-1-yl)-N-(5-methyl-1H-pyrazol-3-yl)-2-[(E)-2-phenylethenyl]pyrimidin-4-amine).

enzastaurin (3-(1-methylindol-3-yl)-4-[1-[1-(pyridin-2-ylmethyl)piperidin-4-yl]indol-3-yl]pyrrole-2,5-dione), epacadostat ((3E)-3-[(3-bromo-4-fluoroanilino)-nitrosomethylidene]-4-[2-(sulfamoyl-amino)ethylamino]-1,2,5-oxadiazole), erlotinib (N-(3-ethynylphenyl)-6,7-bis(2-methoxyethoxy)quinazolin-4-amine), etoposide (4'-Demethylepipodophyllotoxin 9-(4,6-O-ethylidene-β-D-glucopyranoside)), etretinate (ethyl (2E,4E,6E,8E)-9-(4-methoxy-2,3,6-trimethylphenyl)-3,7-dimethylnona-2,4,6,8-tetraenoate), everolimus ((1R,9S,12S,15R,16E,18R,19R,21R,23S,24E,26E,28E,30S,32S,35R)-1,18-Dihydroxy-12-{(2R)-1-[(1S,3R,4R)-4-(2-hydroxyethoxy)-3-methoxycyclohexyl]propan-2-yl}-19,30-dimethoxy-15,17,21,23,29,35-hexamethyl-11,36-dioxa-4-azatricyclo[30.3.1.0$^{4,9}$]-hexatriaconta-16,24,26,28-tetraene-2,3,10,14,20-pentone), EX527 (6-chloro-2,3,4,9-tetrahydro-1H-carbazole-1-carboxamide), fenretinide ((2E,4E,6E,8E)-N-(4-hydroxyphenyl)-3,7-dimethyl-9-(2,6,6-trimethyl-cyclohexen-1-yl)nona-2,4,6,8-tetraenamide), FH535 (2,5-dichloro-N-(2-methyl-4-nitrophenyl)benzenesulfonamide), fingolimod (2-amino-2-[2-(4-octylphenyl)ethyl]propane-1,3-diol), fludarabine ([(2R,3R,4S,5R)-5-(6-amino-2-fluoro-purin-9-yl)-3,4-dihydroxy-oxolan-2-yl]methoxyphosphonic acid).

fotemustine (1-(2-chloroethyl)-3-(1-diethoxyphosphorylethyl)-1-nitrosourea), ganetespib ((5Z)-5-(4-hydroxy-6-oxo-3-propan-2-ylcyclohexa-2,4-dien-1-ylidene)-4-(1-methylindol-5-yl)-1,2,4-triazolidin-3-one), gemcitabine (4-amino-1-[(2R,4R,5R)-3,3-difluoro-4-hydroxy-5-(hydroxymethyl)oxolan-2-yl]pyrimidin-2-one), gilteritinib (6-ethyl-3-[3-methoxy-4-[4-(4-methylpiperazin-1-yl)piperidin-1-yl]anilino]-5-(oxan-4-ylamino)pyrazine-2-carboxamide), glasdegib (1-[(2R,4R)-2-(1H-benzimidazol-2-yl)-1-methylpiperidin-4-yl]-3-(4-cyanophenyl)urea), GSK0660 (methyl 3-[(4-anilino-2-methoxyphenyl)sulfamoyl]thiophene-2-carboxylate),

GSK2132231A,

GSK650394 (2-cyclopentyl-4-(5-phenyl-1H-pyrrolo[2,3-b]pyridin-3-yl)benzoic acid), guadecitabine ((2R,3S,5R)-5-(4-amino-2-oxo-1,3,5-triazin-1(2H)-yl)-2-(hydroxymethyl)-tetrahydrofuran-3-yl (((2S,3R,5R)-5-(2-amino-(6-oxo-1H-purin-9(6H)-yl)-3-hydroxytetrahydrofuran-2-yl)methyl) hydrogen phosphate).

GW0742 (2-[4-[[2-[3-fluoro-4-(trifluoromethyl)phenyl]-4-methyl-1,3-thiazol-5-yl]methylsulfanyl]-2-methylphenoxy]acetic acid), GW2580 (5-[[3-methoxy-4-[(4-methoxyphenyl)methoxy]phenyl]methyl]pyrimidine-2,4-diamine), GW441756 ((3Z)-3-[(1-methylindol-3-yl)methylidene]-1H-pyrrolo[3,2-b]pyridin-2-one), GW9662 (2-chloro-5-nitro-N-phenylbenzamide).

HIF-1i, ibrutinib (1-[(3R)-3-[4-amino-3-(4-phenoxy phenyl)pyrazolo[3,4-d]pyrimidin-1-yl]piperidin-1-yl]prop-2-en-1-one), idarubicin ((7S,9S)-9-acetyl-7-[(2R,4S,5S,6S)-4-amino-5-hydroxy-6-methyloxan-2-yl]oxy-6,9,11-trihydroxy-8,10-dihydro-7H-tetracene-5,12-dione), imatinib (4-[(4-methylpiperazin-1-yl)methyl]-N-(4-methyl-3-{[4-(pyridin-3-yl)pyrimidin-2-yl]amino}phenyl)benzamide), IMD-0354 (N-[3,5-bis(trifluoromethyl)phenyl]-5-chloro-2-hydroxy benzamide), ImmuniCell®, indole-3-carbinol, interferon alfa 2b (intron a; CAS No. 98530-12-2).

interleukin-2 (IL-2)

IPA-3 (1-[(2-hydroxynaphthalen-1-yl)disulfanyl]naphthalen-2-ol), ipatasertinib (GDC-0068; (2S)-2-(4-chlorophenyl)-1-[4-[(5R,7R)-7-hydroxy-5-methyl-6,7-dihydro-5H-cyclopenta[d]pyrimidin-4-yl]piperazin-1-yl]-3-(propan-2-ylamino)propan-1-one), ipilimumab (CAS No. 477202-00-9).

ipilimumab (yervoy; CAS No. 477202-00-9), isotretinoin ((2Z,4E,6E,8E)-3,7-dimethyl-9-(2,6,6-trimethylcyclohexen-1-yl)nona-2,4,6,8-tetraenoic acid), ivosidenib (AG-120; (2R)—N-[(1R)-1-(2-chlorophenyl)-2-[(3,3-difluorocyclobutyl)amino]-2-oxoethyl]-1-(4-cyanopyridin-2-yl)-N-(5-fluoropyridin-3-yl)-5-oxopyrrolidine-2-carboxamide), JZL184 ((4-nitrophenyl) 4-[bis(1,3-benzodioxol-5-yl)-hydroxymethyl]piperidine-1-carboxylate), KU0063794 ([5-[2-[(2R,6S)-2,6-dimethylmorpholin-4-yl]-4-morpholin-4-ylpyrido[2,3-d]pyrimidin-7-yl]-2-methoxyphenyl]methanol), KU-55933 (2-morpholin-4-yl-6-thianthren-1-ylpyran-4-one), L779450 (2-chloro-5-(2-phenyl-5-pyridin-4-yl-1H-imidazol-4-yl)phenol), lapatinib (N-[3-chloro-4-[(3-fluorophenyl)methoxy]phenyl]-6-[5-[(2-methylsulfonylethylamino)methyl]furan-2-yl]quinazolin-4-amine), laromustine (1-[2-chloroethyl(methylsulfonyl)amino]-3-methyl-1-methylsulfonylurea), lenalidomide (3-(7-amino-3-oxo-1H-isoindol-2-yl)piperidine-2,6-dione), lestaurtinib ((5S,6S,8R)-6-Hydroxy-6-(hydroxymethyl)-5-methyl-7,8,14,15-tetrahydro-5H-16-oxa-4b,8a,14-triaza-5,8-methanodibenzo[b,h]cycloocta[jkl]cyclopenta[e]-asindacen-13(6H)-one).

LFM-A13 ((Z)-2-cyano-N-(2,5-dibromophenyl)-3-hydroxybut-2-enamide), linsitinib (OSI906; 3-[8-amino-1-(2-phenylquinolin-7-yl)imidazo[1,5-a]pyrazin-3-yl]-1-methylcyclobutan-1-ol), lirilumab (CAS No. 1000676-41-4),

LSN415169, melphalan ((2S)-2-amino-3-[4-[bis(2-chloroethyl)amino]phenyl]propanoic acid), mercaptopurine (3,7-dihydropurine-6-thione), methotrexate (2S)-2-[(4-{[(2,4-Diaminopteridin-6-yl)methyl](methyl)amino}benzoyl)-amino]pentanedioic acid), midostaurin (PKC-412; (9S,10R,11R,13R)-2,3,10,11,12,13-Hexahydro-1-methoxy-9-methyl-11-(methylamino)-9,13-epoxy-1H,9H-diindolo[1,2,3-gh:3',2',1'-lm]pyrrolo[3,4-j][1,7]benzodiamzonine-1-one).

mitomycin (mitomycin A, mitomycin B, or mitomycin C).

mitoxantrone (1,4-dihydroxy-5,8-bis[2-(2-hydroxyethylamino)ethylamino]-anthracene-9,10-dione).

MK-1775 (1-[6-(2-hydroxypropan-2-yl)pyridin-2-yl]-6-[4-(4-methylpiperazin-1-yl)anilino]-2-prop-2-enylpyrazolo[3,4-d]pyrimidin-3-one), MK-2206 (8-[4-(1-aminocyclobutyl)phenyl]-9-phenyl-2H-[1,2,4]triazolo[3,4-f][1,6]naphthyridin-3-one).

MVax, nilotinib (4-methyl-N-[3-(4-methylimidazol-1-yl)-5-(trifluoromethyl)phenyl]-3-[(4-pyridin-3-ylpyrimidin-2-yl)amino]benzamide).

nilutamide (5,5-dimethyl-3-[4-nitro-3-(trifluoromethyl)phenyl]imidazolidine-2,4-dione), nimustine (3-[(4-amino-2-methylpyrimidin-5-yl)methyl]-1-(2-chloroethyl)-1-nitrosourea), nivolumab (opdivo; BMS-936558; CAS No. 946414-94-4), Nutlin-3 (4-[4,5-bis(4-chlorophenyl)-2-(4-methoxy-2-propan-2-yloxyphenyl)-4,5-dihydroimidazole-1-carbonyl]piperazin-2-one).

NVP-TAE684 (5-chloro-2-N-[2-methoxy-4-[4-(4-methylpiperazin-1-yl)piperidin-1-yl]phenyl]-N-(2-propan-2-ylsulfonylphenyl)pyrimidine-2,4-diamine), OSU-03012 (2-amino-N-[4-[5-phenanthren-2-yl-3-(trifluoromethyl)pyrazol-1-yl]phenyl]acetamide), paclitaxel ((2α,4α,5β,7β,10β,13α)-4,10-Bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate), palbociclib (PD332991; 6-acetyl-8-cyclopentyl-5-methyl-2-[(5-piperazin-1-ylpyridin-2-yl)amino]-pyrido[2,3-d]pyrimidin-7-one), palovarotene (4-[(E)-2-[5,5,8,8-tetramethyl-3-(pyrazol-1-ylmethyl)-6,7-dihydro-naphthalen-2-yl]ethenyl]benzoic acid), panobinostat ((2E)-N-hydroxy-3-[4-({[2-(2-methyl-1H-indol-3-yl)ethyl]amino}methyl)-phenyl]acrylamide).

pazopanib (5-[[4-[(2,3-dimethylindazol-6-yl)-methylamino]pyrimidin-2-yl]amino]-2-methylbenzenesulfonamide), PD173074 (1-tert-butyl-3-[2-[4-(diethylamino)butylamino]-6-(3,5-dimethoxyphenyl)pyrido[2,3-d]pyrimidin-7-yl]urea),

PDR001, pegylated interferon alfa-2b (sylatron; CAS No. 99210-65-8).

pembrolizumiab (keytruda; CAS No. 1374853-91-4), perifosine ((1,1-dimethylpiperidin-1-ium-4-yl) octadecyl phosphate), PF-04217903 (2-[4-[3-(quinolin-6-ylmethyl)triazolo[4,5-b]pyrazin-5-yl]pyrazol-1-yl]ethanol), PF-562271 (N-methyl-N-[3-[[[2-[(2-oxo-1,3-dihydroindol-5-yl)amino]-5-(trifluoromethyl)pyrimidin-4-yl]amino]methyl]pyridin-2-yl]methanesulfonamide), pictilisib (4-[2-(1H-indazol-4-yl)-6-[(4-methylsulfonylpiperazin-1-yl)methyl]thieno[3,2-d]pyrimidin-4-yl]morpholine), PIM-14a (5-[[3-(trifluoromethyl)phenyl]methylidene]-1,3-thiazolidine-2,4-dione), pinometostat ((2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol), pioglitazone (5-[[4-[2-(5-ethylpyridin-2-yl)ethoxy]phenyl]methyl]-1,3-thiazolidine-2,4-dione).

PLX-4720 (N-[3-(5-chloro-1H-pyrrolo[2,3-b]pyridine-3-carbonyl)-2,4-difluorophenyl]propane-1-sulfonamide).

pracinostat ((E)-3-(2-Butyl-1-(2-(diethylamino)ethyl)-1H-benzo[d]imidazol-5-yl)-N-hydroxyacrylamide), QS11 ((2S)-2-[[2-(2,3-dihydro-1H-inden-5-yloxy)-9-[(4-phenylphenyl)methyl]purin-6-yl]amino]-3-phenylpropan-1-ol), quizartinib (1-(5-(tert-Butyl)isoxazol-3-yl)-3-(4-(7-(2-morpholinoethoxy)benzo[d]imidazo-[2,1-b]thiazol-2-yl)phenyl)urea), retinoic acid ((2E,4E,6E,8E)-3,7-dimethyl-9-(2,6,6-trimethylcyclohexen-1-yl)nona-2,4,6,8-tetraenoic acid).

retinol (vitamin A; (2E,4E,6E,8E)-3,7-dimethyl-9-(2,6,6-trimethylcyclohexen-1-yl)nona-2,4,6,8-tetraen-1-ol), ribociclib (7-cyclopentyl-N,N-dimethyl-2-[(5-piperazin-1-ylpyridin-2-yl)amino]pyrrolo-[2,3-d]pyrimidine-6-carboxamide), RK1983 (4-[(1R)-1-aminoethyl]-N-(1H-pyrrolo[2,3-b]pyridin-4-yl)benzamide), ruxolitinib ((3R)-3-cyclopentyl-3-[4-(7H-pyrrolo[2,3-d]pyrimidin-4-yl)pyrazol-1-yl]propanenitrile).
sapacitibine (N-[1-[(2R,3S,4S,5R)-3-cyano-4-hydroxy-5-(hydroxymethyl)oxolan-2-yl]-2-oxopyrimidin-4-yl]hexadecanamide),
selumetinib (AZD-6244; 6-(4-bromo-2-chloroanilino)-7-fluoro-N-(2-hydroxyethoxy)-3-methylbenzimidazole-5-carboxamide),
seviprotimut-L,
silmitasertib (CX4945; 5-(3-chloroanilino)benzo[c][2,6]naphthyridine-8-carboxylic acid).
SNS-032 (N-[5-[(5-tert-butyl-1,3-oxazol-2-yl)methylsulfanyl]-1,3-thiazol-2-yl]piperidine-4-carboxamide),
SNS-314 (1-(3-chlorophenyl)-3-[5-[2-(thieno[3,2-d]pyrimidin-4-ylamino)ethyl]-1,3-thiazol-2-yl]urea),
sorafenib (4-[4-[[4-chloro-3-(trifluoromethyl)phenyl]carbamoylamino]phenoxy]-N-methylpyridine-2-carboxamide),
Src-I1 (6,7-dimethoxy-N-(4-phenoxyphenyl)quinazolin-4-amine),
stibogluconate (2,4:2',4'-O-(oxydistibylidyne)bis[D-gluconic acid] salt).
SU6656 ((3Z)—N,N-dimethyl-2-oxo-3-(4,5,6,7-tetrahydro-1H-indol-2-ylmethylidene)-1H-indole-5-sulfonamide),
sunitinib (N-[2-(diethylamino)ethyl]-5-[(Z)-(5-fluoro-2-oxo-1H-indol-3-ylidene)methyl]-2,4-dimethyl-1H-pyrrole-3-carboxamide),
T0901317 (N-[4-(1,1,1,3,3,3-hexafluoro-2-hydroxypropan-2-yl)phenyl]-N-(2,2,2-trifluoroethyl)benzenesulfonamide),
talimogene laherparepvec (CAS No. 1187560-31-1),
tamatinib (R406; 6-[[5-fluoro-2-(3,4,5-trimethoxyanilino)pyrimidin-4-yl]amino]-2,2-dimethyl-4H-pyrido[3,2-b][1,4]oxazin-3-one),
tamibarotene (4-[(5,5,8,8-tetramethyl-6,7-dihydronaphthalen-2-)yl)carbamoyl]benzoic acid),
tanespimycin (17-AAG; (3R,5S,6R,7S,8E,10S,11S,12Z,14E)-6-hydroxy-5,11-dimethoxy-3,7,9,15-tetramethyl-16,20,22-trioxo-21-(prop-2-enylamino)-17-azabicyclo[16.3.1]docosa-1(21),8,12,14,18-pentaen-10-yl]carbamate),
tazarotene (ethyl 6-[2-(4,4-dimethyl-2,3-dihydrothiochromen-6-yl)ethynyl]pyridine-3-carboxylate),
tazarotenic acid (6-[2-(4,4-dimethyl-2,3-dihydrothiochromen-6-yl)ethynyl]pyridine-3-carboxylic acid).
tazemetostat (N-[(4,6-dimethyl-2-oxo-1H-pyridin-3-yl)methyl]-3-[ethyl(oxan-4-yl)amino]-2-methyl-5-[4-(morpholin-4-ylmethyl)phenyl]benzamide),
TCS 401 (2-[(Carboxycarbon)yl]amino]-4,5,6,7-tetrahydrothieno[2,3-c]pyridine-3-carboxylic acid),
TCS JNK5a (N-(3-cyano-4,5,6,7-tetrahydro-1-benzothiophen-2-yl)naphthalene-1-carboxamide),
temozolomide (3-methyl-4-oxoimidazo[5,1-d][1,2,3,5]tetrazine-8-carboxamide),
tideglusib (TZDZ-8; 4-benzyl-2-naphthalen-1-yl-1,2,4-thiadiazolidine-3,5-dione)
Tie2i,
hipifarnib (6-[(R)-amino-(4-chlorophenyl)-(3-methylimidazol-4-yl)methyl]-4-(3-chlorophenyl)-1-methylquinolin-2-one).
tofacitinib (CP690550; 3-[(3R,4R)-4-methyl-3-[methyl(7H-pyrrolo[2,3-d]pyrimidin-4-yl)amino]piperidin-1-yl]-3-oxopropanenitrile),
topotecan ((S)-10[(dimethylamino)methyl]-4-ethyl-4,9-dihydroxy-1H-pyrano[3',4':6,7]-indolizino[1,2-b]quinoline-3,14(4H,12H)-dione monohydrochloride),
tosedostat (cyclopentyl (2S)-2-[[(2R)-2-[(1 S)-1-hydroxy-2-(hydroxyamino)-2-oxoethyl]-4-methylpentanoyl]amino]-2-phenylacetate),
tozasertib (VX680; 4-benzyl-2-naphthalen-1l-yl-1,2,4-thiadiazolidine-3,5-dione),
trametinib (mekinist; N-[3-[3-cyclopropyl-5-(2-fluoro-4-iodoanilino)-6,8-dimethyl-2,4,7-trioxopyrido-[4,3-d]pyrimidin-1-yl]phenyl]acetamide).
tretinoin (all-trans-Retinoic acid),
U73122 (1-[6-[[[(8R,9S,13S,14S,17S)-3-methoxy-13-methyl-6,7,8,9,11,12,14,15,16,17-decahydrocyclopenta[a]phenanthren-17-yl]amino]hexyl]pyrrole-2,5-dione),
ulixertib (N-[(1S)-1-(3-chlorophenyl)-2-hydroxyethyl]-4-[5-chloro-2-(propan-2-ylamino)-pyridin-4-yl]-1H-pyrrole-2-carboxamide),
vadastuximab talirine ((2R)-3-[(3R)-1-[6-[[(2S)-1-[[(2S)-1-[4-[(6aS)-3-[3-[[(6aS)-2-methoxy-8-(4-methoxyphenyl)-11-oxo-6a,7-dihydropyrrolo[2,1-c][1,4]benzodiazepin-3-yl]oxy]propoxy]-2-methoxy-11-oxo-6a,7-dihydropyrrolo[2,1-c][1,4]benzodiazepin-8-yl]anilino]-1-oxopropan-2-yl]amino]-3-methyl-1-oxobutan-2-yl]amino]-6-oxohexyl]-2,5-dioxopyrrolidin-3-yl]sulfanyl-2-aminopropanoic acid),
valspodar ((3S,6S,9S,12R,15S,18S,21S,24S,30S,33S)-1,4,7,10,12,15,19,25,28-nonamethyl-33-[(E,2R)-2-methylhex-4-enoyl]-6,9,18,24-tetrakis(2-methylpropyl)-3,21,30-tri(propan-2-yl)-1,4,7,10,13,16,19,22,25,28,31-undecazacyclotritriacontane-2,5,8,11,14,17,20,23,26,29,32-undecone),
vasastrol (4-[(E)-4-(4-hydroxyphenyl)hex-3-en-3-yl]phenol),
vatalanib (PTK787; N-(4-chlorophen),1)-4-(pyridin-4-ylmethyl)phthalazin-1-amine),
veliparib (ABT888; 2-[(2R)-2-methylpyrrolidin-2-yl]-1H-benzimidazole-4-carboxamide).
vemurafenib (N-[3-[5-(4-chlorophenyl)-1H-pyrrolo[2,3-b]pyridine-3-carbonyl]-2,4-difluorophenyl]propane-1-sulfonamide),
vemurafenib (zelboraf; N-[3-[5-(4-chlorophenyl)-1H-pyrrolo[2,3-b]pyridine-3-carbonyl]-2,4-difluorophenyl]propane-1-sulfonamide),
venetoclax (4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide),
vinblastine (dimethyl (2β,3β,4β,5α,12β,19α)-15-[(5S,9S)-5-ethyl-5-hydroxy-9-(methoxycarbonyl)-1,4,5,6,7,8,9,10-octahydro-2H-3,7-methanoazacycloundecino[5,4-b]indol-9-yl]-3-hydroxy-16-methoxy-1-methyl-6,7-didehydroaspidospermidine-3,4-dicarboxylate),
vincristine ((3aR,3a1R,4R,5S,5aR,10bR)-Methyl 4-acetoxy-3a-ethyl-9-((5S,7S,9S)-5-ethyl-5-hydroxy-9-(methoxycarbonyl)-2,4,5,6,7,8,9,10-octahydro-1H-3,7-methano[1]-azacycloundecino[5,4-b]indol-9-yl)-6-formyl-5-hydroxy-8-methoxy-3a,3a1,4,5,5a,6,11,12-octahydro-1H-indolizino[8,1-cd]carbazole-5-carboxylate),
vismodegib (GDC0449; 2-chloro-N-(4-chloro-3-pyridin-2-ylphenyl)-4-methylsulfonylbenzamide),
volasertib (N-[4-[4-(cyclopropylmethyl)piperazin-1-yl]cyclohexyl]-4-[[(7R)-7-ethyl-5-methyl-6-oxo-8-propan-2-yl-7H-pteridin-2-yl]amino]-3-methoxybenzamide),
vorinostat (SAHA; N'-hydroxy-N-phenyloctanediamide),
vosaroxin (7-[(3S,4S)-3-methoxy-4-(methylamino)pyrrolidin-1-yl]-4-oxo-1-(1,3-thiazol-2-yl)-1,8-naphthyridine-3-carboxylic acid), VX-702 (6-(N-carbamoyl-2,6-difluoroanilino)-2-(2,4-difluorophenyl)pyridine-3-carboxamide),
Wnti.
XAV939 (2-[4-(trifluoromethyl)phenyl]-1,5,7,8-tetrahydrothiopyrano[4,3-d]pyrimidin-4-one).
XL147 (N-[3-(2,1,3-benzothiadiazol-5-ylamino)quinoxalin-2-yl]-4-methylbenzenesulfonamide),
YM155 (1-(2-methoxyethyl)-2-methyl-3-(pyrazin-2-ylmethyl)-2H-benzo[f]benzimidazole-4,9-dione),
ZM336372 (3-(dimethylamino)-N-[3-[(4-hydroxybenzoyl)amino]-4-methylphenyl]benzamide),
a pharmaceutically acceptable salt thereof, or any combination thereof.

In some embodiments, the one or more additional therapeutic agent comprises a standard-of-care treatment modality for treating AML, a standard-of-care treatment modality for treating melanoma, an epigenetic drug, a targeted therapy, or any combination thereof.

In some embodiments, the one or more additional therapeutic agent comprises an antimetabolite, a topoisomerase II inhibitor, DNA hypomethylating agent, a DNA methyltransferase (DNMT) inhibitor, an HDAC inhibitor, an EZH2 inhibitor, a DOT1L inhibitor, a differentiation agent, a FLT3 inhibitor, a BCL2 inhibitor, a glucocorticoid receptor agonist (GRag), a BCR inhibitor, a corticosteroid, or any combination thereof.

In some embodiments, the one or more additional therapeutic agent comprises Ara-C, CHOP, Daunorubicin, Azacitidine, Decitabine, Pracinostat, Panobinostat, Tazemetostat, Pinometostat, All trans retinoic acid (ATRA), Gilteritinib, Midostaurin, Venetoclax, AG-120, AG-221, Cytarabine, Midostaurin, pembrolizumab, ipilimumab, dacarbazine, temozolomide, interleukin-2, nivolumab, vemurafenib, dabrafenib, trametinib, carmustine, cisplatin, interferon alfa-2b, cobimetinib, Dexamethasone, Prednisolone, Pomalidomide, Lenalidomide, Thalidomide, Ixazomib, Bortezomib, Carfilzomib, Melphalan, Vincristine, Mafosfamide, Etoposide, Doxorubicin, Bendamustine, Trametinib, Idelalisib, Ibrutinib, Tamatinib, Alisertib, Enzastaurin, Ipatasertib, doxorubicin, cytarabine, vincristine, everolimus, alisertib, topotecan, etoposide, carboplatin, entinostat, panobinostat, romidepsin, palbociclib, abemaciclib, selumetinib, trametinib, MK-2206, Vorinostat, Navitoclax, Rituximab, Obatoclax, atezolizumab, ABT-199, Velcade, Dasatinib, GSK1070916, GSK690693, Sorafenib, Omipalisib, Ruxolitinib, Fedratinib, JQ1, Methotrexate, Tofacitinib, OG-L002, GSK J4, Ribociclib, or any combination thereof.

In some embodiments, the one or more additional therapeutic agent comprises an antimetabolite, a topoisomerase II inhibitor, a DNA hypomethylating agent, an HDAC inhibitor, an EZH2 inhibitor, a DOT1L inhibitor, a differentiation agent, an FLT3 inhibitor, or a BCL2 inhibitor.

In some embodiments, the one or more additional therapeutic agent comprises cytarabine (Ara-C), daunorubicin, azacitidine, decitabine, pracinostat, panobinostat, tazemetostat, pinometostat, all-trans retinoic acid (ATRA), gilteritinib, midostaurin, venetoclax, pembrolizumab, ipilimumab, dacarbazine, temozolomide, interleukin-2, nivolumab, vemurafenib, dabrafenib, trametinib, carmustine, cisplatin, interferon alfa-2b, cobimetinib, a pharmaceutically acceptable salt thereof, or any combination thereof.

In some embodiments, the cancer is a hematological cancer or a skin cancer.

In some embodiments, the cancer is a skin cancer. In some embodiments, the skin cancer is melanoma.

In some embodiments, the one or more additional therapeutic agent comprises an alkylating agent, a platinum agent, a vinca alkaloid, a taxane (e.g., paclitaxel, docetaxel or cabazitaxel), a RAS pathway inhibitor (e.g., an ERK inhibitor, a MEK1/2 inhibitor, or a BRAF V600E or V600K inhibitor), a Pi3K/Akt pathway inhibitor (e.g., a Pi3K inhibitor, an Akt inhibitor, or an mTOR inhibitor), an immune-oncology drug (e.g., a CTLA-4 inhibitor or a checkpoint inhibitor), a cell cycle checkpoint inhibitor, a cytokine (e.g., an interferon-α2b (IFN-α2b), an interferon-α2b recombinant (e.g., IFN-α2b recombinant), or an IL-2 analog), a tryptophan synthesis inhibitor (e.g., an IDO-1 inhibitor), a therapeutic vaccine, an adoptive cell therapy (e.g., T-cell-based therapy or CAR-T therapy), an epigenetic drug (e.g., an HDAC inhibitor, methyltransferase inhibitor, an EZH2 inhibitor, or a DOT1L inhibitor), a methyl transferase inhibitor (e.g., a DNA methylation inhibitor), a DNA hypomethylating agent, a P-glycoprotein inhibitor, a receptor tyrosine kinase pathway inhibitor (e.g., a c-Kit inhibitor), a serine/threonine kinase inhibitor (e.g., an aurora kinase inhibitor), a cyclin dependent kinase inhibitor (e.g., CDK4/6 inhibitor), a growth factor inhibitor (e.g., a VGEF inhibitor), an immune response protein inhibitor (e.g., a PD-L1 inhibitor), an engineered protein combining Interleukin-2 and diphtheria toxin, a tumor necrosis factor receptor signaling modulator (e.g., an antibody DR5 agonist), a cyclin dependent kinase inhibitor (e.g., a CDK1/5 inhibitor), an acetaldehyde dehydrogenase inhibitor, a pro-apoptotic drug, a melanoma-associated antigen 3 (MAGE-A3) targeting agent, a retinoic acid receptor (RAR) modulator (e.g., an RAR agonist (e.g., an RARα agonist, an RARβ agonist, or an RARγ agonist)), or any combination thereof.

In some embodiments, the one or more additional therapeutic agent comprises dacarbazine, temozolomide, fotemustine, nimustine, melphalan, cisplatin, carboplatin, vinblastine, vincristine, paclitaxel, docetaxel, ulixertib, trametinib, cobimetinib, binimetinib, selumetinib, dabrafenib, vemurafenib, encorafenib, pictilisib, buparlisib, MK-2206, ipatasertinib, everolimus, ipilimumab, pembrolizumab, PDR001, pegylated interferon alfa-2b, interferon alfa 2b, interleukin-2, aldesleukin, epacadostat, seviprotimut-L, MVax, ImmuniCell®, pracinostat, panobinostat, tazemetostat, pinometostat, azacitidine, decitabine, guadecitabine, valspodar, dasatanib, barasertib, palbociclib, ribociclib, bevacizumab, bleomycin, nivolumab, BMS-93559, diphtheria toxin-Interleukin-2 fusion protein, DS-8273a, dasatanib, dinaciclib, disulfiram, elesclomol, GSK2132231A, imatinib, talimogene laherparepvec, a pharmaceutically acceptable salt thereof, or any combination thereof.

In some embodiments, the alkylating agent comprises dacarbazine, temozolomide, fotemustine, nimustine, melphalan, or a pharmaceutically acceptable salt thereof. In some embodiments, the platinum agent comprises cisplatin, carboplatin, or a pharmaceutically acceptable salt thereof. In some embodiments, the vinca alkaloid is vinblastine, vincristine, or a pharmaceutically acceptable salt thereof. In some embodiments, the taxane is paclitaxel, docetaxel, or a pharmaceutically acceptable salt thereof. In some embodiments, the ERK inhibitor is ulixertib or a pharmaceutically acceptable salt thereof. In some embodiments, the MEK1/2 inhibitor is trametinib, cobimetinib, binimetinib, selumetinib, or a pharmaceutically acceptable salt thereof. In some embodiments, the BRAF V600E or V600K inhibitor is dabrafenib, vemurafenib, sorafenib, encorafenib, or a pharmaceutically acceptable salt thereof.

In some embodiments, the Pi3K inhibitor is pictilisib, buparlisib, or a pharmaceutically acceptable salt thereof. In some embodiments, the Akt inhibitor is MK-2206, ipatasertinib, or a pharmaceutically acceptable salt thereof. In some embodiments, the mTOR inhibitor is everolimus or a pharmaceutically acceptable salt thereof. In some embodiments, the CTLA-4 inhibitor is ipilimumab or a pharmaceutically acceptable salt thereof. In some embodiments, the checkpoint inhibitor is nivolumab, pembrolizumab, PDR001, or a pharmaceutically acceptable salt thereof. In some embodiments, the interferon alfa-2b is pegylated interferon alfa-2b. In some embodiments, the interferon alfa-2b recombinant is intron a or interleukin-2. In some embodiments, the IL-2 analog is aldesleukin. In some embodiments, the IDO-1 inhibitor is epacadostat. In some embodiments, the therapeutic vaccine is seviprotimut-L or MVax. In some embodiments, the T-cell-based therapy is ImmuniCell®. In some embodiments, the HDAC inhibitor is pracinostat, panobinostat, or a pharmaceutically acceptable salt thereof. In some embodiments, the EZH2 inhibitor is tazemetostat or a pharmaceutically acceptable salt thereof. In some embodiments, the DOT1L inhibitor is pinometostat or a pharmaceutically acceptable salt thereof. In some embodiments, the DNA hypomethylating agent comprises azacitidine, decitabine, guadecitabine, or a pharmaceutically acceptable salt thereof. In some embodiments, the P-glycoprotein inhibitor is vaspodar or a pharmaceutically acceptable salt thereof. In some embodiments, the c-Kit inhibitor is dasatanib or a pharmaceutically acceptable salt thereof. In some embodiments, the aurora kinase inhibitor is barasertib or a pharmaceutically acceptable salt thereof. In some embodiments, the CDK4/6 inhibitor is palbociclib, ribociclib, or a pharmaceutically acceptable salt thereof. In some embodiments, the VGEF inhibitor is bevacizumab, bleomycin, nivolumab, or a pharmaceutically acceptable salt thereof. In some embodiments, the PD-L1 inhibitor is BMS-93559 or a pharmaceutically acceptable salt thereof. In some embodiments, the engineered protein combining Interleukin-2 and diphtheria toxin is diphtheria toxin-Interleukin-2 fusion protein. In some embodiments, the antibody DR5 agonist is DS-8273a, dasatanib, or a pharmaceutically acceptable salt thereof. In some embodiments, the CDK1/5 inhibitor is dinaciclib or a pharmaceutically acceptable salt thereof. In some embodiments, the acetaldehyde dehydrogenase inhibitor is disulfiram or a pharmaceutically acceptable salt thereof. In some embodiments, the pro-apoptotic drug is elesclomol or a pharmaceutically acceptable salt thereof. In some embodiments, the melanoma-associated antigen 3 (MAGE-A3) targeting agent comprises GSK2132231A, imatinib, talimogene laherparepvec, or a pharmaceutically acceptable salt thereof.

In some embodiments, the one or more additional therapeutic agent comprises melanoma vaccine, Allovectin-7®, autologous dendritic cell vaccine, autologous dendritic cell-allogeneic melanoma tumor cell lysate vaccine, autologous dendritic cells loaded with autologous tumor RNA, autologous dendritic cell-tumor cell immunotherapy (DC-TC), autologous dendritic cell-tumor fusion vaccine, autologous tumor cell vaccine, autologous DNP-modified vaccine (M-Vax), autologous lethally irradiated melanoma cells, BCD-100, BCG vaccine, BMS-936559 (Anti-PD-L1), CADI-05, CancerVax vaccine (CANVAXIN), CB-10-01 (transgenic lymphocyte immunization), *Corynebacterium granulosum* P40 extract, CSF470 vaccine, BCG. Molgramostim, CYT004-MelQbG10, combination of CYT004-MelQbG10 and montanide, D1/3-MAGE-3-His fusion protein, DC/Apo-Nec vaccine, dendritic cell application, dendritic cell therapy, Detox-B adjuvant, DS-8273a, GM2-KLH vaccine, GM-CSF DNA, NSC 683472, gp100 antigen, gp75 DNA vaccine, GRN-1201, HLA-A1-binding MAGE-1/MAGE-3 multipeptide-pulsed autologous dendritic cell vaccine, human gp 100 plasmid DNA vaccine, human tyrosinase, IL15-DC vaccine, mouse TYRP2 DNA, veledimex (INXN-2001; N'-(3,5-dimethylbenzoyl)-N'-[(3R)-2,2-dimethylhexan-3-yl]-2-ethyl-3-methoxybenzohydrazide), KLH conjugates with GD2L and GD3L, liposomal interleukin-2, MART-1 antigen. MART-1, anti-cytotoxic T-lymphocyte-associated antigen-4 monoclonal antibody, MDX-010, MDX-CTLA4 antibody, tyrosinase/gp 100/MART-1 peptides melanoma vaccine, melanoma vaccine modified to express HLA A2/4-1BB ligand, MKC1106-MT, monoclonal antibody 4B5 anti-idiotype vaccine, combination of montanide and melan-A analogue peptide, mouse gp100 plasmid DNA vaccine, nDC vaccination, NY-ESO-1 ISCOMATRIX® vaccine, oblimersen sodium, ofatumumab, OVA BiP peptide, PBMC reinfusion, PEG IFN alfa-2b, peptide vaccine, peptide-pulsed dendritic cells, pIL-12, POL-103A, recombinant CD40-ligand, recombinant human Hsp110-gp100 chaperone complex vaccine, recombinant interferon alfa, recombinant interferon alfa-2b, recombinant interferon alpha-1b, recombinant interferon beta, sargramostim, TBI-1401(HF10), therapeutic autologous lymphocytes, TriMix-DC, TriMix-DC and ipilimumab, TRX518, tyrosinase peptide, vaccine consisting of a peptide derived from the protein IDO, ziv-aflibercept, MelaFind®, 4SC-202 in combination with pembrolizumab, ABI-007, acetaminophen, ACY-241, adjuvant chemotherapy by fotemustin, flibercept, anti-CD137 (4-1BB) (BMS-663513), anti-CTLA4 monoclonal antibody and HDI, APO866, atezolizumab, atorvastatin, combination of bevacizumab and ipilimumab cohort 1, combination of BKM120 and vemurafenib (PLX4032), BMS-936558 (MDX1106-04), boronophenylalanine-fructose complex, combination of BRAF inhibitor dabrafenib and MEK inhibitor trametinib, buthionine sulfoximine, CC 5013, cilengitide, combination of varlilumab and ipilimumab, CP 870,893. CPG 7909 injection, CR011-vcMMAE, cyclophosphamide, combination of dacarbazine and genasense, dasatinib, dendritic cell-gp100-MART-1 antigen vaccine, denosumab, depsipeptide, disulfiram (DSF), combination of E7050 and lenvatinib, elesclomol (STA-4783), fentanyl sublingual spray, gamma-secretase, notch signalling pathway inhibitor RO4929097, Genasense) (G3139, oblimersen sodium), granulocyte-macrophage colony-stimulating factor (GM-CSF), GSK 2132231A, GSK1120212. GSK2118436, HSPPC-96, oncophage, hu14.18-IL2, hydroxychloroquine, imexon, imiquimod, IMP321, INC280, indocyanine green, indoximod, INO-1001, L191L2, combination of ipilimumab and interleukin-2, INXN-1001, irinotecan, isolated limb perfusion, combination of L19IL2 and L19TNF, lenvatinib, LGX818, lomustine, masitinib, MDX-010 (anti-CTLA4) monoclonal antibody, MEK162, methylphenidate, nilotinib, combination of nivolumab and ipilimumab, OBP-301, omaveloxolone, combination of pazopanib and paclitaxel, peginterferon alfa-2b, pegIntron, pegylated interferon alfa-2a, pegylated interferon-alfa 2b (PEG Intron), combination of pembrolizumab and epacadostat, combination of pembrolizumab and high dose interferon alfa-2b (HDI), combination of pembrolizumab and all-trans retinoic acid, PF-06688992, placebo, PLX3397, propranolol, PV-10 (10% rose bengal disodium), combination of ranibizumab and TTT (ICG based), ranibizumab, recombinant interleukin-21, resiquimod, riluzole, rituxan, RO5185426, RTA 402, saracatinib, combination of sorafenib (Nexavar) and dacarbazine, sorafenib (Nexavar; BAY43-9006), sorafenib tosylate. STA-9090, sunitinib malate, SX-682, tanespimycin, tasisulam, combination of TIL and IL2, combination of timolol and LCP, TLPLDC, TMZ, tremelimumab, vitamin D, vitamin D3 (colecalciferol), XL888, YM155, IGIMRT, ionizing radiation (IR) therapy, proton radiation therapy, radiotherapy, WBRT, whole brain radiation, a pharmaceutically acceptable salt thereof, or any combination thereof.

In some embodiments, the one or more additional therapeutic agent comprises a tyrosine kinase inhibitor (e.g., an Abl inhibitor or an AblT351I inhibitor), an AhR agonist, a Pi3K/Akt pathway inhibitor (e.g., an Akt inhibitor), an alkylating agent, an AMPK agonist, and AMPK antagonist, an androgen receptor, an antimetabolite, an ARFGAP inhibitor, an arsenic derivative, an indoleamine 2,3-dioxygenase inhibitor, a receptor tyrosine kinase inhibitor (e.g., an ALK inhibitor), a serine/threonine kinase inhibitor (e.g., an ATM inhibitor, an aurora kinase inhibitor (e.g., an aurora kinase A inhibitor, an aurora kinase B inhibitor, or an aurora kinase C inhibitor), or a Plk inhibitor), a BCR inhibitor, a BCR-Abl inhibitor, an inhibitor of negative regulator of apoptosis (e.g. a BIRC5 inhibitor), a BMP signaling antagonist, a Wnt signaling inhibitor (e.g., a beta-catenin inhibitor), an inhibitor of a protein involved in apoptosis (e.g., a BCL2 inhibitor or a Bcl-x inhibitor), a non-receptor tyrosine kinase inhibitor (e.g., a BTK inhibitor), a cyclin dependent kinase inhibitor (e.g., a CDK inhibitor, a CDK2 inhibitor, a CDK4 inhibitor, a CDK6 inhibitor, a CDK7 inhibitor, or a CDK9 inhibitor), a Chk inhibitor (e.g., a CHk1 inhibitor, or a Chk2 inhibitor), a receptor tyrosine kinase pathway inhibitor (e.g., a c-Kit inhibitor), a casein kinase inhibitor (a CK2a inhibitor), a CSF1R inhibitor (e.g., a c-fms inhibitor), an EAR inhibitor, a receptor tyrosine kinase inhibitor (e.g., a HER inhibitor (e.g., a HER2 inhibitor), an ErbB inhibitor (e.g., an ErbB-2 inhibitor, an ErbB-3 inhibitor, or an ErbB-4 inhibitor), an FAK inhibitor (e.g., an FAK1 inhibitor or an FAK2 inhibitor), a fatty acid synthase, an FGF signaling inhibitor (e.g., an FGFR1 inhibitor or an FGFR3 inhibitor), an FTI inhibitor, a growth factor signaling inhibitor (e.g., an FGF inhibitor, a VEGF inhibitor or an FLT inhibitor (e.g., an FLT1 inhibitor, an FLT2 inhibitor, an FLT3 inhibitor or an FLT4 inhibitor)), a protein-trosine kinase inhibitor (e.g., a Fyn inhibitor), a gamma secretase, a serine-threonine kinase inhibitor (e.g., a GSK-3 inhibitor), an HDAC inhibitor, an Hh pathway inhibitor, an HIFa inhibitor, an HSP inducer (e.g., an HSP70 inducer), an HSP inhibitor (e.g., an HSP90 inhibitor), a receptor tyrosine kinase inhibitor (e.g., an IGF-1R inhibitor), an IKK inhibitor, an InR inhibitor, a JAK/STAT signaling inhibitor (e.g., a JAK1 inhibitor, a JAK2 inhibitor, or a JAK3 inhibitor), a JNK signaling inhibitor (e.g., a JNK inhibitor), a KSP inhibitor, a LXR inhibitor, a tyrosine protein kinase inhibitor (e.g., a Lyn inhibitor), a lipase inhibitor (e.g., a MAGL inhibitor), a ubiquitin ligase inhibitor (e.g., an MDM2 inhibitor), a MAP Kinase signaling inhibitor (e.g., a MEK inhibitor), a receptor tyrosine kinase inhibitor (e.g., a MET inhibitor), a methyl transferase inhibitor (e.g., a DNA hypomethylating agent), a microtubule agent (e.g., a taxane or a vinca alkaloid), an mTOR kinase inhibitor, an NAMPRT inhibitor, a PAK inhibitor, a PARP inhibitor, a pyruvate dehydrogenase kinase inhibitor (e.g., a PDK1 inhibitor), a PDGF signaling inhibitor (e.g., a PDGFb inhibitor or a PDGFR inhibitor), a Pi3K inhibitor, a MAP kinase inhibitor (e.g., a p38 inhibitor), a tumor suppressor protein inhibitor (e.g., a p53 inhibitor), a serine/threonine kinase inhibitor (e.g., a PIM inhibitor), a PKC-beta inhibitor, a PLC inhibitor, a a serine/threonine kinase inhibitor (e.g., a PLK1 inhibitor), a peroxisome proliferator-activated receptor agonist (e.g. a PPARd agonist or a PPARg agonist), a peroxisome proliferator-activated receptor antagonist (e.g., a PPARG antagonist), a PPARg antagonist, a proteasome inhibitor, protein tyrosine phosphatase inhibitor (e.g., a PTP-1B inhibitor), a Raf inhibitor (e.g., a BRAF V600E or V600K inhibitor, or a c-Raf inhibitor), a proto-oncogene inhibitor (e.g., a RET inhibitor), a ROCK inhibitor, an RSK inhibitor (e.g., an RSK1 inhibitor, an RSK2 inhibitor, an RSK3 inhibitor, an RSK5 inhibitor), a nuclear receptor inhibitor (e.g., an RXR inhibitor), a SGK inhibitor, an inisotal phosphatase inhibitor (a SHIP inhibitor (e.g., a SHIP1 inhibitor or a SHIP2 inhibitor), a SIRT1 inhibitor, a S1PR inhibitor, a Src inhibitor, a survivin inhibitor, a tyrosine kinase inhibitor (e.g., a Syk inhibitor), a tankyrase inhibitor (e.g., a tankyrase 1 inhibitor or a tankyrase 2 inhibitor), a receptor tyrosine kinase inhibitor (e.g., a TIE-2 inhibitor), a TORC inhibitor (e.g., a TORC 1 inhibitor or a TORC2 inhibitor), a tumor necfrosis factor inhibitor (e.g., a TNFa inhibitor), a topoisomerase inhibitor, a receptor tyrosine kinase inhibitor (e.g., a TrkA inhibitor), a tyrosine kinase inhibitor (e.g., aTyk2 inhibitor), a VEGF signaling inhibitor (e.g., a VEGFR-1 inhibitor, a VEGFR-2 inhibitor, a VEGFR-3 inhibitor, or a VEGFR-4 inhibitor), a checkpoint kinase inhibitor (e.g., a Wee-1 inhibitor), proto-oncogene inhibitor (e.g., a Yes inhibitor), an inhibitor of a protein involved in apoptosis (e.g., a XIAP inhibitor), a retinoic acid receptor (RAR) modulator (e.g., an RAR agonist (e.g., an RARα agonist, an RARβ agonist, or an RARγ agonist)), or any combination thereof.

In some embodiments, the one or more additional therapeutic agent comprises ara-C, all trans retinoic acid (ATRA), bexarotene, bortezomib, cisplatin, tofacitinib, crizotinib, cytarabine, dasatanib, daunorubicin, decitabine, docetaxel, erlotinib, etoposide, enasidenib, everolimus, fingolimod, fludarabine, gemcitabine, gilteritinib, ivosidenib, ruxolitinib, lapatinib, lenalidomide, nilotinib, nilutamide, pazopanib, pioglitazone, PLX-4720, sorafenib, stibogluconate, sunitinib, temozolomide, vincristine, venetoclax, vismodegib, vorinostat, AZD7762, CHIR265, IMD-0354, Nutlin-3, OSU-03012, PF-04217903, PF-562271, SNS-032, SNS-314, ABT263, bivanib, silmitasertib, darinaparsin, ENMD-2076, EX527, daporinad, indole-3-carbinol, lestaurtinib. MK-1775, MK-2206, Dactolisib, RKI983, selumetinib, tideglusib, tozasertib, veliparib, VX-702, XL147, YM155, cediranib, dovitinib, enzastaurin, midostaurin, linsitinib, palbociclib, perifosine ((1,1-dimethylpiperidin-1-ium-4-yl) octadecyl phosphate), elesclomol, tamatinib, tanespimycin, tipifamib, vatalanib, A769662, AS252424, BI-78D3, BI-D1870, BMS-536924, C75, dorsomorphin, embelin, FH535, GSK0660, GSK650394, GW0742, GW2580, GW441756, GW9662, HIF-1i, IPA-3, TCS JNK5a, JZL184, KU0063794, KU-55933, L779450. LFM-A13, LSN415169, NVP-TAE684, PD173074, PIM-1 4a, QS11, Src-I1, SU6656, T0901317, TCS 401, Tie2i, U73122, vasastrol, Wnti, XAV939, ZM336372, a pharmaceutically acceptable salt thereof, or any combination thereof.

In some embodiments, the RAR agonist is 9CDHRA, alitretinoin, AC-261066, AC-55649, acitretin, adapalene, arotinoid acid, tretinoin. AM-580, BMS-493, BMS-753, BMS-961, CD-1530, CD-2314, CD-437, Ch-55, EC 23, etretinate, fenretinide, isotretinoin, palovarotene, retinoic acid, retinol, tamibarotene, tazarotene, tazarotenic acid, a pharmaceutically acceptable salt thereof, or any combination thereof.

In some embodiments, the cancer is a hematological cancer. In some embodiments, the hematological cancer is acute myeloid leukemia (AML) or chronic lymphocytic leukemia (CLL). In some embodiments, the hematological cancer is acute myeloid leukemia (AML).

In some embodiments, the one or more additional therapeutic agent comprises an antimetabolite, a topoisomerase inhibitor (e.g., a topoisomerase II inhibitor, a topoisomerase I inhibitor), a methyl transferase inhibitor (e.g., a DNA methylation inhibitor), a DNA hypomethylating agent, an histone deacetylase (HDAC) inhibitor, a histone methyltransferase inhibitor (e.g., an EZH2 inhibitor, a DOT1L inhibitor), a cellular differentiation agent, a tyrosine kinase inhibitor (e.g., an FLT3 inhibitor), an inhibitor of anti-apoptotic proteins (e.g., a BCL2 inhibitor), an inhibitor of an adaptive immune response protein (e.g., a CTLA-4 inhibitor), a cell surface receptor inhibitor (e.g., an anti-CD33 ADC), a sulfatase inhibitor (e.g., a IDH1 inhibitor or an IDH2 inhibitor), an alkylating agent, a serine/threonine protein kinase inhibitor (e.g., a PLK-1 inhibitor, an aurora inhibitor), a non-receptor tyrosine kinase inhibitor (e.g., a BTK inhibitor), an immunoglobulin like receptor inhibitor (e.g., an anti-KIR antibody), a Hedgehog pathway inhibitor, a P-glycoprotein inhibitor, an inhibitor of an immunomodulator, a receptor tyrosine kinase pathway inhibitor (e.g., a c-Kit inhibitor), a cyclin dependent kinase inhibitor (e.g., a CDK4/6 inhibitor), a RAS pathway inhibitor (e.g., an ERK inhibitor, a MEK1/2 inhibitor, or a BRAF V600E or V600K inhibitor), an PI3K/Akt pathway inhibitor (e.g., an Akt inhibitor), a heat shock protein inhibitor (e.g., an Hsp90 inhibitor), an aminopeptidase inhibitor, a Jak/Stat pathway inhibitor (e.g., a Jak2 inhibitor), a farnesyl transferase inhibitor, or any combination thereof.

In some embodiments, the one or more additional therapeutic agent comprises a humanized monoclonal anti-CD52 antibody, an IL-15 superagonist, a VGEF inhibitor, an anti-CD33 antibody, an allogeneic myeloid progenitor cell, a humanized antibody inhibitor of complement, an inhibitor of TNF alpha, an antibody that targets the extracellular domain of Fms-like tyrosine kinase (FLT3. CD 135 or FLK2), an anti RSV antibody, an anti-CD20 antibody, an anti-CD200 antibody, an injectable bivalent DNA vaccine, a WT1/PRAME vaccination, an antimetabolite, an FLT3 inhibitor, an anthracycline, a XIAP antisense oligonucleotide, a VGFR inhibitor, a cKIT inhibitor, a PDGFR inhibitor, a TK inhibitor, an IL-2 receptor agonist, an IL-15 agonist, a CDK9 inhibitor, a folate analog, a blocker of tetrahydrofolate synthesis, a topoisomerase II inhibitor, a DNA intercalator, an mutant p53 reactivator, a CD-70 blocker, a KSP inhibitor, an arsenic trioxide, an IL-1beta inhibitor, a cytarabine prodrug, a PD-1 inhibitor, a PD-L1 inhibitor, an HDAC inhibitor, a retinoic acid receptor (RAR) modulator, an AXL kinase inhibitor, a PI3K inhibitor, a CXCR4 antagonist, a proteasome inhibitor, an antibody drug conjugate, a protein kinase C modulator, an ERK inhibitor, a DNA intercalator, an alkylating agent, a recombinant human FLIT3 ligand, a CHK1 inhibitor, an aminopeptidase inhibitor, an antiangiogenic agent, an antimetabolite, a mitochondrial TCA cycle inhibitor, a PDGFR inhibitor, an anticoagulant, an immunosuppressant, an anticholinergic, an anti-CD38 antibody, a glucocorticoid receptor agonist, an anti-mitotic, a SYK inhibitor, an mTOR inhibitor, a G-CSF, a calcineurim inhibitor, an AKT inhibitor, a BTK inhibitor, a JAKISTAT inhibitor, an IDO inhibitor, a pan PIM inhibitor, an IDO inhibitor, a RARalpha specific agonist, an anti CD123 antibody, an anti-KIR antibody, an antiCD56 antibody-drug conjugate, a GSK-3 inhibitor, an aurora kinase inhibitor, a BCR-ABL tyrosine kinase inhibitor, a VEGFR/FGFR/PDGFR inhibitor, a BCL2 inhibitor, a bromodomain inhibitor, a CDK4/6 inhibitor, a multitarget receptor tyrosine kinase inhibitor, a PLK-1 inhibitor, an IMiD, a CBP/Beta-catenin antagonist, an anti-CD20, a JAK2/FLT3 inhibitor, a PIM/FLT3 inhibitor, an XPO1 inhibitor, an multikinase inhibitor, a parp inhibitor, an LSD inhibitor, a wee1 inhibitor, or a P-gp modulator, or any combination thereof.

In some embodiments, the second therapeutic agent comprises alemtuzumab, ALT-803, bevacizumab, BI 836858, BPX-501 and AP1903, Campath-1H, CLT-008, daclizumab, eculizumab, etanercept, filgrastim, FLYSYN, Nivolumab, palivizumab, rituximab, Samalizumab, VCL-CB01, WT1/PRAME vaccination, 8-chloro-adenosine, AC220, aclacinomycin, AEG35156, AG-013736 (Axitinib), AKN-028, Aldesleukin, ALT-803, Alvocidib, aminopterin, Amonafide+cytarabine, amsacrine, APR-246, ARGX-110 with AZA, ARRY-520, Arsenic Trioxide, AS101, ASP2215, Astarabine (BST-236), Atorvastatin, Avelumab, Axitinib, belinostat, bexarotene, BGB324. BKM120, BL-8040, Bortezomib, Brentuximab Vedotin, bryostatin 1, BVD-523, carboplatin, carmustine, CDX-301, CEP-701, Chidamide, CHK1 Inhibitor SCH 900776, CHR-2797, cilengitide, CP-4055, CPI-613, CPX-351, crenolanib, CX-01, cyclophosphamide, Cyclosporin A, cyproheptadine hydrochloride, Daratumumab, dexamethasone, docetaxel, Dovitinib (TKI258), Entinostat, Entospletinib, Everolimus, F901318. Filgastrim, FK506, fluconazole, Gemcitabine Hydrochloride, Gilteritinib, Gleevec®, GSK21110183, hydroxyurea, Ibrutinib, idarubicin, ifosfamide, INCB018424, INCB024360, INCB053914, Indoximod, IRX5183, Ixazomib, JNJ-56022473, laromustine, LDE225, Lenograstim, Leuprolide, Levetiracetam, Lirilumab. Lomustine, Lorvotuzumab Mertansine (IMGN901), LY2090314, methylprednisolone, MGCD0103, MLN8237, mycophenolate mofetil, NILOTINIB, nintedanib and AML induction, Obatoclax, OTX015, paclitaxel. Palbociclib, panobinostat, Pazopanib, PCM-075, Phase 1—OXi4503+cytarabine, Phase 2—OXi4503+cytarabine, Pixantrone IV infusion, Pomalidomide, Ponatinib, Pracinostat, prednisone, PRI-724, PXD101, rapamycin, Reylimid, rigosertib, Rituximab, SB1518, SEL24, Selinexor, Sorafenib, Sunitinib, SY-1425 (tamibarotene), Tacrolimus, talazoparib, tandutinib, Temozolomide, temsirolimus, thioguanine, thiotepa, tranylcypromine, treosulfan, triple kinase inhibitor BIBF1120, vosaroxin, WEE1 Inhibitor AZD1775, XL999, or zosuquidar trihydrochloride, or any combination thereof. In some embodiments, the one or more additional therapeutic agent comprises ara-C, daunorubicin, mitoxantrone, clofarabine, fludarabine, cladribine, etoposide, mercaptopurine, methotrexate, azacitidine, decitabine, guadecitabine, pracinostat, panobinostat, tazemetostat, pinometostat, all-trans retinoic acid, arsenic trioxide, gilteritinib, quizartinib, midostaurin, venetoclax, ipilimumab, vadastuximab talirine, ivosidenib, enasidenib, laromustine, sapacitibine, vosaroxin, topotecan, mitomycin, volasertib, ibrutinib, lirilumab, glasdegib, valspodar, lenalidomide, dasatanib, barasertib, palbociclib, ribociclib, ulixertib, trametinib, cobimetinib, binimetinib, selumetinib, dabrafenib, vemurafenib, encorafenib, MK-2206, ganetespib, tosedostat, ruxolitinib, tipifarnib, a pharmaceutically acceptable salt thereof, or any combination thereof.

In some embodiments, the cancer is myelodysplastic syndromes (MDS),

In some embodiments, the one or more additional therapeutic agent comprises an immunomodulatory drug (IMiD), a methyl transferase inhibitor (e.g., a DNA methylation inhibitor (e.g., a DNA hypomethylating agent)), an antimetabolite, a topoisomerase II inhibitor, or any combination thereof.

In some embodiments, the one or more additional therapeutic agent comprises lenalidomide, azacitidine, decitabine, guadecitabine, ara-C, daunorubicin, idarubicin, a pharmaceutically acceptable salt thereof, or any combination thereof.

In some embodiments, administration of the combination comprising the EHMT2 inhibitor and the one or more additional therapeutic agent inhibits dimethylation of histone 3 at lysine residue 9 (i.e., H3K9me2).

In some embodiments, the one or more additional therapeutic agent comprises an anticancer agents or a chemotherapeutic agent. In some embodiments, the one or more additional therapeutic agent comprises a glucocorticoid. In some embodiments, the one or more additional therapeutic agent comprises prednisone, prednisolone, cyclophosphamide, vincristine, doxorubicin, mafosfamide, cisplatin, AraC, everolimus, decitabine, dexamethasone, or a functional analog thereof, a derivative thereof, a prodrug thereof, or a metabolite thereof. In some embodiments, the one or more additional therapeutic agent comprises prednisone or its active metabolite (e.g., prednisolone).

In some embodiments, the one or more additional therapeutic agent comprises a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in wwvw.cancer.org/docroot/cdg/cdg_0.asp.

In some embodiments, the one or more additional therapeutic agent comprises an agent selected from CHOP (e.g., cyclophosphamide, hydroxydaunorubicin, oncovin, and prednisone or prednisolone) and R-CHOP (e.g., rituximab, cyclophosphamide, hydroxydaunorubicin, oncovin, prednisone or prednisolone). In some embodiments, the one or more additional therapeutic agent comprises prednisone or prednisolone.

In some embodiments, the one or more additional therapeutic agent comprises an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033): matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P 154; WHI-P 131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Reylimid); bexarotene (Targretin); thalidomide (Thalomid); temsirolimus (Torisel); arsenic trioxide (Trisenox); verteporfin (Visudyne); mimosine (Leucenol); (IM tegafur-0.4 M 5-chloro-2,4-dihydroxypyrimidine-1 M potassium oxonate) or lovastatin.

In some embodiments, the one or more additional therapeutic agent comprises a cytokine, e.g., G-CSF (granulocyte colony stimulating factor). In some embodiments, a compound of the present disclosure, or a pharmaceutically acceptable salt, prodrug, metabolite, analog or derivative thereof, is administered in combination with radiation therapy. Radiation therapy can also be administered in combination with a compound of the present disclosure and one or more additional therapeutic agent described herein as part of a multiple agent therapy. In some embodiments, a compound of the present disclosure, or a pharmaceutically acceptable salt, prodrug, metabolite, analog or derivative thereof, is administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In some embodiments, the one or more additional therapeutic agent comprises an HDAC inhibitor. In certain embodiments, the one or more additional therapeutic agent comprises chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®. Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®. Vidaza™, vincristine sulfate, VM 26, Xeloda® and Zanosar®); biologics (such as Alpha Interferon, Bacillus Calmette-Guerin, Bexxar®, Campath®. Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Velcade® and Zevalin™); small molecules (such as Tykerb®); corticosteroids (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); or radiopharmaceuticals (such as Iodotope®, Metastron®, Phosphocol® and Samarium SM-153).

Representative compounds of the present disclosure include compounds listed in Tables 1-6, 6A, and 7, and tautomers and salts thereof.

TABLE 1

| Compound No. | Structure |
|---|---|
| 1 | 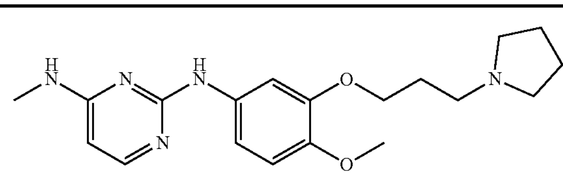 |

TABLE 1-continued
| Compound No. | Structure |
|---|---|
| 2 | 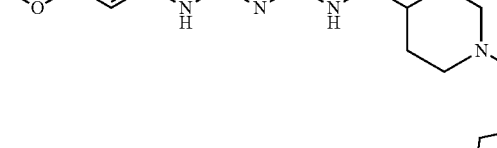 |
| 3 | 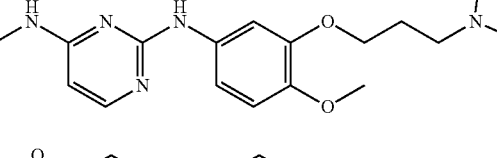 |
| 4 | 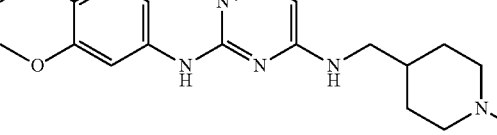 |
| 5 | 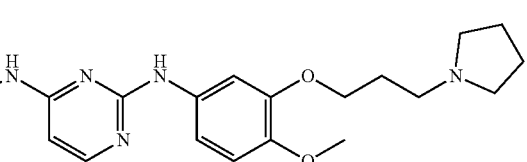 |
| 6 | 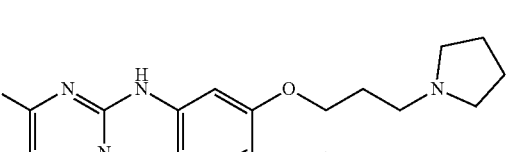 |
| 7 | 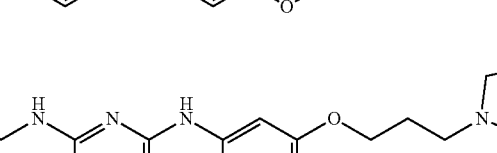 |
| 8 | 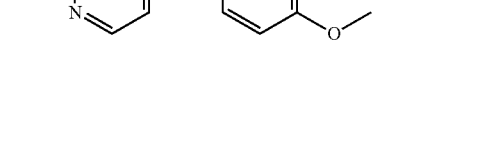 |
| 9 | 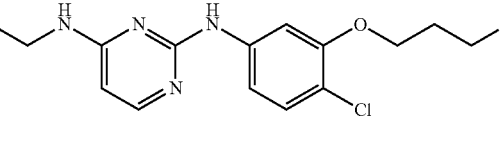 |

TABLE 1-continued
| Compound No. | Structure |
|---|---|
| 10 | 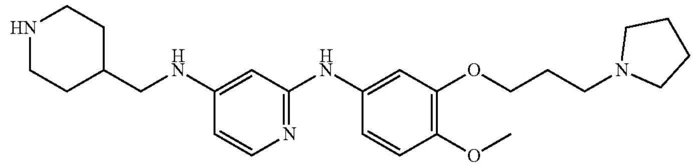 [SMILES: COc1ccc(Nc2cc(NCC3CCNCC3)ccn2)cc1OCCCN1CCCC1] |
| 11 | 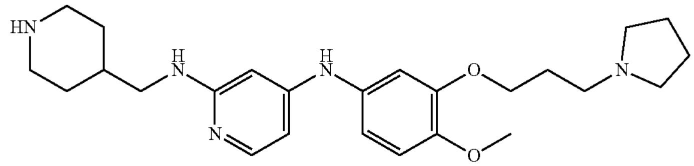 |
| 12 | 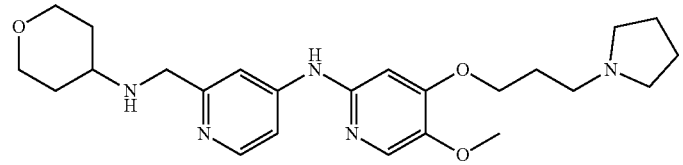 [SMILES: COc1cnc(Nc2ccnc(CNC3CCOCC3)c2)cc1OCCCN1CCCC1] |
| 13 | 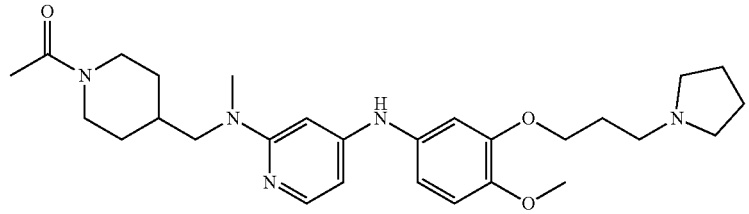 [SMILES: COc1ccc(Nc2ccnc(N(C)CC3CCN(C(C)=O)CC3)c2)cc1OCCCN1CCCC1] |
| 14 | 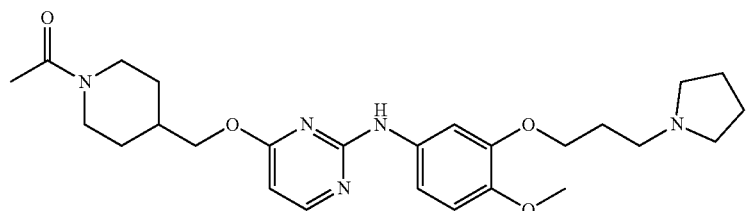 |
| 15 | 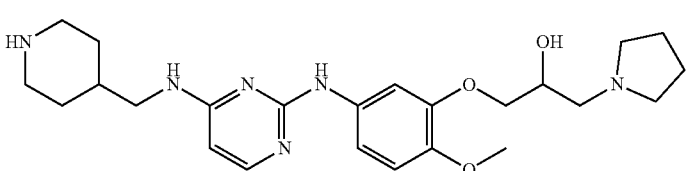 |
| 16 | 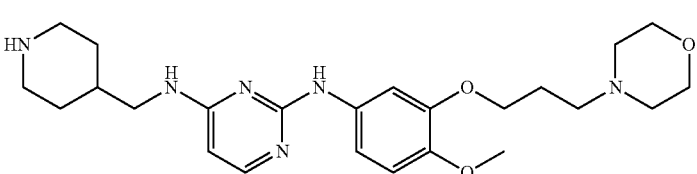 |
| 17 | 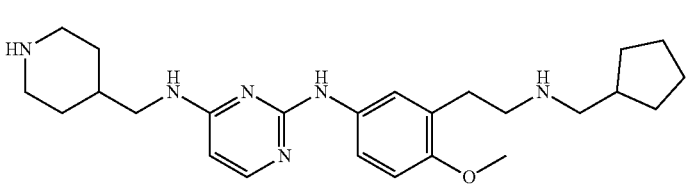 [SMILES: COc1ccc(Nc2nccc(NCC3CCNCC3)n2)cc1CCNCC1CCCC1] |

TABLE 1-continued
| Compound No. | Structure |
|---|---|
| 18 | 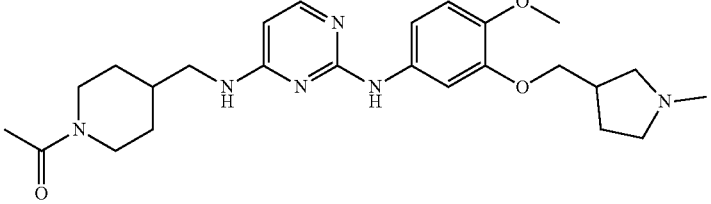 |
| 19 | 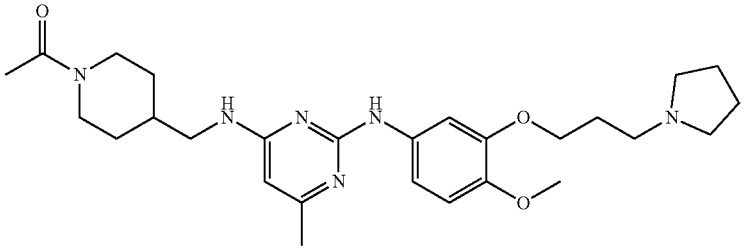 [SMILES: COc1ccc(Nc2nc(C)cc(NCC3CCN(C(C)=O)CC3)n2)cc1OCCCN1CCCC1] |
| 20 | 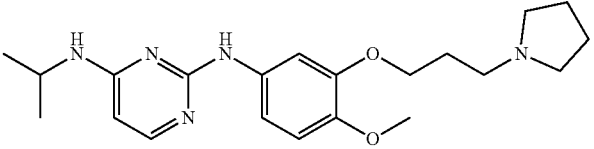 [SMILES: COc1ccc(Nc2nccc(NC(C)C)n2)cc1OCCCN1CCCC1] |
| 21 | 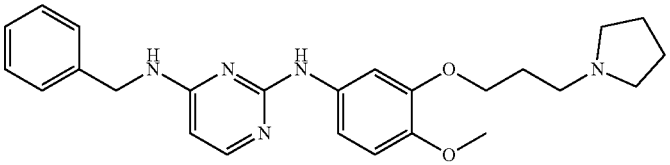 [SMILES: COc1ccc(Nc2nccc(NCc3ccccc3)n2)cc1OCCCN1CCCC1] |
| 22 | 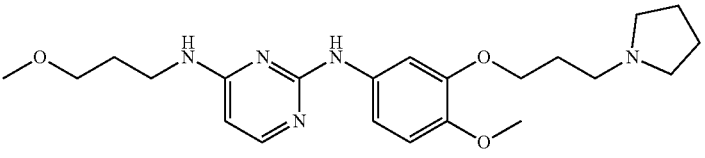 [SMILES: COCCCNc1ccnc(Nc2ccc(OC)c(OCCCN3CCCC3)c2)n1] |
| 23 | 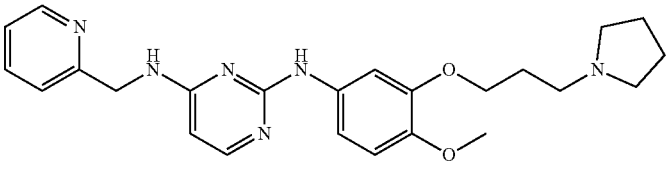 [SMILES: COc1ccc(Nc2nccc(NCc3ccccn3)n2)cc1OCCCN1CCCC1] |
| 24 | 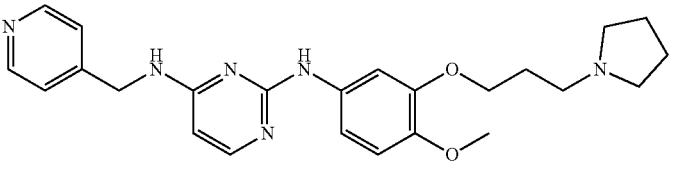 [SMILES: COc1ccc(Nc2nccc(NCc3ccncc3)n2)cc1OCCCN1CCCC1] |
| 25 | 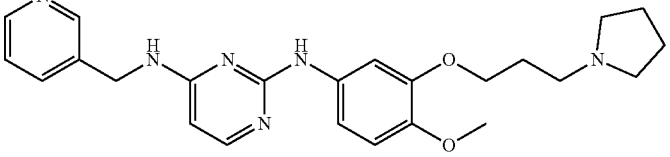 |

TABLE 1-continued

| Compound No. | Structure |
|---|---|
| 26 | 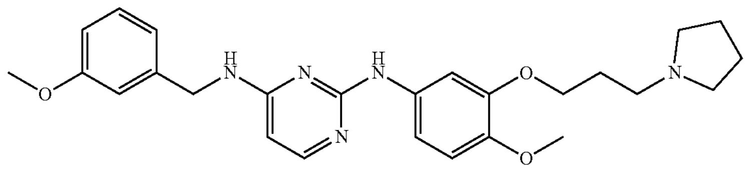 [SMILES: COc1cccc(CNc2ccnc(Nc3ccc(OC)c(OCCCN4CCCC4)c3)n2)c1] |
| 27 | 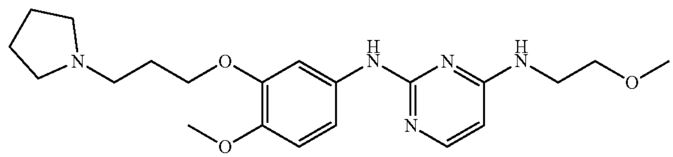 [SMILES: COCCNc1ccnc(Nc2ccc(OC)c(OCCCN3CCCC3)c2)n1] |
| 28 | 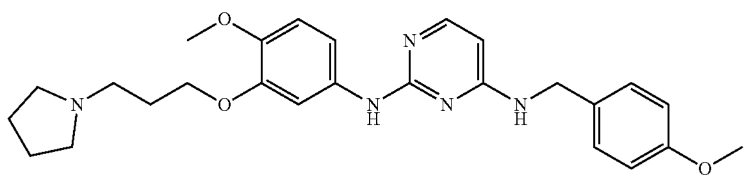 [SMILES: COc1ccc(CNc2ccnc(Nc3ccc(OC)c(OCCCN4CCCC4)c3)n2)cc1] |
| 29 | 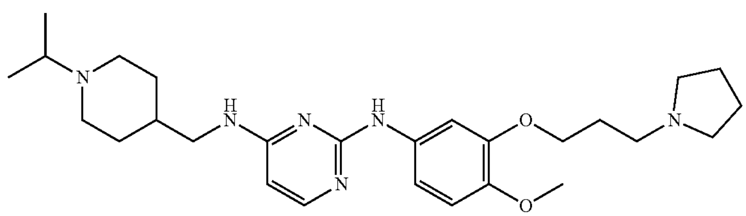 [SMILES: COc1ccc(Nc2nccc(NCC3CCN(C(C)C)CC3)n2)cc1OCCCN1CCCC1] |
| 30 | 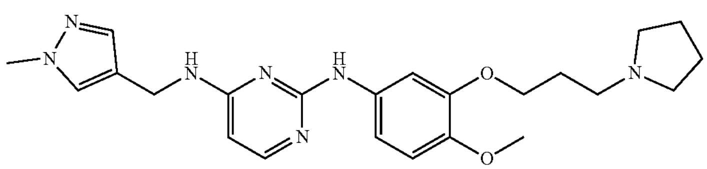 [SMILES: COc1ccc(Nc2nccc(NCc3cnn(C)c3)n2)cc1OCCCN1CCCC1] |
| 31 | 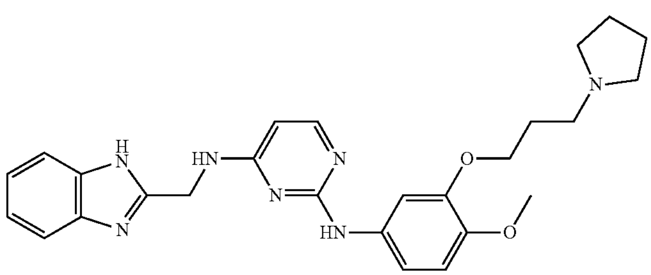 [SMILES: COc1ccc(Nc2nccc(NCc3nc4ccccc4[nH]3)n2)cc1OCCCN1CCCC1] |
| 32 | 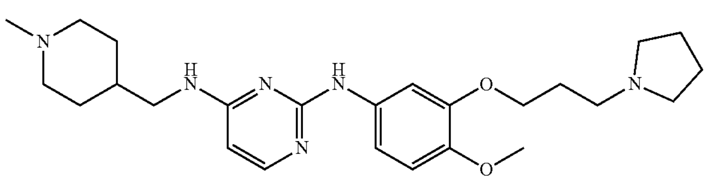 [SMILES: COc1ccc(Nc2nccc(NCC3CCN(C)CC3)n2)cc1OCCCN1CCCC1] |

TABLE 1-continued

| Compound No. | Structure |
|---|---|
| 33 | 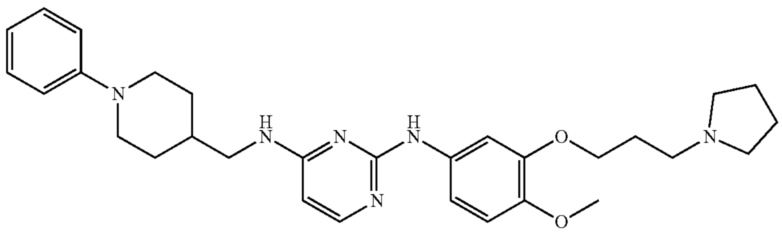 [SMILES: COc1ccc(Nc2nccc(NCC3CCN(c4ccccc4)CC3)n2)cc1OCCCN1CCCC1] |
| 34 | 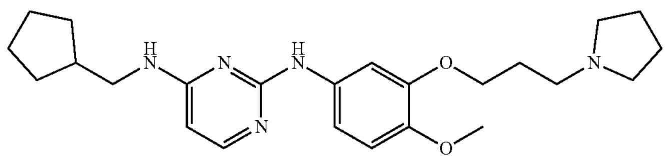 [SMILES: COc1ccc(Nc2nccc(NCC3CCCC3)n2)cc1OCCCN1CCCC1] |
| 35 | 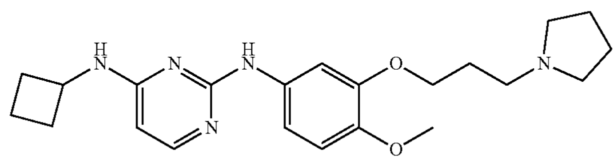 [SMILES: COc1ccc(Nc2nccc(NC3CCC3)n2)cc1OCCCN1CCCC1] |
| 36 | 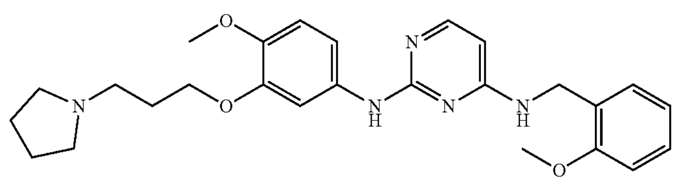 [SMILES: COc1ccccc1CNc1ccnc(Nc2ccc(OC)c(OCCCN3CCCC3)c2)n1] |
| 37 | 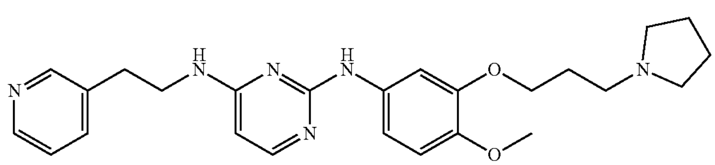 [SMILES: COc1ccc(Nc2nccc(NCCc3cccnc3)n2)cc1OCCCN1CCCC1] |
| 38 | 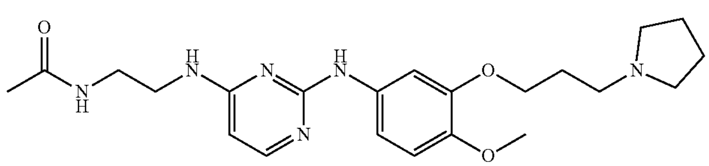 [SMILES: COc1ccc(Nc2nccc(NCCNC(C)=O)n2)cc1OCCCN1CCCC1] |
| 39 | 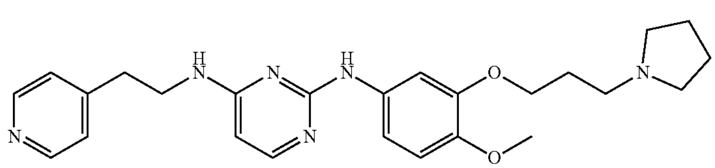 [SMILES: COc1ccc(Nc2nccc(NCCc3ccncc3)n2)cc1OCCCN1CCCC1] |
| 40 | 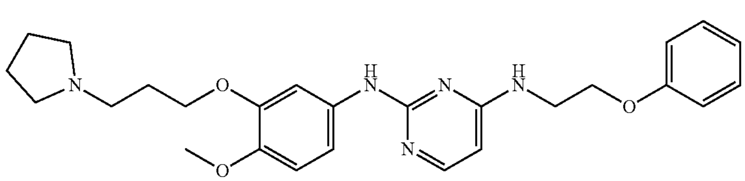 [SMILES: COc1ccc(Nc2nccc(NCCOc3ccccc3)n2)cc1OCCCN1CCCC1] |

TABLE 1-continued
| Compound No. | Structure |
|---|---|
| 41 | 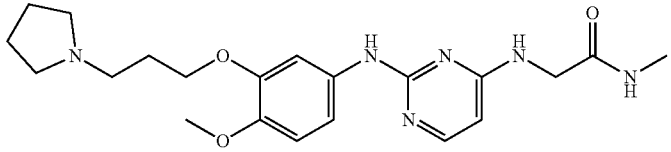 [SMILES: CNC(=O)CNc1ccnc(Nc2ccc(OC)c(OCCCN3CCCC3)c2)n1] |
| 42 | 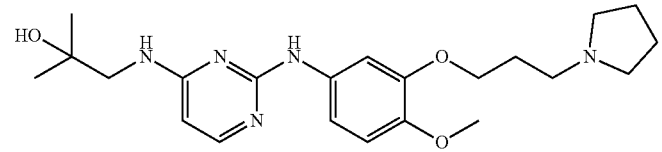 [SMILES: COc1ccc(Nc2nccc(NCC(C)(C)O)n2)cc1OCCCN1CCCC1] |
| 43 | 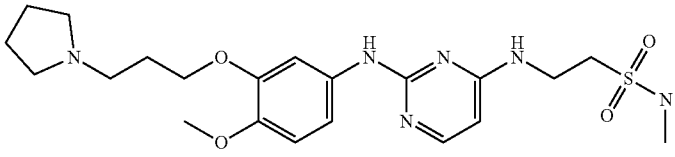 |
| 44 | 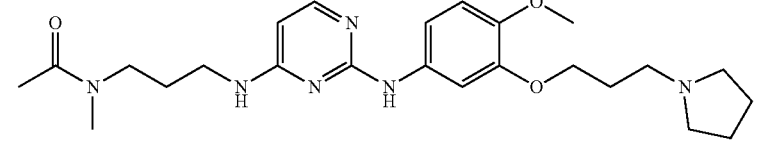 |
| 45 | 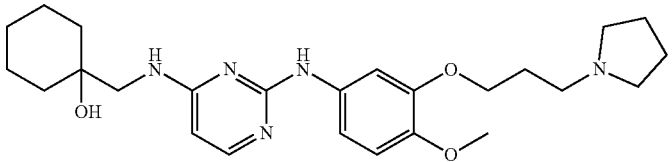 [SMILES: COc1ccc(Nc2nccc(NCC3(O)CCCCC3)n2)cc1OCCCN1CCCC1] |
| 46 | 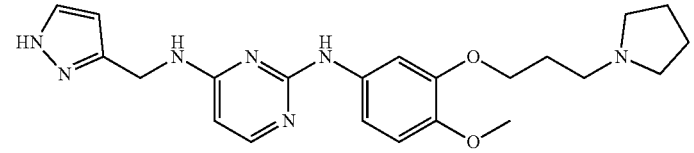 [SMILES: COc1ccc(Nc2nccc(NCc3cc[nH]n3)n2)cc1OCCCN1CCCC1] |
| 47 | 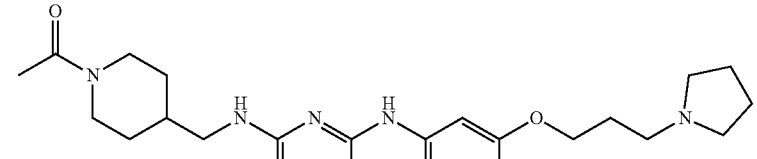 |
| 48 | 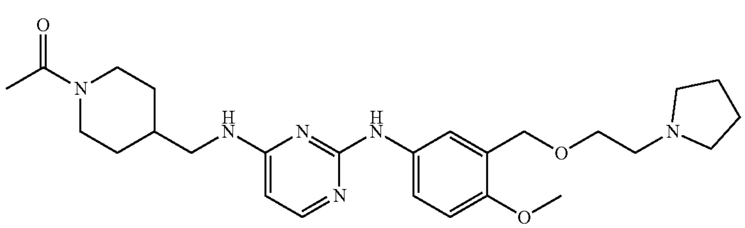 [SMILES: COc1ccc(Nc2nccc(NCC3CCN(C(C)=O)CC3)n2)cc1OCCCN1CCCC1] |

TABLE 1-continued

| Compound No. | Structure |
|---|---|
| 49 | (structure) |
| 50 | (structure) |
| 51 | (structure) |
| 52 | (structure) |
| 53 | (structure) |
| 54 | (structure) |
| 55 | (structure) |
| 56 | (structure) |

TABLE 1-continued

| Compound No. | Structure |
|---|---|
| 57 | *(chemical structure)* |
| 58 | *(chemical structure)* |
| 59 | *(chemical structure)* |
| 60 | *(chemical structure)* |
| 61 | *(chemical structure)* |
| 62 | *(chemical structure)* |
| 63 | *(chemical structure)* |
| 64 | *(chemical structure)* |
| 65 | *(chemical structure)* |

TABLE 1-continued

| Compound No. | Structure |
|---|---|
| 66 | 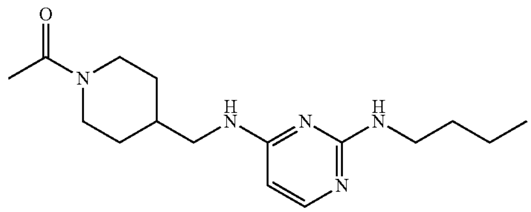 [SMILES: CCCCNc1nccc(NCC2CCN(C(C)=O)CC2)n1] |
| 67 | 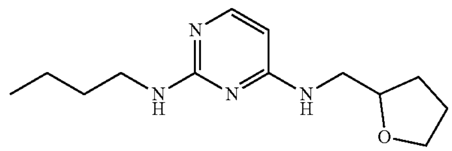 [SMILES: CCCCNc1nccc(NCC2CCCO2)n1] |
| 68 | 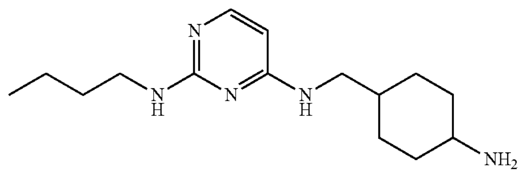 [SMILES: CCCCNc1nccc(NCC2CCC(N)CC2)n1] |
| 69 | 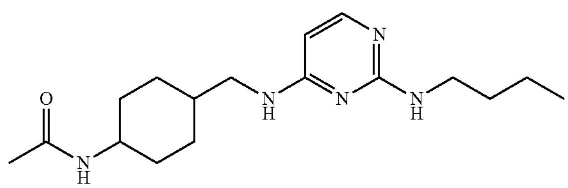 [SMILES: CCCCNc1nccc(NCC2CCC(NC(C)=O)CC2)n1] |
| 70 | 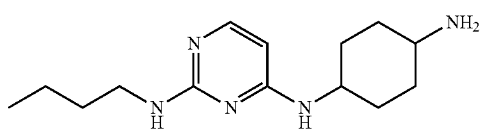 [SMILES: CCCCNc1nccc(NC2CCC(N)CC2)n1] |
| 71 | 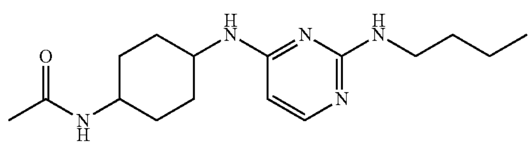 [SMILES: CCCCNc1nccc(NC2CCC(NC(C)=O)CC2)n1] |
| 72 | 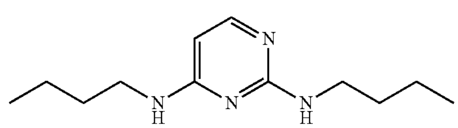 [SMILES: CCCCNc1ccnc(NCCCC)n1] |
| 73 | 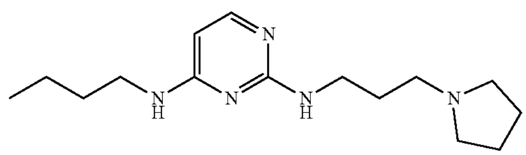 [SMILES: CCCCNc1ccnc(NCCCN2CCCC2)n1] |
| 74 | 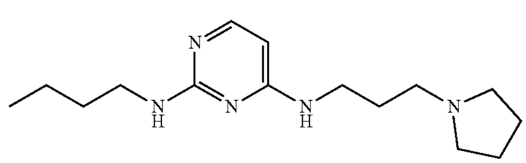 [SMILES: CCCCNc1nccc(NCCCN2CCCC2)n1] |

TABLE 1-continued

| Compound No. | Structure |
|---|---|
| 75 | 2-((2-methoxyethyl)amino)pyrimidin-4-amine |
| 76 | N2-butyl-N4-(3-(dimethylamino)propyl)pyrimidine-2,4-diamine |
| 77 | N4-butyl-N2-(3-aminopropyl)pyrimidine-2,4-diamine |
| 78 | N2-(3-(dimethylamino)propyl)-N4-butylpyrimidine-2,4-diamine |
| 79 | N2-butyl-N4-(3-aminopropyl)pyrimidine-2,4-diamine |
| 80 | 2-(butylamino)pyrimidine-4-carboxamide |
| 81 | 2-(butylamino)-N-(tetrahydro-2H-pyran-4-yl)pyrimidine-4-carboxamide |
| 82 | N2-butyl-5-phenylpyrimidine-2,4-diamine |
| 83 | 2-(butylamino)-4-((piperidin-4-ylmethyl)amino)pyrimidine-5-carbonitrile |

TABLE 1-continued

| Compound No. | Structure |
|---|---|
| 84 | 5-cyano-N4-butyl-N2-(piperidin-4-ylmethyl)pyrimidine-2,4-diamine |
| 85 | 2-(butylamino)-6-{[(piperidin-4-yl)methyl]amino}pyrimidine-4-carboxamide |
| 86 | N2-butyl-6-methyl-N4-(piperidin-4-ylmethyl)pyrimidine-2,4-diamine |
| 87 | N4-butyl-N2-[(1-methylpiperidin-4-yl)methyl]pyrimidine-2,4-diamine |
| 88 | N2-{3-[3-(pyrrolidin-1-yl)propoxy]phenyl}-N4-(piperidin-4-ylmethyl)pyrimidine-2,4-diamine |
| 89 | 2-(butylamino)-4-{[(piperidin-4-yl)methyl]amino}pyrimidine-5-carboxamide |
| 90 | N4-(piperidin-4-ylmethyl)-N2-{4-methoxy-3-[3-(pyrrolidin-1-yl)propoxy]phenyl}pyrimidine-2,4-diamine |
| 91 | N2-butyl-5-methyl-N4-(piperidin-4-ylmethyl)pyrimidine-2,4-diamine |

TABLE 1-continued
| Compound No. | Structure |
|---|---|
| 92 | 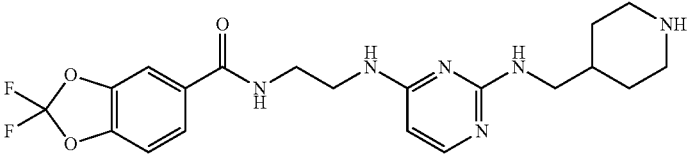 [SMILES: O=C(NCCNc1ccnc(NCC2CCNCC2)n1)c1ccc2c(c1)OC(F)(F)O2] |
| 93 | 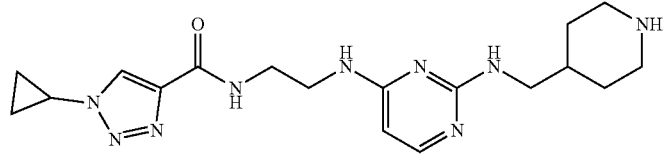 [SMILES: O=C(NCCNc1ccnc(NCC2CCNCC2)n1)c1cn(C2CC2)nn1] |
| 94 | 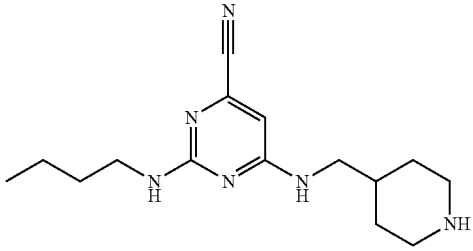 [SMILES: CCCCNc1nc(C#N)cc(NCC2CCNCC2)n1] |
| 95 | 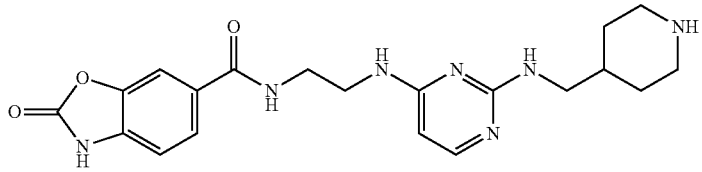 [SMILES: O=C(NCCNc1ccnc(NCC2CCNCC2)n1)c1ccc2[nH]c(=O)oc2c1] |
| 96 | 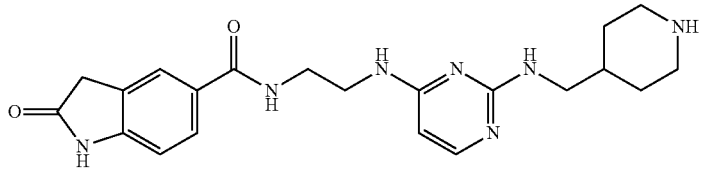 [SMILES: O=C1Cc2cc(C(=O)NCCNc3ccnc(NCC4CCNCC4)n3)ccc2N1] |
| 97 | 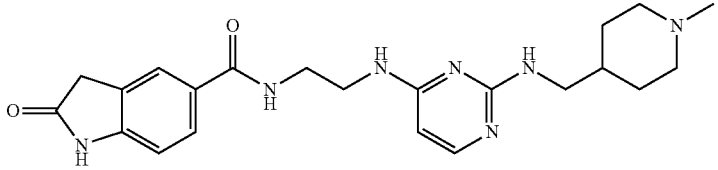 [SMILES: CN1CCC(CNc2nccc(NCCNC(=O)c3ccc4c(c3)CC(=O)N4)n2)CC1] |
| 98 | 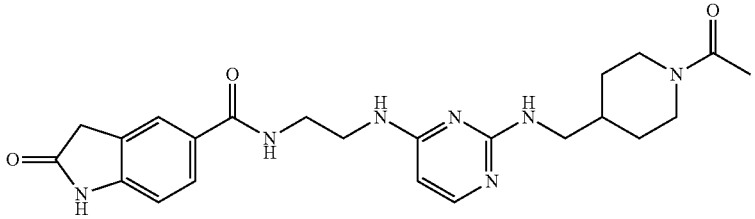 [SMILES: CC(=O)N1CCC(CNc2nccc(NCCNC(=O)c3ccc4c(c3)CC(=O)N4)n2)CC1] |

TABLE 1-continued

| Compound No. | Structure |
|---|---|
| 99 | 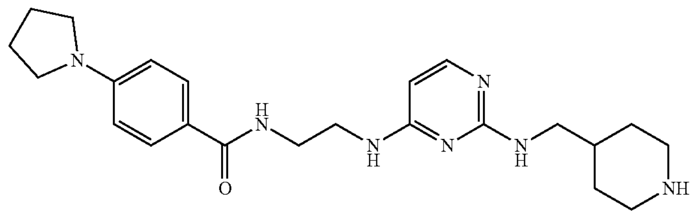 [SMILES: O=C(NCCNc1ccnc(NCC2CCNCC2)n1)c1ccc(N2CCCC2)cc1] |
| 100 | 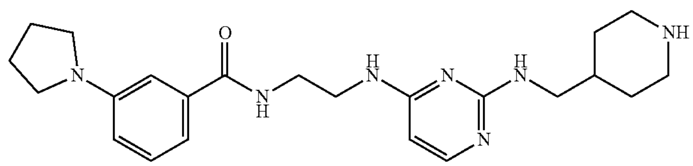 [SMILES: O=C(NCCNc1ccnc(NCC2CCNCC2)n1)c1cccc(N2CCCC2)c1] |
| 101 | 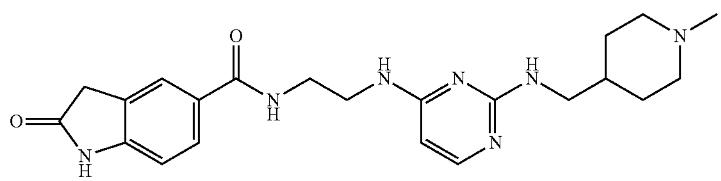 [SMILES: CN1CCC(CNc2nccc(NCCNC(=O)c3ccc4c(c3)CC(=O)N4)n2)CC1] |
| 102 | 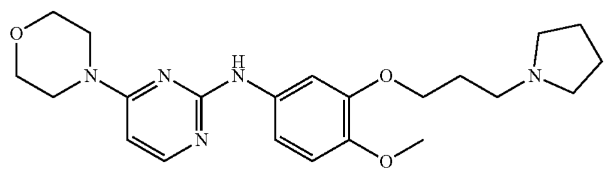 [SMILES: COc1ccc(Nc2nccc(N3CCOCC3)n2)cc1OCCCN1CCCC1] |
| 103 | 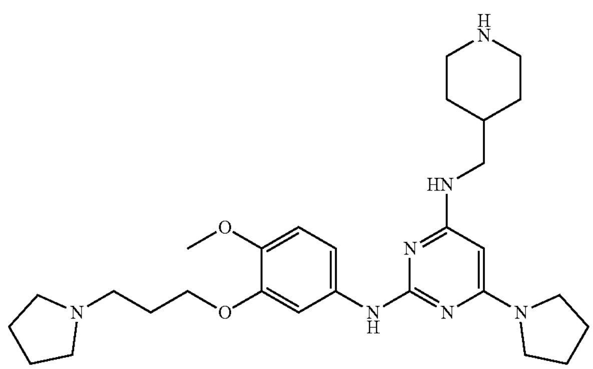 [SMILES: COc1ccc(Nc2nc(NCC3CCNCC3)cc(N3CCCC3)n2)cc1OCCCN1CCCC1] |
| 104 | 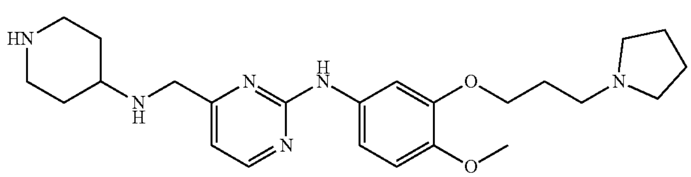 [SMILES: COc1ccc(Nc2nccc(CNC3CCNCC3)n2)cc1OCCCN1CCCC1] |
| 105 | 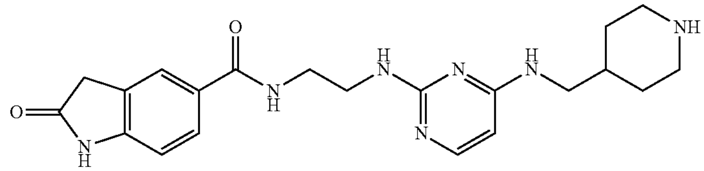 [SMILES: O=C1Cc2cc(C(=O)NCCNc3nccc(NCC4CCNCC4)n3)ccc2N1] |

TABLE 1-continued
| Compound No. | Structure |
|---|---|
| 106 | 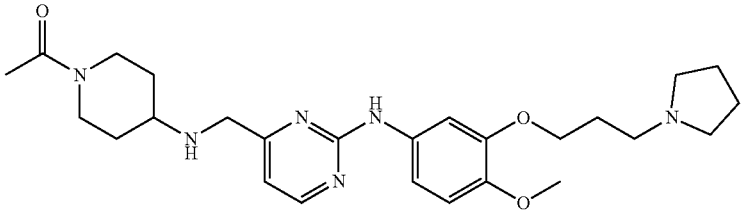 [SMILES: COc1ccc(Nc2nccc(CNC3CCN(C(C)=O)CC3)n2)cc1OCCCN1CCCC1] |
| 107 | 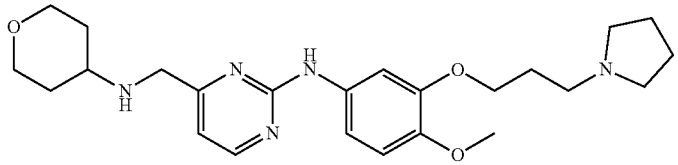 [SMILES: COc1ccc(Nc2nccc(CNC3CCOCC3)n2)cc1OCCCN1CCCC1] |
| 108 | 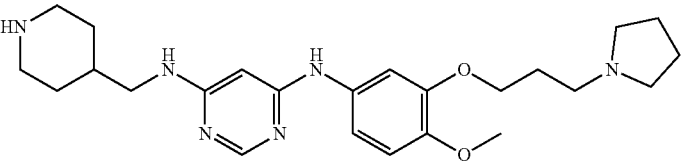 |
| 109 | 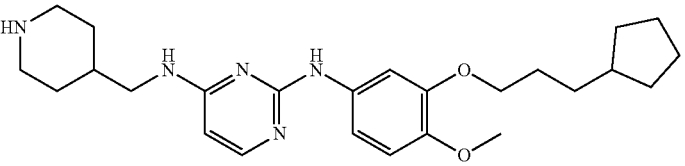 [SMILES: COc1ccc(Nc2nccc(NCC3CCNCC3)n2)cc1OCCCC1CCCC1] |
| 110 | 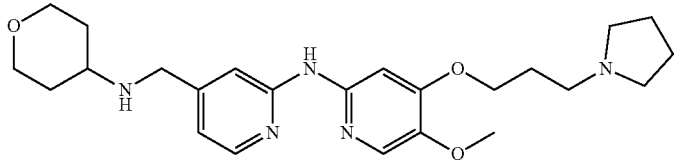 [SMILES: COc1cnc(Nc2cc(CNC3CCOCC3)ccn2)cc1OCCCN1CCCC1] |
| 111 | 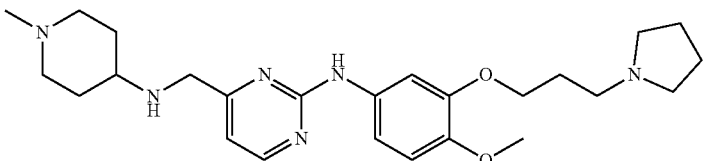 |
| 112 | 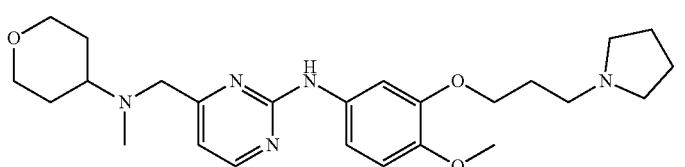 |
| 113 | 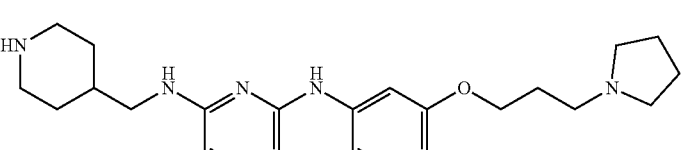 |

TABLE 1-continued

| Compound No. | Structure |
|---|---|
| 114 | 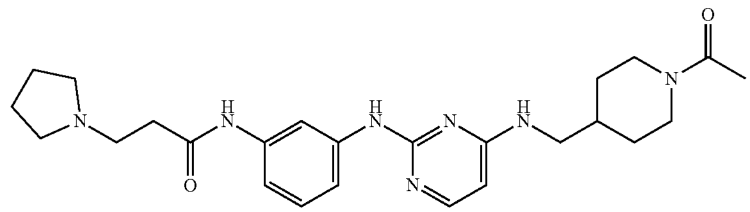 [SMILES: CC(=O)N1CCC(CNc2ccnc(Nc3cccc(NC(=O)CCN4CCCC4)c3)n2)CC1] |
| 115 | 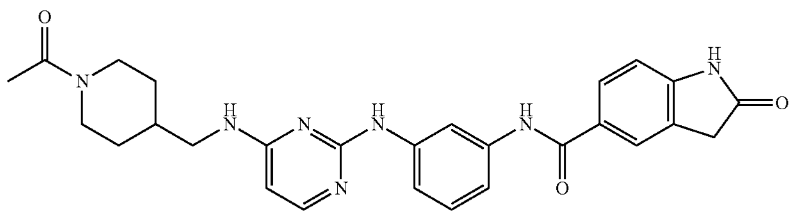 [SMILES: CC(=O)N1CCC(CNc2ccnc(Nc3cccc(NC(=O)c4ccc5c(c4)CC(=O)N5)c3)n2)CC1] |
| 116 | 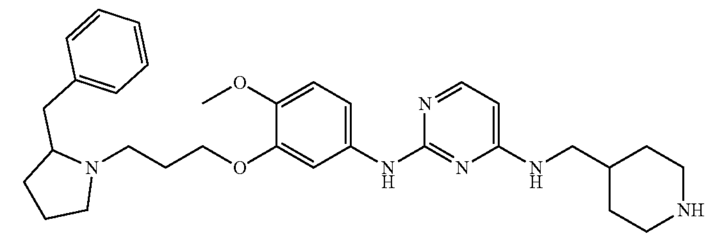 [SMILES: COc1ccc(Nc2nccc(NCC3CCNCC3)n2)cc1OCCCN1CCCC1Cc1ccccc1] |
| 117 | 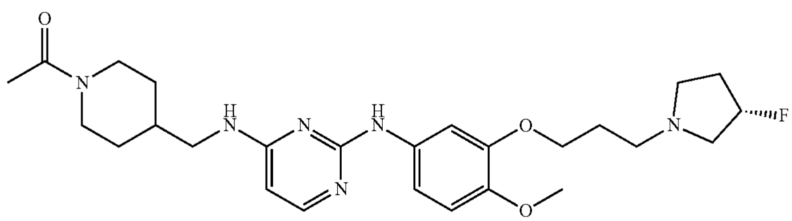 [SMILES: COc1ccc(Nc2nccc(NCC3CCN(C(C)=O)CC3)n2)cc1OCCCN1CC[C@H](F)C1] |
| 118 | 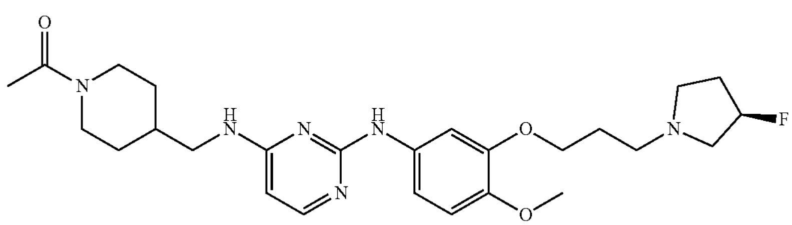 [SMILES: COc1ccc(Nc2nccc(NCC3CCN(C(C)=O)CC3)n2)cc1OCCCN1CC[C@@H](F)C1] |
| 119 | 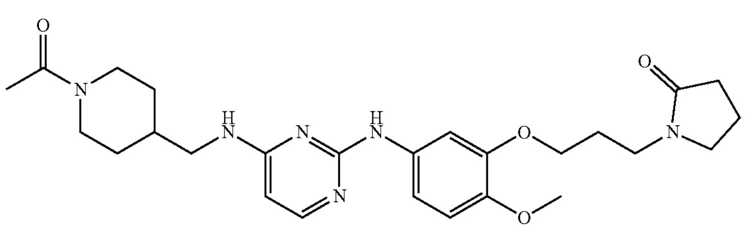 [SMILES: COc1ccc(Nc2nccc(NCC3CCN(C(C)=O)CC3)n2)cc1OCCCN1CCCC1=O] |
| 120 | 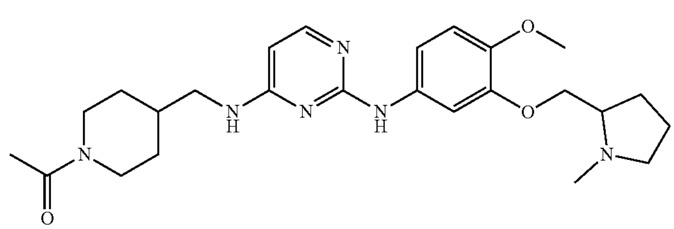 [SMILES: COc1ccc(Nc2nccc(NCC3CCN(C(C)=O)CC3)n2)cc1OCC1CCCN1C] |

TABLE 1-continued

| Compound No. | Structure |
|---|---|
| 121 | 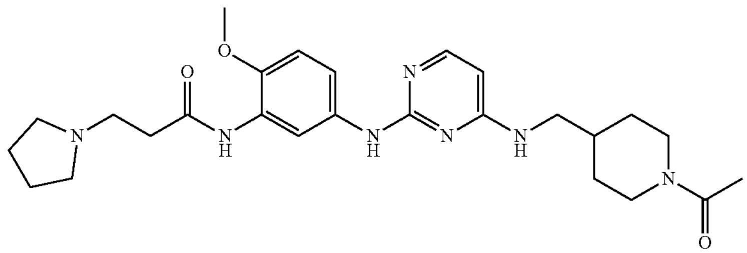 [SMILES: COc1ccc(Nc2nccc(NCC3CCN(C(C)=O)CC3)n2)cc1NC(=O)CCN1CCCC1] |
| 122 | 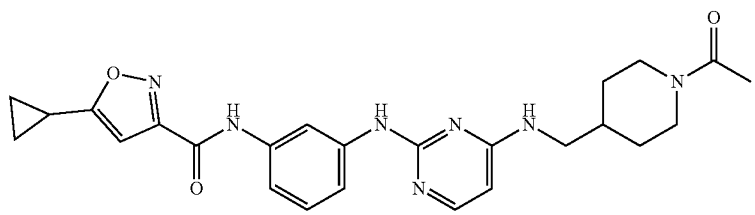 [SMILES: CC(=O)N1CCC(CNc2ccnc(Nc3cccc(NC(=O)c4cc(C5CC5)on4)c3)n2)CC1] |
| 123 | 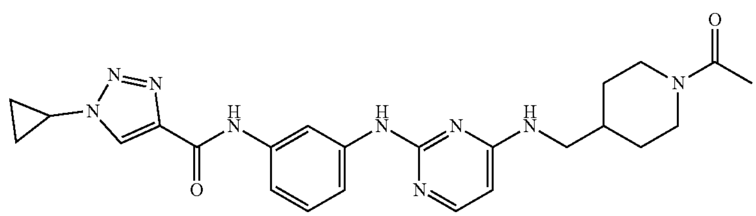 [SMILES: CC(=O)N1CCC(CNc2ccnc(Nc3cccc(NC(=O)c4cn(C5CC5)nn4)c3)n2)CC1] |
| 124 | 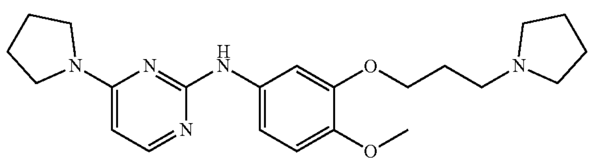 [SMILES: COc1ccc(Nc2nccc(N3CCCC3)n2)cc1OCCCN1CCCC1] |
| 125 | 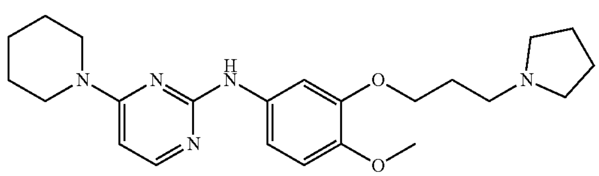 [SMILES: COc1ccc(Nc2nccc(N3CCCCC3)n2)cc1OCCCN1CCCC1] |
| 126 | 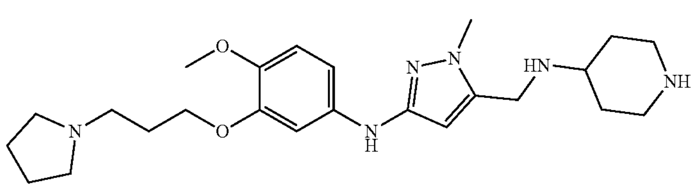 [SMILES: COc1ccc(Nc2cc(CNC3CCNCC3)n(C)n2)cc1OCCCN1CCCC1] |
| 127 | 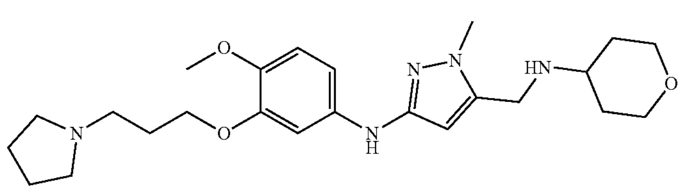 [SMILES: COc1ccc(Nc2cc(CNC3CCOCC3)n(C)n2)cc1OCCCN1CCCC1] |

TABLE 1-continued
| Compound No. | Structure |
|---|---|
| 128 | 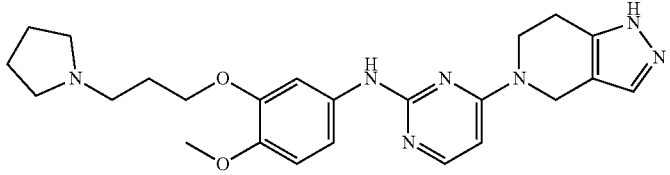 [SMILES: COc1ccc(Nc2nccc(N3CCc4[nH]ncc4C3)n2)cc1OCCCN1CCCC1] |
| 129 | 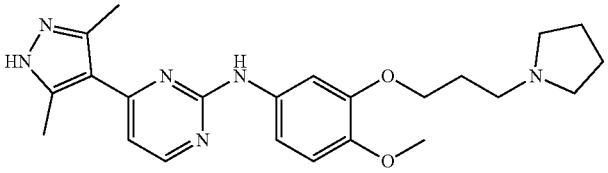 [SMILES: COc1ccc(Nc2nccc(-c3c(C)n[nH]c3C)n2)cc1OCCCN1CCCC1] |
| 130 | 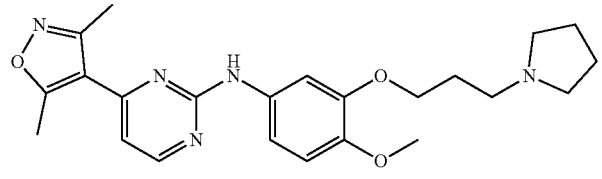 [SMILES: COc1ccc(Nc2nccc(-c3c(C)noc3C)n2)cc1OCCCN1CCCC1] |
| 131 | 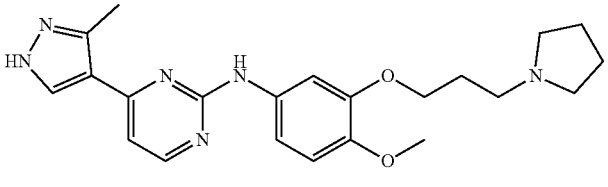 [SMILES: COc1ccc(Nc2nccc(-c3c[nH]nc3C)n2)cc1OCCCN1CCCC1] |
| 132 | 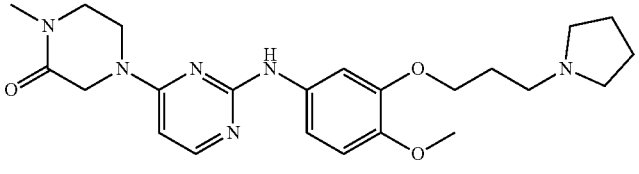 [SMILES: COc1ccc(Nc2nccc(N3CCN(C)C(=O)C3)n2)cc1OCCCN1CCCC1] |
| 133 | 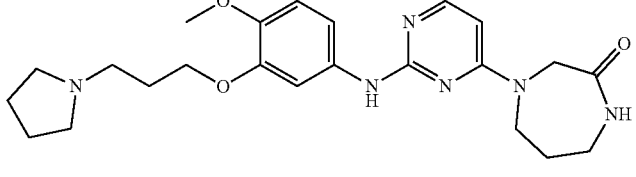 |
| 134 | 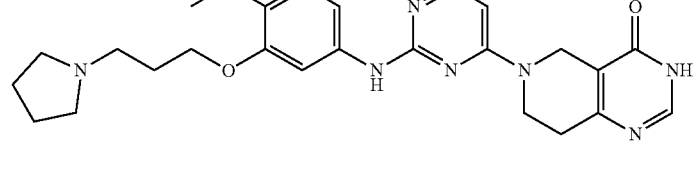 |
| 135 | 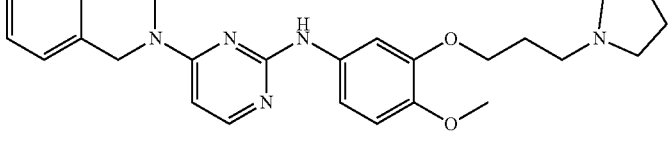 |

TABLE 1-continued

| Compound No. | Structure |
|---|---|
| 136 | 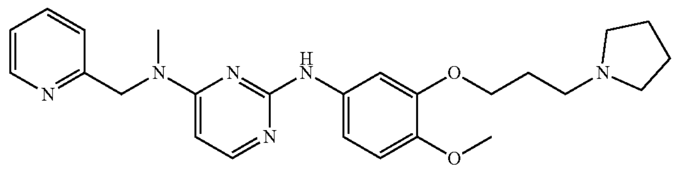 [SMILES: COc1ccc(Nc2nccc(N(C)Cc3ccccn3)n2)cc1OCCCN1CCCC1] |
| 137 | 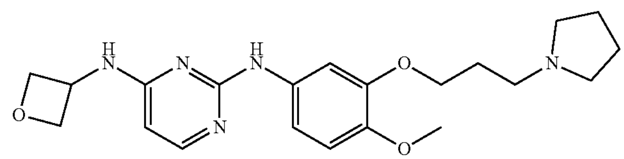 [SMILES: COc1ccc(Nc2nccc(NC3COC3)n2)cc1OCCCN1CCCC1] |
| 138 | 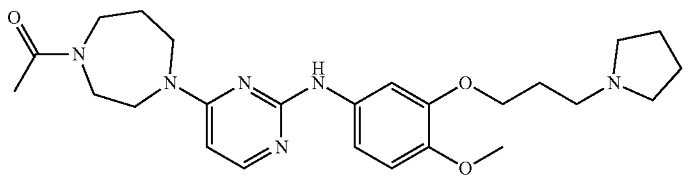 [SMILES: COc1ccc(Nc2nccc(N3CCCN(C(C)=O)CC3)n2)cc1OCCCN1CCCC1] |
| 139 | 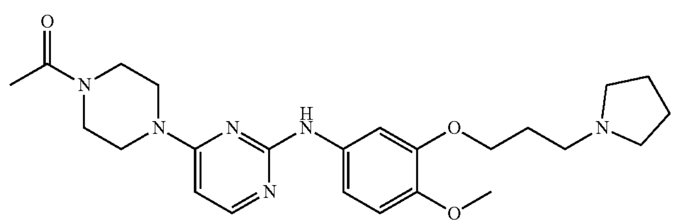 [SMILES: COc1ccc(Nc2nccc(N3CCN(C(C)=O)CC3)n2)cc1OCCCN1CCCC1] |
| 140 | 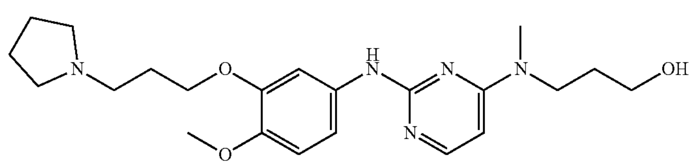 [SMILES: COc1ccc(Nc2nccc(N(C)CCCO)n2)cc1OCCCN1CCCC1] |
| 141 | 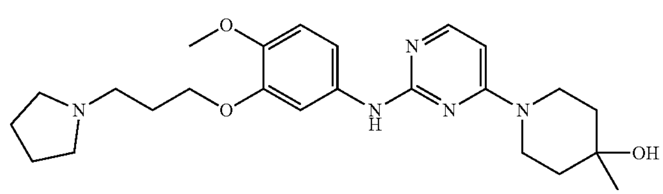 [SMILES: COc1ccc(Nc2nccc(N3CCC(C)(O)CC3)n2)cc1OCCCN1CCCC1] |
| 142 | 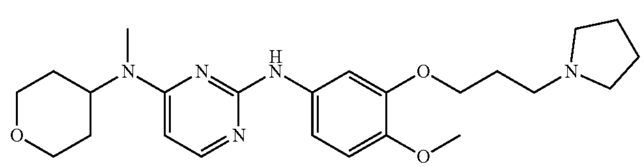 [SMILES: COc1ccc(Nc2nccc(N(C)C3CCOCC3)n2)cc1OCCCN1CCCC1] |
| 143 | 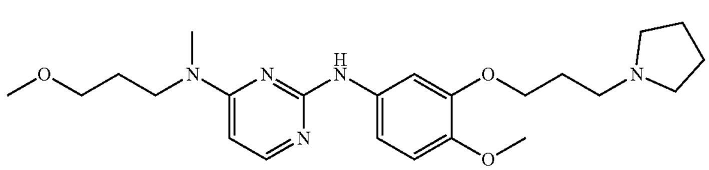 [SMILES: COCCCN(C)c1ccnc(Nc2ccc(OC)c(OCCCN3CCCC3)c2)n1] |

TABLE 1-continued

| Compound No. | Structure |
|---|---|
| 144 | 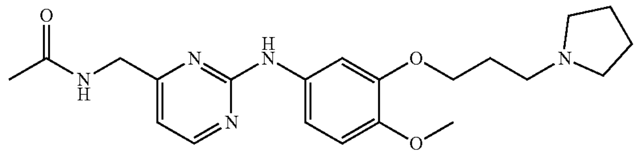 [SMILES: COc1ccc(Nc2nccc(CNC(C)=O)n2)cc1OCCCN1CCCC1] |
| 145 | 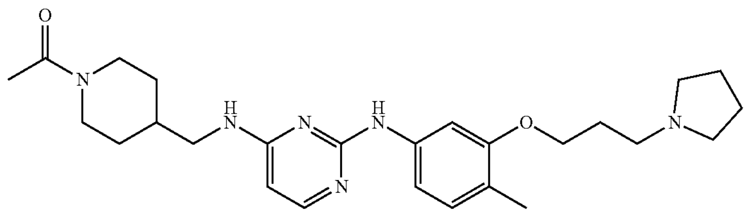 [SMILES: CC(=O)N1CCC(CNc2ccnc(Nc3ccc(C)c(OCCCN4CCCC4)c3)n2)CC1] |
| 146 | 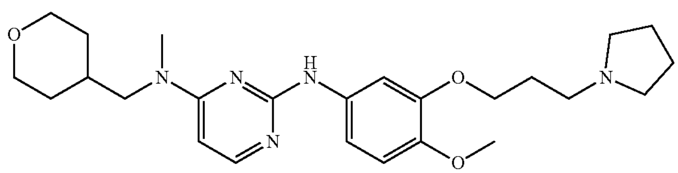 [SMILES: COc1ccc(Nc2nccc(N(C)CC3CCOCC3)n2)cc1OCCCN1CCCC1] |
| 147 | 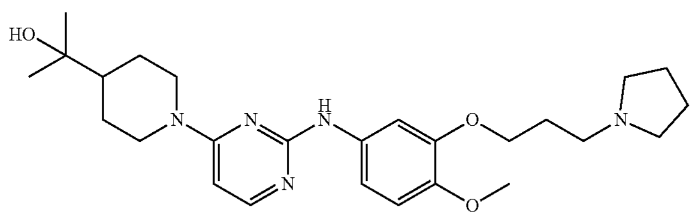 [SMILES: COc1ccc(Nc2nccc(N3CCC(C(C)(C)O)CC3)n2)cc1OCCCN1CCCC1] |
| 148 | 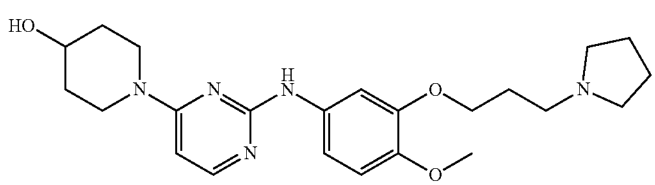 [SMILES: COc1ccc(Nc2nccc(N3CCC(O)CC3)n2)cc1OCCCN1CCCC1] |
| 149 | 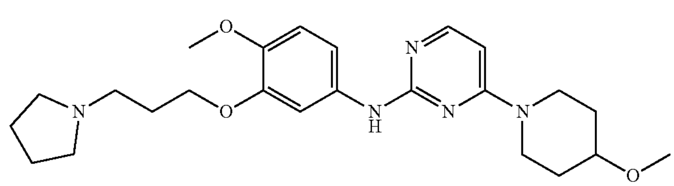 [SMILES: COc1ccc(Nc2nccc(N3CCC(OC)CC3)n2)cc1OCCCN1CCCC1] |
| 150 | 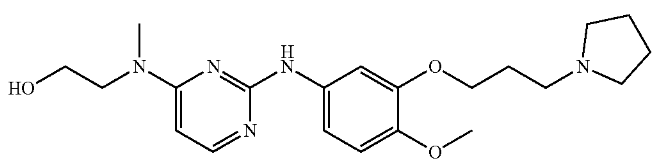 [SMILES: COc1ccc(Nc2nccc(N(C)CCO)n2)cc1OCCCN1CCCC1] |
| 151 | 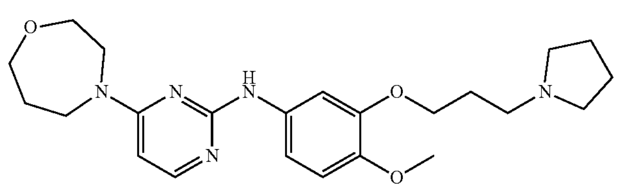 [SMILES: COc1ccc(Nc2nccc(N3CCCOCC3)n2)cc1OCCCN1CCCC1] |

TABLE 1-continued
| Compound No. | Structure |
|---|---|
| 152 | 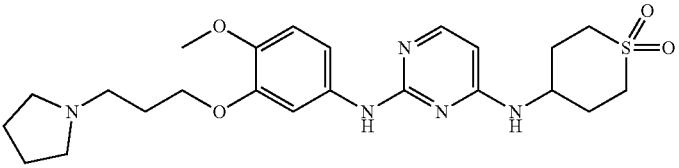 [SMILES: COc1ccc(Nc2nccc(NC3CCS(=O)(=O)CC3)n2)cc1OCCCN1CCCC1] |
| 153 | 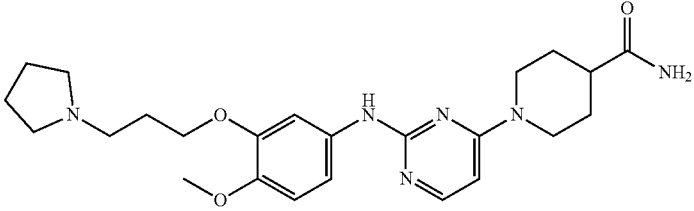 [SMILES: COc1ccc(Nc2nccc(N3CCC(C(N)=O)CC3)n2)cc1OCCCN1CCCC1] |
| 154 | 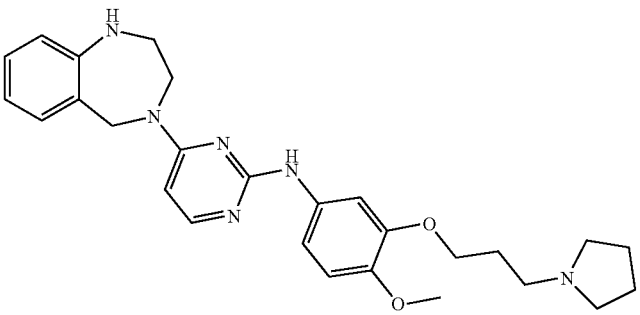 [SMILES: COc1ccc(Nc2nccc(N3CCNc4ccccc4C3)n2)cc1OCCCN1CCCC1] |
| 155 | 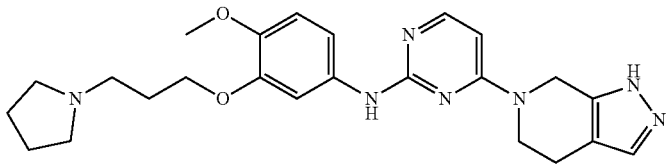 [SMILES: COc1ccc(Nc2nccc(N3CCc4cn[nH]c4C3)n2)cc1OCCCN1CCCC1] |
| 156 | 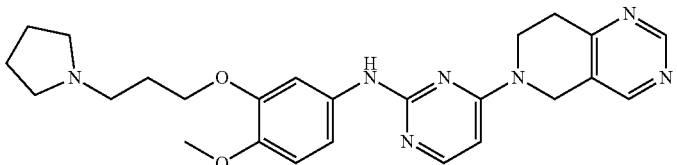 |
| 157 | 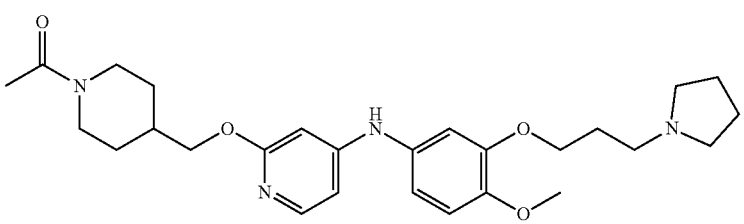 [SMILES: COc1ccc(Nc2ccnc(OCC3CCN(C(C)=O)CC3)c2)cc1OCCCN1CCCC1] |
| 158 | 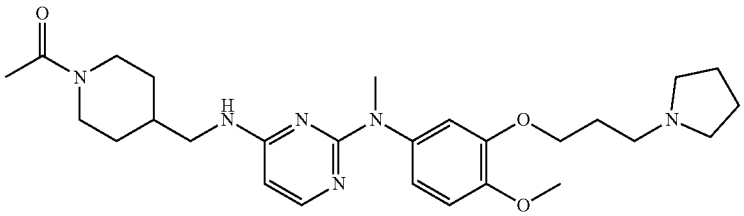 [SMILES: COc1ccc(N(C)c2nccc(NCC3CCN(C(C)=O)CC3)n2)cc1OCCCN1CCCC1] |

TABLE 1-continued
| Compound No. | Structure |
|---|---|
| 159 | 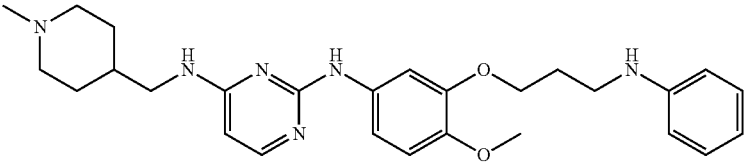 [SMILES: COc1ccc(Nc2nccc(NCC3CCN(C)CC3)n2)cc1OCCCNc1ccccc1] |
| 160 | 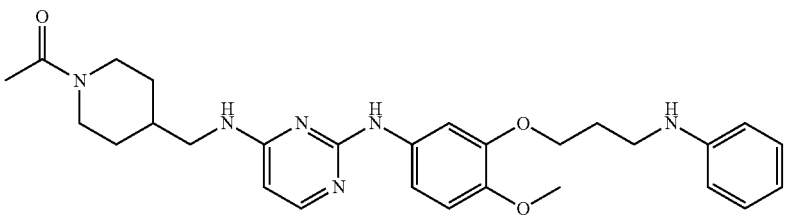 [SMILES: COc1ccc(Nc2nccc(NCC3CCN(C(C)=O)CC3)n2)cc1OCCCNc1ccccc1] |
| 161 | 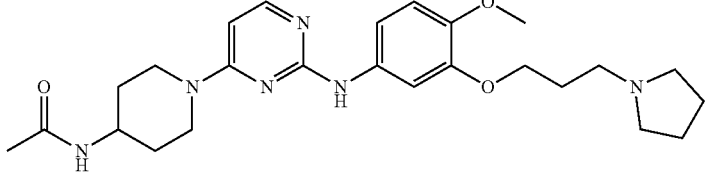 |
| 162 | 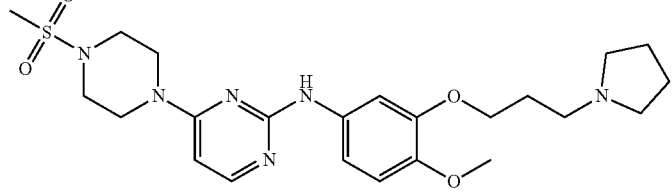 |
| 163 | 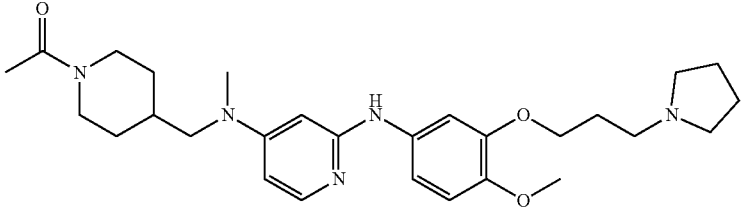 [SMILES: COc1ccc(Nc2cc(N(C)CC3CCN(C(C)=O)CC3)ccn2)cc1OCCCN1CCCC1] |
| 164 | 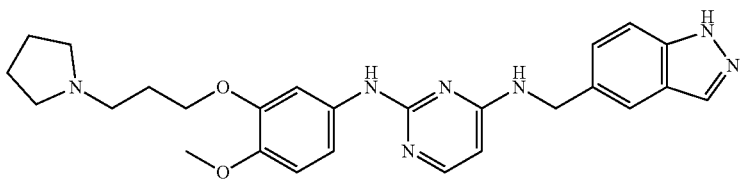 [SMILES: COc1ccc(Nc2nccc(NCc3ccc4[nH]ncc4c3)n2)cc1OCCCN1CCCC1] |
| 165 | 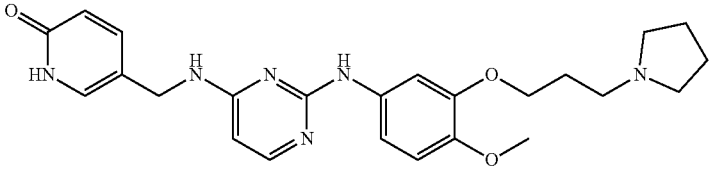 [SMILES: COc1ccc(Nc2nccc(NCc3ccc(=O)[nH]c3)n2)cc1OCCCN1CCCC1] |

TABLE 1-continued
| Compound No. | Structure |
|---|---|
| 166 | 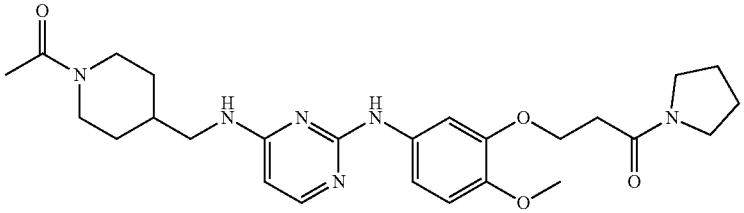 [SMILES: COc1ccc(Nc2nccc(NCC3CCN(C(C)=O)CC3)n2)cc1OCCC(=O)N1CCCC1] |
| 167 | 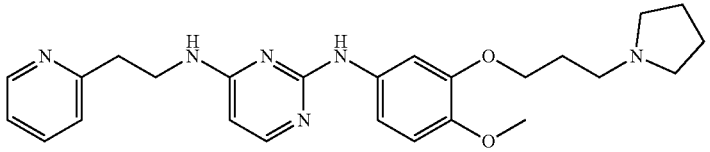 [SMILES: COc1ccc(Nc2nccc(NCCc3ccccn3)n2)cc1OCCCN1CCCC1] |
| 168 | 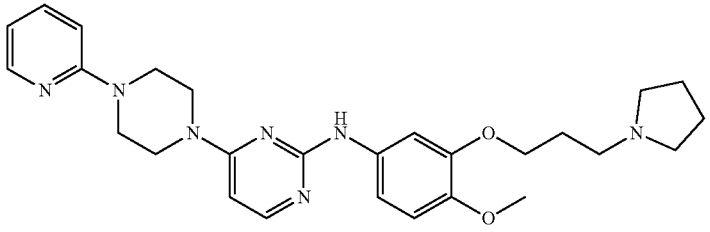 [SMILES: COc1ccc(Nc2nccc(N3CCN(c4ccccn4)CC3)n2)cc1OCCCN1CCCC1] |
| 169 | 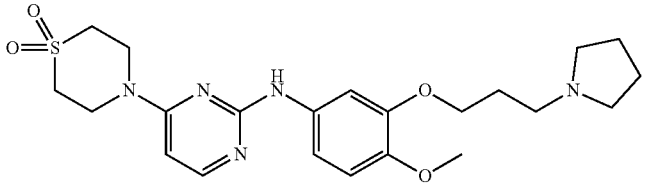 [SMILES: COc1ccc(Nc2nccc(N3CCS(=O)(=O)CC3)n2)cc1OCCCN1CCCC1] |
| 170 | 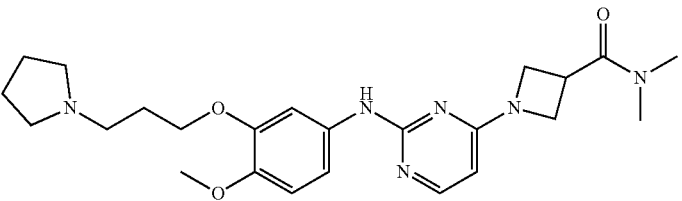 [SMILES: COc1ccc(Nc2nccc(N3CC(C(=O)N(C)C)C3)n2)cc1OCCCN1CCCC1] |
| 171 | 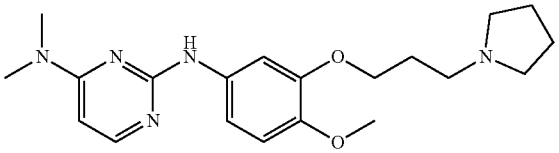 |
| 172 | 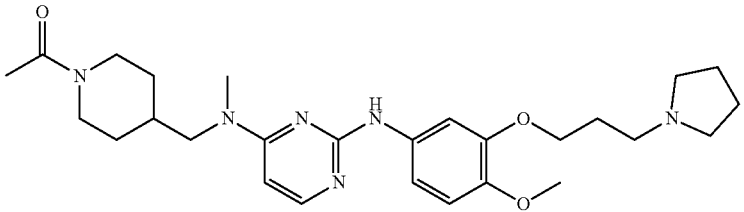 [SMILES: COc1ccc(Nc2nccc(N(C)CC3CCN(C(C)=O)CC3)n2)cc1OCCCN1CCCC1] |

TABLE 1-continued

| Compound No. | Structure |
|---|---|
| 173 | 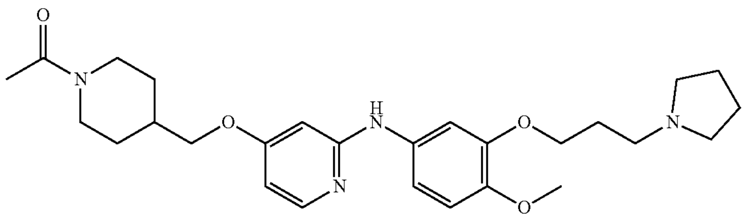 [SMILES: COc1ccc(Nc2cc(OCC3CCN(C(C)=O)CC3)ccn2)cc1OCCCN1CCCC1] |
| 174 | 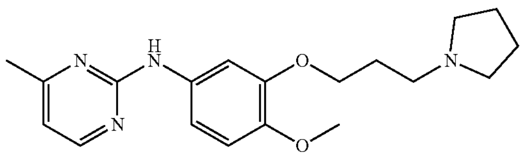 [SMILES: COc1ccc(Nc2nccc(C)n2)cc1OCCCN1CCCC1] |
| 175 | 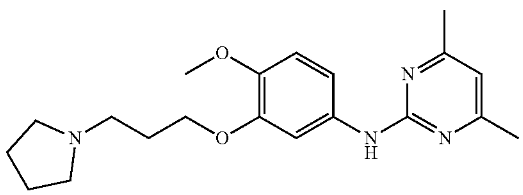 [SMILES: COc1ccc(Nc2nc(C)cc(C)n2)cc1OCCCN1CCCC1] |
| 176 | 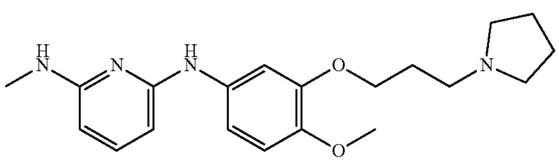 |
| 177 | 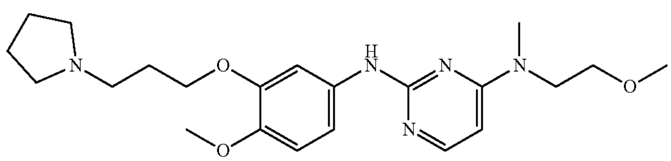 [SMILES: COCCN(C)c1ccnc(Nc2ccc(OC)c(OCCCN3CCCC3)c2)n1] |
| 178 | 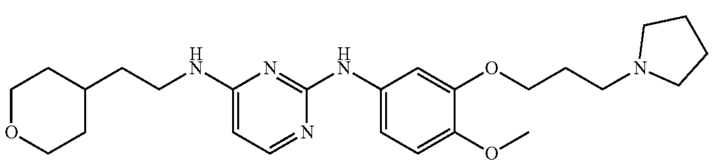 [SMILES: COc1ccc(Nc2nccc(NCCC3CCOCC3)n2)cc1OCCCN1CCCC1] |
| 179 | 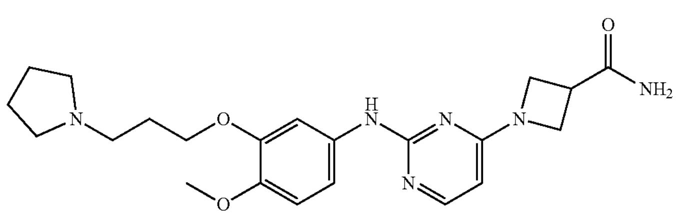 [SMILES: COc1ccc(Nc2nccc(N3CC(C(N)=O)C3)n2)cc1OCCCN1CCCC1] |
| 180 | 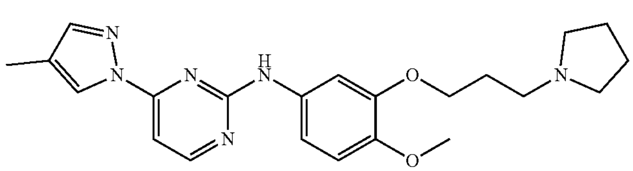 [SMILES: COc1ccc(Nc2nccc(-n3cc(C)cn3)n2)cc1OCCCN1CCCC1] |

TABLE 1-continued

| Compound No. | Structure |
|---|---|
| 181 | 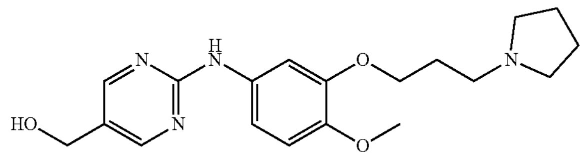 [SMILES: COc1ccc(Nc2ncc(CO)cn2)cc1OCCCN1CCCC1] |
| 182 | 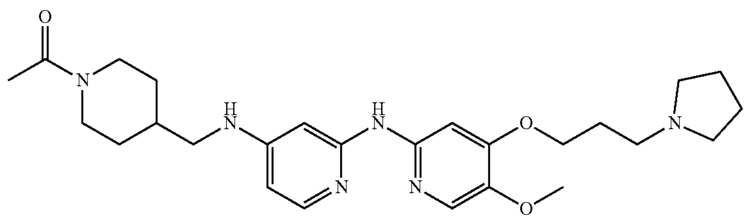 [SMILES: COc1cnc(Nc2cc(NCC3CCN(C(C)=O)CC3)ccn2)cc1OCCCN1CCCC1] |
| 183 | 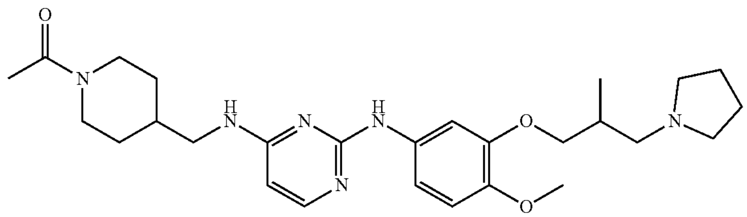 [SMILES: COc1ccc(Nc2nccc(NCC3CCN(C(C)=O)CC3)n2)cc1OCC(C)CN1CCCC1] |
| 184 | 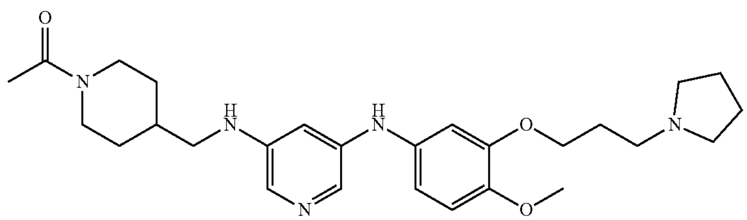 [SMILES: COc1ccc(Nc2cncc(NCC3CCN(C(C)=O)CC3)c2)cc1OCCCN1CCCC1] |
| 185 | 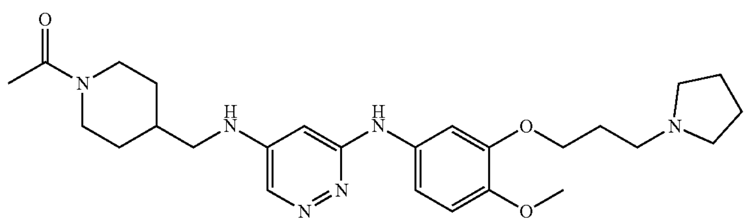 [SMILES: COc1ccc(Nc2cc(NCC3CCN(C(C)=O)CC3)cnn2)cc1OCCCN1CCCC1] |
| 186 | 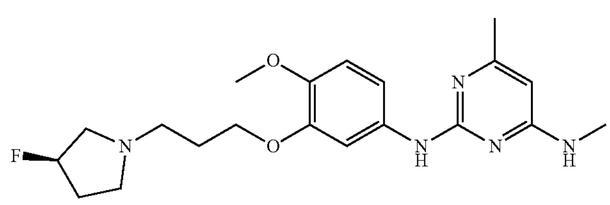 [SMILES: CNc1cc(C)nc(Nc2ccc(OC)c(OCCCN3CC[C@@H](F)C3)c2)n1] |
| 187 | 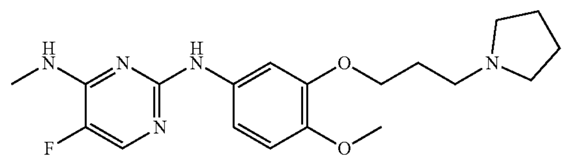 [SMILES: CNc1nc(Nc2ccc(OC)c(OCCCN3CCCC3)c2)ncc1F] |
| 188 | 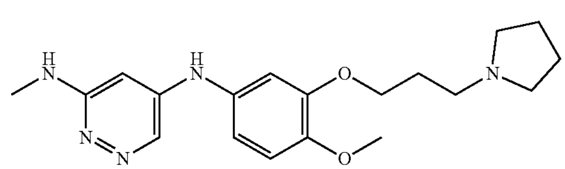 [SMILES: CNc1cc(Nc2ccc(OC)c(OCCCN3CCCC3)c2)cnn1] |

TABLE 1-continued

| Compound No. | Structure |
|---|---|
| 190 | 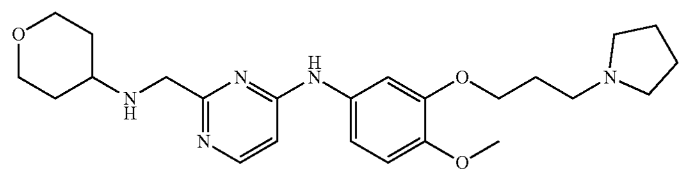 [SMILES: COc1ccc(Nc2ccnc(CNC3CCOCC3)n2)cc1OCCCN1CCCC1] |
| 191 | 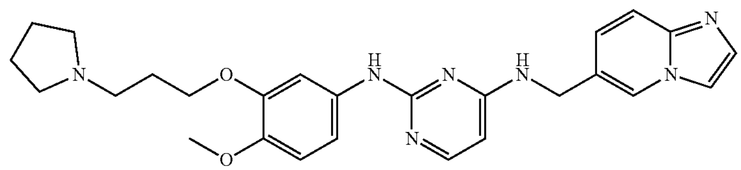 [SMILES: COc1ccc(Nc2nccc(NCc3ccc4nccn4c3)n2)cc1OCCCN1CCCC1] |
| 192 | 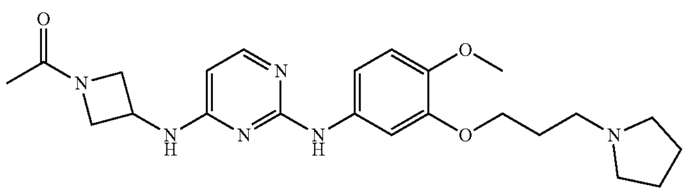 [SMILES: COc1ccc(Nc2nccc(NC3CN(C(C)=O)C3)n2)cc1OCCCN1CCCC1] |
| 193 | 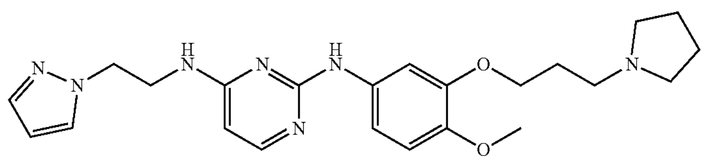 [SMILES: COc1ccc(Nc2nccc(NCCn3cccn3)n2)cc1OCCCN1CCCC1] |
| 194 | 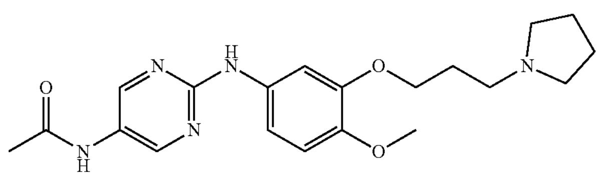 [SMILES: COc1ccc(Nc2ncc(NC(C)=O)cn2)cc1OCCCN1CCCC1] |
| 195 | 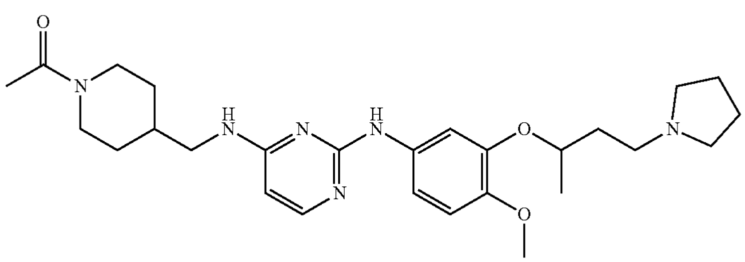 [SMILES: COc1ccc(Nc2nccc(NCC3CCN(C(C)=O)CC3)n2)cc1OC(C)CCN1CCCC1] |
| 196 | 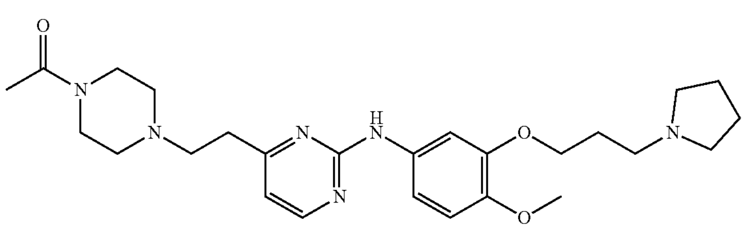 [SMILES: COc1ccc(Nc2nccc(CCN3CCN(C(C)=O)CC3)n2)cc1OCCCN1CCCC1] |

TABLE 1-continued

| Compound No. | Structure |
|---|---|
| 197 | 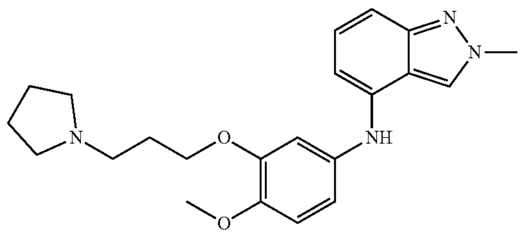 [SMILES: COc1ccc(Nc2cccc3nn(C)cc23)cc1OCCCN1CCCC1] |
| 199 | 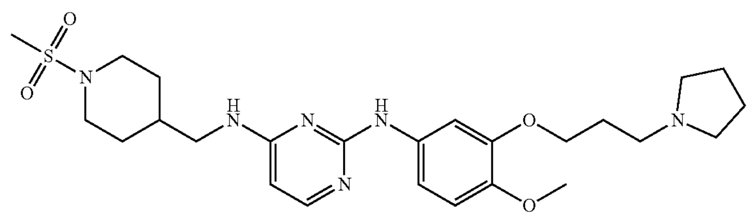 [SMILES: COc1ccc(Nc2nccc(NCC3CCN(S(C)(=O)=O)CC3)n2)cc1OCCCN1CCCC1] |
| 200 | 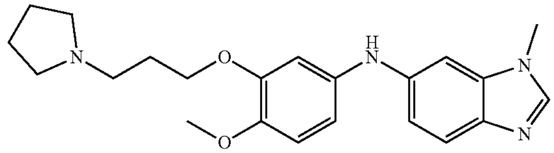 [SMILES: COc1ccc(Nc2ccc3ncn(C)c3c2)cc1OCCCN1CCCC1] |
| 201 | 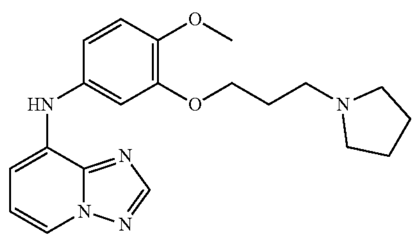 [SMILES: COc1ccc(Nc2cccn3ncnc23)cc1OCCCN1CCCC1] |
| 202 | 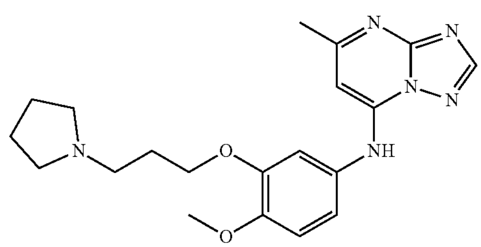 [SMILES: COc1ccc(Nc2cc(C)nc3ncnn23)cc1OCCCN1CCCC1] |
| 203 | 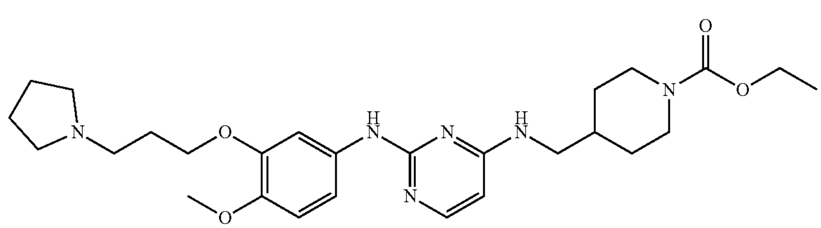 [SMILES: CCOC(=O)N1CCC(CNc2ccnc(Nc3ccc(OC)c(OCCCN4CCCC4)c3)n2)CC1] |
| 204 | 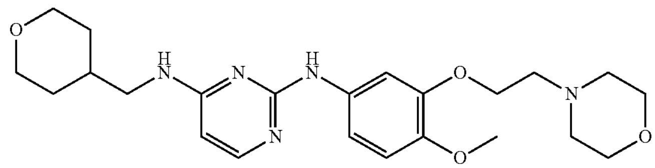 [SMILES: COc1ccc(Nc2nccc(NCC3CCOCC3)n2)cc1OCCN1CCOCC1] |

TABLE 1-continued

| Compound No. | Structure |
|---|---|
| 205 | 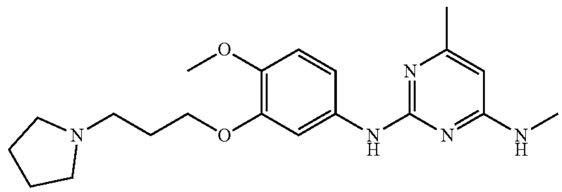 [SMILES: CNc1cc(C)nc(Nc2ccc(OC)c(OCCCN3CCCC3)c2)n1] |
| 206 | 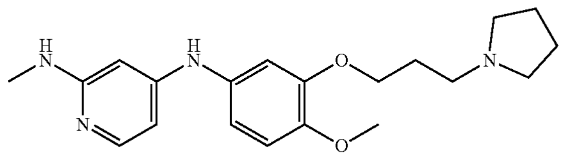 [SMILES: CNc1cc(Nc2ccc(OC)c(OCCCN3CCCC3)c2)ccn1] |
| 207 | 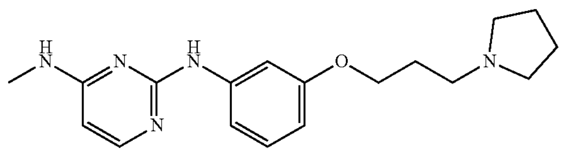 [SMILES: CNc1ccnc(Nc2cccc(OCCCN3CCCC3)c2)n1] |
| 208 | 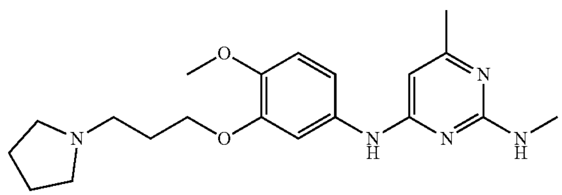 [SMILES: CNc1nc(C)cc(Nc2ccc(OC)c(OCCCN3CCCC3)c2)n1] |
| 209 | 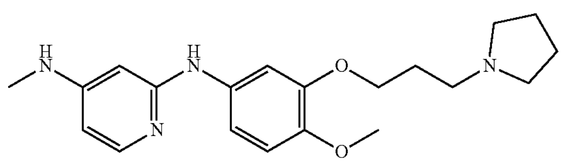 |
| 210 | 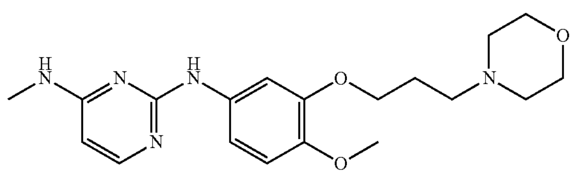 [SMILES: CNc1ccnc(Nc2ccc(OC)c(OCCCN3CCOCC3)c2)n1] |
| 211 | 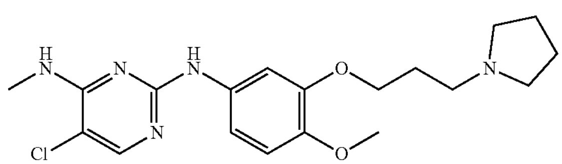 [SMILES: CNc1nc(Nc2ccc(OC)c(OCCCN3CCCC3)c2)ncc1Cl] |
| 212 | 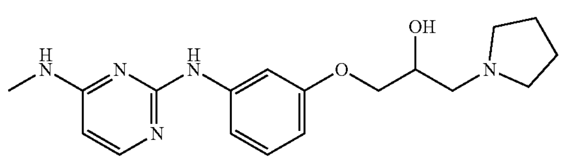 |
| 213 | 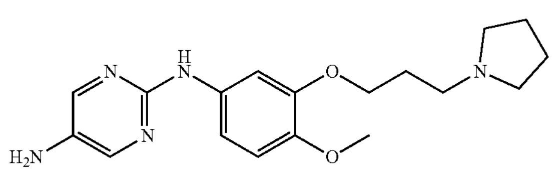 [SMILES: COc1ccc(Nc2ncc(N)cn2)cc1OCCCN1CCCC1] |

TABLE 1-continued

| Compound No. | Structure |
|---|---|
| 214 | 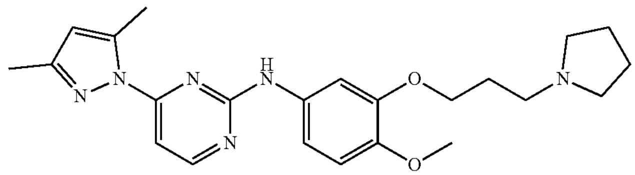 [SMILES: COc1ccc(Nc2nccc(-n3nc(C)cc3C)n2)cc1OCCCN1CCCC1] |
| 215 | 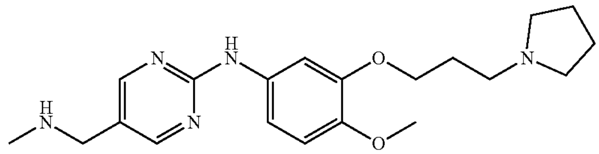 [SMILES: CNCc1cnc(Nc2ccc(OC)c(OCCCN3CCCC3)c2)nc1] |
| 216 | 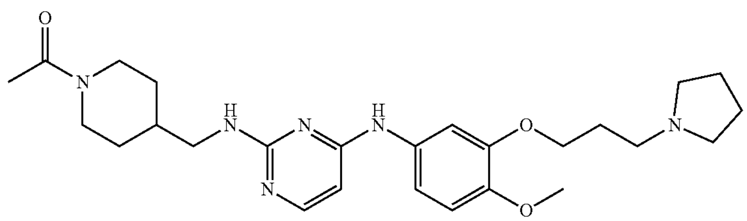 [SMILES: COc1ccc(Nc2ccnc(NCC3CCN(C(C)=O)CC3)n2)cc1OCCCN1CCCC1] |
| 217 | 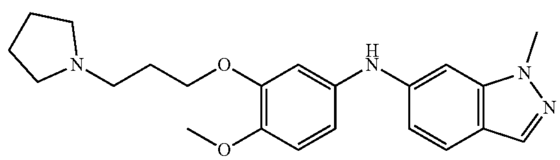 [SMILES: COc1ccc(Nc2ccc3cnn(C)c3c2)cc1OCCCN1CCCC1] |
| 218 | 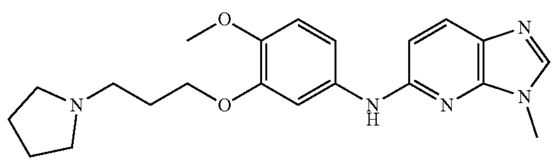 [SMILES: COc1ccc(Nc2ccc3ncn(C)c3n2)cc1OCCCN1CCCC1] |
| 219 | 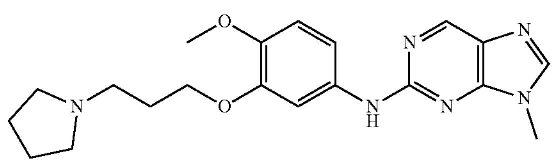 |
| 220 | 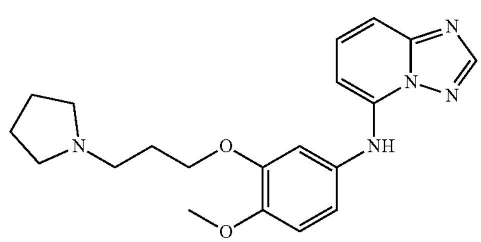 [SMILES: COc1ccc(Nc2cccc3ncnn23)cc1OCCCN1CCCC1] |
| 221 | 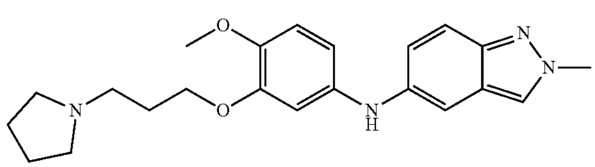 [SMILES: COc1ccc(Nc2ccc3nn(C)cc3c2)cc1OCCCN1CCCC1] |

TABLE 1-continued

| Compound No. | Structure |
|---|---|
| 222 | 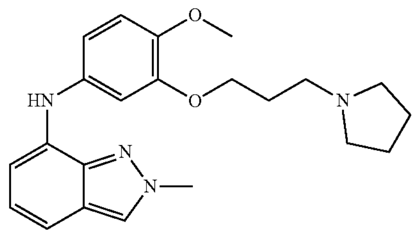 [SMILES: COc1ccc(Nc2cccc3cn(C)nc23)cc1OCCCN1CCCC1] |
| 223 | 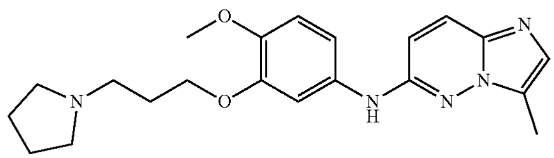 [SMILES: COc1ccc(Nc2ccc3ncc(C)n3n2)cc1OCCCN1CCCC1] |
| 224 | 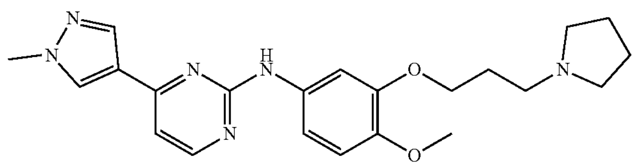 [SMILES: COc1ccc(Nc2nccc(-c3cnn(C)c3)n2)cc1OCCCN1CCCC1] |
| 225 | 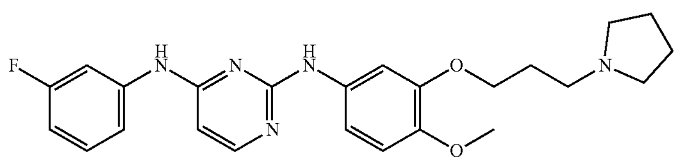 [SMILES: COc1ccc(Nc2nccc(Nc3cccc(F)c3)n2)cc1OCCCN1CCCC1] |
| 226 | 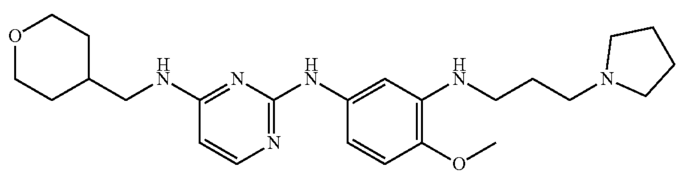 [SMILES: COc1ccc(Nc2nccc(NCC3CCOCC3)n2)cc1NCCCN1CCCC1] |
| 227 | 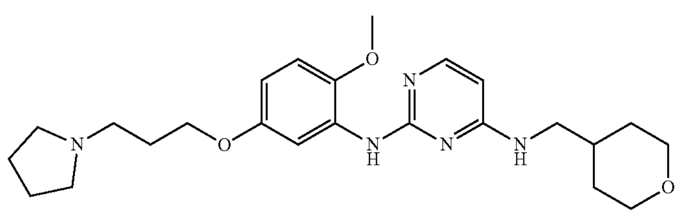 [SMILES: COc1ccc(OCCCN2CCCC2)cc1Nc1nccc(NCC2CCOCC2)n1] |
| 228 | 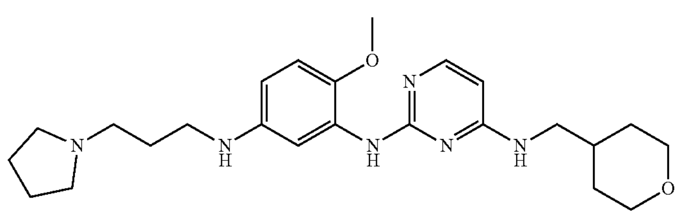 [SMILES: COc1ccc(NCCCN2CCCC2)cc1Nc1nccc(NCC2CCOCC2)n1] |
| 229 | 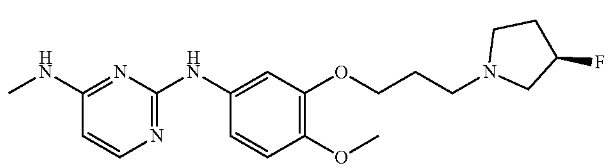 [SMILES: CNc1ccnc(Nc2ccc(OC)c(OCCCN3CC[C@@H](F)C3)c2)n1] |

TABLE 1-continued

| Compound No. | Structure |
|---|---|
| 230 | 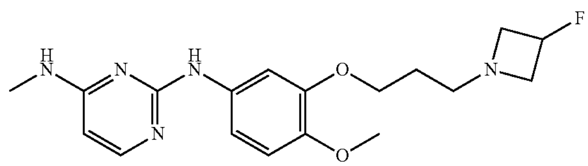 [SMILES: CNc1ccnc(Nc2ccc(OC)c(OCCCN3CC(F)C3)c2)n1] |
| 231 | 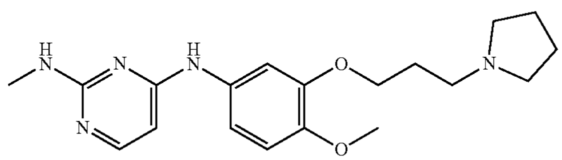 |
| 232 | 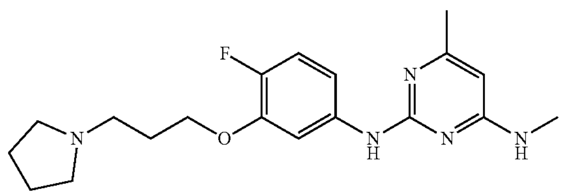 [SMILES: CNc1cc(C)nc(Nc2ccc(F)c(OCCCN3CCCC3)c2)n1] |
| 233 | 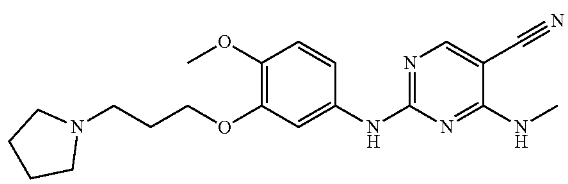 [SMILES: CNc1nc(Nc2ccc(OC)c(OCCCN3CCCC3)c2)ncc1C#N] |
| 234 | 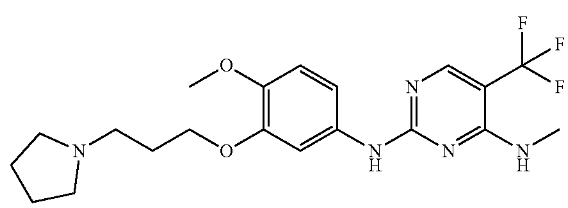 [SMILES: CNc1nc(Nc2ccc(OC)c(OCCCN3CCCC3)c2)ncc1C(F)(F)F] |
| 235 | 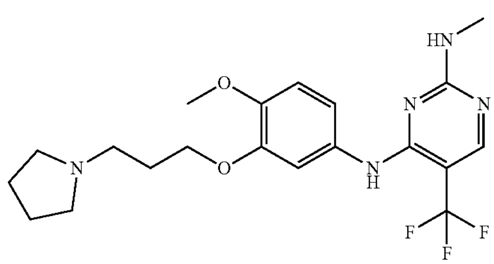 [SMILES: CNc1ncc(C(F)(F)F)c(Nc2ccc(OC)c(OCCCN3CCCC3)c2)n1] |
| 236 | 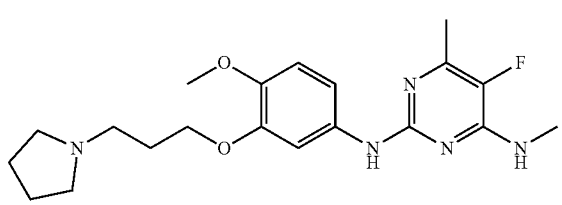 [SMILES: CNc1nc(Nc2ccc(OC)c(OCCCN3CCCC3)c2)nc(C)c1F] |
| 237 | 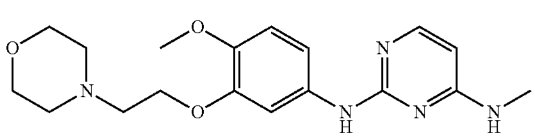 [SMILES: CNc1ccnc(Nc2ccc(OC)c(OCCN3CCOCC3)c2)n1] |

TABLE 1-continued

| Compound No. | Structure |
|---|---|
| 238 | 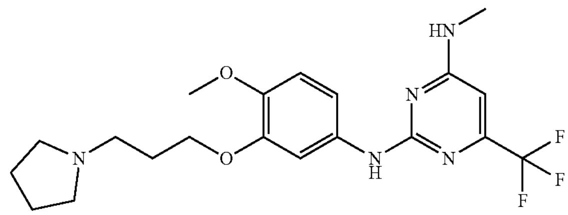 [SMILES: CNc1cc(C(F)(F)F)nc(Nc2ccc(OC)c(OCCCN3CCCC3)c2)n1] |
| 239 | 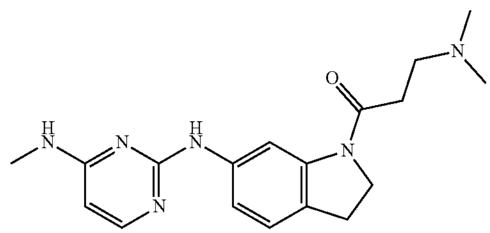 |
| 240 | 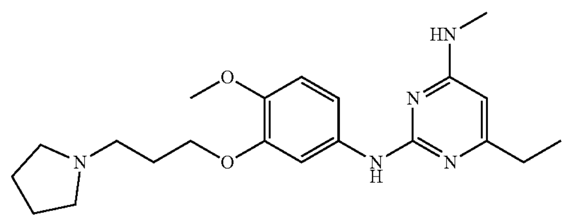 [SMILES: CCc1cc(NC)nc(Nc2ccc(OC)c(OCCCN3CCCC3)c2)n1] |
| 241 | 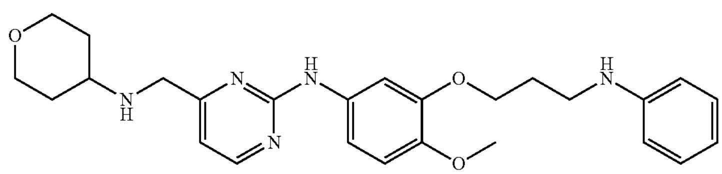 [SMILES: COc1ccc(Nc2nccc(CNC3CCOCC3)n2)cc1OCCCNc1ccccc1] |
| 242 | 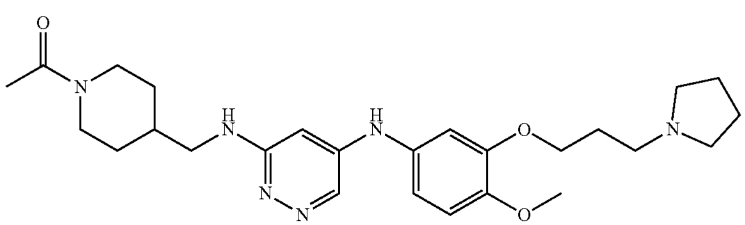 [SMILES: COc1ccc(Nc2cnnc(NCC3CCN(C(C)=O)CC3)c2)cc1OCCCN1CCCC1] |
| 243 | 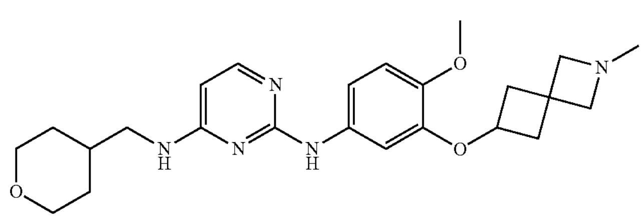 [SMILES: COc1ccc(Nc2nccc(NCC3CCOCC3)n2)cc1OC1CC2(C1)CN(C)C2] |
| 244 | 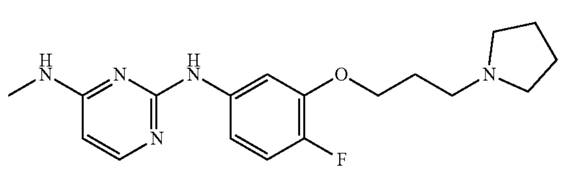 [SMILES: CNc1ccnc(Nc2ccc(F)c(OCCCN3CCCC3)c2)n1] |

TABLE 1-continued

| Compound No. | Structure |
|---|---|
| 245 | 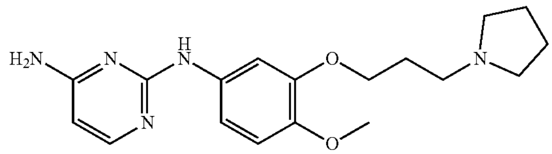 [SMILES: COc1ccc(Nc2nccc(N)n2)cc1OCCCN1CCCC1] |
| 246 | 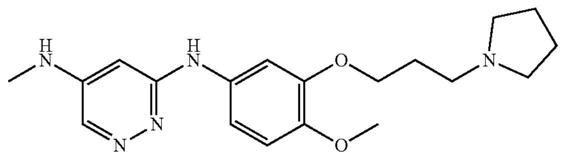 [SMILES: CNc1cnnc(Nc2ccc(OC)c(OCCCN3CCCC3)c2)c1] |
| 247 | 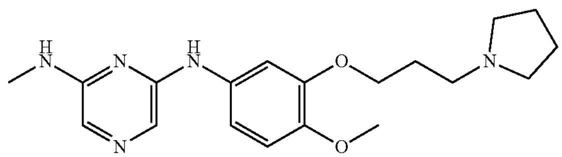 [SMILES: CNc1cncc(Nc2ccc(OC)c(OCCCN3CCCC3)c2)n1] |
| 248 | 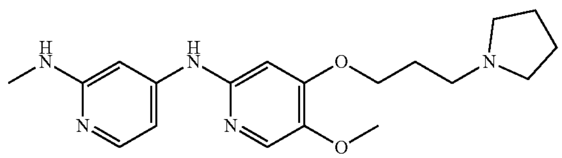 [SMILES: CNc1cc(Nc2cc(OCCCN3CCCC3)c(OC)cn2)ccn1] |
| 249 | 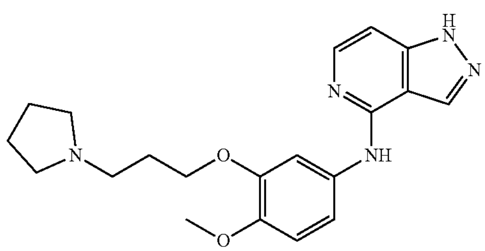 [SMILES: COc1ccc(Nc2nccc3[nH]ncc23)cc1OCCCN1CCCC1] |
| 250 | 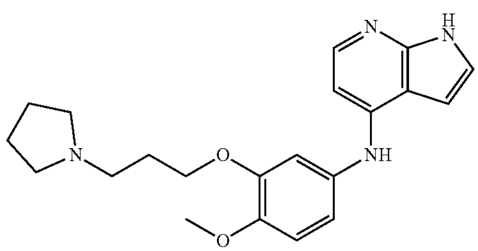 [SMILES: COc1ccc(Nc2ccnc3[nH]ccc23)cc1OCCCN1CCCC1] |
| 251 | 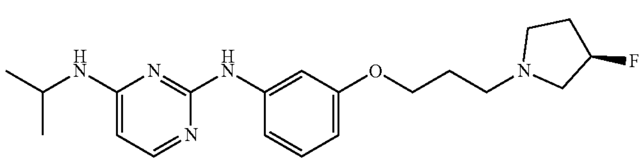 [SMILES: CC(C)Nc1ccnc(Nc2cccc(OCCCN3CC[C@@H](F)C3)c2)n1] |
| 252 | 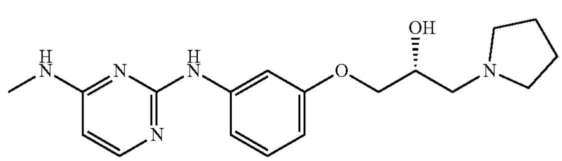 |

TABLE 1-continued

| Compound No. | Structure |
|---|---|
| 253 | 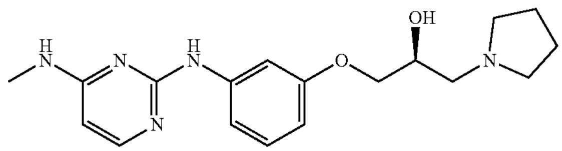 [SMILES: CNc1ccnc(Nc2cccc(OC[C@@H](O)CN3CCCC3)c2)n1] |
| 254 | 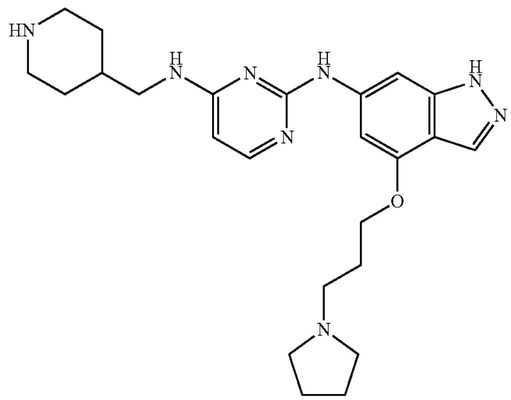 [SMILES: c1cc(NCC2CCNCC2)nc(Nc2cc(OCCCN3CCCC3)c3cn[nH]c3c2)n1] |
| 255 | 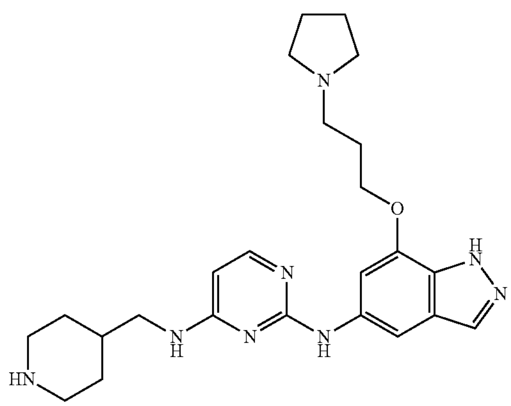 [SMILES: c1cc(NCC2CCNCC2)nc(Nc2cc(OCCCN3CCCC3)c3[nH]ncc3c2)n1] |
| 256 | 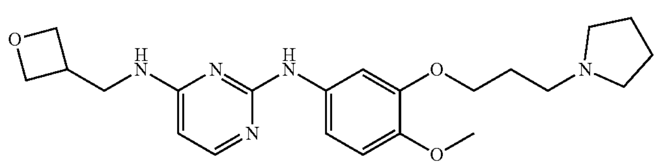 [SMILES: COc1ccc(Nc2nccc(NCC3COC3)n2)cc1OCCCN1CCCC1] |
| 257 | 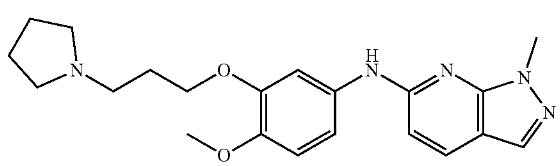 [SMILES: COc1ccc(Nc2ccc3cnn(C)c3n2)cc1OCCCN1CCCC1] |
| 258 | 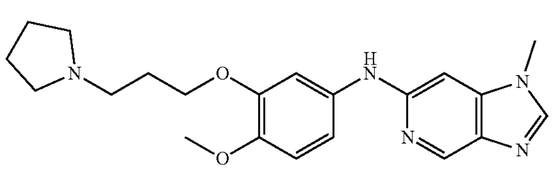 [SMILES: COc1ccc(Nc2cc3c(cn2)ncn3C)cc1OCCCN1CCCC1] |

TABLE 1-continued

| Compound No. | Structure |
| --- | --- |
| 259 | 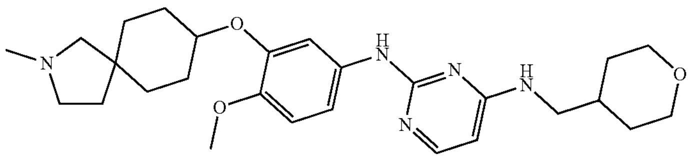 [SMILES: COc1ccc(Nc2nccc(NCC3CCOCC3)n2)cc1OC1CCC2(CC1)CCN(C)C2] |
| 260 | 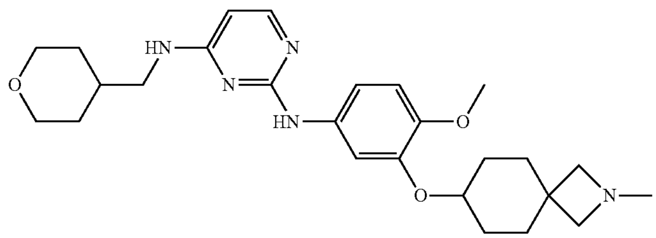 [SMILES: COc1ccc(Nc2nccc(NCC3CCOCC3)n2)cc1OC1CCC2(CC1)CN(C)C2] |
| 261 | 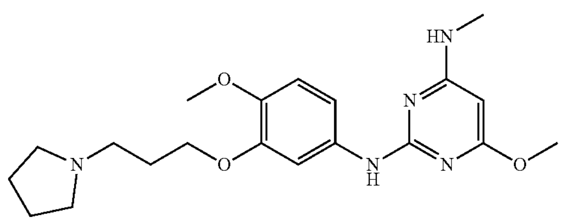 [SMILES: CNc1cc(OC)nc(Nc2ccc(OC)c(OCCCN3CCCC3)c2)n1] |
| 262a | 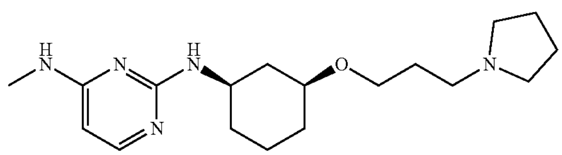 [SMILES: CNc1ccnc(N[C@@H]2CCC[C@H](OCCCN3CCCC3)C2)n1] |
| 262b | 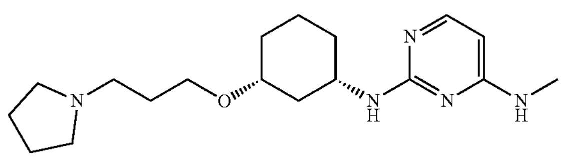 [SMILES: CNc1ccnc(N[C@H]2CCC[C@@H](OCCCN3CCCC3)C2)n1] |
| 263 | 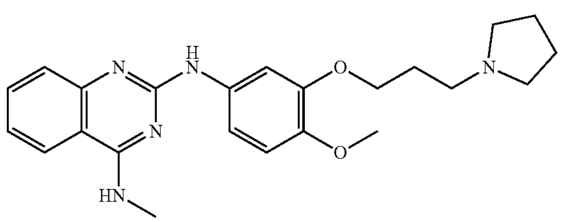 [SMILES: CNc1nc(Nc2ccc(OC)c(OCCCN3CCCC3)c2)nc2ccccc12] |
| 264 | 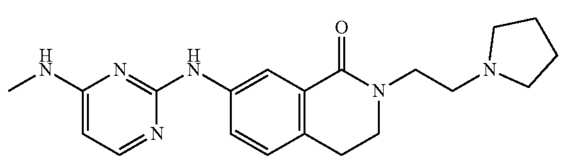 [SMILES: CNc1ccnc(Nc2ccc3c(c2)C(=O)N(CCN2CCCC2)CC3)n1] |
| 265 | 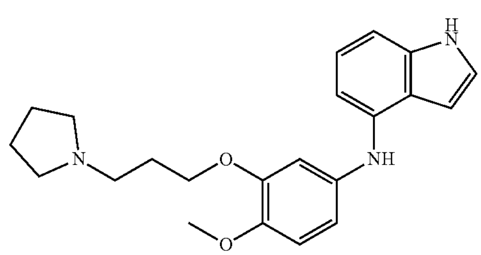 [SMILES: COc1ccc(Nc2cccc3[nH]ccc23)cc1OCCCN1CCCC1] |

TABLE 1-continued

| Compound No. | Structure |
|---|---|
| 266 | 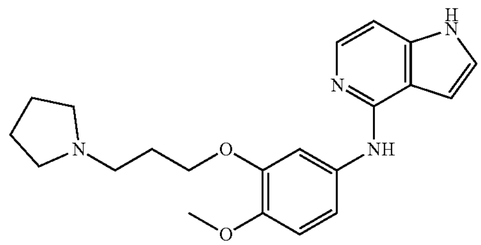 [SMILES: COc1ccc(Nc2nccc3[nH]ccc23)cc1OCCCN1CCCC1] |
| 267 | 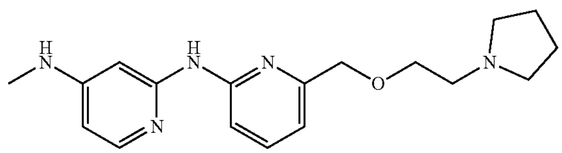 [SMILES: CNc1ccnc(Nc2cccc(COCCN3CCCC3)n2)c1] |
| 268 | 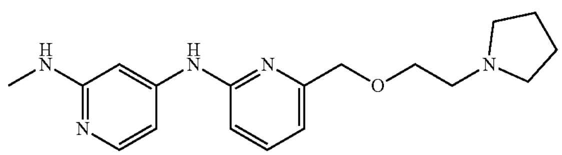 [SMILES: CNc1cc(Nc2cccc(COCCN3CCCC3)n2)ccn1] |
| 269 | 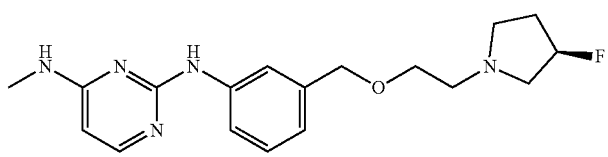 [SMILES: CNc1ccnc(Nc2cccc(COCCN3CC[C@@H](F)C3)c2)n1] |
| 271 | 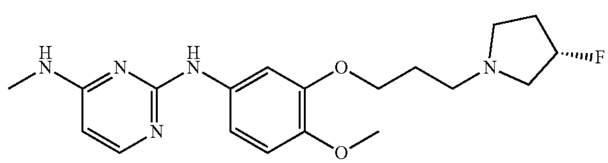 [SMILES: CNc1ccnc(Nc2ccc(OC)c(OCCCN3CC[C@H](F)C3)c2)n1] |
| 272 | 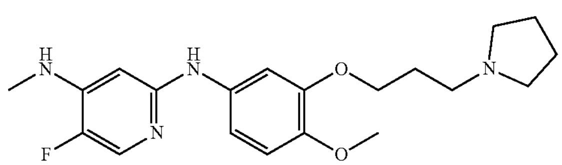 [SMILES: CNc1cc(Nc2ccc(OC)c(OCCCN3CCCC3)c2)ncc1F] |
| 273 | 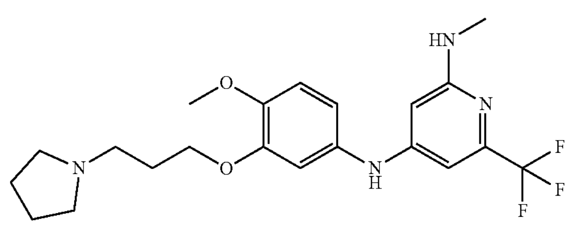 [SMILES: CNc1cc(Nc2ccc(OC)c(OCCCN3CCCC3)c2)cc(C(F)(F)F)n1] |
| 274 | 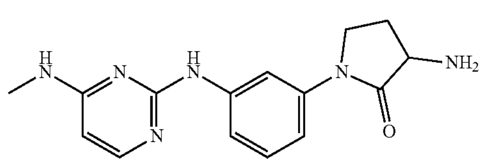 [SMILES: CNc1ccnc(Nc2cccc(N3CCC(N)C3=O)c2)n1] |

TABLE 1-continued

| Compound No. | Structure |
|---|---|
| 275 | 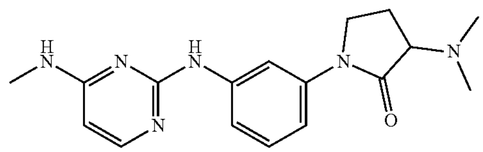 |
| 276 | 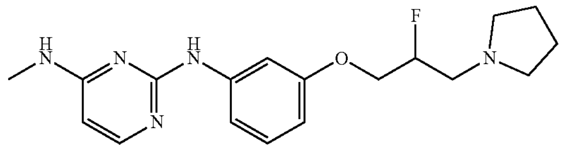 [SMILES: CNc1ccnc(Nc2cccc(OCC(F)CN3CCCC3)c2)n1] |
| 277 | 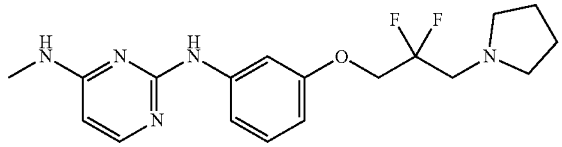 [SMILES: CNc1ccnc(Nc2cccc(OCC(F)(F)CN3CCCC3)c2)n1] |
| 278 | 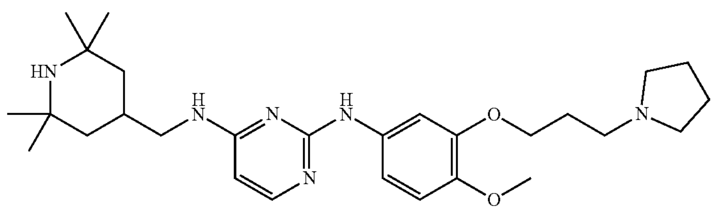 [SMILES: COc1ccc(Nc2nccc(NCC3CC(C)(C)NC(C)(C)C3)n2)cc1OCCCN1CCCC1] |
| 279 | 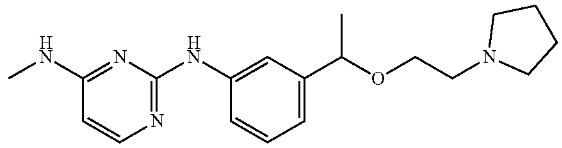 [SMILES: CNc1ccnc(Nc2cccc(C(C)OCCN3CCCC3)c2)n1] |
| 280 | 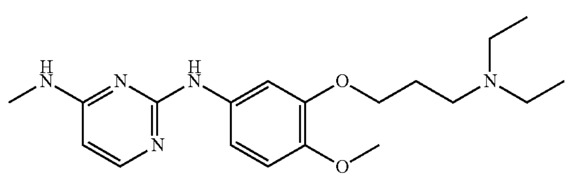 [SMILES: CCN(CC)CCCOc1cc(Nc2nccc(NC)n2)ccc1OC] |
| 281 | 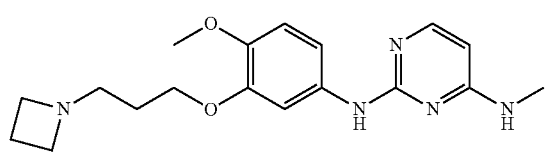 [SMILES: CNc1ccnc(Nc2ccc(OC)c(OCCCN3CCC3)c2)n1] |
| 282 | 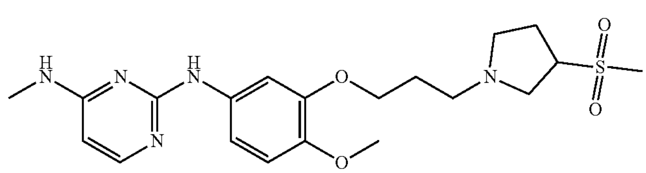 |
| 283 | 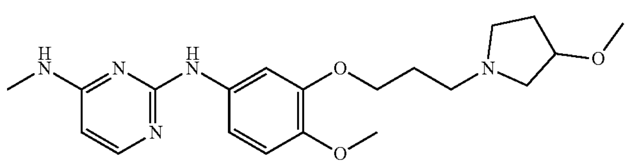 |

| Compound No. | Structure |
|---|---|
| 284 | 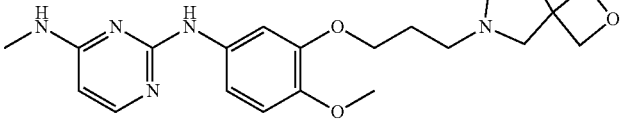 |
| 285 | 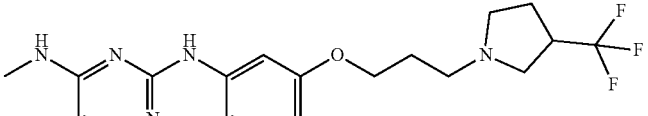 |
| 286 | 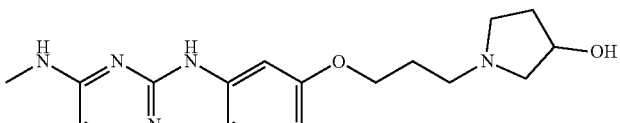 |
| 287 | 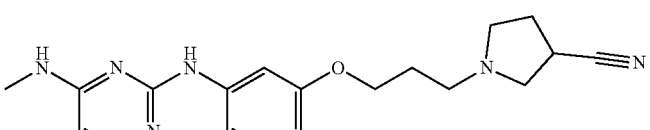 |
| 288 | 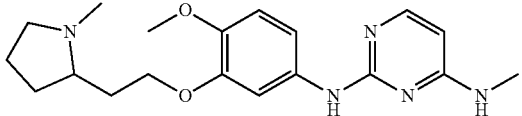 [SMILES: CNc1ccnc(Nc2ccc(OC)c(OCCC3CCCN3C)c2)n1] |
| 289 | 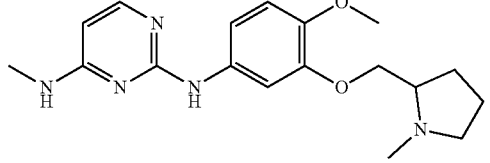 |
| 290 | 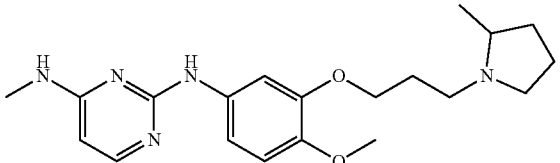 |
| 291 | 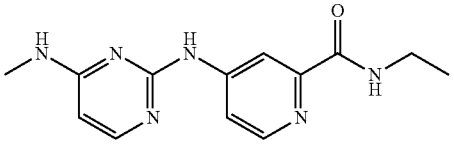 [SMILES: CCNC(=O)c1cc(Nc2nccc(NC)n2)ccn1] |
| 292 | 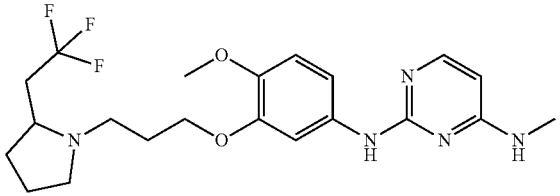 [SMILES: CNc1ccnc(Nc2ccc(OC)c(OCCCN3CCCC3CC(F)(F)F)c2)n1] |

TABLE 1-continued

| Compound No. | Structure |
|---|---|
| 293 | 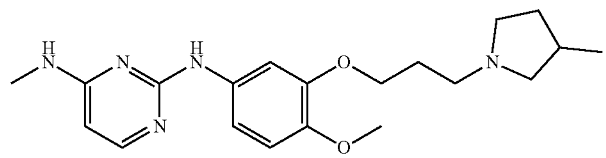 |
| 294 | 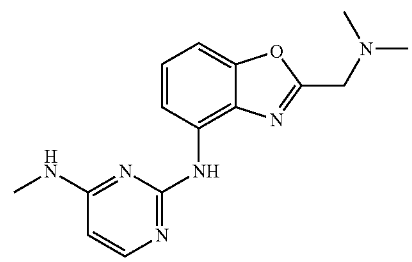 |
| 295 | 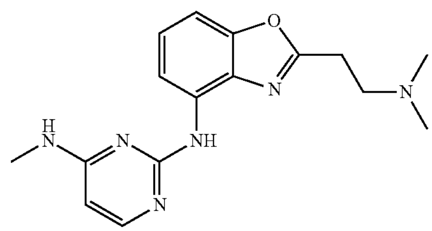 |
| 296 | 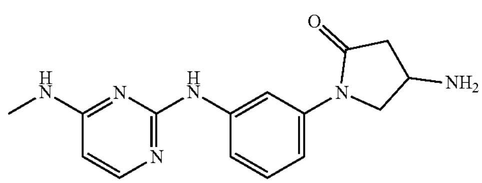 [SMILES: CNc1ccnc(Nc2cccc(N3CC(N)CC3=O)c2)n1] |
| 297 | 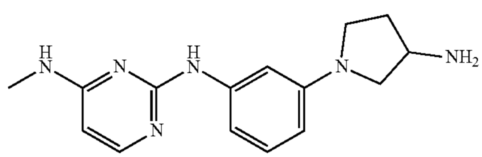 [SMILES: CNc1ccnc(Nc2cccc(N3CCC(N)C3)c2)n1] |
| 298 | 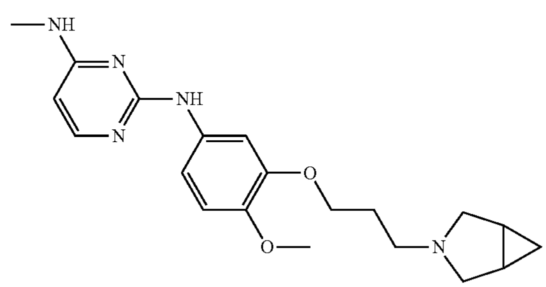 [SMILES: CNc1ccnc(Nc2ccc(OC)c(OCCCN3CC4CC4C3)c2)n1] |
| 299 | 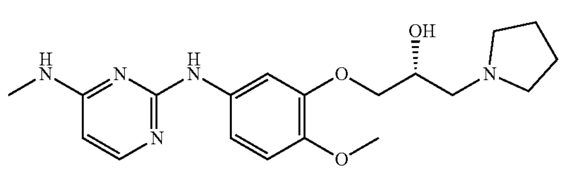 [SMILES: CNc1ccnc(Nc2ccc(OC)c(OC[C@H](O)CN3CCCC3)c2)n1] |

TABLE 1-continued

| Compound No. | Structure |
|---|---|
| 300 | 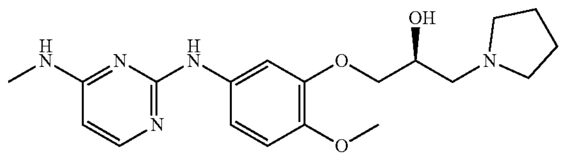 [SMILES: CNc1ccnc(Nc2ccc(OC)c(OC[C@@H](O)CN3CCCC3)c2)n1] |
| 301 | 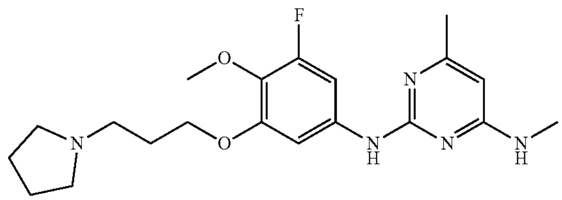 [SMILES: CNc1cc(C)nc(Nc2cc(F)c(OC)c(OCCCN3CCCC3)c2)n1] |
| 302 | 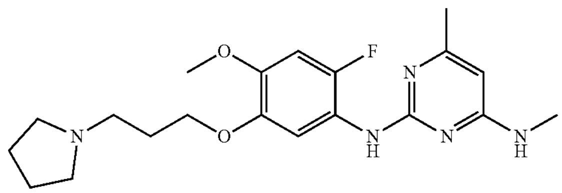 [SMILES: CNc1cc(C)nc(Nc2cc(OCCCN3CCCC3)c(OC)cc2F)n1] |
| 303 | 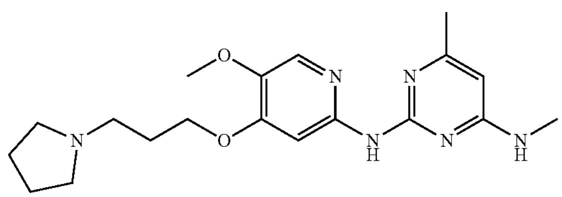 [SMILES: CNc1cc(C)nc(Nc2cc(OCCCN3CCCC3)c(OC)cn2)n1] |
| 304 | 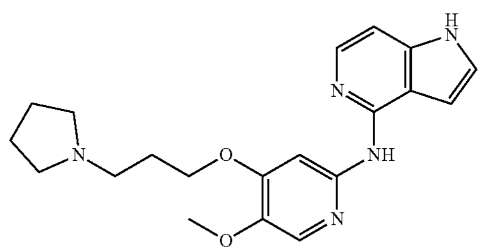 |
| 305 | 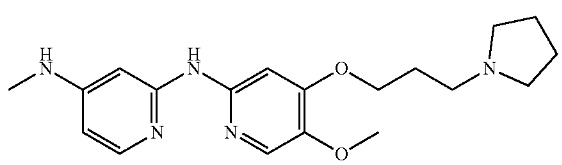 |
| 306 | 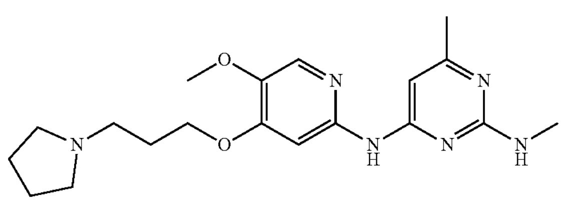 [SMILES: CNc1nc(C)cc(Nc2cc(OCCCN3CCCC3)c(OC)cn2)n1] |
| 307 | 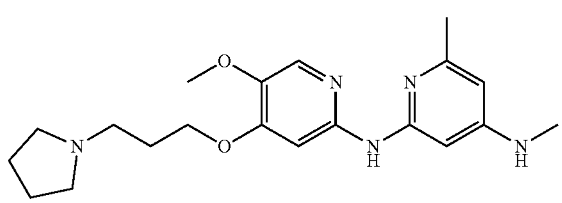 [SMILES: CNc1cc(C)nc(Nc2cc(OCCCN3CCCC3)c(OC)cn2)c1] |

TABLE 1-continued

| Compound No. | Structure |
| --- | --- |
| 308 | 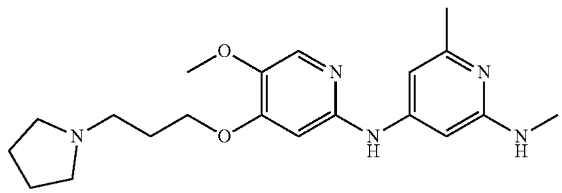 [SMILES: CNc1cc(Nc2cc(OCCCN3CCCC3)c(OC)cn2)cc(C)n1] |
| 309 | 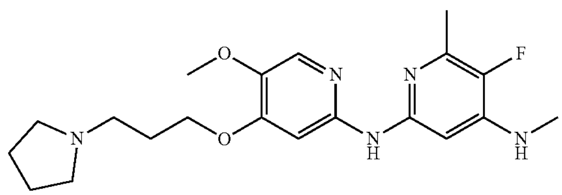 [SMILES: CNc1cc(Nc2cc(OCCCN3CCCC3)c(OC)cn2)nc(C)c1F] |
| 310 | 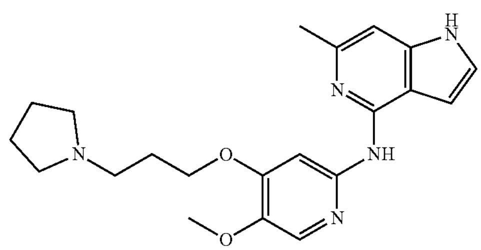 [SMILES: COc1cnc(Nc2nc(C)cc3[nH]ccc23)cc1OCCCN1CCCC1] |
| 311 | 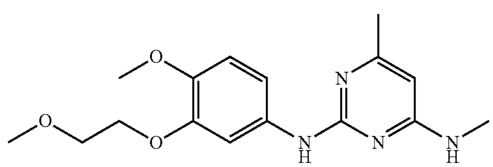 |
| 312 | 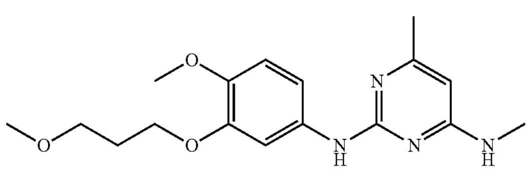 |
| 313 | 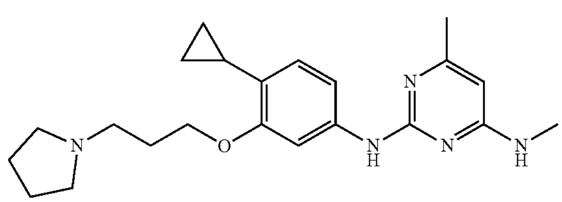 [SMILES: CNc1cc(C)nc(Nc2ccc(C3CC3)c(OCCCN3CCCC3)c2)n1] |
| 314 | 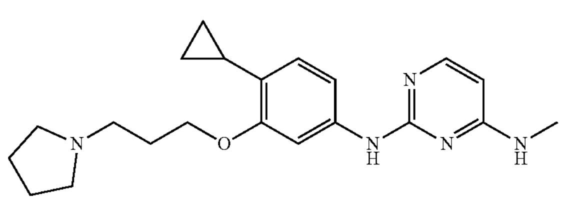 [SMILES: CNc1ccnc(Nc2ccc(C3CC3)c(OCCCN3CCCC3)c2)n1] |

TABLE 1-continued

| Compound No. | Structure |
|---|---|
| 315 | 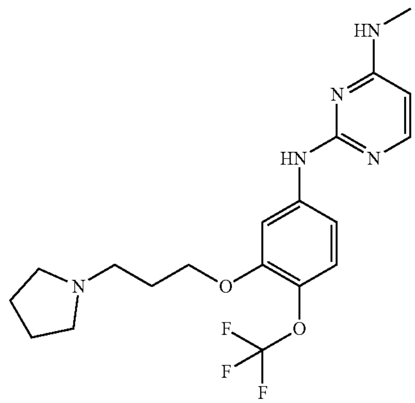 [SMILES: CNc1ccnc(Nc2ccc(OC(F)(F)F)c(OCCCN3CCCC3)c2)n1] |
| 316 | 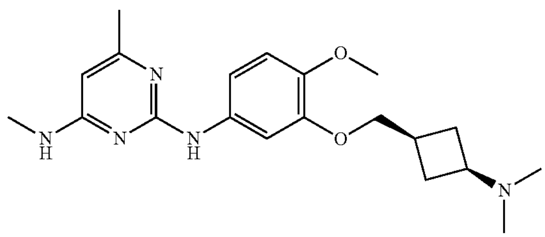 |
| 317 | 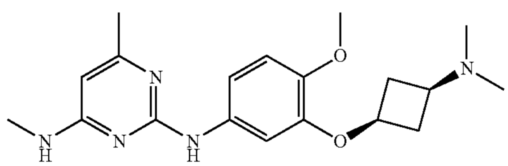 |
| 318 | 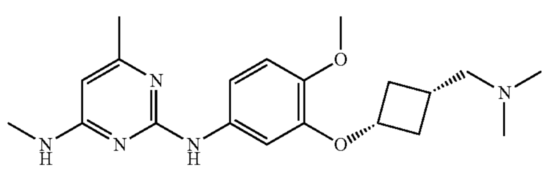 |
| 319 | 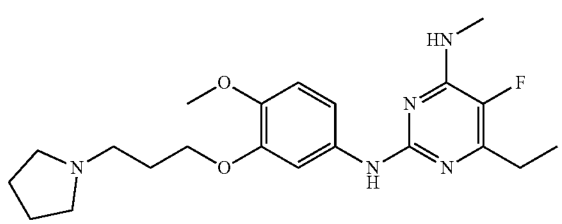 [SMILES: CCc1nc(Nc2ccc(OC)c(OCCCN3CCCC3)c2)nc(NC)c1F] |
| 320 | 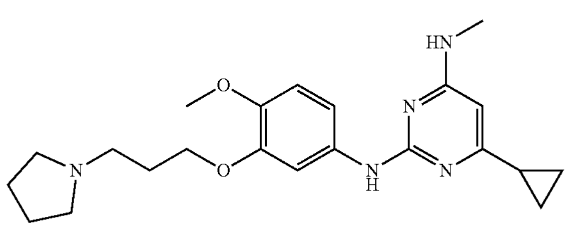 [SMILES: CNc1cc(C2CC2)nc(Nc2ccc(OC)c(OCCCN3CCCC3)c2)n1] |

TABLE 1-continued

| Compound No. | Structure |
|---|---|
| 321 | 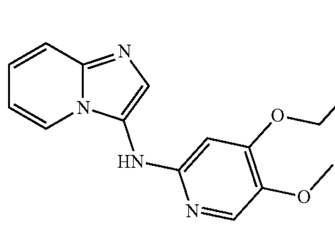 |
| 322 | 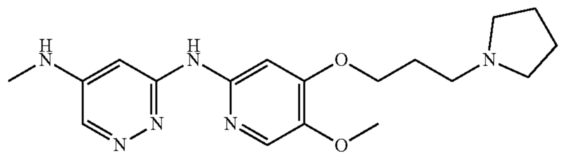 |
| 323 | 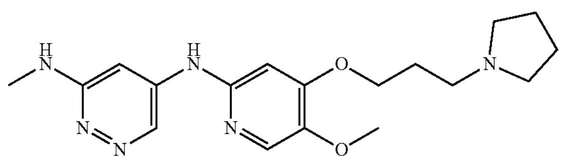 [SMILES: CNc1cc(Nc2cc(OCCCN3CCCC3)c(OC)cn2)cnn1] |
| 324 | 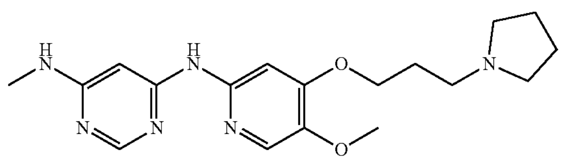 |
| 325 | 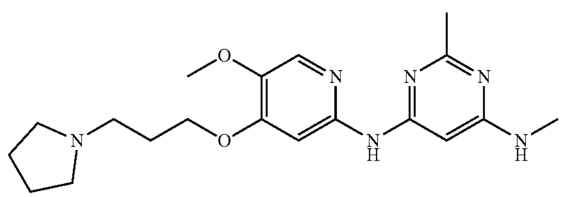 [SMILES: CNc1cc(Nc2cc(OCCCN3CCCC3)c(OC)cn2)nc(C)n1] |
| 326 | 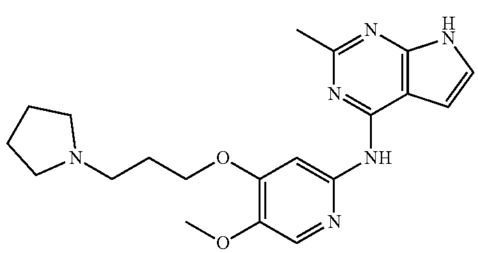 |
| 327 | 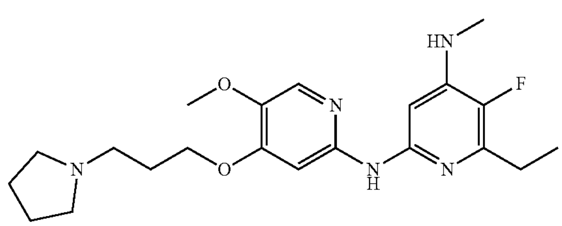 [SMILES: CCc1nc(Nc2cc(OCCCN3CCCC3)c(OC)cn2)cc(NC)c1F] |

| Compound No. | Structure |
|---|---|
| 328 | 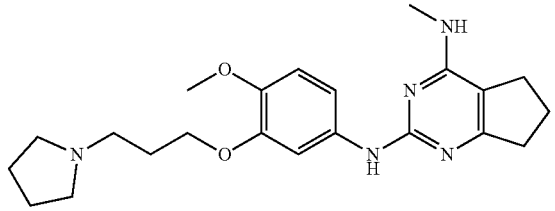 [SMILES: CNc1nc(Nc2ccc(OC)c(OCCCN3CCCC3)c2)nc2c1CCC2] |
| 329 | 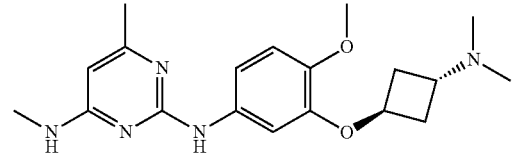 |
| 330 | 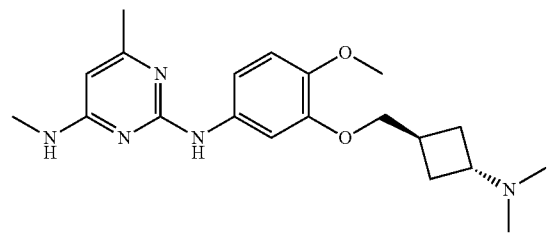 |
| 331 | 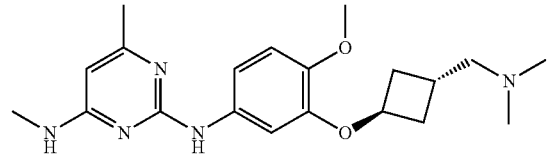 |
| 332 | 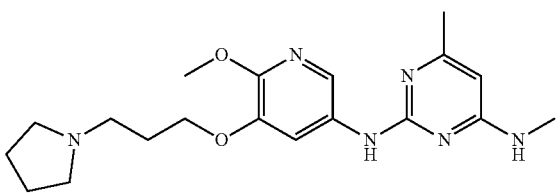 [SMILES: CNc1cc(C)nc(Nc2cnc(OC)c(OCCCN3CCCC3)c2)n1] |
| 333 | 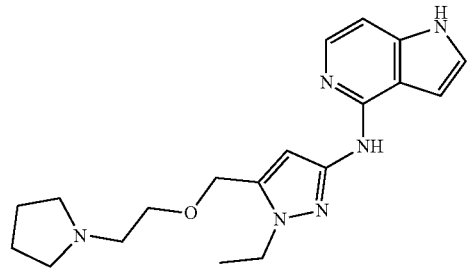 [SMILES: CCn1nc(Nc2nccc3[nH]ccc23)cc1COCCN1CCCC1] |
| 334 | 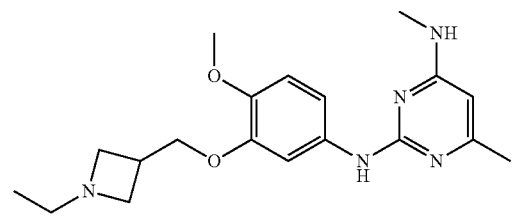 [SMILES: CCN1CC(COc2cc(Nc3nc(C)cc(NC)n3)ccc2OC)C1] |

TABLE 1-continued
| Compound No. | Structure |
|---|---|
| 334x | 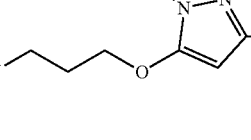 |
| 335 | 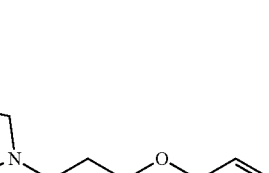 |
| 336 | 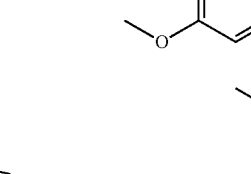 |
| 337 | 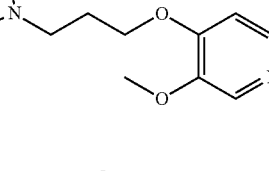 |
The compounds of Table 1 are the compounds found in U.S. Application No. 62/402,997, the entire contents of which are incorporated herein by reference.
TABLE 2
| Compound No. | Structure |
|---|---|
| 338 | 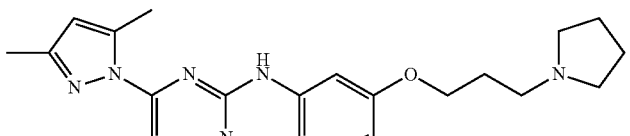 |
| 339 | 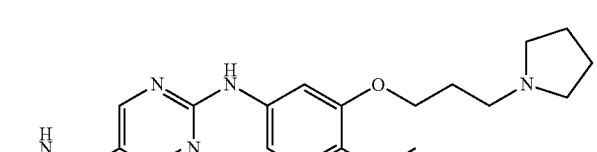 |

TABLE 2-continued

| Compound No. | Structure |
|---|---|
| 340 | 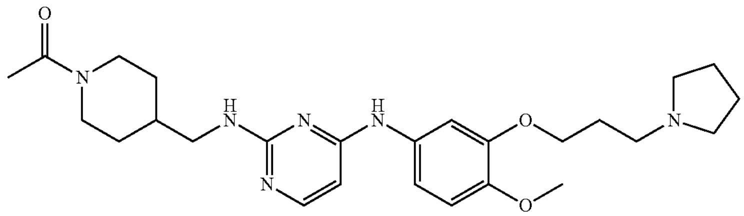 [SMILES: COc1ccc(Nc2ccnc(NCC3CCN(C(C)=O)CC3)n2)cc1OCCCN1CCCC1] |
| 341 | 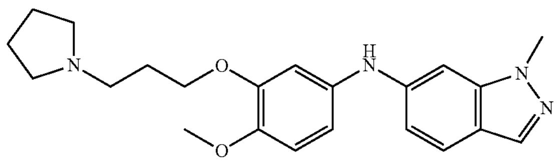 [SMILES: COc1ccc(Nc2ccc3cnn(C)c3c2)cc1OCCCN1CCCC1] |
| 342 | 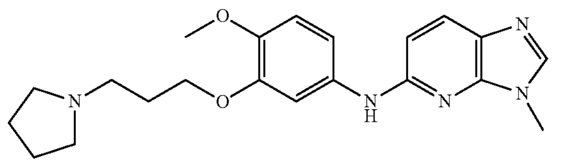 [SMILES: COc1ccc(Nc2ccc3ncn(C)c3n2)cc1OCCCN1CCCC1] |
| 343 | 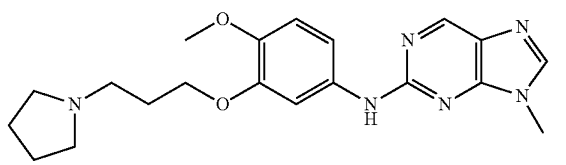 [SMILES: COc1ccc(Nc2ncc3ncn(C)c3n2)cc1OCCCN1CCCC1] |
| 344 | 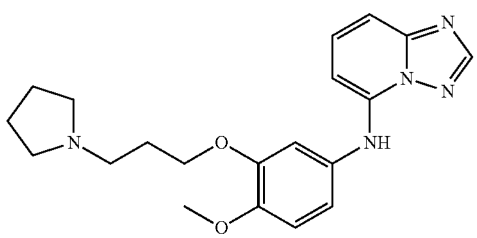 [SMILES: COc1ccc(Nc2cccc3ncnn23)cc1OCCCN1CCCC1] |
| 345 | 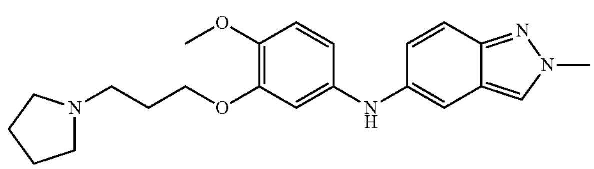 [SMILES: COc1ccc(Nc2ccc3nn(C)cc3c2)cc1OCCCN1CCCC1] |
| 346 | 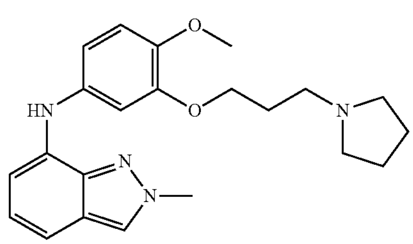 [SMILES: COc1ccc(Nc2cccc3cn(C)nc23)cc1OCCCN1CCCC1] |
| 347 | 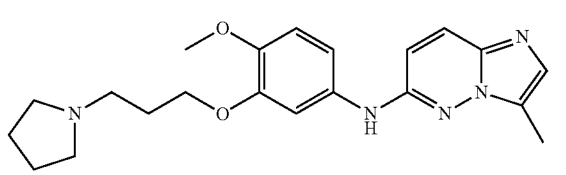 [SMILES: COc1ccc(Nc2ccc3ncc(C)n3n2)cc1OCCCN1CCCC1] |

US 11,672,800 B2
237                                                                                238
TABLE 2-continued
| Compound No. | Structure |
|---|---|
| 348 | 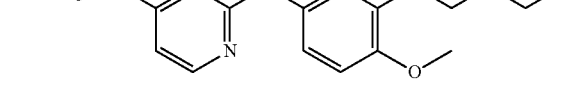 |
| 349 | 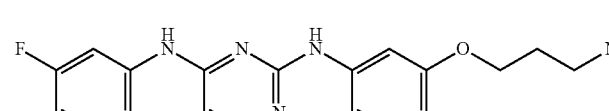 |
| 350 | 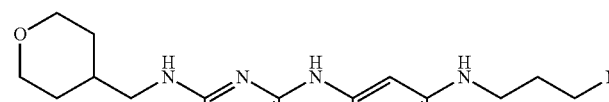 |
| 351 | 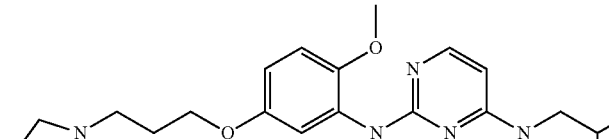 |
| 352 | 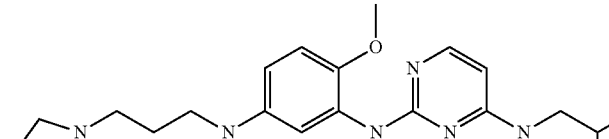 |
| 353 | 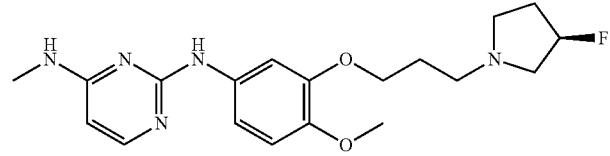 [SMILES: CNc1ccnc(Nc2ccc(OC)c(OCCCN3CC[C@@H](F)C3)c2)n1] |
| 354 | 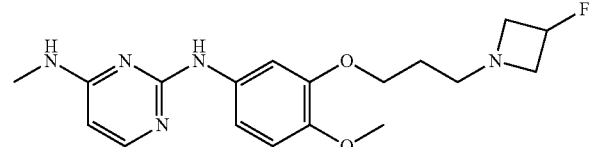 |
| 355 | 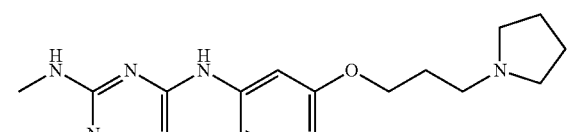 |

TABLE 2-continued
| Compound No. | Structure |
|---|---|
| 356 | 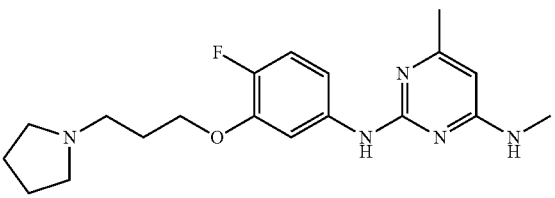 [SMILES: CNc1cc(C)nc(Nc2ccc(F)c(OCCCN3CCCC3)c2)n1] |
| 357 | 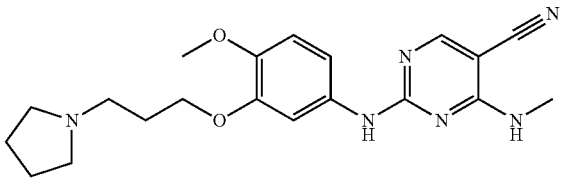 [SMILES: CNc1nc(Nc2ccc(OC)c(OCCCN3CCCC3)c2)ncc1C#N] |
| 358 | 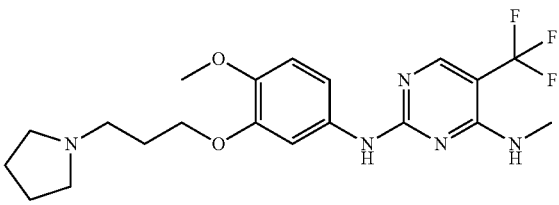 [SMILES: CNc1nc(Nc2ccc(OC)c(OCCCN3CCCC3)c2)ncc1C(F)(F)F] |
| 359 | 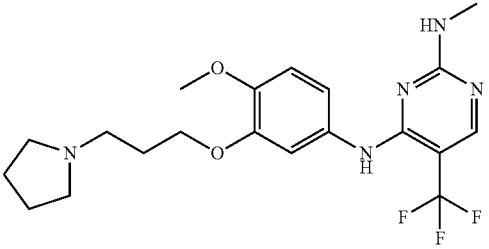 [SMILES: CNc1ncc(C(F)(F)F)c(Nc2ccc(OC)c(OCCCN3CCCC3)c2)n1] |
| 360 | 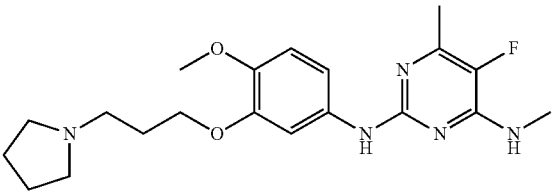 [SMILES: CNc1nc(Nc2ccc(OC)c(OCCCN3CCCC3)c2)nc(C)c1F] |
| 361 | 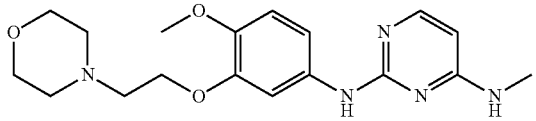 [SMILES: CNc1ccnc(Nc2ccc(OC)c(OCCN3CCOCC3)c2)n1] |
| 362 | 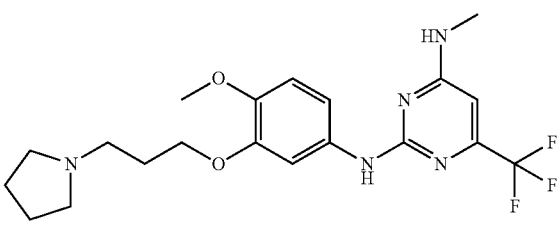 [SMILES: CNc1cc(C(F)(F)F)nc(Nc2ccc(OC)c(OCCCN3CCCC3)c2)n1] |

TABLE 2-continued

| Compound No. | Structure |
|---|---|
| 363 | 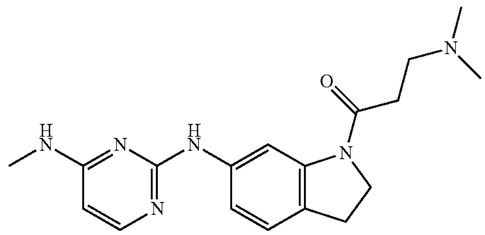 |
| 364 | 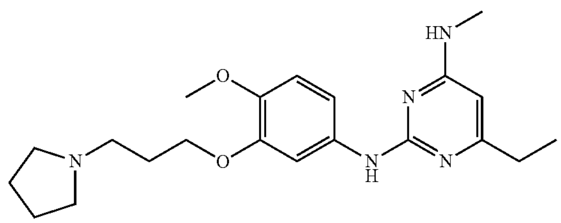 [SMILES: CCc1cc(NC)nc(Nc2ccc(OC)c(OCCCN3CCCC3)c2)n1] |
| 365 | 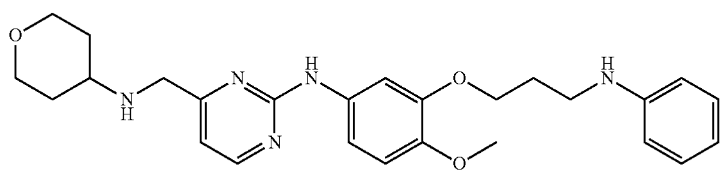 [SMILES: COc1ccc(Nc2nccc(CNC3CCOCC3)n2)cc1OCCCNc1ccccc1] |
| 366 | 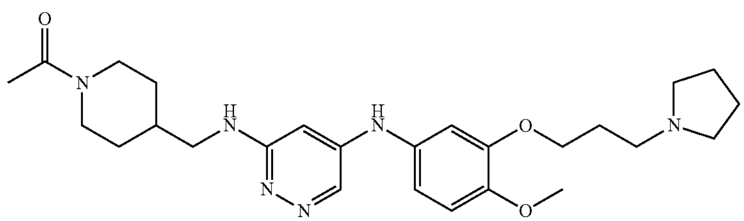 [SMILES: COc1ccc(Nc2cnnc(NCC3CCN(C(C)=O)CC3)c2)cc1OCCCN1CCCC1] |
| 367 | 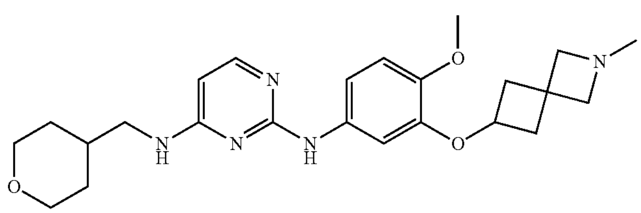 [SMILES: COc1ccc(Nc2nccc(NCC3CCOCC3)n2)cc1OC1CC2(C1)CN(C)C2] |
| 368 | 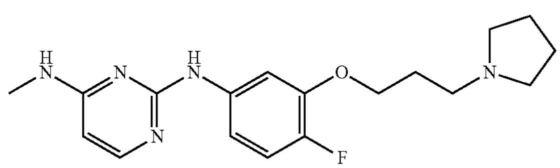 [SMILES: CNc1ccnc(Nc2ccc(F)c(OCCCN3CCCC3)c2)n1] |
| 369 | 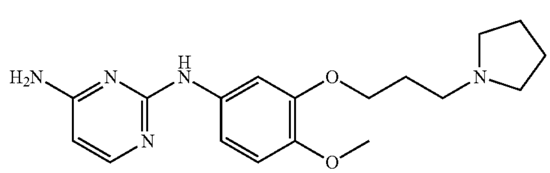 [SMILES: COc1ccc(Nc2nccc(N)n2)cc1OCCCN1CCCC1] |
| 370 | 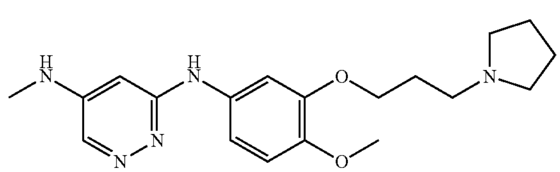 [SMILES: CNc1cnnc(Nc2ccc(OC)c(OCCCN3CCCC3)c2)c1] |

TABLE 2-continued

| Compound No. | Structure |
|---|---|
| 371 | (structure) |
| 372 | (structure) |
| 373 | (structure) |
| 374 | (structure) |
| 375 | (structure) |
| 376 | (structure) |
| 377 | (structure) |
| 378 | (structure) |

TABLE 2-continued

| Compound No. | Structure |
|---|---|
| 379 | 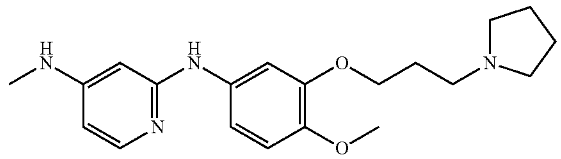 [SMILES: CNc1ccnc(Nc2ccc(OC)c(OCCCN3CCCC3)c2)c1] |
| 380 | 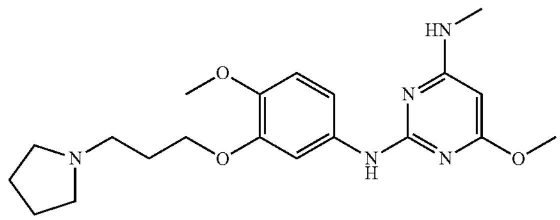 [SMILES: CNc1cc(OC)nc(Nc2ccc(OC)c(OCCCN3CCCC3)c2)n1] |
| 381 | 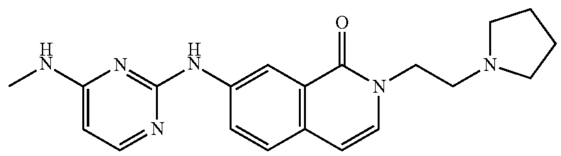 [SMILES: CNc1ccnc(Nc2ccc3ccn(CCN4CCCC4)c(=O)c3c2)n1] |
| 382 | 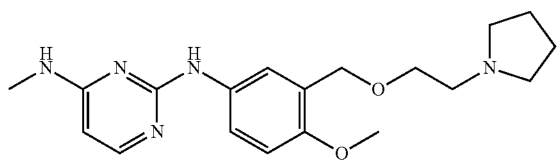 [SMILES: CNc1ccnc(Nc2ccc(OC)c(COCCN3CCCC3)c2)n1] |
| 383 | 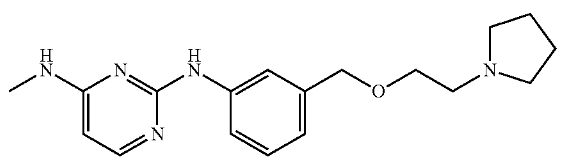 [SMILES: CNc1ccnc(Nc2cccc(COCCN3CCCC3)c2)n1] |
| 384 | 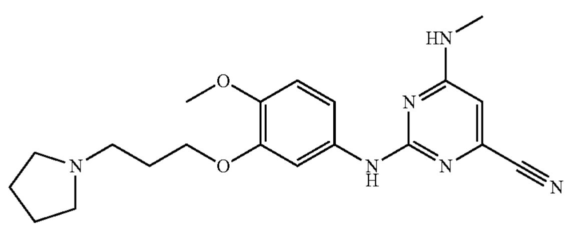 [SMILES: CNc1cc(C#N)nc(Nc2ccc(OC)c(OCCCN3CCCC3)c2)n1] |
| 385 | 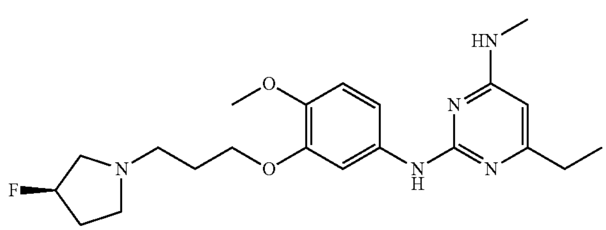 [SMILES: CCc1cc(NC)nc(Nc2ccc(OC)c(OCCCN3CC[C@@H](F)C3)c2)n1] |
| 386 | 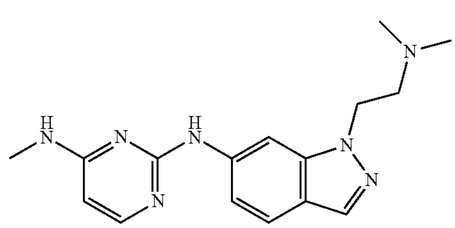 |

TABLE 2-continued

| Compound No. | Structure |
|---|---|
| 387 | 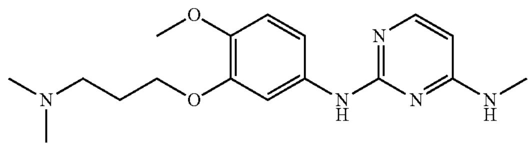 |
| 388 | 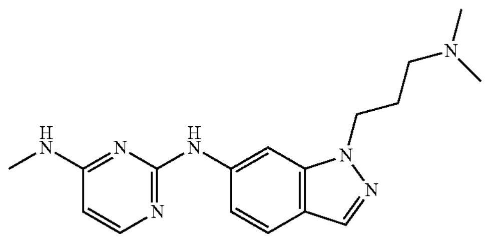 |
| 389 | 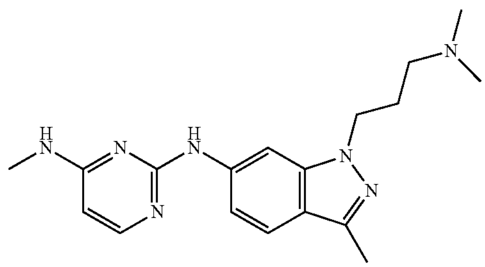 |
| 390 | 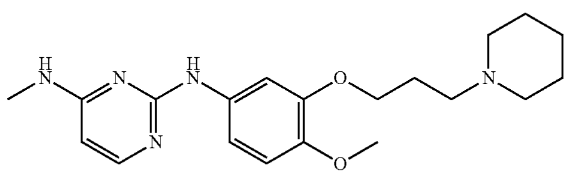 [SMILES: CNc1ccnc(Nc2ccc(OC)c(OCCCN3CCCCC3)c2)n1] |
| 391 | 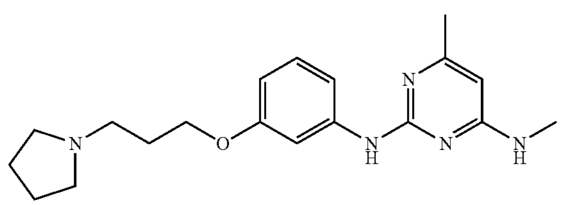 [SMILES: CNc1cc(C)nc(Nc2cccc(OCCCN3CCCC3)c2)n1] |
| 392 | 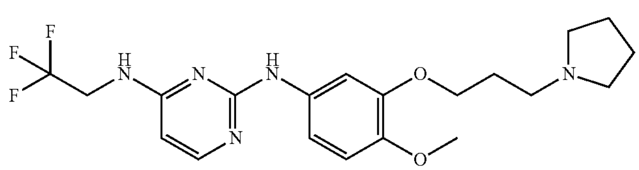 [SMILES: COc1ccc(Nc2nccc(NCC(F)(F)F)n2)cc1OCCCN1CCCC1] |
| 393 | 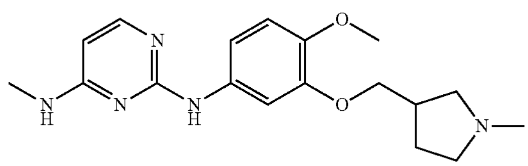 |
| 394 | 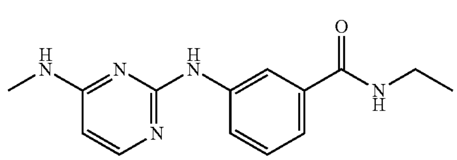 |

TABLE 2-continued

| Compound No. | Structure |
| --- | --- |
| 395 | *(chemical structure)* |
| 396 | *(chemical structure)* |
| 397 | *(chemical structure)* |
| 398 | *(chemical structure)* |
| 399 | *(chemical structure)* |
| 400 | *(chemical structure)* |
| 401 | *(chemical structure)* |
| 402 | *(chemical structure)* |

TABLE 2-continued

| Compound No. | Structure |
|---|---|
| 403 | 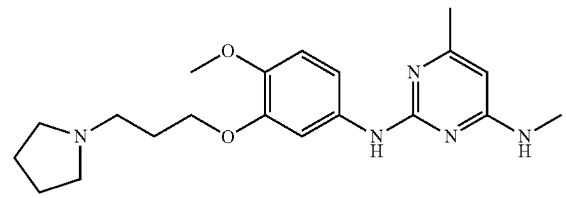 [SMILES: CNc1cc(C)nc(Nc2ccc(OC)c(OCCCN3CCCC3)c2)n1] |
| 404 | 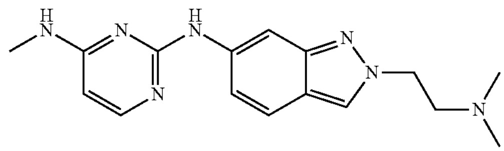 |
| 405 | 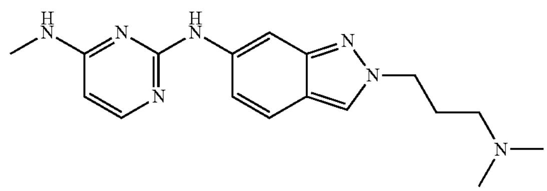 |
| 406 | 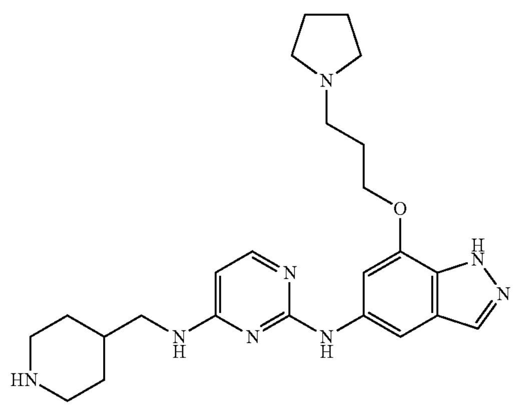 [SMILES: c1cc(NCC2CCNCC2)nc(Nc2cc(OCCCN3CCCC3)c3[nH]ncc3c2)n1] |
| 407 | 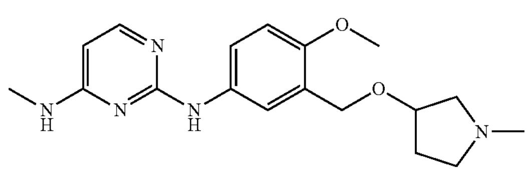 |
| 408 | 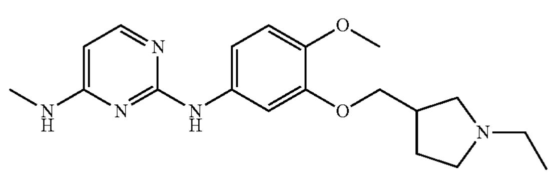 |
| 409 | 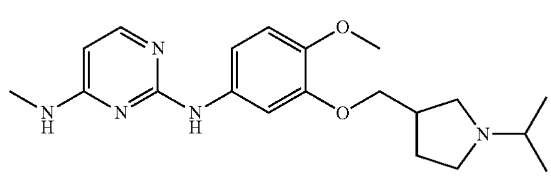 [SMILES: CNc1ccnc(Nc2ccc(OC)c(OCC3CCN(C(C)C)C3)c2)n1] |

TABLE 2-continued

| Compound No. | Structure |
|---|---|
| 410 | 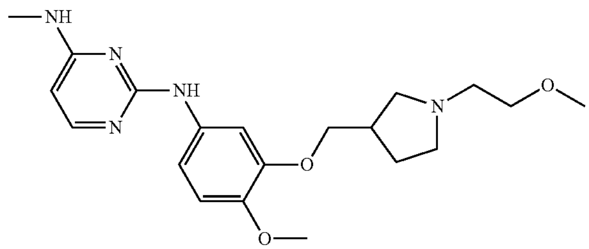 |
| 411 | 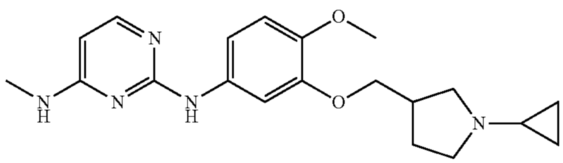 [SMILES: CNc1ccnc(Nc2ccc(OC)c(OCC3CCN(C4CC4)C3)c2)n1] |
| 412 | 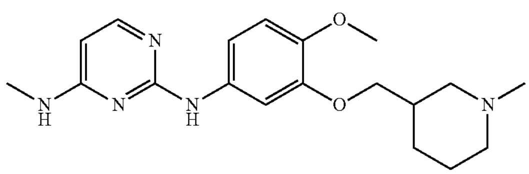 |
| 413 | 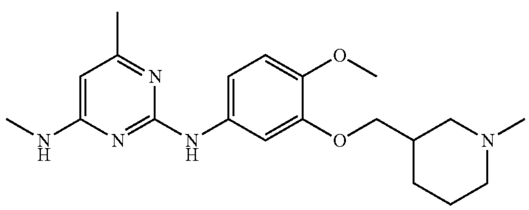 |
| 414 | 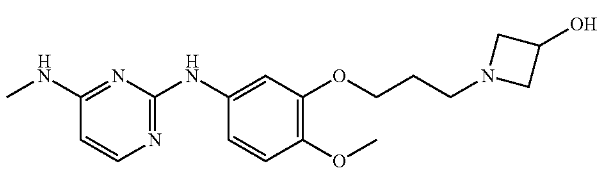 [SMILES: CNc1ccnc(Nc2ccc(OC)c(OCCCN3CC(O)C3)c2)n1] |
| 415 | 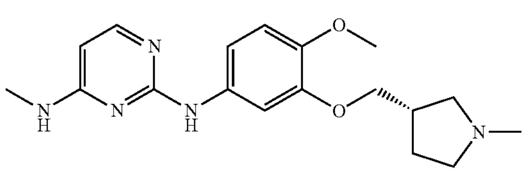 |
| 416 | 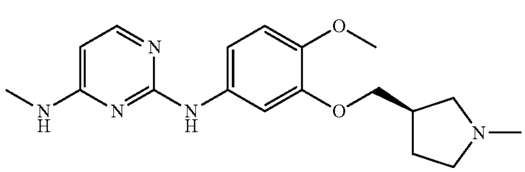 |
| 417 | 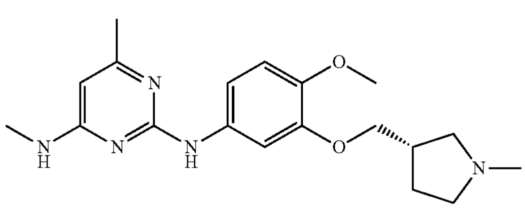 |

TABLE 2-continued
| Compound No. | Structure |
|---|---|
| 418 | 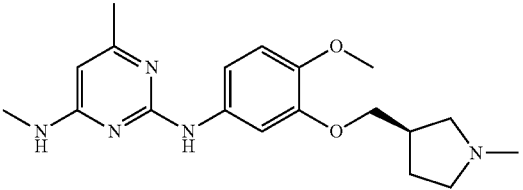 |
| 419 | 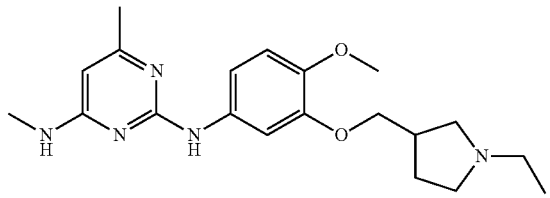 [SMILES: CCN1CCC(COc2cc(Nc3nc(C)cc(NC)n3)ccc2OC)C1] |
| 420 | 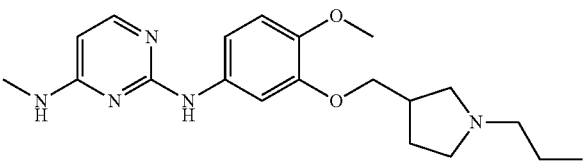 [SMILES: CCCN1CCC(COc2cc(Nc3nccc(NC)n3)ccc2OC)C1] |
| 421 | 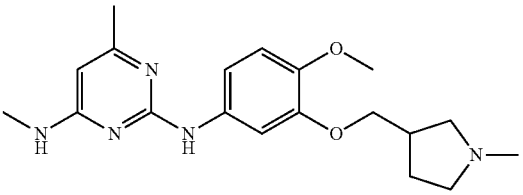 |
| 422 | 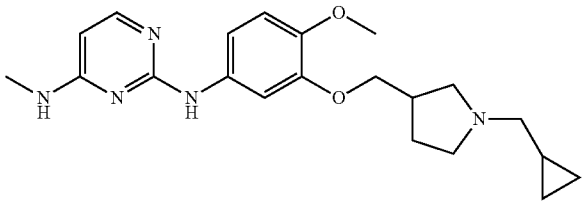 [SMILES: CNc1ccnc(Nc2ccc(OC)c(OCC3CCN(CC4CC4)C3)c2)n1] |
| 423 | 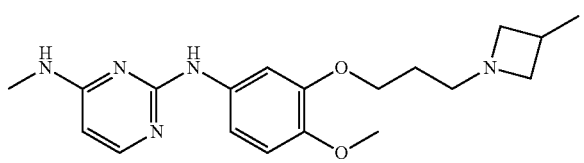 |
| 424 | 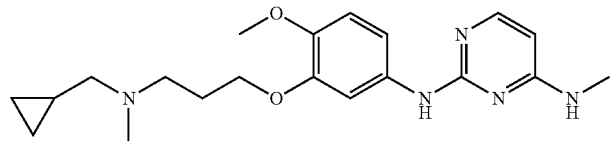 [SMILES: CNc1ccnc(Nc2ccc(OC)c(OCCCN(C)CC3CC3)c2)n1] |
| 425 | 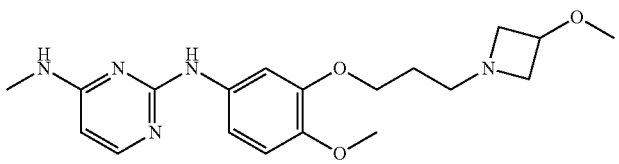 |

TABLE 2-continued

| Compound No. | Structure |
|---|---|
| 426 | 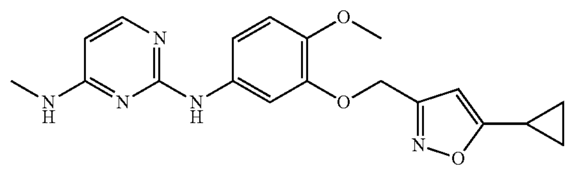 [SMILES: CNc1ccnc(Nc2ccc(OC)c(OCc3cc(C4CC4)on3)c2)n1] |
| 427 | 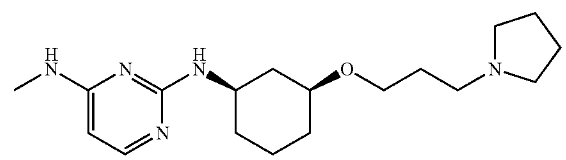 [SMILES: CNc1ccnc(N[C@@H]2CCC[C@H](OCCCN3CCCC3)C2)n1] |
| 428 | 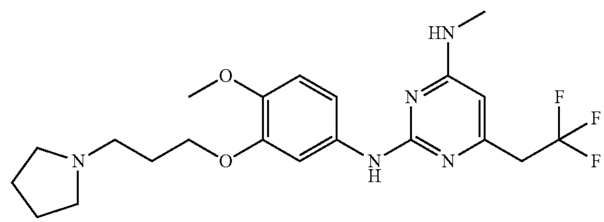 [SMILES: CNc1cc(CC(F)(F)F)nc(Nc2ccc(OC)c(OCCCN3CCCC3)c2)n1] |
| 429 | 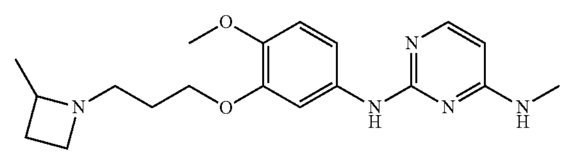 |
| 430 | 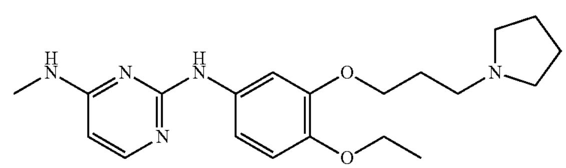 [SMILES: CCOc1ccc(Nc2nccc(NC)n2)cc1OCCCN1CCCC1] |
| 431 | 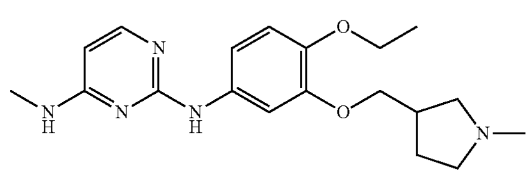 |
| 432 | 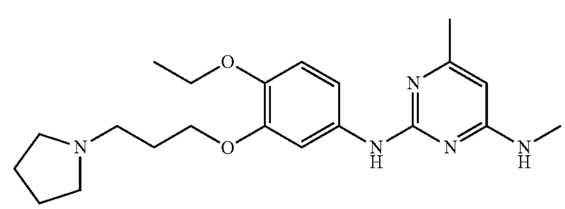 [SMILES: CCOc1ccc(Nc2nc(C)cc(NC)n2)cc1OCCCN1CCCC1] |
| 433 | 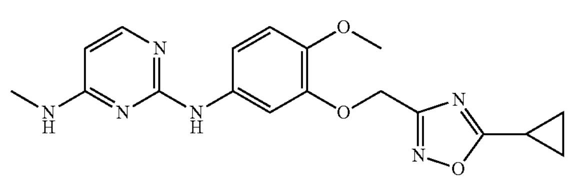 [SMILES: CNc1ccnc(Nc2ccc(OC)c(OCc3noc(C4CC4)n3)c2)n1] |

TABLE 2-continued

| Compound No. | Structure |
|---|---|
| 434 | 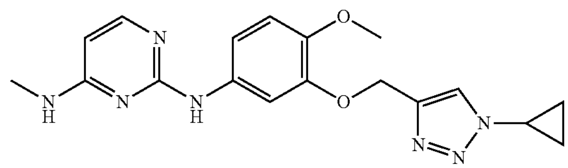 [SMILES: CNc1ccnc(Nc2ccc(OC)c(OCc3cn(C4CC4)nn3)c2)n1] |
| 435 | 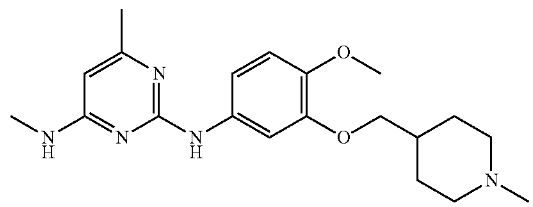 |
| 436 | 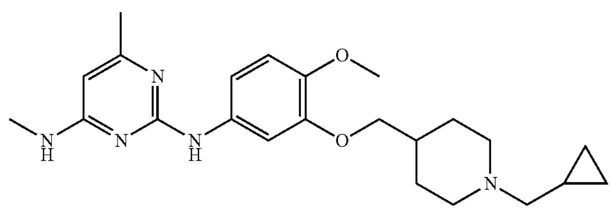 [SMILES: CNc1cc(C)nc(Nc2ccc(OC)c(OCC3CCN(CC4CC4)CC3)c2)n1] |
| 437 | 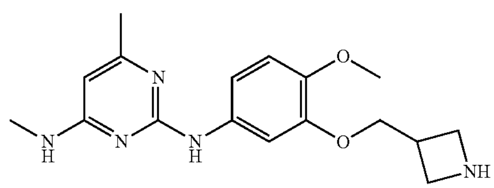 [SMILES: CNc1cc(C)nc(Nc2ccc(OC)c(OCC3CNC3)c2)n1] |
| 438 | 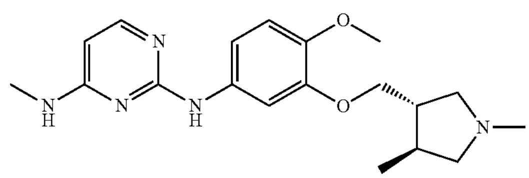 |
| 439 | 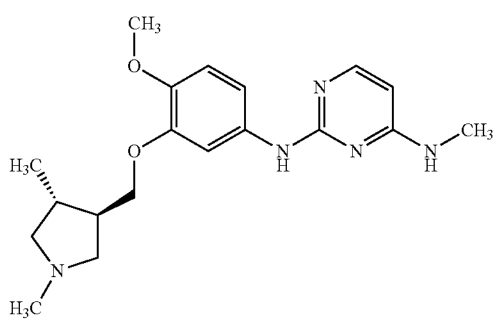 [SMILES: CNc1ccnc(Nc2ccc(OC)c(OC[C@H]3CN(C)C[C@@H]3C)c2)n1] |
| 440 | 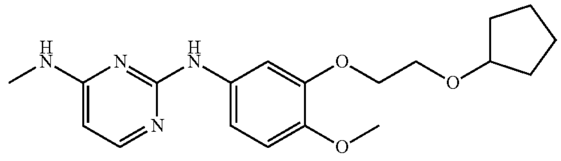 [SMILES: CNc1ccnc(Nc2ccc(OC)c(OCCOC3CCCC3)c2)n1] |

| Compound No. | Structure |
|---|---|
| 441 | [chemical structure] |
| 442 | [chemical structure] |
| 443 | [chemical structure] |
| 444 | [chemical structure] |
| 445 | [chemical structure] |
| 446 | [chemical structure] |
| 447 | [chemical structure] |

TABLE 2-continued

| Compound No. | Structure |
|---|---|
| 448 | 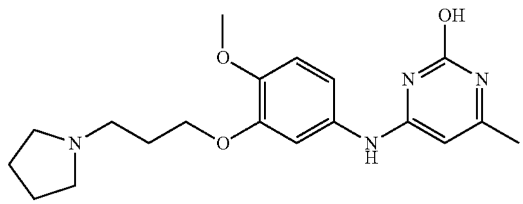 [SMILES: COc1ccc(Nc2cc(C)nc(O)n2)cc1OCCCN1CCCC1] |
| 449 | 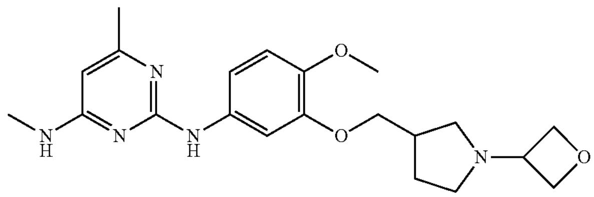 [SMILES: CNc1cc(C)nc(Nc2ccc(OC)c(OCC3CCN(C4COC4)C3)c2)n1] |
| 450 | 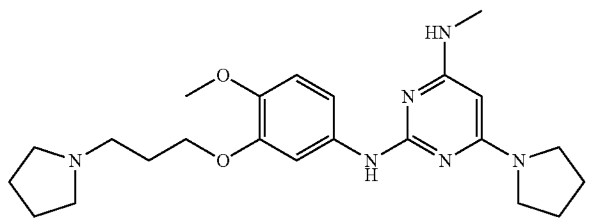 [SMILES: CNc1cc(N2CCCC2)nc(Nc2ccc(OC)c(OCCCN3CCCC3)c2)n1] |
| 451 | 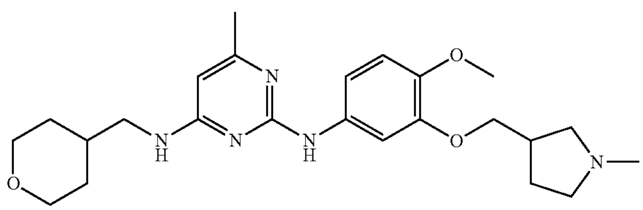 [SMILES: COc1ccc(Nc2nc(C)cc(NCC3CCOCC3)n2)cc1OCC1CCN(C)C1] |
| 452 | 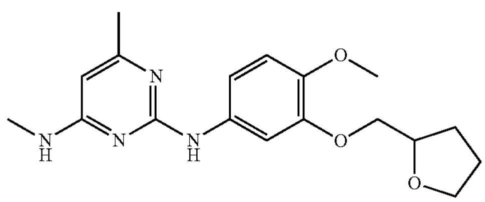 [SMILES: CNc1cc(C)nc(Nc2ccc(OC)c(OCC3CCCO3)c2)n1] |
| 453 | 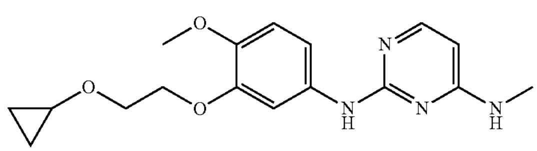 [SMILES: CNc1ccnc(Nc2ccc(OC)c(OCCOC3CC3)c2)n1] |
| 454 | 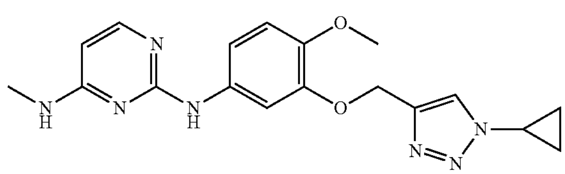 [SMILES: CNc1ccnc(Nc2ccc(OC)c(OCc3cn(C4CC4)nn3)c2)n1] |
| 455 | 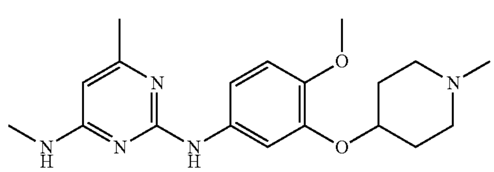 |

TABLE 2-continued
| Compound No. | Structure |
|---|---|
| 456 | 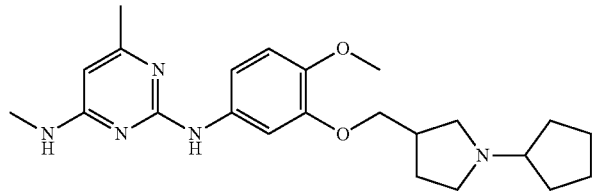 [SMILES: CNc1cc(C)nc(Nc2ccc(OC)c(OCC3CCN(C4CCCC4)C3)c2)n1] |
| 457 | 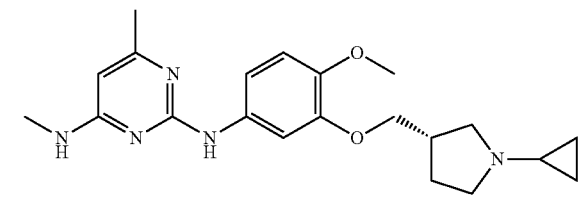 [SMILES: CNc1cc(C)nc(Nc2ccc(OC)c(OC[C@H]3CCN(C4CC4)C3)c2)n1] |
| 458 | 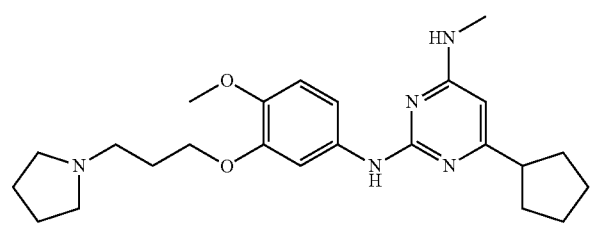 [SMILES: CNc1cc(C2CCCC2)nc(Nc2ccc(OC)c(OCCCN3CCCC3)c2)n1] |
| 459 | 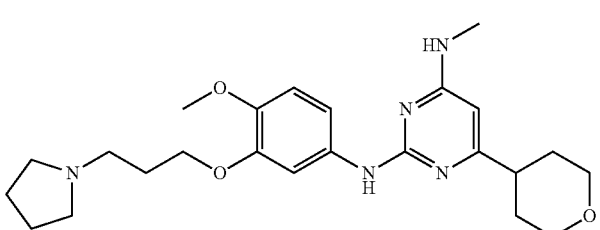 |
| 460 | 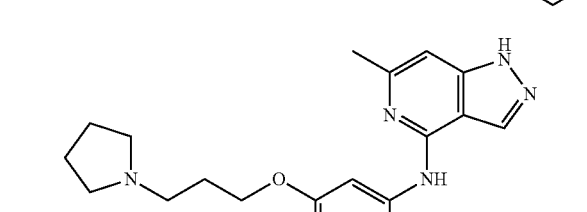 |
| 461 | 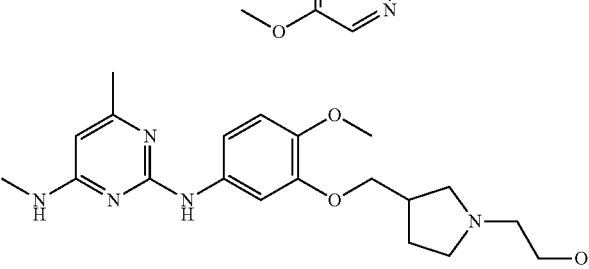 |
| 462 | 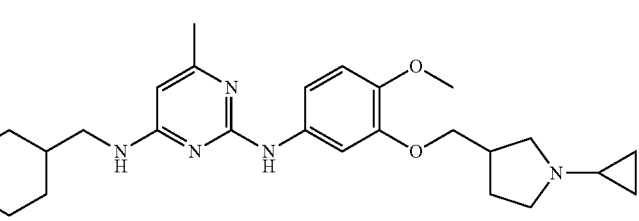 |

TABLE 2-continued
| Compound No. | Structure |
|---|---|
| 463 | 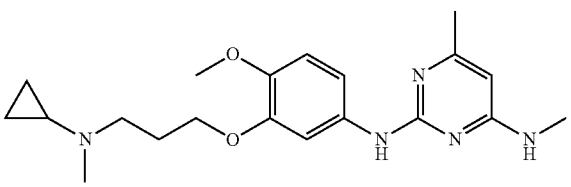 [SMILES: CNc1cc(C)nc(Nc2ccc(OC)c(OCCCN(C)C3CC3)c2)n1] |
| 464 | 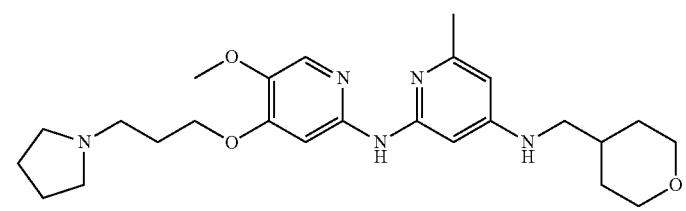 [SMILES: COc1cnc(Nc2cc(NCC3CCOCC3)cc(C)n2)cc1OCCCN1CCCC1] |
| 465 | 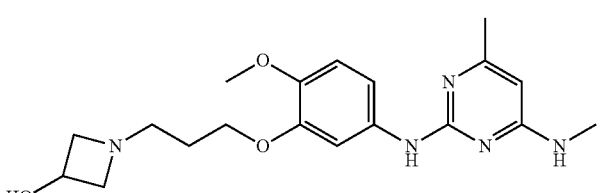 |
| 466 | 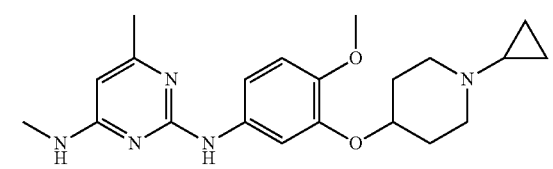 [SMILES: CNc1cc(C)nc(Nc2ccc(OC)c(OC3CCN(C4CC4)CC3)c2)n1] |
| 467 | 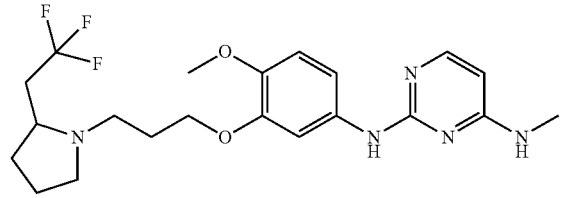 [SMILES: CNc1ccnc(Nc2ccc(OC)c(OCCCN3CCCC3CC(F)(F)F)c2)n1] |
| 468 | 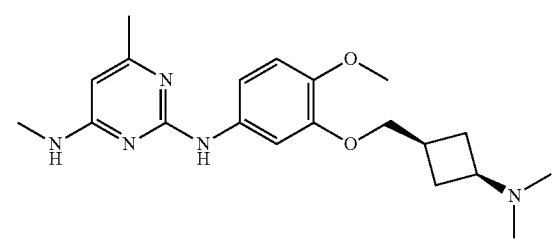 |
| 469 | 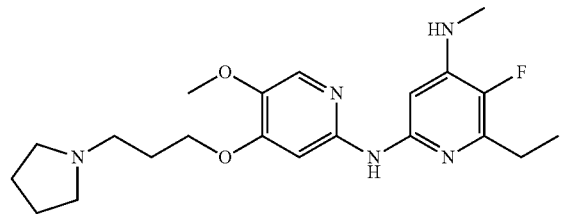 [SMILES: CCc1nc(Nc2cc(OCCCN3CCCC3)c(OC)cn2)cc(NC)c1F] |

TABLE 2-continued

| Compound No. | Structure |
|---|---|
| 470 | 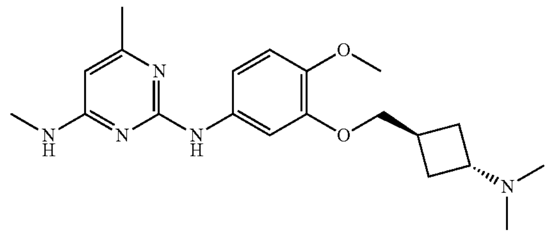 |
| 471 | 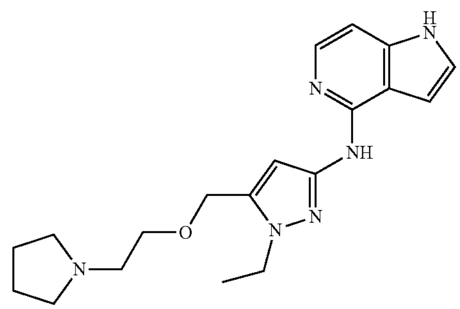 [SMILES: CCn1nc(Nc2nccc3[nH]ccc23)cc1COCCN1CCCC1] |
| 472 | 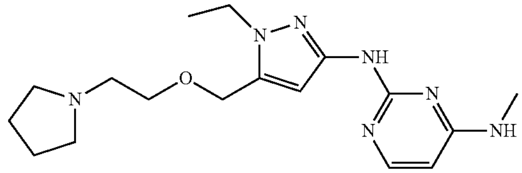 [SMILES: CCn1nc(Nc2nccc(NC)n2)cc1COCCN1CCCC1] |
| 473 | 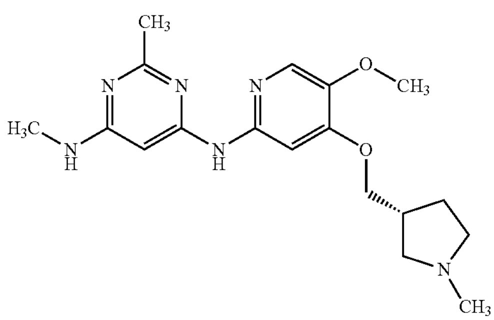 [SMILES: CNc1cc(Nc2cc(OC[C@@H]3CCN(C)C3)c(OC)cn2)nc(C)n1] |
| 474 | 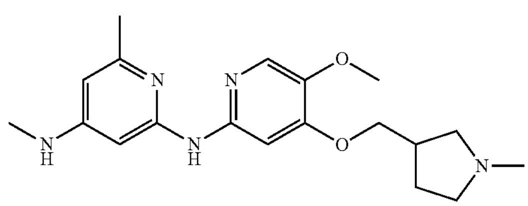 |
| 475 | 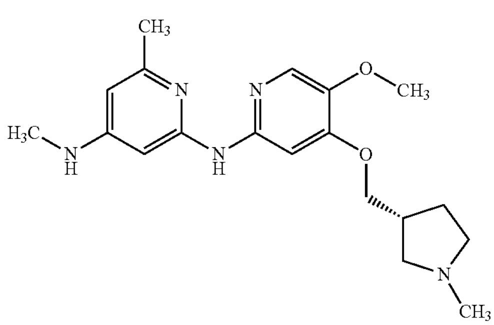 [SMILES: CNc1cc(C)nc(Nc2cc(OC[C@@H]3CCN(C)C3)c(OC)cn2)c1] |

TABLE 2-continued

| Compound No. | Structure |
|---|---|
| 476 | 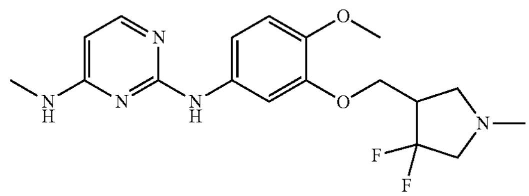 |
| 477 | 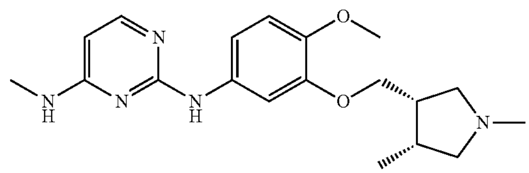 |
| 478 | 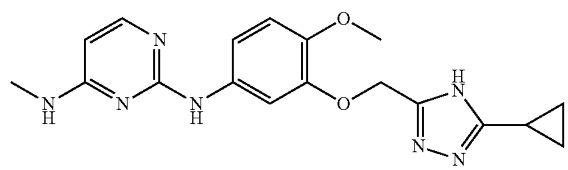 [SMILES: CNc1ccnc(Nc2ccc(OC)c(OCc3nnc(C4CC4)[nH]3)c2)n1] |
| 479 | 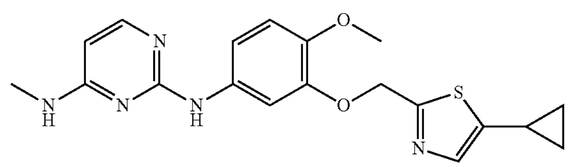 [SMILES: CNc1ccnc(Nc2ccc(OC)c(OCc3ncc(C4CC4)s3)c2)n1] |
| 480 | 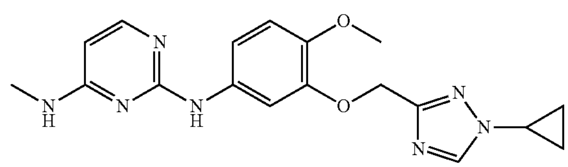 [SMILES: CNc1ccnc(Nc2ccc(OC)c(OCc3ncn(C4CC4)n3)c2)n1] |
| 481 | 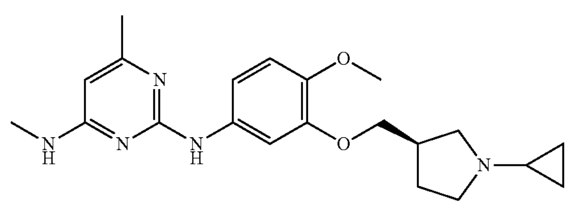 [SMILES: CNc1cc(C)nc(Nc2ccc(OC)c(OC[C@@H]3CCN(C4CC4)C3)c2)n1] |
| 482 | 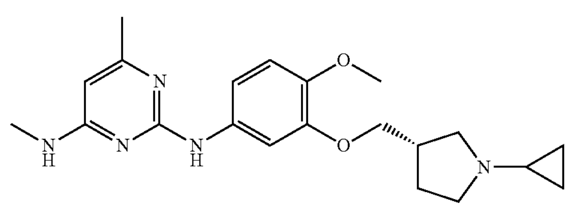 [SMILES: CNc1cc(C)nc(Nc2ccc(OC)c(OC[C@H]3CCN(C4CC4)C3)c2)n1] |
| 483 | 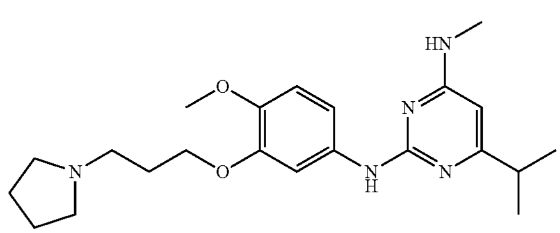 [SMILES: CNc1cc(C(C)C)nc(Nc2ccc(OC)c(OCCCN3CCCC3)c2)n1] |

US 11,672,800 B2
TABLE 2-continued
| Compound No. | Structure |
|---|---|
| 484 | 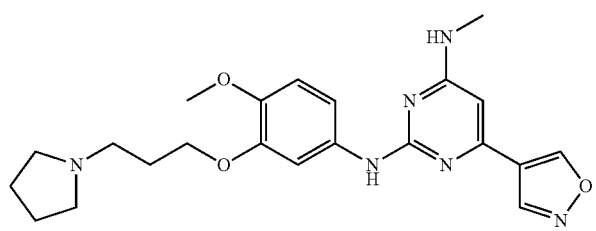 [SMILES: CNc1cc(-c2cnoc2)nc(Nc2ccc(OC)c(OCCCN3CCCC3)c2)n1] |
| 485 | 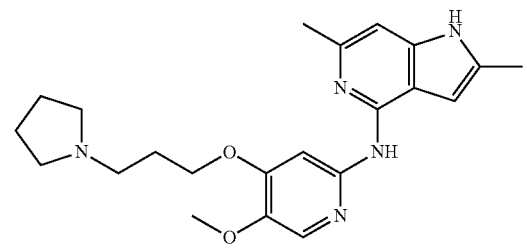 [SMILES: COc1cnc(Nc2nc(C)cc3[nH]c(C)cc23)cc1OCCCN1CCCC1] |
| 486 | 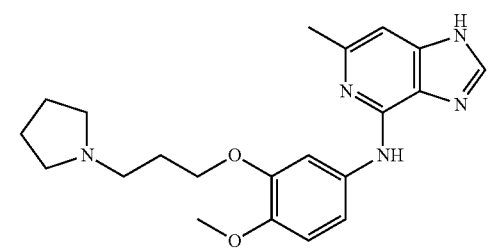 [SMILES: COc1ccc(Nc2nc(C)cc3[nH]cnc23)cc1OCCCN1CCCC1] |
| 487 | 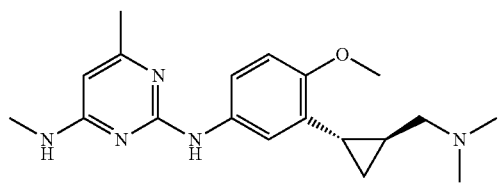 |
| 488 | 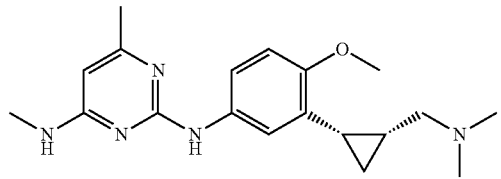 |
| 489 | 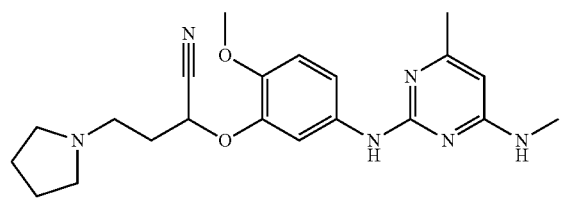 [SMILES: CNc1cc(C)nc(Nc2ccc(OC)c(OC(C#N)CCN3CCCC3)c2)n1] |
| 490 | 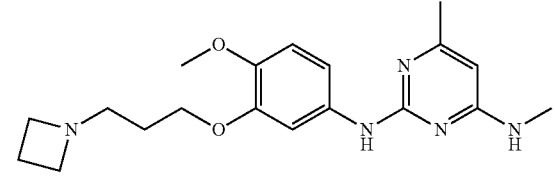 [SMILES: CNc1cc(C)nc(Nc2ccc(OC)c(OCCCN3CCC3)c2)n1] |

TABLE 2-continued

| Compound No. | Structure |
|---|---|
| 491 | 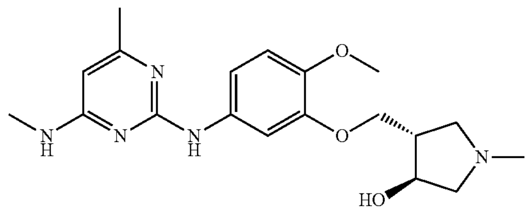 |
| 492 | 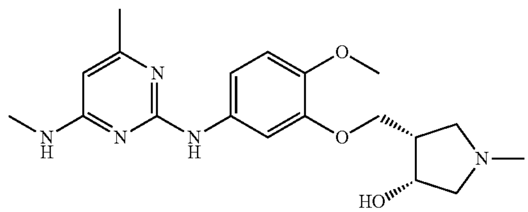 |
| 493 | 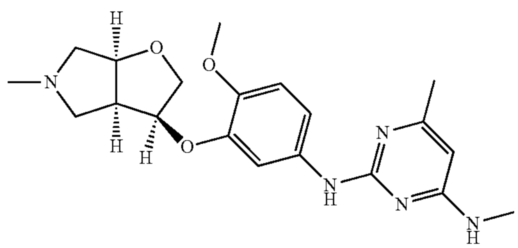 |
| 494 | 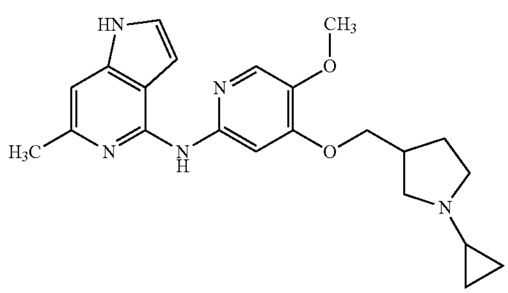 [SMILES: COc1cnc(Nc2nc(C)cc3[nH]ccc23)cc1OCC1CCN(C2CC2)C1] |
| 494a | 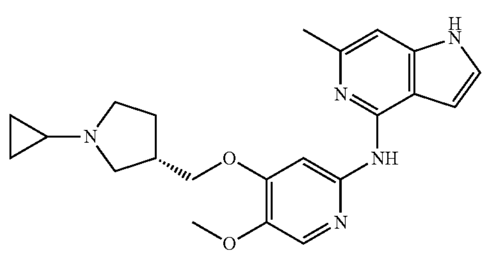 [SMILES: COc1cnc(Nc2nc(C)cc3[nH]ccc23)cc1OC[C@H]1CCN(C2CC2)C1] |
| 495 | 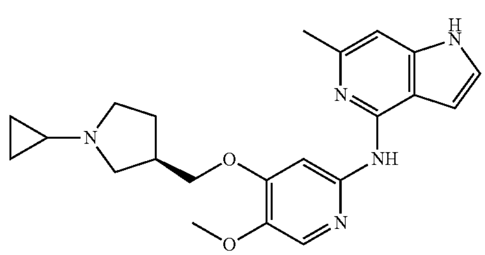 [SMILES: COc1cnc(Nc2nc(C)cc3[nH]ccc23)cc1OC[C@@H]1CCN(C2CC2)C1] |

TABLE 2-continued
| Compound No. | Structure |
|---|---|
| 496 | 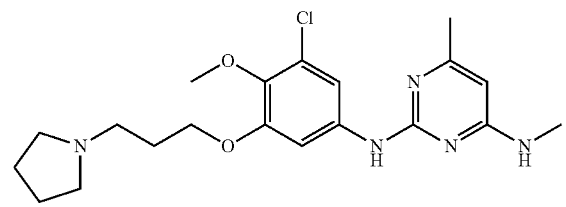 [SMILES: CNc1cc(C)nc(Nc2cc(Cl)c(OC)c(OCCCN3CCCC3)c2)n1] |
| 497 | 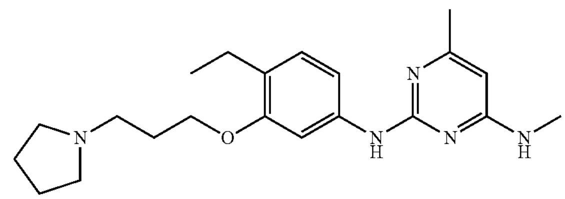 [SMILES: CCc1ccc(Nc2nc(C)cc(NC)n2)cc1OCCCN1CCCC1] |
| 498 | 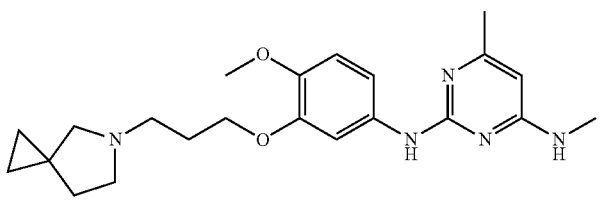 [SMILES: CNc1cc(C)nc(Nc2ccc(OC)c(OCCCN3CCC4(CC4)C3)c2)n1] |
| 499 | 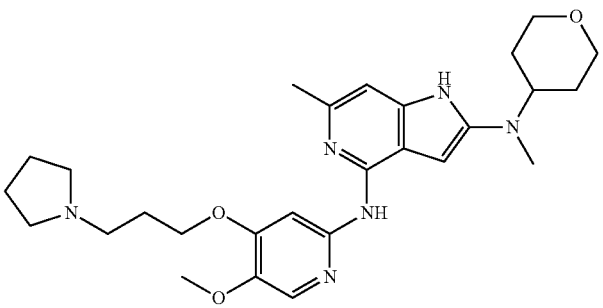 [SMILES: COc1cnc(Nc2nc(C)cc3[nH]c(N(C)C4CCOCC4)cc23)cc1OCCCN1CCCC1] |
| 500 | 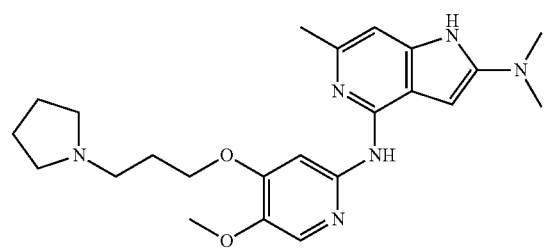 [SMILES: COc1cnc(Nc2nc(C)cc3[nH]c(N(C)C)cc23)cc1OCCCN1CCCC1] |
| 501 | 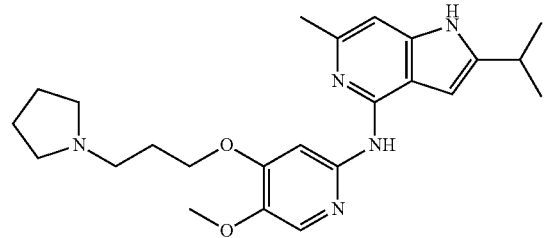 |

TABLE 2-continued

| Compound No. | Structure |
|---|---|
| 502 | 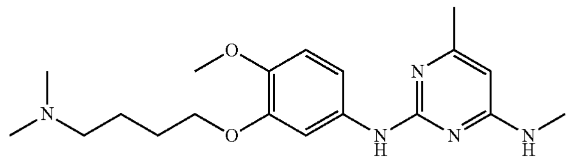 |
| 503 | 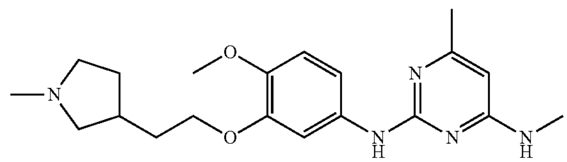 |
| 504 | 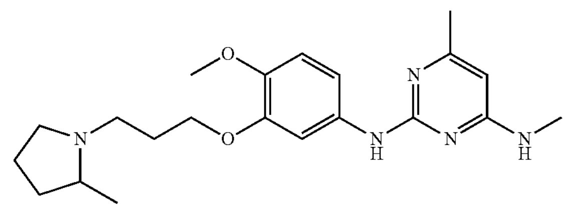 [SMILES: CNc1cc(C)nc(Nc2ccc(OC)c(OCCCN3CCCC3C)c2)n1] |
| 505 | 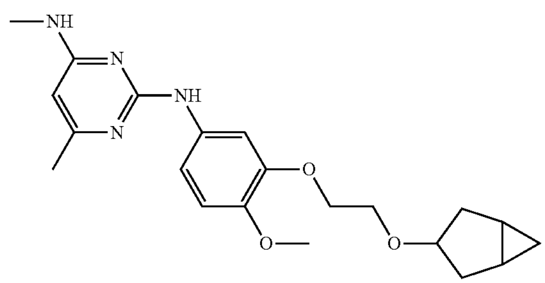 [SMILES: CNc1cc(C)nc(Nc2ccc(OC)c(OCCOC3CC4CC4C3)c2)n1] |
| 506 | 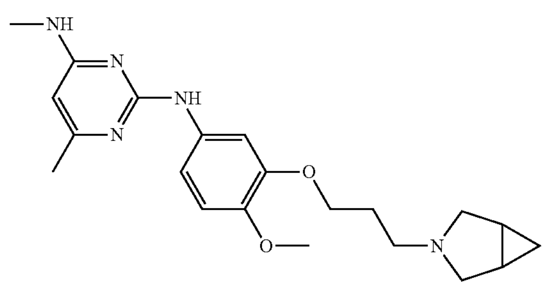 |
| 507 | 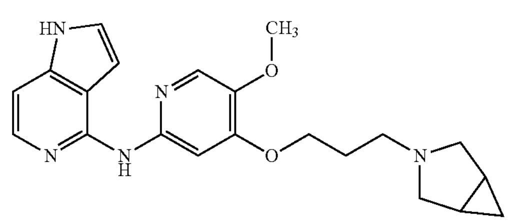 [SMILES: COc1cnc(Nc2nccc3[nH]ccc23)cc1OCCCN1CC2CC2C1] |
| 508 | 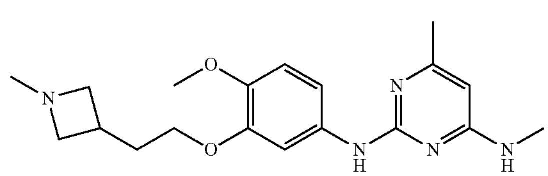 |

TABLE 2-continued

| Compound No. | Structure |
|---|---|
| 509 | 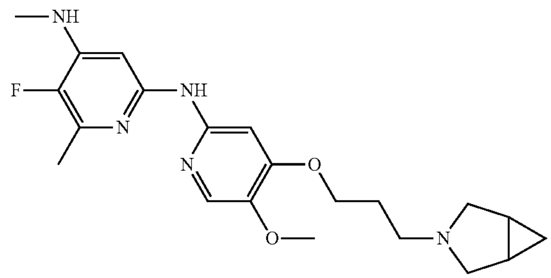 [SMILES: CNc1cc(Nc2cc(OCCCN3CC4CC4C3)c(OC)cn2)nc(C)c1F] |
| 510 | 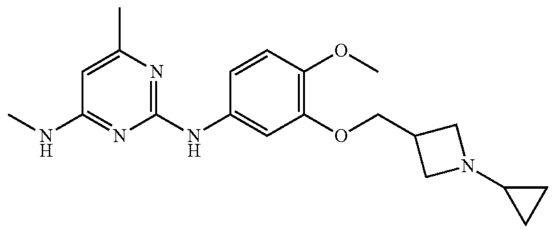 [SMILES: CNc1cc(C)nc(Nc2ccc(OC)c(OCC3CN(C4CC4)C3)c2)n1] |
| 511 | 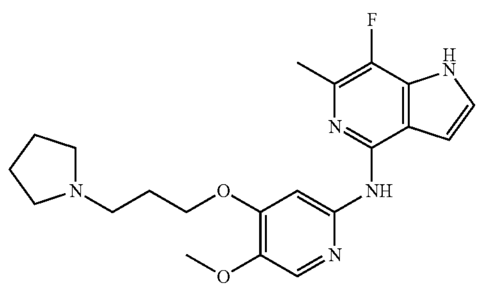 [SMILES: COc1cnc(Nc2nc(C)c(F)c3[nH]ccc23)cc1OCCCN1CCCC1] |
| 512 | 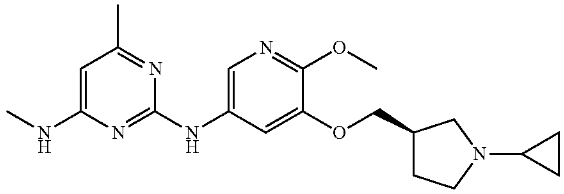 [SMILES: CNc1cc(C)nc(Nc2cnc(OC)c(OC[C@@H]3CCN(C4CC4)C3)c2)n1] |
| 513 | 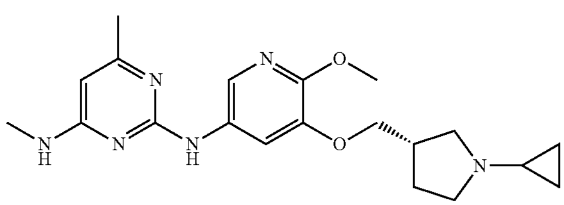 [SMILES: CNc1cc(C)nc(Nc2cnc(OC)c(OC[C@H]3CCN(C4CC4)C3)c2)n1] |
| 514 | 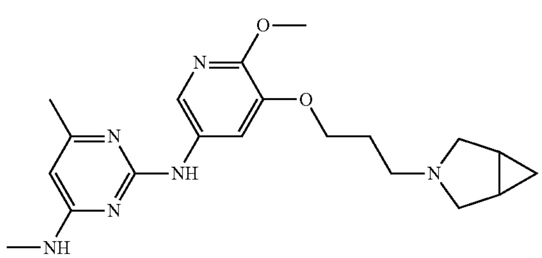 [SMILES: CNc1cc(C)nc(Nc2cnc(OC)c(OCCCN3CC4CC4C3)c2)n1] |

TABLE 2-continued

| Compound No. | Structure |
|---|---|
| 515 | 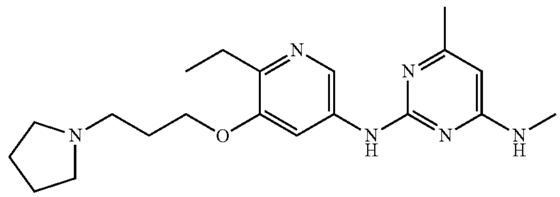 [SMILES: CCc1ncc(Nc2nc(C)cc(NC)n2)cc1OCCCN1CCCC1] |
| 516 | 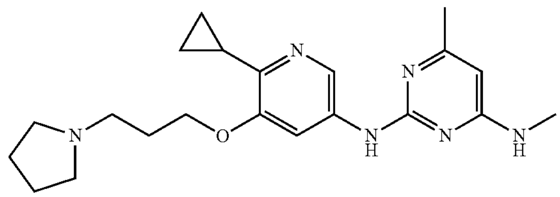 [SMILES: CNc1cc(C)nc(Nc2cnc(C3CC3)c(OCCCN3CCCC3)c2)n1] |
| 517a | 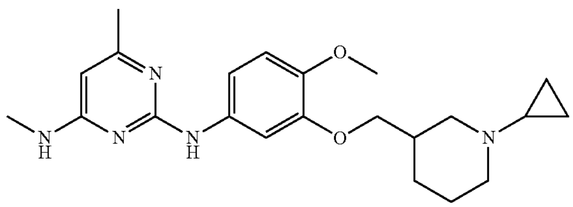 [SMILES: CNc1cc(C)nc(Nc2ccc(OC)c(OC[C@H]3CCCN(C4CC4)C3)c2)n1] |
| 517b | 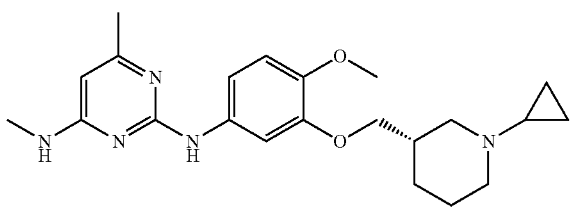 |

The compounds of Table 2 are the compounds found in U.S. Application No. 62/402,997, the entire contents of which are incorporated herein by reference.

TABLE 3

| Compound No. | Structure |
|---|---|
| 270 | 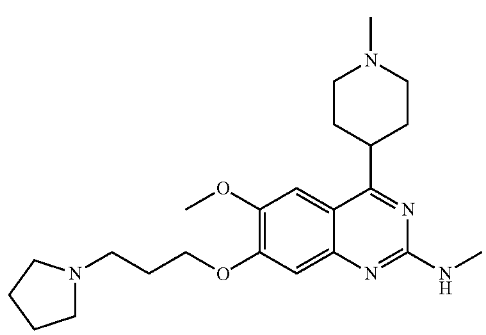 |

TABLE 3-continued
| Compound No. | Structure |
|---|---|
| 518 | 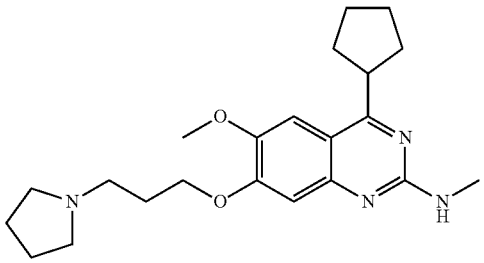 [SMILES: CNc1nc(C2CCCC2)c2cc(OC)c(OCCCN3CCCC3)cc2n1] |
| 519 | 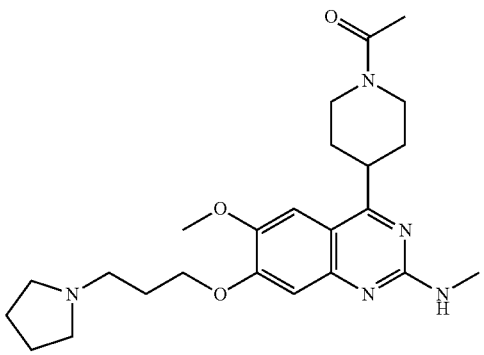 [SMILES: CNc1nc(C2CCN(C(C)=O)CC2)c2cc(OC)c(OCCCN3CCCC3)cc2n1] |
| 520 | 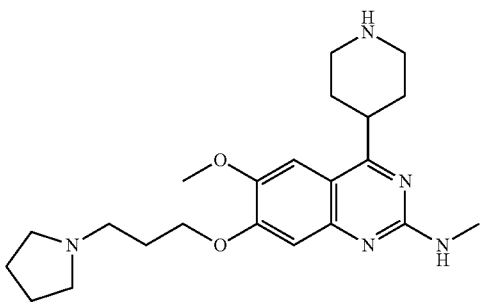 [SMILES: CNc1nc(C2CCNCC2)c2cc(OC)c(OCCCN3CCCC3)cc2n1] |
| 521 | 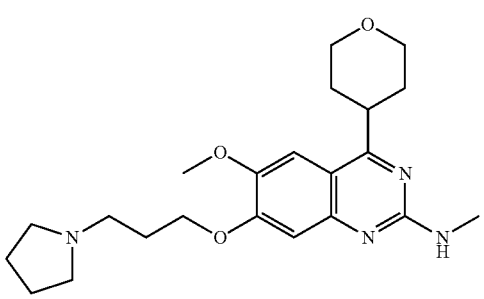 [SMILES: CNc1nc(C2CCOCC2)c2cc(OC)c(OCCCN3CCCC3)cc2n1] |
| 522 | 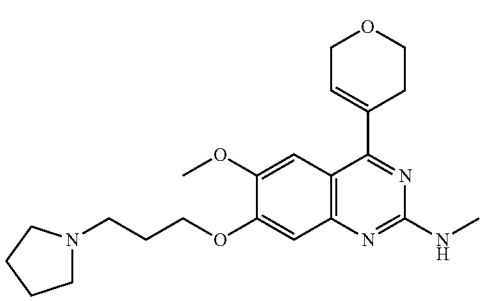 [SMILES: CNc1nc(C2=CCOCC2)c2cc(OC)c(OCCCN3CCCC3)cc2n1] |

TABLE 3-continued

| Compound No. | Structure |
| --- | --- |
| 523 | 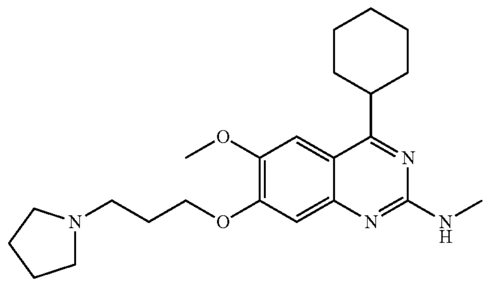 [SMILES: CNc1nc(C2CCCCC2)c2cc(OC)c(OCCCN3CCCC3)cc2n1] |
| 524 | 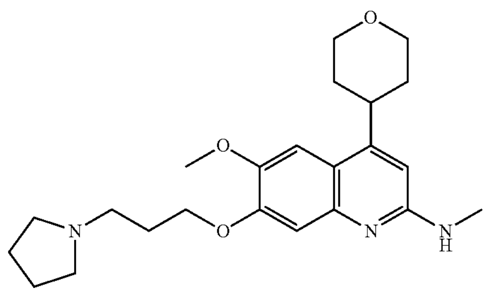 [SMILES: CNc1cc(C2CCOCC2)c2cc(OC)c(OCCCN3CCCC3)cc2n1] |
| 525 | 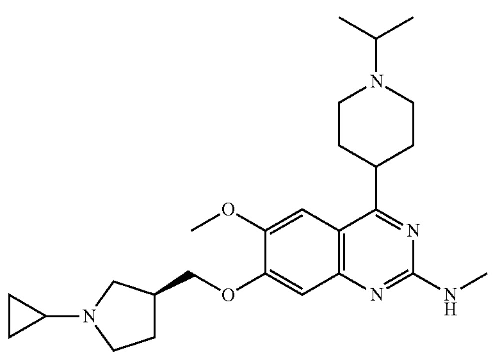 [SMILES: CNc1nc(C2CCN(C(C)C)CC2)c2cc(OC)c(OC[C@H]3CCN(C4CC4)C3)cc2n1] |
| 526 | 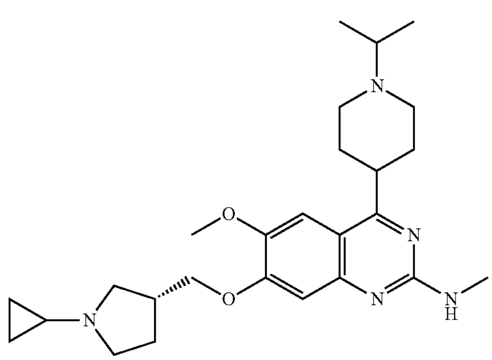 [SMILES: CNc1nc(C2CCN(C(C)C)CC2)c2cc(OC)c(OC[C@@H]3CCN(C4CC4)C3)cc2n1] |

TABLE 3-continued

| Compound No. | Structure |
|---|---|
| 527 | 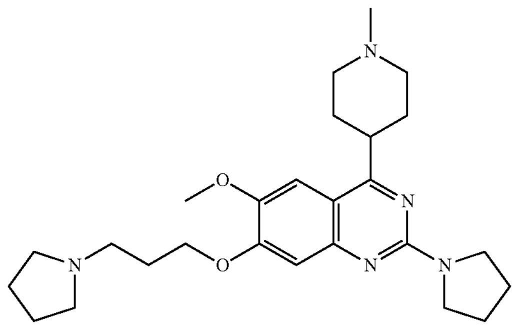 [SMILES: COc1cc2c(C3CCN(C)CC3)nc(N3CCCC3)nc2cc1OCCCN1CCCC1] |
| 528 | 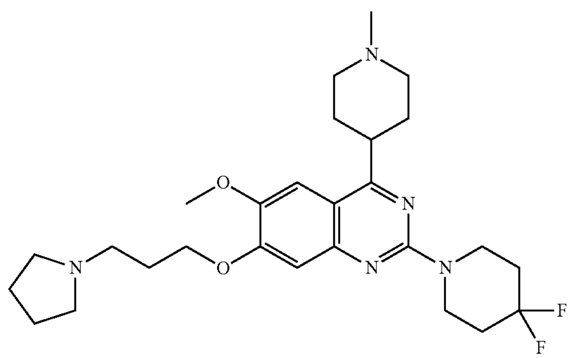 [SMILES: COc1cc2c(C3CCN(C)CC3)nc(N3CCC(F)(F)CC3)nc2cc1OCCCN1CCCC1] |
| 529 | 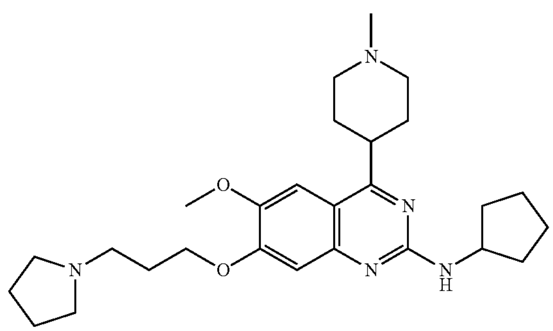 [SMILES: COc1cc2c(C3CCN(C)CC3)nc(NC3CCCC3)nc2cc1OCCCN1CCCC1] |
| 530 | 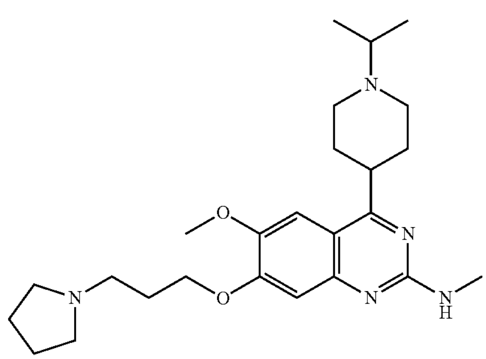 [SMILES: CNc1nc(C2CCN(C(C)C)CC2)c2cc(OC)c(OCCCN3CCCC3)cc2n1] |

TABLE 3-continued

| Compound No. | Structure |
|---|---|
| 531 | 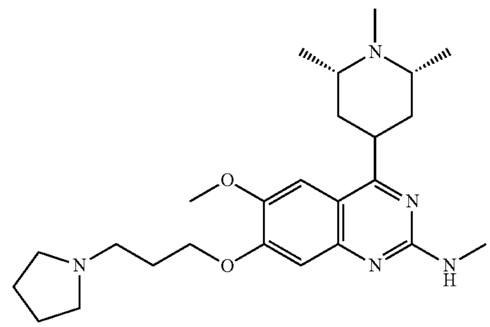 [SMILES: CNc1nc(C2C[C@@H](C)N(C)[C@@H](C)C2)c2cc(OC)c(OCCCN3CCCC3)cc2n1] |
| 532 | 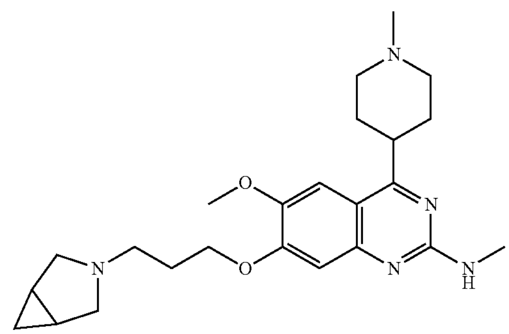 [SMILES: CNc1nc(C2CCN(C)CC2)c2cc(OC)c(OCCCN3CC4CC4C3)cc2n1] |
| 533 | 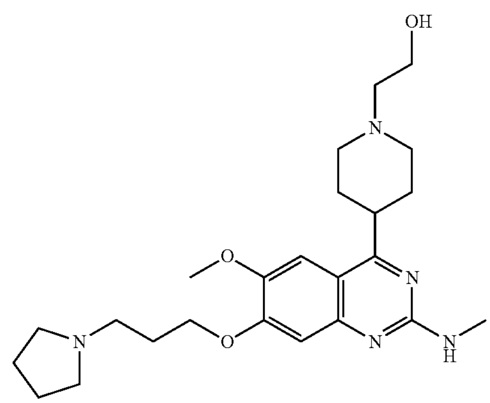 [SMILES: CNc1nc(C2CCN(CCO)CC2)c2cc(OC)c(OCCCN3CCCC3)cc2n1] |
| 534 | 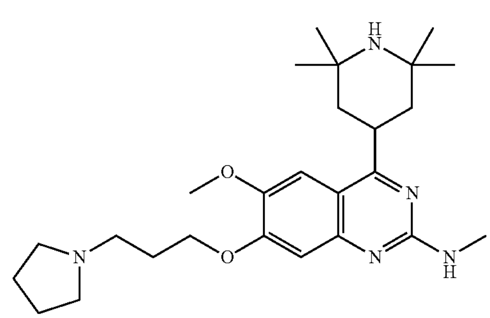 [SMILES: CNc1nc(C2CC(C)(C)NC(C)(C)C2)c2cc(OC)c(OCCCN3CCCC3)cc2n1] |

TABLE 3-continued

| Compound No. | Structure |
|---|---|
| 535 | 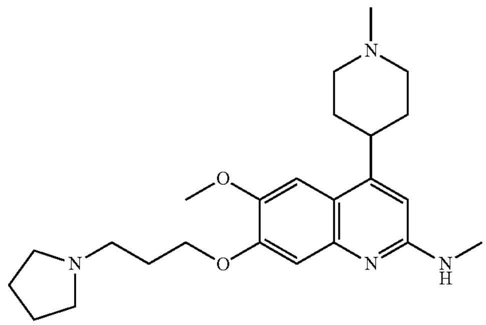 [SMILES: CNc1cc(C2CCN(C)CC2)c2cc(OC)c(OCCCN3CCCC3)cc2n1] |
| 536 | 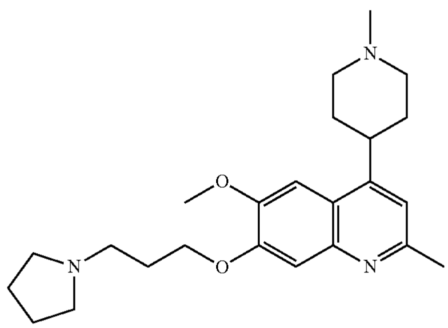 [SMILES: COc1cc2c(C3CCN(C)CC3)cc(C)nc2cc1OCCCN1CCCC1] |
| 537 | 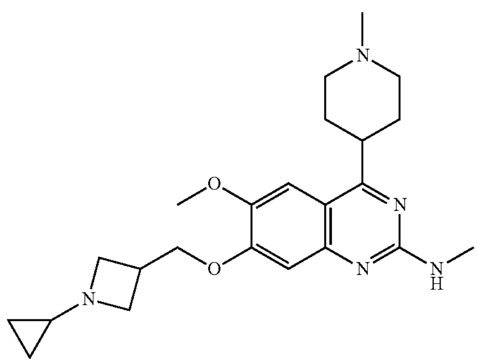 [SMILES: CNc1nc(C2CCN(C)CC2)c2cc(OC)c(OCC3CN(C4CC4)C3)cc2n1] |
| 538 | 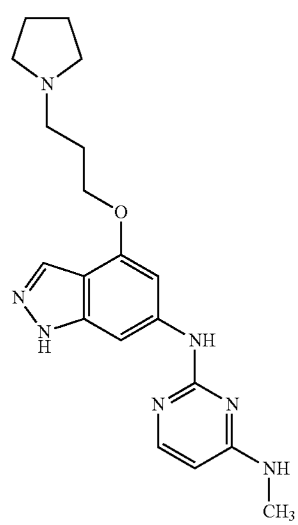 [SMILES: CNc1ccnc(Nc2cc(OCCCN3CCCC3)c3cn[nH]c3c2)n1] |

TABLE 3-continued
| Compound No. | Structure |
|---|---|
| 539 | 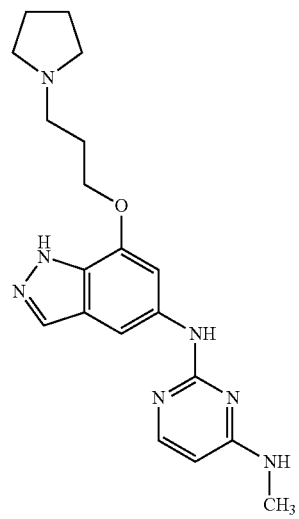 [SMILES: CNc1ccnc(Nc2cc(OCCCN3CCCC3)c3[nH]ncc3c2)n1] |
| 540 | 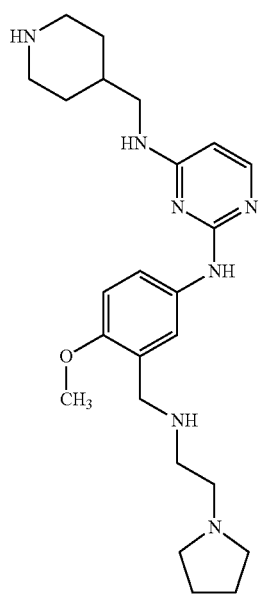 [SMILES: COc1ccc(Nc2nccc(NCC3CCNCC3)n2)cc1CNCCN1CCCC1] |
| 541 | 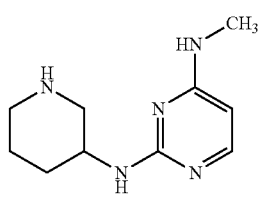 |
| 542 | 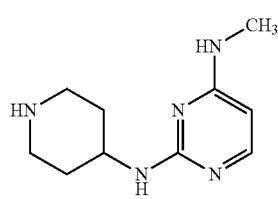 |

TABLE 3-continued

| Compound No. | Structure |
|---|---|
| 543 | N2-butyl-N4-methylpyrimidine-2,4-diamine |
| 544 | N2-(3-propylpiperidin-3-yl)-N4-methylpyrimidine-2,4-diamine |
| 545 | N2-(4-propylpiperidin-4-yl)-N4-methylpyrimidine-2,4-diamine |
| 546 | N2-(3-methylpiperidin-3-yl)-N4-methylpyrimidine-2,4-diamine |
| 547 | N2-(4-methylpiperidin-4-yl)-N4-methylpyrimidine-2,4-diamine |
| 548 | N2-((1S,3R)-3-aminocyclopentyl)-N4-methylpyrimidine-2,4-diamine |
| 549 | N2-(1-butyl-3-methylpiperidin-3-yl)-N4-methylpyrimidine-2,4-diamine |

TABLE 3-continued

| Compound No. | Structure |
|---|---|
| 550 | 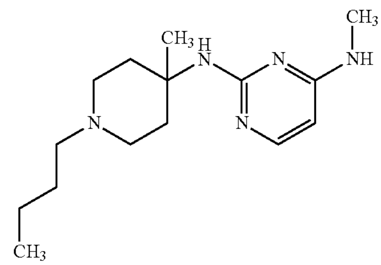 [SMILES: CCCCN1CCC(C)(Nc2nccc(NC)n2)CC1] |
| 551 | 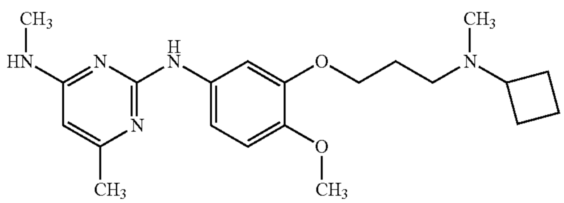 [SMILES: CNc1cc(C)nc(Nc2ccc(OC)c(OCCCN(C)C3CCC3)c2)n1] |
| 552 | 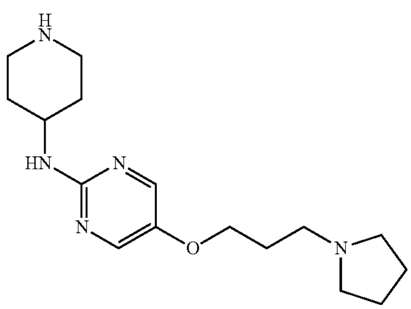 [SMILES: c1nc(NC2CCNCC2)ncc1OCCCN1CCCC1] |
| 553 | 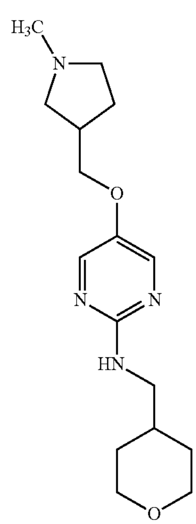 [SMILES: CN1CCC(COc2cnc(NCC3CCOCC3)nc2)C1] |

TABLE 3-continued
| Compound No. | Structure |
|---|---|
| 554 | 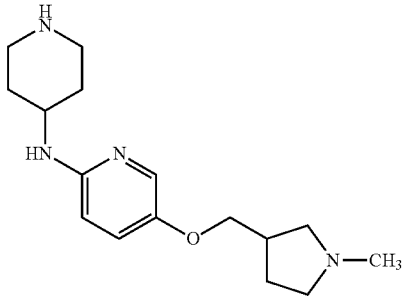 [SMILES: CN1CCC(COc2ccc(NC3CCNCC3)nc2)C1] |
| 555 | 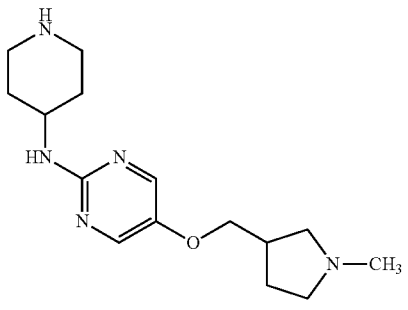 [SMILES: CN1CCC(COc2cnc(NC3CCNCC3)nc2)C1] |
| 556 | 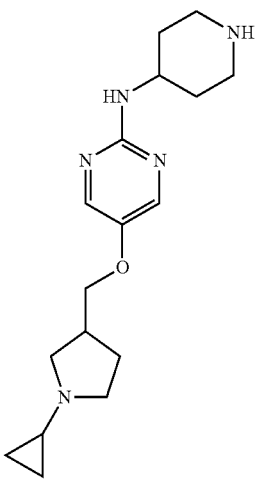 [SMILES: c1nc(NC2CCNCC2)ncc1OCC1CCN(C2CC2)C1] |

TABLE 3-continued
| Compound No. | Structure |
|---|---|
| 557 | 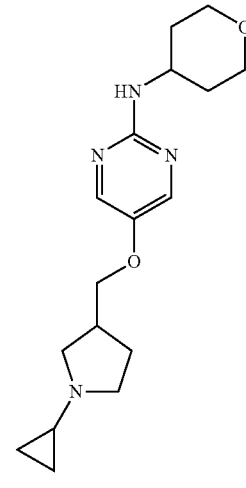 |
| 558 | 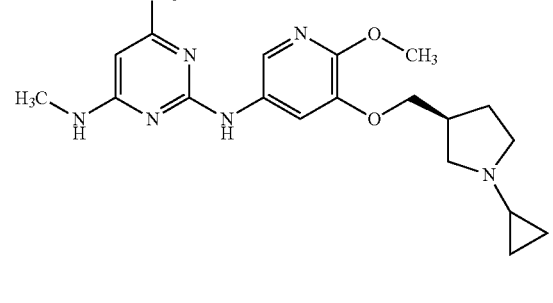 |
| 559 | 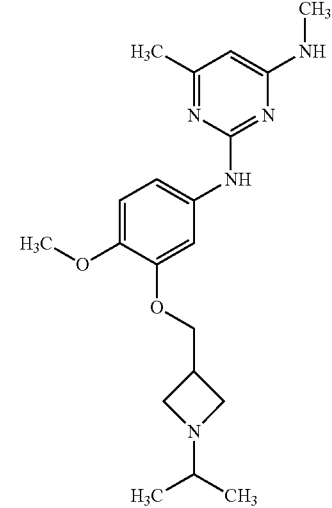 |

TABLE 3-continued
| Compound No. | Structure |
|---|---|
| 560 | 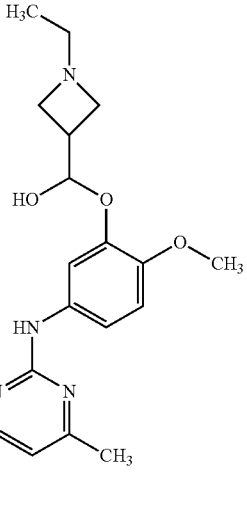 |
| 561 | 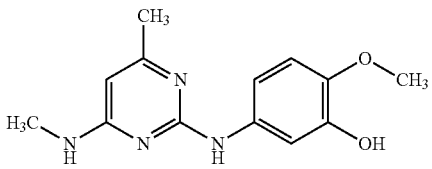 |
| 562 | 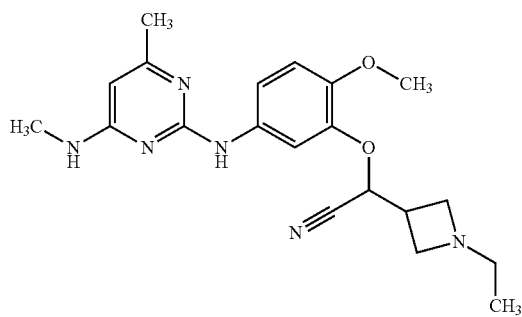 [SMILES: CCN1CC(C(C#N)Oc2cc(Nc3nc(C)cc(NC)n3)ccc2OC)C1] |
| 563 | 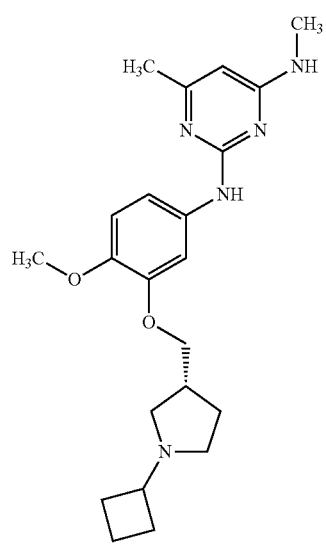 |

TABLE 3-continued

| Compound No. | Structure |
|---|---|
| 564 | 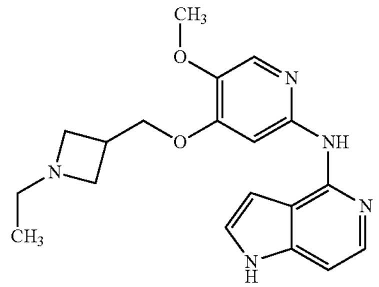 [SMILES: CCN1CC(COc2cc(Nc3nccc4[nH]ccc34)ncc2OC)C1] |
| 565 | 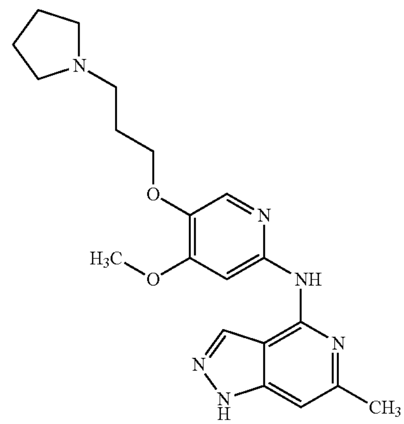 [SMILES: COc1cc(Nc2nc(C)cc3[nH]ncc23)ncc1OCCCN1CCCC1] |
| 566 | 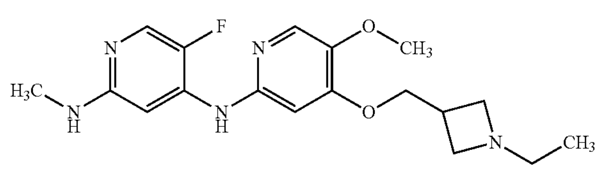 [SMILES: CCN1CC(COc2cc(Nc3cc(NC)ncc3F)ncc2OC)C1] |
| 567 | 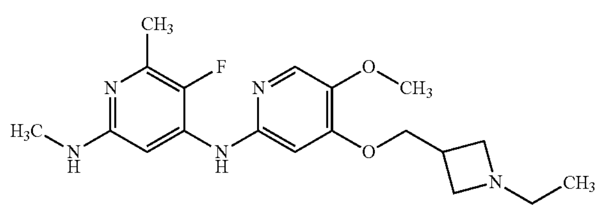 [SMILES: CCN1CC(COc2cc(Nc3cc(NC)nc(C)c3F)ncc2OC)C1] |
| 568 | 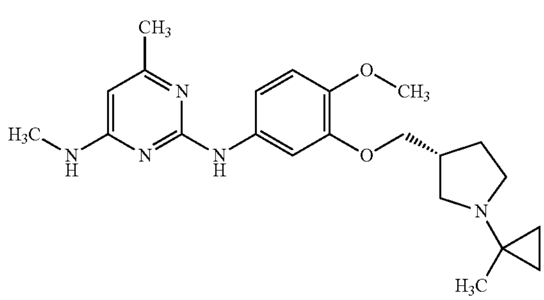 [SMILES: CNc1cc(C)nc(Nc2ccc(OC)c(OC[C@@H]3CCN(C4(C)CC4)C3)c2)n1] |

TABLE 3-continued

| Compound No. | Structure |
|---|---|
| 569 | 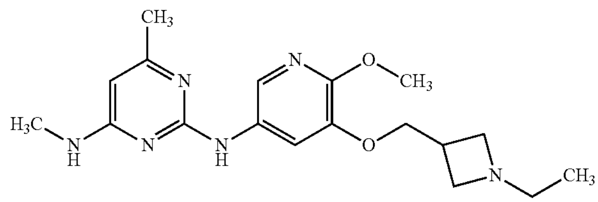 [SMILES: CCN1CC(COc2cc(Nc3nc(C)cc(NC)n3)cnc2OC)C1] |
| 570 | 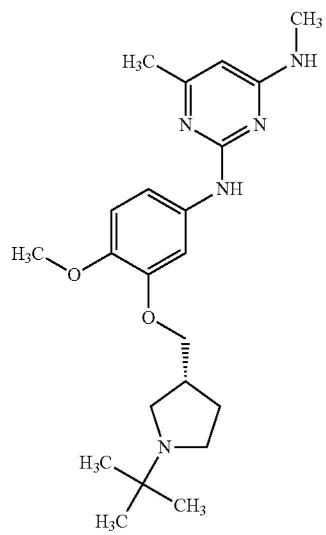 |
| 571 | 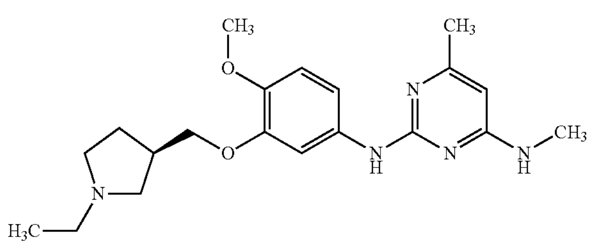 [SMILES: CCN1CC[C@@H](COc2cc(Nc3nc(C)cc(NC)n3)ccc2OC)C1] |
| 572 | 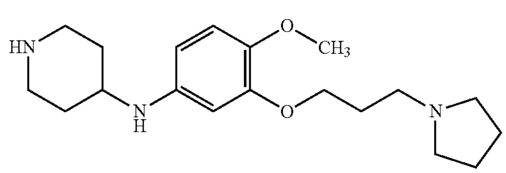 [SMILES: COc1ccc(NC2CCNCC2)cc1OCCCN1CCCC1] |
| 573 | 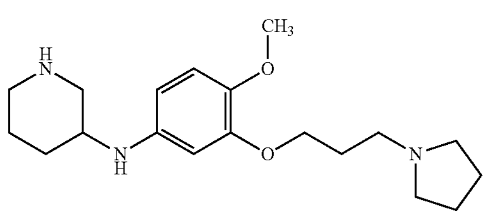 [SMILES: COc1ccc(NC2CCCNC2)cc1OCCCN1CCCC1] |

TABLE 3-continued
| Compound No. | Structure |
|---|---|
| 574 | 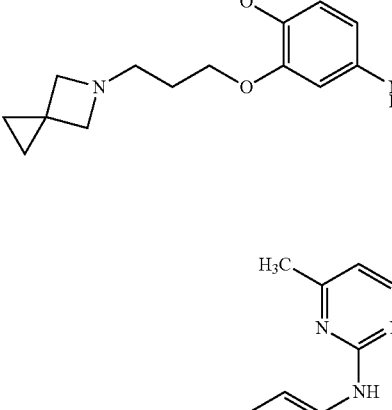 |
| 575 | 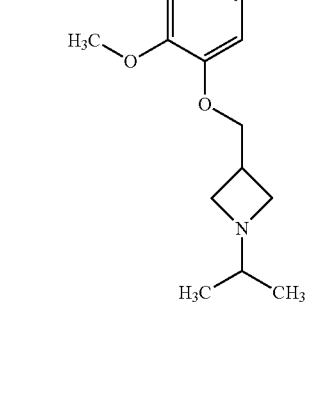 |
| 576 | 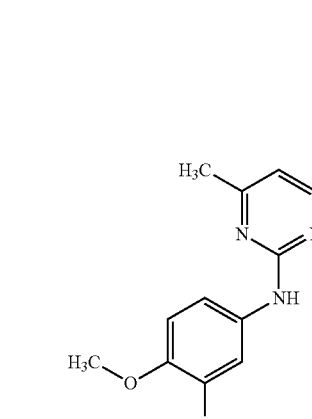 |

TABLE 3-continued
| Compound No. | Structure |
|---|---|
| 577 | 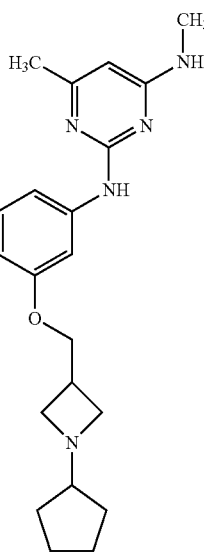 |
| 578 | 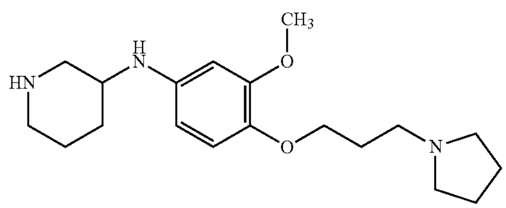 [SMILES: COc1cc(NC2CCCNC2)ccc1OCCCN1CCCC1] |
| 579 | 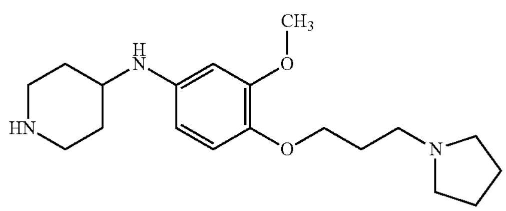 [SMILES: COc1cc(NC2CCNCC2)ccc1OCCCN1CCCC1] |
| 580 | 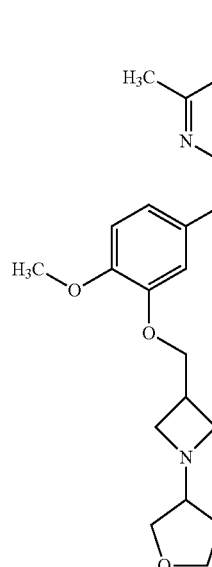 |

TABLE 3-continued

| Compound No. | Structure |
| --- | --- |
| 581 | 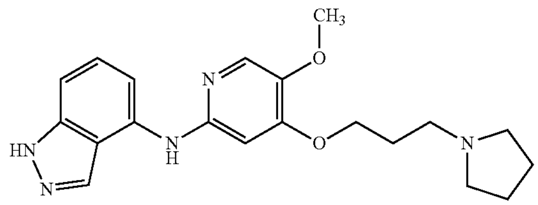 [SMILES: COc1cnc(Nc2cccc3[nH]ncc23)cc1OCCCN1CCCC1] |
| 582 | 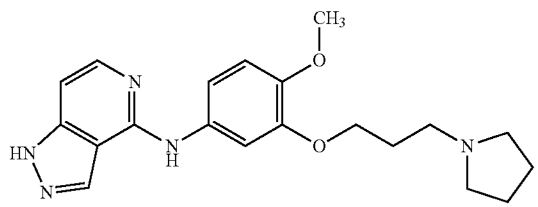 [SMILES: COc1ccc(Nc2nccc3[nH]ncc23)cc1OCCCN1CCCC1] |
| 583 | 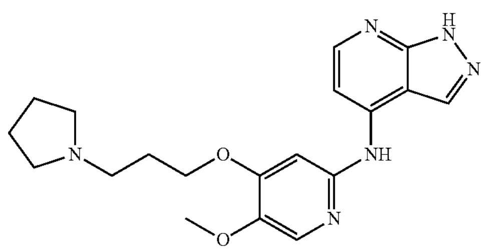 [SMILES: COc1cnc(Nc2ccnc3[nH]ncc23)cc1OCCCN1CCCC1] |
| 584 | 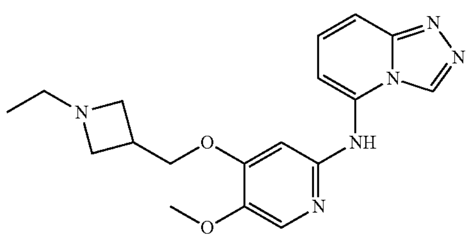 [SMILES: CCN1CC(COc2cc(Nc3cccc4nncn34)ncc2OC)C1] |
| 585 | 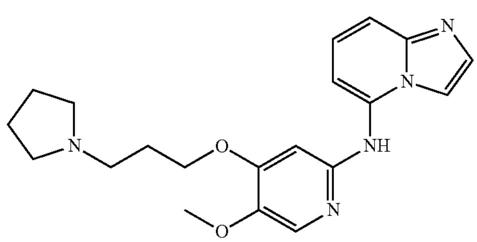 [SMILES: COc1cnc(Nc2cccc3nccn23)cc1OCCCN1CCCC1] |
| 586 | 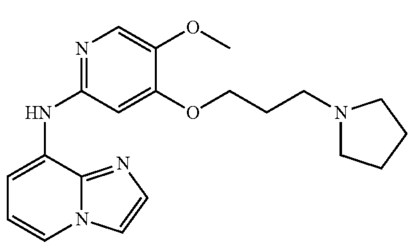 [SMILES: COc1cnc(Nc2cccn3ccnc23)cc1OCCCN1CCCC1] |

TABLE 3-continued

| Compound No. | Structure |
|---|---|
| 587 | 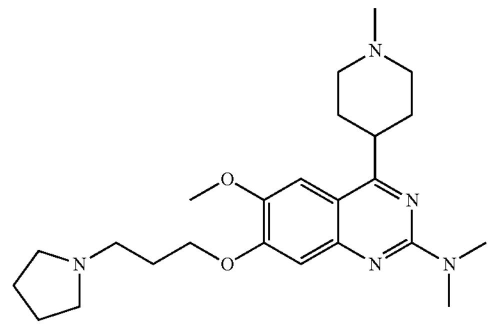 [SMILES: COc1cc2c(C3CCN(C)CC3)nc(N(C)C)nc2cc1OCCCN1CCCC1] |
| 588 | 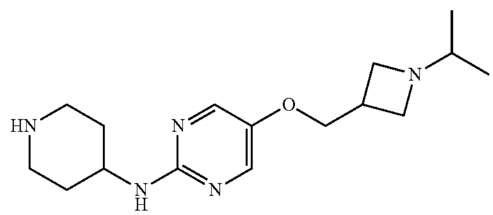 [SMILES: CC(C)N1CC(COc2cnc(NC3CCNCC3)nc2)C1] |
| 589 | 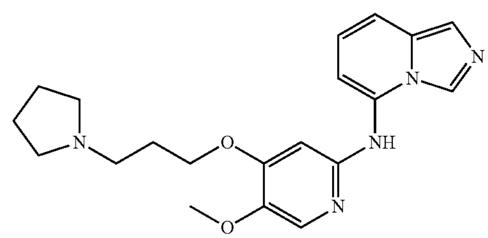 [SMILES: COc1cnc(Nc2cccc3cncn23)cc1OCCCN1CCCC1] |
| 590 | 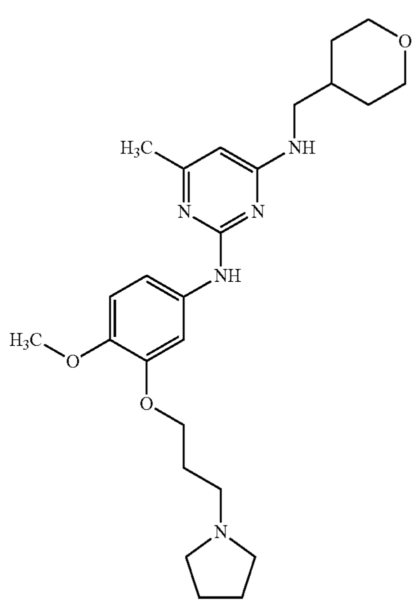 [SMILES: COc1ccc(Nc2nc(C)cc(NCC3CCOCC3)n2)cc1OCCCN1CCCC1] |

TABLE 3-continued
| Compound No. | Structure |
|---|---|
| 591 | 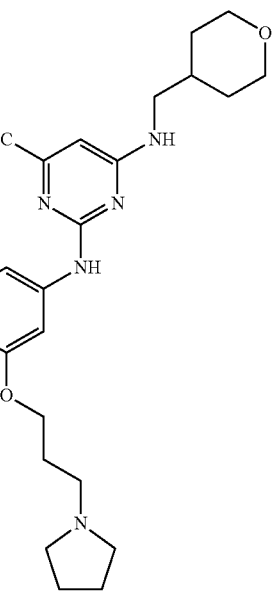 |
| 592 | 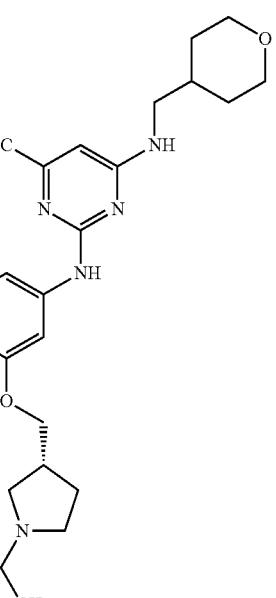 |
| 593 | 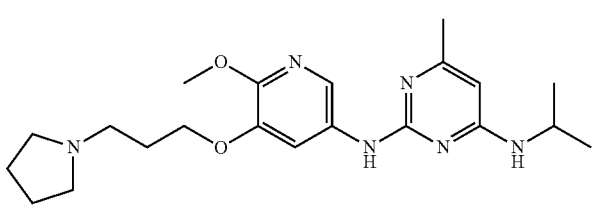 [SMILES: COc1ncc(Nc2nc(C)cc(NC(C)C)n2)cc1OCCCN1CCCC1] |

TABLE 3-continued
| Compound No. | Structure |
|---|---|
| 594 | 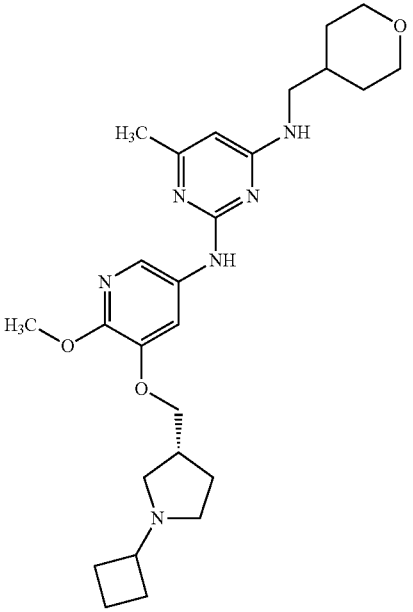 [SMILES: COc1ncc(Nc2nc(C)cc(NCC3CCOCC3)n2)cc1OC[C@@H]1CCN(C2CCC2)C1] |
| 595 | 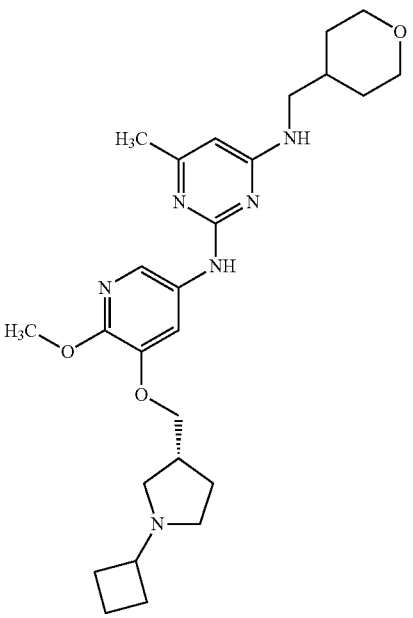 [SMILES: COc1ncc(Nc2nc(C)cc(NCC3CCOCC3)n2)cc1OC[C@@H]1CCN(C2CCC2)C1] |
| 596 | 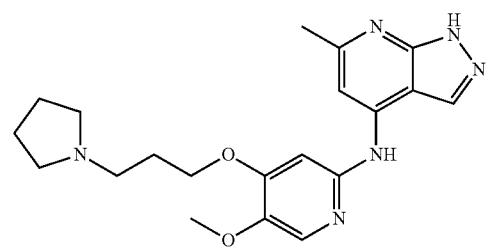 [SMILES: COc1cnc(Nc2cc(C)nc3[nH]ncc23)cc1OCCCN1CCCC1] |

TABLE 3-continued
| Compound No. | Structure |
|---|---|
| 597 | 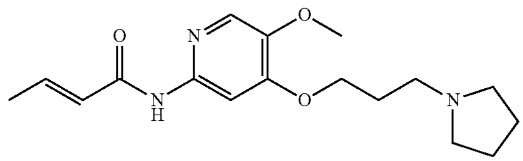 [SMILES: C/C=C/C(=O)Nc1cc(OCCCN2CCCC2)c(OC)cn1] |
| 598 | 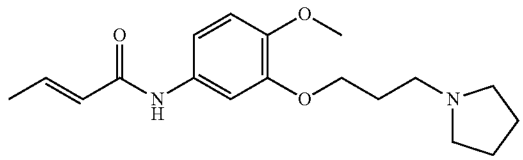 [SMILES: C/C=C/C(=O)Nc1ccc(OC)c(OCCCN2CCCC2)c1] |
| 599 | 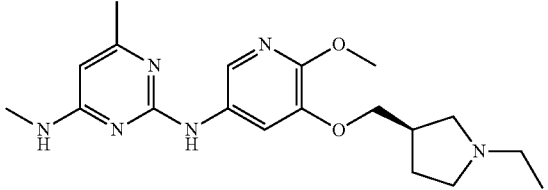 [SMILES: CCN1CC[C@@H](COc2cc(Nc3nc(C)cc(NC)n3)cnc2OC)C1] |
| 600 | 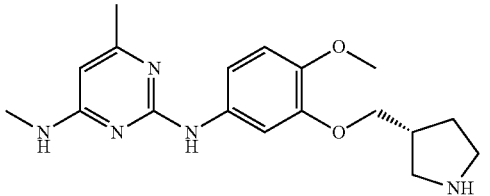 [SMILES: CNc1cc(C)nc(Nc2ccc(OC)c(OC[C@@H]3CCNC3)c2)n1] |
| 601 | 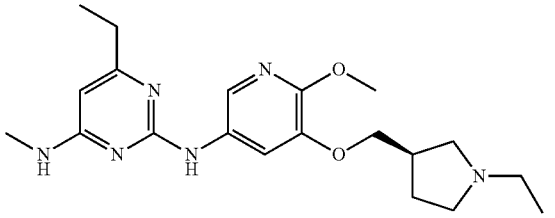 [SMILES: CCc1cc(NC)nc(Nc2cnc(OC)c(OC[C@@H]3CCN(CC)C3)c2)n1] |
| 602 | 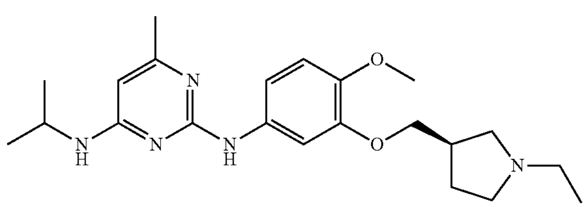 [SMILES: CCN1CC[C@@H](COc2cc(Nc3nc(C)cc(NC(C)C)n3)ccc2OC)C1] |
| 603 | 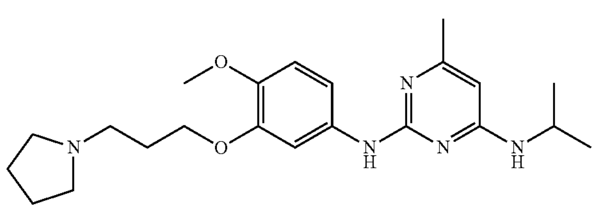 [SMILES: COc1ccc(Nc2nc(C)cc(NC(C)C)n2)cc1OCCCN1CCCC1] |

TABLE 3-continued
| Compound No. | Structure |
|---|---|
| 604 | 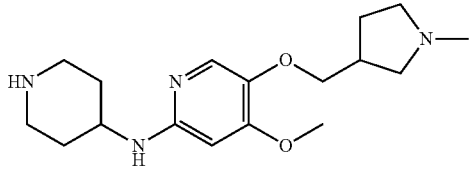 [SMILES: COc1cc(NC2CCNCC2)ncc1OCC1CCN(C)C1] |
| 605 | 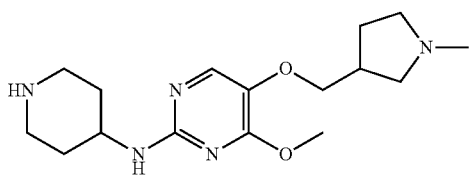 |
| 606 | 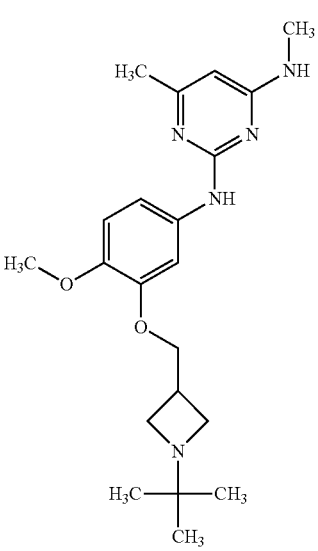 |
| 607 | 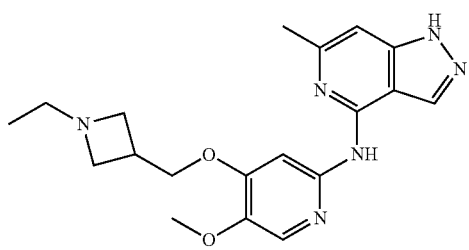 [SMILES: CCN1CC(COc2cc(Nc3nc(C)cc4[nH]ncc34)ncc2OC)C1] |
| 608 | 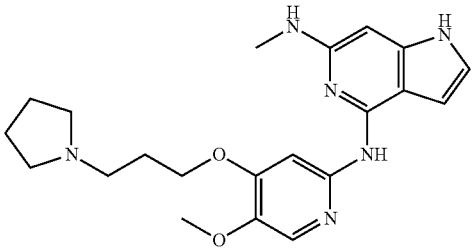 [SMILES: CNc1cc2[nH]ccc2c(Nc2cc(OCCCN3CCCC3)c(OC)cn2)n1] |

TABLE 3-continued

| Compound No. | Structure |
|---|---|
| 609 | 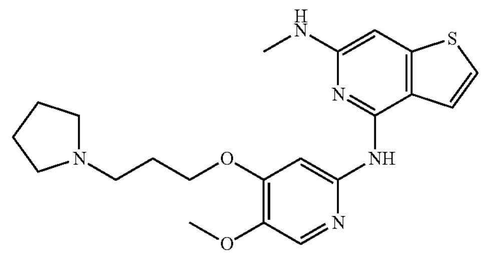 [SMILES: CNc1cc2sccc2c(Nc2cc(OCCCN3CCCC3)c(OC)cn2)n1] |
| 610 | 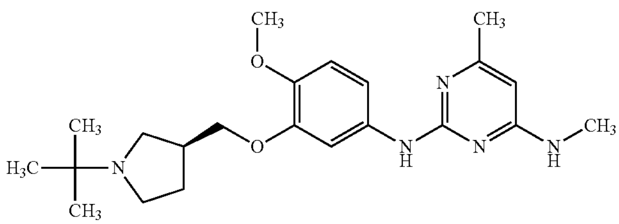 [SMILES: CNc1cc(C)nc(Nc2ccc(OC)c(OC[C@H]3CCN(C(C)(C)C)C3)c2)n1] |
| 611 | 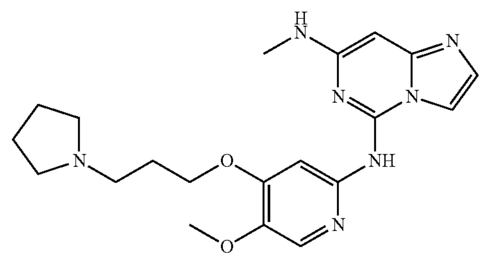 [SMILES: CNc1cc2nccn2c(Nc2cc(OCCCN3CCCC3)c(OC)cn2)n1] |
| 612 | 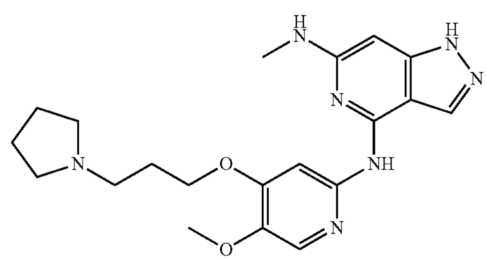 [SMILES: CNc1cc2[nH]ncc2c(Nc2cc(OCCCN3CCCC3)c(OC)cn2)n1] |
| 613 | 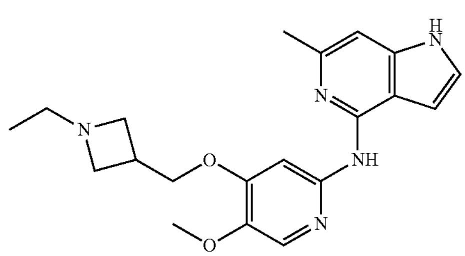 [SMILES: CCN1CC(COc2cc(Nc3nc(C)cc4[nH]ccc34)ncc2OC)C1] |
| 614 | 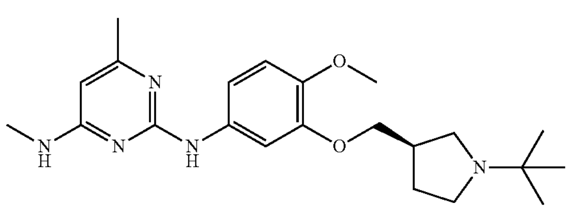 [SMILES: CNc1cc(C)nc(Nc2ccc(OC)c(OC[C@@H]3CCN(C(C)(C)C)C3)c2)n1] |

TABLE 3-continued

| Compound No. | Structure |
|---|---|
| 615 | 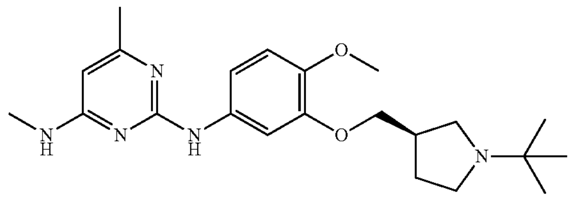 [SMILES: CNc1cc(C)nc(Nc2ccc(OC)c(OC[C@@H]3CCN(C(C)(C)C)C3)c2)n1] |
| 616 | 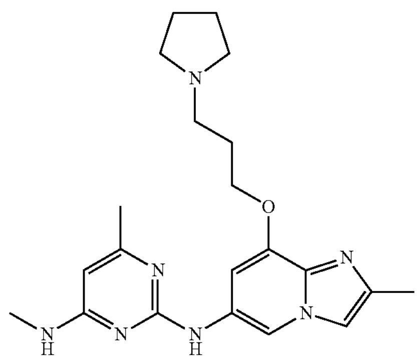 |
| 617 | 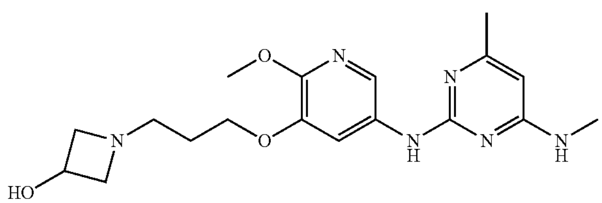 [SMILES: CNc1cc(C)nc(Nc2cnc(OC)c(OCCCN3CC(O)C3)c2)n1] |
| 618 | 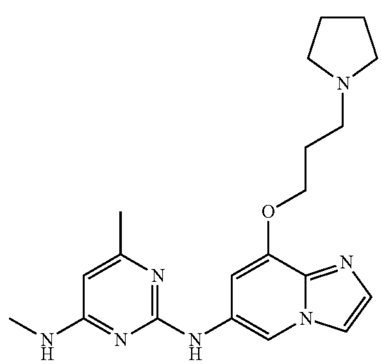 [SMILES: CNc1cc(C)nc(Nc2cc(OCCCN3CCCC3)c3nccn3c2)n1] |
| 619 | 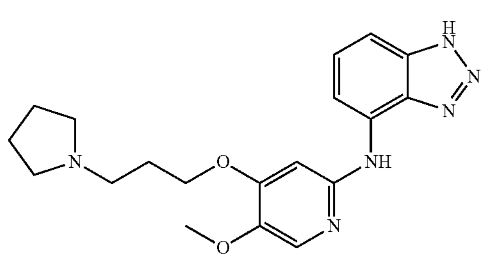 [SMILES: COc1cnc(Nc2cccc3[nH]nnc23)cc1OCCCN1CCCC1] |

TABLE 3-continued

| Compound No. | Structure |
|---|---|
| 620 | 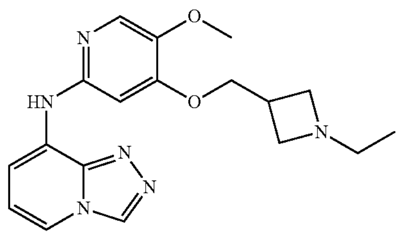 [SMILES: CCN1CC(COc2cc(Nc3cccn4cnnc34)ncc2OC)C1] |
| 621 | 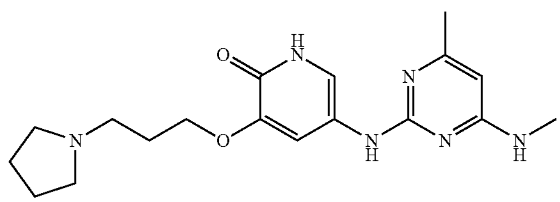 [SMILES: CNc1cc(C)nc(Nc2c[nH]c(=O)c(OCCCN3CCCC3)c2)n1] |
| 622 | 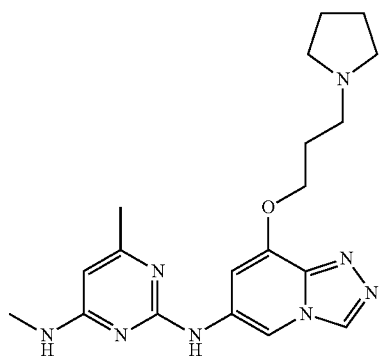 [SMILES: CNc1cc(C)nc(Nc2cc(OCCCN3CCCC3)c3nncn3c2)n1] |
| 623 | 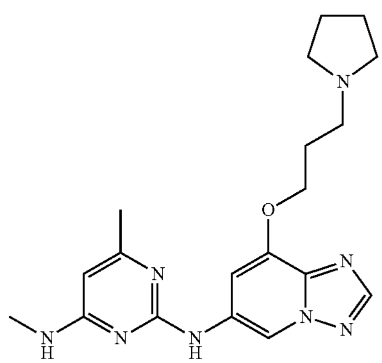 [SMILES: CNc1cc(C)nc(Nc2cc(OCCCN3CCCC3)c3ncnn3c2)n1] |
| 624 | 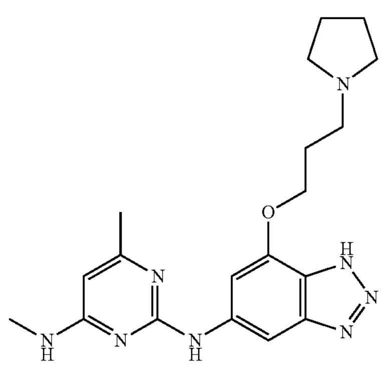 [SMILES: CNc1cc(C)nc(Nc2cc(OCCCN3CCCC3)c3[nH]nnc3c2)n1] |

TABLE 3-continued

| Compound No. | Structure |
|---|---|
| 625 | 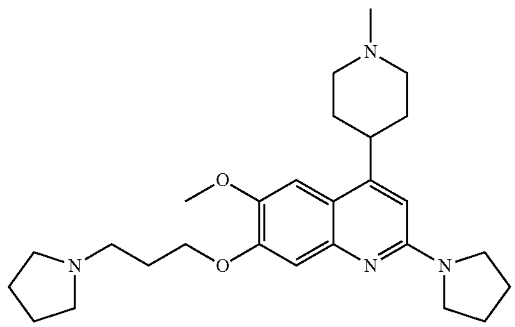 [SMILES: COc1cc2c(C3CCN(C)CC3)cc(N3CCCC3)nc2cc1OCCCN1CCCC1] |
| 626 | 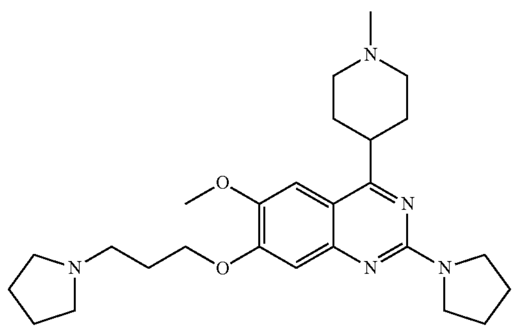 [SMILES: COc1cc2c(C3CCN(C)CC3)nc(N3CCCC3)nc2cc1OCCCN1CCCC1] |
| 627 | 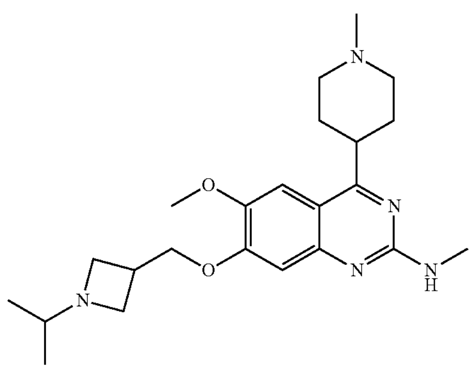 [SMILES: CNc1nc(C2CCN(C)CC2)c2cc(OC)c(OCC3CN(C(C)C)C3)cc2n1] |
| 628 | 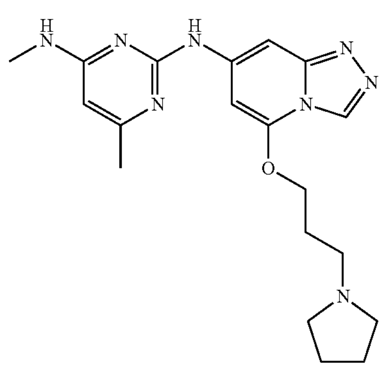 [SMILES: CNc1cc(C)nc(Nc2cc(OCCCN3CCCC3)n3cnnc3c2)n1] |

TABLE 3-continued

| Compound No. | Structure |
|---|---|
| 629 | 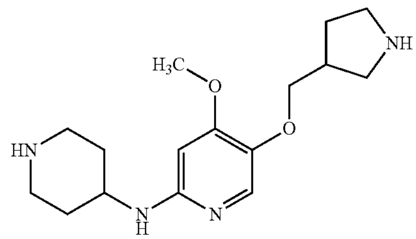 [SMILES: COc1cc(NC2CCNCC2)ncc1OCC1CCNC1] |
| 630 | 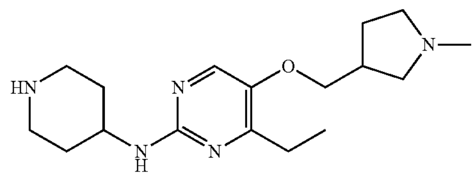 [SMILES: CCc1nc(NC2CCNCC2)ncc1OCC1CCN(C)C1] |
| 631 | 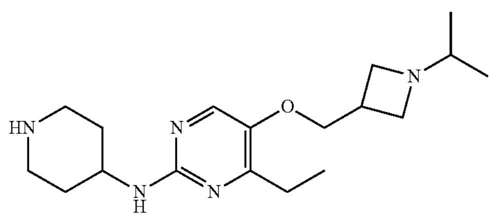 [SMILES: CCc1nc(NC2CCNCC2)ncc1OCC1CN(C(C)C)C1] |
| 632 | 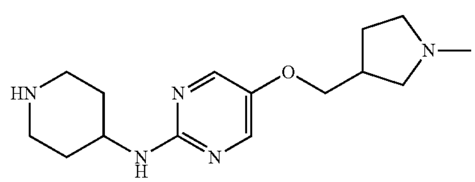 [SMILES: CN1CCC(COc2cnc(NC3CCNCC3)nc2)C1] |
| 633 | 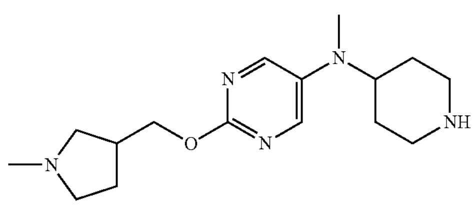 [SMILES: CN1CCC(COc2ncc(N(C)C3CCNCC3)cn2)C1] |
| 634 | 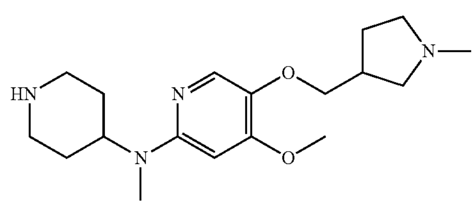 [SMILES: COc1cc(N(C)C2CCNCC2)ncc1OCC1CCN(C)C1] |
| 635 | 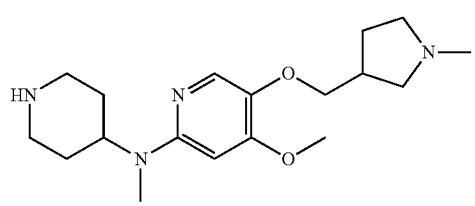 [SMILES: COc1cc(N(C)C2CCNCC2)ncc1OCC1CCN(C)C1] |

TABLE 3-continued

| Compound No. | Structure |
|---|---|
| 636 | 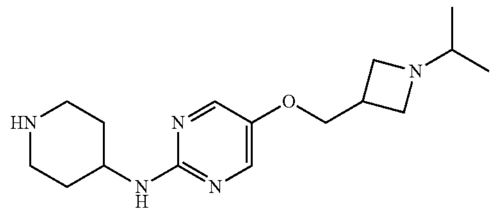 [SMILES: CC(C)N1CC(COc2cnc(NC3CCNCC3)nc2)C1] |
| 637 | 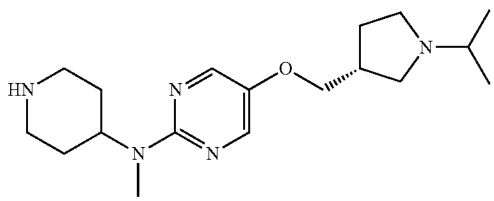 [SMILES: CC(C)N1CC[C@@H](COc2cnc(N(C)C3CCNCC3)nc2)C1] |
| 638 | 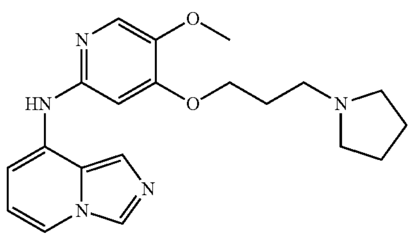 [SMILES: COc1cnc(Nc2cccn3cncc23)cc1OCCCN1CCCC1] |
| 639 | 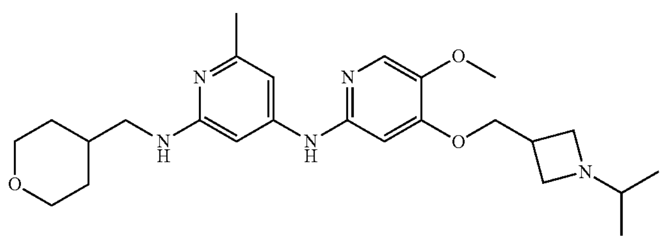 [SMILES: COc1cnc(Nc2cc(C)nc(NCC3CCOCC3)c2)cc1OCC1CN(C(C)C)C1] |
| 640 | 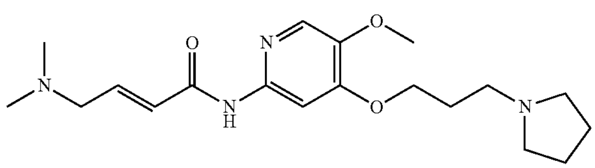 [SMILES: COc1cnc(NC(=O)/C=C/CN(C)C)cc1OCCCN1CCCC1] |
| 641 | 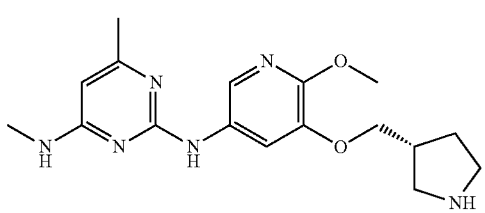 [SMILES: CNc1cc(C)nc(Nc2cnc(OC)c(OC[C@@H]3CCNC3)c2)n1] |
| 642 | 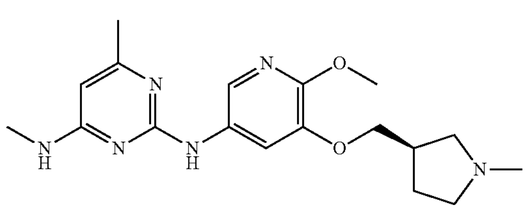 |

TABLE 3-continued
| Compound No. | Structure |
|---|---|
| 643 | 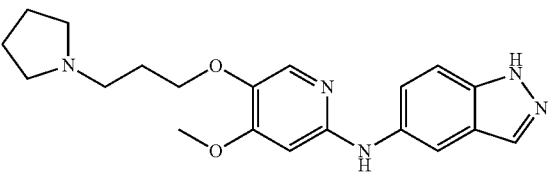 [SMILES: COc1cc(Nc2ccc3[nH]ncc3c2)ncc1OCCCN1CCCC1] |
| 644 | 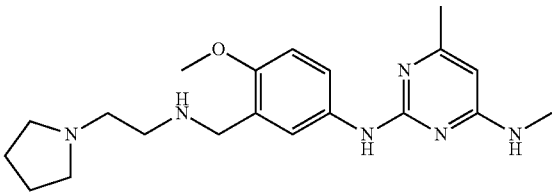 [SMILES: CNc1cc(C)nc(Nc2ccc(OC)c(CNCCN3CCCC3)c2)n1] |
| 645 | 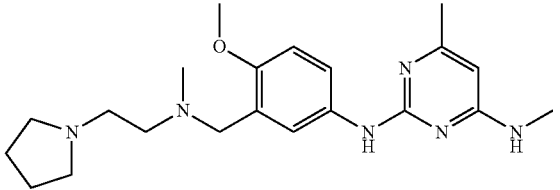 [SMILES: CNc1cc(C)nc(Nc2ccc(OC)c(CN(C)CCN3CCCC3)c2)n1] |
| 646 | 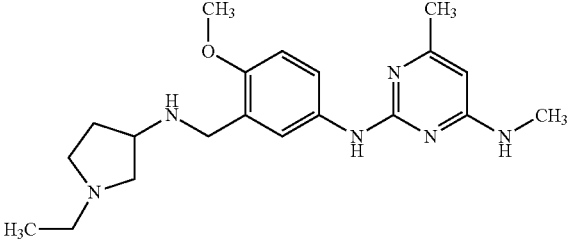 [SMILES: CCN1CCC(NCc2cc(Nc3nc(C)cc(NC)n3)ccc2OC)C1] |
| 647 | 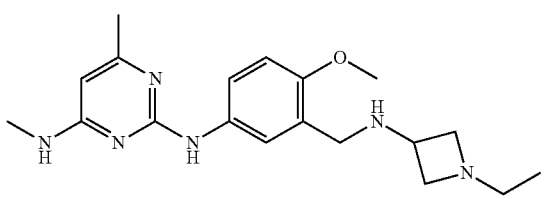 [SMILES: CCN1CC(NCc2cc(Nc3nc(C)cc(NC)n3)ccc2OC)C1] |
| 648 | 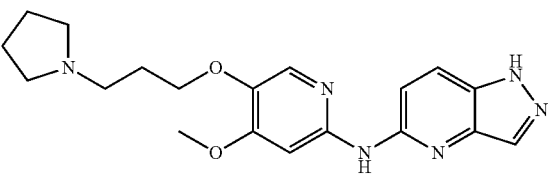 [SMILES: COc1cc(Nc2ccc3[nH]ncc3n2)ncc1OCCCN1CCCC1] |
| 649 | 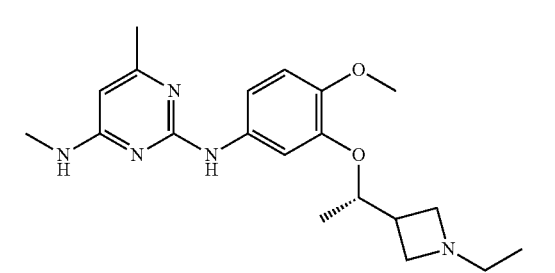 [SMILES: CCN1CC([C@H](C)Oc2cc(Nc3nc(C)cc(NC)n3)ccc2OC)C1] |

TABLE 3-continued

| Compound No. | Structure |
|---|---|
| 650 | 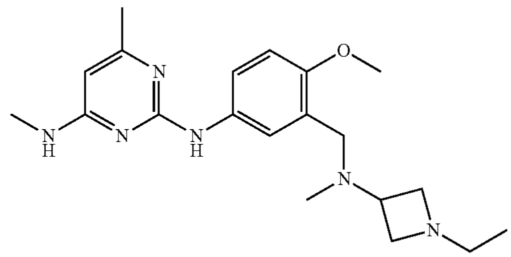 [SMILES: CCN1CC(N(C)Cc2cc(Nc3nc(C)cc(NC)n3)ccc2OC)C1] |
| 651 | 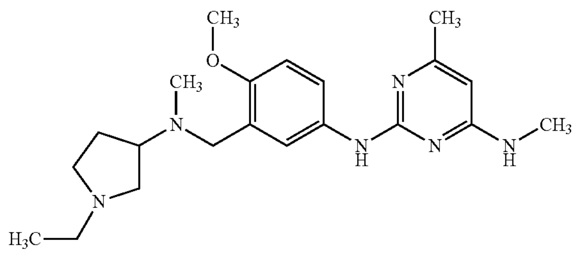 [SMILES: CCN1CCC(N(C)Cc2cc(Nc3nc(C)cc(NC)n3)ccc2OC)C1] |
| 652 | 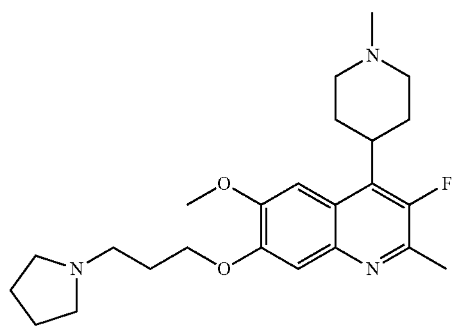 [SMILES: COc1cc2c(C3CCN(C)CC3)c(F)c(C)nc2cc1OCCCN1CCCC1] |
| 653 | 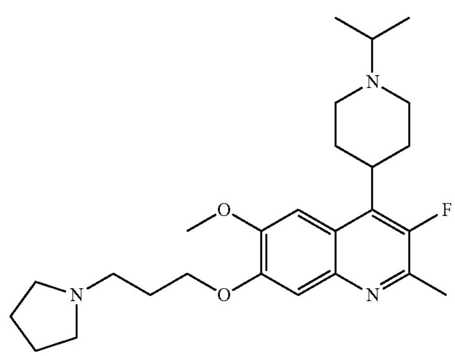 [SMILES: COc1cc2c(C3CCN(C(C)C)CC3)c(F)c(C)nc2cc1OCCCN1CCCC1] |
| 654 | 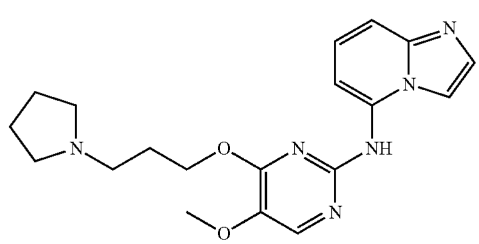 [SMILES: COc1cnc(Nc2cccc3nccn23)nc1OCCCN1CCCC1] |

TABLE 3-continued

| Compound No. | Structure |
|---|---|
| 655 | 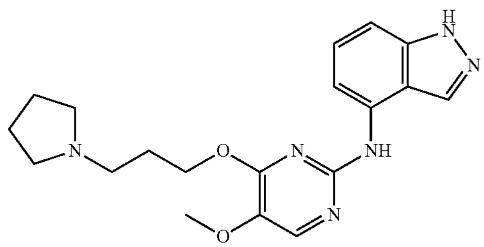 [SMILES: COc1cnc(Nc2cccc3[nH]ncc23)nc1OCCCN1CCCC1] |
| 656 | 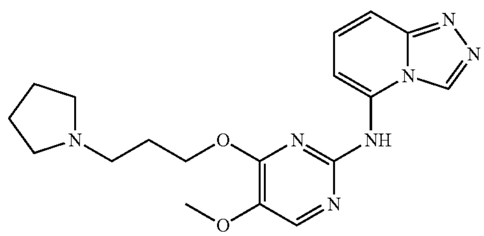 [SMILES: COc1cnc(Nc2cccc3nncn23)nc1OCCCN1CCCC1] |
| 657 | 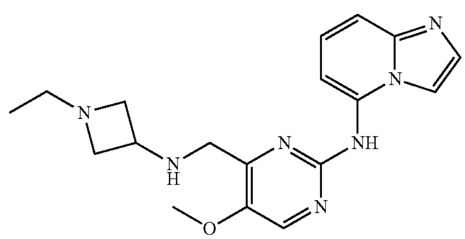 [SMILES: CCN1CC(NCc2nc(Nc3cccc4nccn34)ncc2OC)C1] |
| 658 | 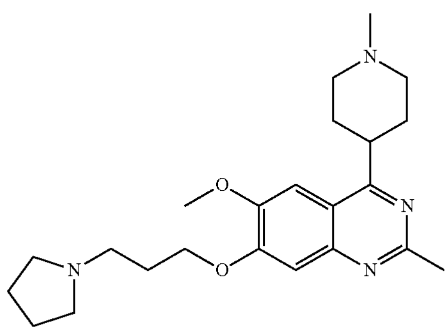 [SMILES: COc1cc2c(C3CCN(C)CC3)nc(C)nc2cc1OCCCN1CCCC1] |
| 659 | 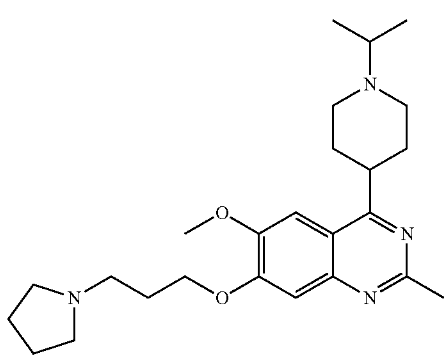 [SMILES: COc1cc2c(C3CCN(C(C)C)CC3)nc(C)nc2cc1OCCCN1CCCC1] |

TABLE 3-continued

| Compound No. | Structure |
|---|---|
| 660 | 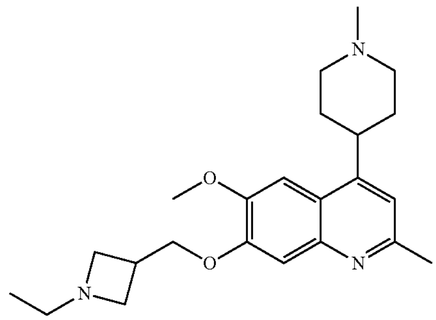 [SMILES: CCN1CC(COc2cc3nc(C)cc(C4CCN(C)CC4)c3cc2OC)C1] |
| 661 | 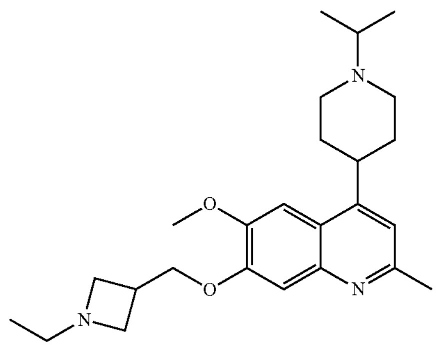 [SMILES: CCN1CC(COc2cc3nc(C)cc(C4CCN(C(C)C)CC4)c3cc2OC)C1] |
| 662 | 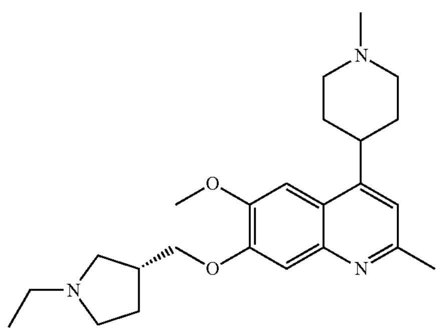 [SMILES: CCN1CC[C@@H](COc2cc3nc(C)cc(C4CCN(C)CC4)c3cc2OC)C1] |
| 663 | 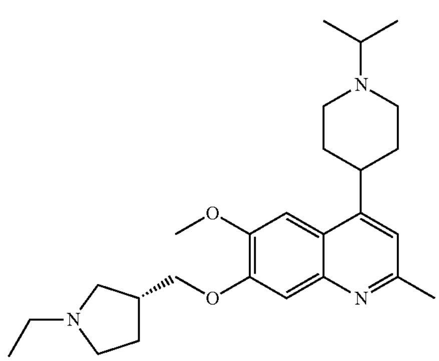 [SMILES: CCN1CC[C@@H](COc2cc3nc(C)cc(C4CCN(C(C)C)CC4)c3cc2OC)C1] |

TABLE 3-continued

| Compound No. | Structure |
|---|---|
| 664 | 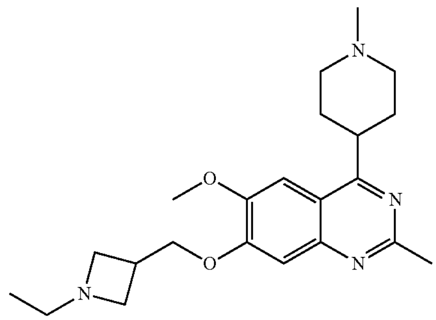 [SMILES: CCN1CC(COc2cc3nc(C)nc(C4CCN(C)CC4)c3cc2OC)C1] |
| 665 | 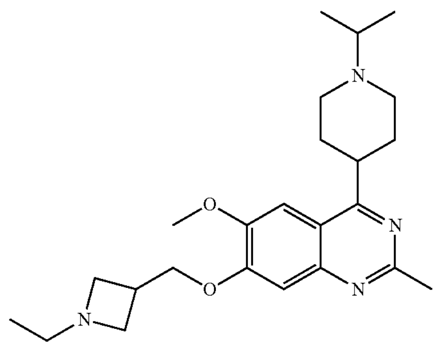 [SMILES: CCN1CC(COc2cc3nc(C)nc(C4CCN(C(C)C)CC4)c3cc2OC)C1] |
| 666 | 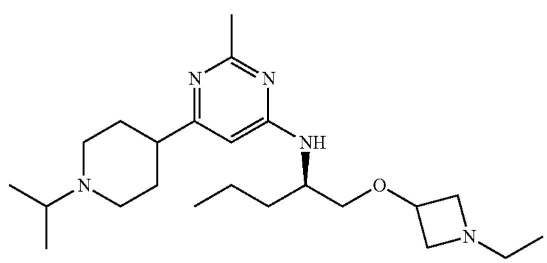 [SMILES: CCC[C@H](COC1CN(CC)C1)Nc1cc(C2CCN(C(C)C)CC2)nc(C)n1] |
| 667 | 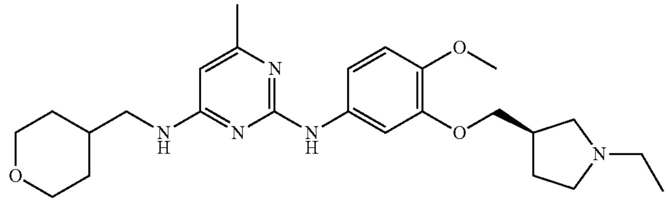 [SMILES: CCN1CC[C@@H](COc2cc(Nc3nc(C)cc(NCC4CCOCC4)n3)ccc2OC)C1] |
| 668 | 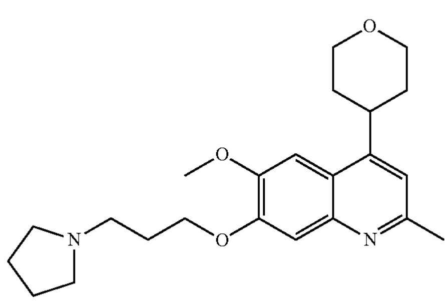 [SMILES: COc1cc2c(C3CCOCC3)cc(C)nc2cc1OCCCN1CCCC1] |

TABLE 3-continued
| Compound No. | Structure |
|---|---|
| 669 | 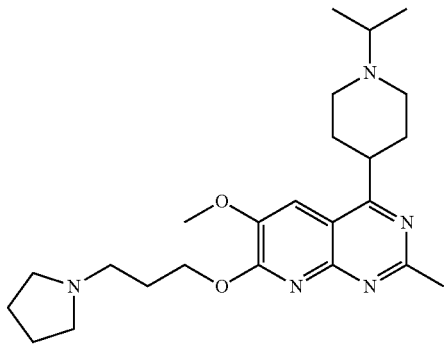 [SMILES: COc1cc2c(C3CCN(C(C)C)CC3)nc(C)nc2nc1OCCCN1CCCC1] |
| 670 | 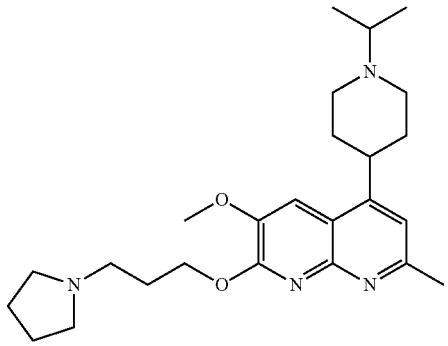 [SMILES: COc1cc2c(C3CCN(C(C)C)CC3)cc(C)nc2nc1OCCCN1CCCC1] |
| 671 | 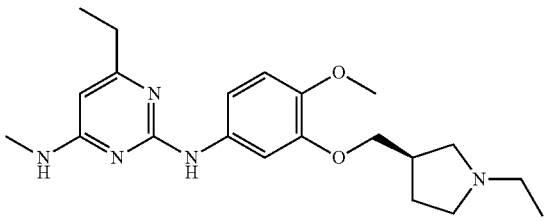 [SMILES: CCc1cc(NC)nc(Nc2ccc(OC)c(OC[C@@H]3CCN(CC)C3)c2)n1] |
| 672 | 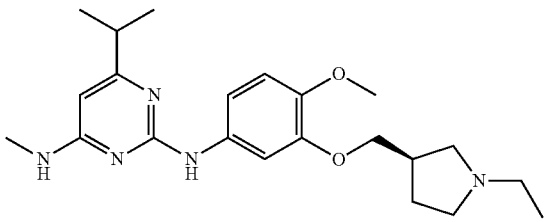 [SMILES: CCN1CC[C@@H](COc2cc(Nc3nc(NC)cc(C(C)C)n3)ccc2OC)C1] |
| 673 | 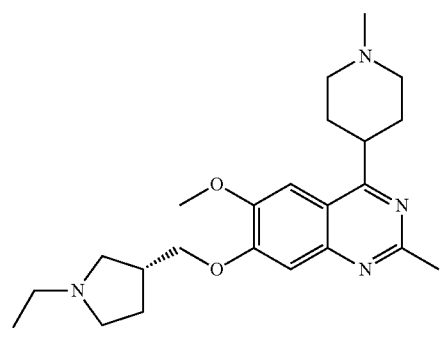 [SMILES: CCN1CC[C@@H](COc2cc3nc(C)nc(C4CCN(C)CC4)c3cc2OC)C1] |

TABLE 3-continued
| Compound No. | Structure |
|---|---|
| 674 | 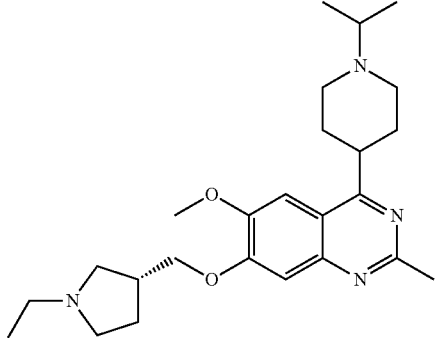 [SMILES: CCN1CC[C@@H](COc2cc3nc(C)nc(C4CCN(C(C)C)CC4)c3cc2OC)C1] |
| 675 | 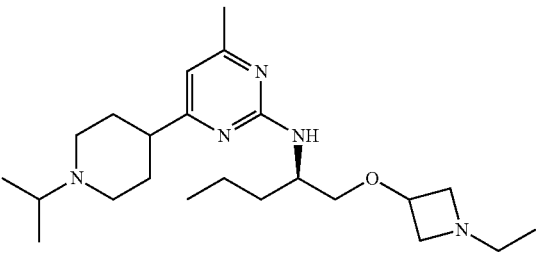 [SMILES: CCC[C@H](COC1CN(CC)C1)Nc1nc(C)cc(C2CCN(C(C)C)CC2)n1] |
| 676 | 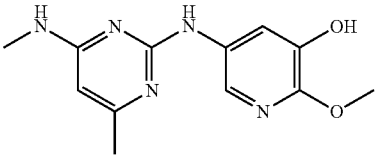 |
| 677 | 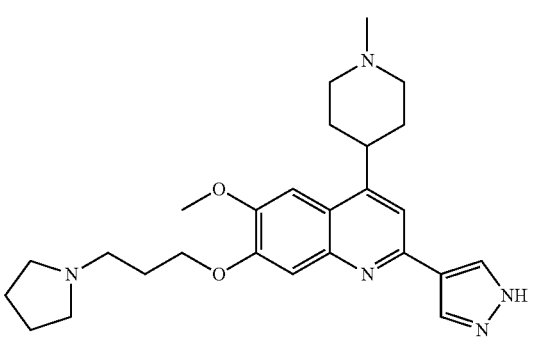 [SMILES: COc1cc2c(C3CCN(C)CC3)cc(-c3cn[nH]c3)nc2cc1OCCCN1CCCC1] |
| 678 | 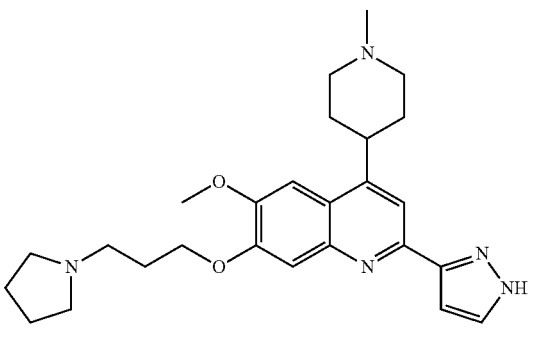 [SMILES: COc1cc2c(C3CCN(C)CC3)cc(-c3cc[nH]n3)nc2cc1OCCCN1CCCC1] |

TABLE 3-continued

| Compound No. | Structure |
|---|---|
| 679 | 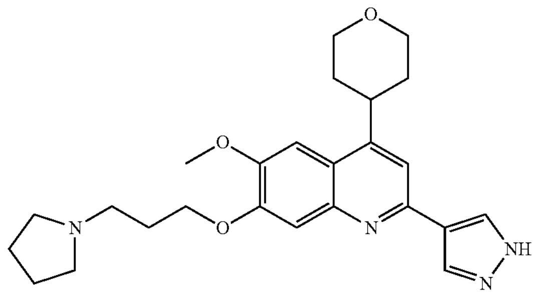 [SMILES: COc1cc2c(C3CCOCC3)cc(-c3cn[nH]c3)nc2cc1OCCCN1CCCC1] |
| 680 | 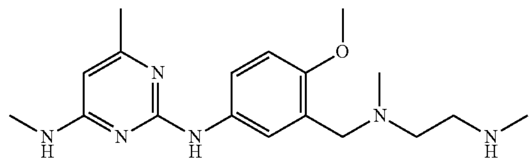 |
| 681 | 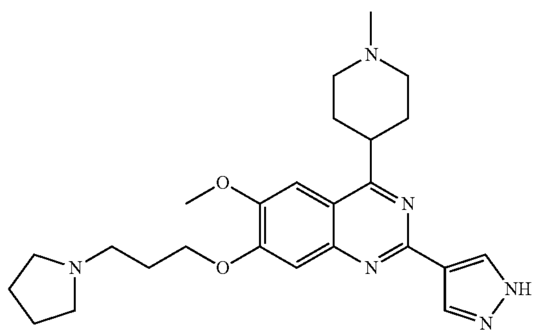 [SMILES: COc1cc2c(C3CCN(C)CC3)nc(-c3cn[nH]c3)nc2cc1OCCCN1CCCC1] |
| 682 | 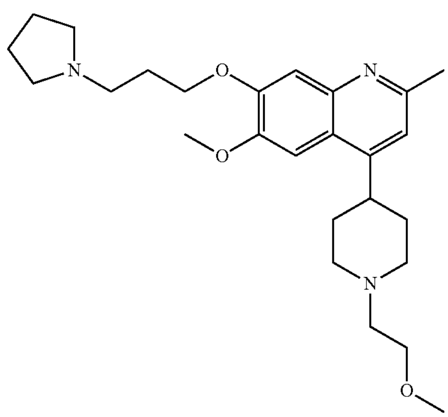 [SMILES: COCCN1CCC(c2cc(C)nc3cc(OCCCN4CCCC4)c(OC)cc23)CC1] |
| 683 | 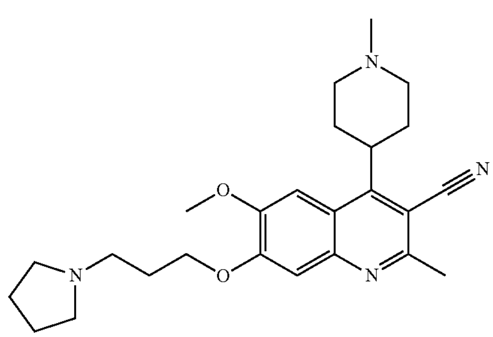 [SMILES: COc1cc2c(C3CCN(C)CC3)c(C#N)c(C)nc2cc1OCCCN1CCCC1] |

TABLE 3-continued
| Compound No. | Structure |
|---|---|
| 684 | 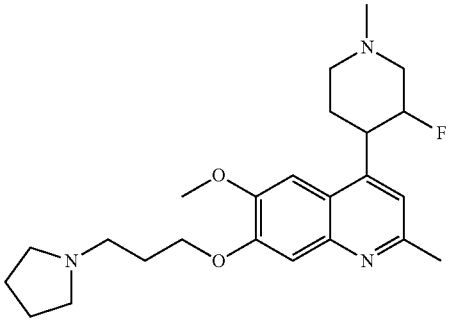 [SMILES: COc1cc2c(C3CCN(C)CC3F)cc(C)nc2cc1OCCCN1CCCC1] |
| 685 | 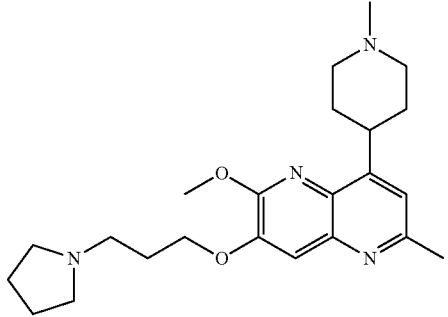 [SMILES: COc1nc2c(C3CCN(C)CC3)cc(C)nc2cc1OCCCN1CCCC1] |
| 686 | 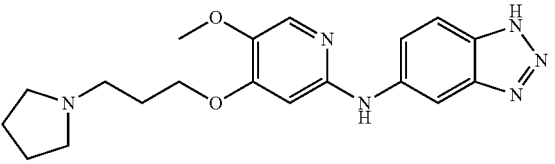 [SMILES: COc1cnc(Nc2ccc3[nH]nnc3c2)cc1OCCCN1CCCC1] |
| 687 | 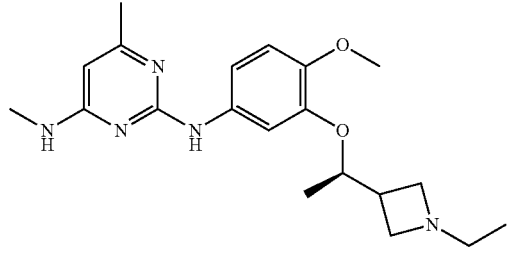 [SMILES: CCN1CC([C@@H](C)Oc2cc(Nc3nc(C)cc(NC)n3)ccc2OC)C1] |
| 688 | 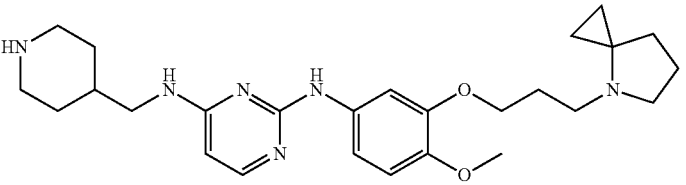 [SMILES: COc1ccc(Nc2nccc(NCC3CCNCC3)n2)cc1OCCCN1CCCC12CC2] |
| 689 | 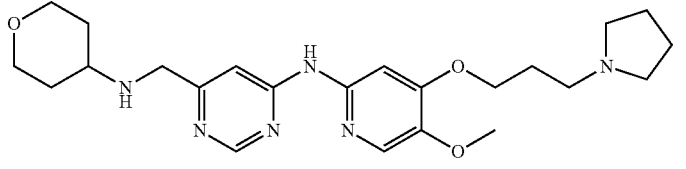 [SMILES: COc1cnc(Nc2cc(CNC3CCOCC3)ncn2)cc1OCCCN1CCCC1] |

TABLE 3-continued
| Compound No. | Structure |
|---|---|
| 690 | 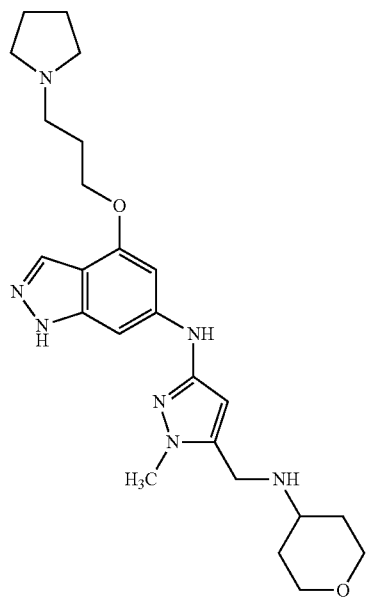 [SMILES: Cn1nc(Nc2cc(OCCCN3CCCC3)c3cn[nH]c3c2)cc1CNC1CCOCC1] |
| 691 | 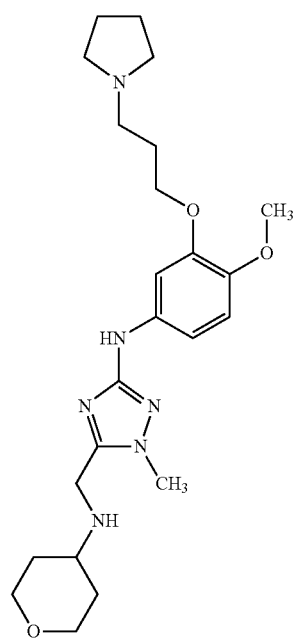 [SMILES: COc1ccc(Nc2nc(CNC3CCOCC3)n(C)n2)cc1OCCCN1CCCC1] |

TABLE 3-continued
| Compound No. | Structure |
|---|---|
| 692 | 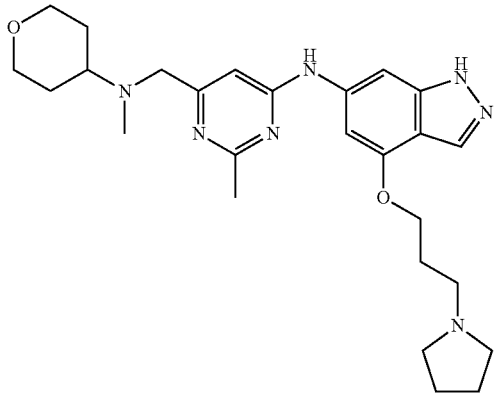 [SMILES: Cc1nc(CN(C)C2CCOCC2)cc(Nc2cc(OCCCN3CCCC3)c3cn[nH]c3c2)n1] |
| 693 | 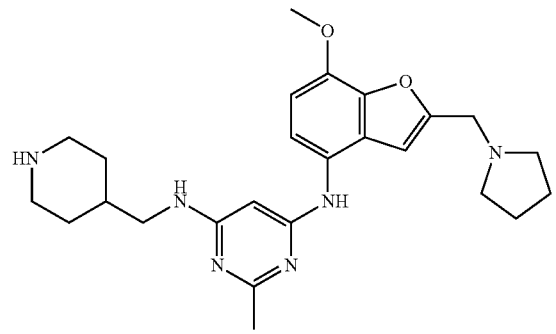 [SMILES: COc1ccc(Nc2cc(NCC3CCNCC3)nc(C)n2)c2cc(CN3CCCC3)oc12] |
| 694 | 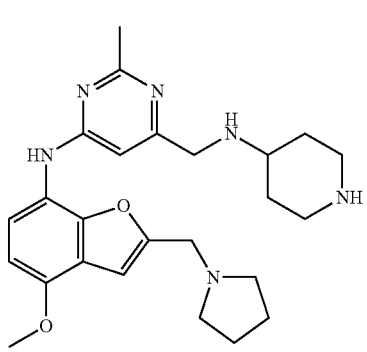 [SMILES: COc1ccc(Nc2cc(CNC3CCNCC3)nc(C)n2)c2oc(CN3CCCC3)cc12] |
| 695 | 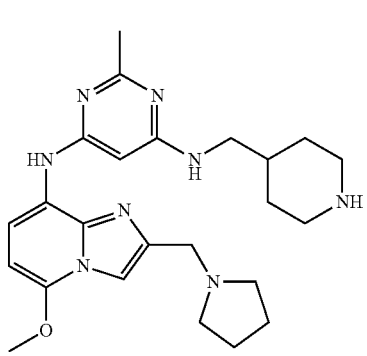 [SMILES: COc1ccc(Nc2cc(NCC3CCNCC3)nc(C)n2)c2nc(CN3CCCC3)cn12] |

TABLE 3-continued
| Compound No. | Structure |
|---|---|
| 696 | 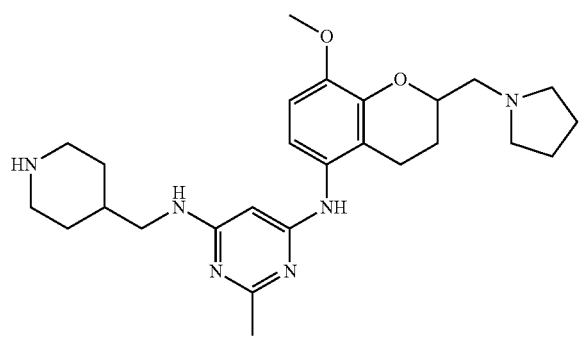 [SMILES: COc1ccc(Nc2cc(NCC3CCNCC3)nc(C)n2)c2c1OC(CN1CCCC1)CC2] |
| 697 | 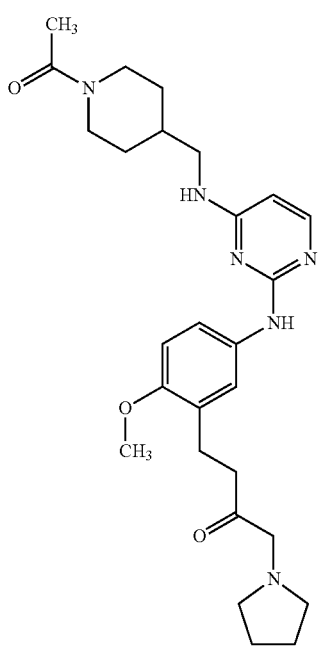 [SMILES: COc1ccc(Nc2nccc(NCC3CCN(C(C)=O)CC3)n2)cc1CCC(=O)CN1CCCC1] |
| 698 | 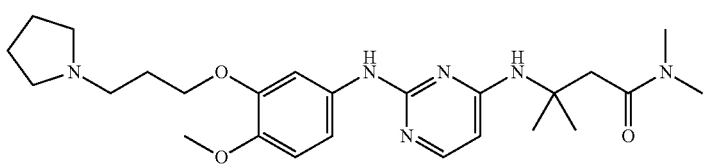 [SMILES: COc1ccc(Nc2nccc(NC(C)(C)CC(=O)N(C)C)n2)cc1OCCCN1CCCC1] |
| 699 | 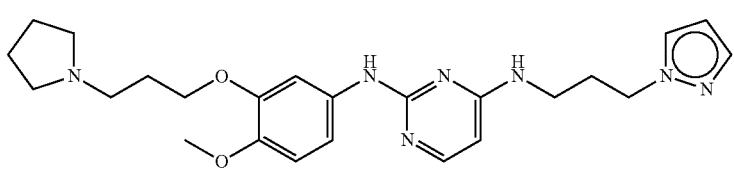 |

TABLE 3-continued
| Compound No. | Structure |
|---|---|
| 700 | 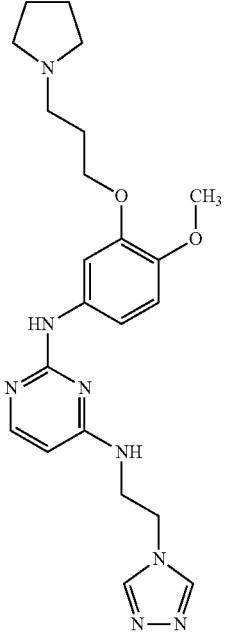 [SMILES: COc1ccc(Nc2nccc(NCCn3cnnc3)n2)cc1OCCCN1CCCC1] |
| 701 | 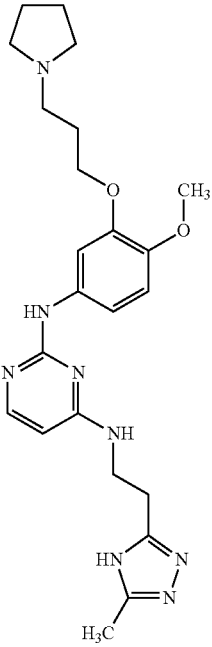 [SMILES: COc1ccc(Nc2nccc(NCCc3nnc(C)[nH]3)n2)cc1OCCCN1CCCC1] |
| 702 | 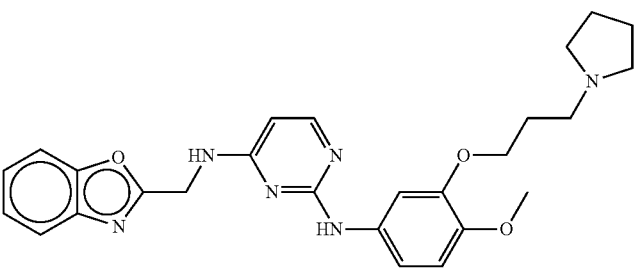 |

TABLE 3-continued

| Compound No. | Structure |
|---|---|
| 703 | 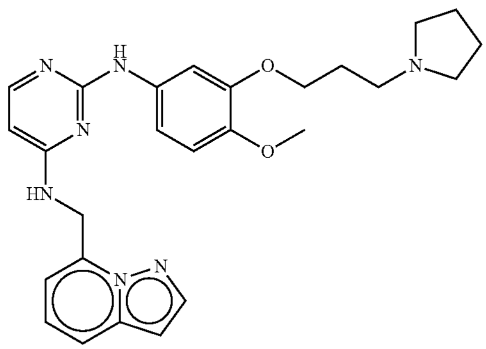 |
| 704 | 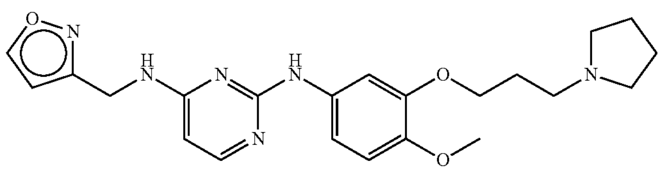 |
| 705 | 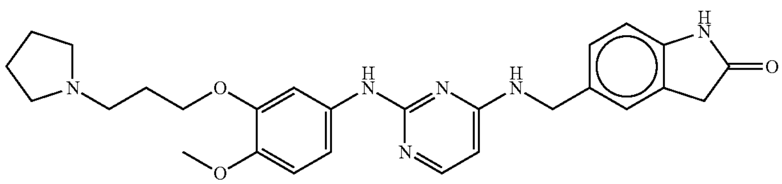 |
| 706 | 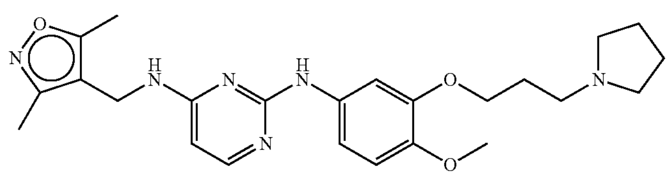 |
| 707 | 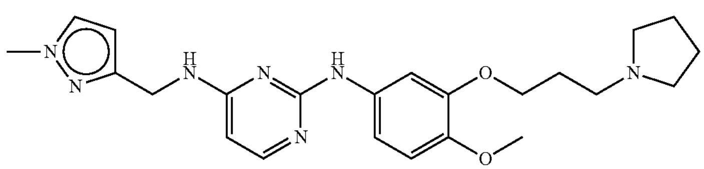 |
| 708 | 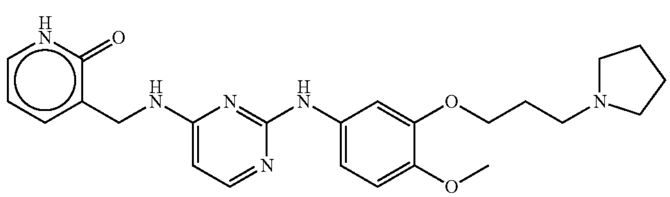 |
| 709 | 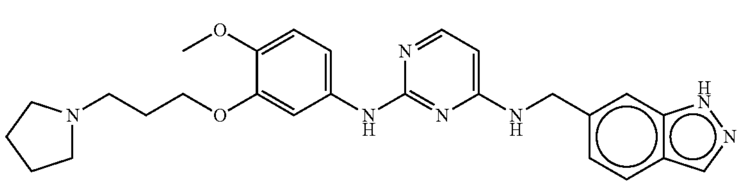 |

TABLE 3-continued

| Compound No. | Structure |
|---|---|
| 710 | 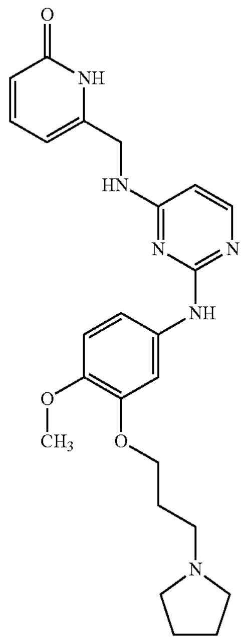 [SMILES: COc1ccc(Nc2nccc(NCc3cccc(=O)[nH]3)n2)cc1OCCCN1CCCC1] |
| 711 | 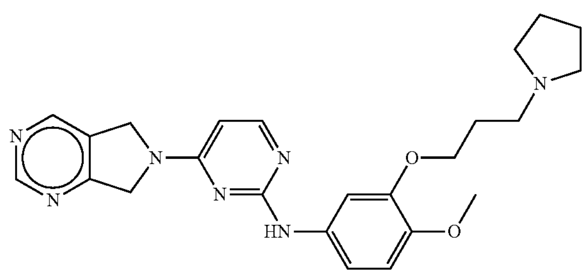 |
| 712 | 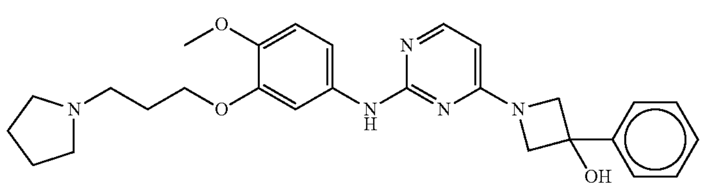 |
| 713 | 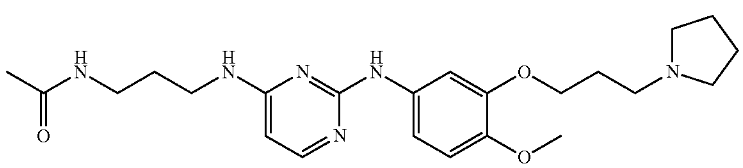 [SMILES: COc1ccc(Nc2nccc(NCCCNC(C)=O)n2)cc1OCCCN1CCCC1] |
| 714 | 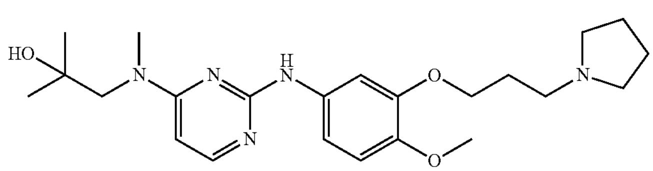 [SMILES: COc1ccc(Nc2nccc(N(C)CC(C)(C)O)n2)cc1OCCCN1CCCC1] |

TABLE 3-continued
| Compound No. | Structure |
|---|---|
| 715 | 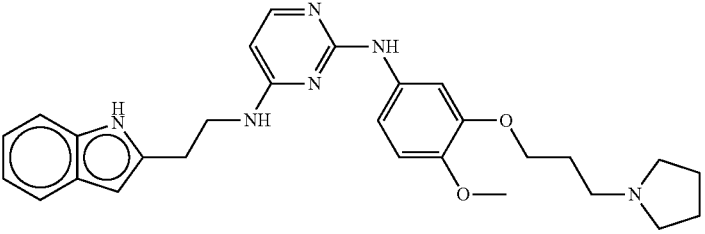 |
| 716 | 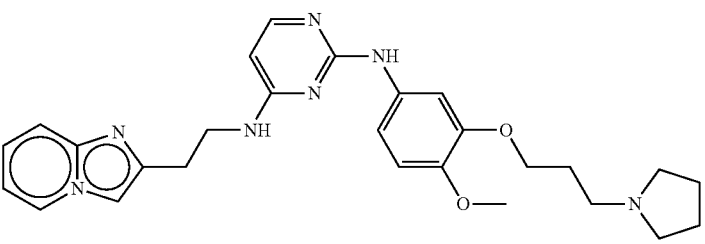 |
| 717 | 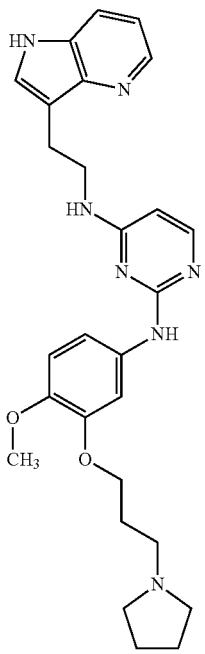 [SMILES: COc1ccc(Nc2nccc(NCCc3c[nH]c4cccnc34)n2)cc1OCCCN1CCCC1] |

TABLE 3-continued
| Compound No. | Structure |
|---|---|
| 718 | 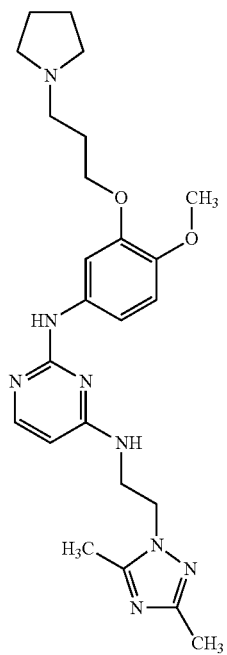 [SMILES: COc1ccc(Nc2nccc(NCCn3nc(C)nc3C)n2)cc1OCCCN1CCCC1] |
| 719 | 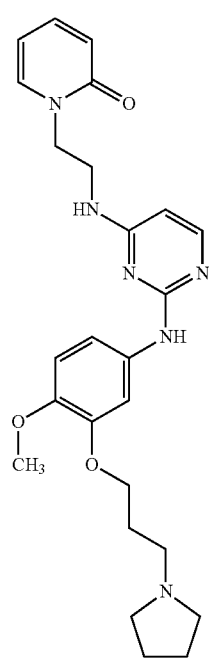 |

TABLE 3-continued
| Compound No. | Structure |
|---|---|
| 720 | 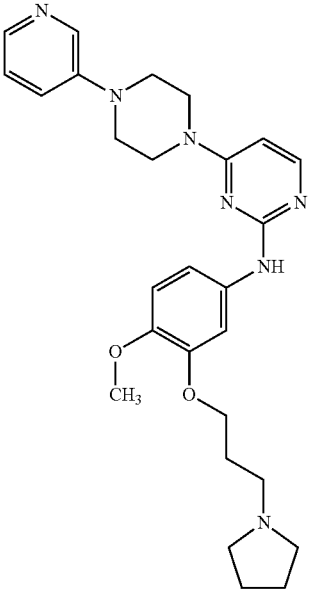 [SMILES: COc1ccc(Nc2nccc(N3CCN(c4cccnc4)CC3)n2)cc1OCCCN1CCCC1] |
| 721 | 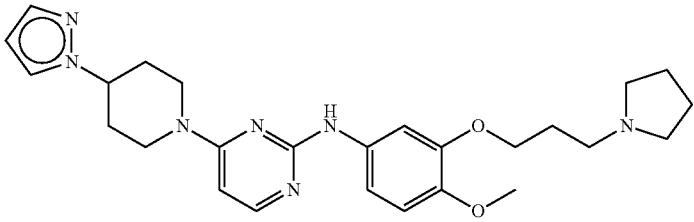 |
| 722 | 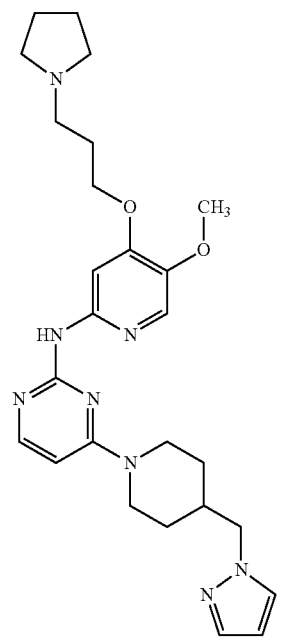 [SMILES: COc1cnc(Nc2nccc(N3CCC(Cn4cccn4)CC3)n2)cc1OCCCN1CCCC1] |

TABLE 3-continued

| Compound No. | Structure |
|---|---|
| 723 | 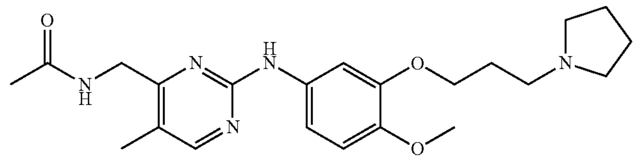 [SMILES: COc1ccc(Nc2ncc(C)c(CNC(C)=O)n2)cc1OCCCN1CCCC1] |
| 724 | 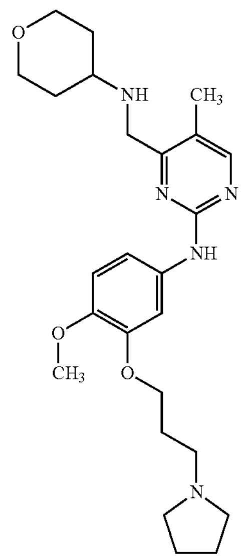 [SMILES: COc1ccc(Nc2ncc(C)c(CNC3CCOCC3)n2)cc1OCCCN1CCCC1] |
| 725 | 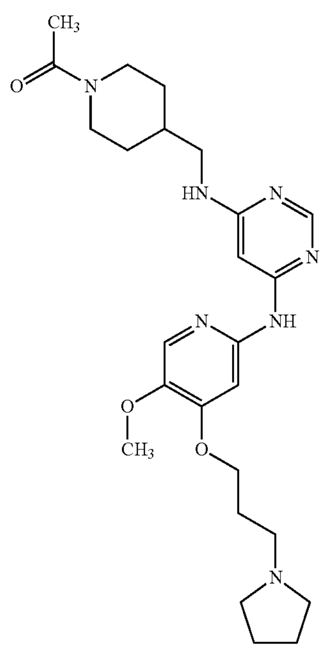 [SMILES: COc1cnc(Nc2cc(NCC3CCN(C(C)=O)CC3)ncn2)cc1OCCCN1CCCC1] |

TABLE 3-continued
| Compound No. | Structure |
|---|---|
| 726 | 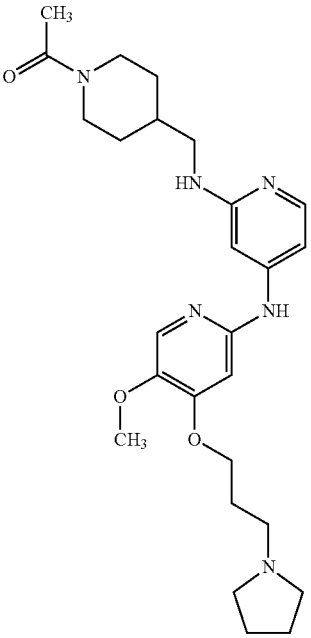 [SMILES: COc1cnc(Nc2ccnc(NCC3CCN(C(C)=O)CC3)c2)cc1OCCCN1CCCC1] |
| 727 | 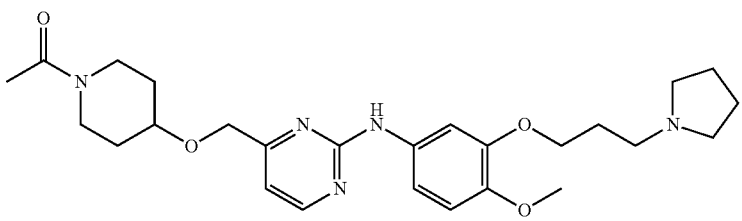 [SMILES: COc1ccc(Nc2nccc(COC3CCN(C(C)=O)CC3)n2)cc1OCCCN1CCCC1] |
| 728 | 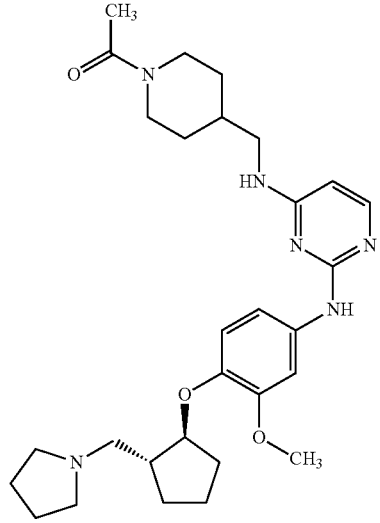 [SMILES: COc1cc(Nc2nccc(NCC3CCN(C(C)=O)CC3)n2)ccc1O[C@H]1CCC[C@@H]1CN1CCCC1] |

TABLE 3-continued

| Compound No. | Structure |
|---|---|
| 729 | 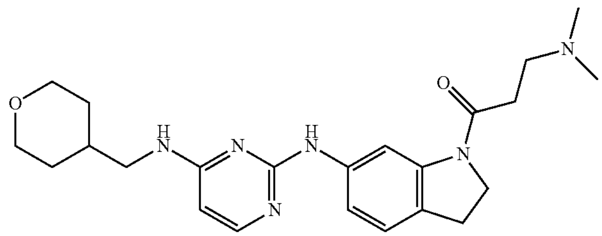 [SMILES: CN(C)CCC(=O)N1CCc2ccc(Nc3nccc(NCC4CCOCC4)n3)cc21] |
| 730 | 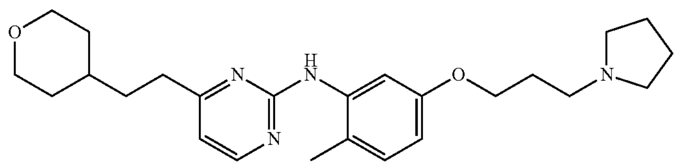 [SMILES: Cc1ccc(OCCCN2CCCC2)cc1Nc1nccc(CCC2CCOCC2)n1] |
| 731 | 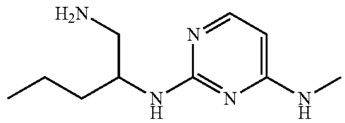 |
| 732 | 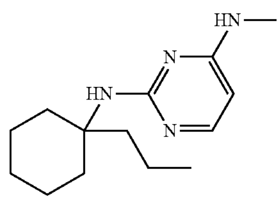 [SMILES: CCCC1(Nc2nccc(NC)n2)CCCCC1] |
| 733 | 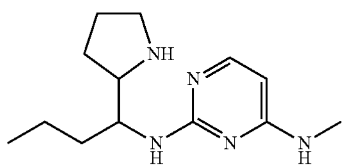 [SMILES: CCCC(Nc1nccc(NC)n1)C1CCCN1] |
| 734 | 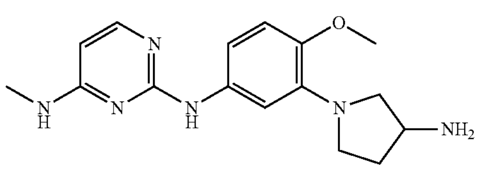 [SMILES: CNc1ccnc(Nc2ccc(OC)c(N3CCC(N)C3)c2)n1] |
| 735 | 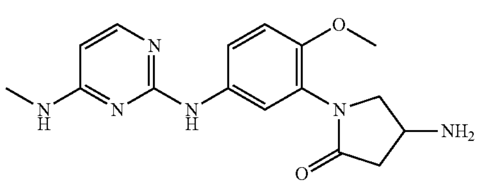 [SMILES: CNc1ccnc(Nc2ccc(OC)c(N3CC(N)CC3=O)c2)n1] |
| 736 | 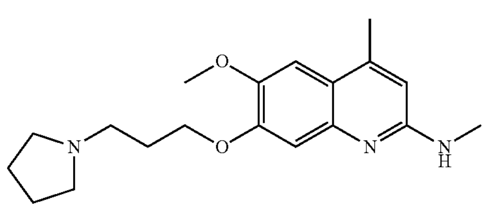 [SMILES: CNc1cc(C)c2cc(OC)c(OCCCN3CCCC3)cc2n1] |

TABLE 3-continued

| Compound No. | Structure |
|---|---|
| 737 | 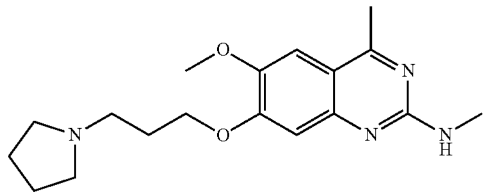 [SMILES: CNc1nc(C)c2cc(OC)c(OCCCN3CCCC3)cc2n1] |
| 738 | 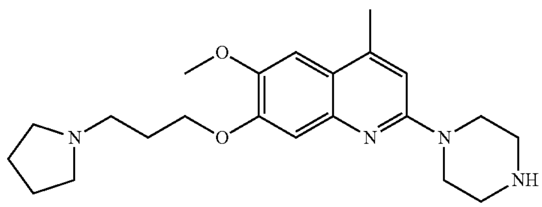 [SMILES: COc1cc2c(C)cc(N3CCNCC3)nc2cc1OCCCN1CCCC1] |
| 739 | 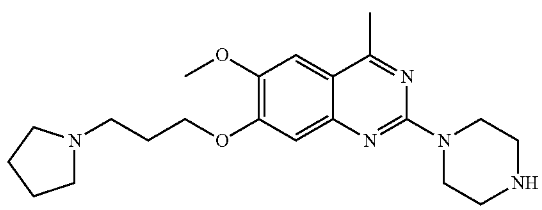 [SMILES: COc1cc2c(C)nc(N3CCNCC3)nc2cc1OCCCN1CCCC1] |
| 740 | 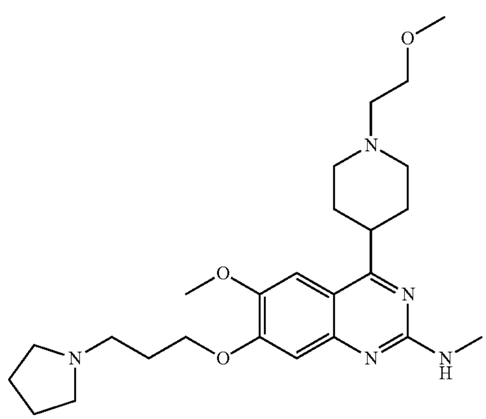 [SMILES: CNc1nc(C2CCN(CCOC)CC2)c2cc(OC)c(OCCCN3CCCC3)cc2n1] |
| 741 | 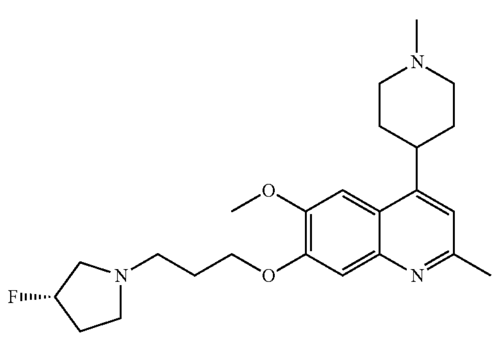 [SMILES: COc1cc2c(C3CCN(C)CC3)cc(C)nc2cc1OCCCN1CC[C@H](F)C1] |

TABLE 3-continued
| Compound No. | Structure |
|---|---|
| 742 | 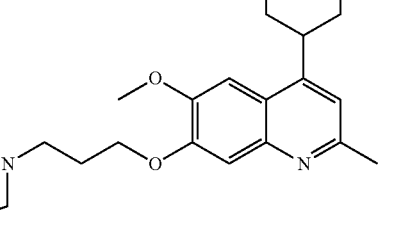 |
| 743 | 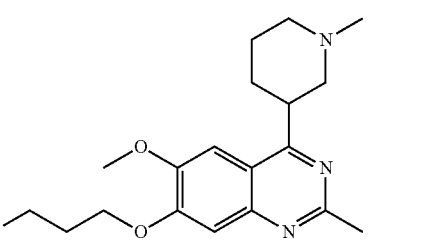 |
| 744 | 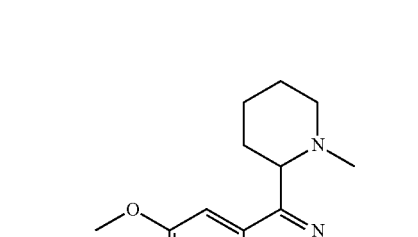 |
| 745 | 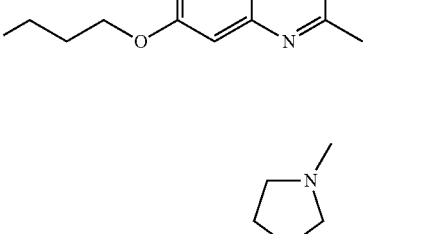 |
| 746 | 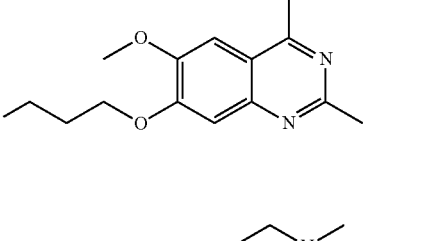 |

TABLE 3-continued

| Compound No. | Structure |
|---|---|
| 747 | 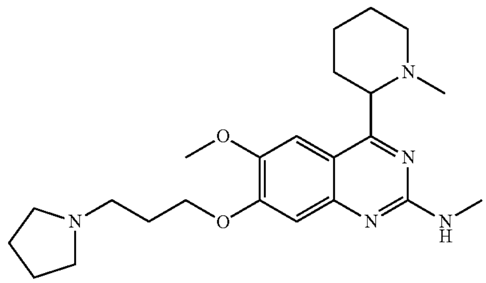 [SMILES: CNc1nc(C2CCCCN2C)c2cc(OC)c(OCCCN3CCCC3)cc2n1] |
| 748 | 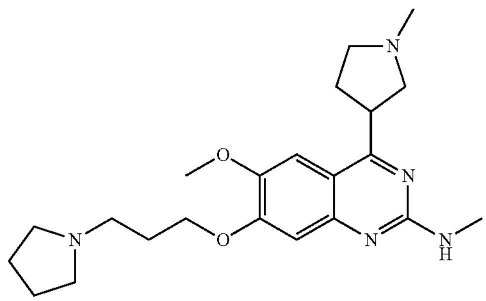 [SMILES: CNc1nc(C2CCN(C)C2)c2cc(OC)c(OCCCN3CCCC3)cc2n1] |
| 749 | 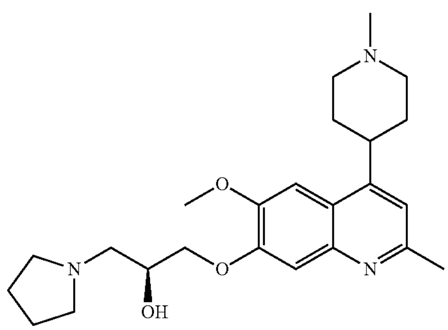 [SMILES: COc1cc2c(C3CCN(C)CC3)cc(C)nc2cc1OC[C@@H](O)CN1CCCC1] |
| 750 | 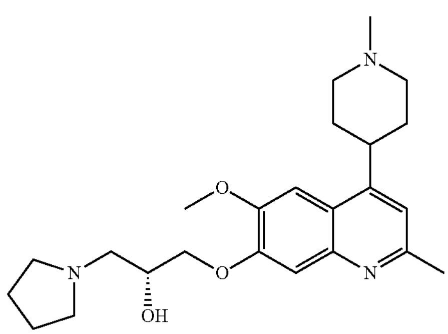 [SMILES: COc1cc2c(C3CCN(C)CC3)cc(C)nc2cc1OC[C@H](O)CN1CCCC1] |

TABLE 3-continued
| Compound No. | Structure |
|---|---|
| 751 | 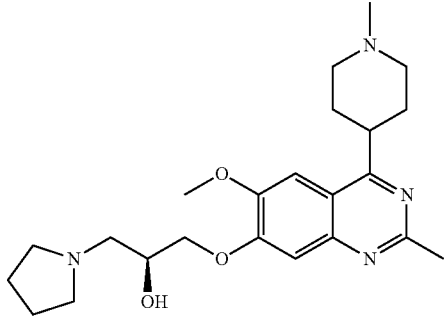 [SMILES: COc1cc2c(C3CCN(C)CC3)nc(C)nc2cc1OC[C@@H](O)CN1CCCC1] |
| 752 | 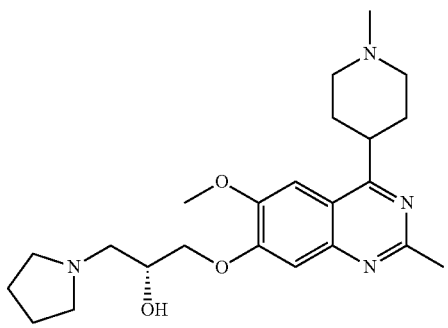 [SMILES: COc1cc2c(C3CCN(C)CC3)nc(C)nc2cc1OC[C@H](O)CN1CCCC1] |
| 753 | 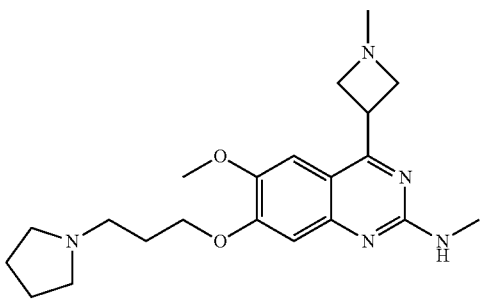 [SMILES: CNc1nc(C2CN(C)C2)c2cc(OC)c(OCCCN3CCCC3)cc2n1] |
| 754 | 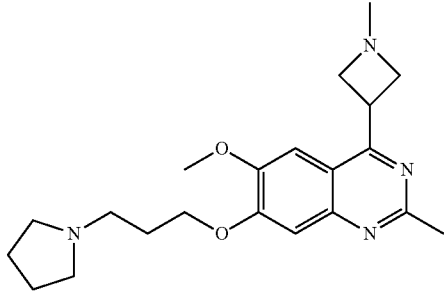 [SMILES: COc1cc2c(C3CN(C)C3)nc(C)nc2cc1OCCCN1CCCC1] |

TABLE 3-continued

| Compound No. | Structure |
|---|---|
| 755 | 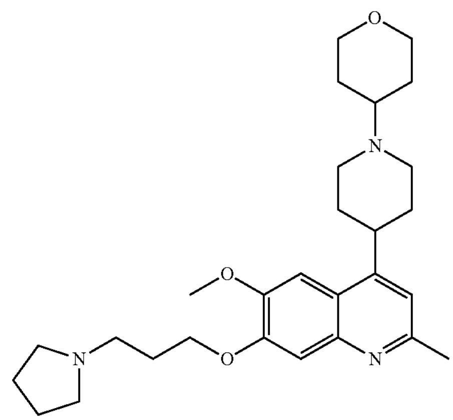 [SMILES: COc1cc2c(C3CCN(C4CCOCC4)CC3)cc(C)nc2cc1OCCCN1CCCC1] |
| 756 | 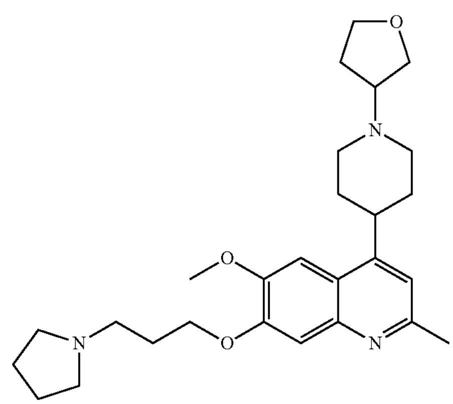 [SMILES: COc1cc2c(C3CCN(C4CCOC4)CC3)cc(C)nc2cc1OCCCN1CCCC1] |
| 757 | 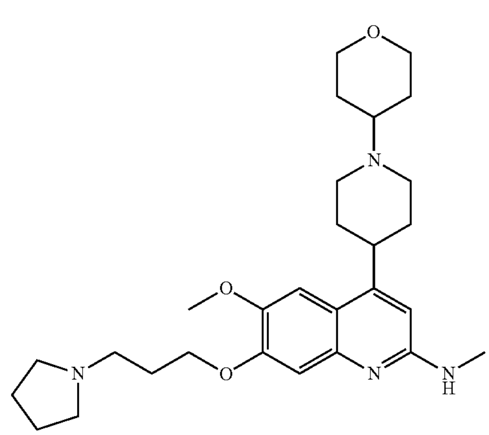 [SMILES: CNc1cc(C2CCN(C3CCOCC3)CC2)c2cc(OC)c(OCCCN3CCCC3)cc2n1] |

TABLE 3-continued

| Compound No. | Structure |
|---|---|
| 758 | (structure) |
| 759 | (structure) |
| 760 | (structure) |
| 761 | (structure) |

TABLE 3-continued

| Compound No. | Structure |
|---|---|
| 762 | 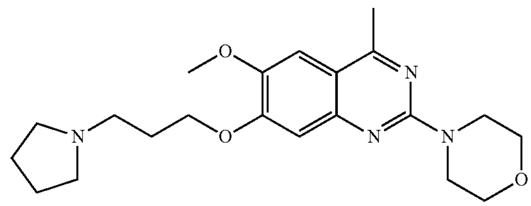 [SMILES: COc1cc2c(C)nc(N3CCOCC3)nc2cc1OCCCN1CCCC1] |
| 763 | 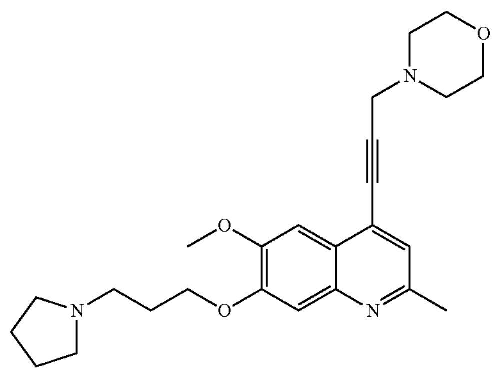 [SMILES: COc1cc2c(C#CCN3CCOCC3)cc(C)nc2cc1OCCCN1CCCC1] |
| 764 | 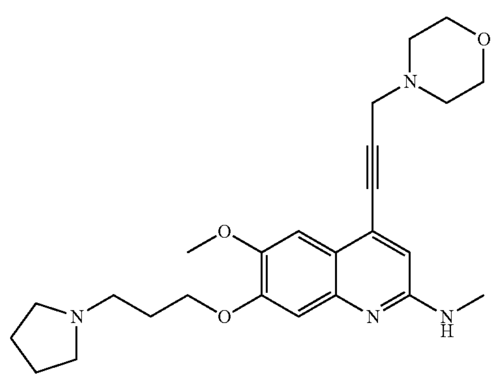 [SMILES: CNc1cc(C#CCN2CCOCC2)c2cc(OC)c(OCCCN3CCCC3)cc2n1] |
| 765 | 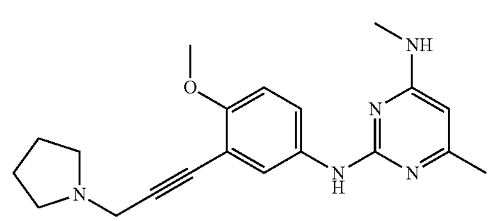 [SMILES: CNc1cc(C)nc(Nc2ccc(OC)c(C#CCN3CCCC3)c2)n1] |

The compounds of Table 3 are the compounds found in U.S. Application No. 62/402,997, the entire contents of which are incorporated herein by reference.

TABLE 4

| Compound No. | Structure |
| --- | --- |
| A1 | 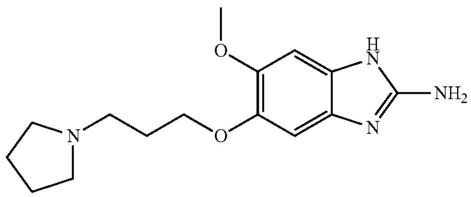 [SMILES: COc1cc2[nH]c(N)nc2cc1OCCCN1CCCC1] |
| A2 | 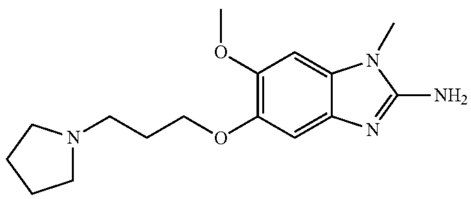 [SMILES: COc1cc2c(cc1OCCCN1CCCC1)nc(N)n2C] |
| A3 | 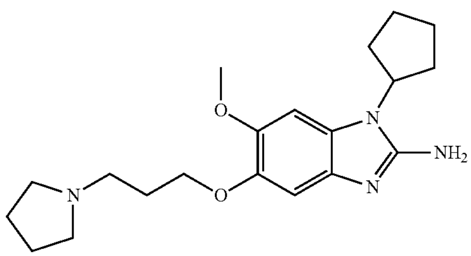 [SMILES: COc1cc2c(cc1OCCCN1CCCC1)nc(N)n2C1CCCC1] |
| A4 | 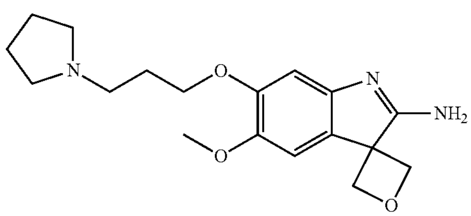 [SMILES: COc1cc2c(cc1OCCCN1CCCC1)N=C(N)C21COC1] |
| A5 | 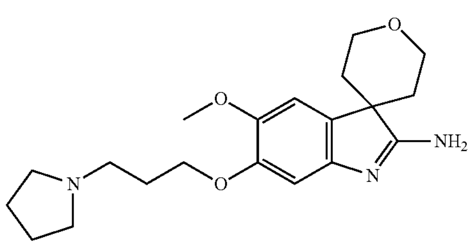 [SMILES: COc1cc2c(cc1OCCCN1CCCC1)N=C(N)C21CCOCC1] |
| A6 | 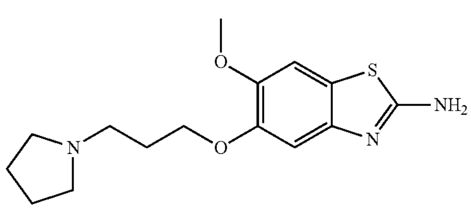 [SMILES: COc1cc2sc(N)nc2cc1OCCCN1CCCC1] |

TABLE 4-continued

| Compound No. | Structure |
|---|---|
| A7 | 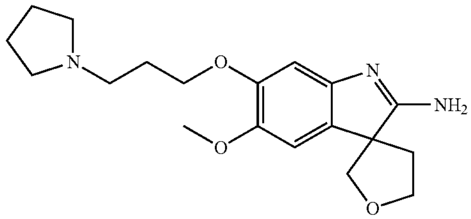 [SMILES: COc1cc2c(cc1OCCCN1CCCC1)N=C(N)C21CCOC1] |
| A8 | 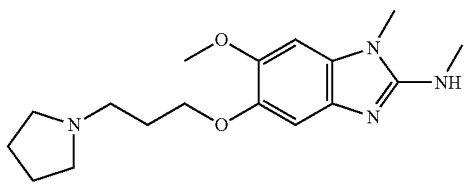 [SMILES: CNc1nc2cc(OCCCN3CCCC3)c(OC)cc2n1C] |
| A9 | 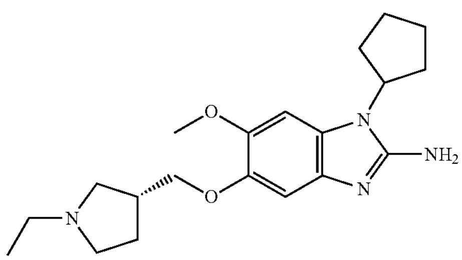 [SMILES: CCN1CC[C@@H](COc2cc3nc(N)n(C4CCCC4)c3cc2OC)C1] |
| A10 | 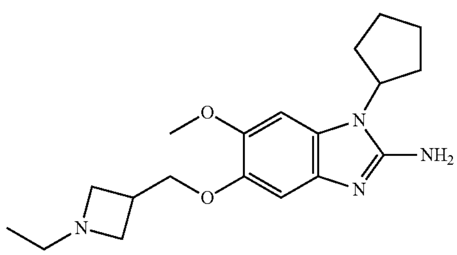 [SMILES: CCN1CC(COc2cc3nc(N)n(C4CCCC4)c3cc2OC)C1] |
| A11 | 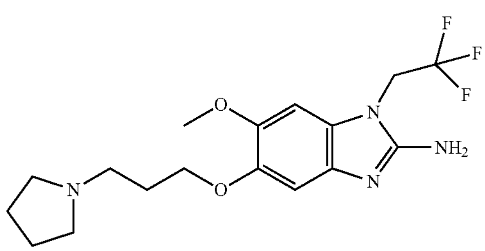 [SMILES: COc1cc2c(cc1OCCCN1CCCC1)nc(N)n2CC(F)(F)F] |
| A12 | 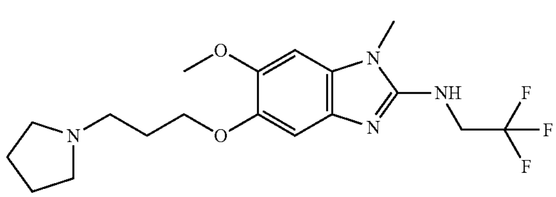 [SMILES: COc1cc2c(cc1OCCCN1CCCC1)nc(NCC(F)(F)F)n2C] |

US 11,672,800 B2
TABLE 4-continued
| Compound No. | Structure |
|---|---|
| A13 | 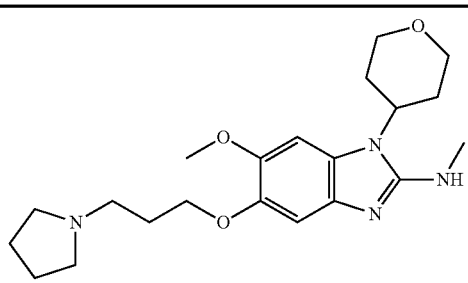 |
| A14 | 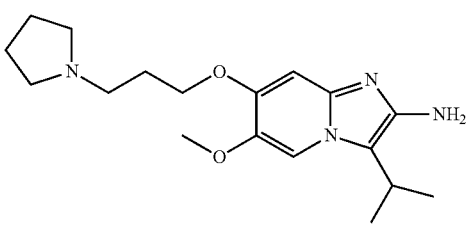 [SMILES: COc1cn2c(C(C)C)c(N)nc2cc1OCCCN1CCCC1] |
| A15 | 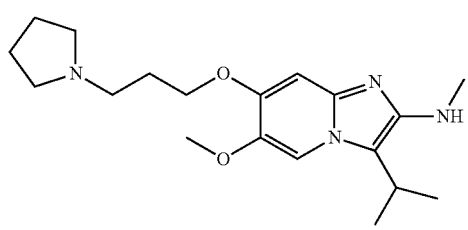 [SMILES: CNc1nc2cc(OCCCN3CCCC3)c(OC)cn2c1C(C)C] |
| A16 | 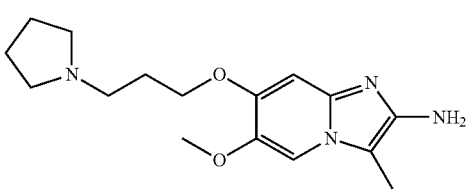 [SMILES: COc1cn2c(C)c(N)nc2cc1OCCCN1CCCC1] |
| A17 | 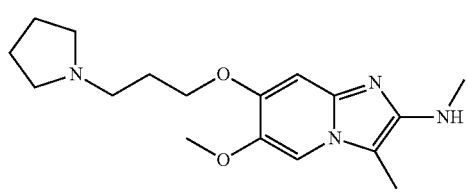 [SMILES: CNc1nc2cc(OCCCN3CCCC3)c(OC)cn2c1C] |
| A18 | 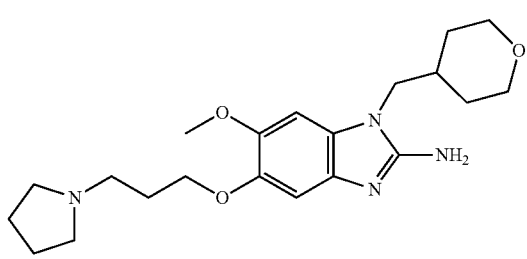 [SMILES: COc1cc2c(cc1OCCCN1CCCC1)nc(N)n2CC1CCOCC1] |
| A19 | 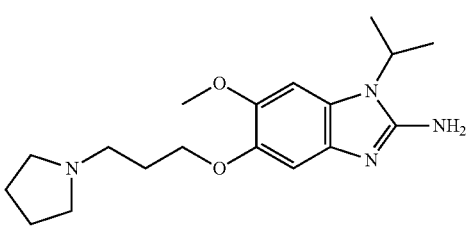 [SMILES: COc1cc2c(cc1OCCCN1CCCC1)nc(N)n2C(C)C] |

TABLE 4-continued

| Compound No. | Structure |
|---|---|
| A20 | 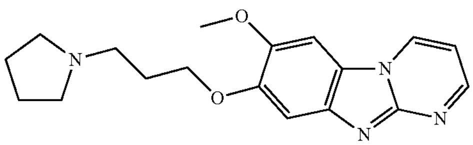 [SMILES: COc1cc2c(cc1OCCCN1CCCC1)nc1ncccn12] |
| A21 | 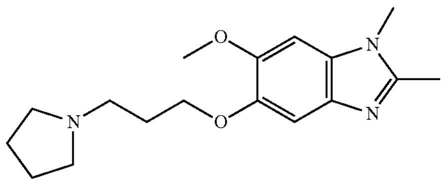 [SMILES: COc1cc2c(cc1OCCCN1CCCC1)nc(C)n2C] |
| A22 | 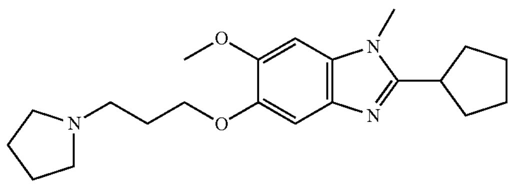 [SMILES: COc1cc2c(cc1OCCCN1CCCC1)nc(C1CCCC1)n2C] |
| A23 | 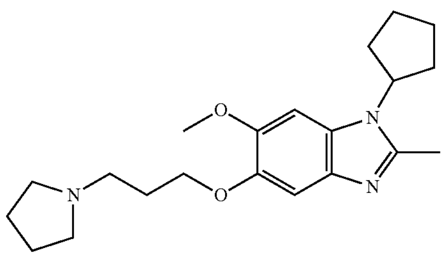 [SMILES: COc1cc2c(cc1OCCCN1CCCC1)nc(C)n2C1CCCC1] |
| A24 | 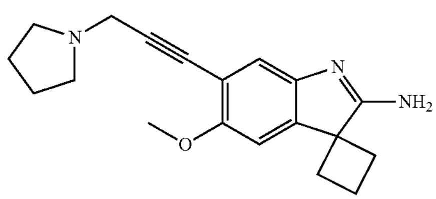 [SMILES: COc1cc2c(cc1C#CCN1CCCC1)N=C(N)C21CCC1] |
| A25 | 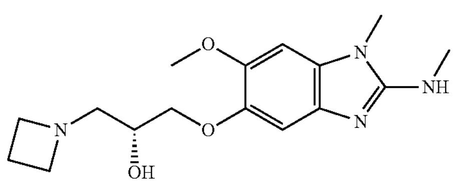 [SMILES: CNc1nc2cc(OC[C@H](O)CN3CCC3)c(OC)cc2n1C] |
| A26 | 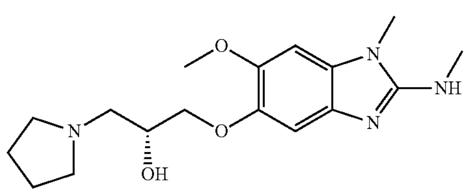 [SMILES: CNc1nc2cc(OC[C@H](O)CN3CCCC3)c(OC)cc2n1C] |
| A27 | 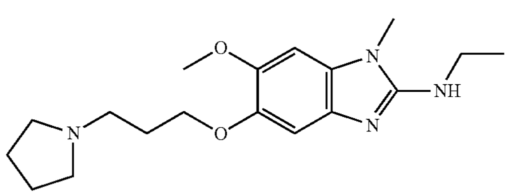 [SMILES: CCNc1nc2cc(OCCCN3CCCC3)c(OC)cc2n1C] |

TABLE 4-continued

| Compound No. | Structure |
| --- | --- |
| A28 | 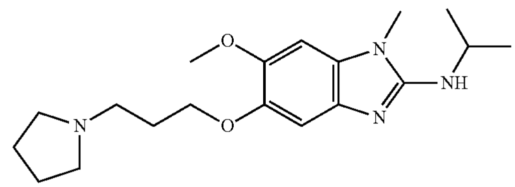 [SMILES: COc1cc2c(cc1OCCCN1CCCC1)nc(NC(C)C)n2C] |
| A29 | 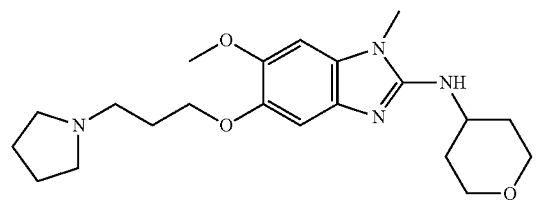 [SMILES: COc1cc2c(cc1OCCCN1CCCC1)nc(NC1CCOCC1)n2C] |
| A30 | 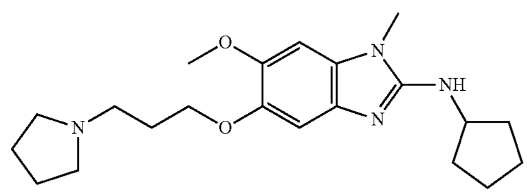 [SMILES: COc1cc2c(cc1OCCCN1CCCC1)nc(NC1CCCC1)n2C] |
| A31 | 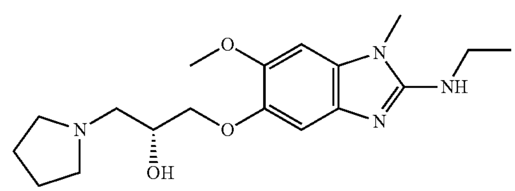 [SMILES: CCNc1nc2cc(OC[C@H](O)CN3CCCC3)c(OC)cc2n1C] |
| A32 | 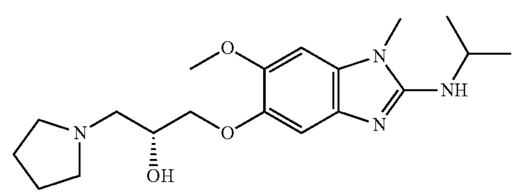 [SMILES: COc1cc2c(cc1OC[C@H](O)CN1CCCC1)nc(NC(C)C)n2C] |
| A33 | 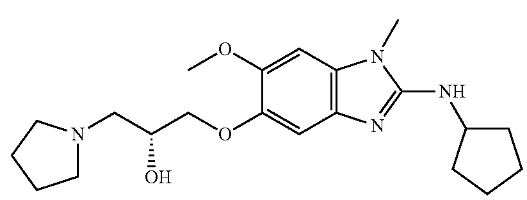 [SMILES: COc1cc2c(cc1OC[C@H](O)CN1CCCC1)nc(NC1CCCC1)n2C] |
| A34 | 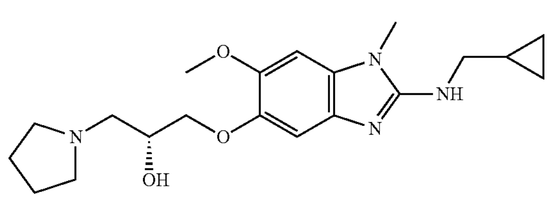 [SMILES: COc1cc2c(cc1OC[C@H](O)CN1CCCC1)nc(NCC1CC1)n2C] |

TABLE 4-continued

| Compound No. | Structure |
| --- | --- |
| A35 | 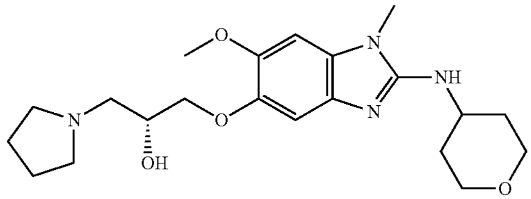 [SMILES: COc1cc2c(cc1OC[C@H](O)CN1CCCC1)nc(NC1CCOCC1)n2C] |
| A36 | 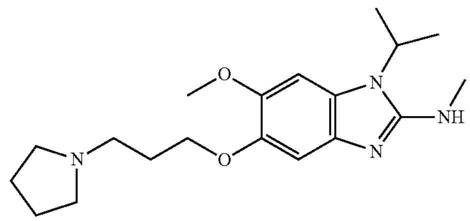 [SMILES: CNc1nc2cc(OCCCN3CCCC3)c(OC)cc2n1C(C)C] |
| A37 | 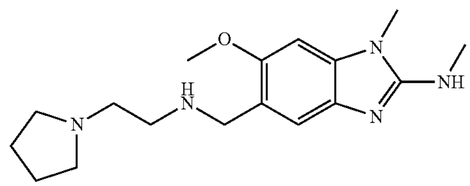 [SMILES: CNc1nc2cc(CNCCN3CCCC3)c(OC)cc2n1C] |
| A38 | 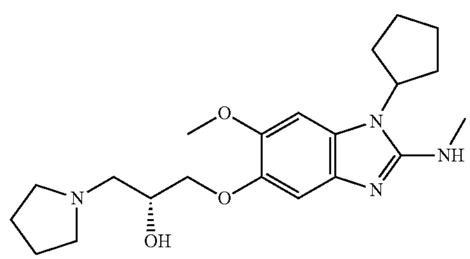 [SMILES: CNc1nc2cc(OC[C@H](O)CN3CCCC3)c(OC)cc2n1C1CCCC1] |
| A39 | 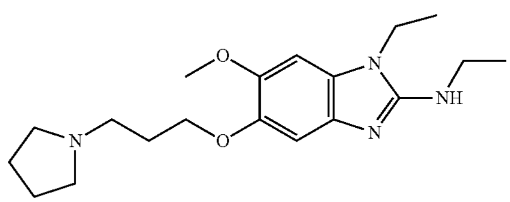 [SMILES: CCNc1nc2cc(OCCCN3CCCC3)c(OC)cc2n1CC] |
| A40 | 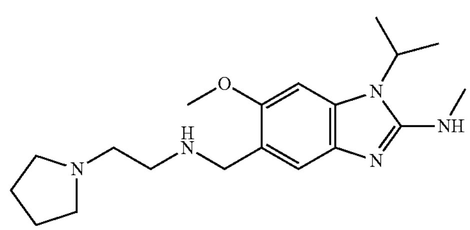 [SMILES: CNc1nc2cc(CNCCN3CCCC3)c(OC)cc2n1C(C)C] |
| A41 | 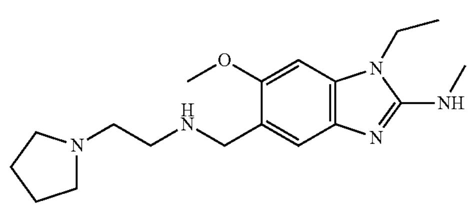 [SMILES: CCn1c(NC)nc2cc(CNCCN3CCCC3)c(OC)cc21] |

TABLE 4-continued
| Compound No. | Structure |
|---|---|
| A42 | 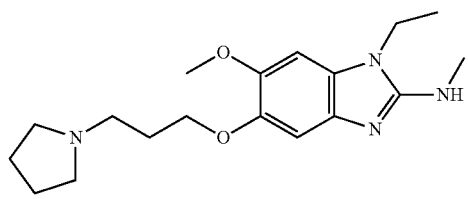 [SMILES: CCn1c(NC)nc2cc(OCCCN3CCCC3)c(OC)cc21] |
| A43 | 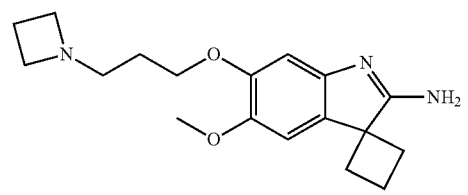 [SMILES: COc1cc2c(cc1OCCCN1CCC1)N=C(N)C21CCC1] |
| A44 | 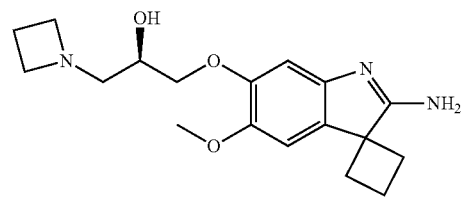 [SMILES: COc1cc2c(cc1OC[C@H](O)CN1CCC1)N=C(N)C21CCC1] |
| A45 | 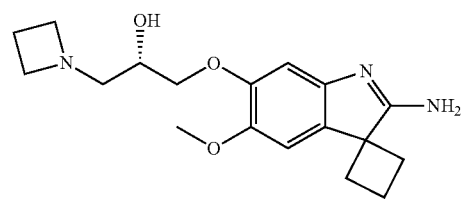 [SMILES: COc1cc2c(cc1OC[C@@H](O)CN1CCC1)N=C(N)C21CCC1] |
| A46 | 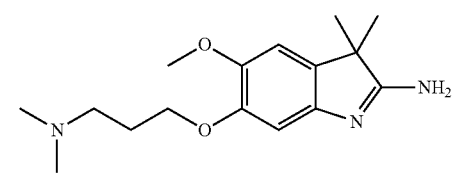 [SMILES: COc1cc2c(cc1OCCCN(C)C)N=C(N)C2(C)C] |
| A47 | 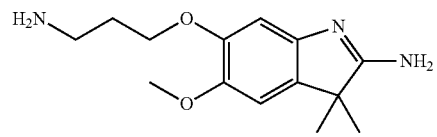 [SMILES: COc1cc2c(cc1OCCCN)N=C(N)C2(C)C] |
| A48 | 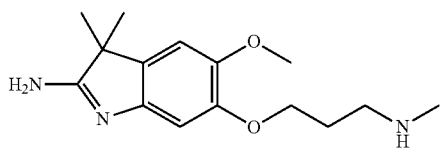 [SMILES: CNCCCOc1cc2c(cc1OC)C(C)(C)C(N)=N2] |
| A49 | 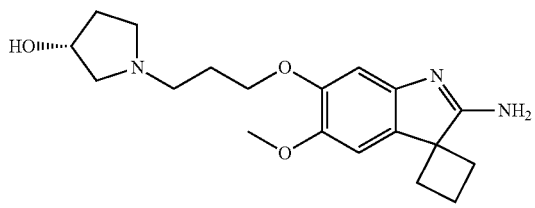 [SMILES: COc1cc2c(cc1OCCCN1CC[C@@H](O)C1)N=C(N)C21CCC1] |

TABLE 4-continued

| Compound No. | Structure |
|---|---|
| A50 | 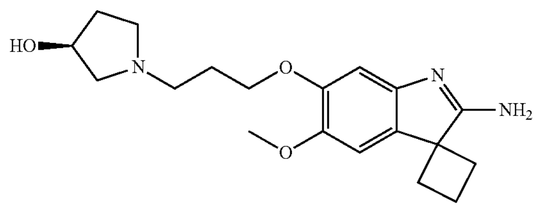 [SMILES: COc1cc2c(cc1OCCCN1CC[C@H](O)C1)N=C(N)C21CCC1] |
| A51 | 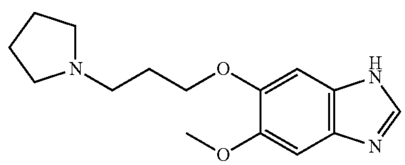 [SMILES: COc1cc2nc[nH]c2cc1OCCCN1CCCC1] |
| A52 | 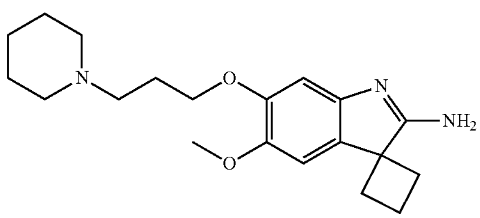 [SMILES: COc1cc2c(cc1OCCCN1CCCCC1)N=C(N)C21CCC1] |
| A53 | 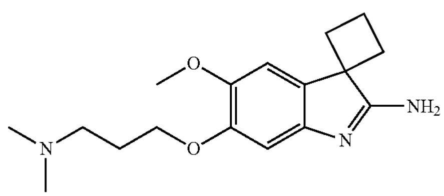 [SMILES: COc1cc2c(cc1OCCCN(C)C)N=C(N)C21CCC1] |
| A54 | 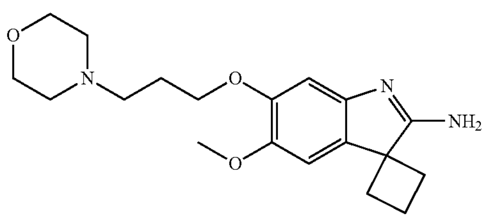 [SMILES: COc1cc2c(cc1OCCCN1CCOCC1)N=C(N)C21CCC1] |
| A55 | 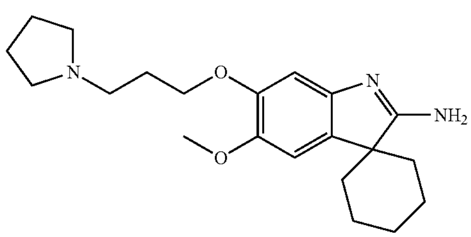 [SMILES: COc1cc2c(cc1OCCCN1CCCC1)N=C(N)C21CCCCC1] |
| A56 | 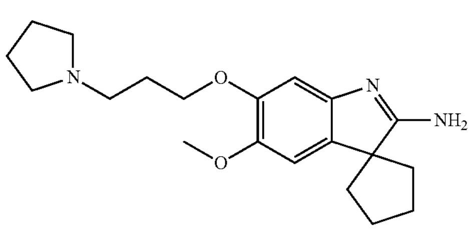 [SMILES: COc1cc2c(cc1OCCCN1CCCC1)N=C(N)C21CCCC1] |

TABLE 4-continued

| Compound No. | Structure |
|---|---|
| A57 | 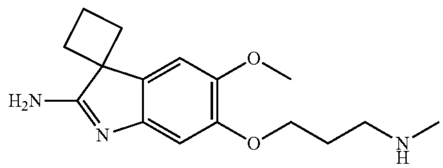 [SMILES: CNCCCOc1cc2c(cc1OC)C1(CCC1)C(N)=N2] |
| A58 | 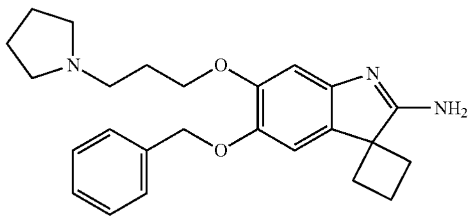 [SMILES: NC1=Nc2cc(OCCCN3CCCC3)c(OCc3ccccc3)cc2C12CCC2] |
| A59 | 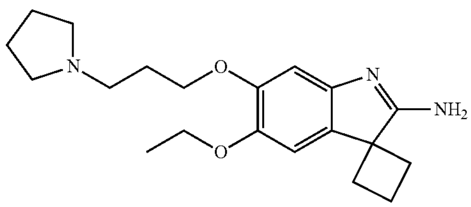 [SMILES: CCOc1cc2c(cc1OCCCN1CCCC1)N=C(N)C21CCC1] |
| A60 | 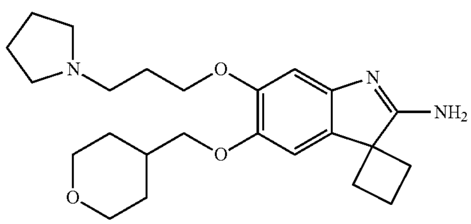 [SMILES: NC1=Nc2cc(OCCCN3CCCC3)c(OCC3CCOCC3)cc2C12CCC2] |
| A61 | 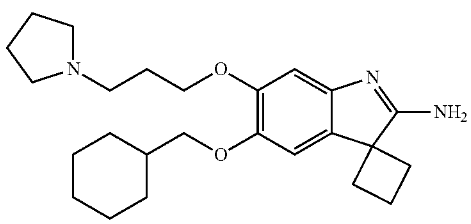 [SMILES: NC1=Nc2cc(OCCCN3CCCC3)c(OCC3CCCCC3)cc2C12CCC2] |
| A62 | 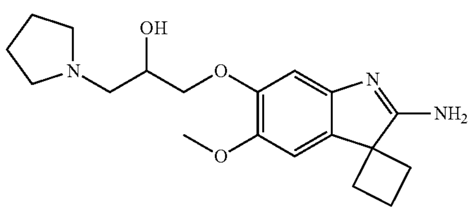 [SMILES: COc1cc2c(cc1OCC(O)CN1CCCC1)N=C(N)C21CCC1] |
| A63 | 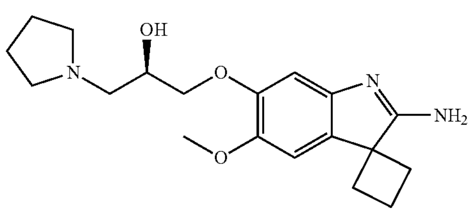 [SMILES: COc1cc2c(cc1OC[C@H](O)CN1CCCC1)N=C(N)C21CCC1] |

TABLE 4-continued

| Compound No. | Structure |
|---|---|
| A64 | 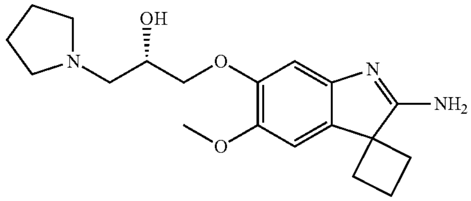 |
| A65 | 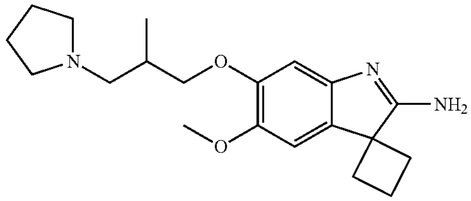 [SMILES: COc1cc2c(cc1OCC(C)CN1CCCC1)N=C(N)C21CCC1] |
| A66 | 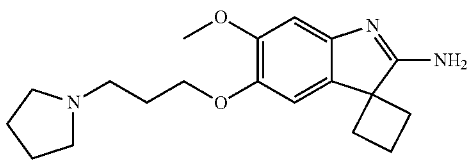 [SMILES: COc1cc2c(cc1OCCCN1CCCC1)C1(CCC1)C(N)=N2] |
| A67 | 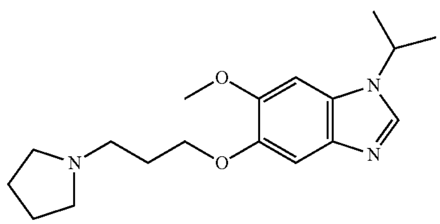 [SMILES: COc1cc2c(cc1OCCCN1CCCC1)ncn2C(C)C] |
| A68 | 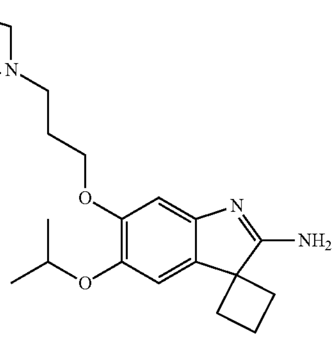 |
| A69 | 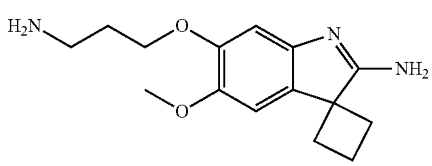 [SMILES: COc1cc2c(cc1OCCCN)N=C(N)C21CCC1] |
| A70 | 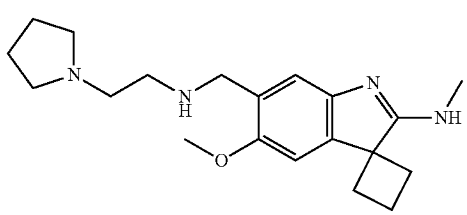 [SMILES: CNC1=Nc2cc(CNCCN3CCCC3)c(OC)cc2C12CCC2] |

TABLE 4-continued

| Compound No. | Structure |
| --- | --- |
| A71 | 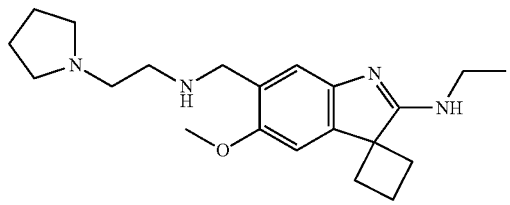 [SMILES: CCNC1=Nc2cc(CNCCN3CCCC3)c(OC)cc2C12CCC2] |
| A72 | 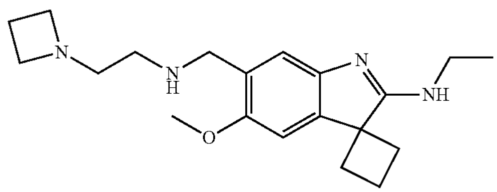 [SMILES: CCNC1=Nc2cc(CNCCN3CCC3)c(OC)cc2C12CCC2] |
| A73 | 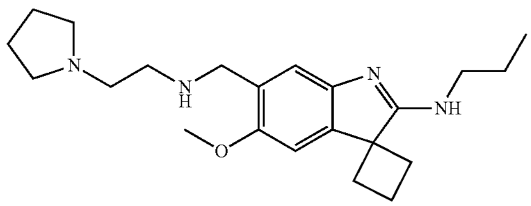 [SMILES: CCCNC1=Nc2cc(CNCCN3CCCC3)c(OC)cc2C12CCC2] |
| A74 | 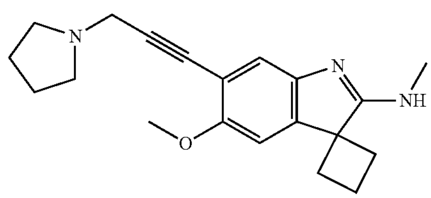 [SMILES: CNC1=Nc2cc(C#CCN3CCCC3)c(OC)cc2C12CCC2] |
| A75 | 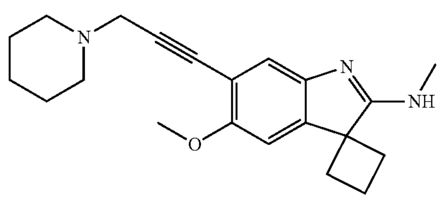 [SMILES: CNC1=Nc2cc(C#CCN3CCCCC3)c(OC)cc2C12CCC2] |
| A76 | 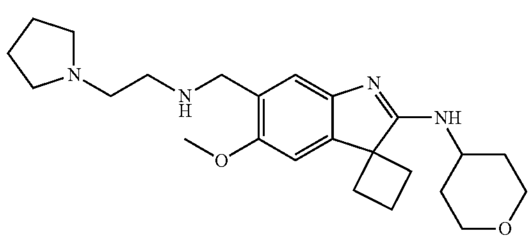 [SMILES: COc1cc2c(cc1CNCCN1CCCC1)N=C(NC1CCOCC1)C21CCC1] |
| A77 | 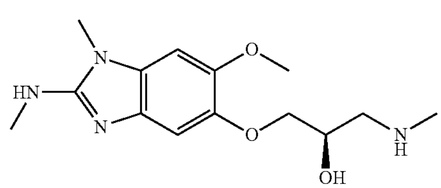 |

417 418
TABLE 4-continued
| Compound No. | Structure |
|---|---|
| A78 | 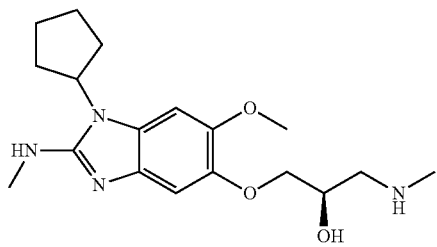 |
| A79 | 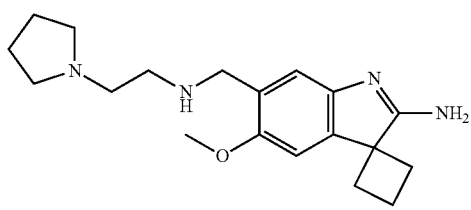 [SMILES: COc1cc2c(cc1CNCCN1CCCC1)N=C(N)C21CCC1] |
| A80 | 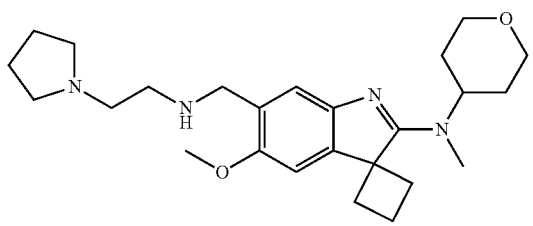 [SMILES: COc1cc2c(cc1CNCCN1CCCC1)N=C(N(C)C1CCOCC1)C21CCC1] |
| A81 | 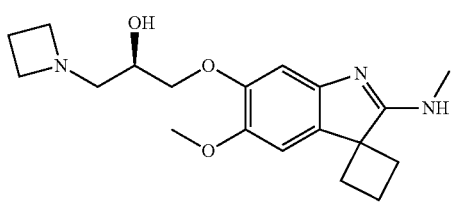 [SMILES: CNC1=Nc2cc(OC[C@H](O)CN3CCC3)c(OC)cc2C12CCC2] |
| A82 | 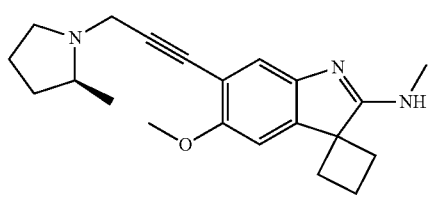 [SMILES: CNC1=Nc2cc(C#CCN3CCC[C@@H]3C)c(OC)cc2C12CCC2] |
| A83 | 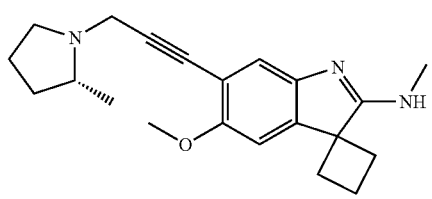 [SMILES: CNC1=Nc2cc(C#CCN3CCC[C@H]3C)c(OC)cc2C12CCC2] |
| A84 | 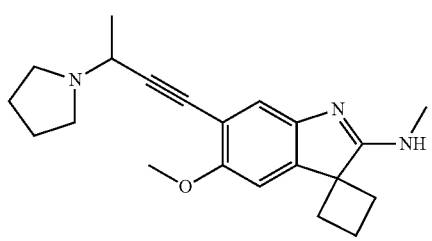 |

TABLE 4-continued

| Compound No. | Structure |
|---|---|
| A85 | 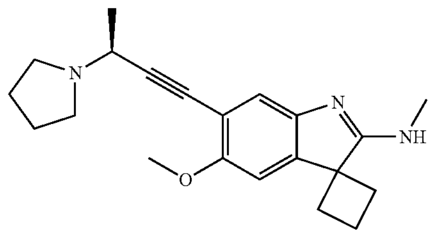 |
| A86 | 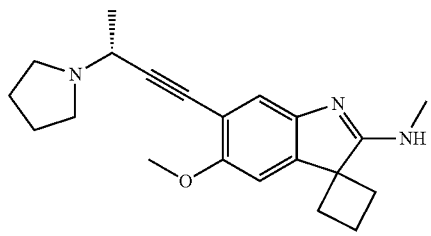 [SMILES: CNC1=Nc2cc(C#CC(C)N3CCCC3)c(OC)cc2C12CCC2] |
| A87 | 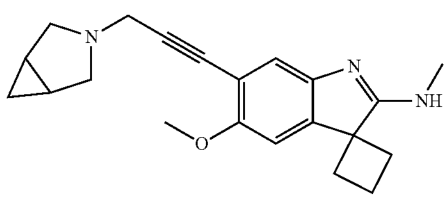 [SMILES: CNC1=Nc2cc(C#CCN3CC4CC4C3)c(OC)cc2C12CCC2] |
| A88 | 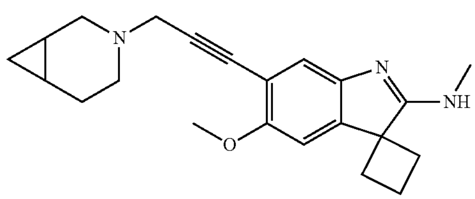 [SMILES: CNC1=Nc2cc(C#CCN3CCC4CC4C3)c(OC)cc2C12CCC2] |
| A89 | 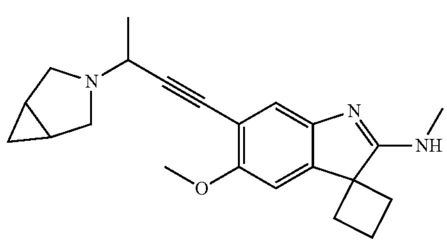 |
| A90 | 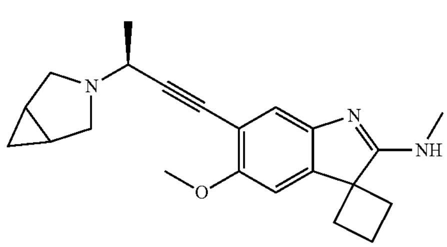 [SMILES: CNC1=Nc2cc(C#C[C@H](C)N3CC4CC4C3)c(OC)cc2C12CCC2] |

TABLE 4-continued
| Compound No. | Structure |
|---|---|
| A91 | 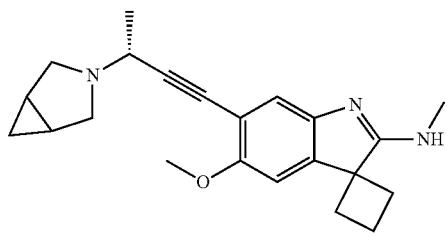 [SMILES: CNC1=Nc2cc(C#C[C@@H](C)N3CC4CC4C3)c(OC)cc2C12CCC2] |
| A92 | 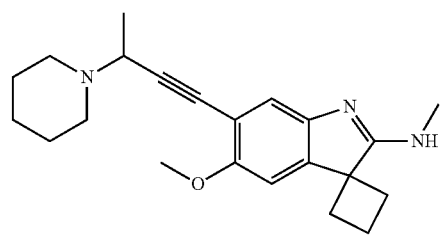 [SMILES: CNC1=Nc2cc(C#CC(C)N3CCCCC3)c(OC)cc2C12CCC2] |
| A93 | 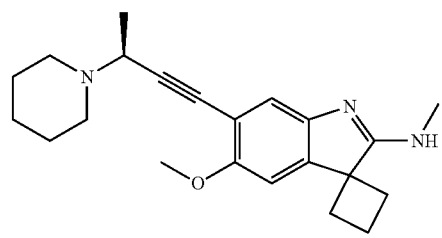 [SMILES: CNC1=Nc2cc(C#C[C@H](C)N3CCCCC3)c(OC)cc2C12CCC2] |
| A94 | 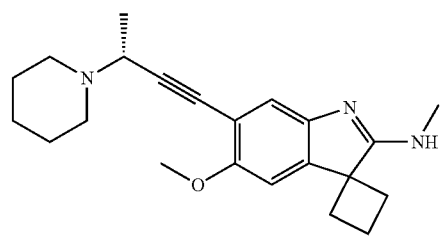 [SMILES: CNC1=Nc2cc(C#C[C@@H](C)N3CCCCC3)c(OC)cc2C12CCC2] |
| A95 | 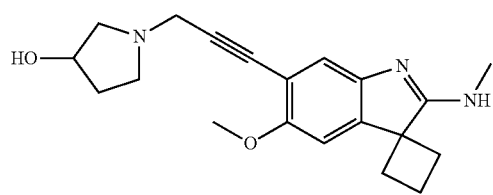 [SMILES: CNC1=Nc2cc(C#CCN3CCC(O)C3)c(OC)cc2C12CCC2] |
| A96 | 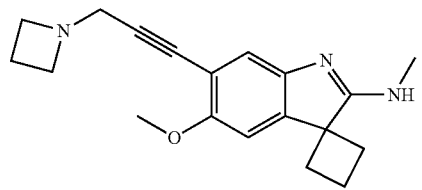 [SMILES: CNC1=Nc2cc(C#CCN3CCC3)c(OC)cc2C12CCC2] |
| A97 | 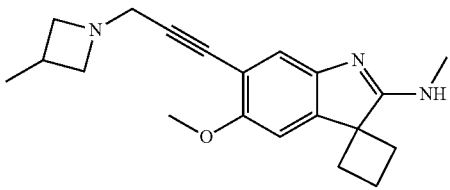 |

TABLE 4-continued
| Compound No. | Structure |
|---|---|
| A98 | 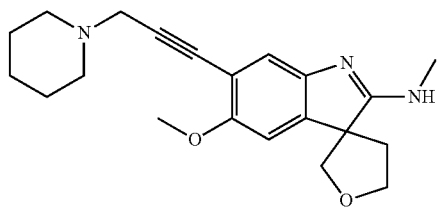 [SMILES: CNC1=Nc2cc(C#CCN3CCCCC3)c(OC)cc2C12CCOC2] |
| A99 | 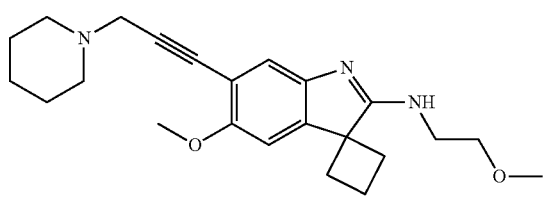 [SMILES: COCCNC1=Nc2cc(C#CCN3CCCCC3)c(OC)cc2C12CCC2] |
| A100 | 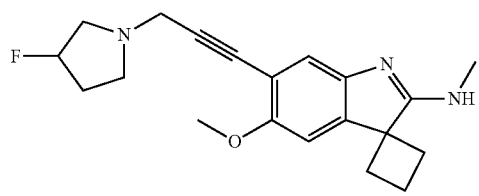 [SMILES: CNC1=Nc2cc(C#CCN3CCC(F)C3)c(OC)cc2C12CCC2] |
| A101 | 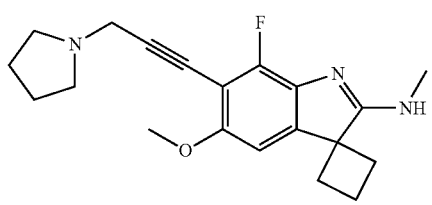 [SMILES: CNC1=Nc2c(cc(OC)c(C#CCN3CCCC3)c2F)C12CCC2] |
| A106 | 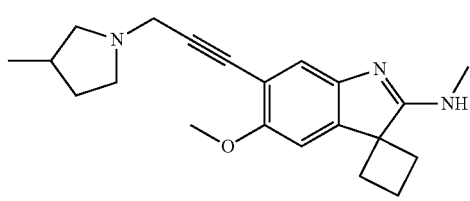 |
| A107 | 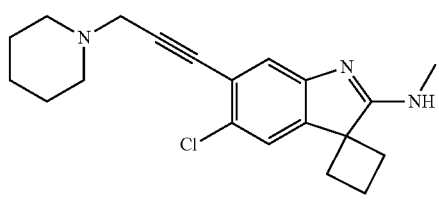 [SMILES: CNC1=Nc2cc(C#CCN3CCCCC3)c(Cl)cc2C12CCC2] |
| A110 | 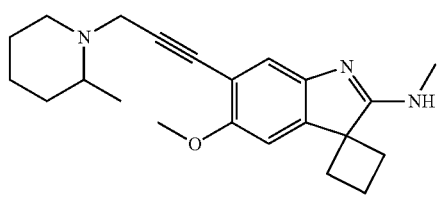 [SMILES: CNC1=Nc2cc(C#CCN3CCCCC3C)c(OC)cc2C12CCC2] |

TABLE 4-continued
| Compound No. | Structure |
|---|---|
| A111 | 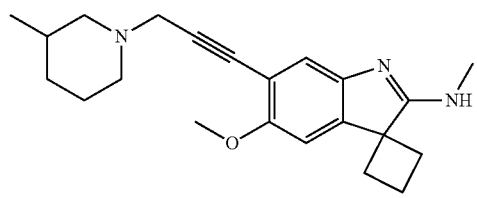 |
| A112 | 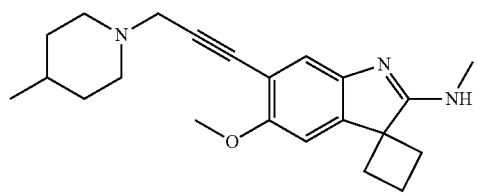 |
| A113 | 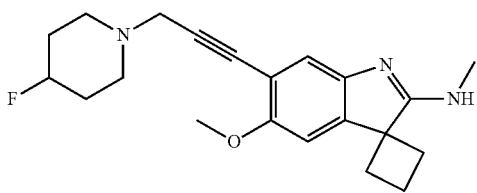 [SMILES: CNC1=Nc2cc(C#CCN3CCC(F)CC3)c(OC)cc2C12CCC2] |
| A114 | 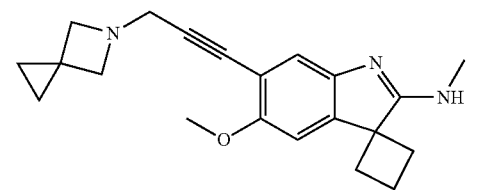 [SMILES: CNC1=Nc2cc(C#CCN3CC4(CC4)C3)c(OC)cc2C12CCC2] |
| A115 | 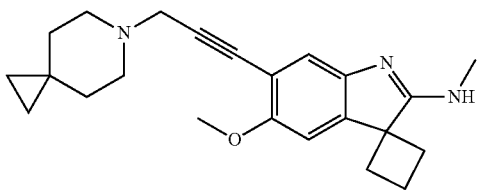 [SMILES: CNC1=Nc2cc(C#CCN3CCC4(CC3)CC4)c(OC)cc2C12CCC2] |
| A116 | 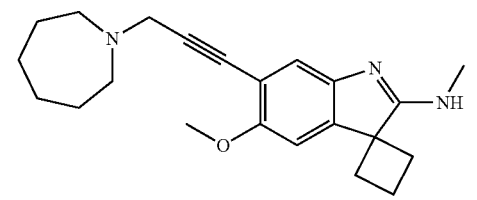 [SMILES: CNC1=Nc2cc(C#CCN3CCCCCC3)c(OC)cc2C12CCC2] |
| A117 | 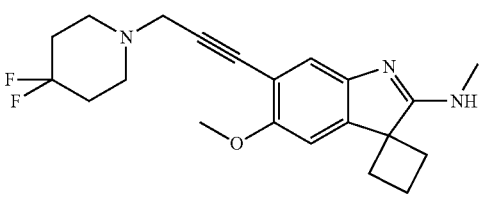 [SMILES: CNC1=Nc2cc(C#CCN3CCC(F)(F)CC3)c(OC)cc2C12CCC2] |

TABLE 4-continued
| Compound No. | Structure |
|---|---|
| A118 | 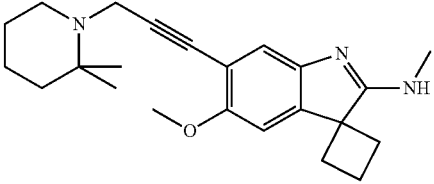 [SMILES: CNC1=Nc2cc(C#CCN3CCCCC3(C)C)c(OC)cc2C12CCC2] |
| A119 | 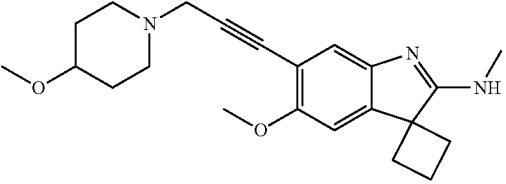 |
| A120 | 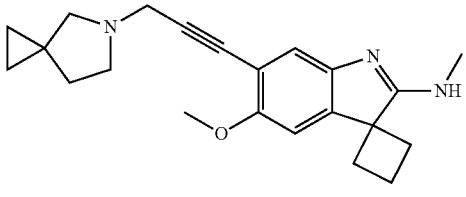 [SMILES: CNC1=Nc2cc(C#CCN3CCC4(CC4)C3)c(OC)cc2C12CCC2] |
| A121 | 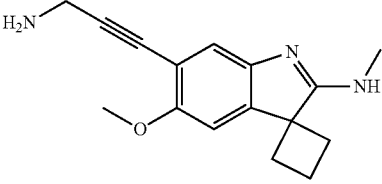 [SMILES: CNC1=Nc2cc(C#CCN)c(OC)cc2C12CCC2] |
| A122 | 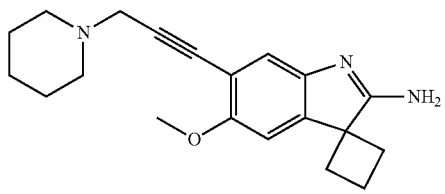 [SMILES: COc1cc2c(cc1C#CCN1CCCCC1)N=C(N)C21CCC1] |
| A123 | 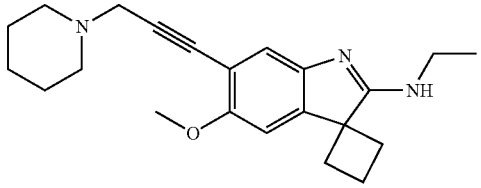 [SMILES: CCNC1=Nc2cc(C#CCN3CCCCC3)c(OC)cc2C12CCC2] |
| A124 | 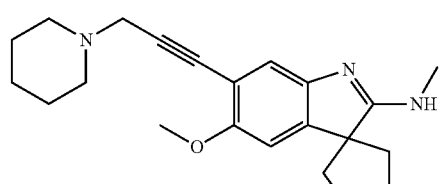 |

TABLE 4-continued
| Compound No. | Structure |
|---|---|
| A125 | 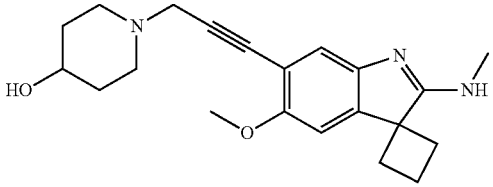 [SMILES: CNC1=Nc2cc(C#CCN3CCC(O)CC3)c(OC)cc2C12CCC2] |
| A126 | 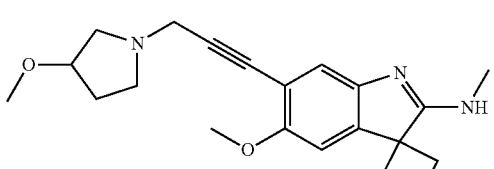 |
| A127 | 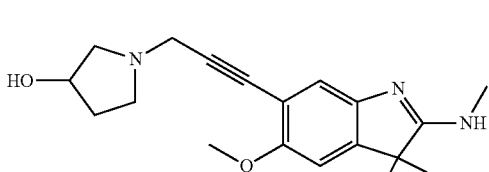 |
| A128 | 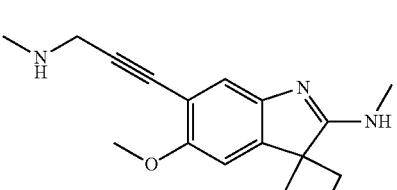 |
| A129 | 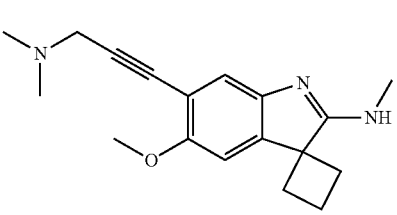 |
| A130 | 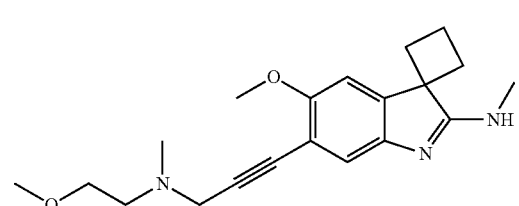 |
| A131 | 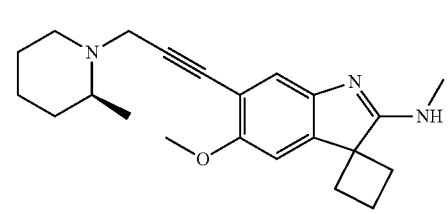 [SMILES: CNC1=Nc2cc(C#CCN3CCCC[C@@H]3C)c(OC)cc2C12CCC2] |

TABLE 4-continued

| Compound No. | Structure |
|---|---|
| A132 | 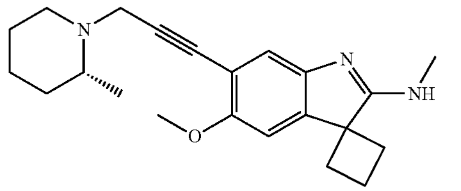 [SMILES: CNC1=Nc2cc(C#CCN3CCCC[C@H]3C)c(OC)cc2C12CCC2] |
| A133 | 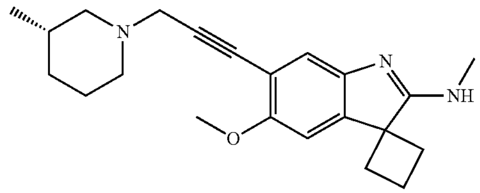 |
| A134 | 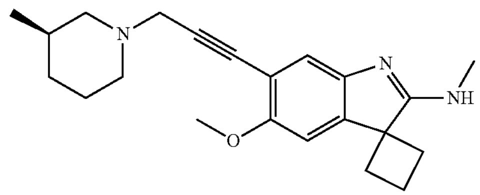 |
| A135 | 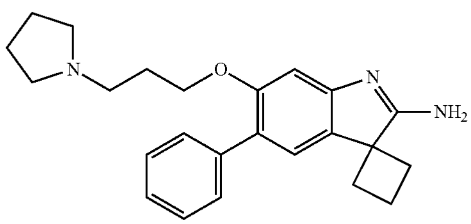 [SMILES: NC1=Nc2cc(OCCCN3CCCC3)c(-c3ccccc3)cc2C12CCC2] |
| A136 | 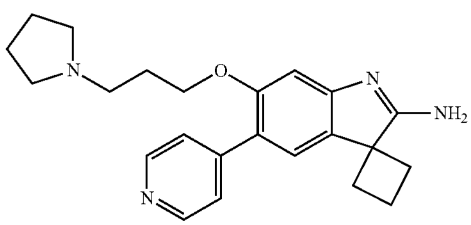 |
| A137 | 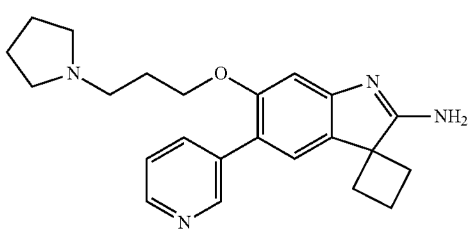 [SMILES: NC1=Nc2cc(OCCCN3CCCC3)c(-c3cccnc3)cc2C12CCC2] |
| A138 | 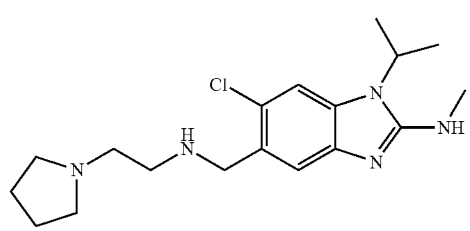 [SMILES: CNc1nc2cc(CNCCN3CCCC3)c(Cl)cc2n1C(C)C] |

TABLE 4-continued

| Compound No. | Structure |
|---|---|
| A139 | 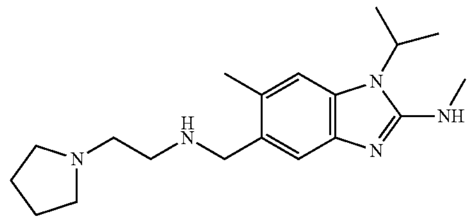 [SMILES: CNc1nc2cc(CNCCN3CCCC3)c(C)cc2n1C(C)C] |
| A140 | 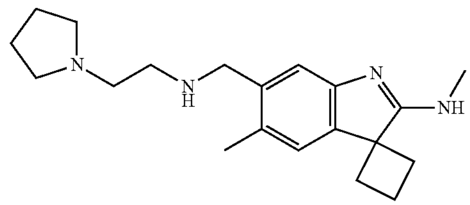 [SMILES: CNC1=Nc2cc(CNCCN3CCCC3)c(C)cc2C12CCC2] |
| A141 | 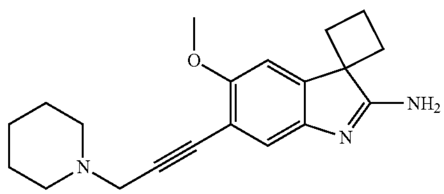 [SMILES: COc1cc2c(cc1C#CCN1CCCCC1)N=C(N)C21CCC1] |

The compounds of Table 4 are the compounds found in U.S. Application Nos. 62/402,863 and 62/509,620, and PCT Appl'n No. PCT/US2017/054468, the entire contents of which are incorporated herein by reference.

TABLE 5

| Compound No. | Structure |
|---|---|
| B1 | 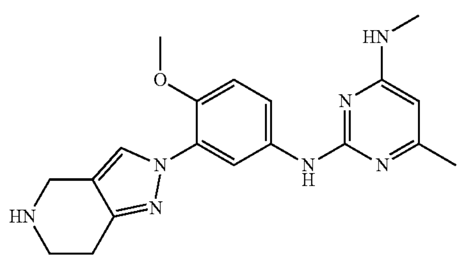 [SMILES: CNc1cc(C)nc(Nc2ccc(OC)c(-n3cc4c(n3)CCNC4)c2)n1] |
| B2 | 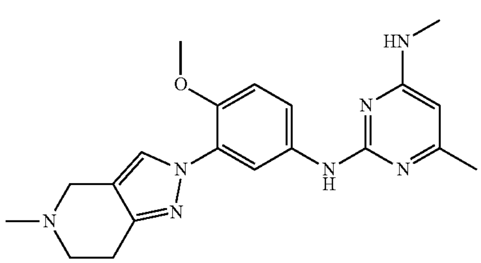 |

TABLE 5-continued
| Compound No. | Structure |
|---|---|
| B3 | 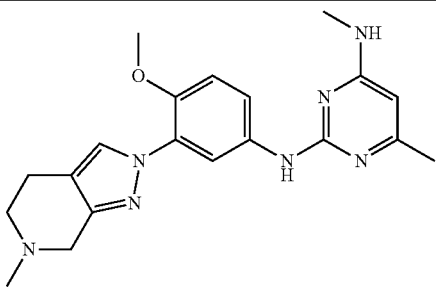 |
| B4 | 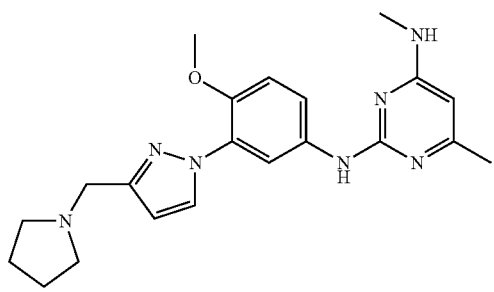 [SMILES: CNc1cc(C)nc(Nc2ccc(OC)c(-n3ccc(CN4CCCC4)n3)c2)n1] |
| B5 | 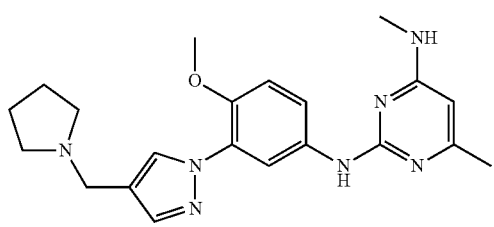 [SMILES: CNc1cc(C)nc(Nc2ccc(OC)c(-n3cc(CN4CCCC4)cn3)c2)n1] |
| B6 | 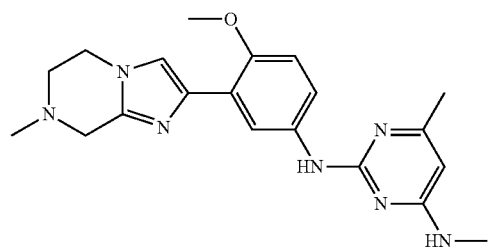 |
| B7 | 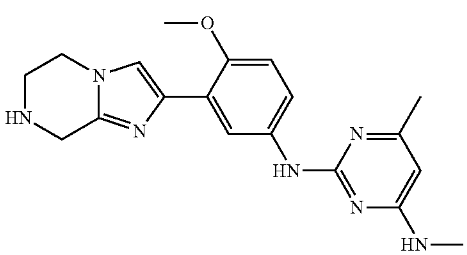 [SMILES: CNc1cc(C)nc(Nc2ccc(OC)c(-c3cn4c(n3)CNCC4)c2)n1] |
| B8 | 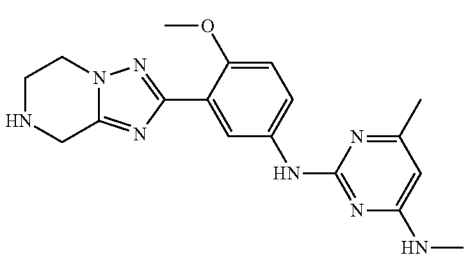 |

TABLE 5-continued

| Compound No. | Structure |
|---|---|
| B9 | 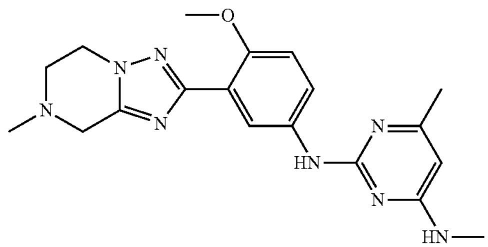 |
| B10 | 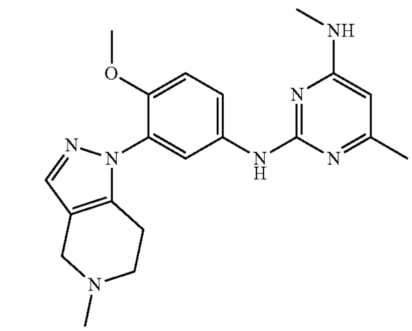 [SMILES: CNc1cc(C)nc(Nc2ccc(OC)c(-n3ncc4c3CCN(C)C4)c2)n1] |
| B11 | 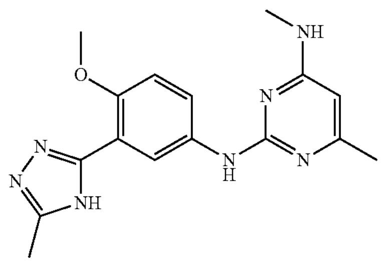 [SMILES: CNc1cc(C)nc(Nc2ccc(OC)c(-c3nnc(C)[nH]3)c2)n1] |
| B12 | 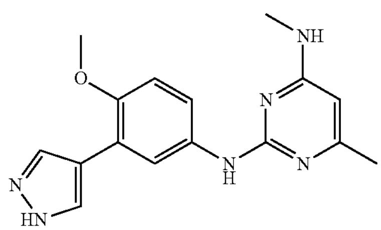 [SMILES: CNc1cc(C)nc(Nc2ccc(OC)c(-c3cn[nH]c3)c2)n1] |
| B13 | 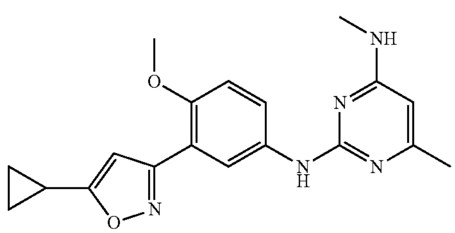 [SMILES: CNc1cc(C)nc(Nc2ccc(OC)c(-c3cc(C4CC4)on3)c2)n1] |
| B14 | 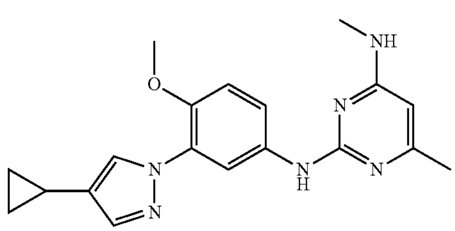 [SMILES: CNc1cc(C)nc(Nc2ccc(OC)c(-n3cc(C4CC4)cn3)c2)n1] |

TABLE 5-continued

| Compound No. | Structure |
|---|---|
| B15 | 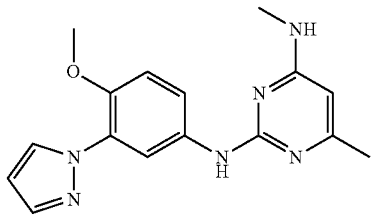 [SMILES: CNc1cc(C)nc(Nc2ccc(OC)c(-n3cccn3)c2)n1] |
| B16 | 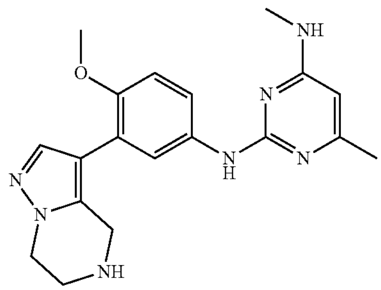 [SMILES: CNc1cc(C)nc(Nc2ccc(OC)c(-c3cnn4c3CNCC4)c2)n1] |
| B17 | 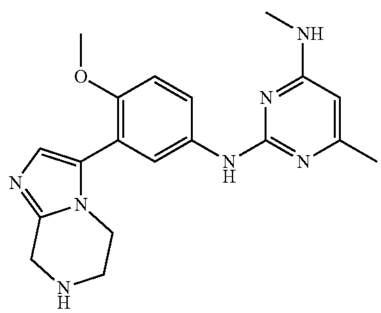 [SMILES: CNc1cc(C)nc(Nc2ccc(OC)c(-c3cnc4n3CCNC4)c2)n1] |
| B18 | 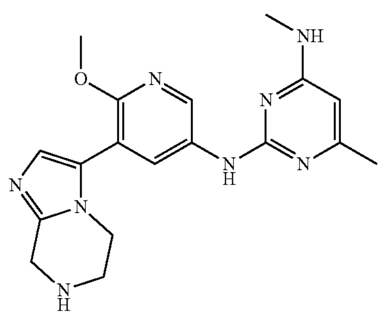 [SMILES: CNc1cc(C)nc(Nc2cnc(OC)c(-c3cnc4n3CCNC4)c2)n1] |
| B19 | 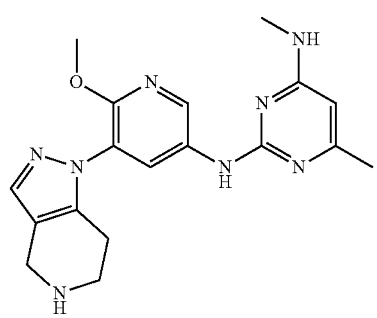 [SMILES: CNc1cc(C)nc(Nc2cnc(OC)c(-n3ncc4c3CCNC4)c2)n1] |

TABLE 5-continued

| Compound No. | Structure |
|---|---|
| B20 | 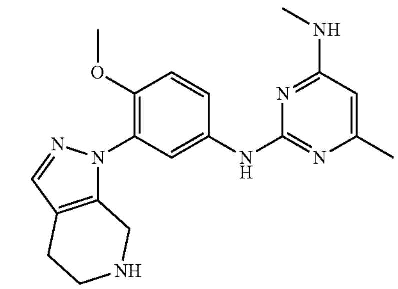 [SMILES: CNc1cc(C)nc(Nc2ccc(OC)c(-n3ncc4c3CNCC4)c2)n1] |
| B21 | 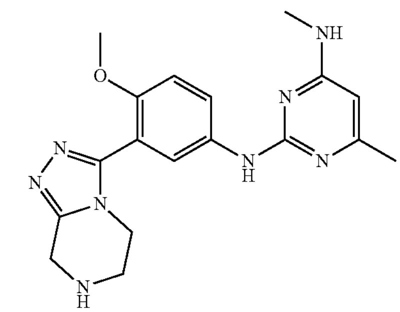 [SMILES: CNc1cc(C)nc(Nc2ccc(OC)c(-c3nnc4n3CCNC4)c2)n1] |
| B22 | 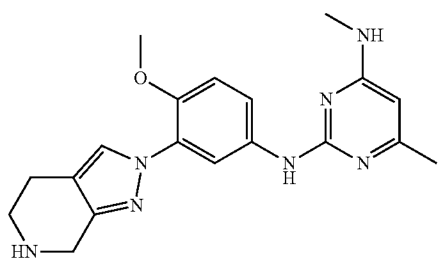 [SMILES: CNc1cc(C)nc(Nc2ccc(OC)c(-n3cc4c(n3)CNCC4)c2)n1] |
| B23 | 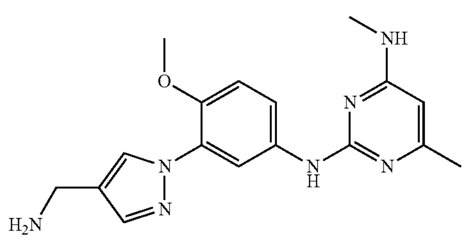 [SMILES: CNc1cc(C)nc(Nc2ccc(OC)c(-n3cc(CN)cn3)c2)n1] |
| B24 | 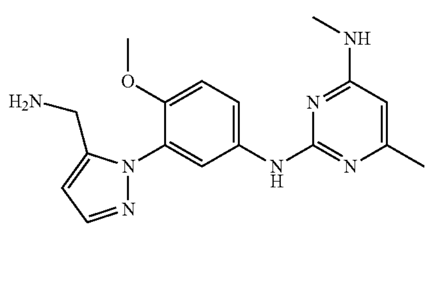 [SMILES: CNc1cc(C)nc(Nc2ccc(OC)c(-n3nccc3CN)c2)n1] |

TABLE 5-continued

| Compound No. | Structure |
|---|---|
| B25 | 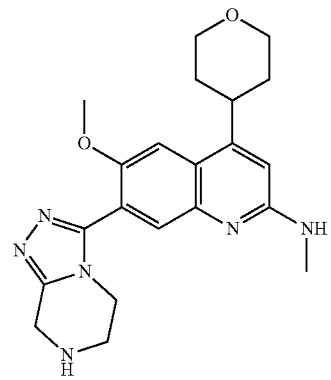 [SMILES: CNc1cc(C2CCOCC2)c2cc(OC)c(-c3nnc4n3CCNC4)cc2n1] |
| B26 | 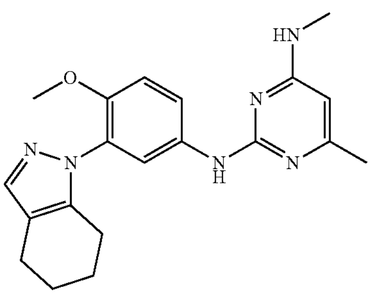 [SMILES: CNc1cc(C)nc(Nc2ccc(OC)c(-n3ncc4c3CCCC4)c2)n1] |
| B27 | 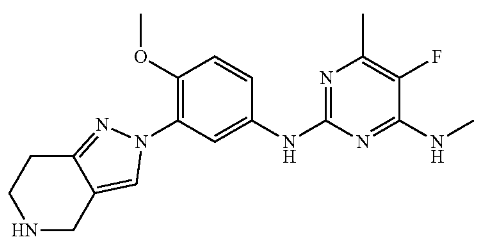 [SMILES: CNc1nc(Nc2ccc(OC)c(-n3cc4c(n3)CCNC4)c2)nc(C)c1F] |
| B28 | 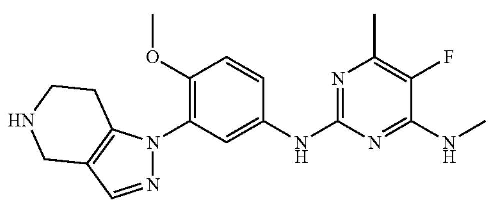 [SMILES: CNc1nc(Nc2ccc(OC)c(-n3ncc4c3CCNC4)c2)nc(C)c1F] |
| B29 | 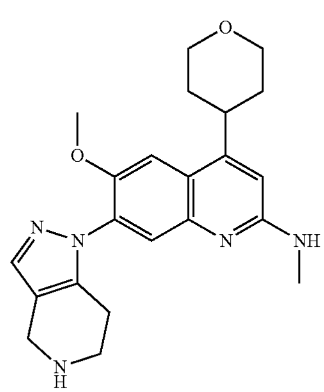 [SMILES: CNc1cc(C2CCOCC2)c2cc(OC)c(-n3ncc4c3CCNC4)cc2n1] |

TABLE 5-continued
| Compound No. | Structure |
|---|---|
| B30 | 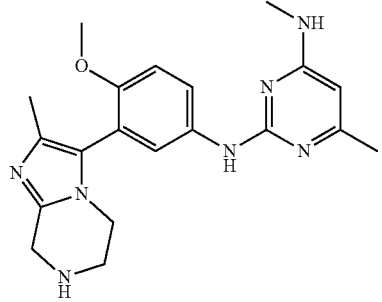 [SMILES: CNc1cc(C)nc(Nc2ccc(OC)c(-c3c(C)nc4n3CCNC4)c2)n1] |
| B31 | 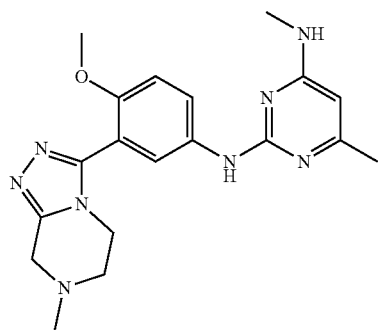 [SMILES: CNc1cc(C)nc(Nc2ccc(OC)c(-c3nnc4n3CCN(C)C4)c2)n1] |
| B32 | 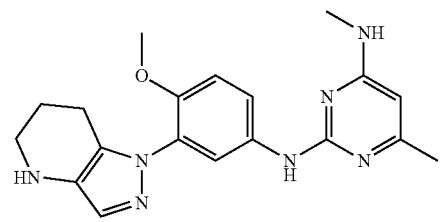 [SMILES: CNc1cc(C)nc(Nc2ccc(OC)c(-n3ncc4c3CCCN4)c2)n1] |
| B33 | 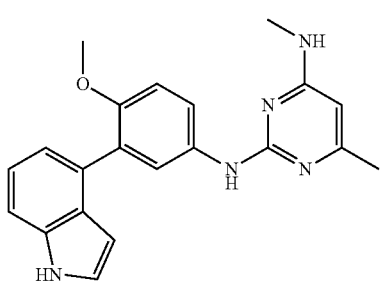 [SMILES: CNc1cc(C)nc(Nc2ccc(OC)c(-c3cccc4[nH]ccc34)c2)n1] |
| B34 | 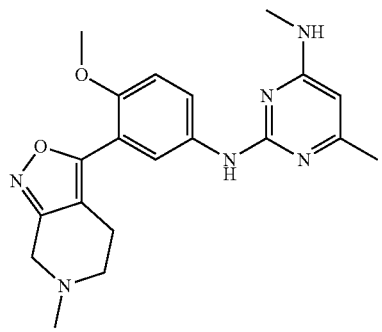 [SMILES: CNc1cc(C)nc(Nc2ccc(OC)c(-c3onc4c3CCN(C)C4)c2)n1] |

TABLE 5-continued

| Compound No. | Structure |
|---|---|
| B35 | 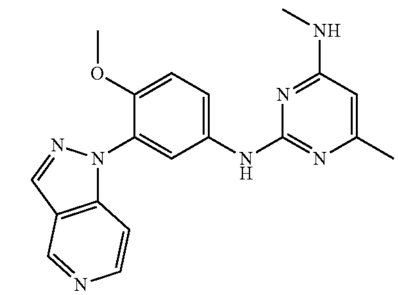 [SMILES: CNc1cc(C)nc(Nc2ccc(OC)c(-n3ncc4cnccc43)c2)n1] |
| B36 | 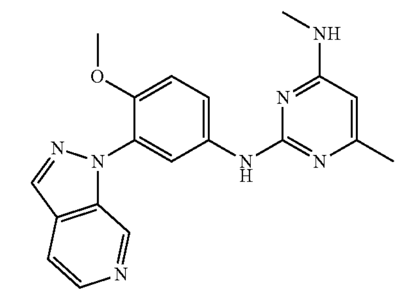 [SMILES: CNc1cc(C)nc(Nc2ccc(OC)c(-n3ncc4ccncc43)c2)n1] |
| B37 | 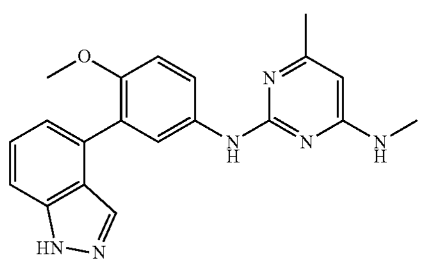 [SMILES: CNc1cc(C)nc(Nc2ccc(OC)c(-c3cccc4[nH]ncc34)c2)n1] |
| B38 | 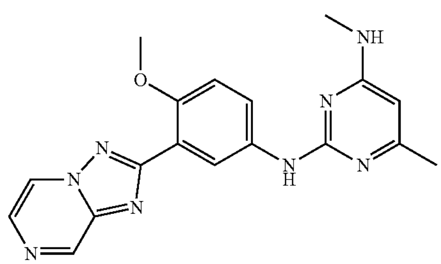 [SMILES: CNc1cc(C)nc(Nc2ccc(OC)c(-c3nc4cnccn4n3)c2)n1] |
| B39 | 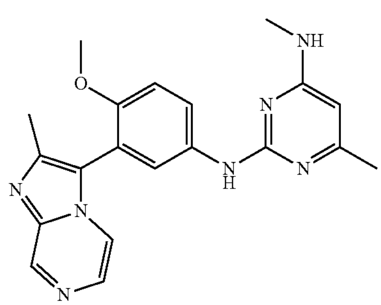 [SMILES: CNc1cc(C)nc(Nc2ccc(OC)c(-c3c(C)nc4cnccn34)c2)n1] |

TABLE 5-continued

| Compound No. | Structure |
|---|---|
| B40 | 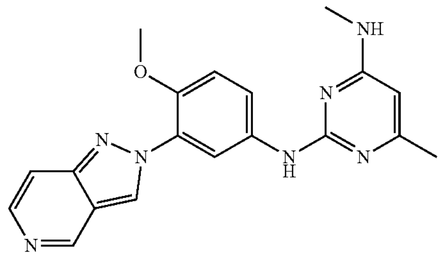 [SMILES: CNc1cc(C)nc(Nc2ccc(OC)c(-n3cc4cnccc4n3)c2)n1] |
| B41 | 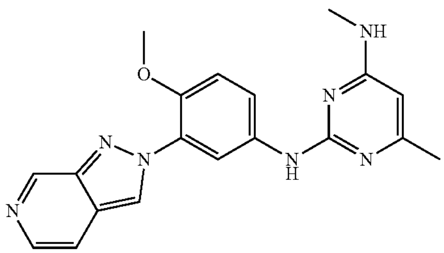 [SMILES: CNc1cc(C)nc(Nc2ccc(OC)c(-n3cc4ccncc4n3)c2)n1] |
| B42 | 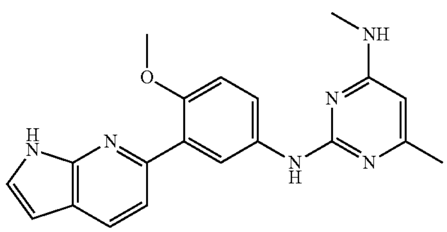 [SMILES: CNc1cc(C)nc(Nc2ccc(OC)c(-c3ccc4cc[nH]c4n3)c2)n1] |
| B43 | 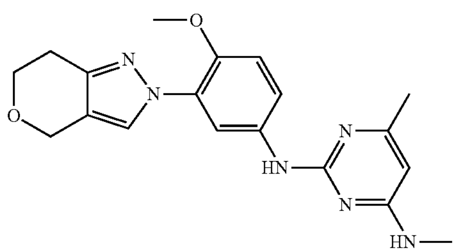 [SMILES: CNc1cc(C)nc(Nc2ccc(OC)c(-n3cc4c(n3)CCOC4)c2)n1] |
| B44 | 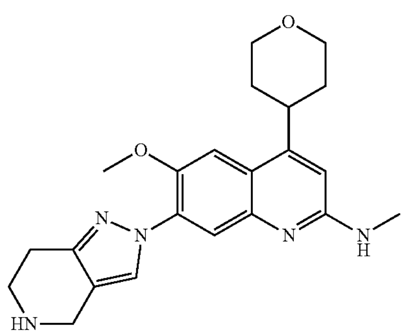 [SMILES: CNc1cc(C2CCOCC2)c2cc(OC)c(-n3cc4c(n3)CCNC4)cc2n1] |
| B45 | 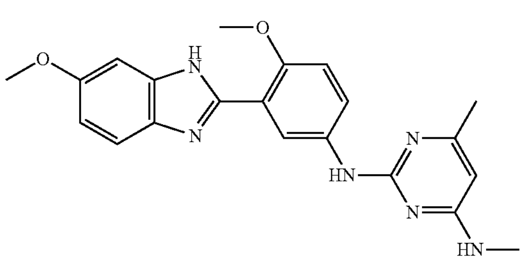 |

TABLE 5-continued
| Compound No. | Structure |
|---|---|
| B46 | 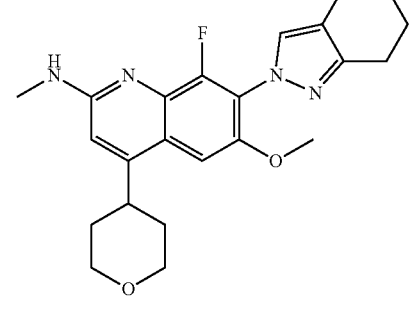 |
| B47 | 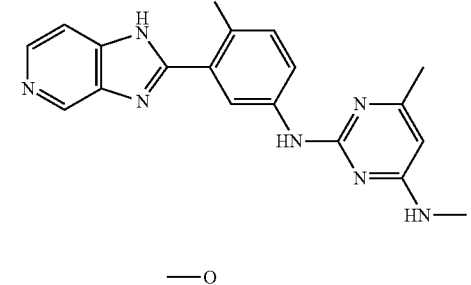 |
| B48 | 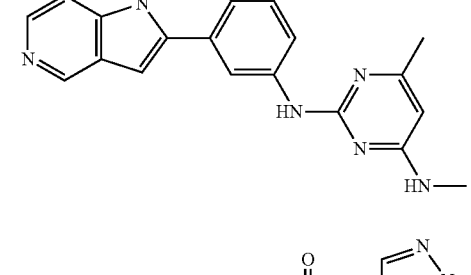 |
| B49 | 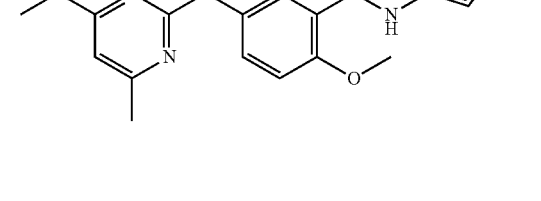 |
| B50 | 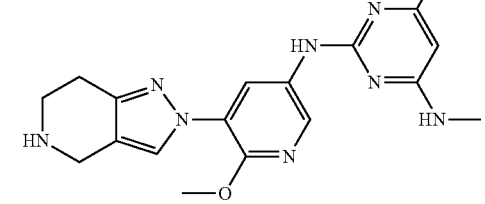 |

TABLE 5-continued

| Compound No. | Structure |
|---|---|
| B51 | 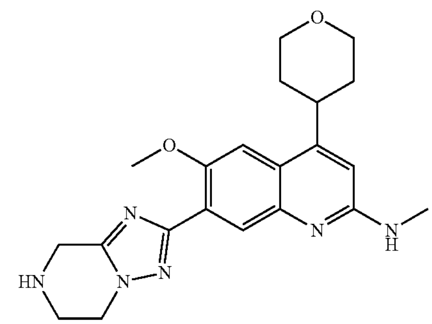 [SMILES: CNc1cc(C2CCOCC2)c2cc(OC)c(-c3nc4n(n3)CCNC4)cc2n1] |
| B52 | 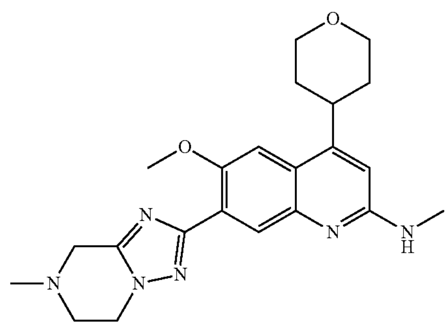 |
| B53 | 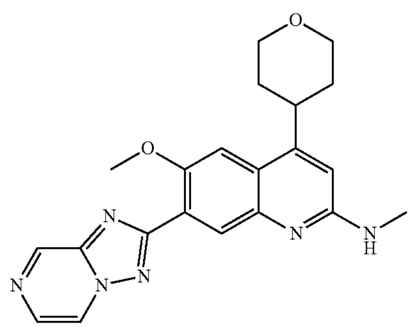 [SMILES: CNc1cc(C2CCOCC2)c2cc(OC)c(-c3nc4cnccn4n3)cc2n1] |
| B54 | 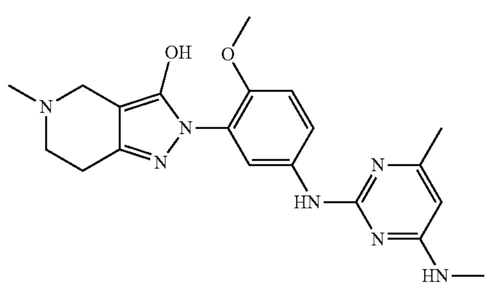 |
| B55 | 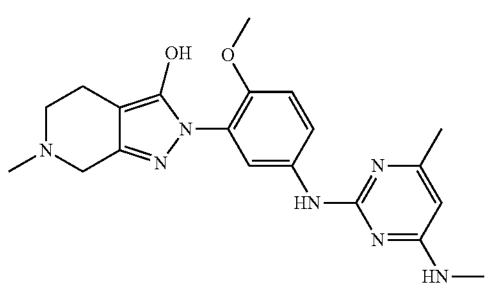 |

TABLE 5-continued

| Compound No. | Structure |
|---|---|
| B56 | 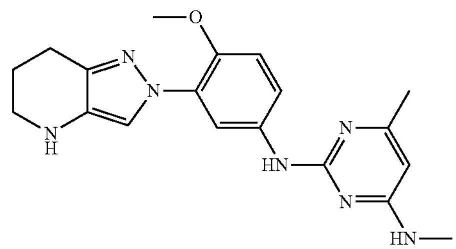 [SMILES: CNc1cc(C)nc(Nc2ccc(OC)c(-n3cc4c(n3)CCCN4)c2)n1] |
| B57 | 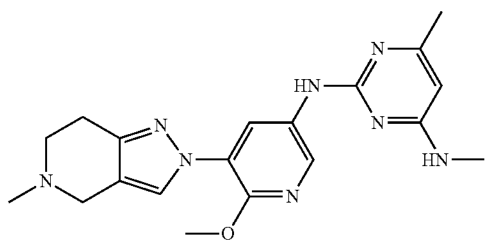 |
| B58 | 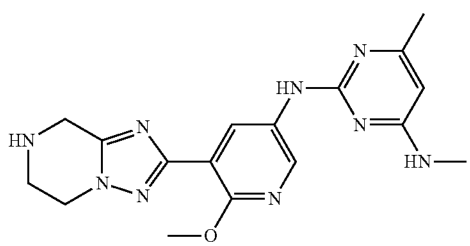 [SMILES: CNc1cc(C)nc(Nc2cnc(OC)c(-c3nc4n(n3)CCNC4)c2)n1] |
| B59 | 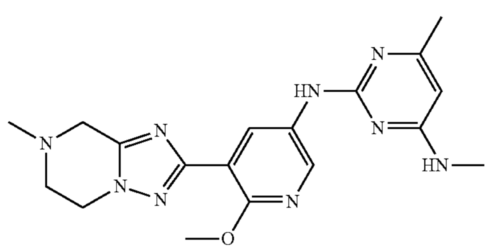 |
| B60 | 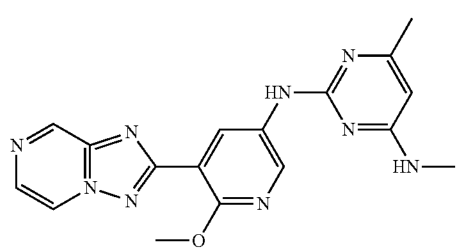 |
| B61 | 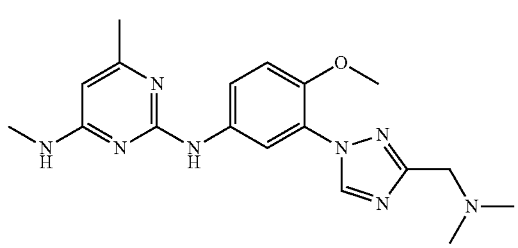 |

TABLE 5-continued

| Compound No. | Structure |
|---|---|
| B62 | 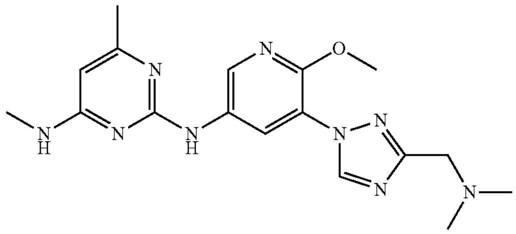 |
| B63 | 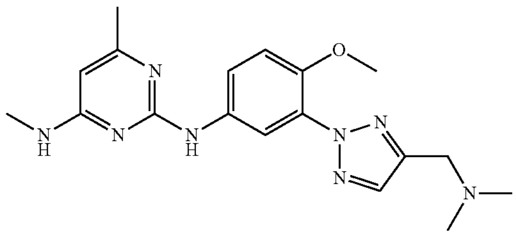 |
| B64 | 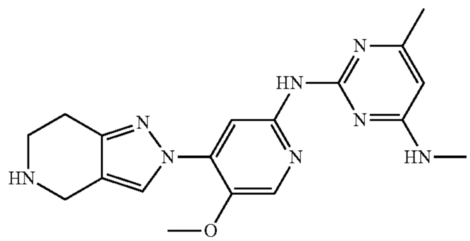 [SMILES: CNc1cc(C)nc(Nc2cc(-n3cc4c(n3)CCNC4)c(OC)cn2)n1] |
| B65 | 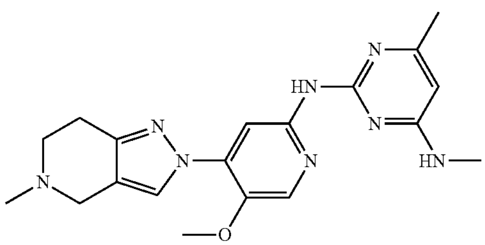 |
| B66 | 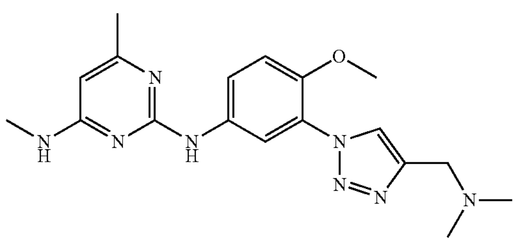 |
| B67 | 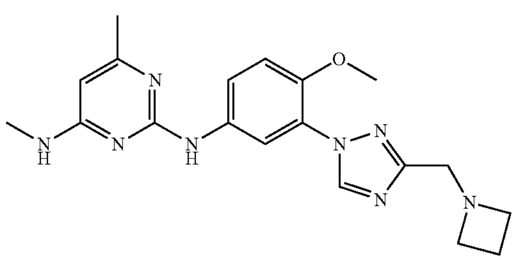 [SMILES: CNc1cc(C)nc(Nc2ccc(OC)c(-n3cnc(CN4CCC4)n3)c2)n1] |

TABLE 5-continued

| Compound No. | Structure |
|---|---|
| B68 | 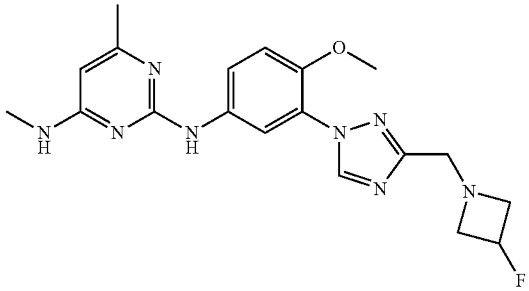 [SMILES: CNc1cc(C)nc(Nc2ccc(OC)c(-n3cnc(CN4CC(F)C4)n3)c2)n1] |
| B69 | 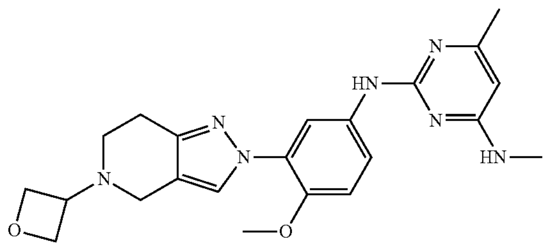 [SMILES: CNc1cc(C)nc(Nc2ccc(OC)c(-n3cc4c(n3)CCN(C3COC3)C4)c2)n1] |
| B70 | 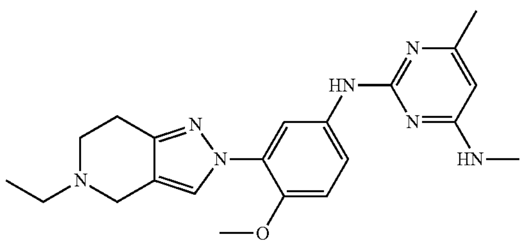 [SMILES: CCN1CCc2nn(-c3cc(Nc4nc(C)cc(NC)n4)ccc3OC)cc2C1] |
| B71 | 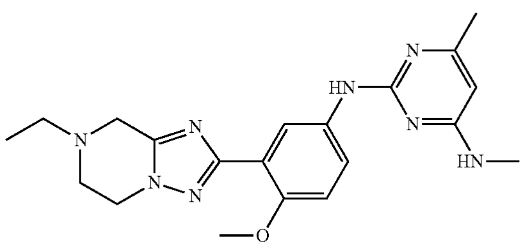 [SMILES: CCN1CCn2nc(-c3cc(Nc4nc(C)cc(NC)n4)ccc3OC)nc2C1] |
| B72 | 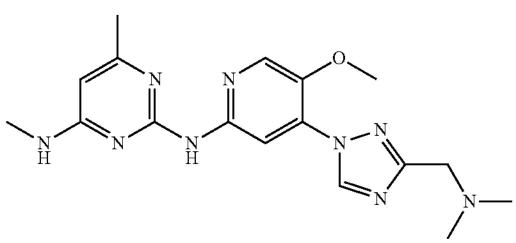 |
| B73 | 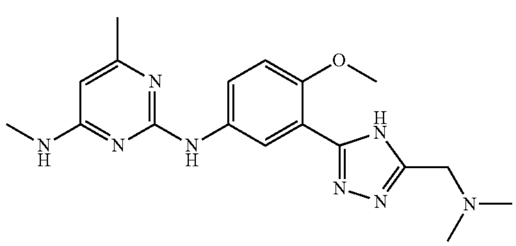 |

TABLE 5-continued

| Compound No. | Structure |
|---|---|
| B74 | 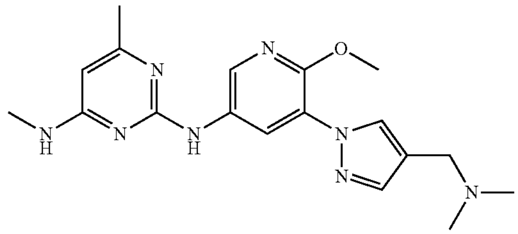 |
| B75 | 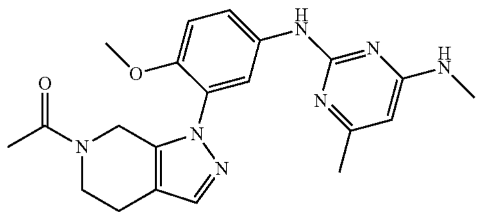 [SMILES: CNc1cc(C)nc(Nc2ccc(OC)c(-n3ncc4c3CN(C(C)=O)CC4)c2)n1] |
| B76 | 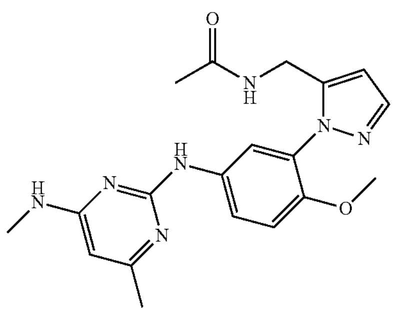 [SMILES: CNc1cc(C)nc(Nc2ccc(OC)c(-n3nccc3CNC(C)=O)c2)n1] |
| B77 | 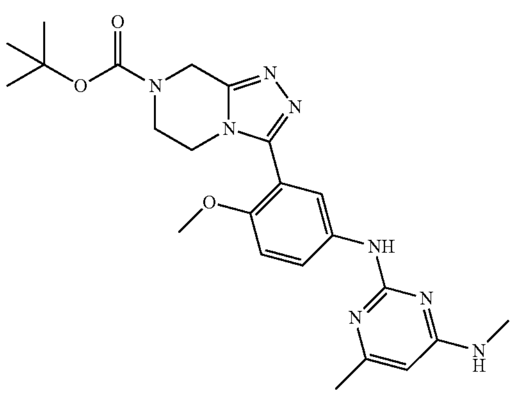 [SMILES: CNc1cc(C)nc(Nc2ccc(OC)c(-c3nnc4n3CCN(C(=O)OC(C)(C)C)C4)c2)n1] |
| B78 | 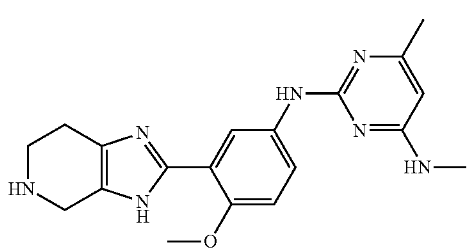 [SMILES: CNc1cc(C)nc(Nc2ccc(OC)c(-c3nc4c([nH]3)CNCC4)c2)n1] |

TABLE 5-continued

| Compound No. | Structure |
|---|---|
| B79 | 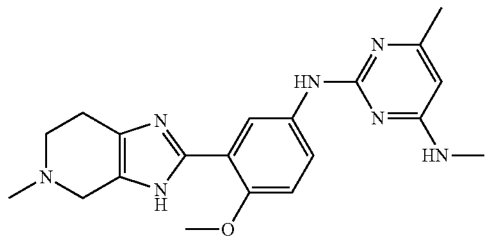 |
| B80 | 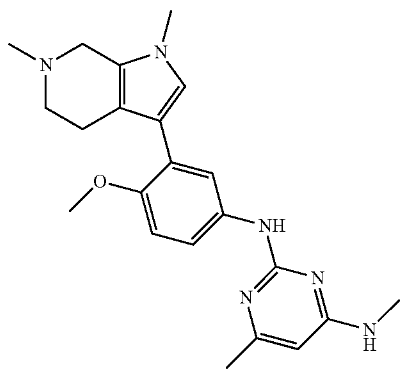 |
| B81 | 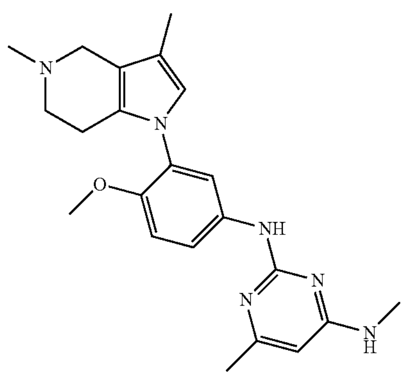 |
| B82 | 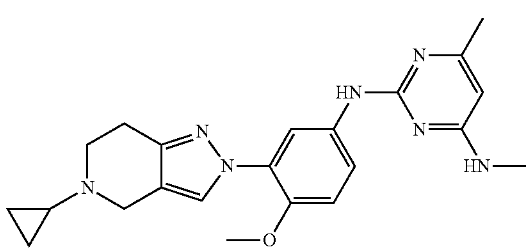 [SMILES: CNc1cc(C)nc(Nc2ccc(OC)c(-n3cc4c(n3)CCN(C3CC3)C4)c2)n1] |
| B83 | 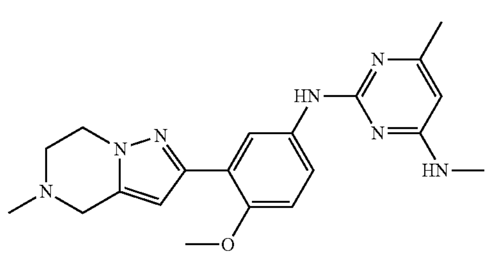 |

TABLE 5-continued
| Compound No. | Structure |
|---|---|
| B84 | 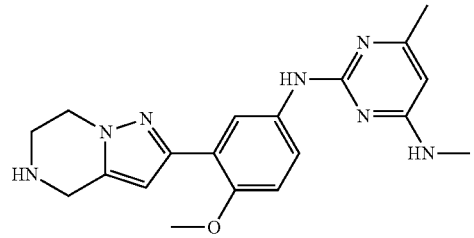 [SMILES: CNc1cc(C)nc(Nc2ccc(OC)c(-c3cc4n(n3)CCNC4)c2)n1] |
| B85 | 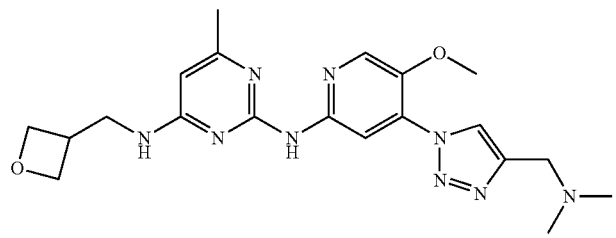 [SMILES: COc1cnc(Nc2nc(C)cc(NCC3COC3)n2)cc1-n1cc(CN(C)C)nn1] |
| B86 | 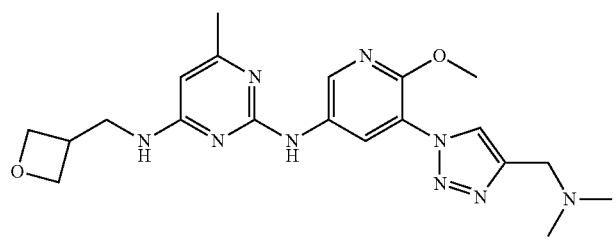 [SMILES: COc1ncc(Nc2nc(C)cc(NCC3COC3)n2)cc1-n1cc(CN(C)C)nn1] |
| B87 | 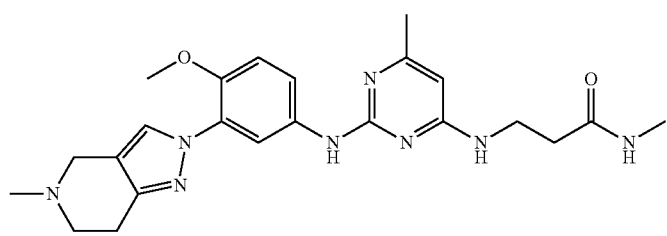 |
| B88 | 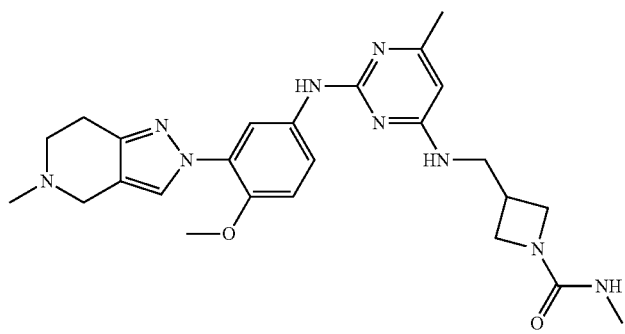 |
| B89 | 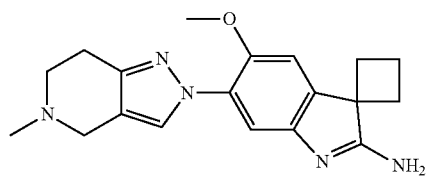 [SMILES: COc1cc2c(cc1-n1cc3c(n1)CCN(C)C3)N=C(N)C21CCC1] |

TABLE 5-continued

| Compound No. | Structure |
| --- | --- |
| B90 | 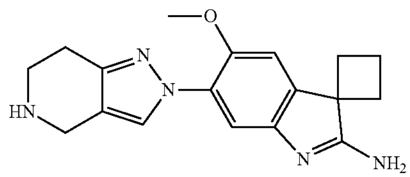 [SMILES: COc1cc2c(cc1-n1cc3c(n1)CCNC3)N=C(N)C21CCC1] |
| B91 | 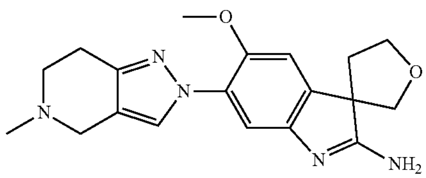 [SMILES: COc1cc2c(cc1-n1cc3c(n1)CCN(C)C3)N=C(N)C21CCOC1] |
| B92 | 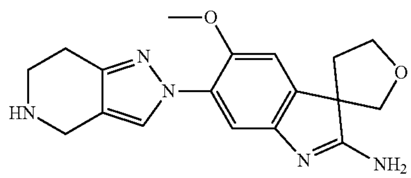 [SMILES: COc1cc2c(cc1-n1cc3c(n1)CCNC3)N=C(N)C21CCOC1] |
| B93 | 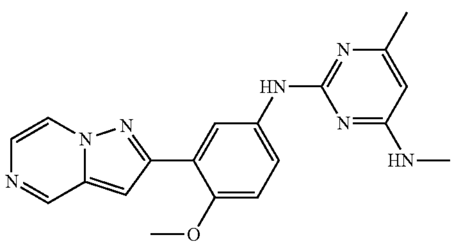 [SMILES: CNc1cc(C)nc(Nc2ccc(OC)c(-c3cc4cnccn4n3)c2)n1] |
| B94 | 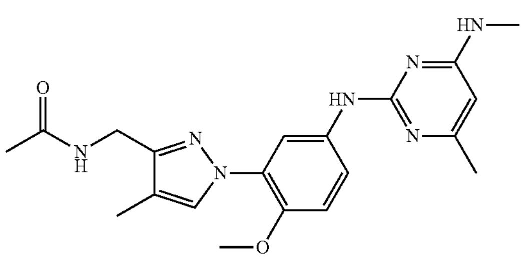 |
| B95 | 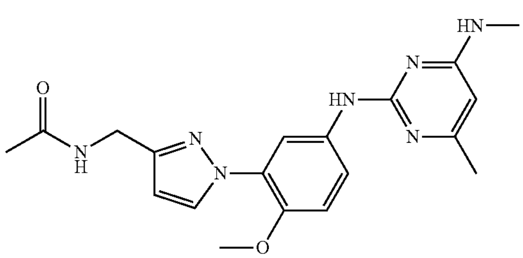 [SMILES: CNc1cc(C)nc(Nc2ccc(OC)c(-n3ccc(CNC(C)=O)n3)c2)n1] |
| B96 | 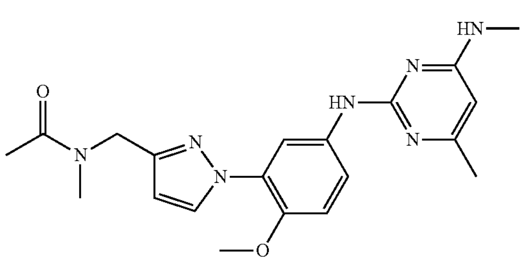 [SMILES: CNc1cc(C)nc(Nc2ccc(OC)c(-n3ccc(CN(C)C(C)=O)n3)c2)n1] |

TABLE 5-continued

| Compound No. | Structure |
|---|---|
| B97 | 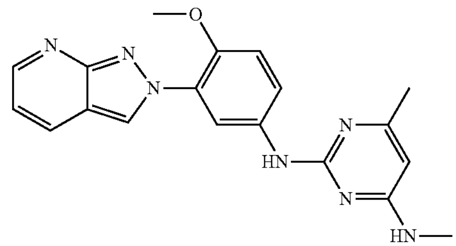 [SMILES: CNc1cc(C)nc(Nc2ccc(OC)c(-n3cc4cccnc4n3)c2)n1] |
| B98 | 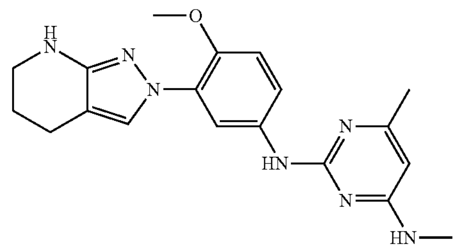 [SMILES: CNc1cc(C)nc(Nc2ccc(OC)c(-n3cc4c(n3)NCCC4)c2)n1] |
| B99 | 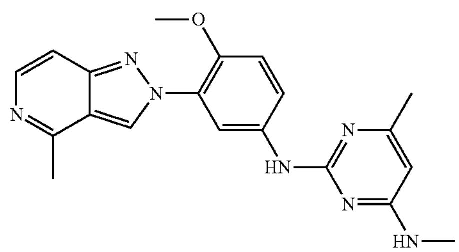 [SMILES: CNc1cc(C)nc(Nc2ccc(OC)c(-n3cc4c(C)nccc4n3)c2)n1] |
| B100 | 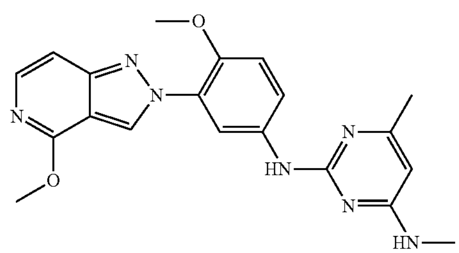 [SMILES: CNc1cc(C)nc(Nc2ccc(OC)c(-n3cc4c(OC)nccc4n3)c2)n1] |
| B101 | 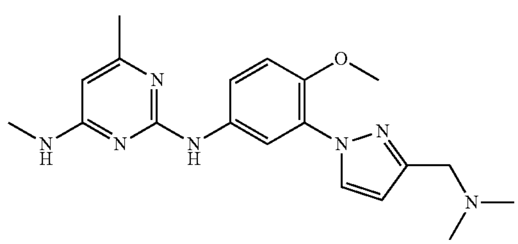 |
| B102 | 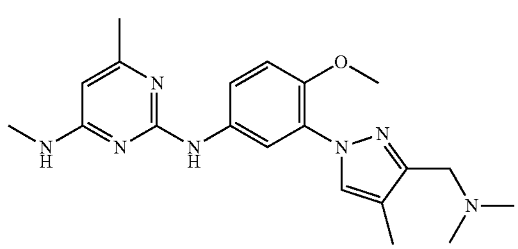 |

TABLE 5-continued

| Compound No. | Structure |
|---|---|
| B103 | 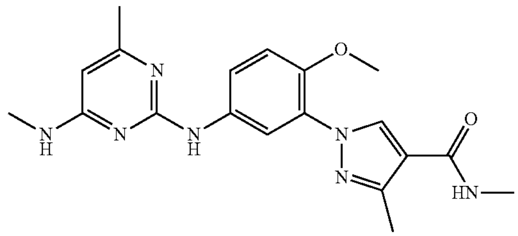 |
| B104 | 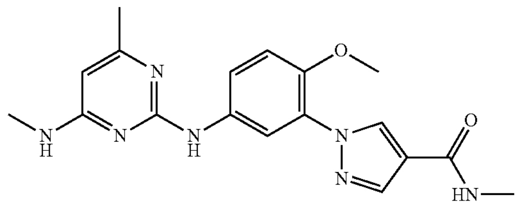 |
| B105 | 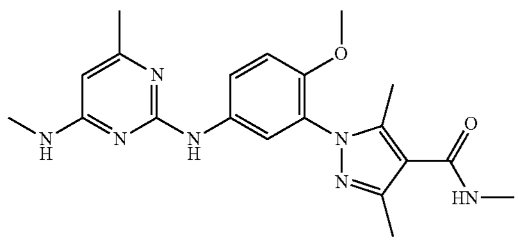 |
| B106 | 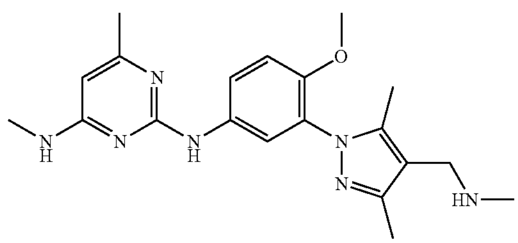 |
| B107 | 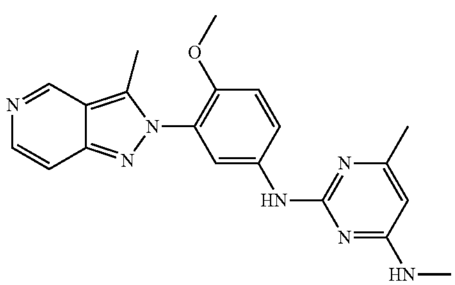 [SMILES: CNc1cc(C)nc(Nc2ccc(OC)c(-n3nc4ccncc4c3C)c2)n1] |
| B108 | 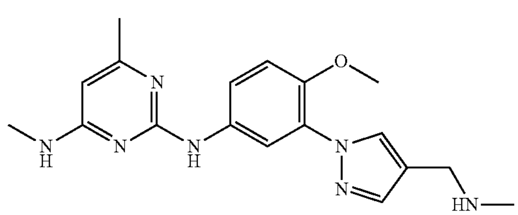 |

TABLE 5-continued
| Compound No. | Structure |
|---|---|
| B109 | 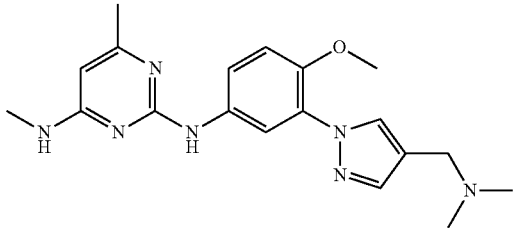 |
| B110 | 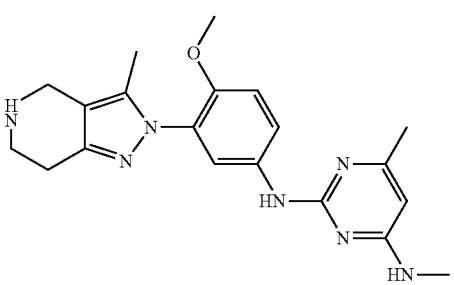 [SMILES: CNc1cc(C)nc(Nc2ccc(OC)c(-n3nc4c(c3C)CNCC4)c2)n1] |
| B111 | 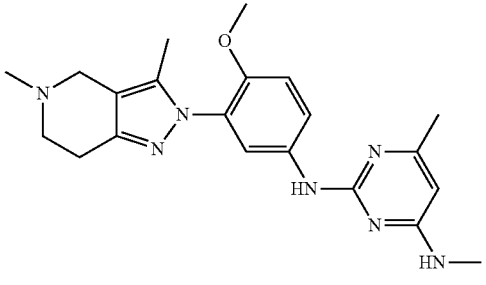 |
| B112 | 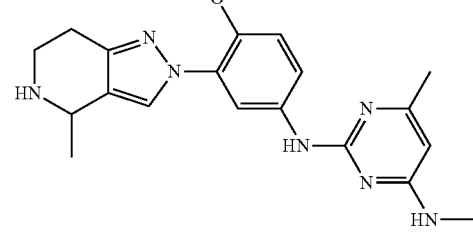 |
| B113 | 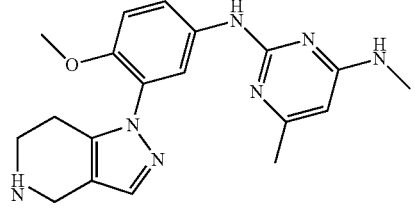 [SMILES: CNc1cc(C)nc(Nc2ccc(OC)c(-n3ncc4c3CCNC4)c2)n1] |
| B114 | 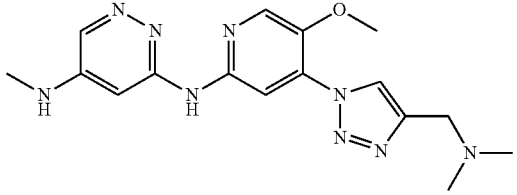 |

TABLE 5-continued

| Compound No. | Structure |
| --- | --- |
| B115 | 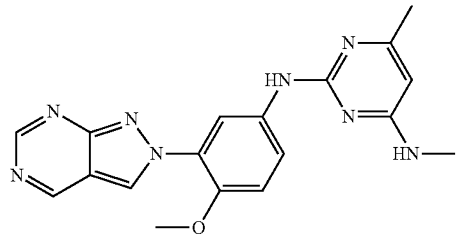 [SMILES: CNc1cc(C)nc(Nc2ccc(OC)c(-n3cc4cncnc4n3)c2)n1] |
| B116 | 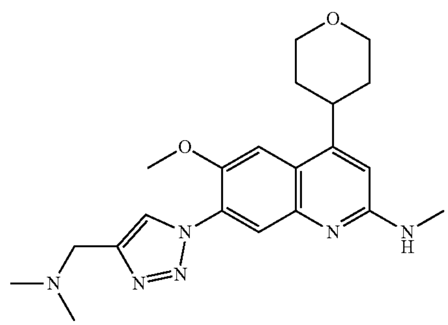 |
| B117 | 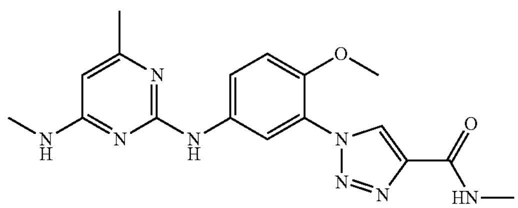 |
| B118 | 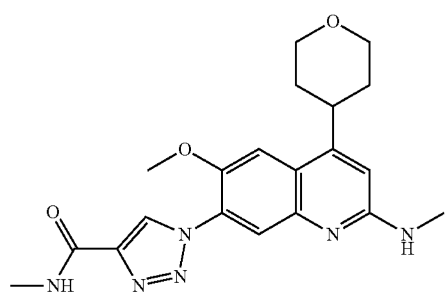 |
| B119 | 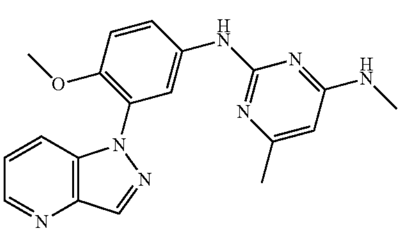 [SMILES: CNc1cc(C)nc(Nc2ccc(OC)c(-n3ncc4ncccc43)c2)n1] |
| B120 | 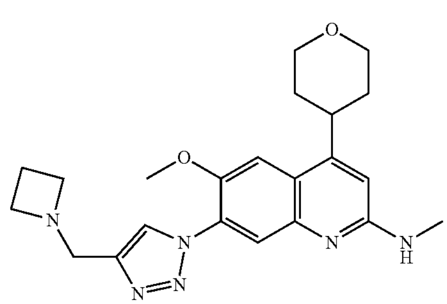 [SMILES: CNc1cc(C2CCOCC2)c2cc(OC)c(-n3cc(CN4CCC4)nn3)cc2n1] |

TABLE 5-continued
| Compound No. | Structure |
|---|---|
| B121 | 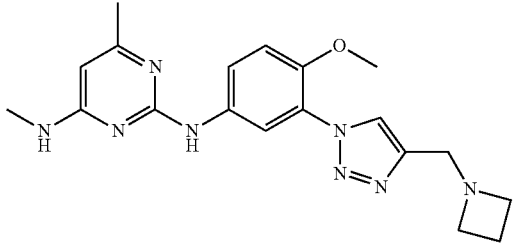 [SMILES: CNc1cc(C)nc(Nc2ccc(OC)c(-n3cc(CN4CCC4)nn3)c2)n1] |
| B122 | 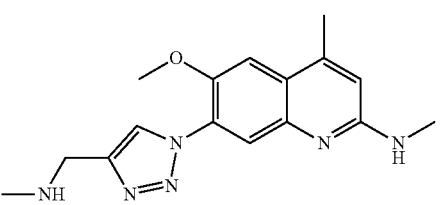 |
| B123 | 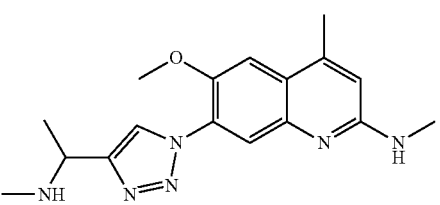 |
| B124 | 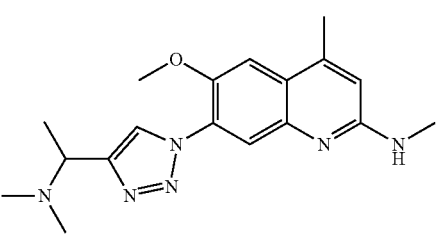 |
| B125 | 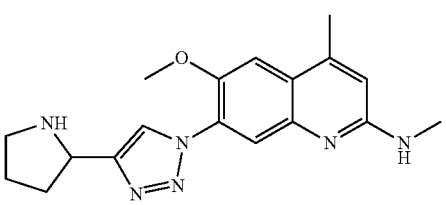 [SMILES: CNc1cc(C)c2cc(OC)c(-n3cc(C4CCCN4)nn3)cc2n1] |
| B126 | 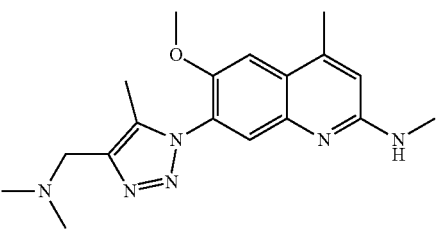 |

TABLE 5-continued
| Compound No. | Structure |
|---|---|
| B127 | 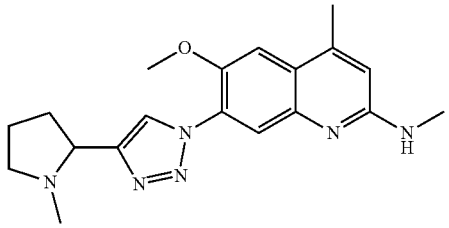 [SMILES: CNc1cc(C)c2cc(OC)c(-n3cc(C4CCCN4C)nn3)cc2n1] |
| B128 | 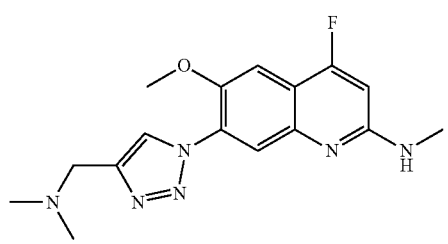 |
| B129 | 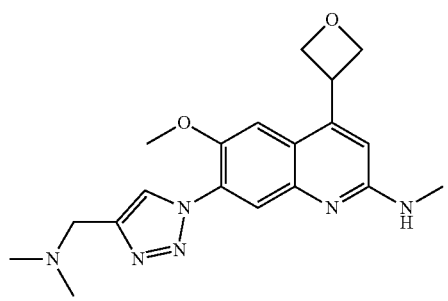 |
| B130 | 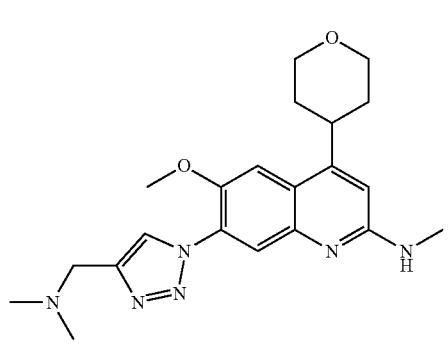 |
| B131 | 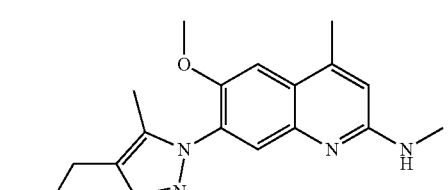 |

TABLE 5-continued

| Compound No. | Structure |
|---|---|
| B132 | 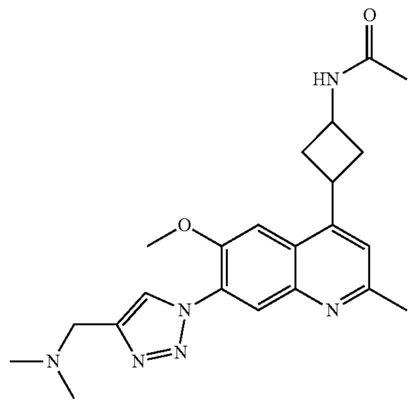 [SMILES: COc1cc2c(C3CC(NC(C)=O)C3)cc(C)nc2cc1-n1cc(CN(C)C)nn1] |
| B133 | 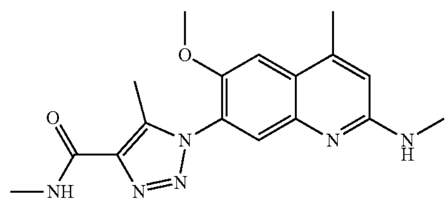 |
| B134 | 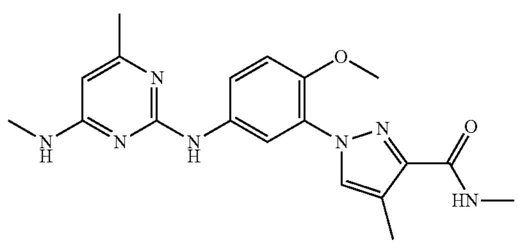 |
| B135 | 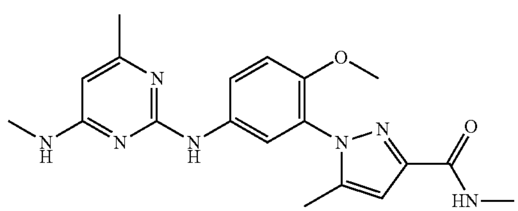 |
| B136 | 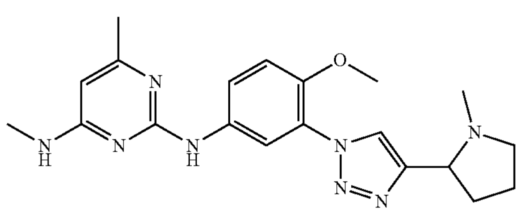 [SMILES: CNc1cc(C)nc(Nc2ccc(OC)c(-n3cc(C4CCCN4C)nn3)c2)n1] |
| B137 | 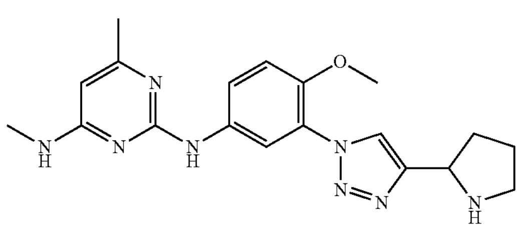 [SMILES: CNc1cc(C)nc(Nc2ccc(OC)c(-n3cc(C4CCCN4)nn3)c2)n1] |

TABLE 5-continued

| Compound No. | Structure |
|---|---|
| B138 | 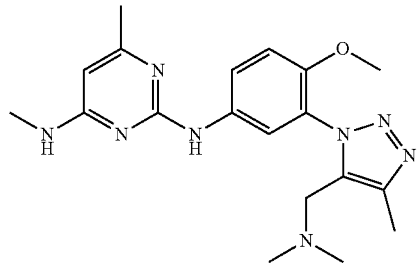 [SMILES: CNc1cc(C)nc(Nc2ccc(OC)c(-n3nnc(C)c3CN(C)C)c2)n1] |
| B139 | 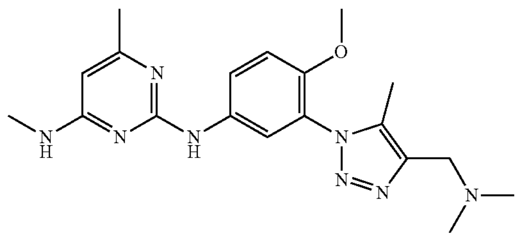 |
| B140 | 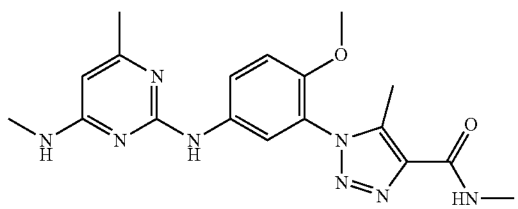 |
| B141 | 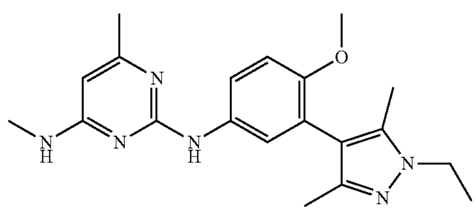 [SMILES: CCn1nc(C)c(-c2cc(Nc3nc(C)cc(NC)n3)ccc2OC)c1C] |
| B142 | 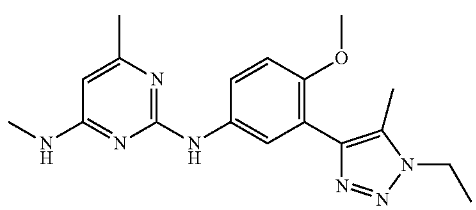 [SMILES: CCn1nnc(-c2cc(Nc3nc(C)cc(NC)n3)ccc2OC)c1C] |
| B143 | 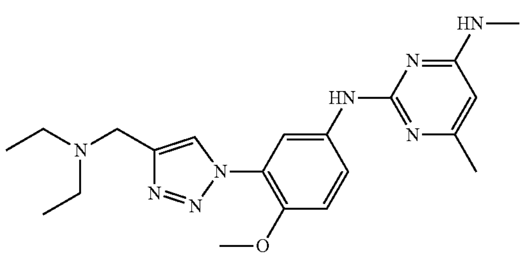 [SMILES: CCN(CC)Cc1cn(-c2cc(Nc3nc(C)cc(NC)n3)ccc2OC)nn1] |

TABLE 5-continued

| Compound No. | Structure |
|---|---|
| B144 | (5-methyl-2H-indazol-2-yl) substituted methoxyphenyl linked to N-methyl-6-methylpyrimidin-4-amine via NH |
| B145 | (5-cyclopropyl-2H-indazol-2-yl) substituted methoxyphenyl linked to N-methyl-6-methylpyrimidin-4-amine via NH |
| B146 | (2H-indazol-2-yl) substituted methoxyphenyl linked to N-methyl-6-methylpyrimidin-4-amine via NH |
| B147 | (5-methyl-2H-pyrazolo[3,4-b]pyridin-2-yl) substituted methoxyphenyl linked to N-methyl-6-methylpyrimidin-4-amine via NH |
| B148 | (5-bromo-2H-indazol-2-yl) substituted methoxyphenyl linked to N-methyl-6-methylpyrimidin-4-amine via NH |
| B149 | (5-methoxy-2H-indazol-2-yl) substituted methoxyphenyl linked to N-methyl-6-methylpyrimidin-4-amine via NH |

TABLE 5-continued

| Compound No. | Structure |
|---|---|
| B150 | 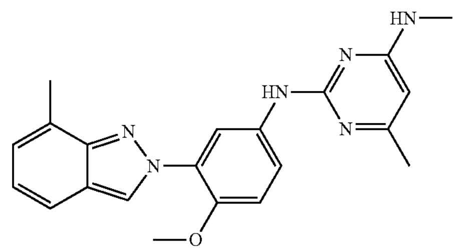 [SMILES: CNc1cc(C)nc(Nc2ccc(OC)c(-n3cc4cccc(C)c4n3)c2)n1] |
| B151 | 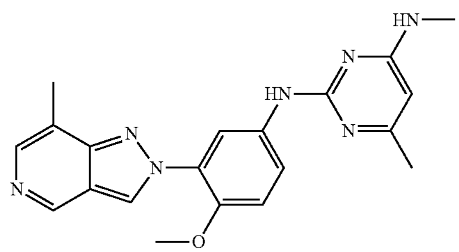 [SMILES: CNc1cc(C)nc(Nc2ccc(OC)c(-n3cc4cncc(C)c4n3)c2)n1] |
| B152 | 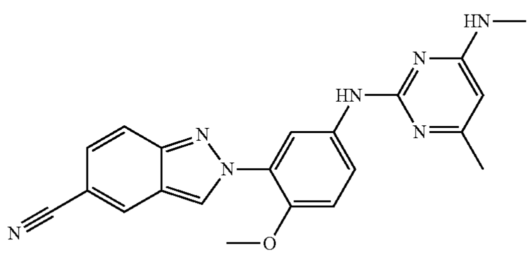 [SMILES: CNc1cc(C)nc(Nc2ccc(OC)c(-n3cc4cc(C#N)ccc4n3)c2)n1] |
| B153 | 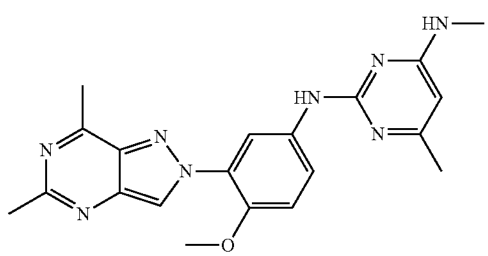 |
| B154 | 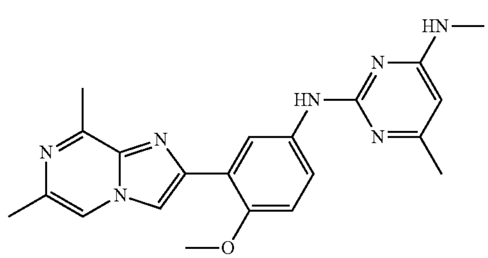 |
| B155 | 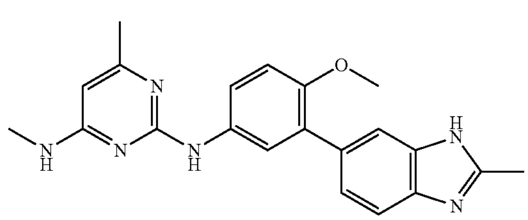 |

TABLE 5-continued

| Compound No. | Structure |
|---|---|
| B156 | 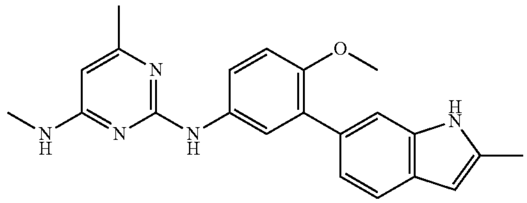 |
| B157 | 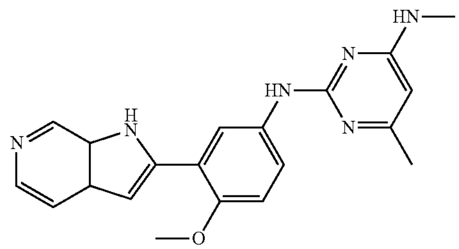 [SMILES: CNc1cc(C)nc(Nc2ccc(OC)c(C3=CC4C=CN=CC4N3)c2)n1] |
| B158 | 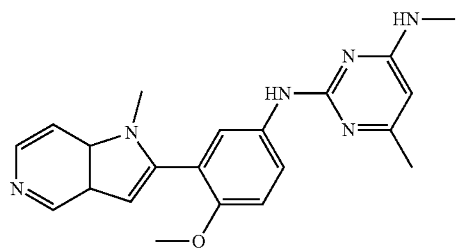 [SMILES: CNc1cc(C)nc(Nc2ccc(OC)c(C3=CC4C=NC=CC4N3C)c2)n1] |
| B159 | 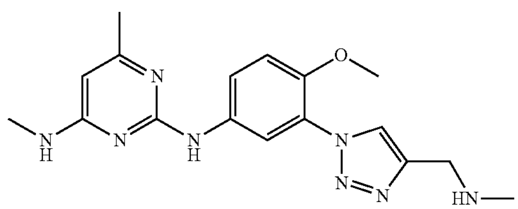 |
| B160 | 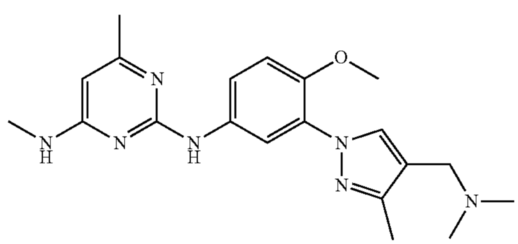 |
| B161 | 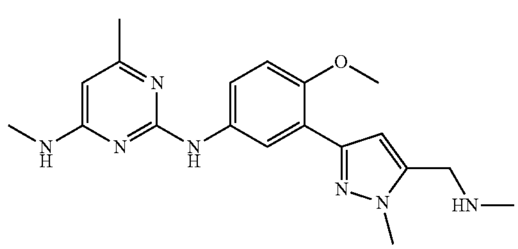 |

TABLE 5-continued

| Compound No. | Structure |
|---|---|
| B162 | 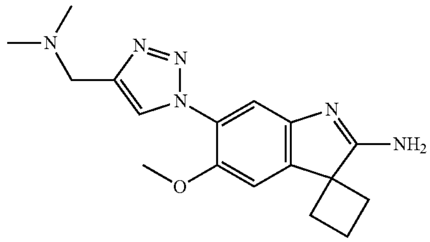 [SMILES: COc1cc2c(cc1-n1cc(CN(C)C)nn1)N=C(N)C21CCC1] |
| B163 | 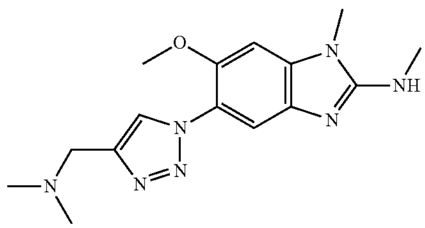 |
| B164 | 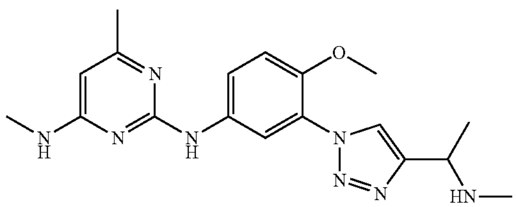 |
| B165 | 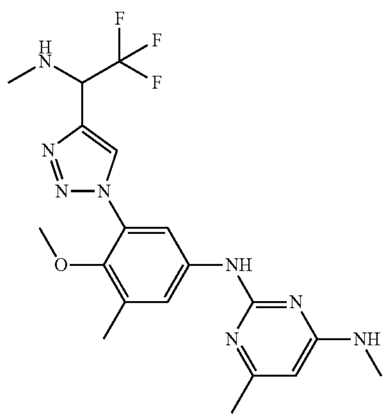 |
| B166 | 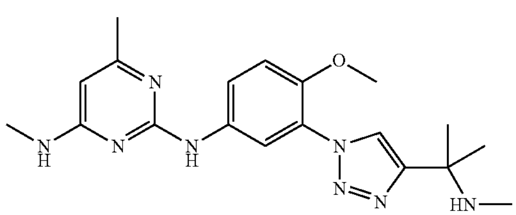 |
| B167 | 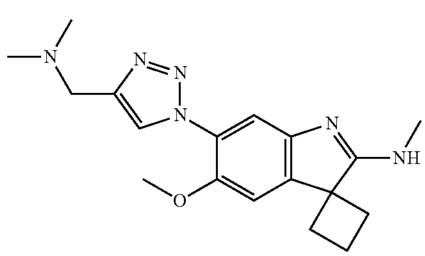 |

TABLE 5-continued

| Compound No. | Structure |
|---|---|
| B168 | 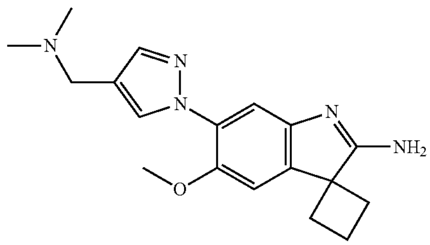 [SMILES: COc1cc2c(cc1-n1cc(CN(C)C)cn1)N=C(N)C21CCC1] |
| B169 | 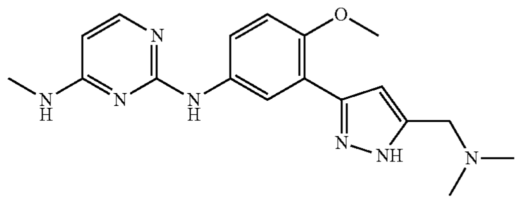 |
| B170 | 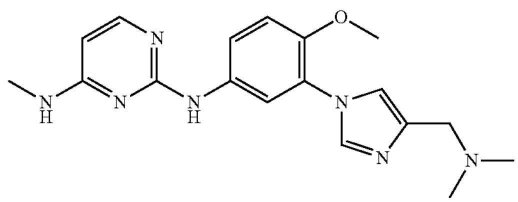 |
| B171 | 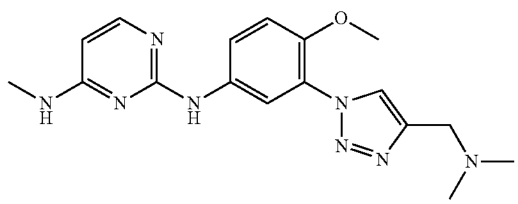 |
| B172 | 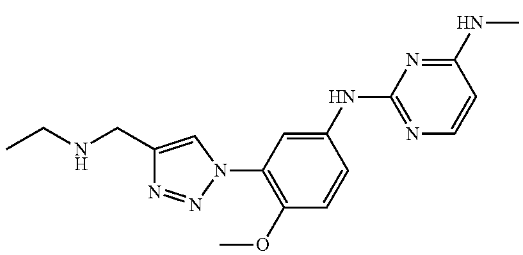 |
| B173 | 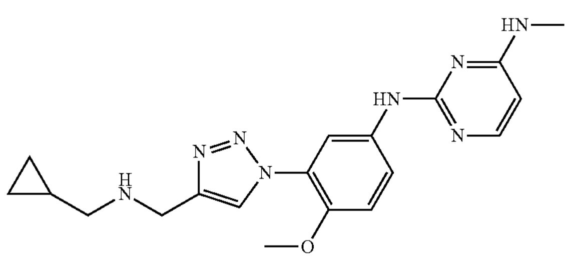 [SMILES: CNc1ccnc(Nc2ccc(OC)c(-n3cc(CNCC4CC4)nn3)c2)n1] |
| B174 | 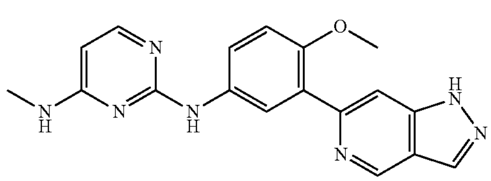 [SMILES: CNc1ccnc(Nc2ccc(OC)c(-c3cc4[nH]ncc4cn3)c2)n1] |

TABLE 5-continued

| Compound No. | Structure |
| --- | --- |
| B175 | 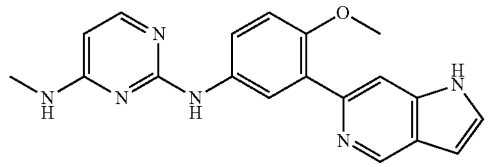 [SMILES: CNc1ccnc(Nc2ccc(OC)c(-c3cc4[nH]ccc4cn3)c2)n1] |
| B176 | 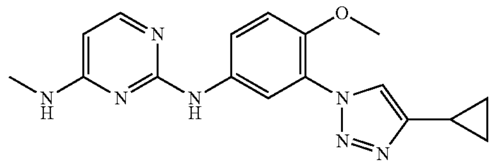 [SMILES: CNc1ccnc(Nc2ccc(OC)c(-n3cc(C4CC4)nn3)c2)n1] |
| B177 | 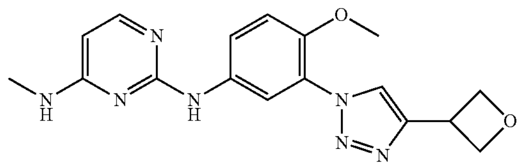 [SMILES: CNc1ccnc(Nc2ccc(OC)c(-n3cc(C4COC4)nn3)c2)n1] |
| B178 | 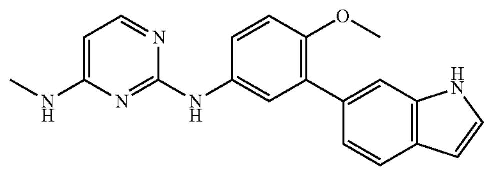 [SMILES: CNc1ccnc(Nc2ccc(OC)c(-c3ccc4cc[nH]c4c3)c2)n1] |
| B179 | 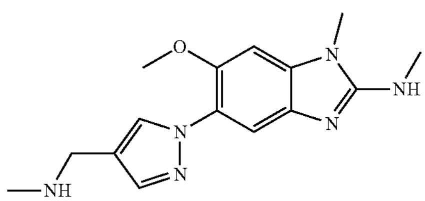 |
| B180 | 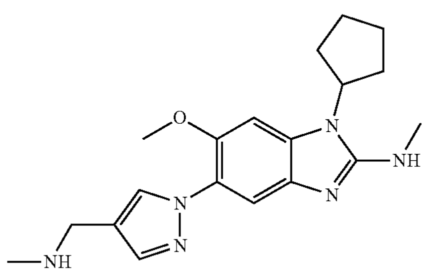 |
| B181 | 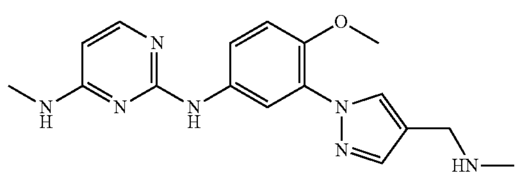 |
| B182 | 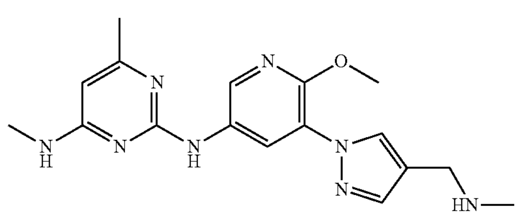 |

TABLE 5-continued

| Compound No. | Structure |
|---|---|
| B183 | (structure) |
| B184 | (structure) |
| B185 | (structure) |
| B186 | (structure) |
| B187 | (structure) |
| B188 | (structure) |

TABLE 5-continued

| Compound No. | Structure |
|---|---|
| B191 | 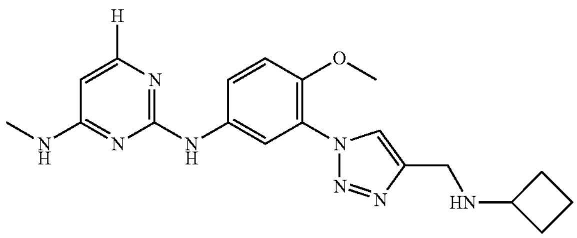 [SMILES: CNc1ccnc(Nc2ccc(OC)c(-n3cc(CNC4CCC4)nn3)c2)n1] |
| B192 | 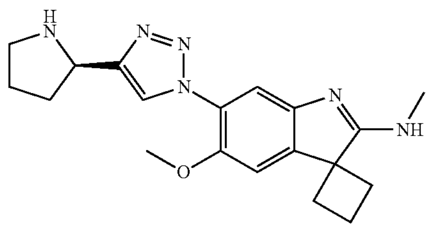 [SMILES: CNC1=Nc2cc(-n3cc([C@H]4CCCN4)nn3)c(OC)cc2C12CCC2] |
| B193 | 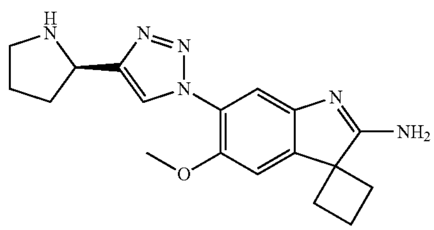 [SMILES: COc1cc2c(cc1-n1cc([C@H]3CCCN3)nn1)N=C(N)C21CCC1] |
| B194 | 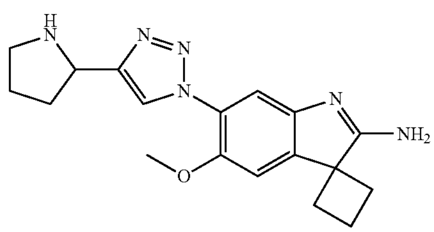 |
| B195 | 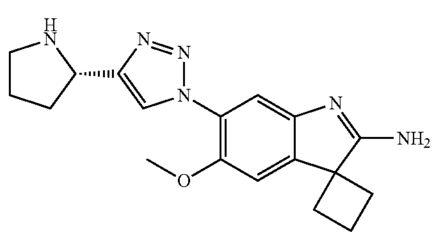 [SMILES: COc1cc2c(cc1-n1cc(C3CCCN3)nn1)N=C(N)C21CCC1] |
| B196 | 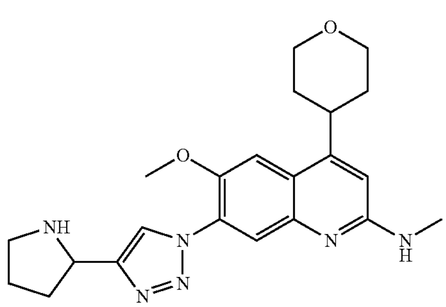 [SMILES: CNc1cc(C2CCOCC2)c2cc(OC)c(-n3cc(C4CCCN4)nn3)cc2n1] |

TABLE 5-continued

| Compound No. | Structure |
|---|---|
| B197 | 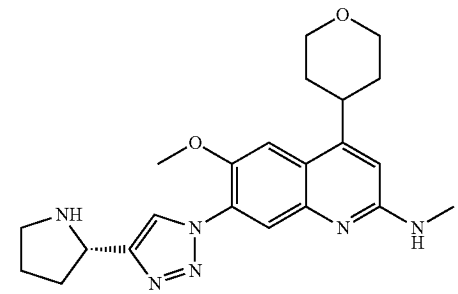 [SMILES: CNc1cc(C2CCOCC2)c2cc(OC)c(-n3cc([C@@H]4CCCN4)nn3)cc2n1] |
| B198 | 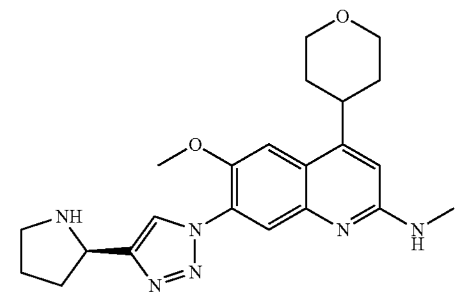 [SMILES: CNc1cc(C2CCOCC2)c2cc(OC)c(-n3cc([C@H]4CCCN4)nn3)cc2n1] |
| B199 | 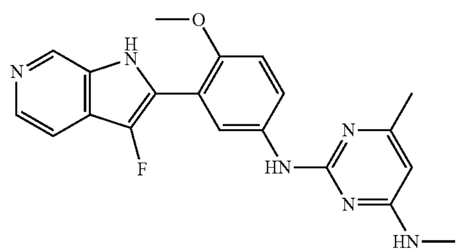 |
| B200 | 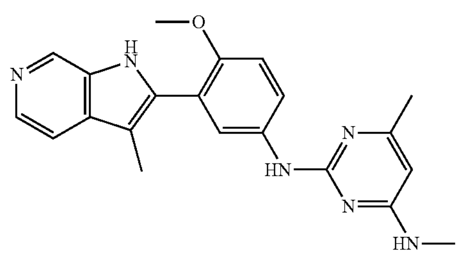 [SMILES: CNc1cc(C)nc(Nc2ccc(OC)c(-c3[nH]c4cnccc4c3F)c2)n1] |
| B201 | 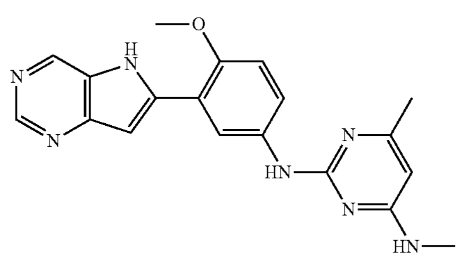 [SMILES: CNc1cc(C)nc(Nc2ccc(OC)c(-c3cc4ncncc4[nH]3)c2)n1] |
| B202 | 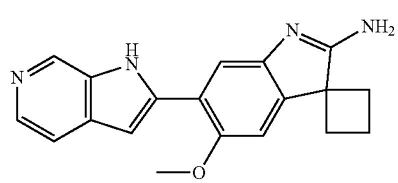 [SMILES: COc1cc2c(cc1-c1cc3ccncc3[nH]1)N=C(N)C21CCC1] |

TABLE 5-continued

| Compound No. | Structure |
|---|---|
| B203 | 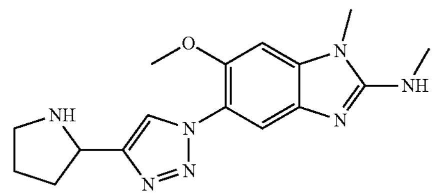 [SMILES: CNc1nc2cc(-n3cc(C4CCCN4)nn3)c(OC)cc2n1C] |
| B204 | 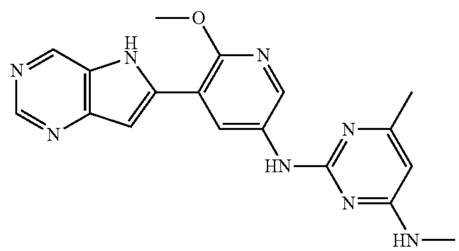 [SMILES: CNc1cc(C)nc(Nc2cnc(OC)c(-c3cc4ncncc4[nH]3)c2)n1] |
| B205 | 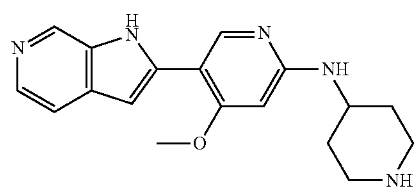 [SMILES: COc1cc(NC2CCNCC2)ncc1-c1cc2ccncc2[nH]1] |
| B206 | 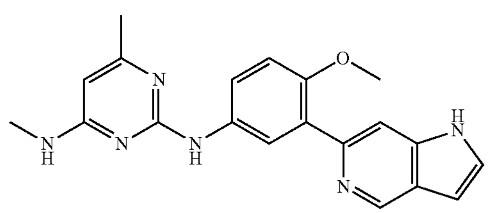 [SMILES: CNc1cc(C)nc(Nc2ccc(OC)c(-c3cc4[nH]ccc4cn3)c2)n1] |
| B207 | 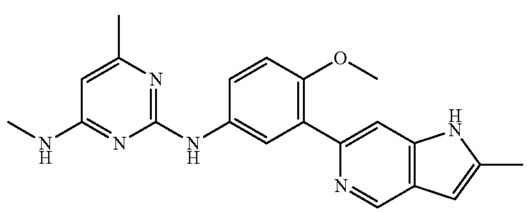 |
| B208 | 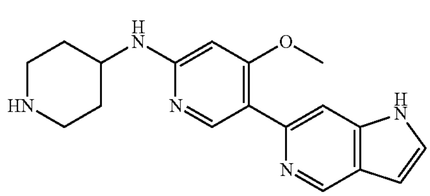 [SMILES: COc1cc(NC2CCNCC2)ncc1-c1cc2[nH]ccc2cn1] |
| B209 | 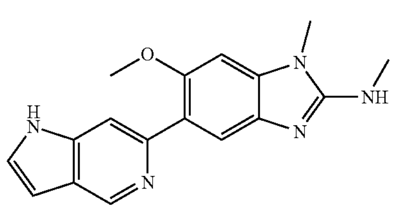 [SMILES: CNc1nc2cc(-c3cc4[nH]ccc4cn3)c(OC)cc2n1C] |

TABLE 5-continued
| Compound No. | Structure |
|---|---|
| B210 | 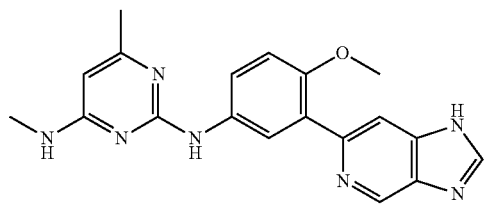 [SMILES: CNc1cc(C)nc(Nc2ccc(OC)c(-c3cc4[nH]cnc4cn3)c2)n1] |
| B211 | 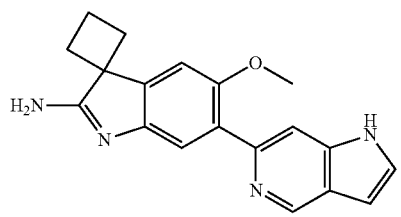 [SMILES: COc1cc2c(cc1-c1cc3[nH]ccc3cn1)N=C(N)C21CCC1] |
| B212 | 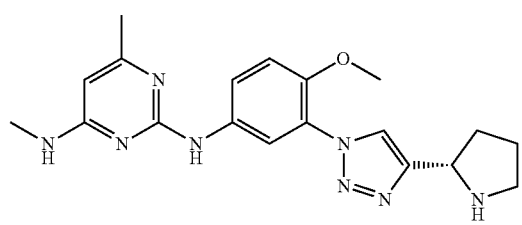 [SMILES: CNc1cc(C)nc(Nc2ccc(OC)c(-n3cc([C@@H]4CCCN4)nn3)c2)n1] |
| B213 | 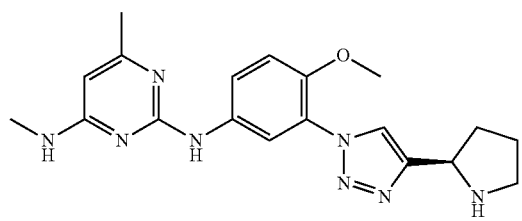 [SMILES: CNc1cc(C)nc(Nc2ccc(OC)c(-n3cc([C@H]4CCCN4)nn3)c2)n1] |
| B214 | 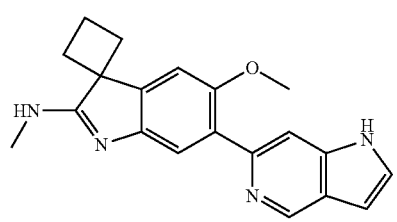 [SMILES: CNC1=Nc2cc(-c3cc4[nH]ccc4cn3)c(OC)cc2C12CCC2] |
| B715 | 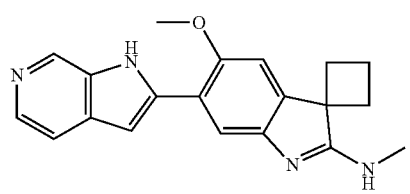 [SMILES: CNC1=Nc2cc(-c3cc4ccncc4[nH]3)c(OC)cc2C12CCC2] |
| B216 | 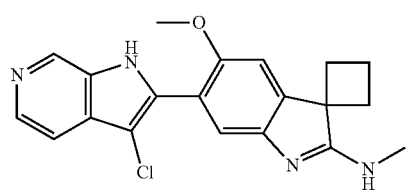 [SMILES: CNC1=Nc2cc(-c3[nH]c4cnccc4c3Cl)c(OC)cc2C12CCC2] |

TABLE 5-continued

| Compound No. | Structure |
|---|---|
| B217 | 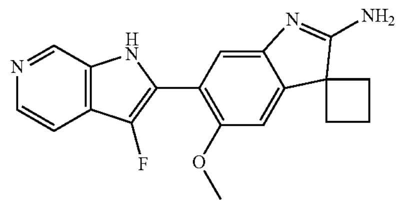 [SMILES: COc1cc2c(cc1-c1[nH]c3cnccc3c1F)N=C(N)C21CCC1] |
| B218 | 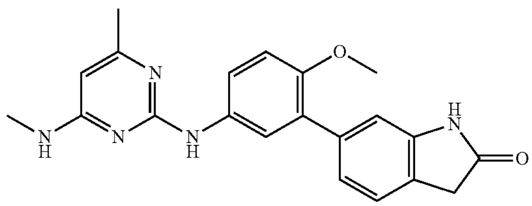 [SMILES: CNc1cc(C)nc(Nc2ccc(OC)c(-c3ccc4c(c3)NC(=O)C4)c2)n1] |
| B219 | 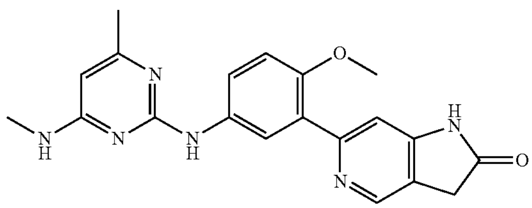 [SMILES: CNc1cc(C)nc(Nc2ccc(OC)c(-c3cc4c(cn3)CC(=O)N4)c2)n1] |
| B220 | 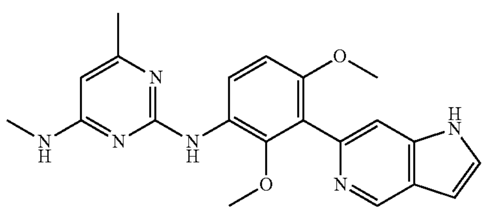 [SMILES: CNc1cc(C)nc(Nc2ccc(OC)c(-c3cc4[nH]ccc4cn3)c2OC)n1] |
| B221 | 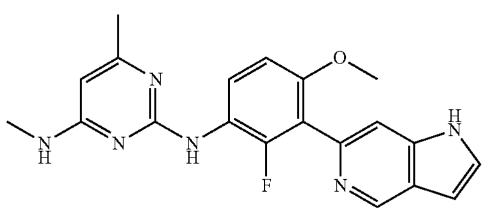 [SMILES: CNc1cc(C)nc(Nc2ccc(OC)c(-c3cc4[nH]ccc4cn3)c2F)n1] |
| B222 | 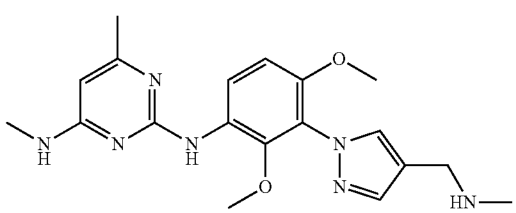 |
| B223 | 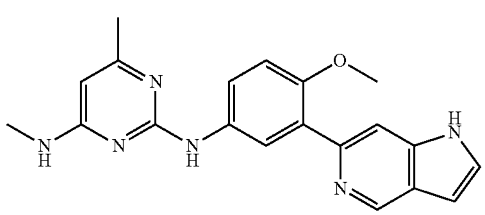 [SMILES: CNc1cc(C)nc(Nc2ccc(OC)c(-c3cc4[nH]ccc4cn3)c2)n1] |

TABLE 5-continued

| Compound No. | Structure |
|---|---|
| B224 | 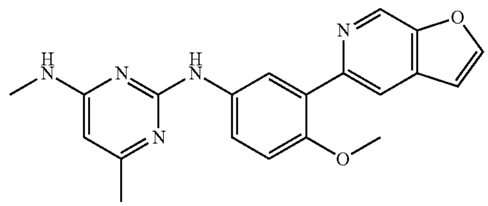 [SMILES: CNc1cc(C)nc(Nc2ccc(OC)c(-c3cc4ccoc4cn3)c2)n1] |
| B225 | 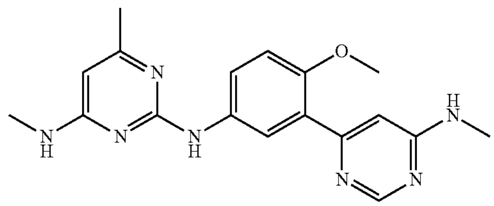 |
| B226 | 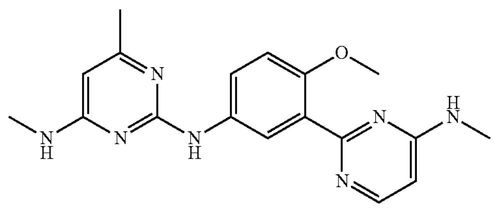 |
| B227 | 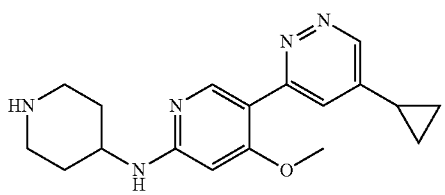 [SMILES: COc1cc(NC2CCNCC2)ncc1-c1cc(C2CC2)cnn1] |
| B228 | 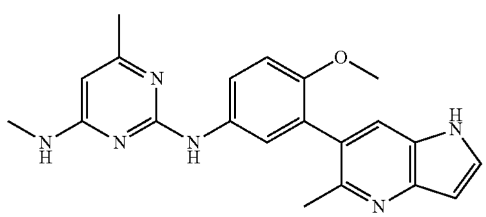 [SMILES: CNc1cc(C)nc(Nc2ccc(OC)c(-c3cc4[nH]ccc4nc3C)c2)n1] |
| B229 | 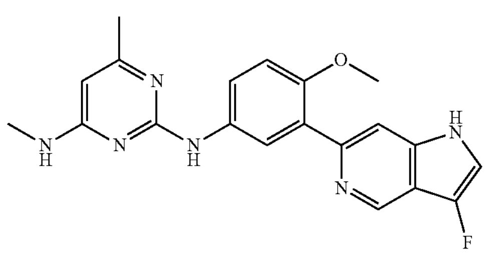 [SMILES: CNc1cc(C)nc(Nc2ccc(OC)c(-c3cc4[nH]cc(F)c4cn3)c2)n1] |
| B230 | 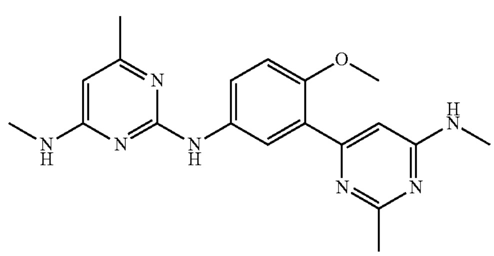 |

TABLE 5-continued

| Compound No. | Structure |
|---|---|
| B231 | 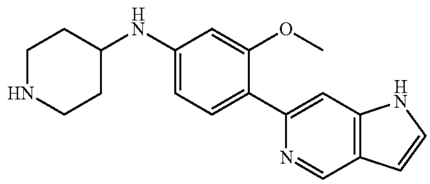 [SMILES: COc1cc(NC2CCNCC2)ccc1-c1cc2[nH]ccc2cn1] |
| B232 | 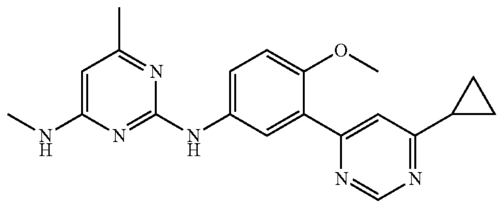 [SMILES: CNc1cc(C)nc(Nc2ccc(OC)c(-c3cc(C4CC4)ncn3)c2)n1] |
| B233 | 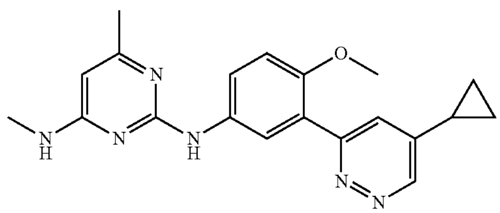 [SMILES: CNc1cc(C)nc(Nc2ccc(OC)c(-c3cc(C4CC4)cnn3)c2)n1] |
| B234 | 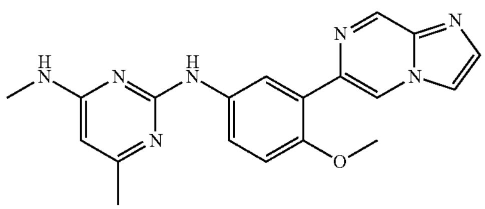 [SMILES: CNc1cc(C)nc(Nc2ccc(OC)c(-c3cn4ccnc4cn3)c2)n1] |
| B235 | 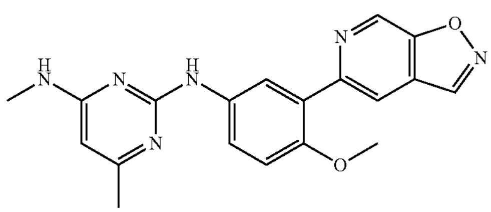 [SMILES: CNc1cc(C)nc(Nc2ccc(OC)c(-c3cc4cnoc4cn3)c2)n1] |
| B236 | 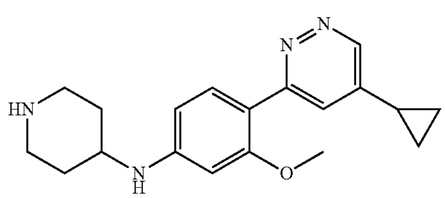 [SMILES: COc1cc(NC2CCNCC2)ccc1-c1cc(C2CC2)cnn1] |
| B237 | 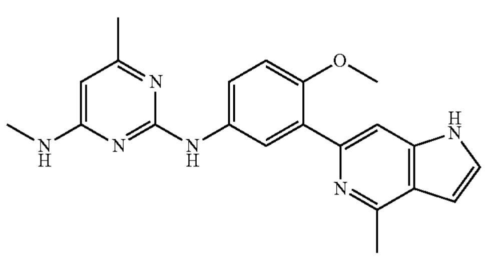 [SMILES: CNc1cc(C)nc(Nc2ccc(OC)c(-c3cc4[nH]ccc4c(C)n3)c2)n1] |

TABLE 5-continued
| Compound No. | Structure |
|---|---|
| B238 | 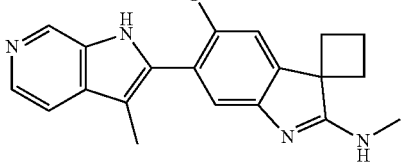 |
| B239 | 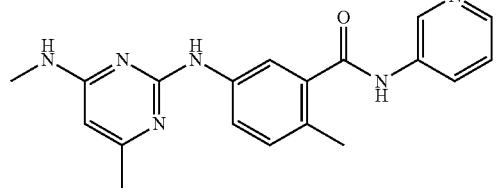 |
| B240 | 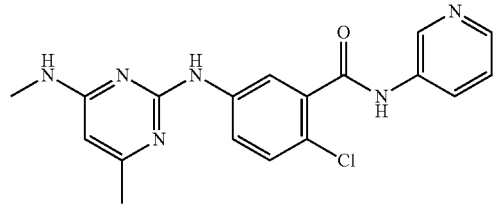 [SMILES: CNc1cc(C)nc(Nc2ccc(C)c(C(=O)Nc3cccnc3)c2)n1] |
| B241 | 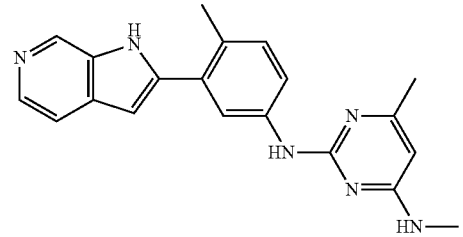 [SMILES: CNc1cc(C)nc(Nc2ccc(C)c(-c3cc4ccncc4[nH]3)c2)n1] |
| B242 | 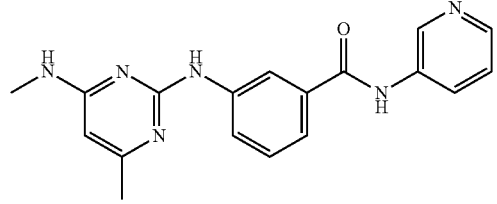 [SMILES: CNc1cc(C)nc(Nc2cccc(C(=O)Nc3cccnc3)c2)n1] |
| B243 | 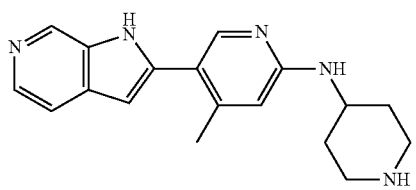 [SMILES: Cc1cc(NC2CCNCC2)ncc1-c1cc2ccncc2[nH]1] |
| B244 | 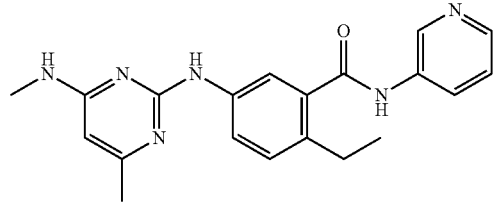 [SMILES: CCc1ccc(Nc2nc(C)cc(NC)n2)cc1C(=O)Nc1cccnc1] |

TABLE 5-continued
| Compound No. | Structure |
|---|---|
| B245 | 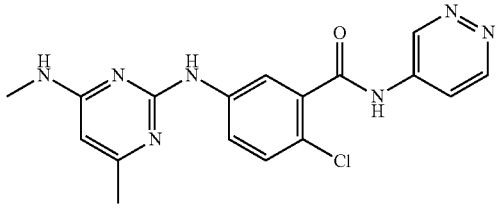 [SMILES: CNc1cc(C)nc(Nc2ccc(Cl)c(C(=O)Nc3ccnnc3)c2)n1] |
| B246 | 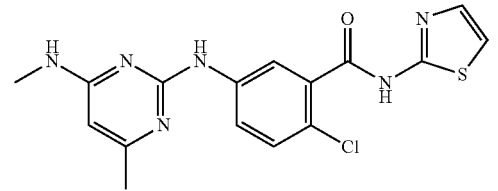 |
| B247 | 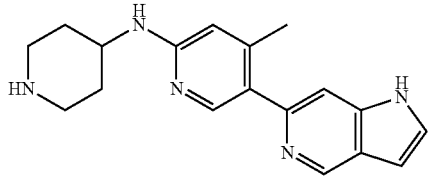 [SMILES: Cc1cc(NC2CCNCC2)ncc1-c1cc2[nH]ccc2cn1] |
| B248 | 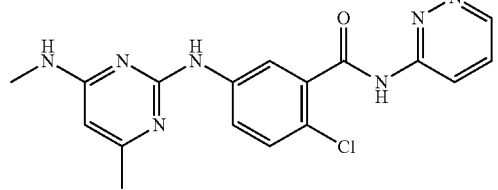 |
| B249 | 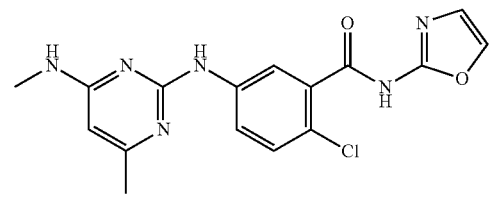 |
| B250 | 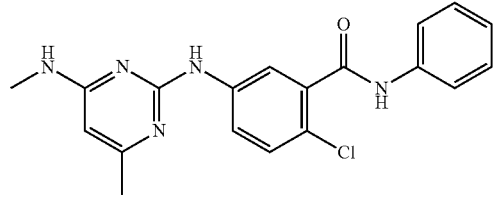 [SMILES: CNc1cc(C)nc(Nc2ccc(Cl)c(C(=O)Nc3ccccc3)c2)n1] |
| B251 | 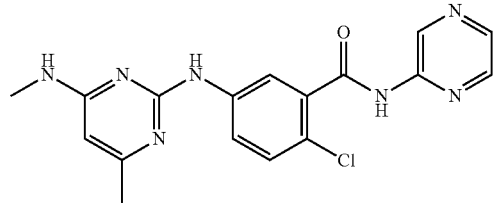 [SMILES: CNc1cc(C)nc(Nc2ccc(Cl)c(C(=O)Nc3cnccn3)c2)n1] |

TABLE 5-continued

| Compound No. | Structure |
|---|---|
| B252 | 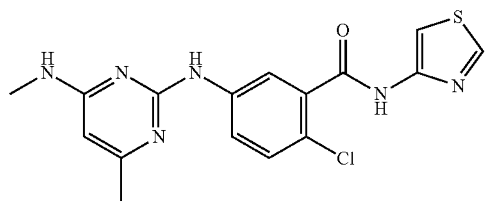 |
| B253 | 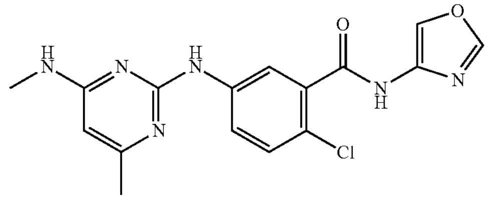 |
| B254 | 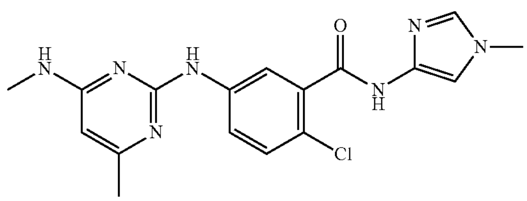 |
| B255 | 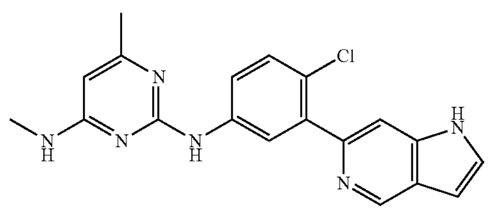 |
| B256 | 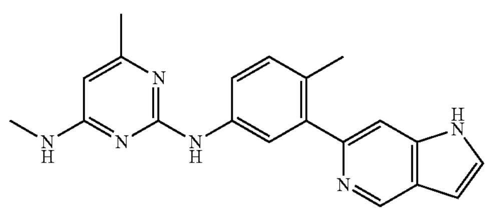 [SMILES: CNc1cc(C)nc(Nc2ccc(C)c(-c3cc4[nH]ccc4cn3)c2)n1] |
| B257 | 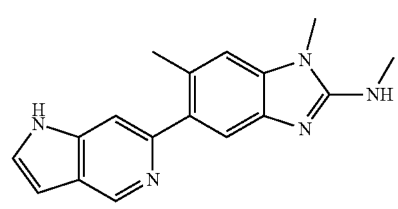 [SMILES: CNc1nc2cc(-c3cc4[nH]ccc4cn3)c(C)cc2n1C] |
| B258 | 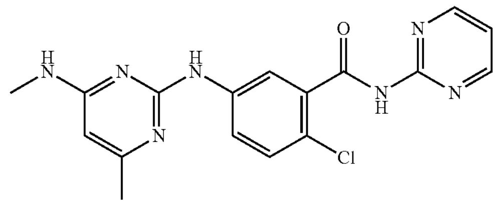 [SMILES: CNc1cc(C)nc(Nc2ccc(Cl)c(C(=O)Nc3ncccn3)c2)n1] |

TABLE 5-continued

| Compound No. | Structure |
|---|---|
| B259 | 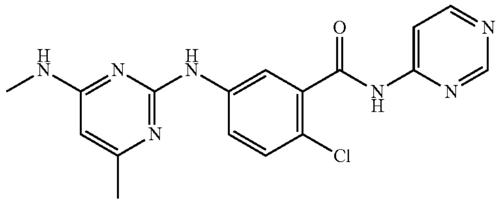 [SMILES: CNc1cc(C)nc(Nc2ccc(Cl)c(C(=O)Nc3ccncn3)c2)n1] |
| B260 | 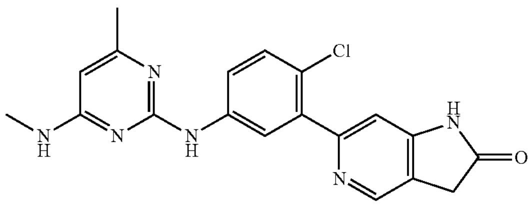 [SMILES: CNc1cc(C)nc(Nc2ccc(Cl)c(-c3cc4c(cn3)CC(=O)N4)c2)n1] |
| B261 | 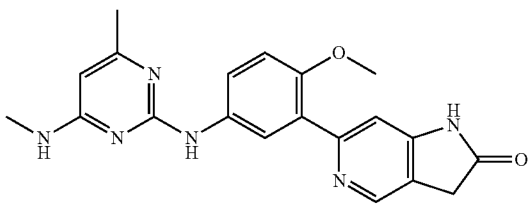 [SMILES: CNc1cc(C)nc(Nc2ccc(OC)c(-c3cc4c(cn3)CC(=O)N4)c2)n1] |
| B262 | 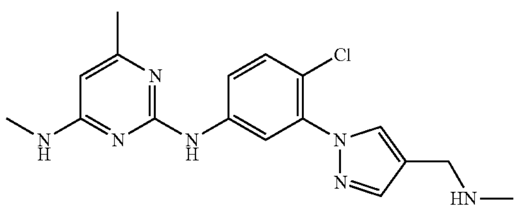 |
| B269 | 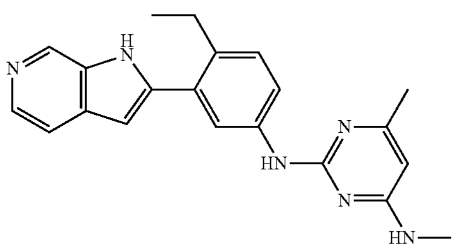 [SMILES: CCc1ccc(Nc2nc(C)cc(NC)n2)cc1-c1cc2ccncc2[nH]1] |
| B271 | 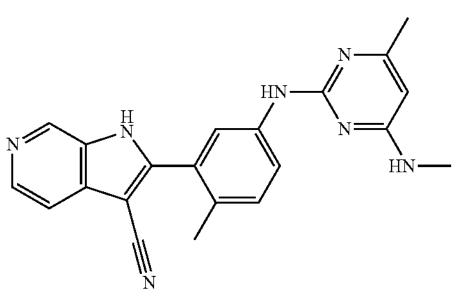 [SMILES: CNc1cc(C)nc(Nc2ccc(C)c(-c3[nH]c4cnccc4c3C#N)c2)n1] |

TABLE 5-continued

| Compound No. | Structure |
| --- | --- |
| B274 | 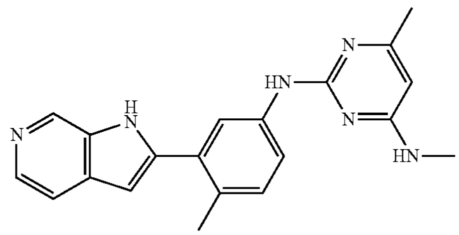 [SMILES: CNc1cc(C)nc(Nc2ccc(C)c(-c3cc4ccncc4[nH]3)c2)n1] |
| B276 | 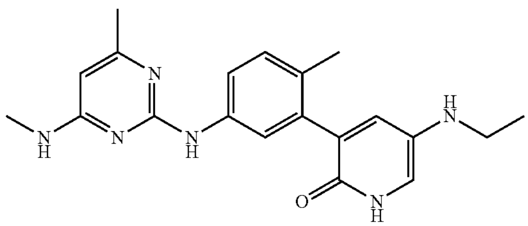 [SMILES: CCNc1c[nH]c(=O)c(-c2cc(Nc3nc(C)cc(NC)n3)ccc2C)c1] |
| B277 | 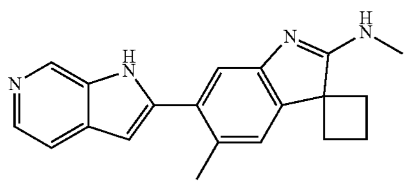 [SMILES: CNC1=Nc2cc(-c3cc4ccncc4[nH]3)c(C)cc2C12CCC2] |
| B278 | 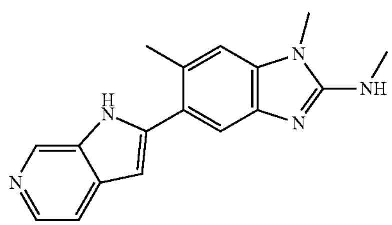 [SMILES: CNc1nc2cc(-c3cc4ccncc4[nH]3)c(C)cc2n1C] |
| B270 | 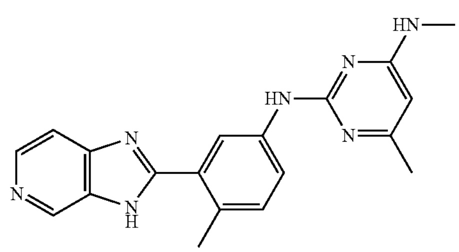 [SMILES: CNc1cc(C)nc(Nc2ccc(C)c(-c3nc4ccncc4[nH]3)c2)n1] |
| B280 | 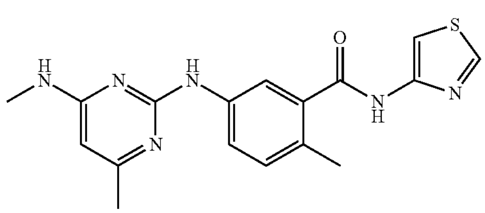 [SMILES: CNc1cc(C)nc(Nc2ccc(C)c(C(=O)Nc3cscn3)c2)n1] |
| B281 | 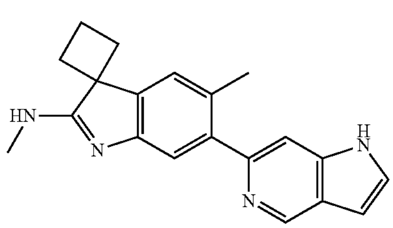 [SMILES: CNC1=Nc2cc(-c3cc4[nH]ccc4cn3)c(C)cc2C12CCC2] |

TABLE 5-continued
| Compound No. | Structure |
|---|---|
| B282 | 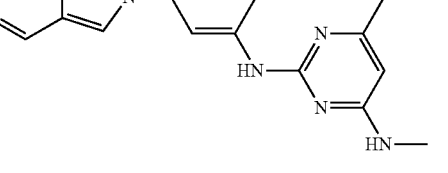 |
| B283 | 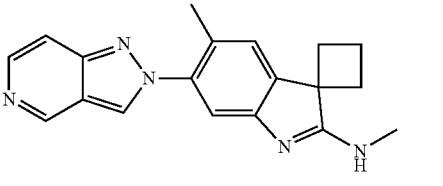 [SMILES: CNC1=Nc2cc(-n3cc4cnccc4n3)c(C)cc2C12CCC2] |
| B284 | 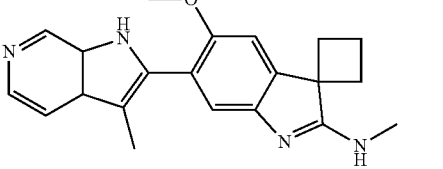 |
| B285 | 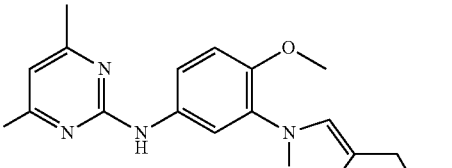 |
| B286 | 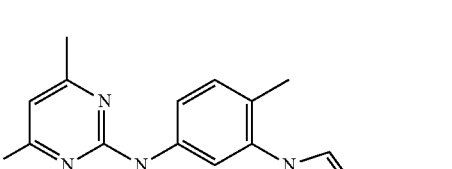 |
| B287 | 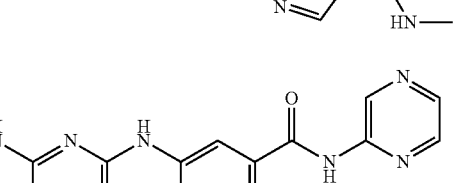 |
| B288 | 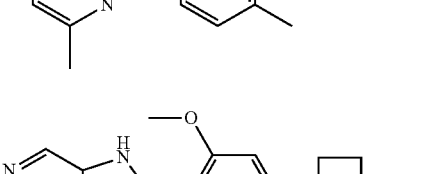 |

TABLE 5-continued
| Compound No. | Structure |
|---|---|
| B289 | 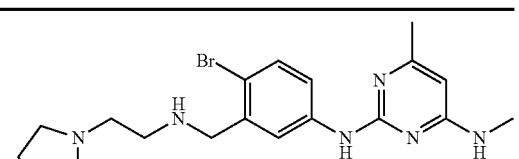 |
| B290 | 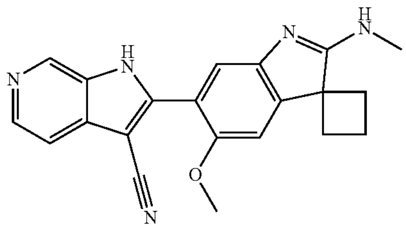 [SMILES: CNC1=Nc2cc(-c3[nH]c4cnccc4c3C#N)c(OC)cc2C12CCC2] |
| B291 | 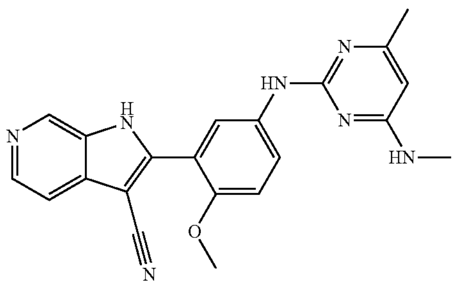 [SMILES: CNc1cc(C)nc(Nc2ccc(OC)c(-c3[nH]c4cnccc4c3C#N)c2)n1] |
The compounds of Table 5 are the compounds found in U.S. Application Nos. 62/436,139 and 62/517,840, the entire contents of which are incorporated herein by reference.
TABLE 6
| Compound No. | Structure |
|---|---|
| C1 | 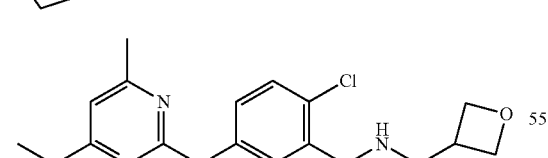 |
| C2 | 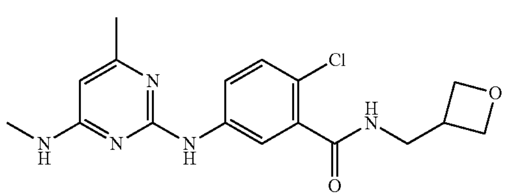 [SMILES: CNc1cc(C)nc(Nc2ccc(Cl)c(C(=O)NCC3COC3)c2)n1] |
| C3 | 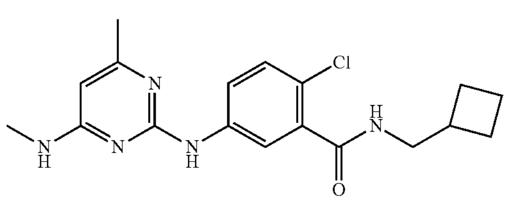 [SMILES: CNc1cc(C)nc(Nc2ccc(Cl)c(C(=O)NCC3CCC3)c2)n1] |
TABLE 6-continued
| Compound No. | Structure |
|---|---|
| C4 | 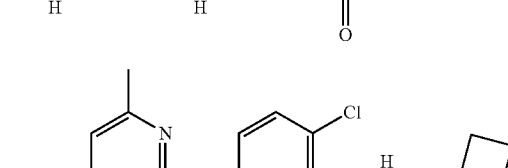 |
| C5 | 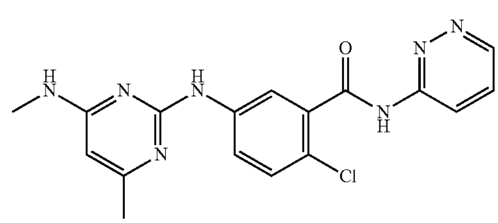 [SMILES: CNc1cc(C)nc(Nc2ccc(Cl)c(C(=O)Nc3cccnn3)c2)n1] |
| C6 | 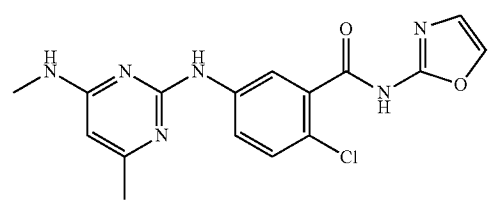 [SMILES: CNc1cc(C)nc(Nc2ccc(Cl)c(C(=O)Nc3ncco3)c2)n1] |

TABLE 6-continued
| Compound No. | Structure |
|---|---|
| C7 | 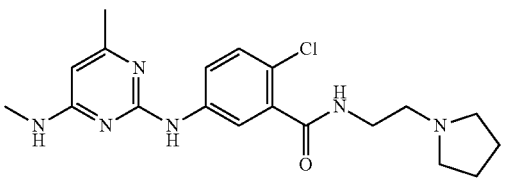 [SMILES: CNc1cc(C)nc(Nc2ccc(Cl)c(C(=O)NCCN3CCCC3)c2)n1] |
| C8 | 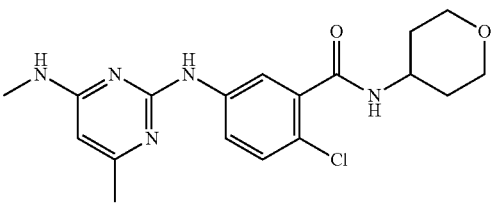 [SMILES: CNc1cc(C)nc(Nc2ccc(Cl)c(C(=O)NC3CCOCC3)c2)n1] |
| C9 | 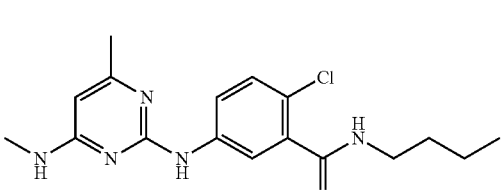 |
| C10 | 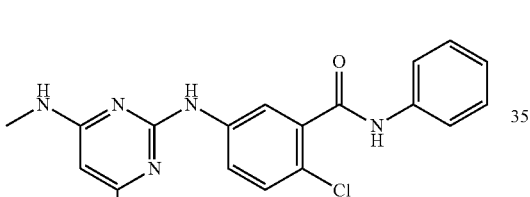 |
| C11 | 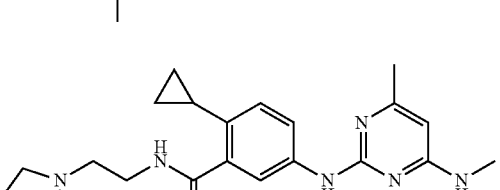 |
| C12 | 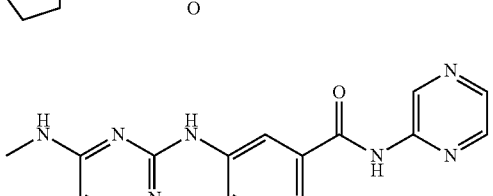 |
| C13 | 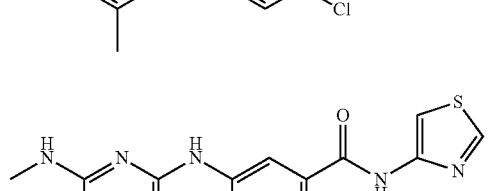 |
| C14 | 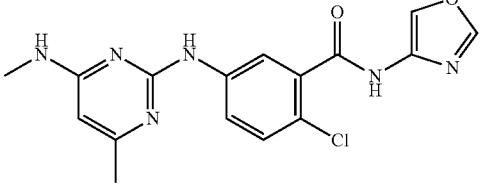 |
| C15 | 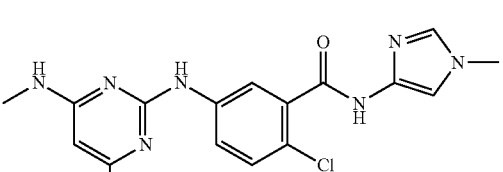 |
| C16 | 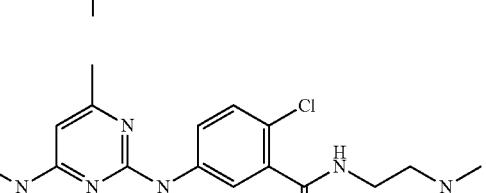 |
| C17 | 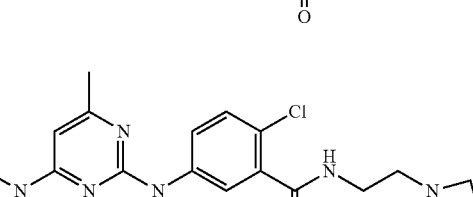 |
| C18 | 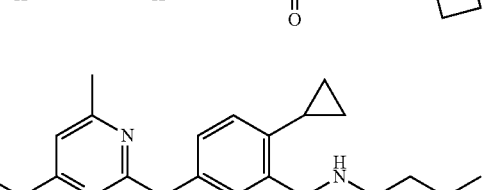 |
| C19 | 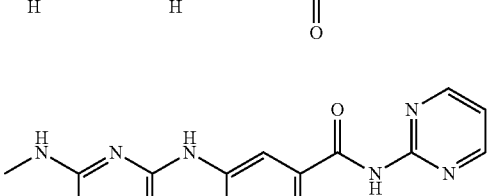 |
| C20 | 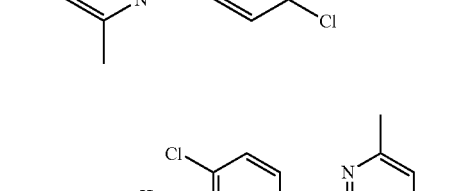 |

TABLE 6-continued

| Compound No. | Structure |
|---|---|
| C21 | |
| C22 | |
| C23 | |
| C24 | |
| C25 | |
| C26 | |
| C27 | |
| C28 | 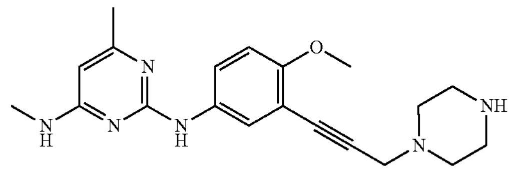 [SMILES: CNc1cc(C)nc(Nc2ccc(OC)c(C#CCN3CCNCC3)c2)n1] |
| C29 | 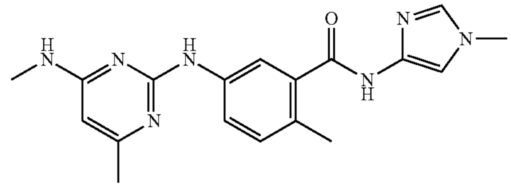 |
| C30 | 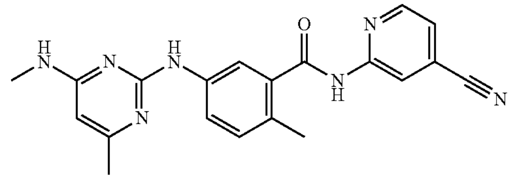 [SMILES: CNc1cc(C)nc(Nc2ccc(C)c(C(=O)Nc3cc(C#N)ccn3)c2)n1] |
| C31 | 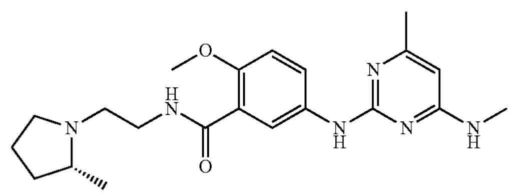 [SMILES: CNc1cc(C)nc(Nc2ccc(OC)c(C(=O)NCCN3CCC[C@H]3C)c2)n1] |
| C32 | 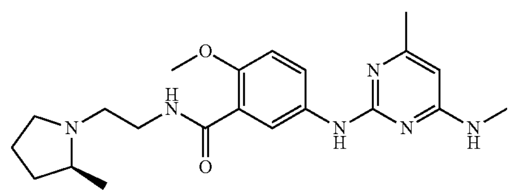 [SMILES: CNc1cc(C)nc(Nc2ccc(OC)c(C(=O)NCCN3CCC[C@@H]3C)c2)n1] |
| C33 | 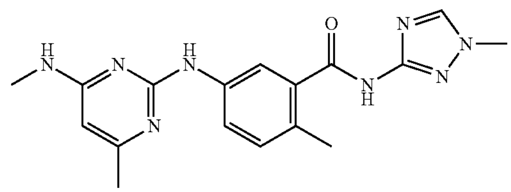 |
| C34 | 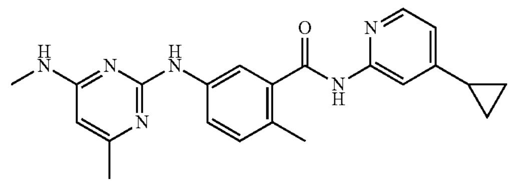 [SMILES: CNc1cc(C)nc(Nc2ccc(C)c(C(=O)Nc3cc(C4CC4)ccn3)c2)n1] |
| C35 | 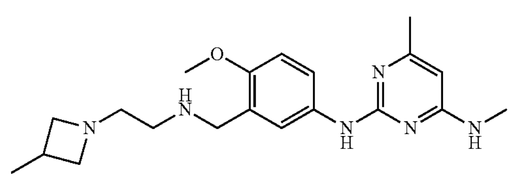 |

TABLE 6-continued
| Compound No. | Structure |
|---|---|
| C36 | 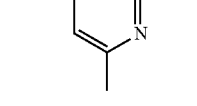 |
| C37 | 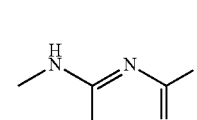 |
| C38 | 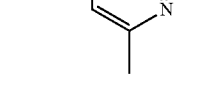 |
| C39 | 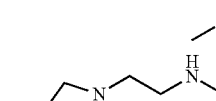 |
| C40 | 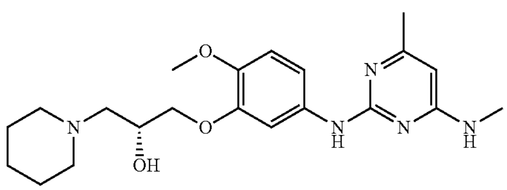 [SMILES: CNc1cc(C)nc(Nc2ccc(OC)c(OC[C@H](O)CN3CCCCC3)c2)n1] |
| C41 | 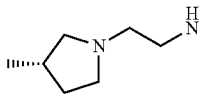 |
| C42 | 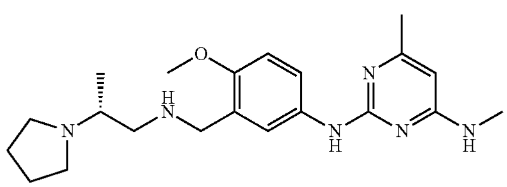 [SMILES: CNc1cc(C)nc(Nc2ccc(OC)c(CNC[C@@H](C)N3CCCC3)c2)n1] |
| C43 | 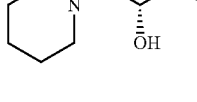 |
| C44 | |
| C45 | |
| C46 | |
| C47 | |
| C48 | |
| C49 | |
| C50 | |

TABLE 6-continued

| Compound No. | Structure |
|---|---|
| C51 | (structure) |
| C52 | (structure) |
| C53 | (structure) |
| C54 | (structure) |
| C55 | (structure) |
| C56 | (structure) |
| C57 | (structure) |
| C58 | (structure) |
| C59 | (structure) |
| C60 | (structure) |
| C61 | (structure) |
| C62 | (structure) |
| C63 | (structure) |
| C64 | (structure) |

TABLE 6-continued
| Compound No. | Structure |
|---|---|
| C65 | 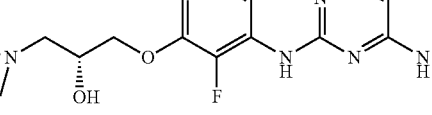 |
| C66 | 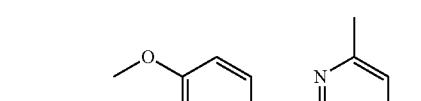 |
| C67 | 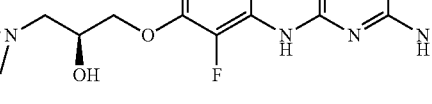 |
| C68 | 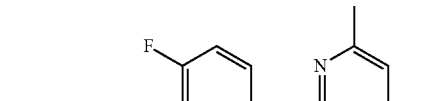 |
| C69 | 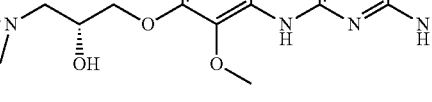 |
| C70 | 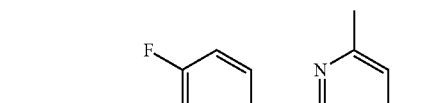 |
| C71 | 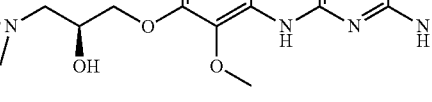 |
| C72 | 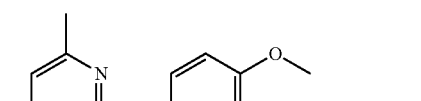 |
| C73 | 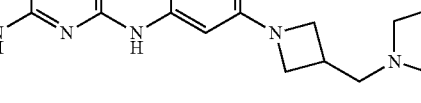 |
| C74 | 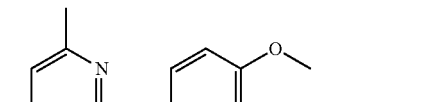 |
| C75 | 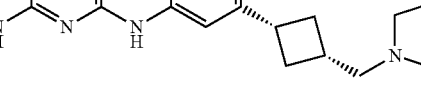 |
| C76 | 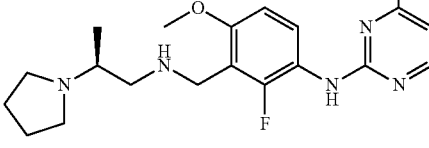 |
| C77 | 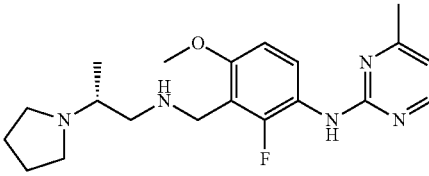 |
| C78 | 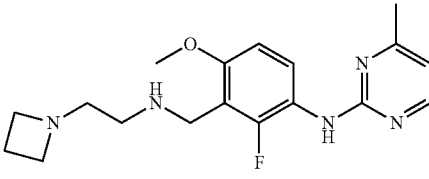 |
The compounds of Table 6 are the compound found in U.S. Application No. 62/573,442, the entire contents of which are incorporated herein by reference.

TABLE 6A
| Compound No. | Structure |
|---|---|
| CA1 | 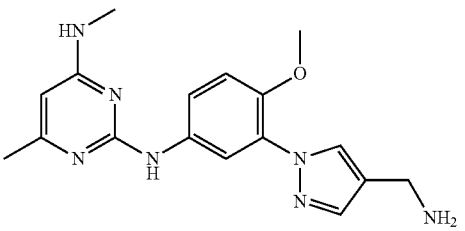 [SMILES: CNc1cc(C)nc(Nc2ccc(OC)c(-n3cc(CN)cn3)c2)n1] |
| CA2 | 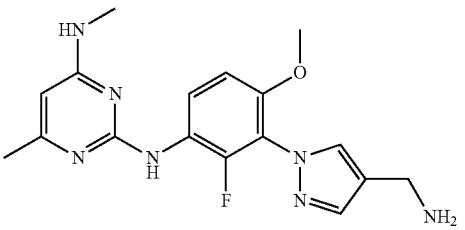 [SMILES: CNc1cc(C)nc(Nc2ccc(OC)c(-n3cc(CN)cn3)c2F)n1] |
| CA3 | 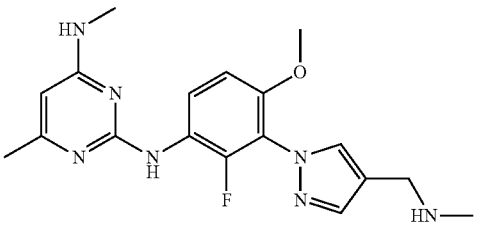 |
| CA4 | 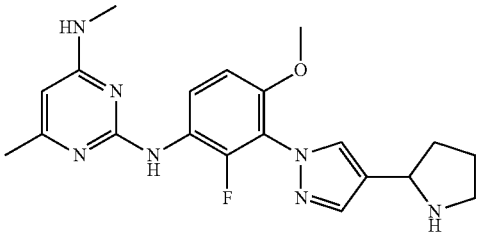 |
| CA4R | 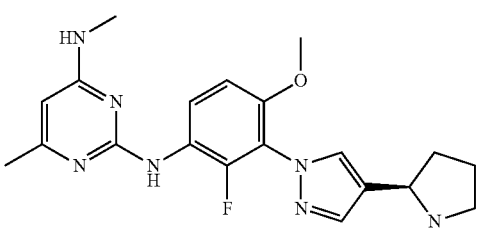 |
| CA4S | 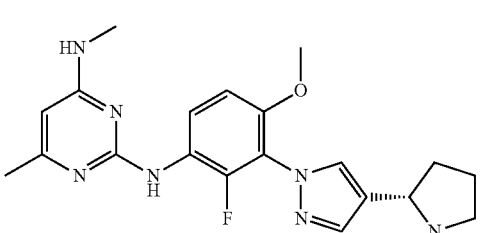 |
TABLE 6A-continued
| Compound No. | Structure |
|---|---|
| CA5 | 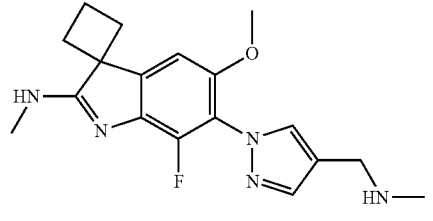 |
| CA6 | 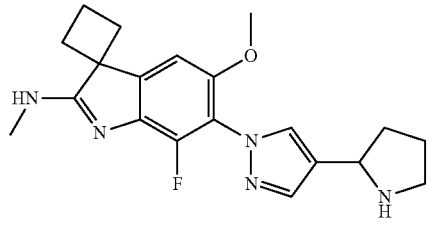 |
| CA6R | 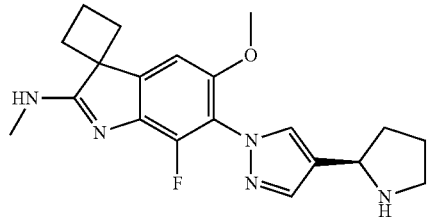 [SMILES: CNC1=Nc2c(cc(OC)c(-n3cc([C@H]4CCCN4)cn3)c2F)C12CCC2] |
| CA6S | 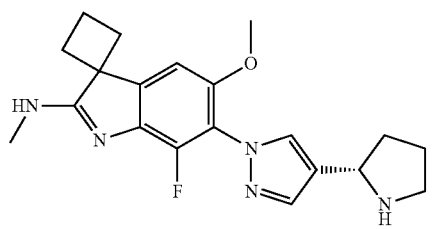 [SMILES: CNC1=Nc2c(cc(OC)c(-n3cc([C@@H]4CCCN4)cn3)c2F)C12CCC2] |
| CA7 | 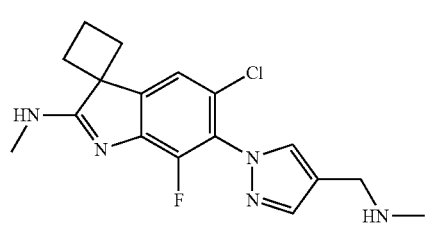 |
| CA8 | 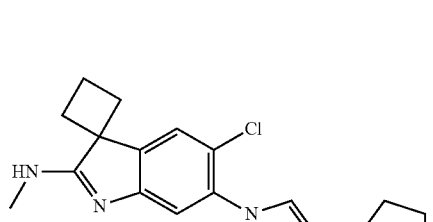 |

TABLE 6A-continued

| Compound No. | Structure |
|---|---|
| CA8R | (structure) |
| CA8S | (structure) |
| CA9 | (structure) |
| CA10 | (structure) |
| CA11 | (structure) |
| CA11R | (structure) |
| CA11S | (structure) |
| CA12 | (structure) |
| CA12R | (structure) |
| CA12S | (structure) |
| CA13 | (structure) |
| CA14 | (structure) |

TABLE 6A-continued

| Compound No. | Structure |
|---|---|
| CA15 | 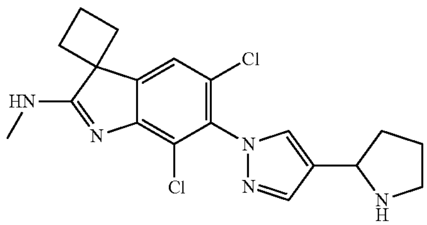 [SMILES: CNC1=Nc2c(cc(Cl)c(-n3cc(C4CCCN4)cn3)c2Cl)C12CCC2] |
| CA15R | 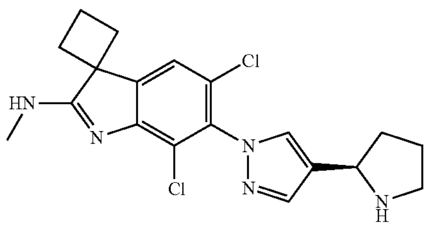 [SMILES: CNC1=Nc2c(cc(Cl)c(-n3cc([C@H]4CCCN4)cn3)c2Cl)C12CCC2] |
| CA15S | 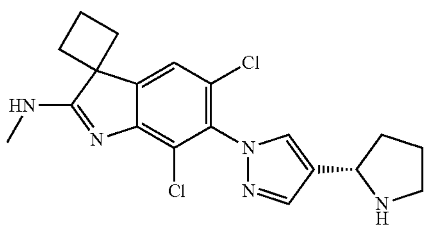 |

TABLE 7

| Compound No. | Structure |
|---|---|
| D1 | |
| D1R | |
| D1S | |
| D2 | 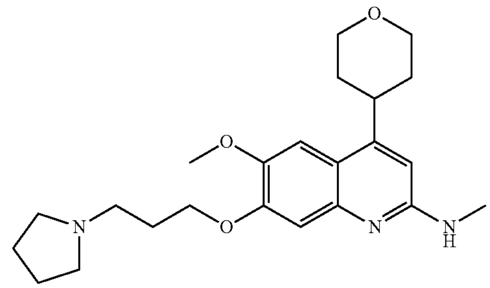 [SMILES: CNc1cc(C2CCOCC2)c2cc(OC)c(OCCCN3CCCC3)cc2n1] |
| D3 | 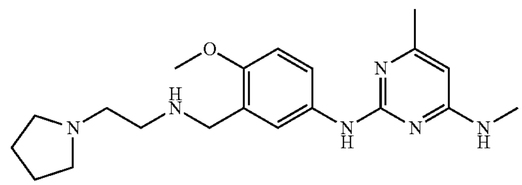 [SMILES: CNc1cc(C)nc(Nc2ccc(OC)c(CNCCN3CCCC3)c2)n1] |
| D4 | 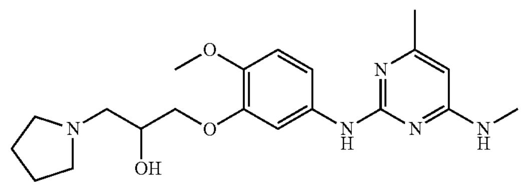 |
| D4R | 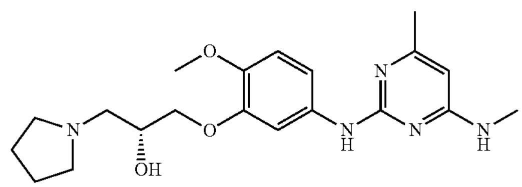 [SMILES: CNc1cc(C)nc(Nc2ccc(OC)c(OC[C@H](O)CN3CCCC3)c2)n1] |
| D4S | 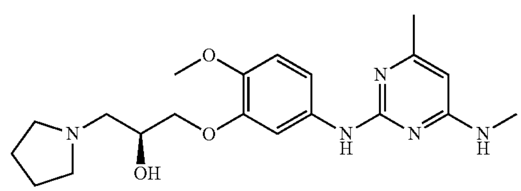 [SMILES: CNc1cc(C)nc(Nc2ccc(OC)c(OC[C@@H](O)CN3CCCC3)c2)n1] |
| D5 | 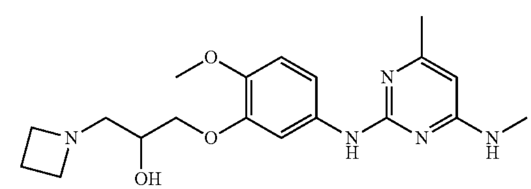 [SMILES: CNc1cc(C)nc(Nc2ccc(OC)c(OCC(O)CN3CCC3)c2)n1] |
| D5R | 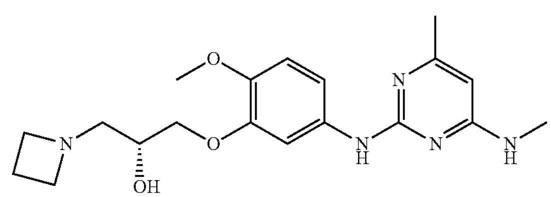 [SMILES: CNc1cc(C)nc(Nc2ccc(OC)c(OC[C@H](O)CN3CCC3)c2)n1] |

TABLE 7-continued

| Compound No. | Structure |
|---|---|
| D5S | (structure: methoxyphenyl ether with azetidinyl-CH2-CH(OH)-CH2-O- linker connected to pyrimidine-NH bearing methyl) |
| D6 | (structure: methoxyphenyl with pyrazole bearing -CH2-NH substituent, connected to methyl-pyrimidine via NH) |

The compounds of Table 7 are the compounds found in U.S. Application No. 62/573,917, the entire contents of which are incorporated herein by reference.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic non-aromatic rings, only one of the rings needs to be non-aromatic (e.g., 1,2,3,4-tetrahydronaphthalenyl or 2,3-dihydroindole).

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, "alkyl linker" or "alkylene linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkylene linker is intended to include $C_1$, $C_2$, $C_3$, $C_4$, $C_5$ and $C_6$ alkylene linker groups. Examples of alkylene linker include, moieties having from one to six carbon atoms, such as, but not limited to, methyl (—CH$_2$—), ethyl (—CH$_2$CH$_2$—), n-propyl (—CH$_2$CH$_2$CH$_2$—), i-propyl (—CHCH$_3$CH$_2$—), n-butyl (—CH$_2$CH$_2$CH$_2$CH$_2$—), s-butyl (—CHCH$_3$CH$_2$CH$_2$—), i-butyl (—C(CH$_3$)$_2$CH$_2$—), n-pentyl (—CH$_2$CH$_2$CH$_2$CH$_2$CH$_2$—), s-pentyl (—CHCH$_3$CH$_2$CH$_2$CH$_2$—) or n-hexyl (—CH$_2$CH$_2$CH$_2$CH$_2$CH$_2$CH$_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups.

In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated." or multicyclic systems with one or more aromatic rings and do not contain any heteroatom in the ring structure. Examples include phenyl, naphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N—O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthridine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein. "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, and [4.4.0]bicyclodecane and [2.2.2]bicyclooctane. A bridged ring occurs when one or more carbon atoms link two non-adjacent carbon atoms. In some embodiments, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., 1-4 heteroatoms selected from N, O and S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl (e.g., benzo[d][1,3]dioxole-5-yl), morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2R moieties, then the group may optionally be substituted with up to two R moieties and R at each occurrence is selected independently from the definition of R. Also, combinations of substituents and/or variables are permissible, but only if such combinations result in stable compounds.

The term "hydroxy" or "hydroxyl" includes groups with an —OH or —O—.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to —$NH_2$. "Alkylamino" includes groups of compounds wherein the nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to two alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present disclosure that contain nitrogens can be converted to N-oxides by treatment with an oxidizing agent (e.g., 3-chloroperoxybenzoic acid (mCPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It should also be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

Furthermore, the structures and other compounds discussed in this disclosure include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. Examples of lactam-lactim tautomerism are as shown below.

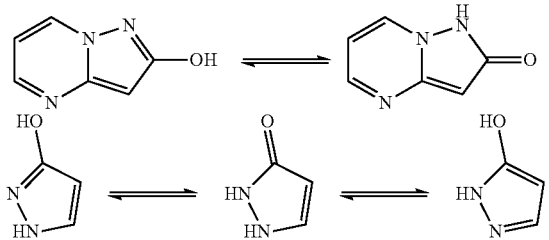

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any Formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (II) are substituted bi-heterocyclic compounds, and have Formula (II) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See. e.g., Patani and LaVoie, *Chem. Rev.* 96, 3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A. B, and/or C, i.e., one or more As, one or more Bs, one or more Cs, or any combination thereof, unless indicated otherwise.

The present disclosure provides methods for the synthesis of the compounds of any of the Formulae described herein. The present disclosure also provides detailed methods for the synthesis of various disclosed compounds of the present disclosure according to the following schemes as well as those shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the respective process or method remains operable. Moreover, two or more steps or actions can be conducted simultaneously.

The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith. M. B., March. J., *March's Advanced Organic Chemistry: Reactions, Mechanisms, and Structure*, 5$^{th}$ edition, John Wiley & Sons; New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

Compounds of the present disclosure can be conveniently prepared by a variety of methods familiar to those skilled in the art.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene. T. W., Wuts, P. G. M., *Protective Groups in Organic Synthesis*, 3$^{rd}$ edition, John Wiley & Sons: New York, 1999.

Compounds of the present disclosure inhibit the histone methyltransferase activity of G9a also known as KMT1C (lysine methyltransferase 1C) or EHMT2 (euchromatic histone methyltransferase 2), or a mutant thereof and, accordingly, in one aspect of the disclosure, certain compounds disclosed herein are candidates for treating, or preventing certain conditions, diseases, and disorders in which EHMT2 plays a role. The present disclosure provides methods for treating conditions and diseases the course of which can be influenced by modulating the methylation status of histones or other proteins, wherein said methylation status is mediated at least in part by the activity of EHMT2. Modulation of the methylation status of histones can in turn influence the level of expression of target genes activated by methylation, and/or target genes suppressed by methylation. The method includes administering to a subject in need of such treatment, a therapeutically effective amount of a compound of the present disclosure, or a pharmaceutically acceptable salt, polymorph, solvate, or stereoisomer thereof.

Unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

In still another aspect, this disclosure relates to a method of modulating the activity of EHMT2, which catalyzes the dimethylation of lysine 9 on histone H3 (H3K9) in a subject in need thereof.

The compound(s) of the present disclosure inhibit the histone methyltransferase activity of EHMT2 or a mutant thereof and, accordingly, the present disclosure also provides methods for treating conditions and diseases the course of which can be influenced by modulating the methylation status of histones or other proteins, wherein said methylation status is mediated at least in part by the activity of EHMT2. In one aspect of the disclosure, certain compounds disclosed herein are candidates for treating, or preventing certain conditions, diseases, and disorders. Modulation of the methylation status of histones can in turn influence the level of expression of target genes activated by methylation, and/or target genes suppressed by methylation.

The method includes administering to a subject in need of such treatment, a therapeutically effective amount of a compound of the present disclosure.

In still another aspect, this disclosure relates to a method of modulating the activity of EHMT2, which catalyzes the dimethylation of lysine 9 on histone H3 (H3K9) in a subject in need thereof. In some embodiments, the method comprises the step of administering to a subject having a cancer expressing a mutant EHMT2 a therapeutically effective amount of a composition comprising a compound described herein and one or more additional therapeutic agent, wherein the combination inhibits histone methyltransferase activity of EHMT2, thereby treating the cancer.

In some embodiments, the EHMT2-mediated cancer is leukemia, prostate carcinoma, hepatocellular carcinoma, lung cancer, or skin cancer.

In some embodiments, the compounds disclosed herein can be used for treating cancer. In some embodiments, the cancer is a hematological cancer. In some embodiments, the cancer is a skin cancer.

In some embodiments, the cancer is brain and/or central nervous system (CNS) cancer, head and/or neck cancer, kidney cancer, ovarian cancer, pancreatic cancer, leukemia, lung cancer, lymphoma, myeloma, sarcoma, breast cancer, prostate cancer, or skin cancer. Preferably, a subject in need thereof is one who had, is having or is predisposed to developing brain and CNS cancer, kidney cancer, ovarian cancer, pancreatic cancer, leukemia, lymphoma, myeloma, skin cancer, and/or sarcoma. Exemplary brain and central CNS cancer includes medulloblastoma, oligodendroglioma, atypical teratoid/rhabdoid tumor, choroid plexus carcinoma, choroid plexus papilloma, ependymoma, glioblastoma, meningioma, neuroglial tumor, oligoastrocytoma, oligodendroglioma, and pineoblastoma. Exemplary ovarian cancer includes ovarian clear cell adenocarcinoma, ovarian endometrioid adenocarcinoma, and ovarian serous adenocarcinoma. Exemplary pancreatic cancer includes pancreatic ductal adenocarcinoma and pancreatic endocrine tumor. Exemplary skin cancer includes basal cell carcinoma, squamous cell carcinoma, melanoma, Kaposi's sarcoma, Merkel cell carcinoma, and sebaceous gland carcinoma. Exemplary sarcoma includes chondrosarcoma, clear cell sarcoma of soft tissue, ewing sarcoma, gastrointestinal stromal tumor, osteosarcoma, rhabdomyosarcoma, and not otherwise specified (NOS) sarcoma. Alternatively, cancers to be treated by the compounds of the present disclosure are non NHL cancers.

In some embodiments, the cancer is acute myeloid leukemia (AML) or chronic lymphocytic leukemia (CLL), medulloblastoma, oligodendroglioma, ovarian clear cell adenocarcinoma, ovarian endometrioid adenocarcinoma, ovarian serous adenocarcinoma, pancreatic ductal adenocarcinoma, pancreatic endocrine tumor, malignant rhabdoid tumor, astrocytoma, atypical teratoid/rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma rhabdomyosarcoma, or not otherwise specified (NOS) sarcoma. Preferably, the cancer is acute myeloid leukemia (AML), chronic lymphocytic leukemia (CLL), medulloblastoma, ovarian clear cell adenocarcinoma, ovarian endometrioid adenocarcinoma, pancreatic ductal adenocarcinoma, malignant rhabdoid tumor, atypical teratoid/rhabdoid tumor, choroid plexus carcinoma, choroid plexus papilloma, glioblastoma, meningioma, pineoblastoma, carcinosarcoma, extrarenal rhabdoid tumor, schwannoma, skin squamous cell carcinoma, melanoma, chondrosarcoma, ewing sarcoma, epithelioid sarcoma, renal medullary carcinoma, diffuse large B-cell lymphoma, follicular lymphoma and/or NOS sarcoma.

As used herein, a "subject" is interchangeable with a "subject in need thereof", both of which refer to a subject having a cancer or a disorder in which EHMT2-mediated protein methylation plays a part, or a subject having an increased risk of developing such cancer or disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In some embodiments, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. A subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition. In some embodiments, the cancer is leukemia, prostate carcinoma, hepatocellular carcinoma, lung cancer, or melanoma.

As used herein, "candidate compound" refers to a compound of the present disclosure, or a pharmaceutically acceptable salt, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present disclosure, or a pharmaceutically acceptable salt, polymorph or solvate thereof. The biological or medical response can be the treatment of cancer. The biological or medical response can be treatment or prevention of a cell proliferative disorder. The biological response or effect can also include a change in cell proliferation or growth that occurs in vitro or in an animal model, as well as other biological changes that are observable in vitro. In vitro or in vivo biological assays can include, but are not limited to, enzymatic activity assays, electrophoretic mobility shift assays, reporter gene assays, in vitro cell viability assays, and the assays described herein.

In some embodiments, an in vitro biological assay that can be used includes the steps of (1) mixing a histone substrate (e.g., an isolated histone sample or an isolated histone peptide representative of human histone H3 residues 1-15) with recombinant EHMT2 enzymes; (2) adding a compound of the disclosure to this mixture; (3) adding non-radioactive and $^3$H-labeled S-Adenosyl methionine (SAM) to start the reaction; (4) adding excessive amount of non-radioactive SAM to stop the reaction; (4) washing off the free non-incorporated $^3$H-SAM; and (5) detecting the quantity of $^3$H-labeled histone substrate by any methods known in the art (e.g., by a PerkinElmer TopCount platereader).

In some embodiments, an in vitro study that can be used includes the steps of (1) treating cancer cells (e.g., breast cancer cells) with a compound of this disclosure; (2) incubating the cells for a set period of time; (3) fixing the cells; (4) treating the cells with primary antibodies that bind to dimethylated histone substrates; (5) treating the cells with a secondary antibody (e.g. an antibody conjugated to an infrared dye); (6) detecting the quantity of bound antibody by any methods known in the art (e.g., by a Licor Odyssey Infrared Scanner).

As used herein. "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, "temporal proximity" refers to that administration of one therapeutic agent (e.g., a compound of the present disclosure) occurs within a time period before or after the administration of another therapeutic agent (e.g., the one or more additional therapeutic agent disclosed herein), such that the therapeutic effect of the one therapeutic agent overlaps with the therapeutic effect of the another therapeutic agent. In some embodiments, the therapeutic effect of the one therapeutic agent completely overlaps with the therapeutic effect of the another therapeutic agent. In some embodiments, "temporal proximity" means that administration of one therapeutic agent occurs within a time period before or after the administration of another therapeutic agent, such that there is a synergistic effect between the one therapeutic agent and the another therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

A compound of the present disclosure, or a pharmaceutically acceptable salt, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning. A Laboratory Manual* ($3^{rd}$ edition), Cold Spring Harbor Press, Cold Spring Harbor, N.Y. (2000). Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the disclosure.

As used herein, "combination therapy" or "co-therapy" includes the administration of a compound of the present disclosure, or a pharmaceutically acceptable salt, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents.

The present disclosure also provides pharmaceutical compositions comprising a compound of any of the Formulae described herein in combination with at least one pharmaceutically acceptable excipient or carrier.

A "pharmaceutical composition" is a formulation containing the compounds of the present disclosure in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In some embodiments, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the disclosure can be administered to a subject in many of the well-known methods currently used for chemotherapeutic treatment. For example, for treatment of cancers, a compound of the disclosure may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water. Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

The pharmaceutical compositions can be included in a container, pack, or dispenser together with instructions for administration.

The compounds of the present disclosure are capable of further forming salts. All of these forms are also contemplated within the scope of the claimed disclosure.

As used herein, "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hdroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids. e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In some embodiments, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated, the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in Remington: the Science and Practice of Pharmacy, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. Several embodiments embraced by the present disclosure having now been described by way of written description, those of skill in the art will recognize that the inventive concepts disclosed herein can be practiced in a variety of embodiments and that the foregoing description and examples below are for purposes of illustration and not limitation of the claims that follow.

Example 1: Synthesis of EHMT2 Inhibitor Compounds

EHMT2 inhibitor compounds useful for the invention defined herein were synthesized or may be synthesized by, e.g., methods described in U.S. Application Nos. 62/323, 602, 62/348,837, 62/402,997, 62/402,863, 62/509,620, 62/436,139, 62/517,840, 62/573,442, and 62/573,917, and PCT Application Nos. PCT/US/027918, PCT/US2017/ 054468, and PCT/US2017/067192, the contents of each of which are incorporated herein by reference in their entireties.

Example 2: In Vitro Combination Studies of EHMT2 Inhibitor Compounds with Other Agents Pretreatment Model: various cell lines were grown in individual flasks with various concentrations of Compound 205 (an EHMT2 inhibitor) for seven days. Cells were then washed and plated to 96 well plates containing standard agents alone, and in combination with Compound 205, and grown for an additional three days. Quantification of proliferation through measurement of cellular adenosine triphosphate (ATP) was performed in a luminescent cell viability assay. Proliferation data was read for luminescence. Calculations of synergy were performed using the Loewe Volume (Chalice Software) and Fa-CI plots were generated with Calcusyn.

Cotreatment Model: various cell lines were directly plated to 96 well plates containing standard agents alone, and in combination with Compound 205, and grown for seven days. Quantification of proliferation through measurement of cellular adenosine triphosphate (ATP) was performed in a luminescent cell viability assay. Proliferation data was read for luminescence.

The results of the combination studies of Compound 205 with other therapies in the pretreatment and cotreatment models described above are summarized in FIG. 1.

Example 3: In Vitro Single-Agent Studies of EHMT2 Inhibitor Compounds

Figure 2:
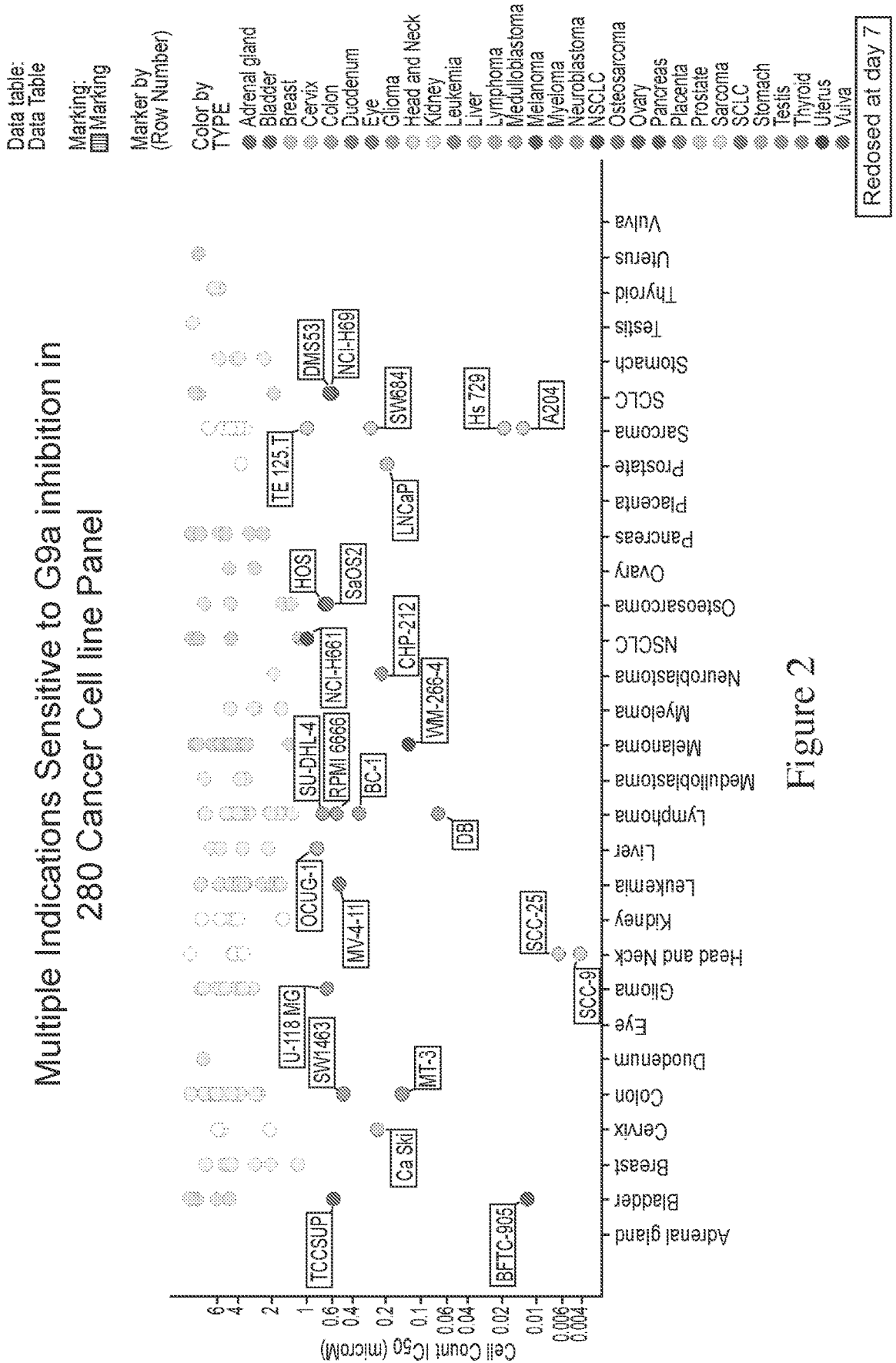
FIG. 2 is a series of schematic diagrams depicting indications which are suitable for treatment via EHMT2 inhibition via a single agent, e.g., an EHMT2 inhibitor.
Figure 2:
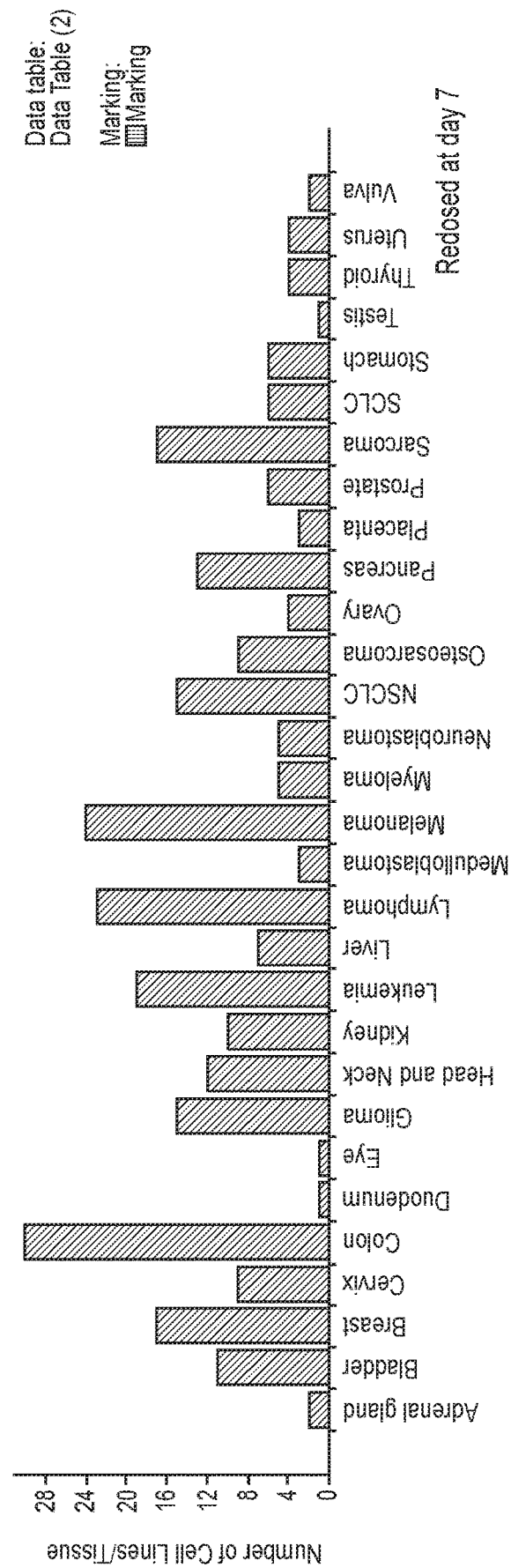
Figure 6:
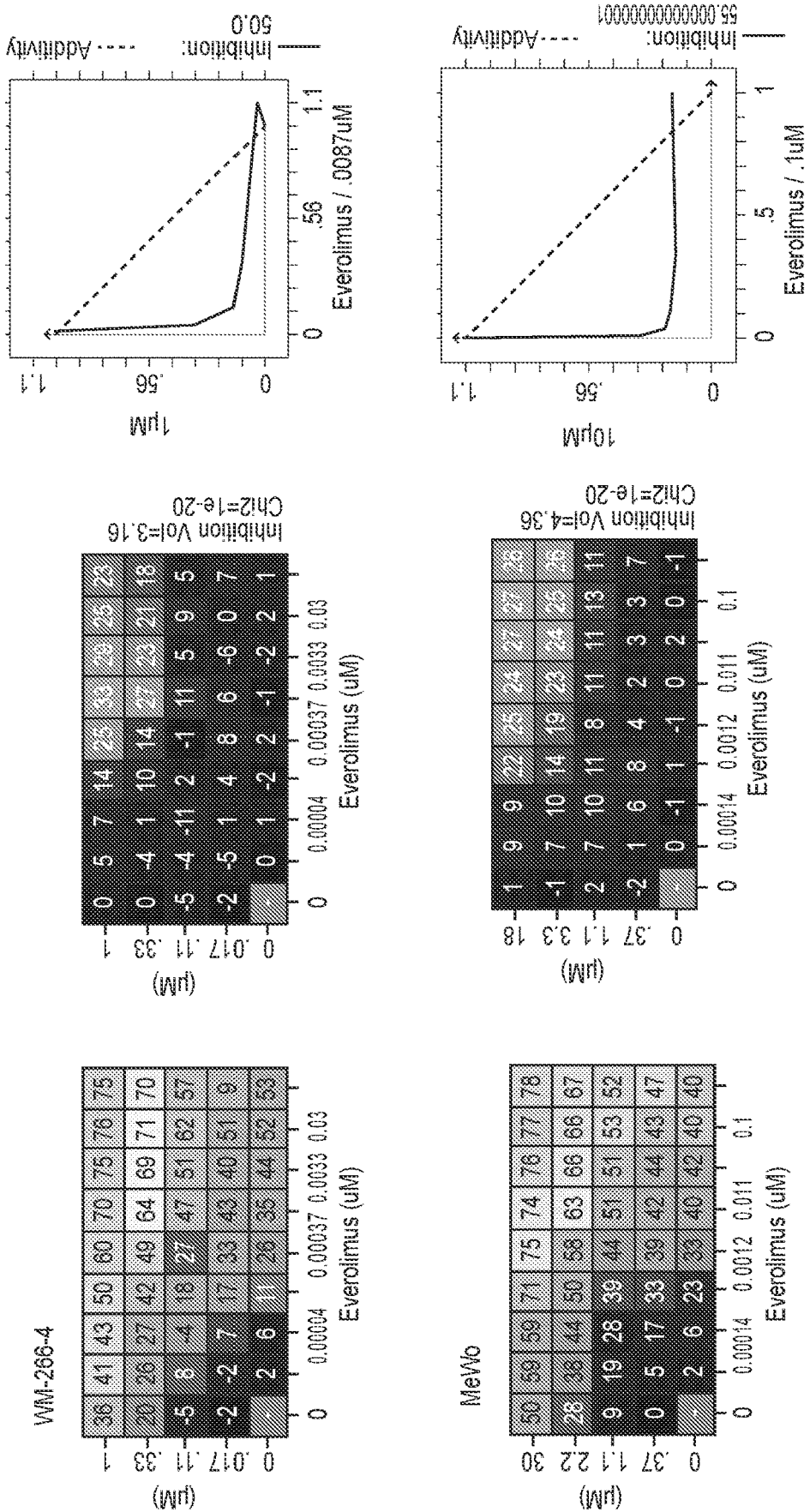
FIG. 6 shows examples of synergy in WM-266-4 and MeWo melanoma cell lines with combination of Compound 205 and Everolimus.

The results of the single-agent studies of an EHMT2 Inhibitor are summarized in FIGS. 2 and 3.

Example 4: In Vitro Combination Studies of EHMT2 Inhibitor Compounds with Other Agents on AML Cell Lines Pretreatment model: Cells were treated in flasks for 7 days in a dose dependent manner with EHMT2 inhibitor Compound 205 followed by a cotreatment phase with a second agent for additional 3 or 7 days as indicated in the schedule (7+3 or 7+7). Cell viability was assessed by the ATP content of the cultures. Synergy was quantified with the Chalice Viewer software by the Loewe excess model. Observed synergies are described in FIG. 4

Cotreatment model: Cell lines AML-193, AP-1060, EOL-1, HL60-Kasumi-1, ML-2, MOLM-16, OCI-AML2, OCI-AML3, and SKM were used. Cells were cotreated in 384-well plates for 7 days in a dose dependent manner with EHMT2 inhibitor Compound 205 and a second agent in a matrix format. Cell viability was assessed by the ATP content of the cultures. Synergy was quantified with the Chalice Viewer software by the Loewe excess model. Observed synergies are described in FIG. 5.

Example 5: In Vitro Combination Studies of EHMT2 Inhibitor Compounds with Other Agents on Melanoma Cell Lines Studies were performed using melanoma cancer cell lines in vitro to evaluate the anti-proliferative effect of combinations of the EHMT2 inhibitor Compound 205 and a second agent. Initial proliferation studies were performed to determine the $IC_{50}$ of Compound 205 in each cell line. For the screen, Compound 205 was used at concentrations bracketed around the $IC_{50}$ value. If 50% inhibitory concentration was not achieved, then Compound 205 was tested starting at 10 μM.

In order to study the effect of dual combination of Compound 205 and a second agent on cell proliferation, cells in log-linear phase growth rate were pre-treated with various concentrations of Compound 205 or DMSO for 7 days in flasks, plated in 384-well plates and co-treated with Compound 205 or DMSO and the second agent serially diluted for additional 7 days (as depicted in FIG. 1). On day 14 plates were developed for endpoint analysis using Cell-Titer Glo to measure ATP content, which was used as an indicator of cell viability. DMSO concentration was kept constant throughout the assay at 0.2% v/v.

The cell lines MeWo and WM-266-4 were obtained from American Type Culture Collection (ATCC; Rockville, Md.) and cultured in EMEM medium containing 10% v/v Fetal Bovine Serum (FBS) and 1% v/v Penicillin/Streptomycin (P/S). All cells were maintained and cultured at 37° C., in a humidified atmosphere and 5% $CO_2$.

Analysis of combinatorial effects and synergy quantification between Compound 205 and a second agent was performed using CHALICE software (Horizon Discovery, Cambridge, UK) was used to determine synergy using the Loewe method (Lehar et al, Mol Syst Biol 2007; 3:80). Loewe volumes greater than 1 denoted synergy and volumes below −1 denoted antagonism. A value between −1 and 1 denoted additivity. Results for combinations of Compound 205 and the compounds tested as second agents are shown in Table 8.

Examples of dose matrix visualization (left), Loewe excess (middle) and isobolograms (right) are shown in FIG. 4 for the two cell lines tested for Compound 205 and Everolimus.

TABLE 8

| | | Cell line | |
|---|---|---|---|
| Modality | Compound | MeWo | WM-266-4 |
| Pi3K inhibitors | BKM120 | SYN | SYN |
| | Pictilisib | SYN | SYN |
| MTOR inhibitor | Everolimus | SYN | SYN |
| AKT inhibitors | MK-2206 | SYN | SYN |
| | GDC-0068 | ADD | SYN |
| BRAF inhibitors | Sorafenib | ADD | SYN |
| MEK1,2 inhibitors | Trametinib | ADD | ADD |
| | Selumetinib | ADD | ADD |
| ERK inhibitor | BVD-523 | ADD | ADD |
| EGFR inhibtor | Erlotinib | SYN | SYN |
| DNMT inhibitor | Decitabine | SYN | SYN |
| cKIT inhibitor | Imatinib | SYN | ADD |
| CDK4/6 inhibitor | Palbociclib | SYN | SYN |

SYN Synergy
ADD Additivity

Example 6: Assessment of In Vitro Long Term Proliferation (LTP) in Human T-Cell Acute Lymphoblastic Leukemia Cell Lines with EHMT2 Inhibitor Compounds Exponentially growing T-cell lymphocytic leukemia (T-ALL) cells were plated, in triplicate, in 96-well plates at the appropriate cell density in a final volume of 150 μl. Cells were incubated in the presence of increasing concentrations of Compound A75. Viable cell number was determined at day 0, 4, 7, 11 and 14 days using Calcein staining and using an Accumen instrument to enumerate the number of cells. On days of cell counts, growth media and Compound A75 were replaced and cells split back to initial density. Total cell number is expressed as split-adjusted viable cells per well. For each cell line, absolute $IC_{50}$ values (concentration of compound at which 50% inhibition occurs) were determined from concentration-dependence curves at 14 days using Graphpad Prism software. Results are shown in Table 9 ("A" means $IC_{50}$<100 nM; "B" means $IC_{50}$ ranging between 100 nM and 1 μM; "C" means $IC_{50}$ ranging between >1 μM and 5 μM; "D" means $IC_{50}$>5 μM and 15 μM).

TABLE 9

| Cell line | 14 day LTP Seeding density | Compound A75 $IC_{50}$ (μM) |
|---|---|---|
| PEER | 250000 | A |
| MOLT-4 | 100000 | B |
| MOLT-16 | 100000 | B |
| CCRF-CEM | 100000 | C |
| Jurkat | 100000 | C |
| SUP-T1 | 200000 | D |
| TALL-1 | 150000 | D |

The inventive concepts described herein can be embodied in other specific forms without departing from the spirit or essential characteristics thereof. The foregoing embodiments are therefore to be considered in all respects illustrative rather than limiting on the various aspects of the disclosure described herein. Scope of the disclosure is thus indicated by the appended claims rather than by the foregoing description, and all changes that come within the meaning and range of equivalency of the claims are intended to be embraced therein.

What is claimed is:
1. A method for treating an acute myeloid leukemia (AML), acute lymphocytic leukemia (ALL), or melanoma comprising administering to a subject in need thereof a compound selected from:
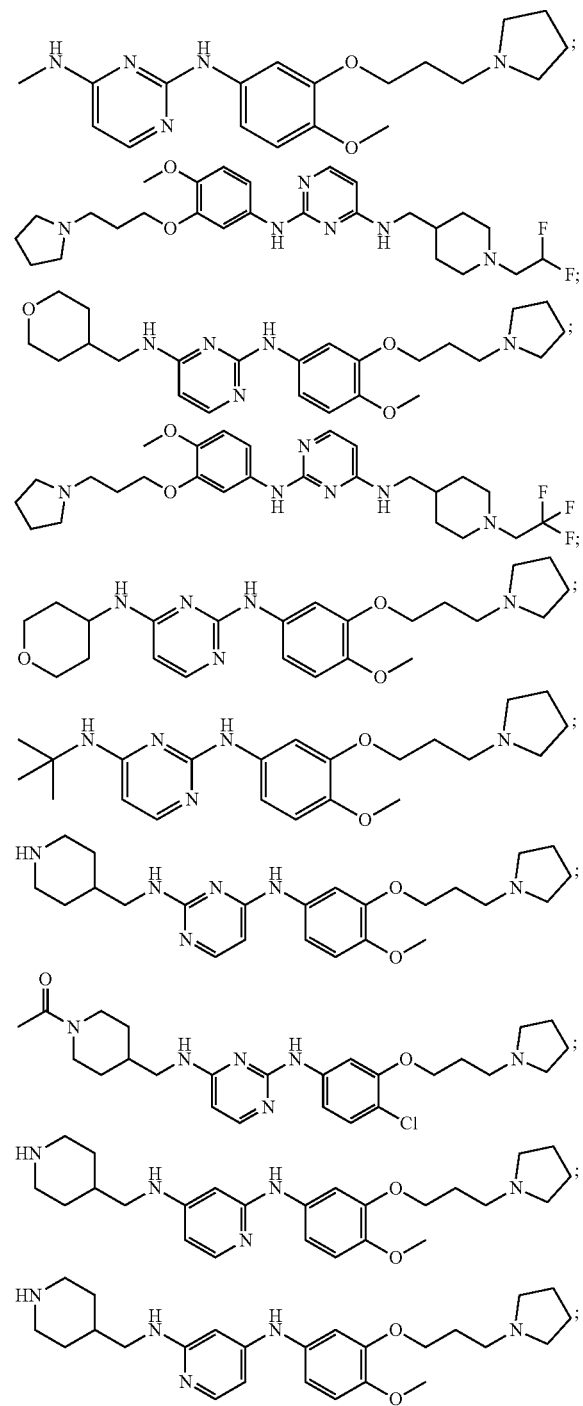
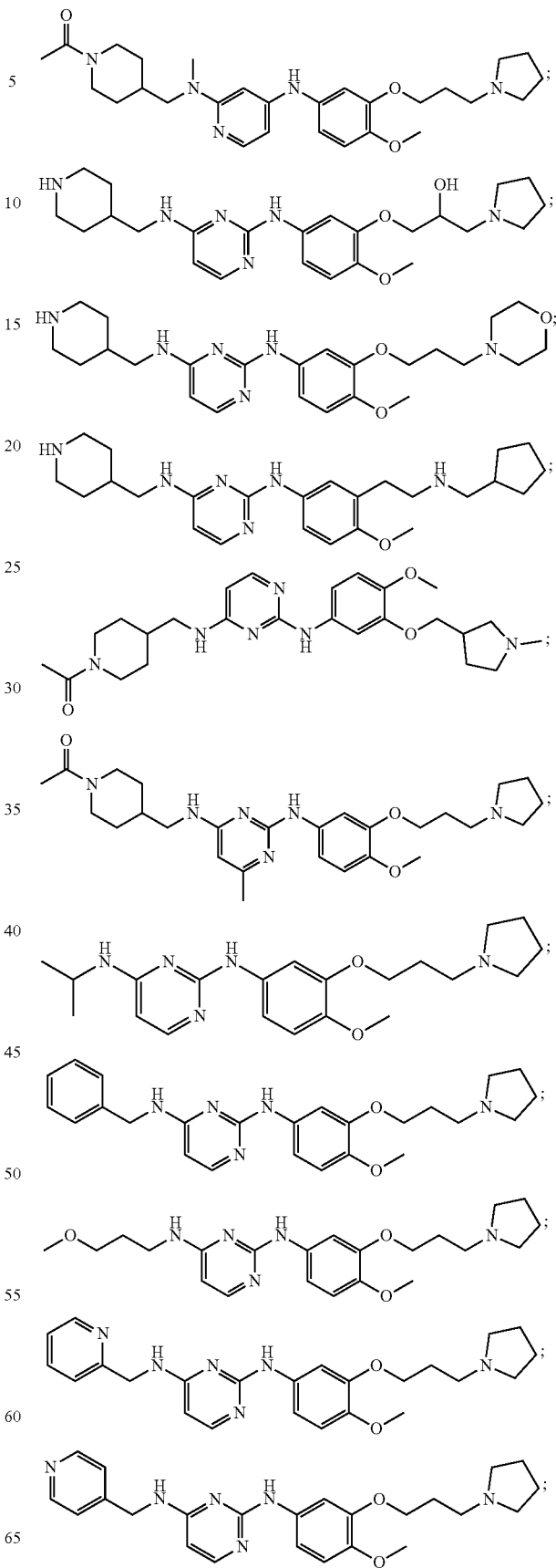

569
-continued
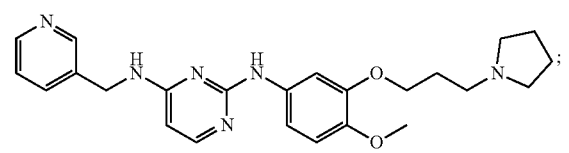
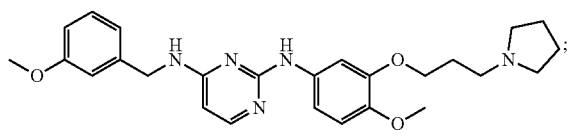
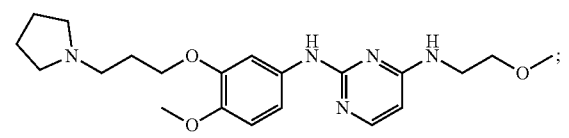
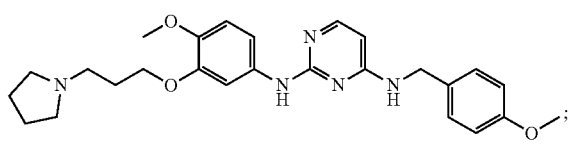
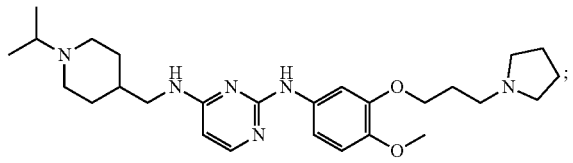
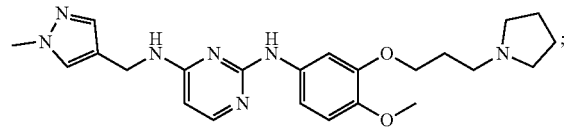
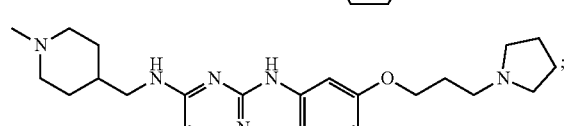

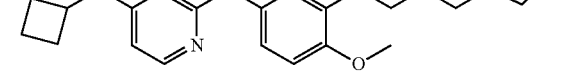
570
-continued
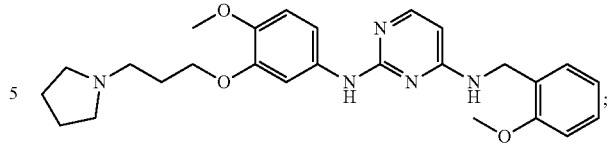

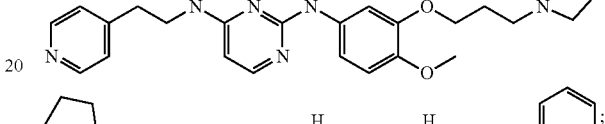
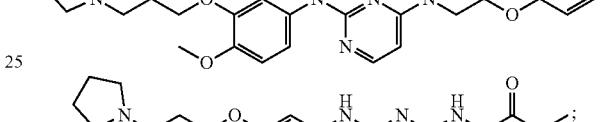
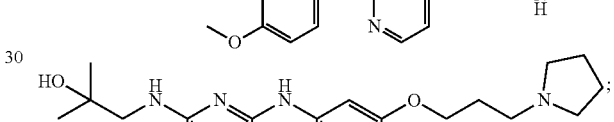
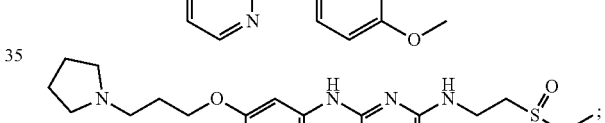
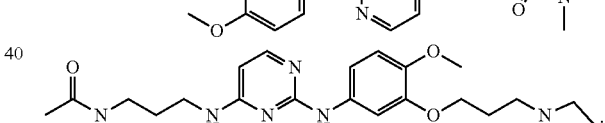
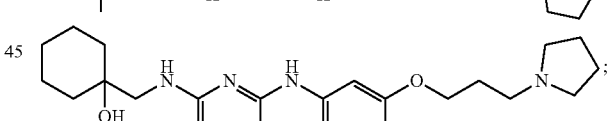
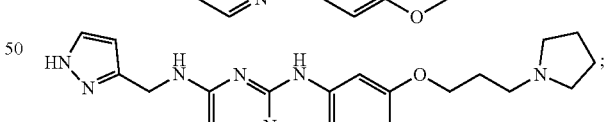
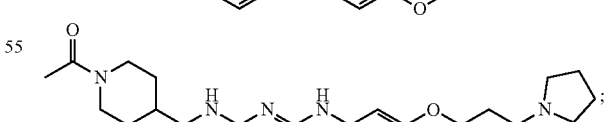
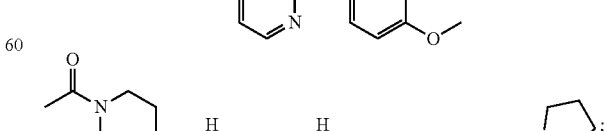
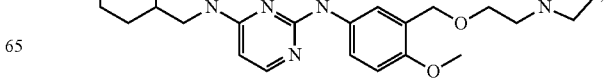

571
-continued
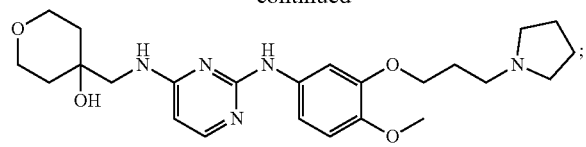
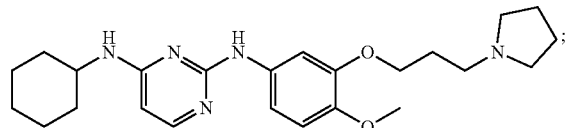
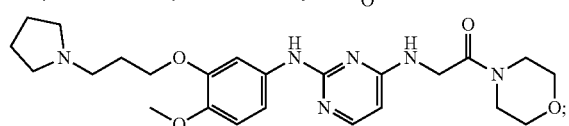
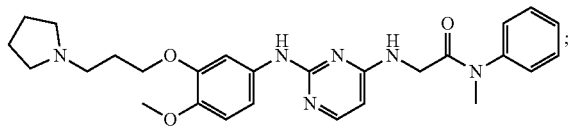
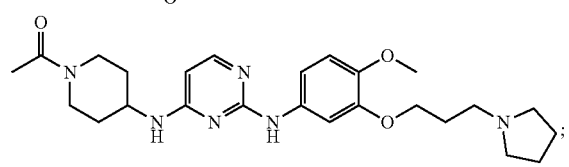
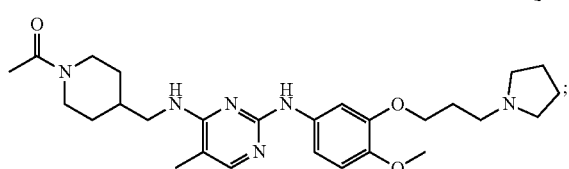
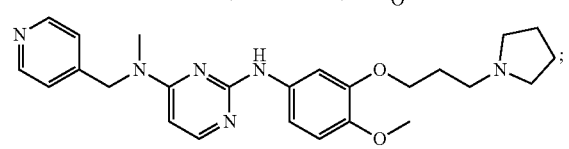
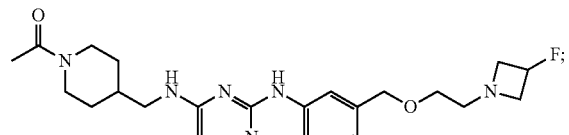
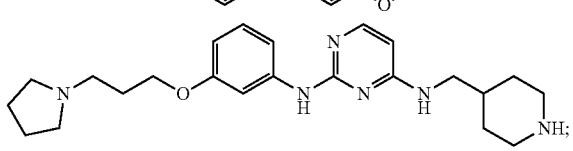
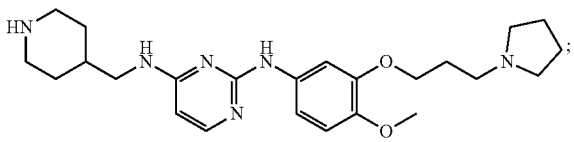
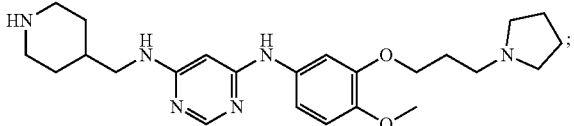
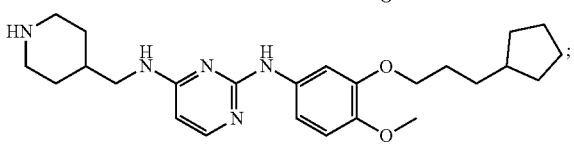
572
-continued
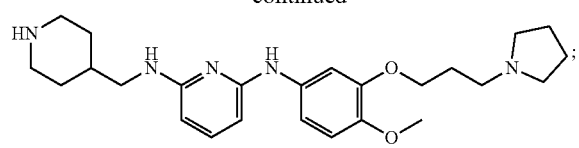
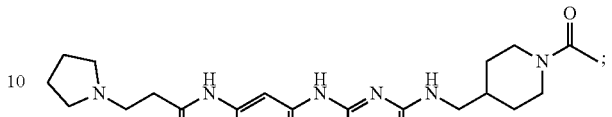
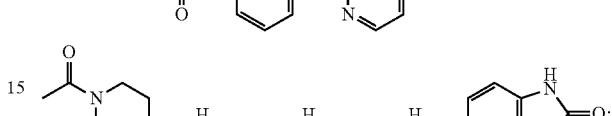
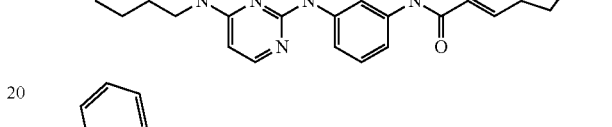
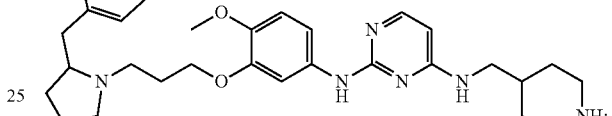
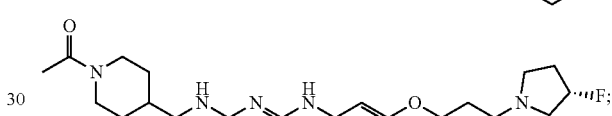
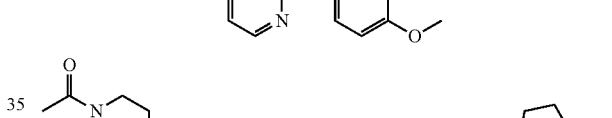
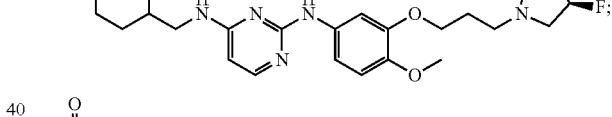
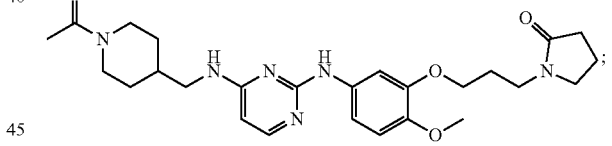
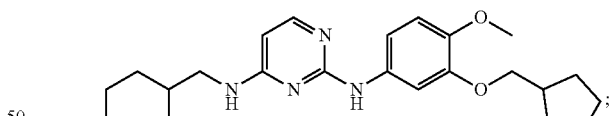
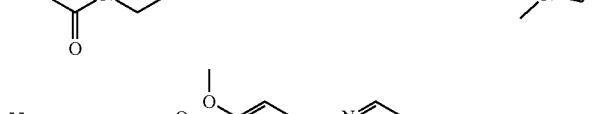
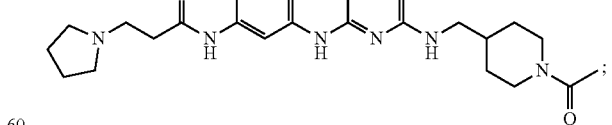
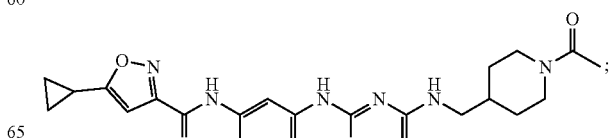

573
-continued
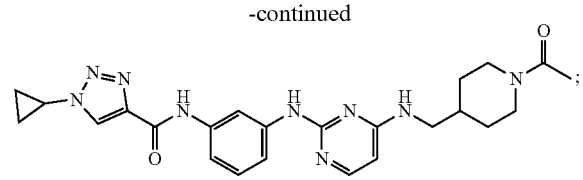
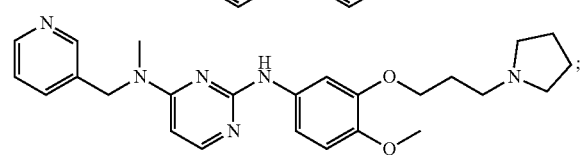
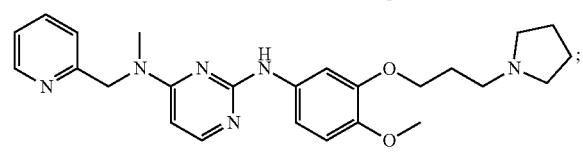
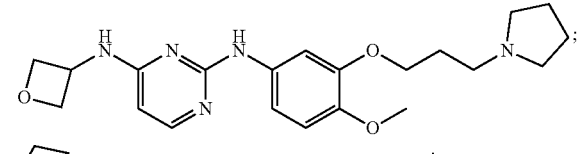
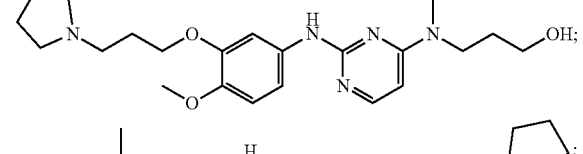
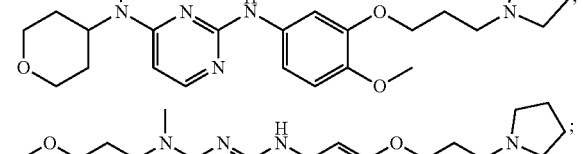
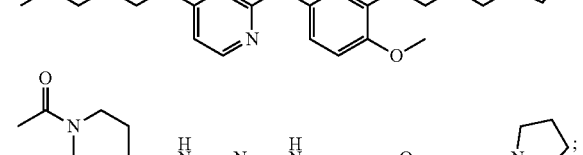
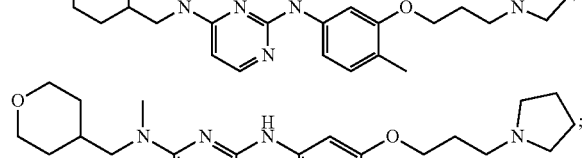
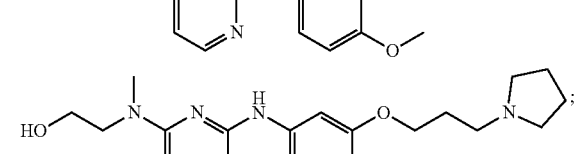
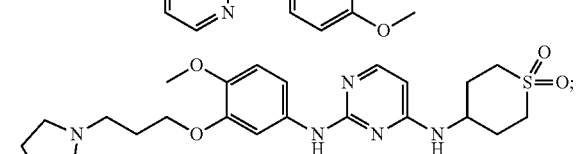
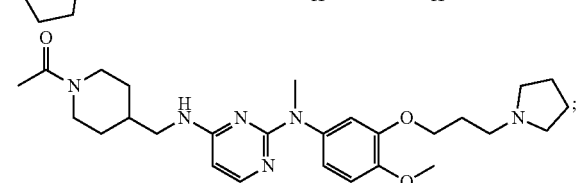
574
-continued
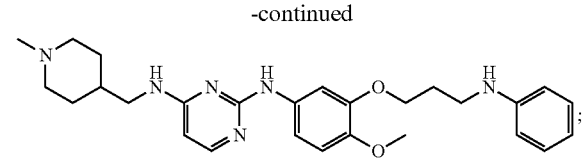
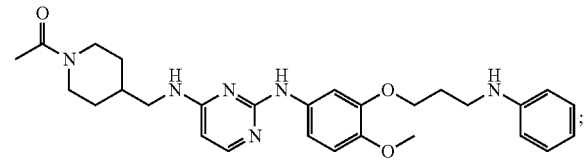
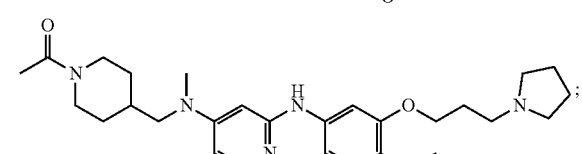
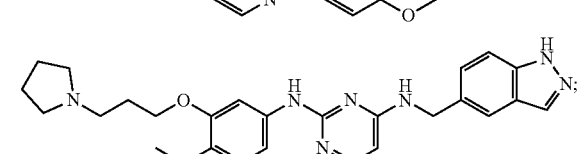
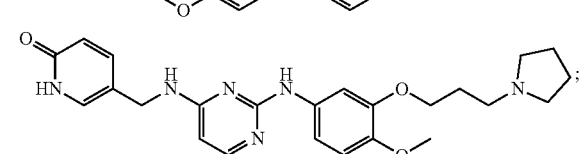
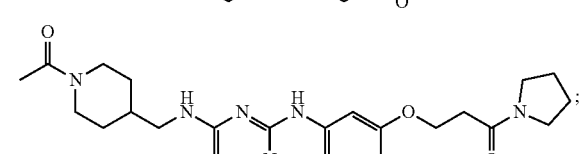
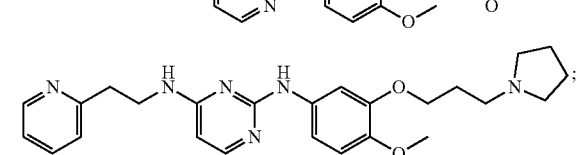
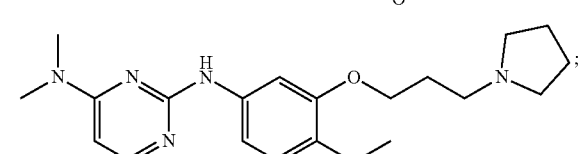
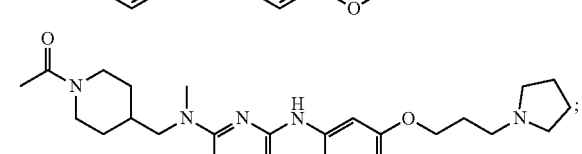
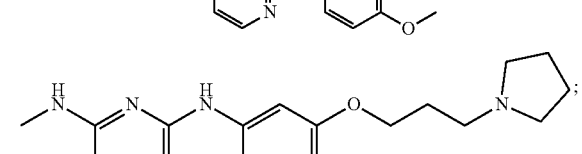
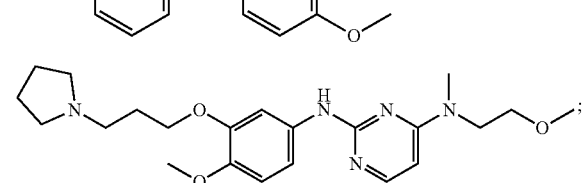

575
-continued
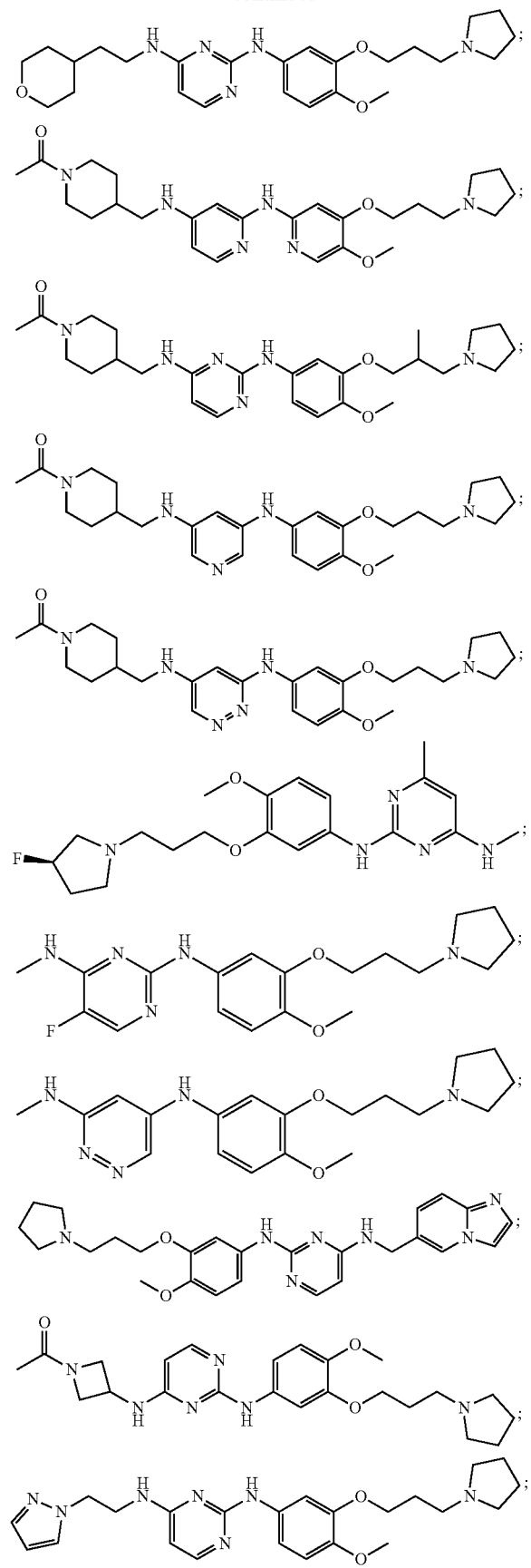
576
-continued
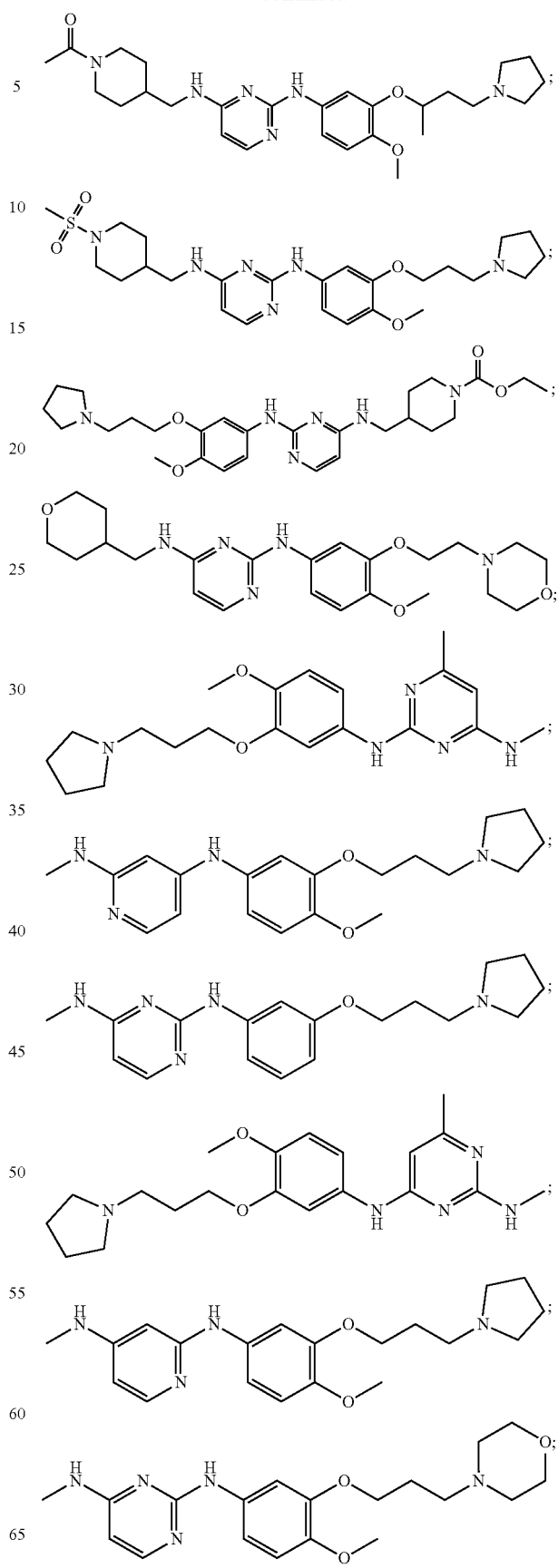

577
-continued
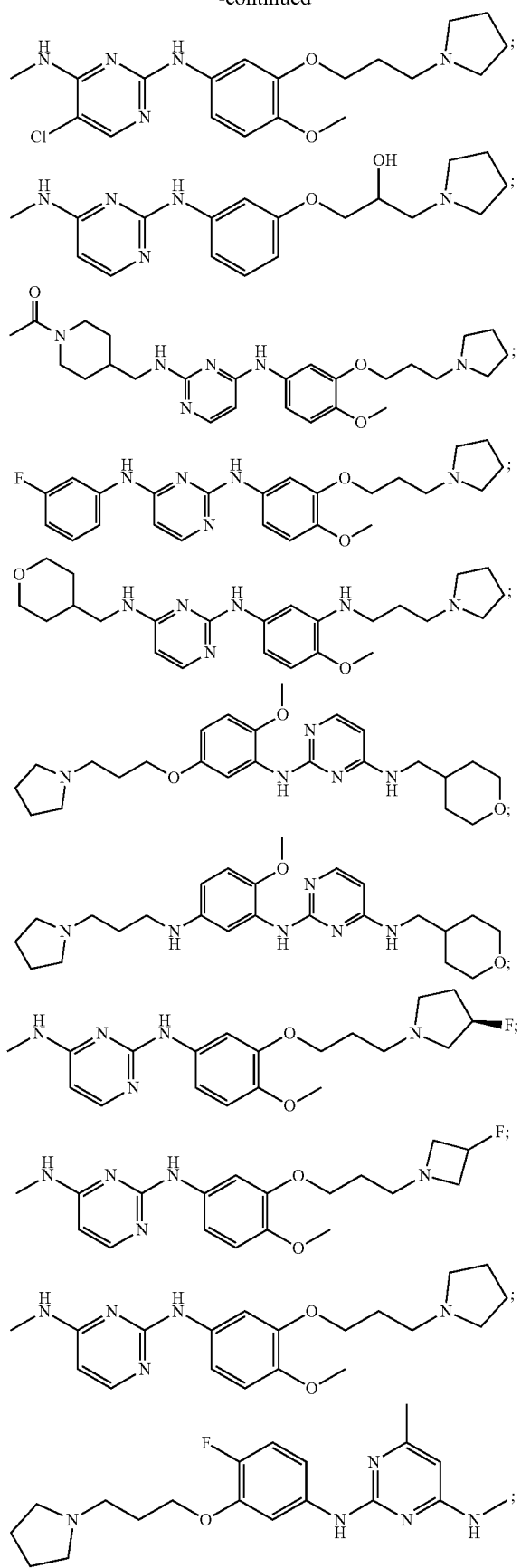
578
-continued
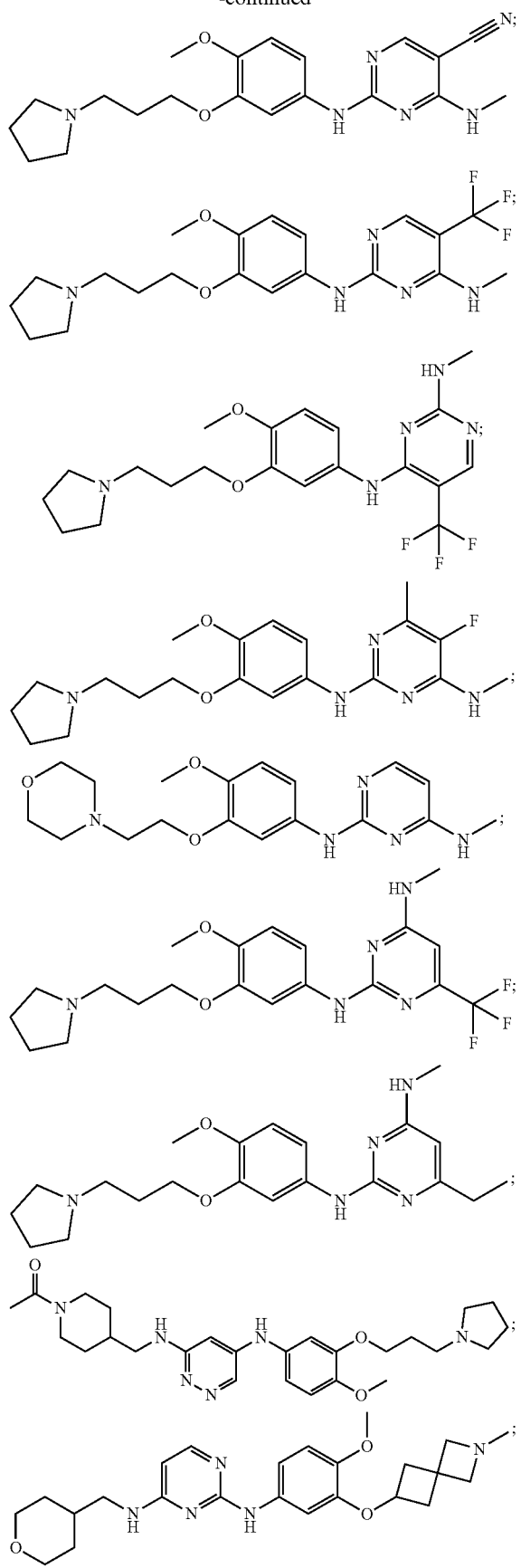

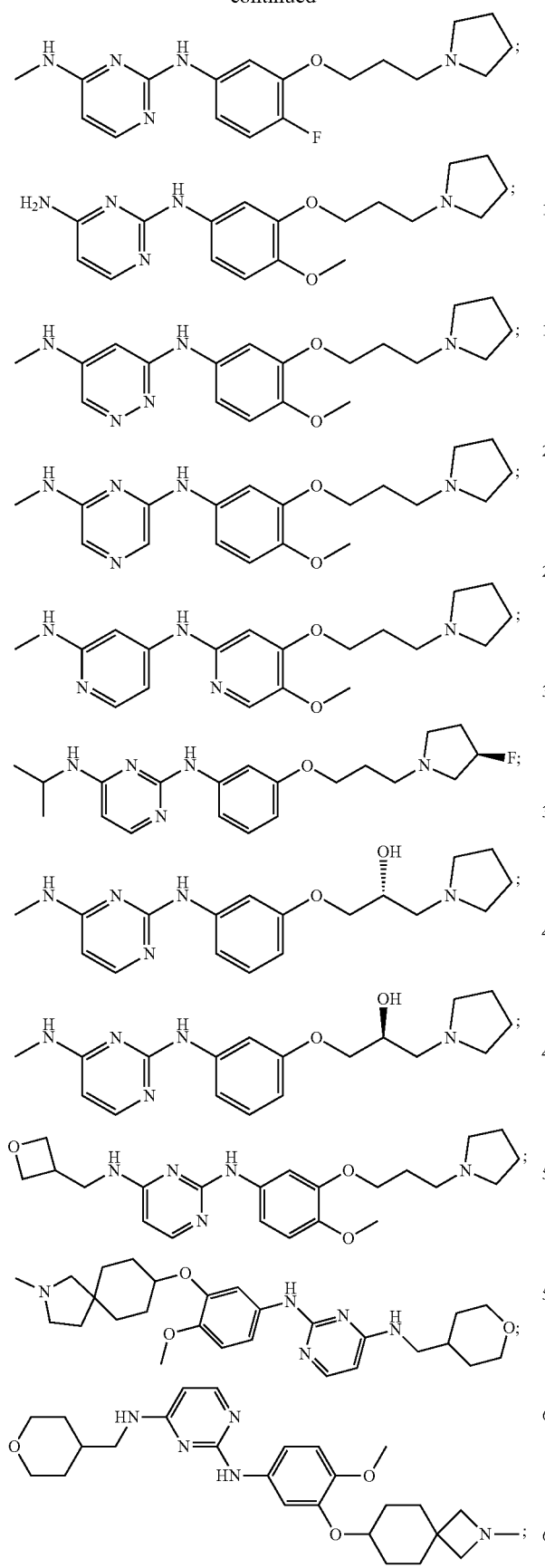
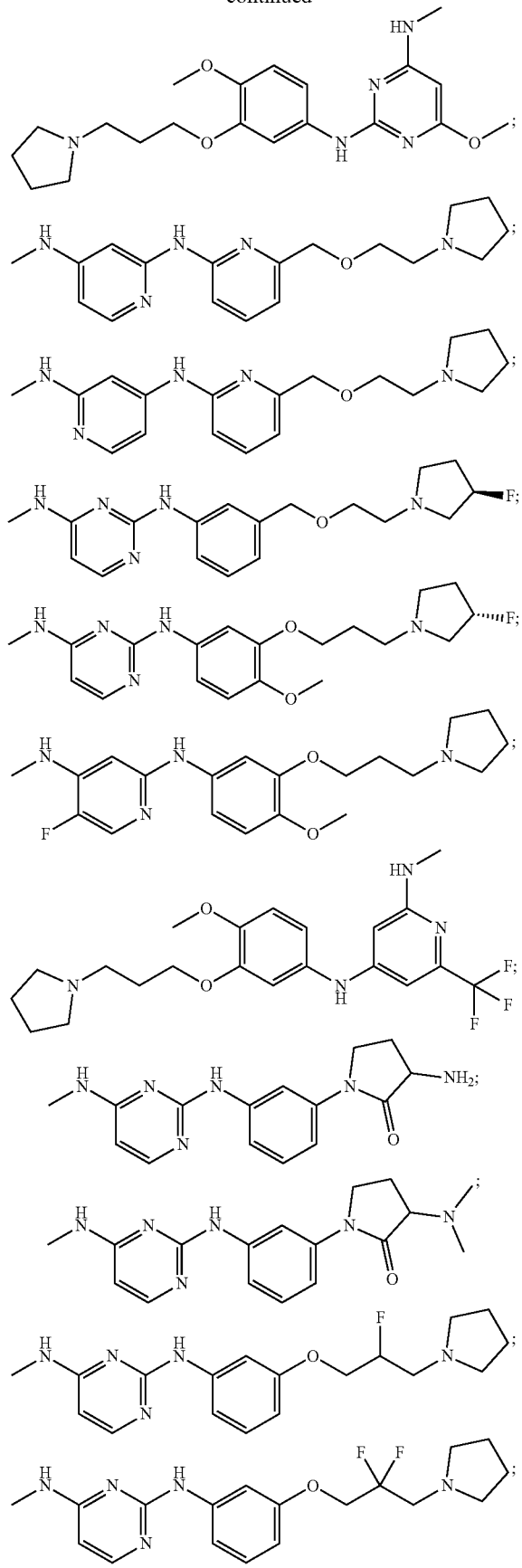

581
-continued
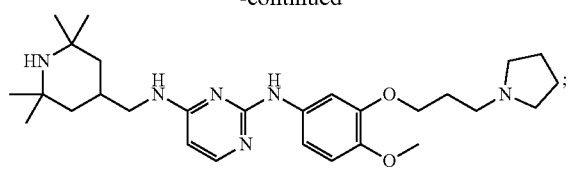
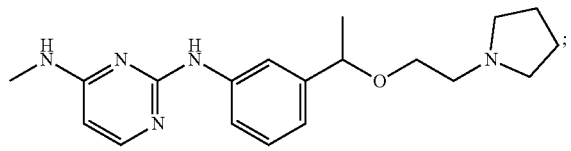
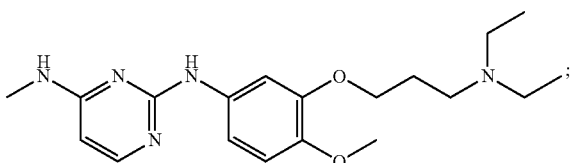
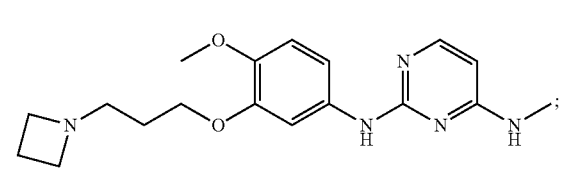
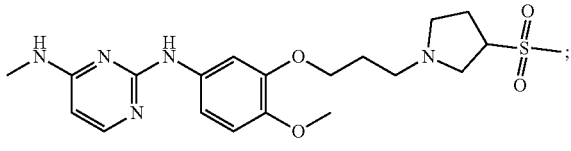
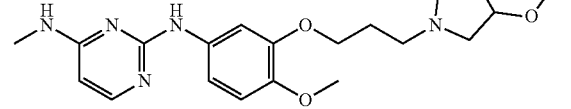
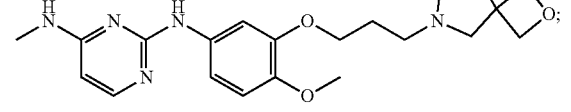
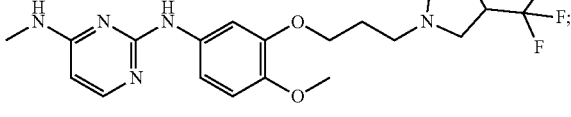
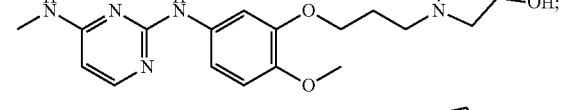
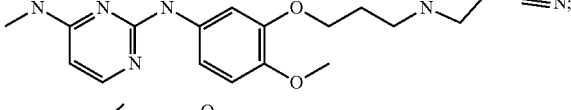
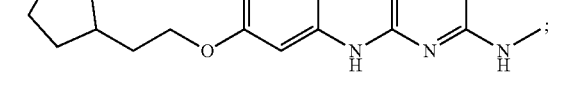
582
-continued
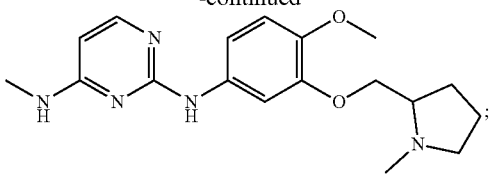
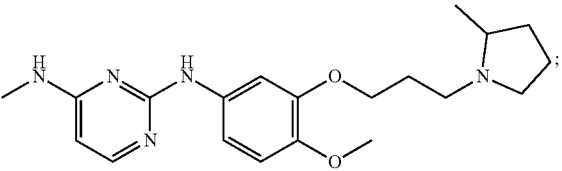
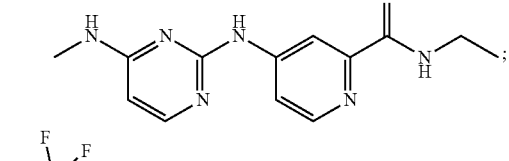
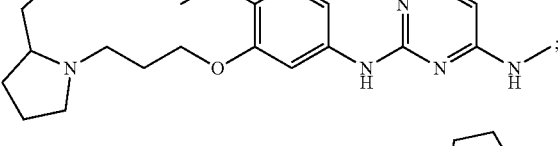
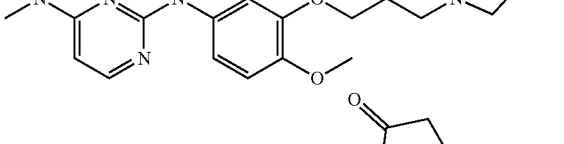
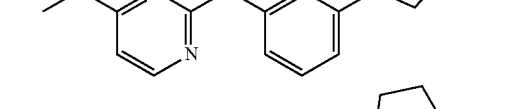
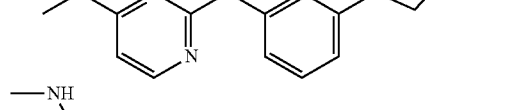
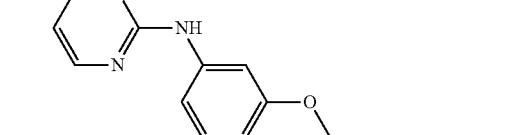
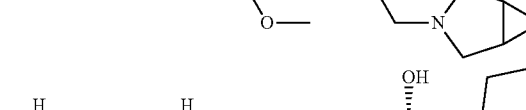
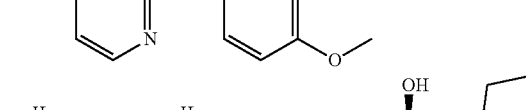
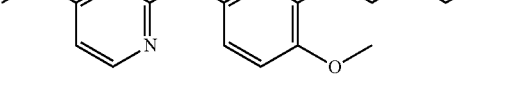

583
-continued
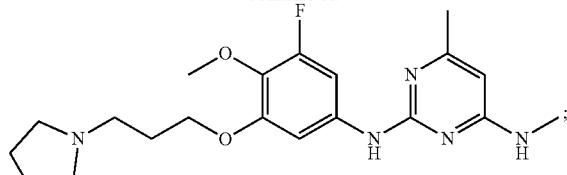
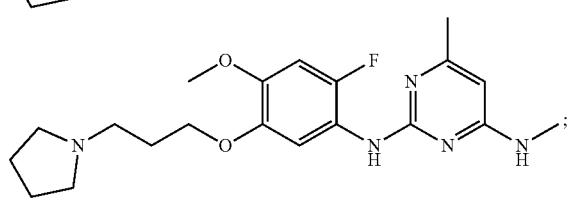
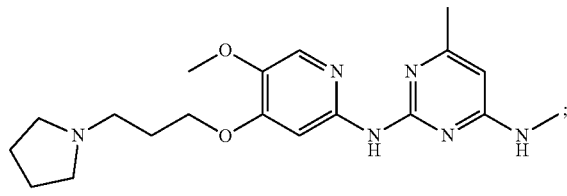
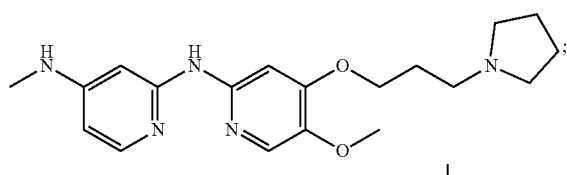
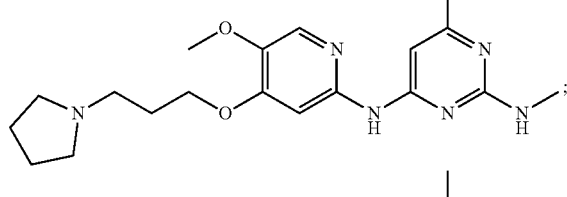
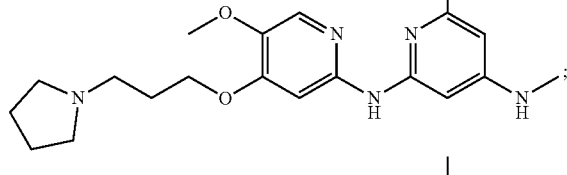
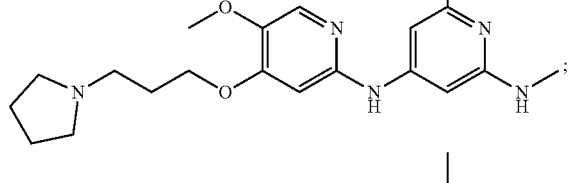
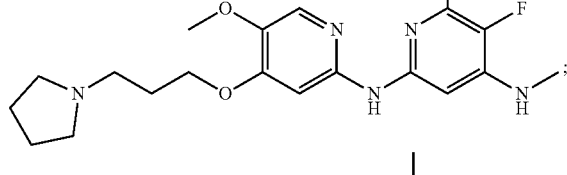
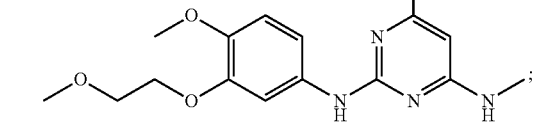
584
-continued
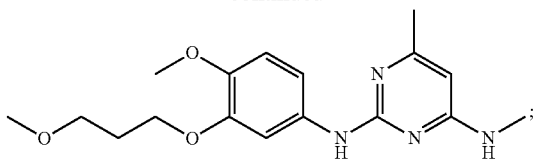
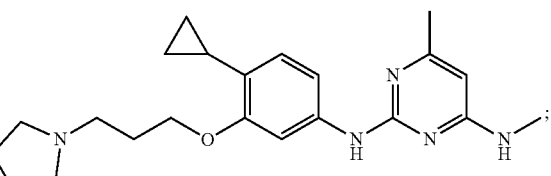
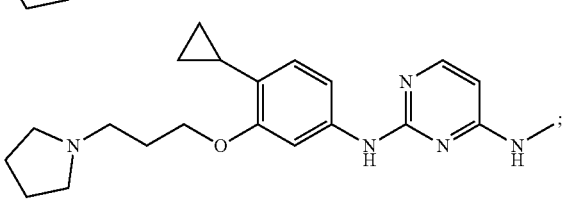
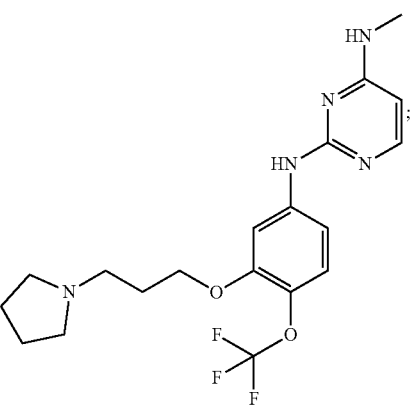
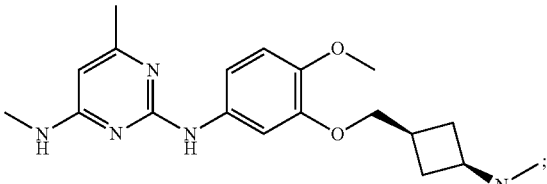
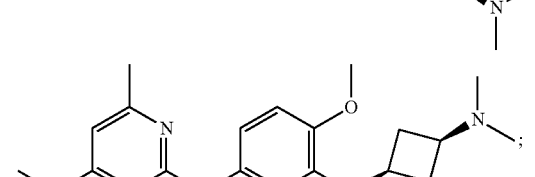
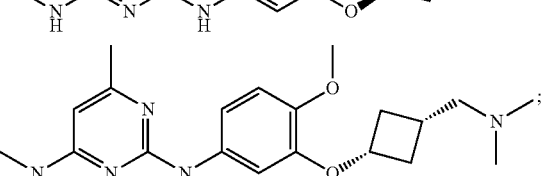
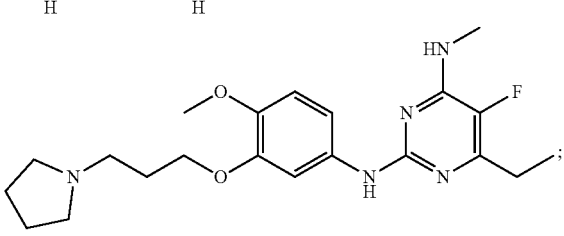

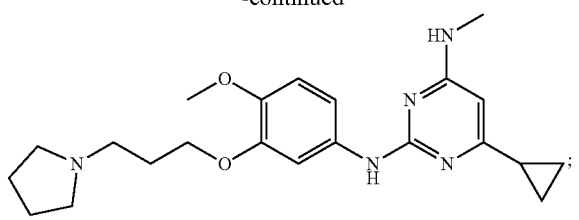
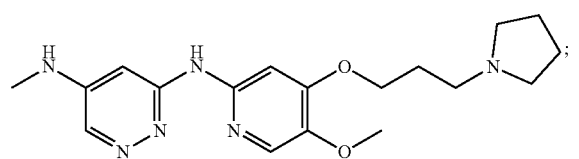
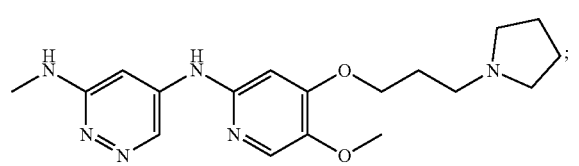
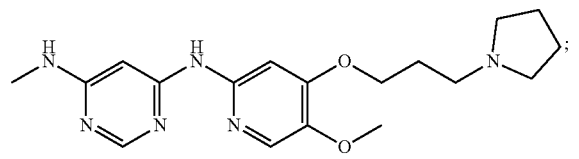
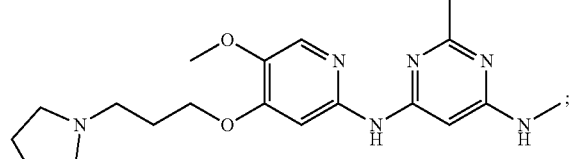
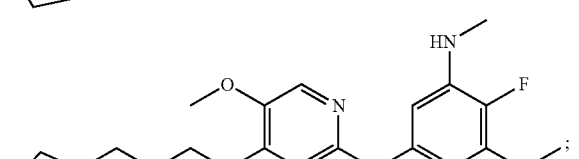
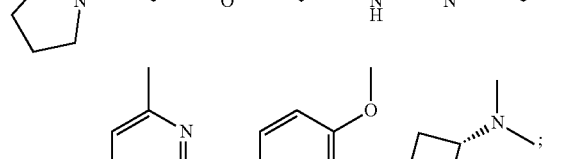
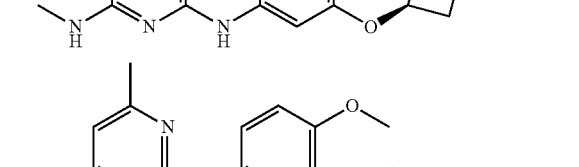
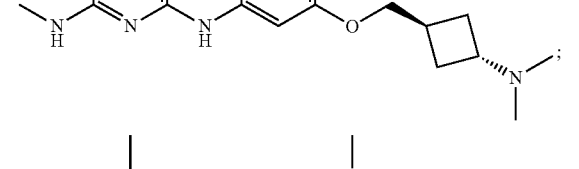
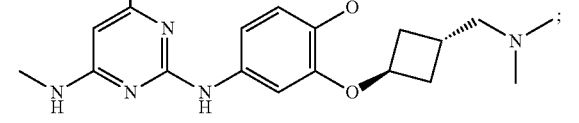
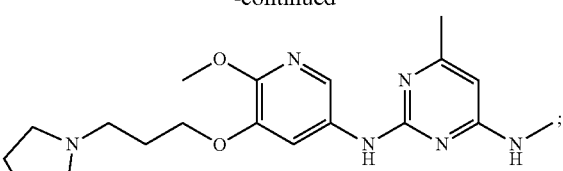
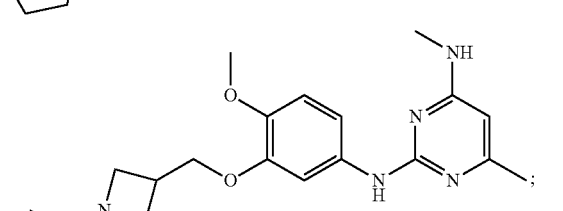
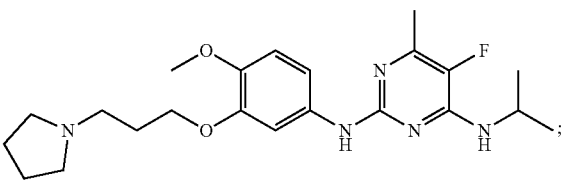
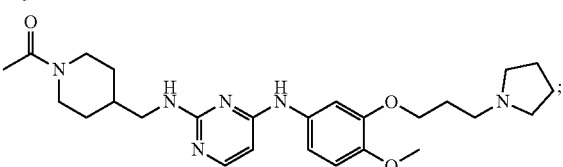
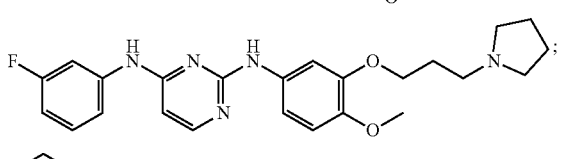
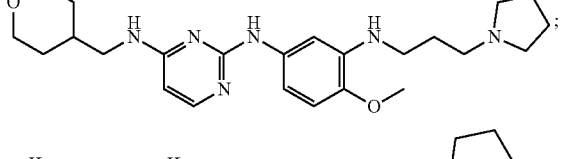
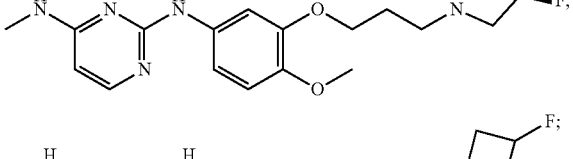
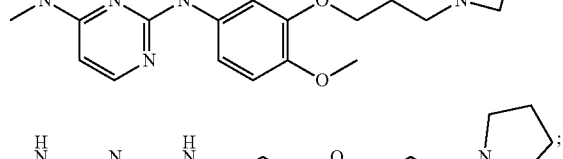
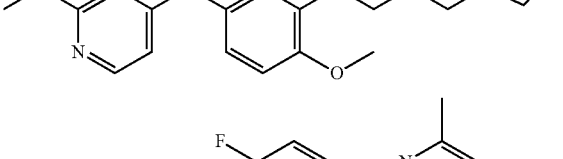
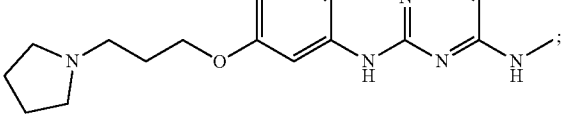

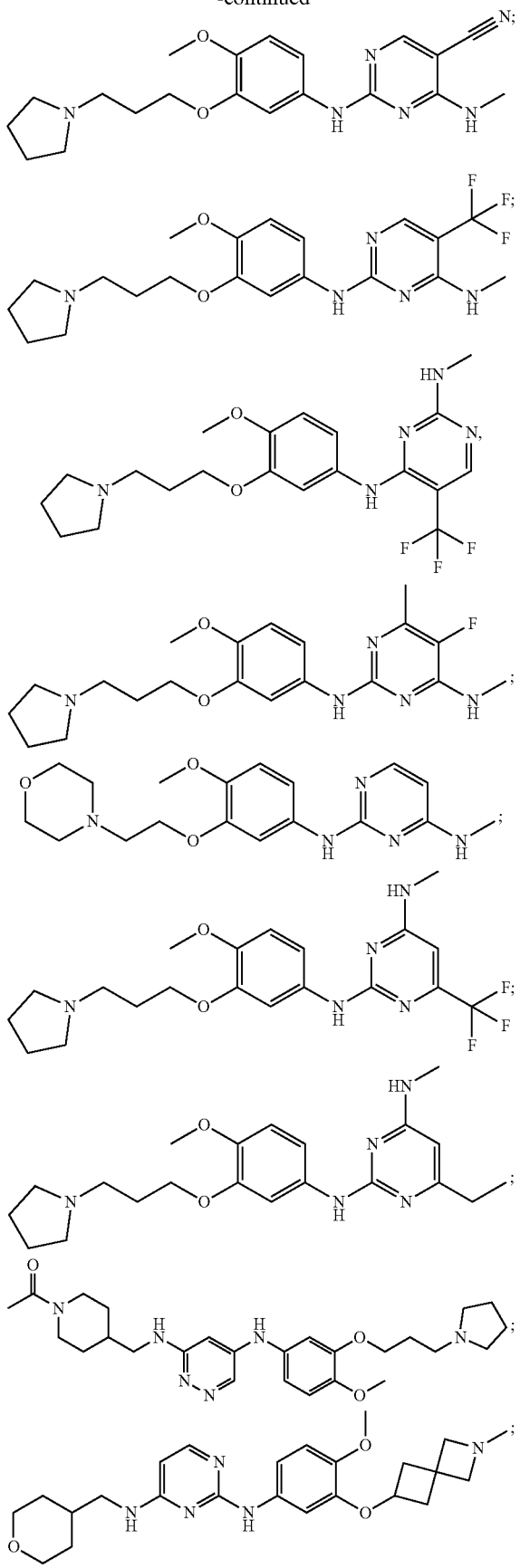
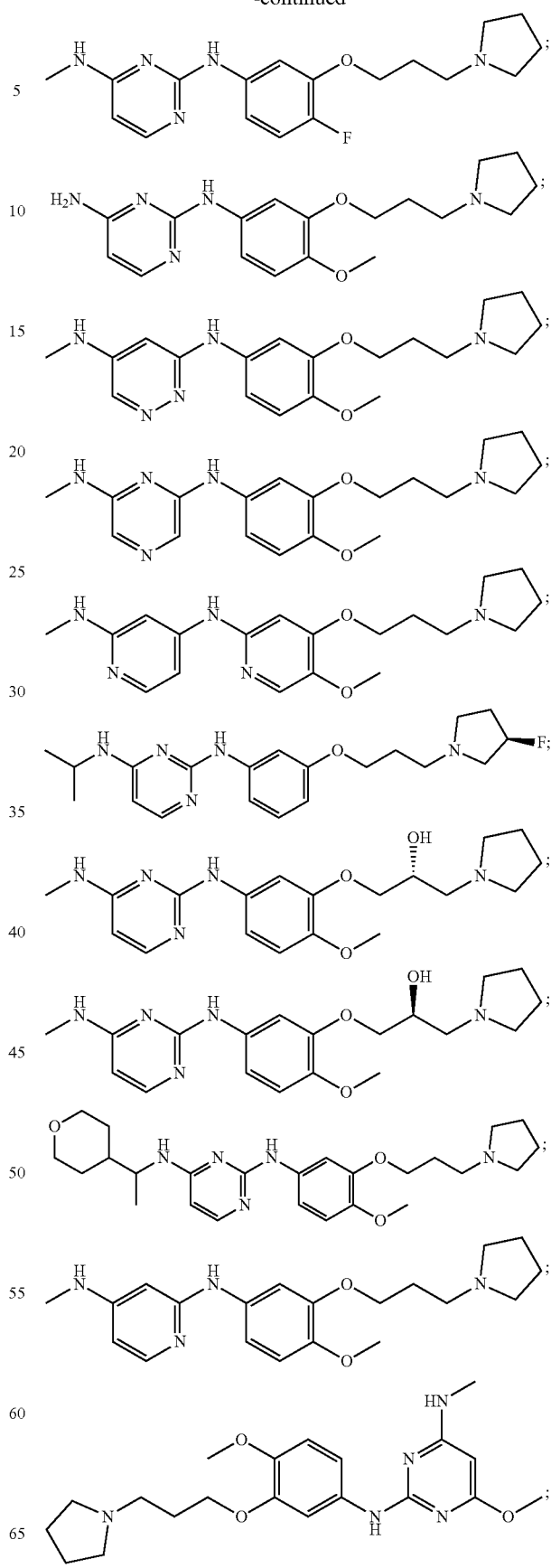

-continued
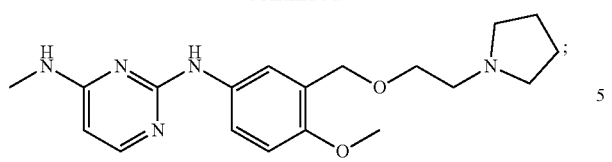
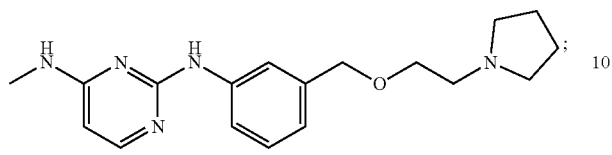
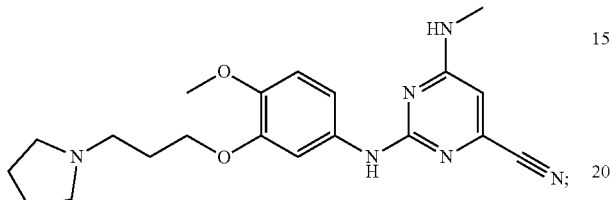
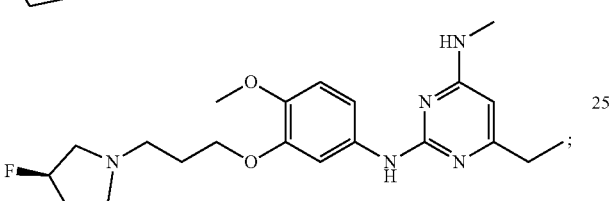
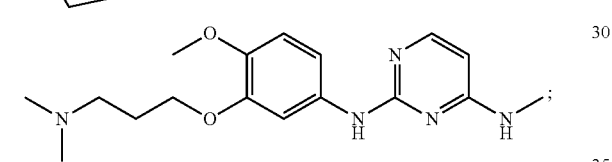
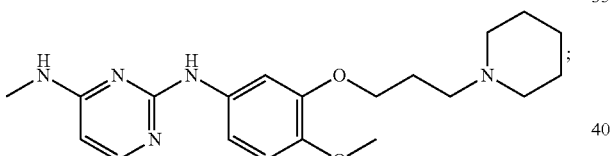
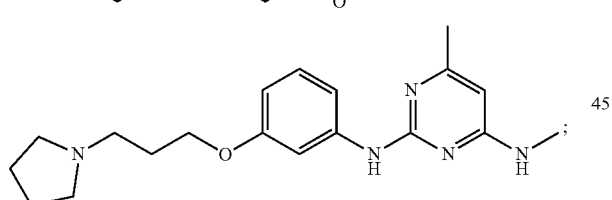
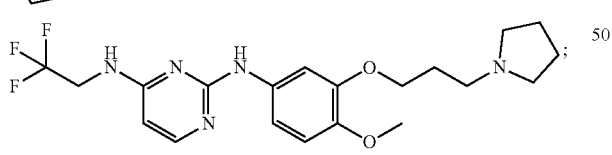
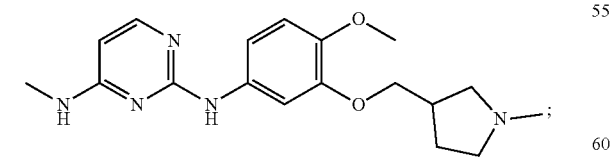
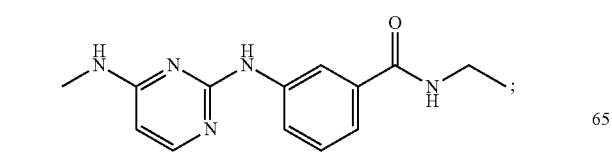
-continued
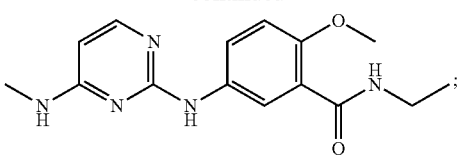
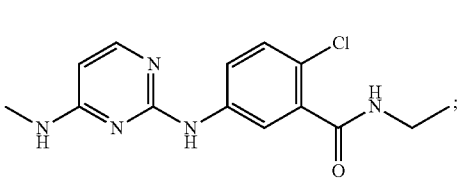
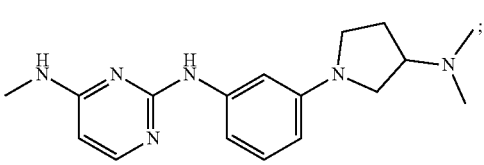
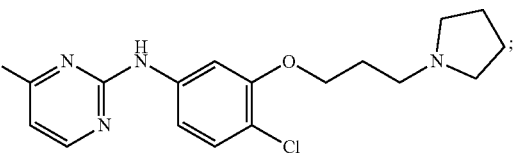
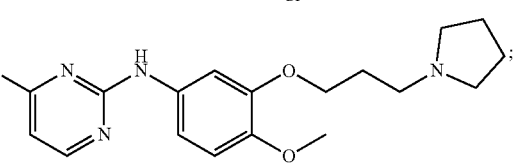
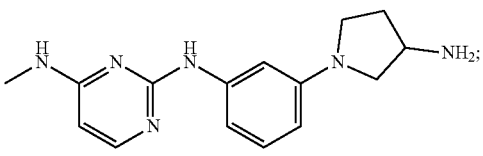
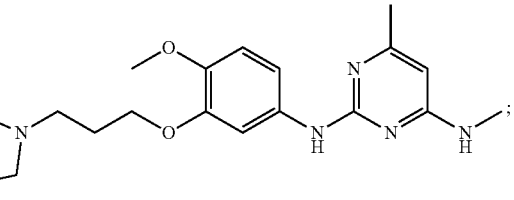
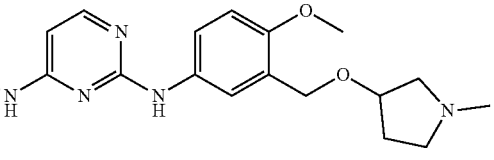
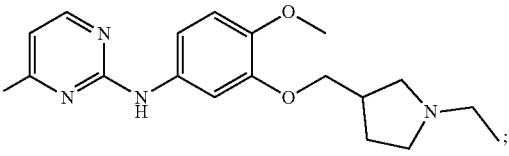
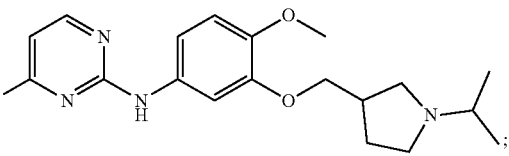

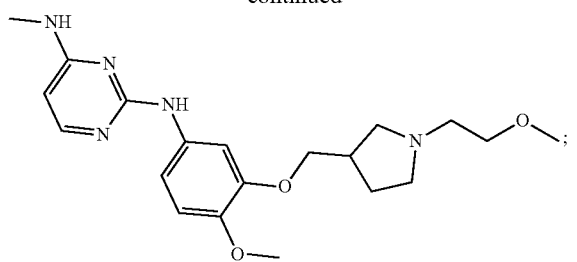
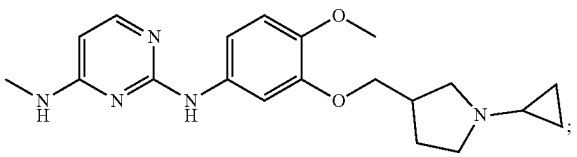
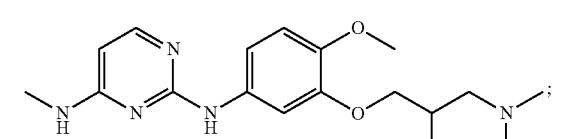
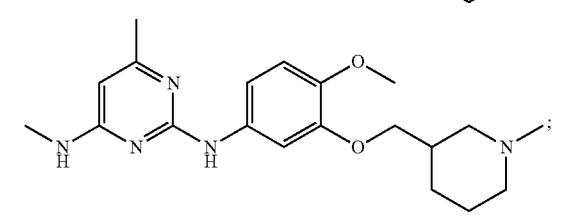
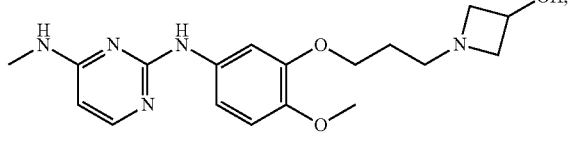
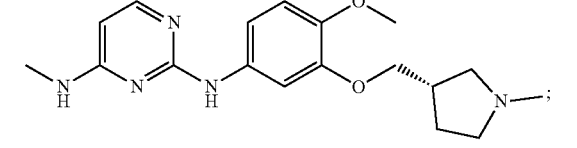
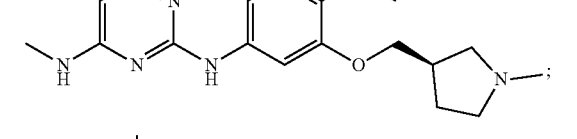
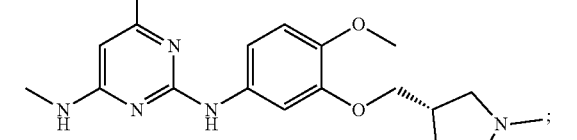
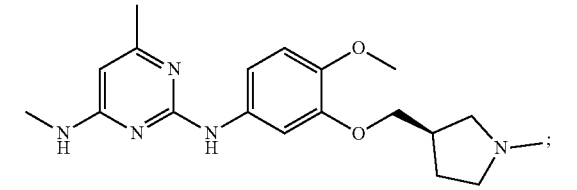
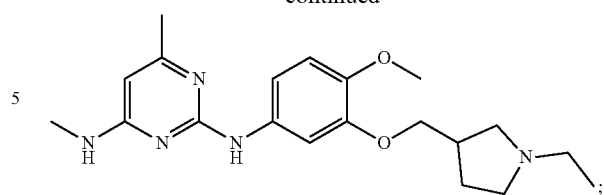
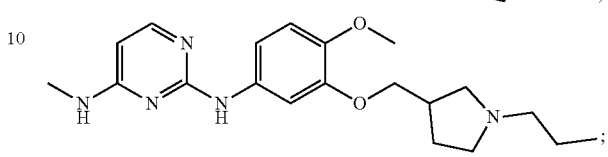
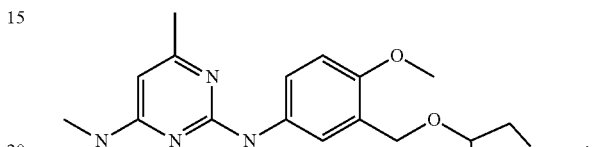
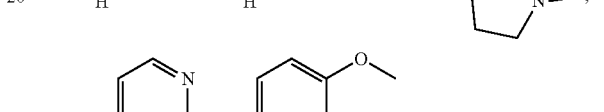
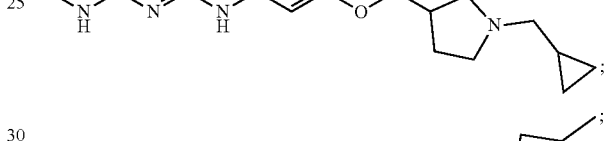
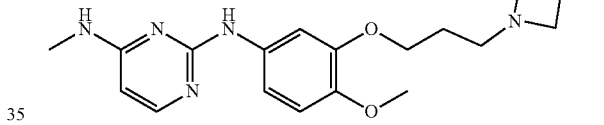
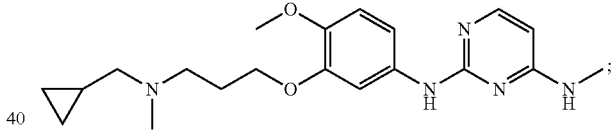
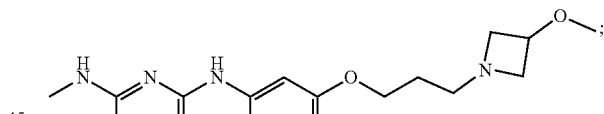
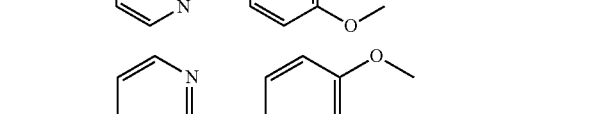
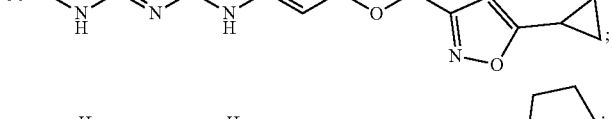
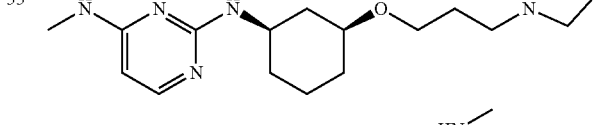
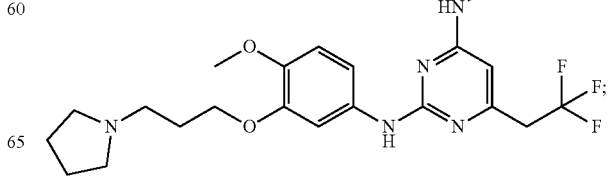

593
-continued
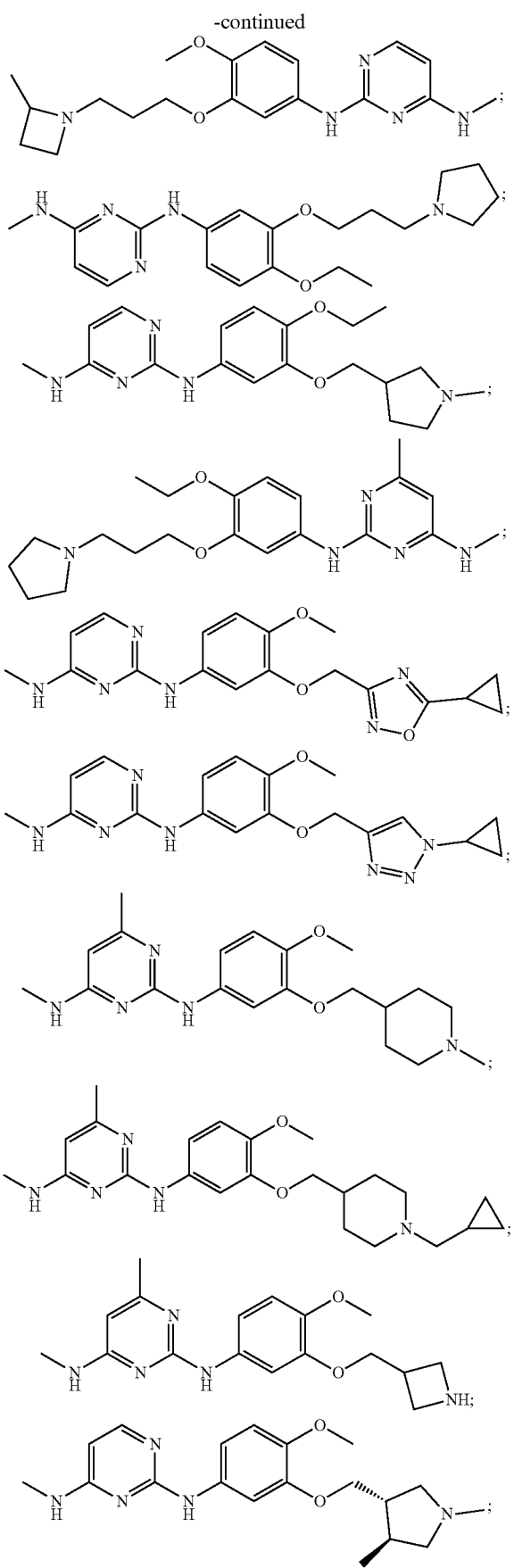
594
-continued
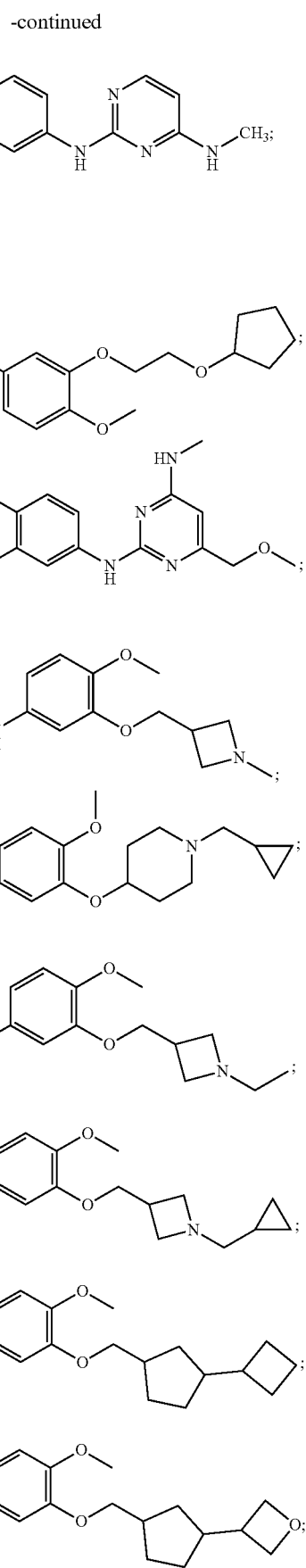

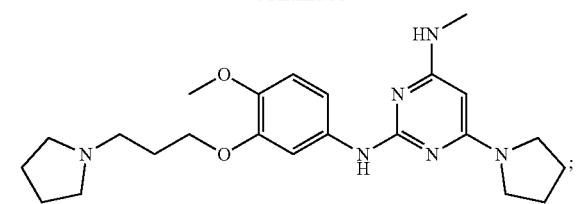
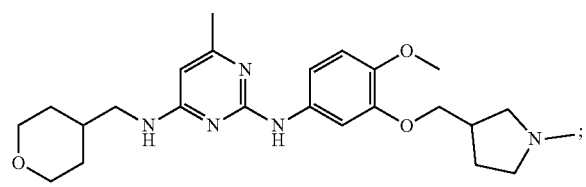
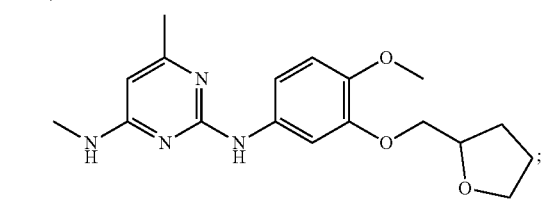
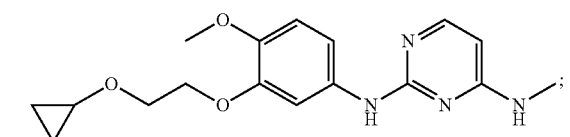
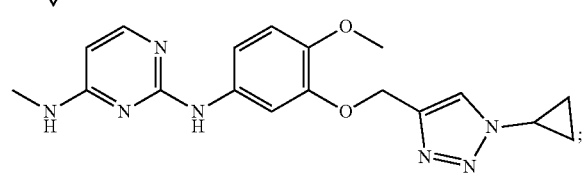
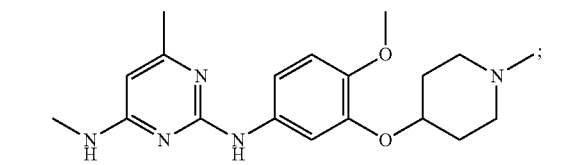
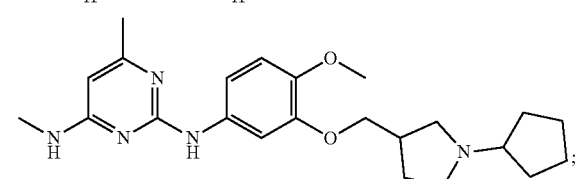
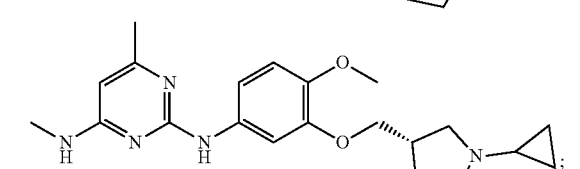
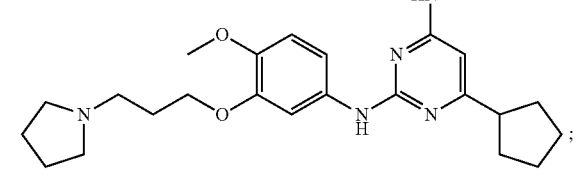
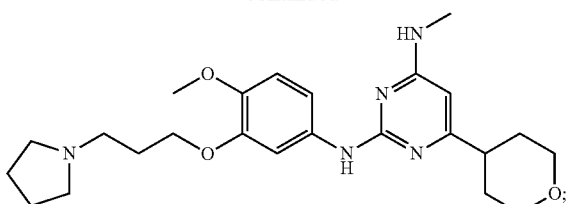
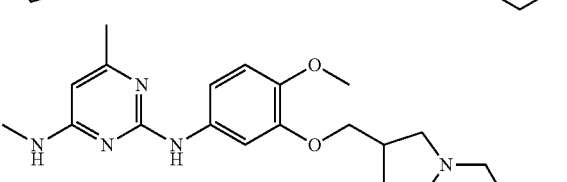
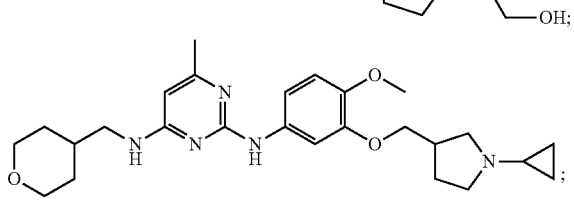
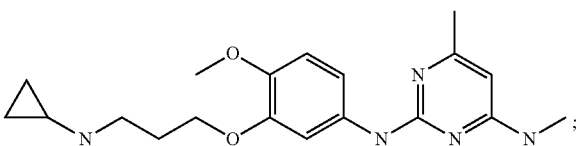
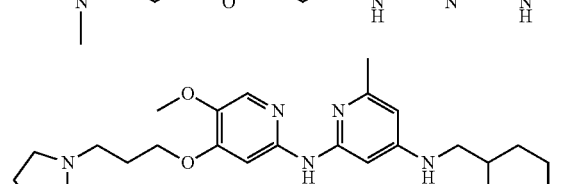
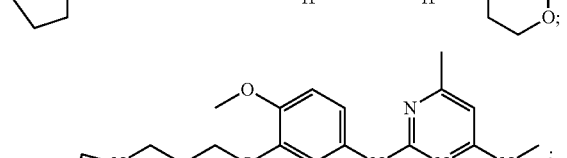
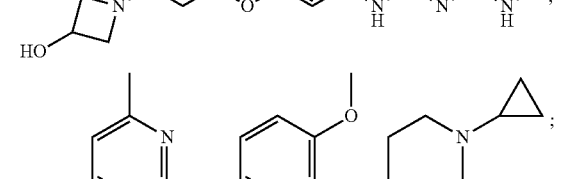
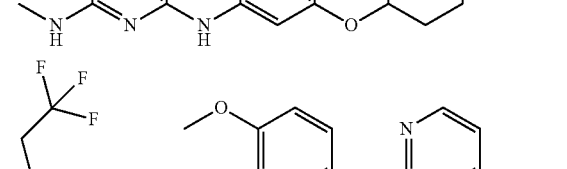
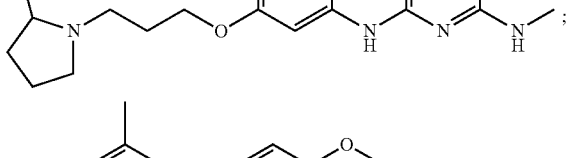
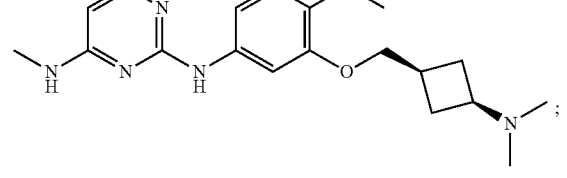

597
-continued
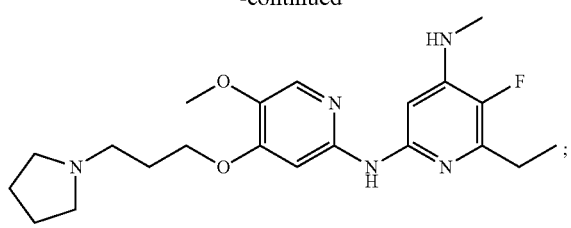
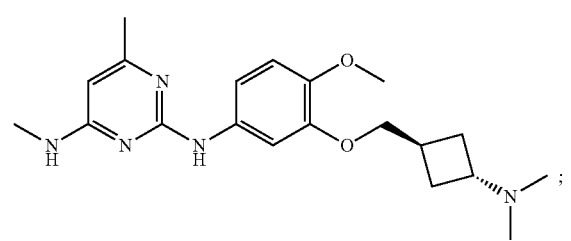
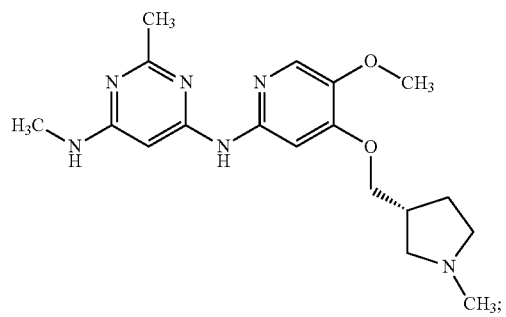
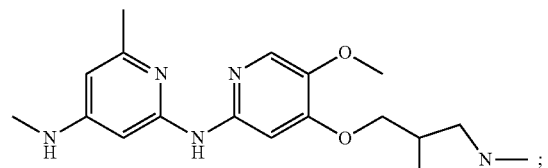
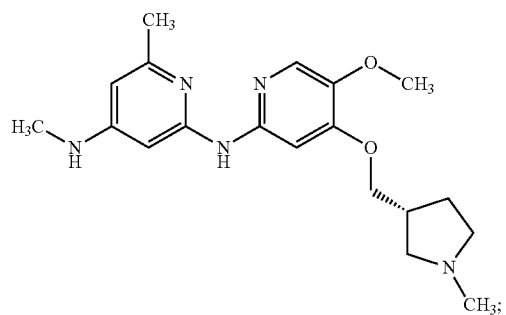
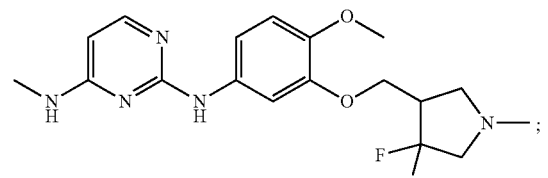
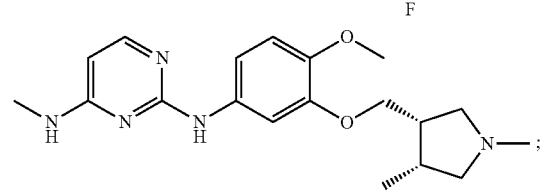
598
-continued
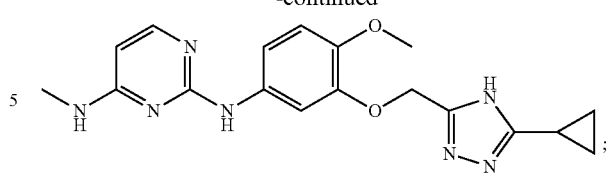
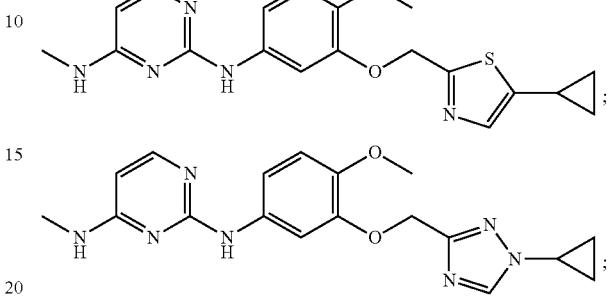
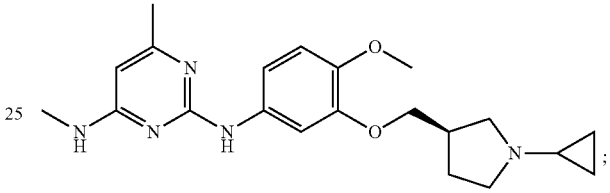
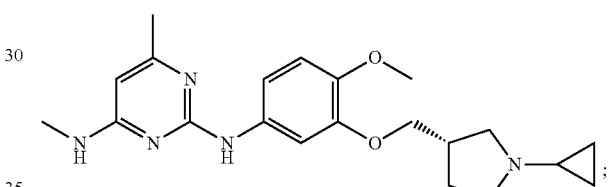
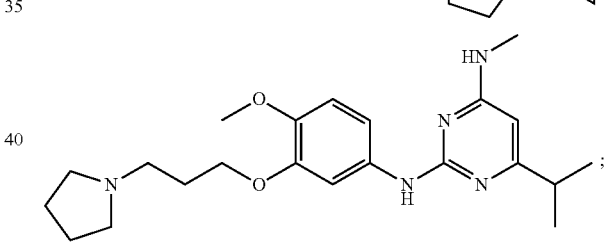
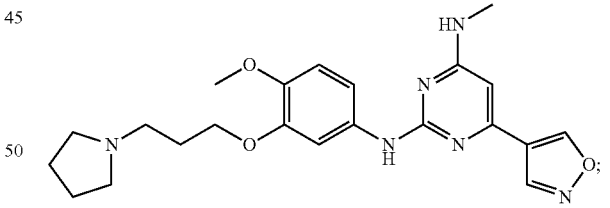
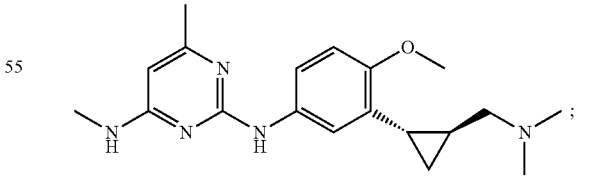
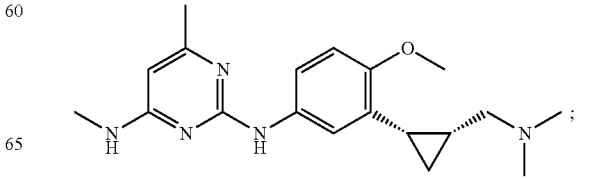

599
-continued
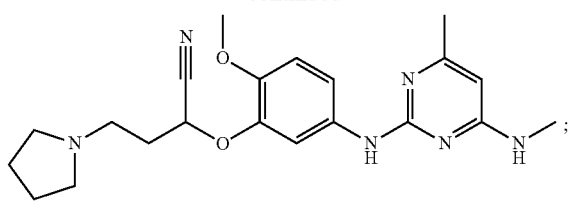
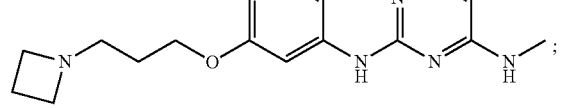
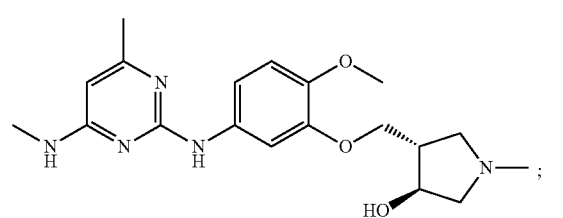
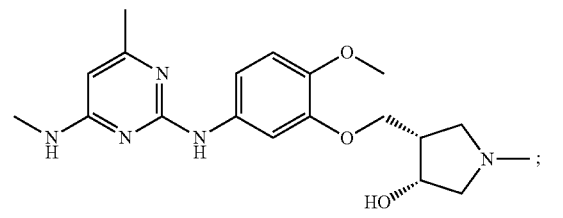
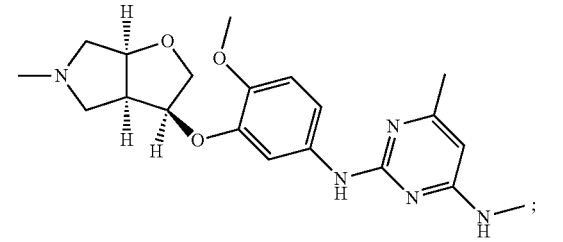
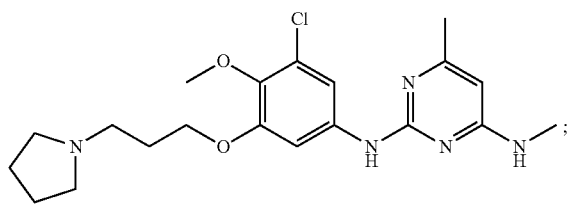
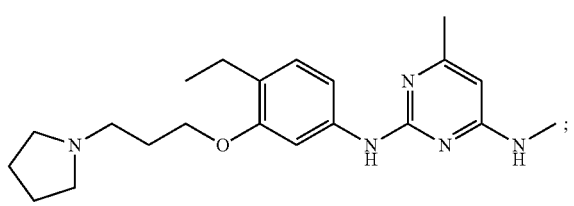
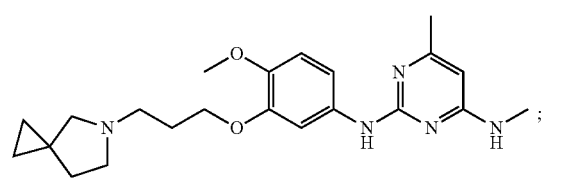
600
-continued
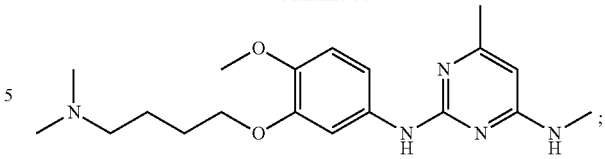
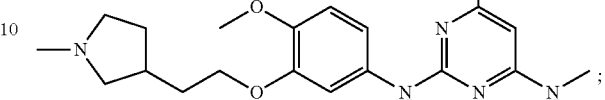
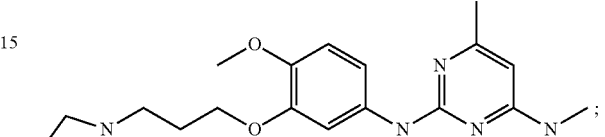
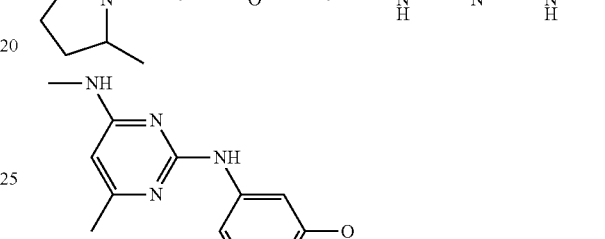
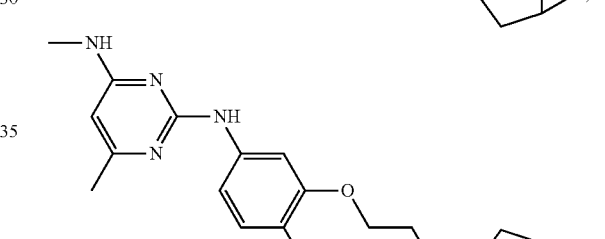
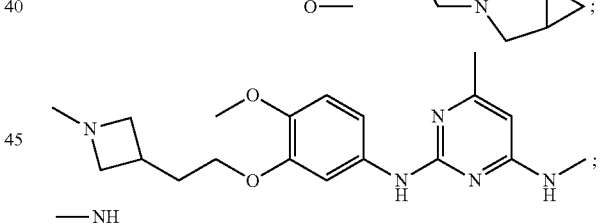
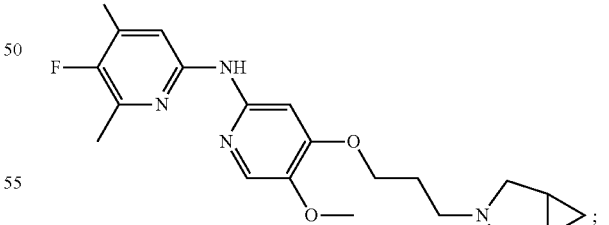
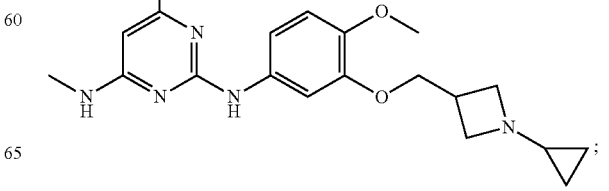

601
-continued
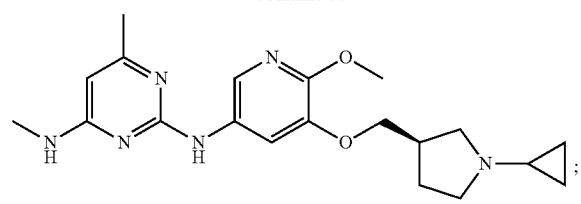
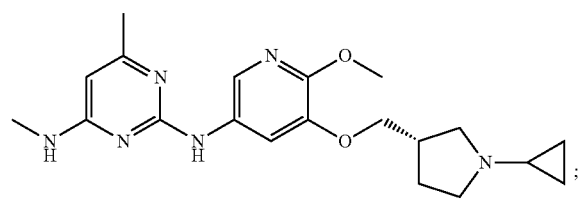
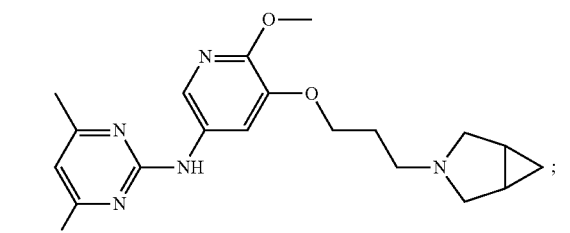
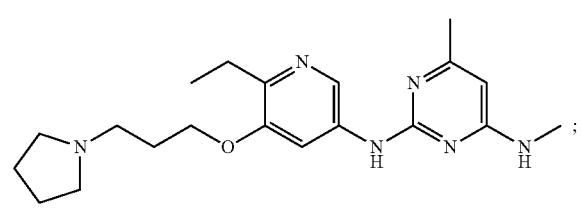
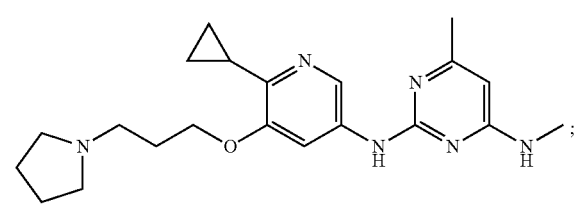
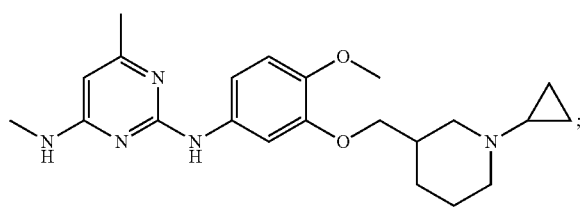
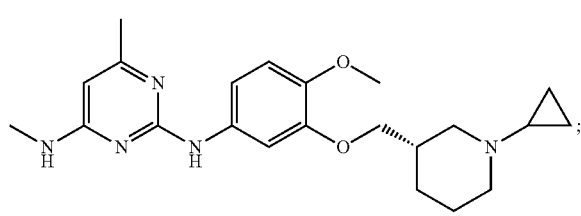
602
-continued
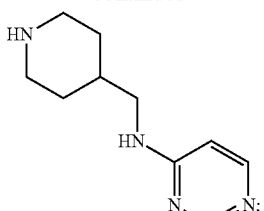
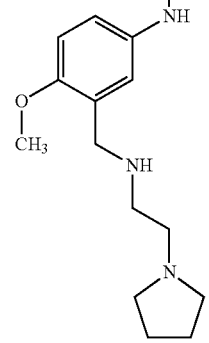
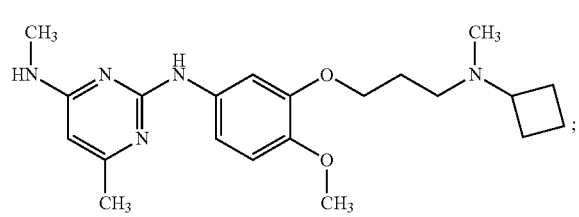
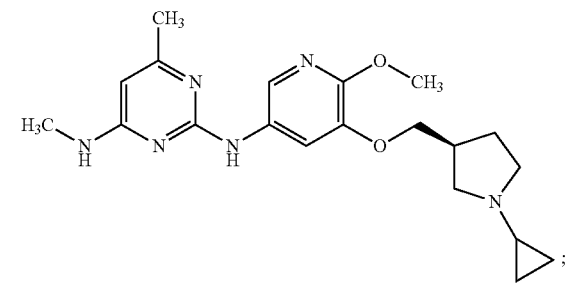
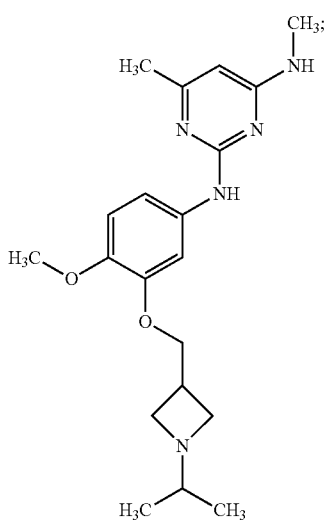

-continued
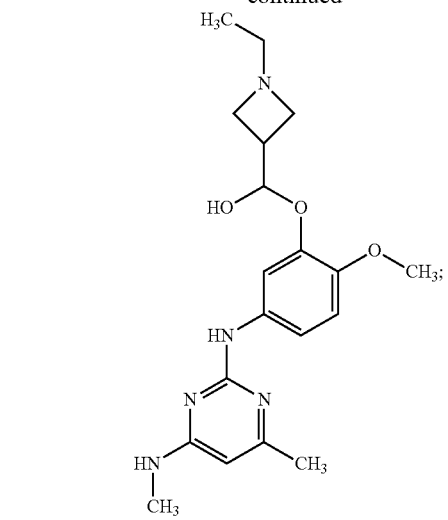
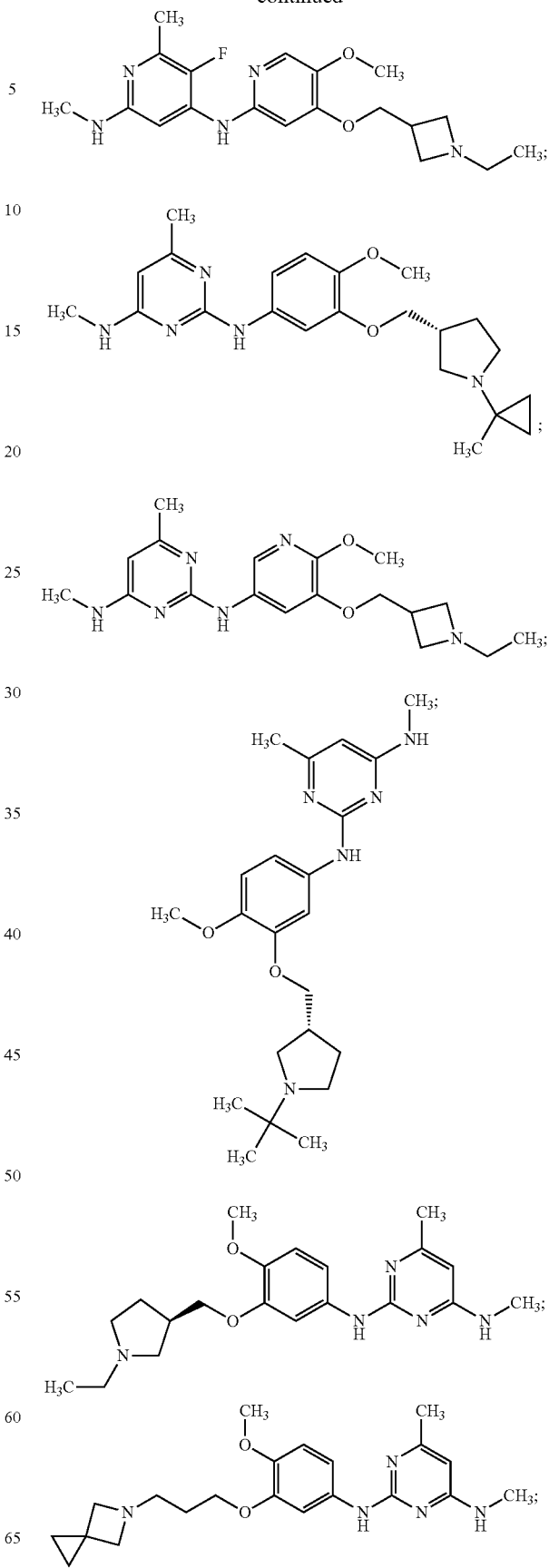

605
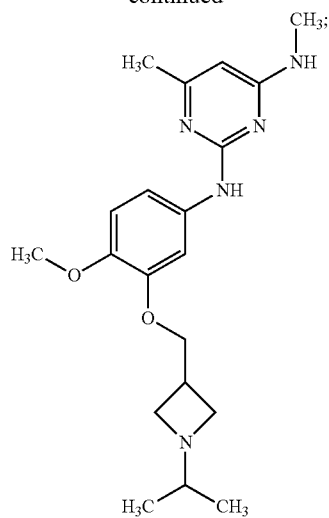
606
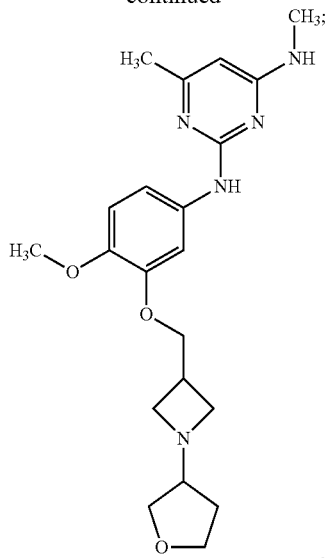
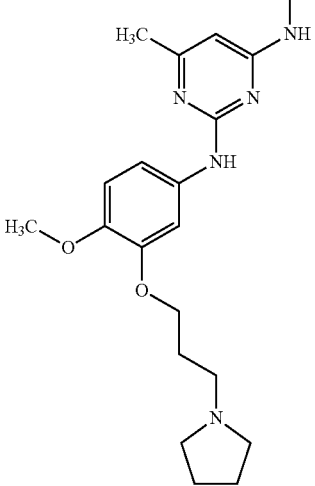
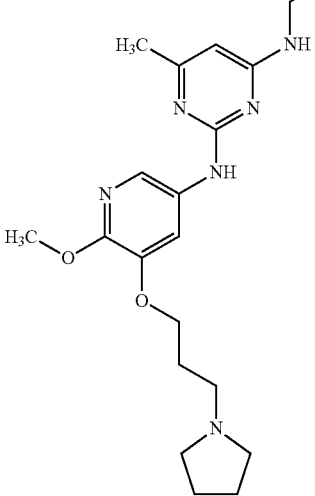

607
-continued
608
-continued
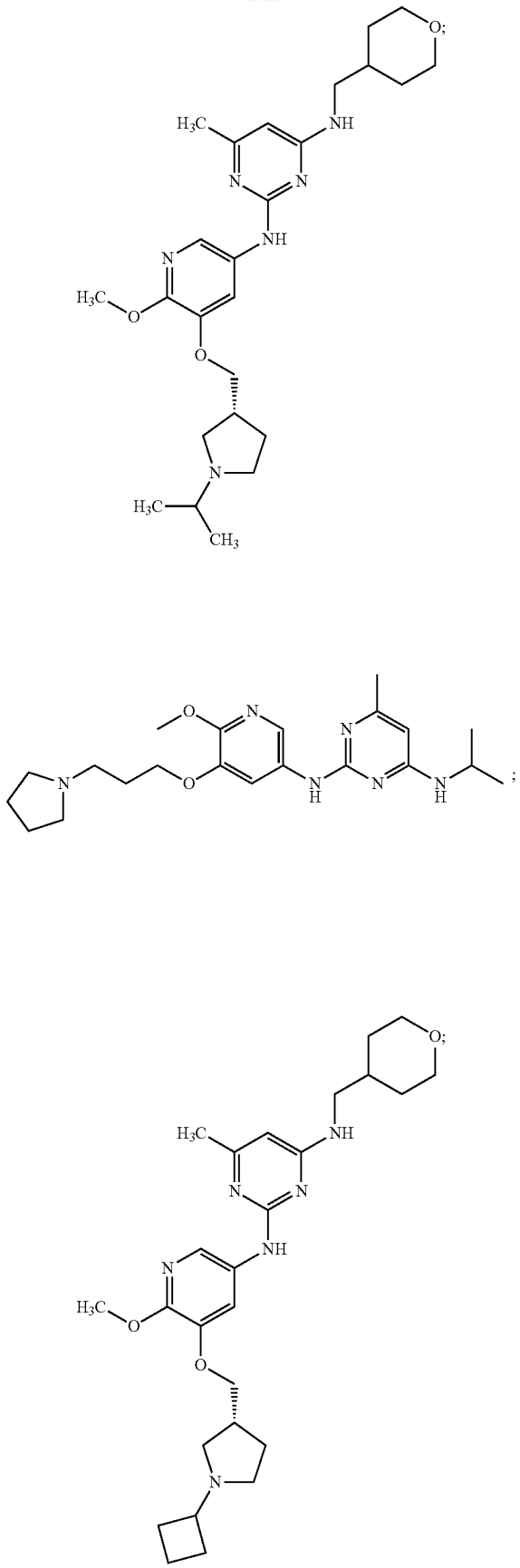
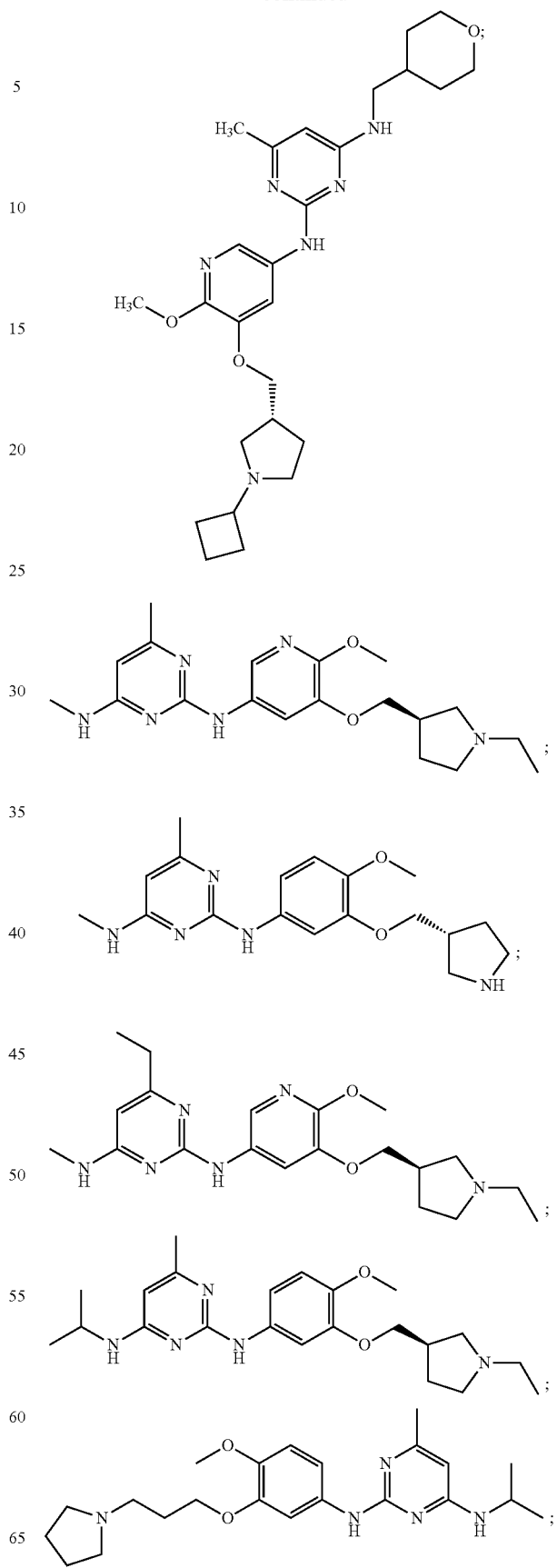

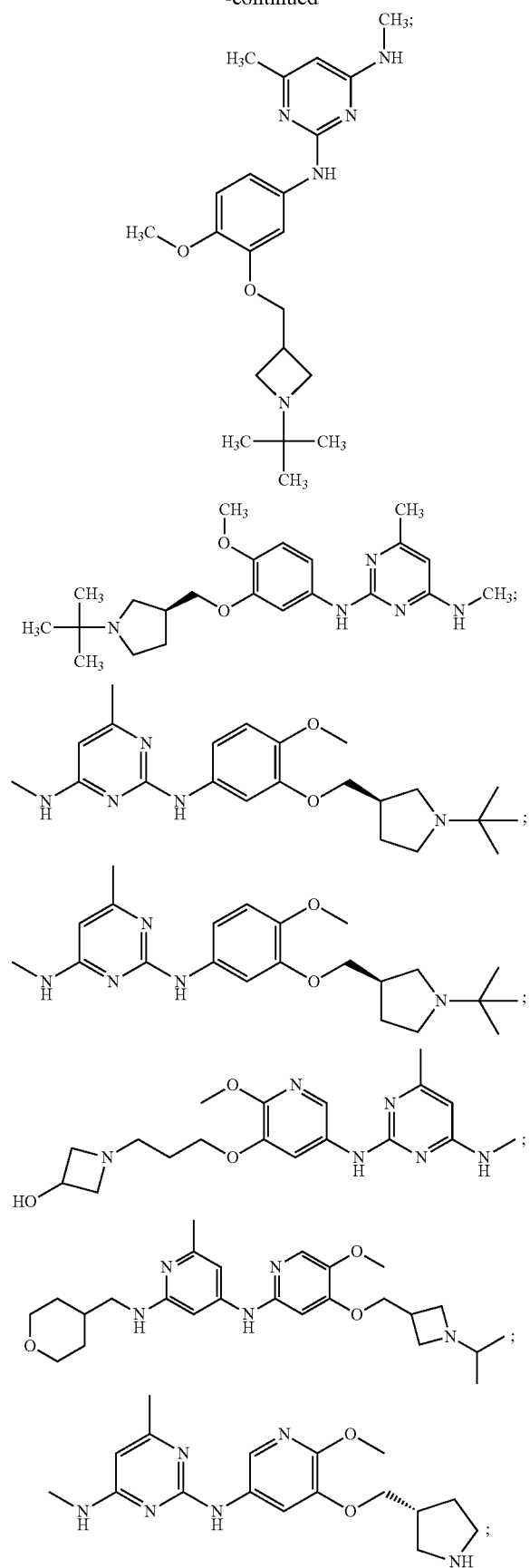
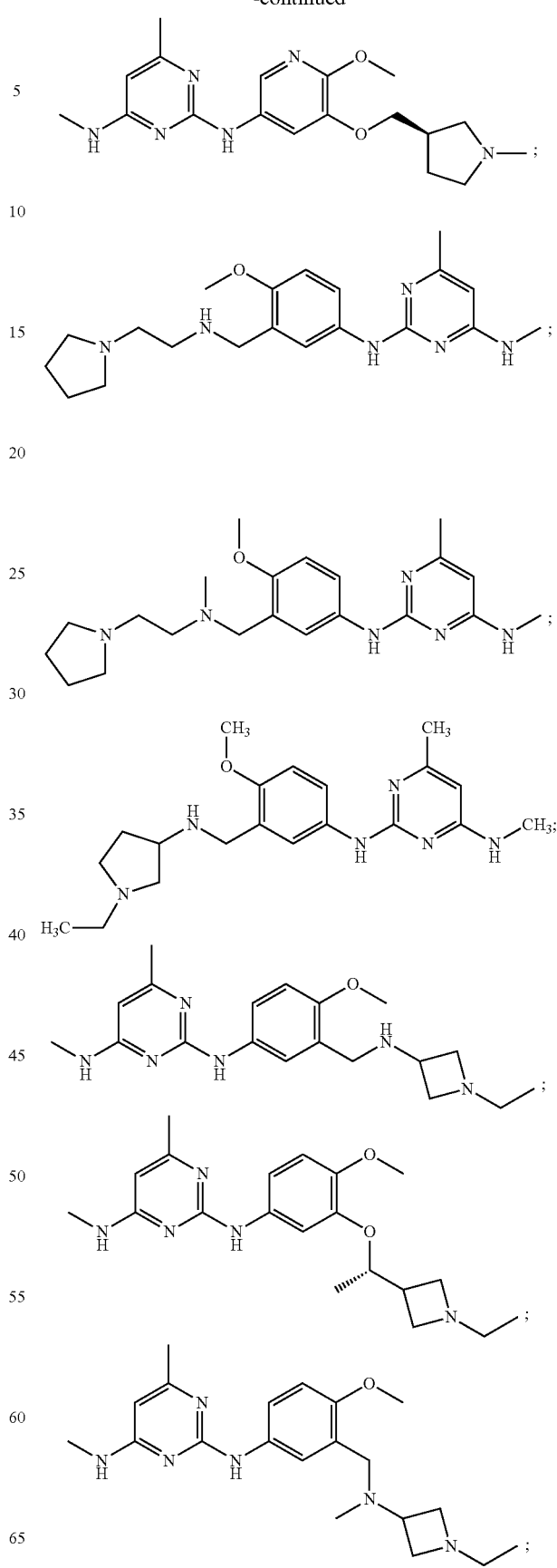

611
-continued
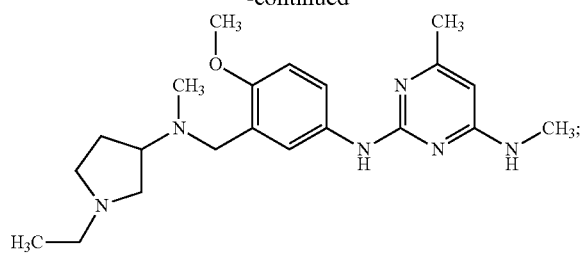
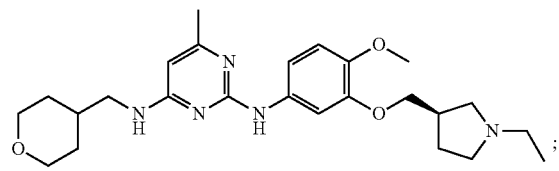
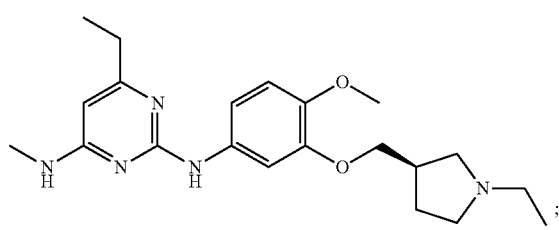
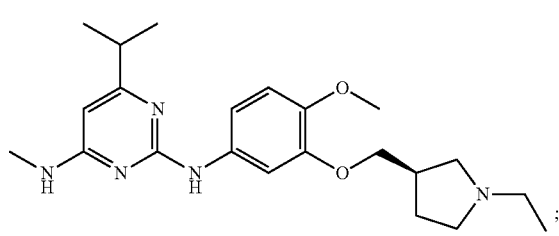
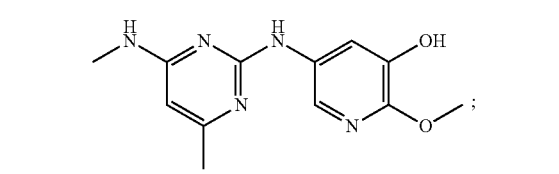
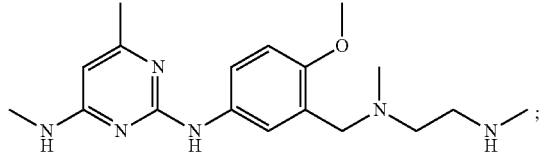
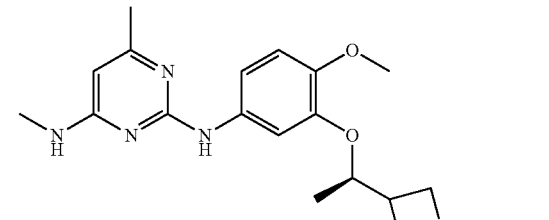
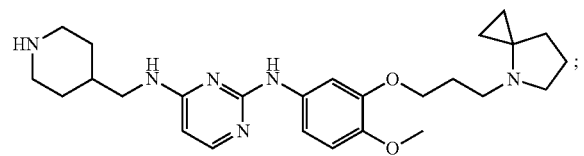
612
-continued
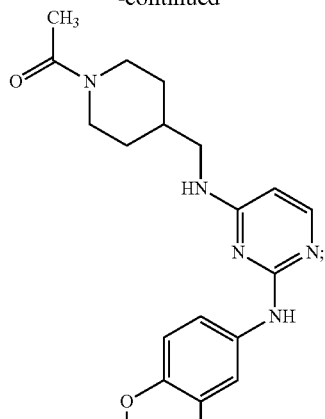
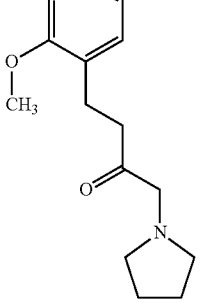
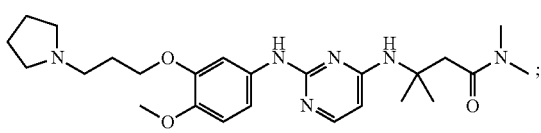
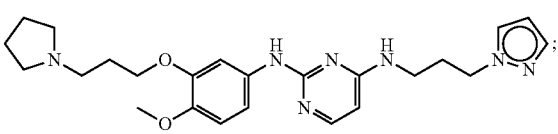
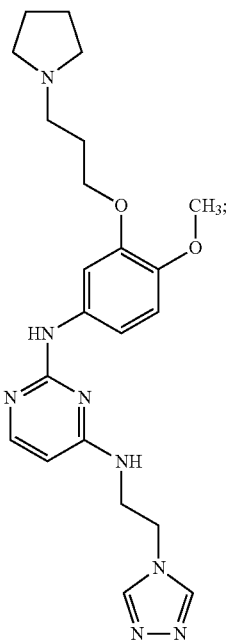

613
-continued
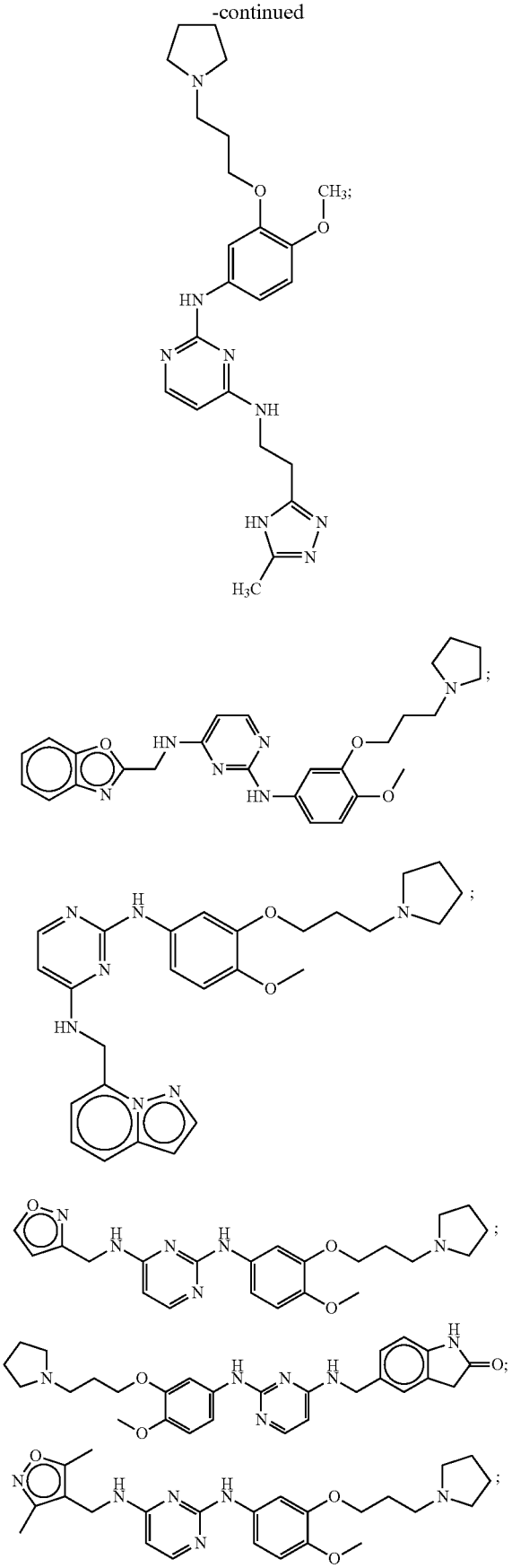
614
-continued
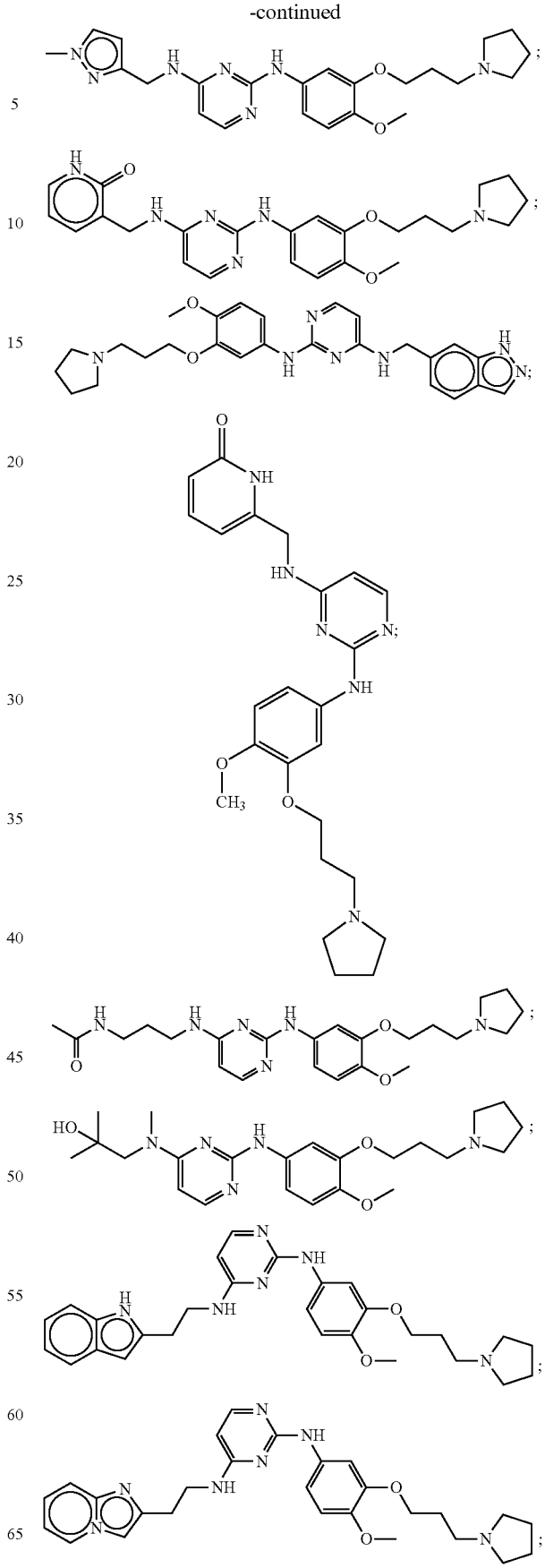

615
-continued
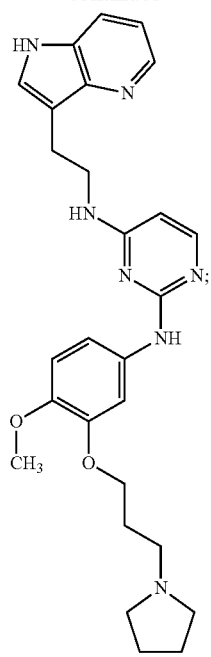
616
-continued
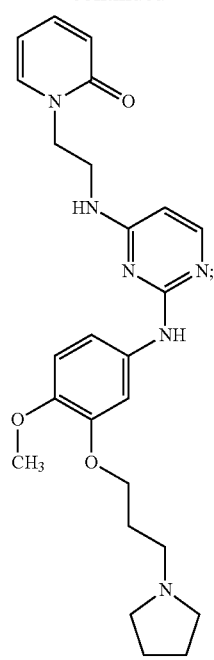
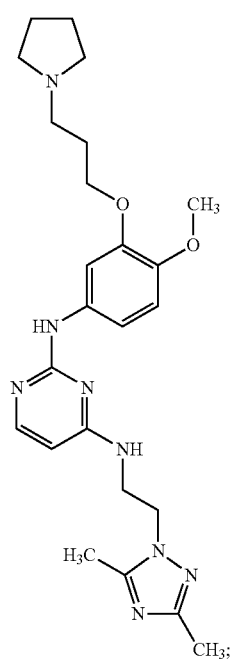
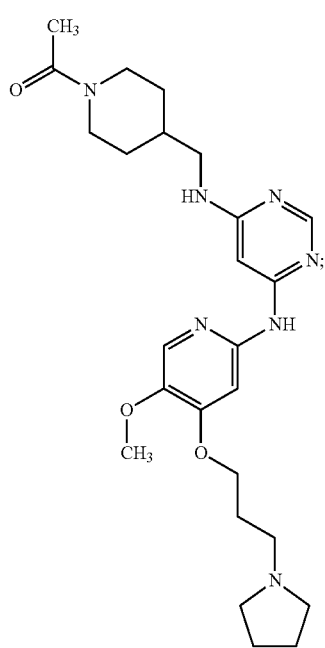

617
-continued
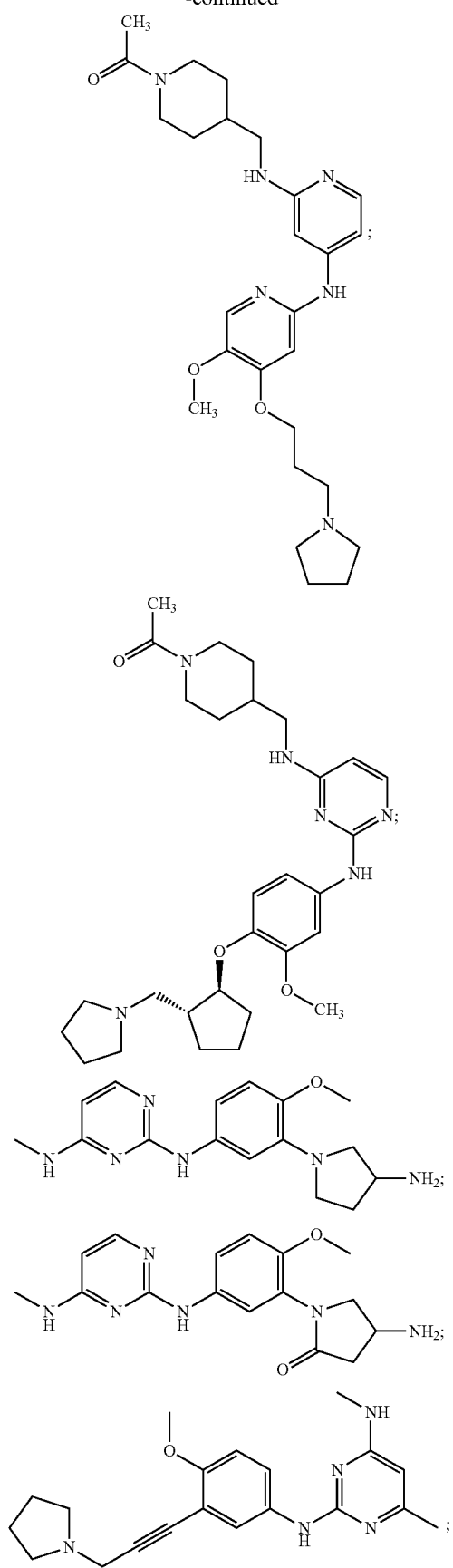
618
-continued
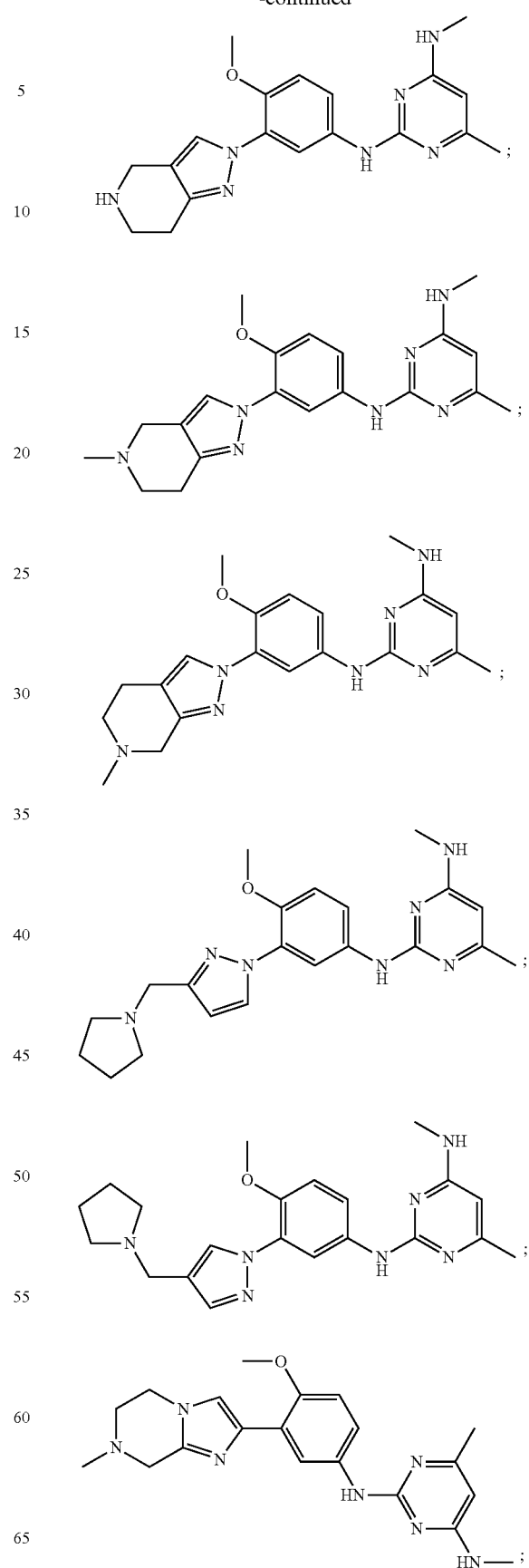

-continued
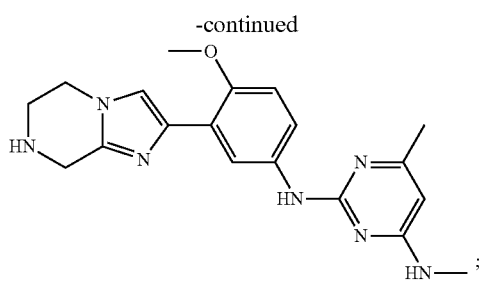
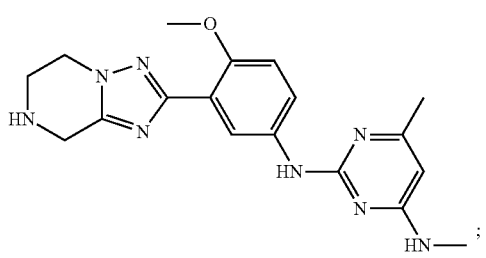
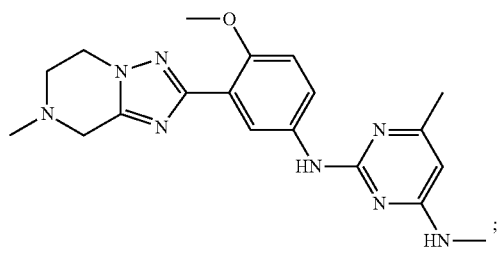
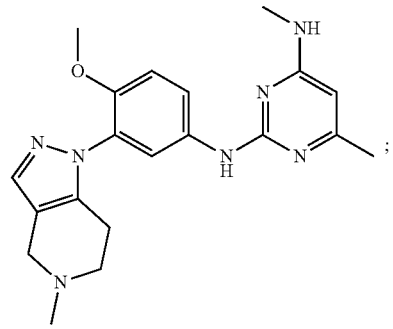
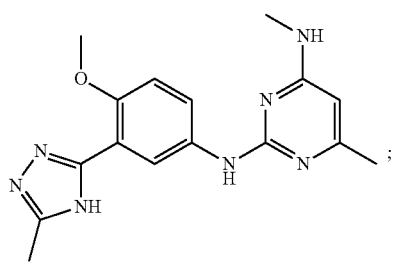
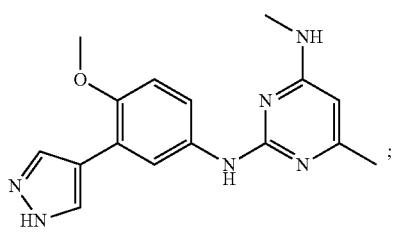
-continued
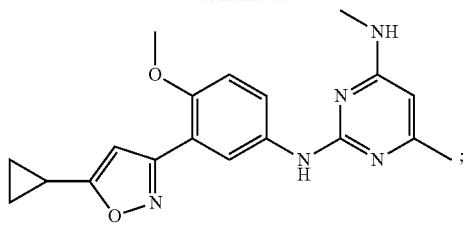

621
-continued
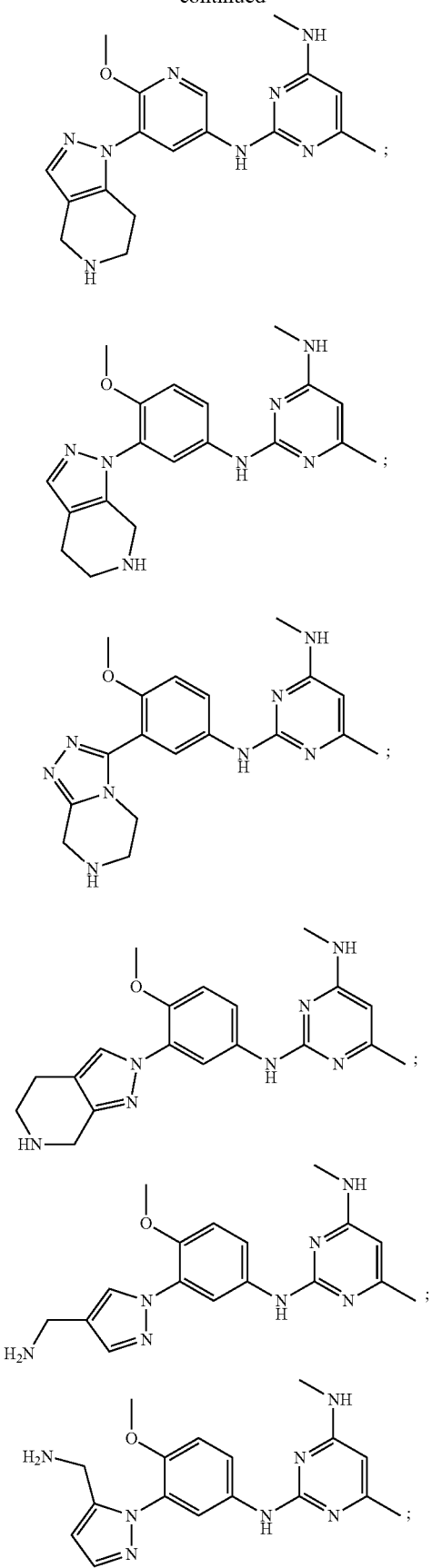
622
-continued
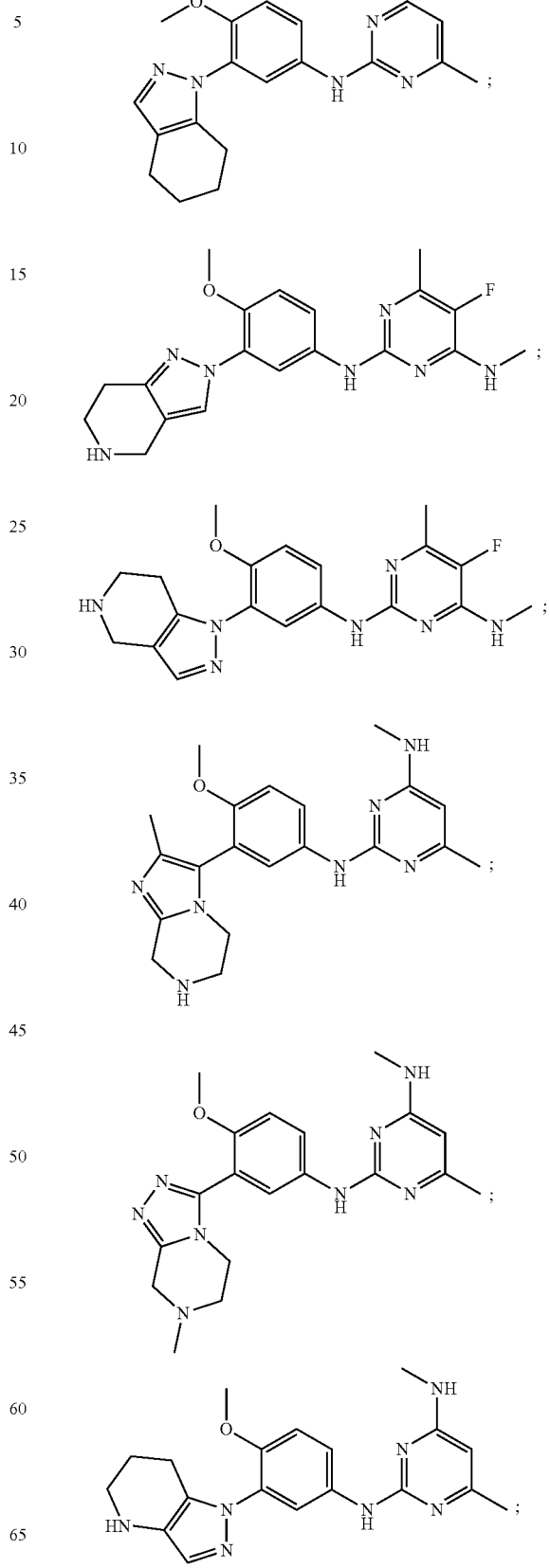

623
-continued
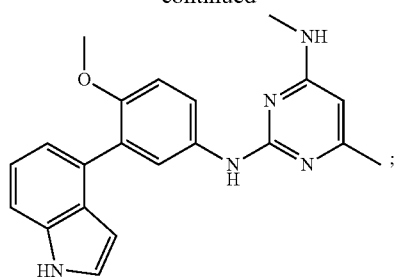
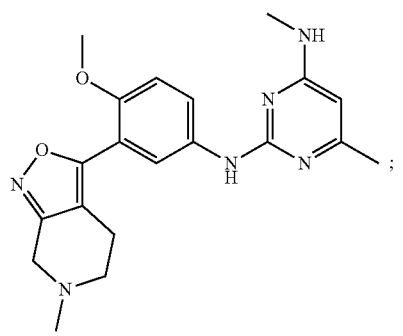
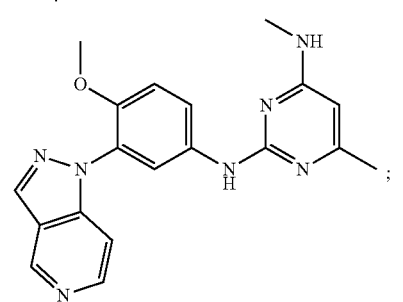
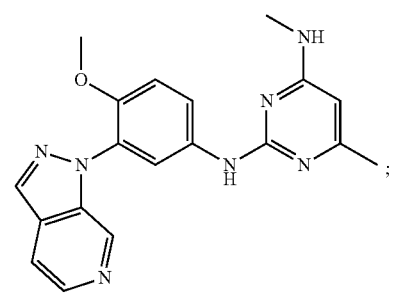
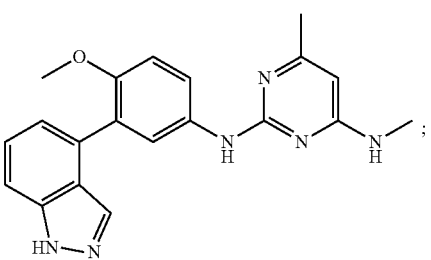
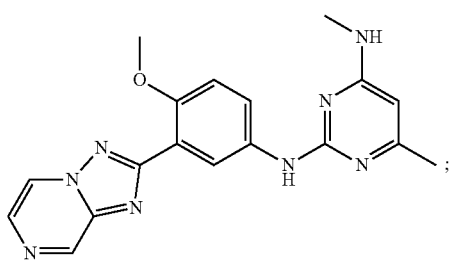
624
-continued
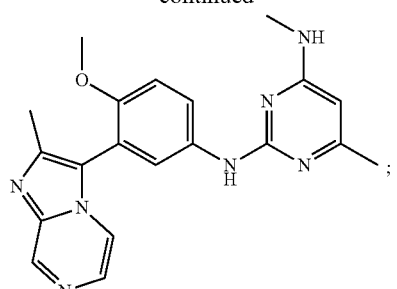
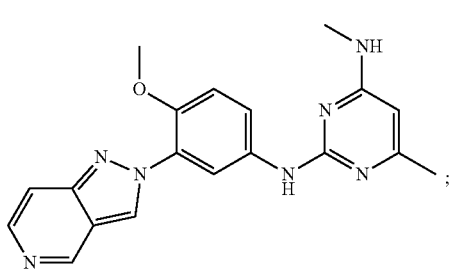
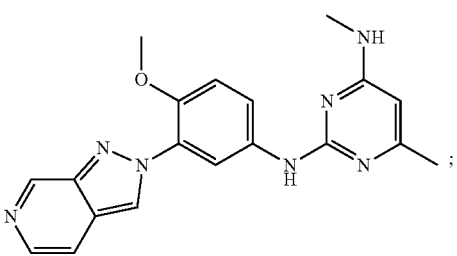
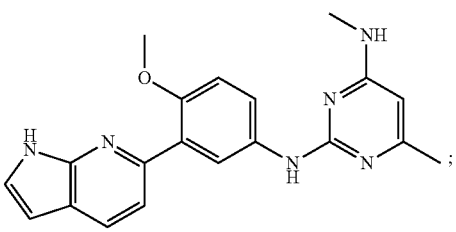
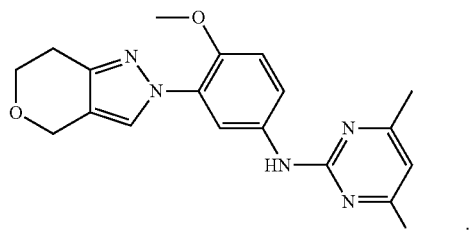
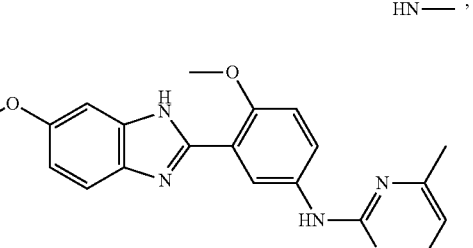

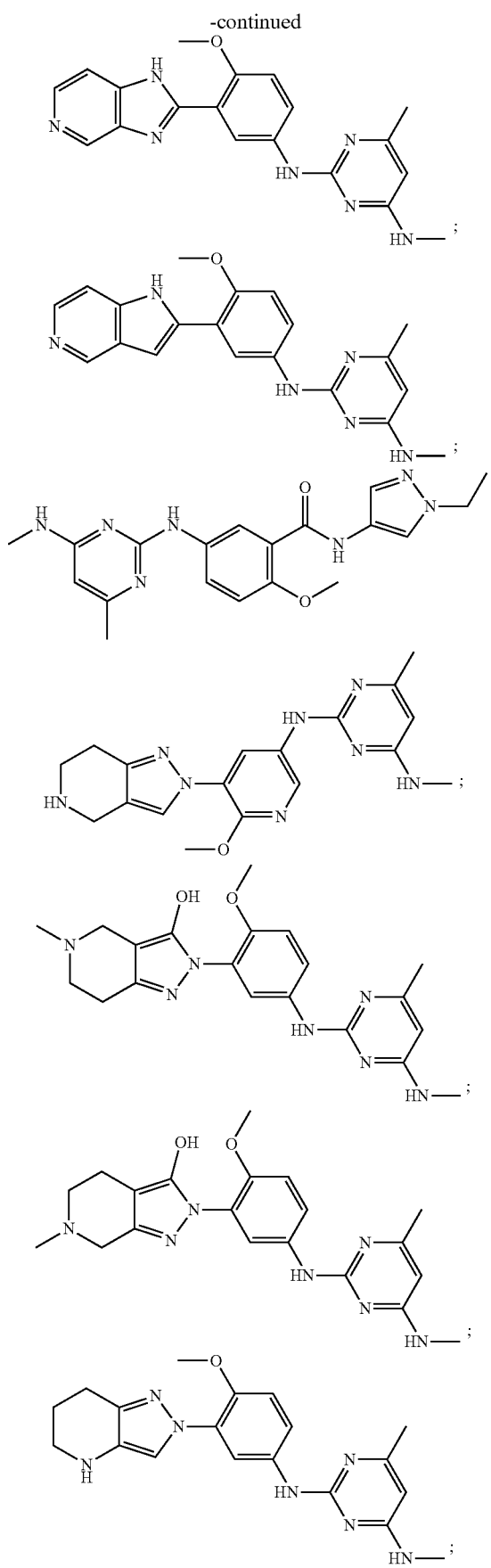
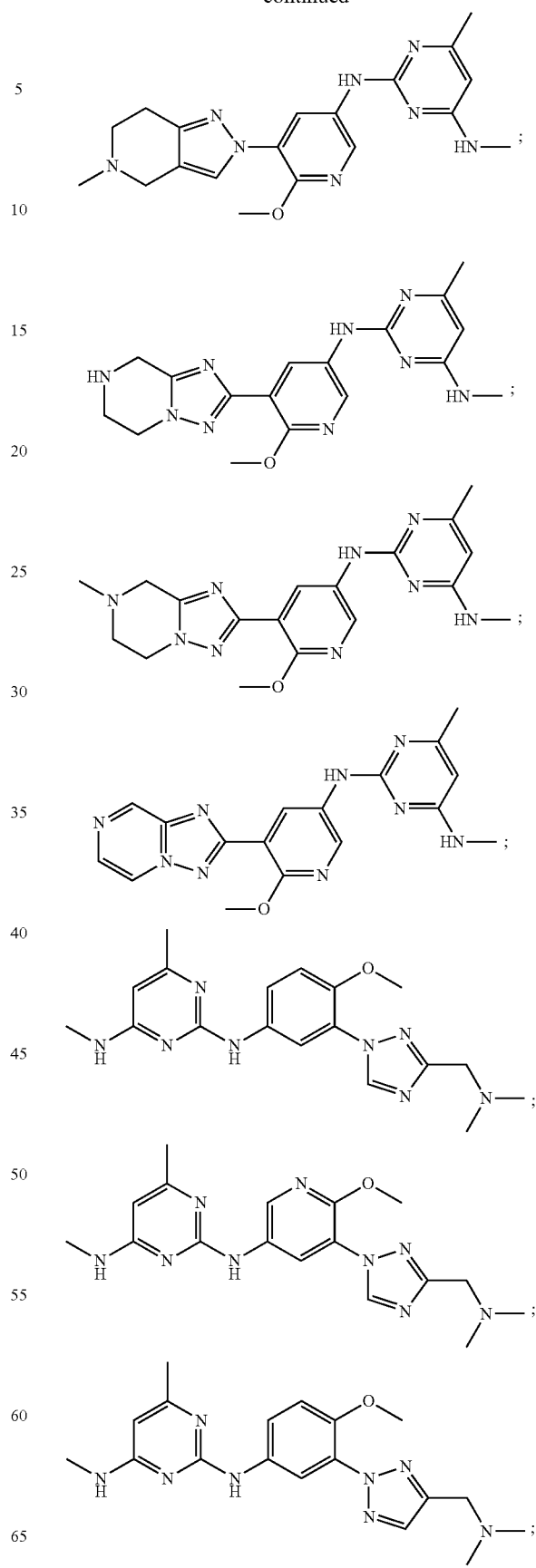

627
-continued
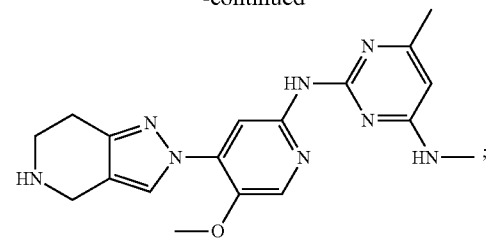
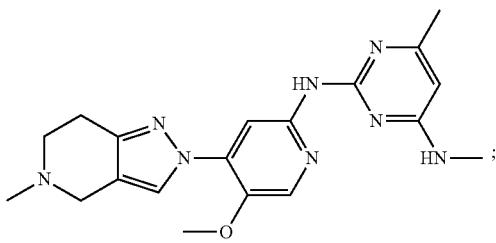
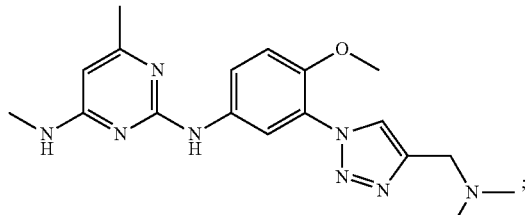
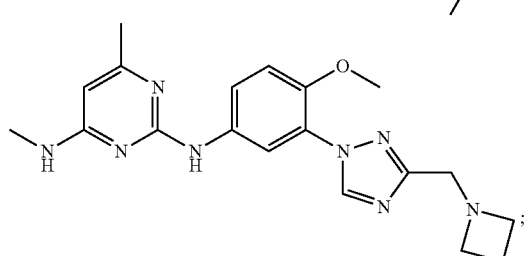
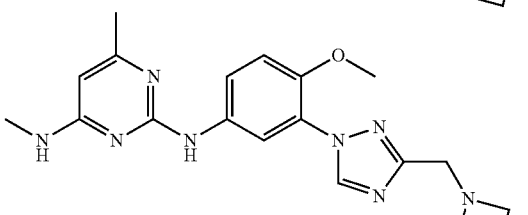
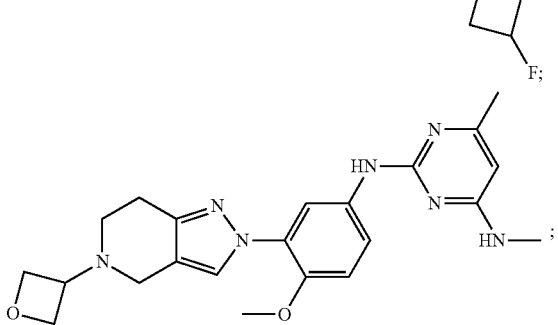
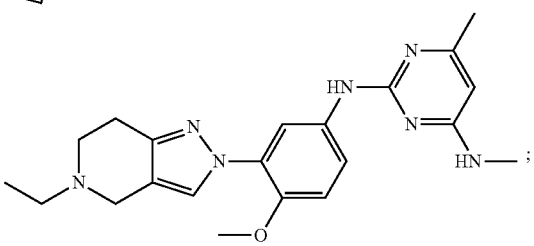
628
-continued
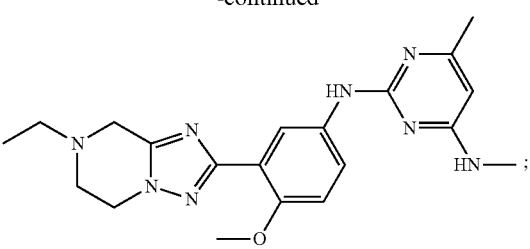
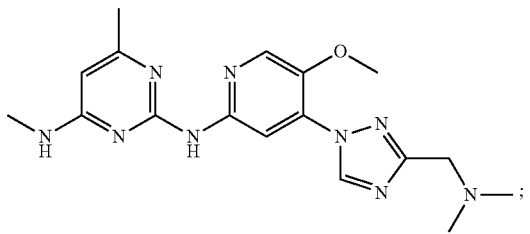
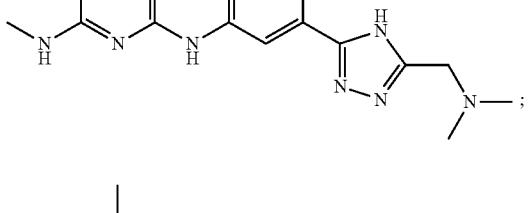
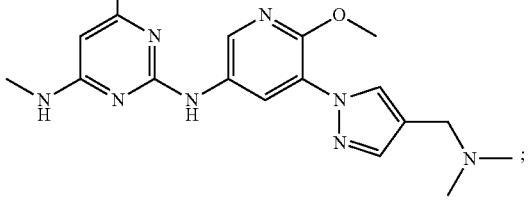
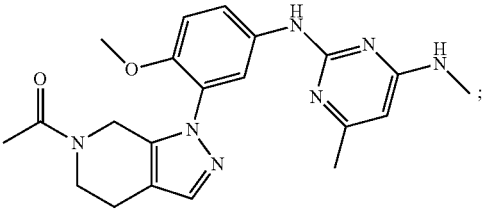
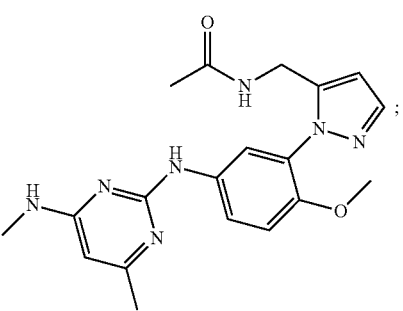

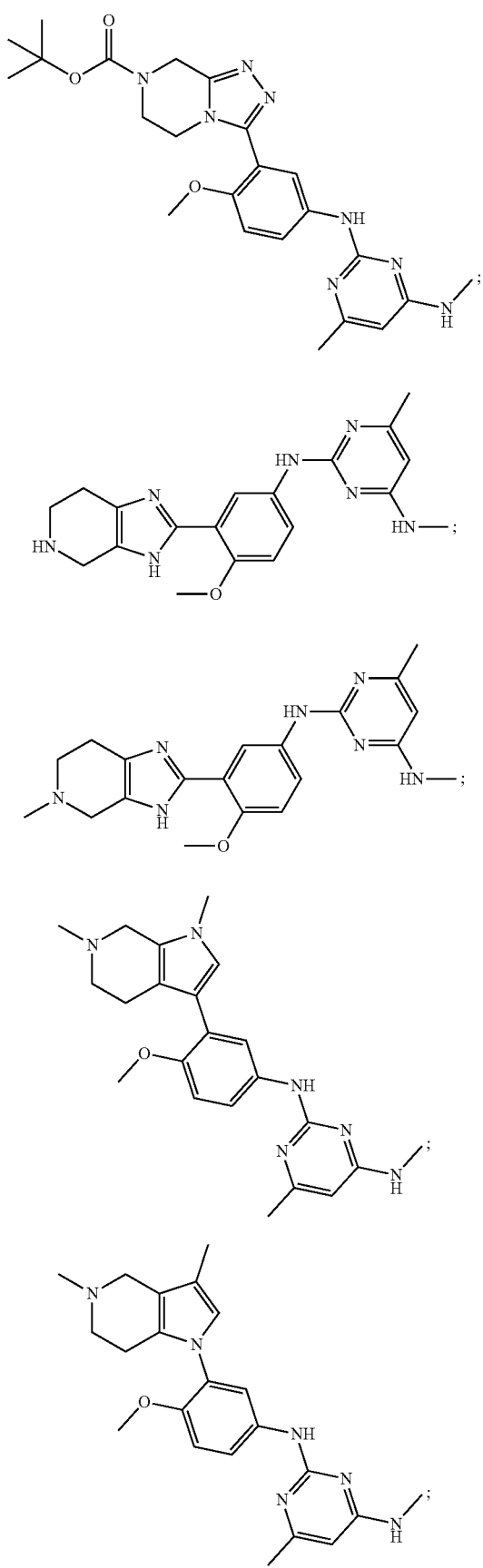
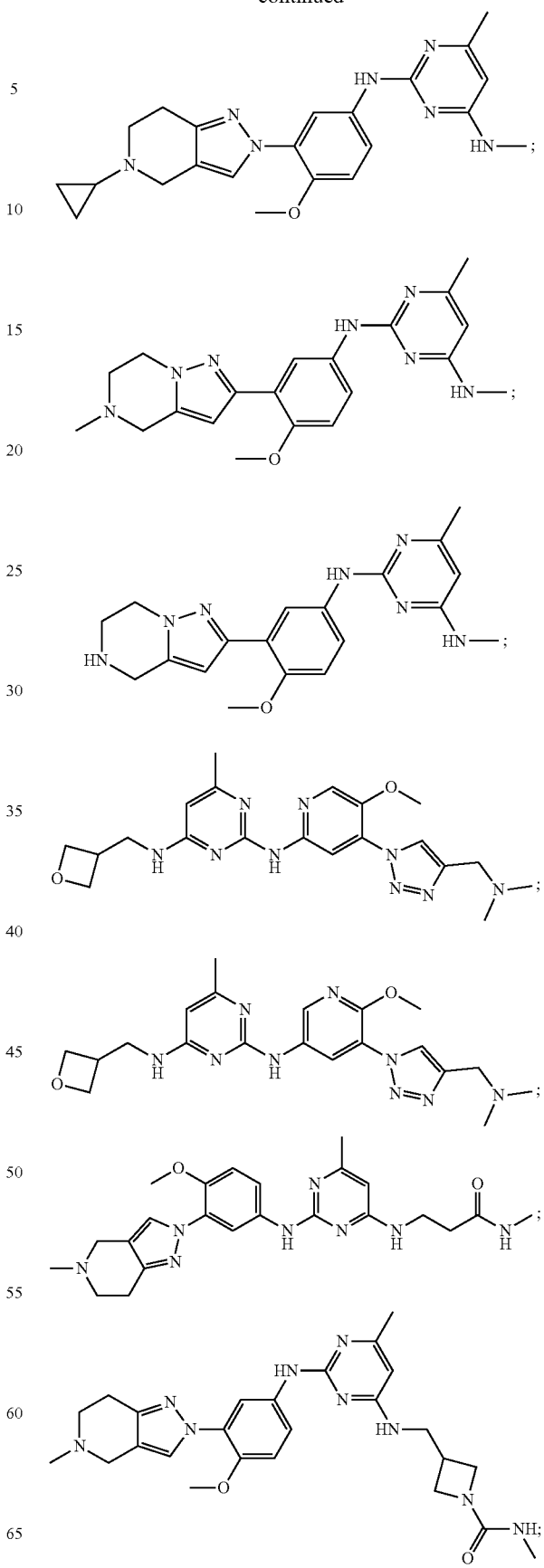

631
-continued
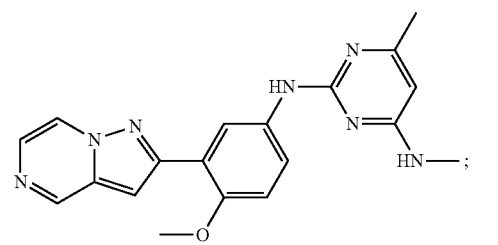
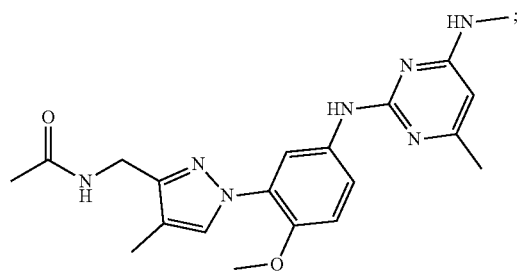
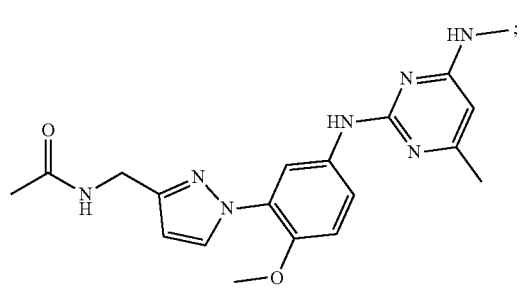
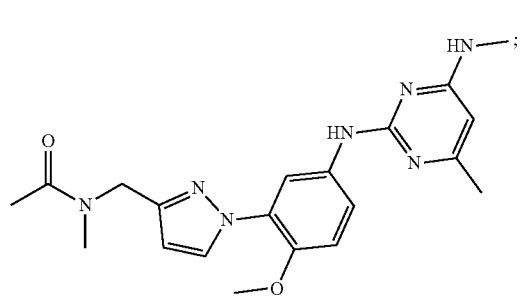
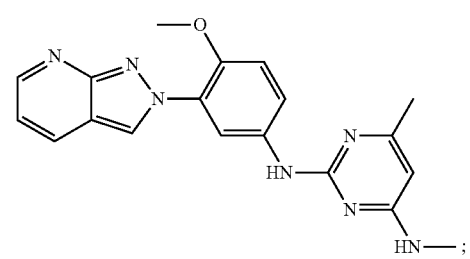
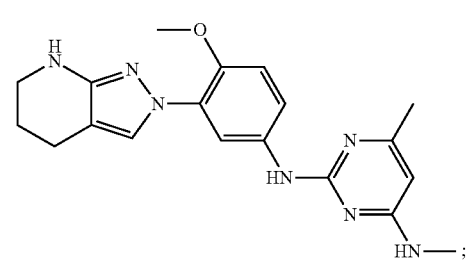
632
-continued
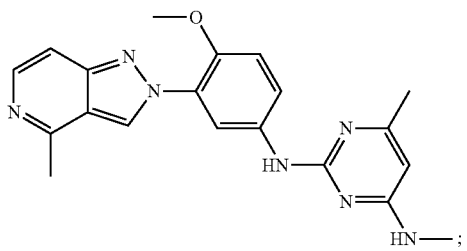
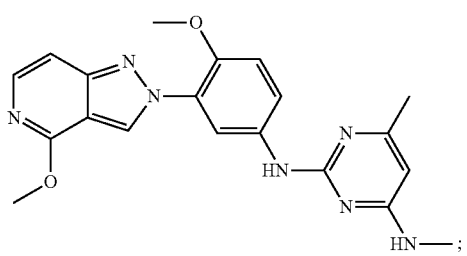
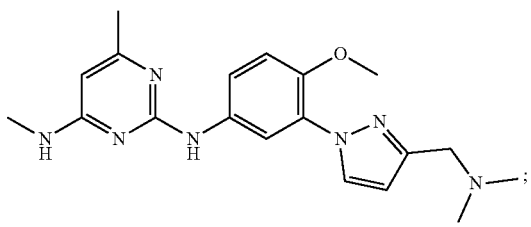
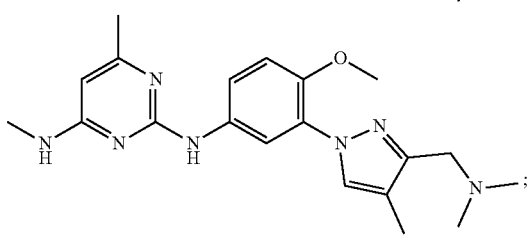
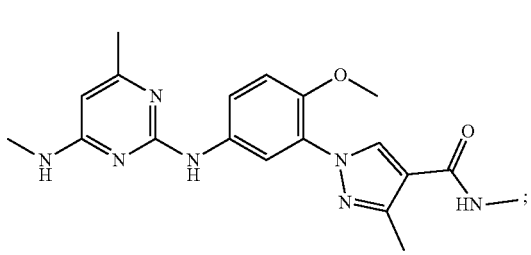
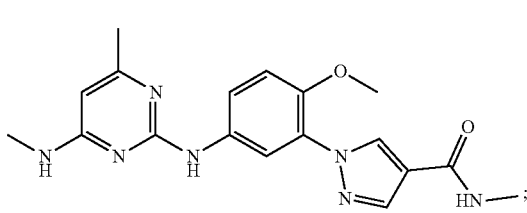
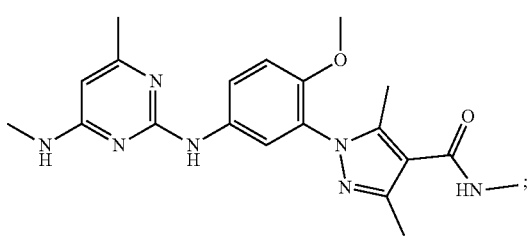

633
-continued
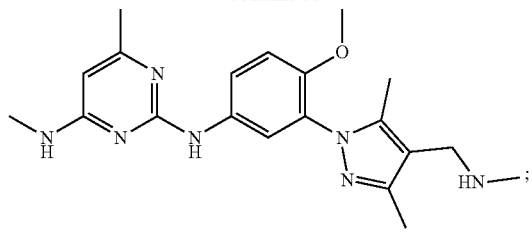
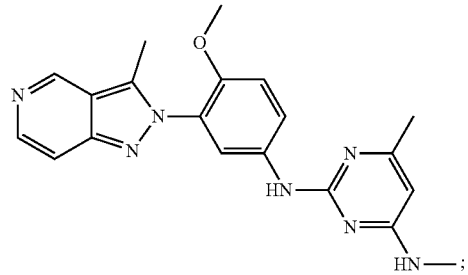
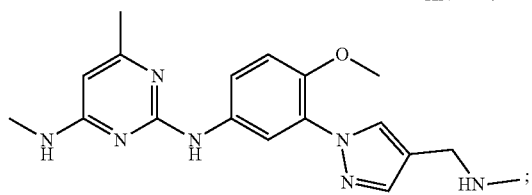
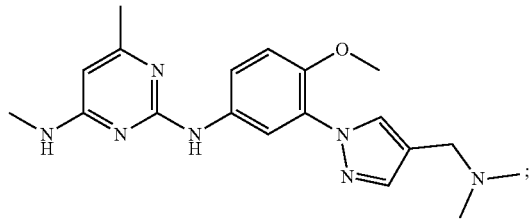
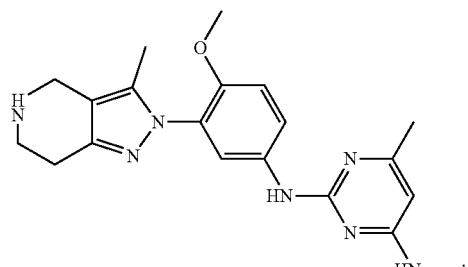
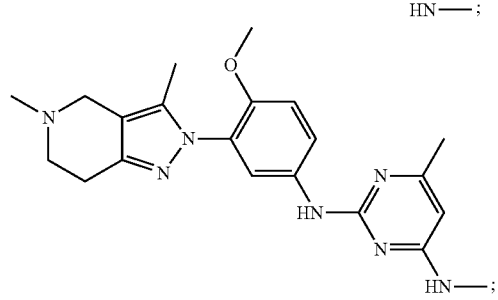
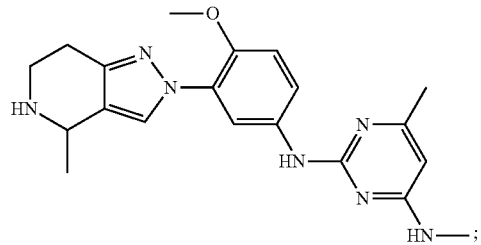
634
-continued
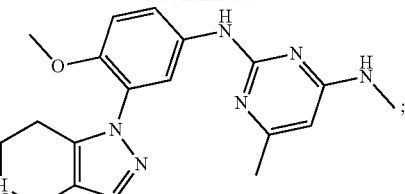
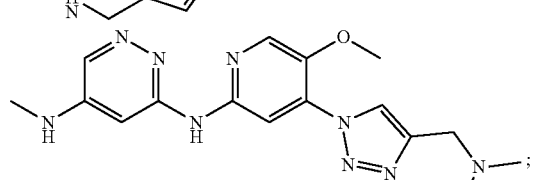
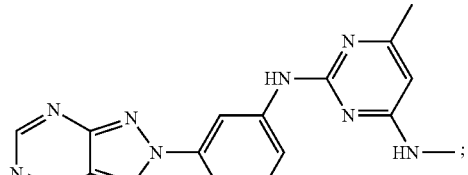
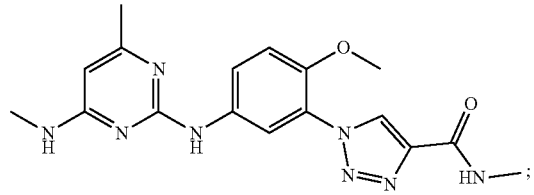
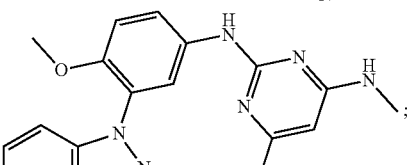
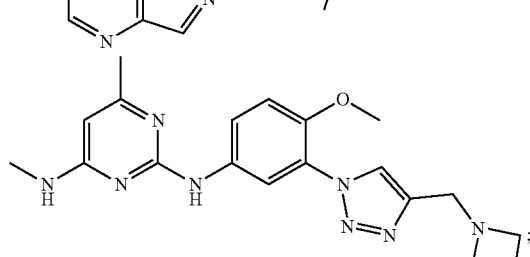
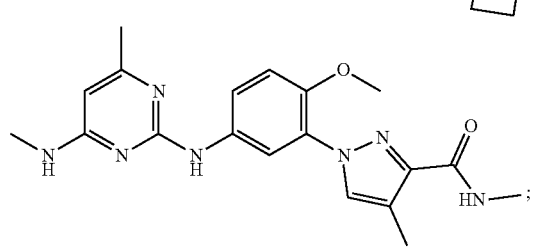
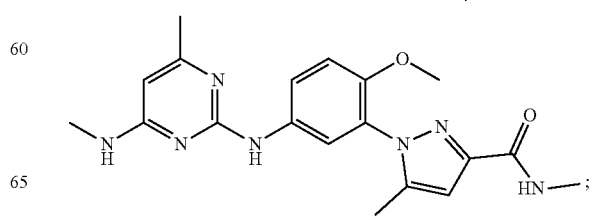

635
-continued
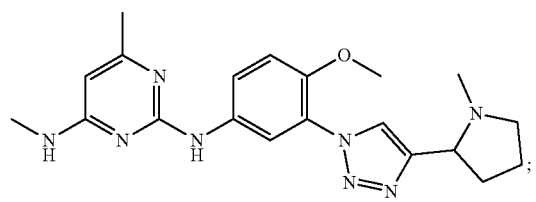
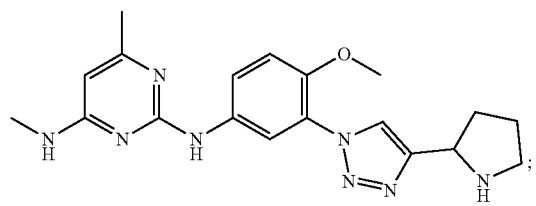
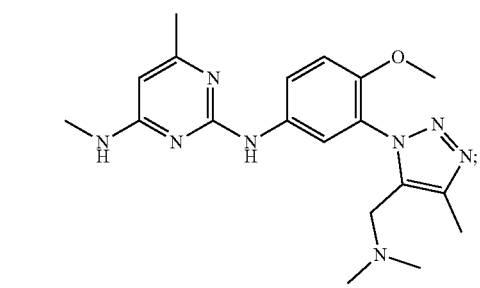
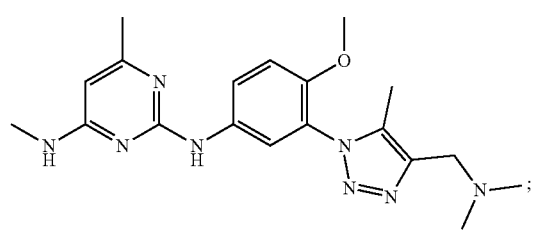
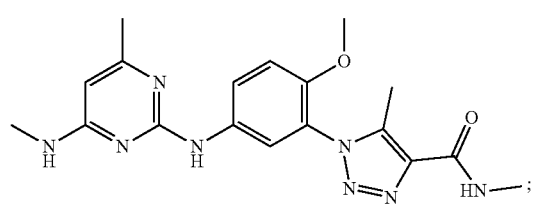
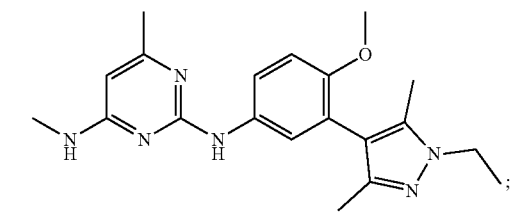
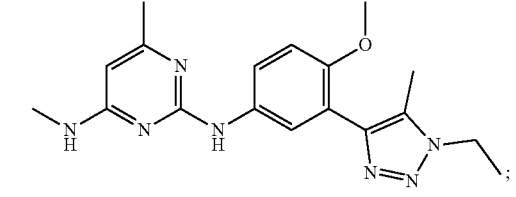
636
-continued
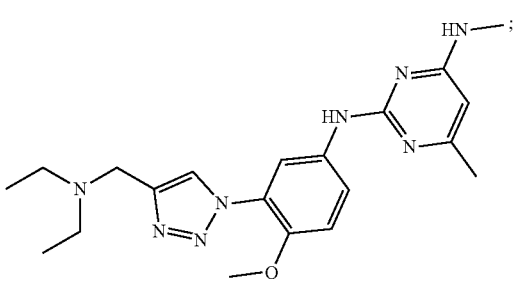
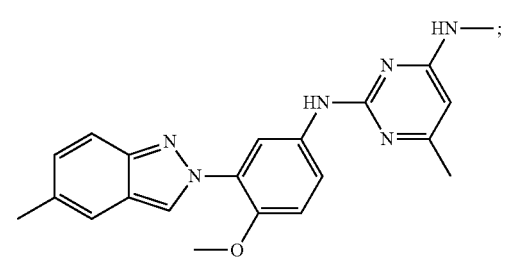
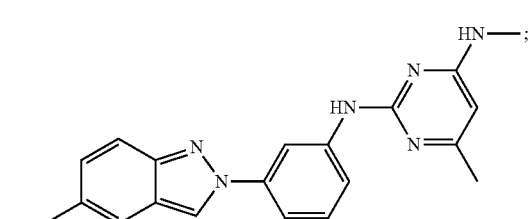
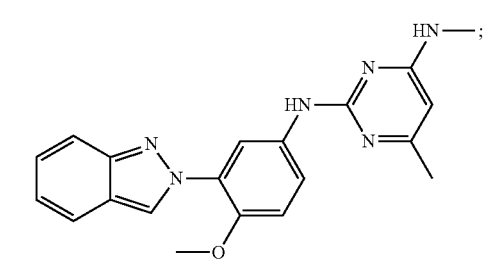
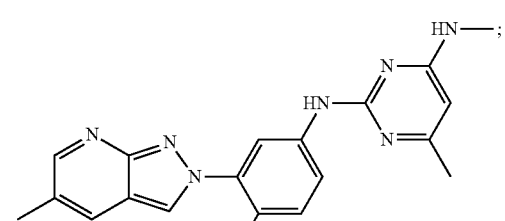
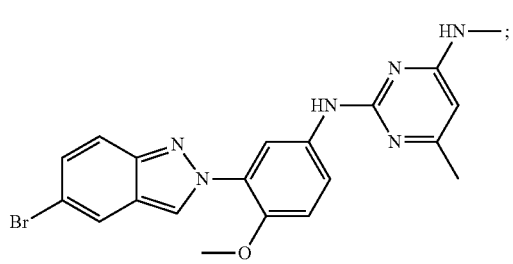

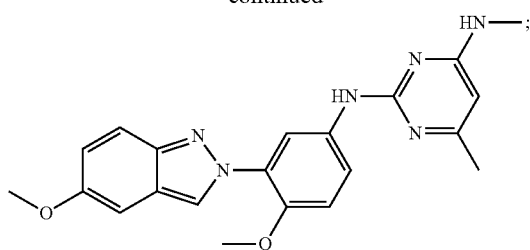
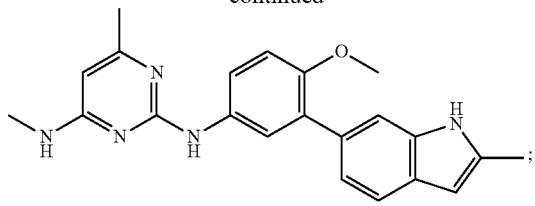
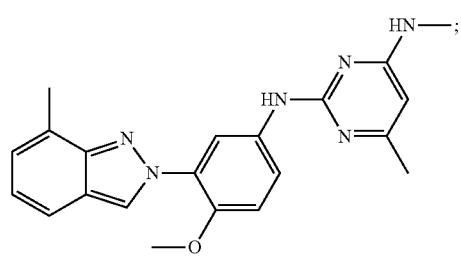
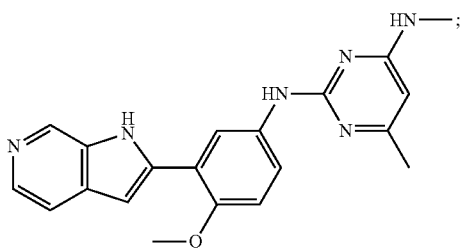
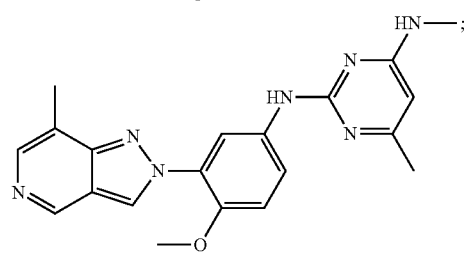
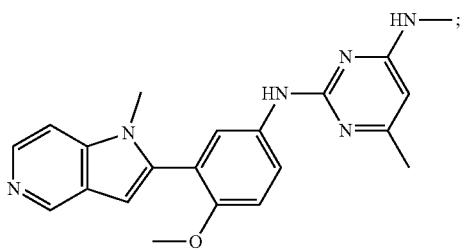
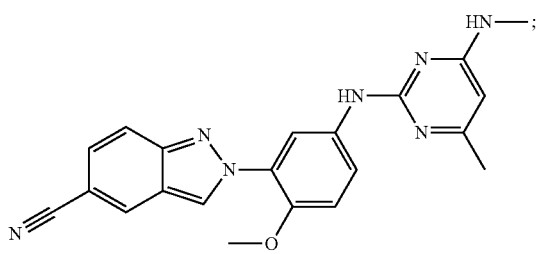
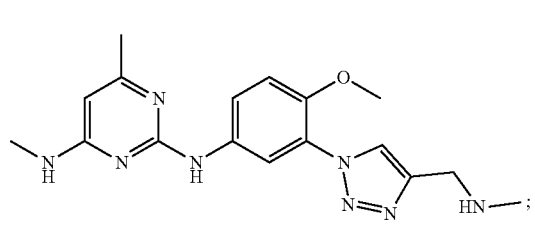
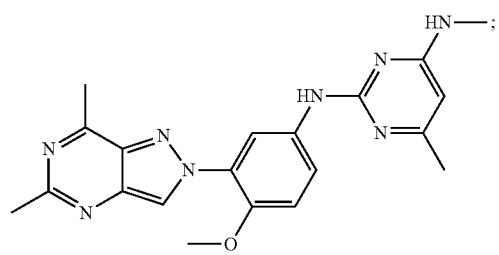
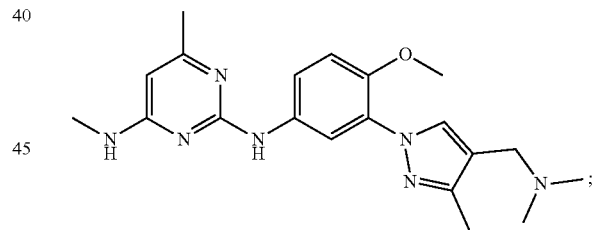
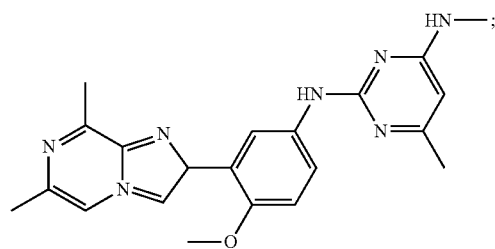
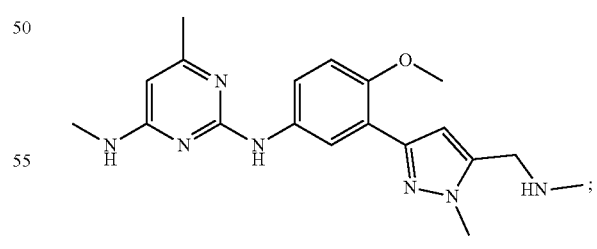
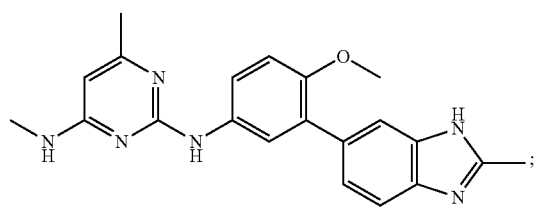
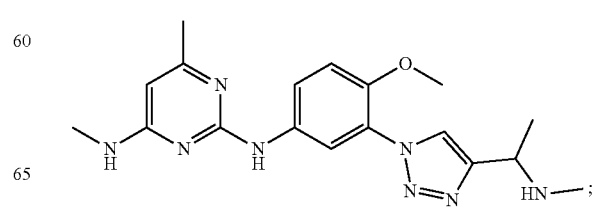

639
-continued
640
-continued
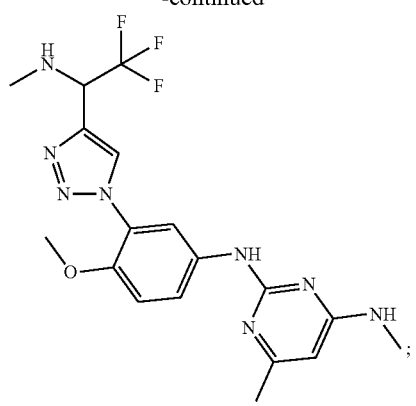
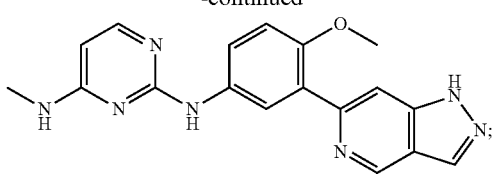
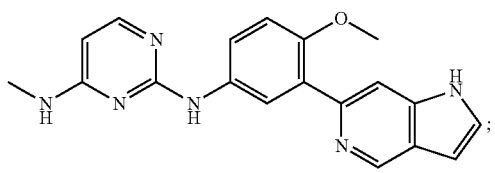
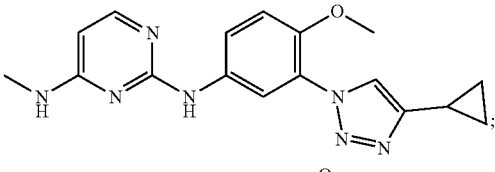
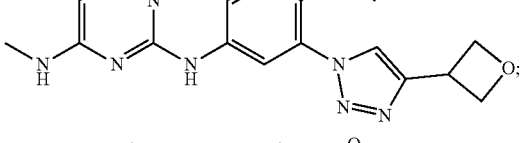
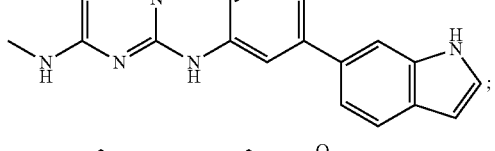
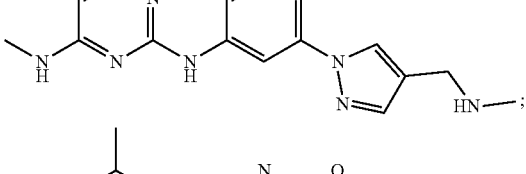
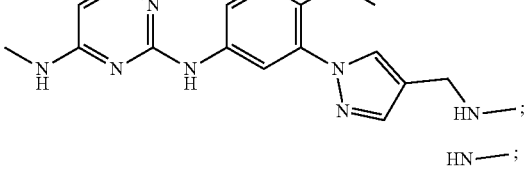
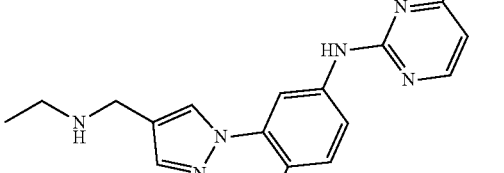
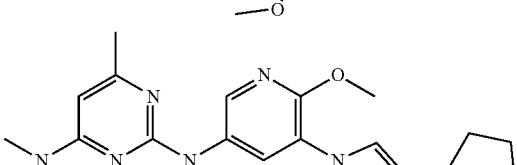

641
-continued
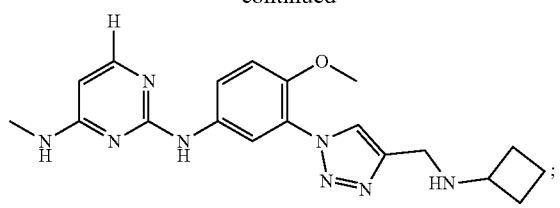
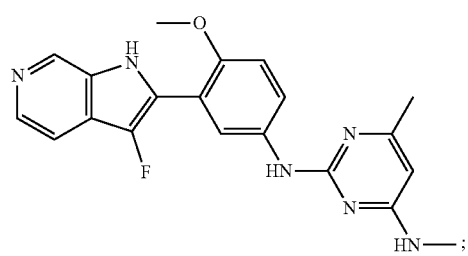
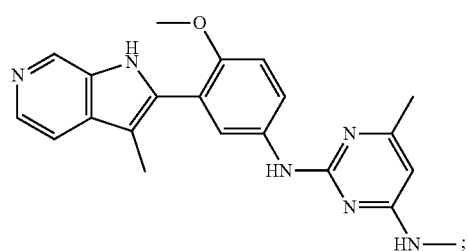
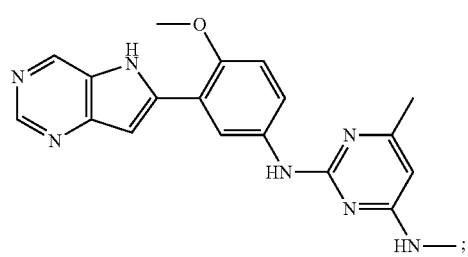
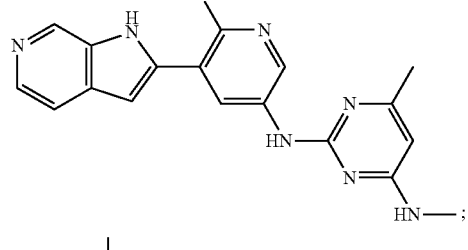
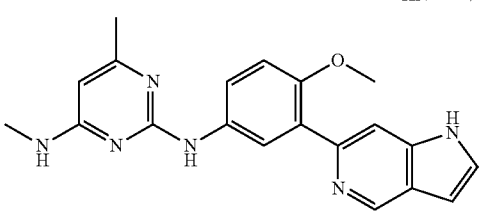
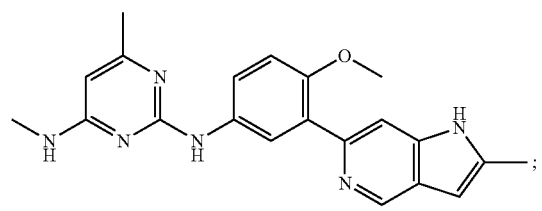
642
-continued
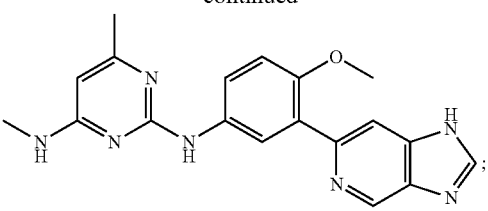
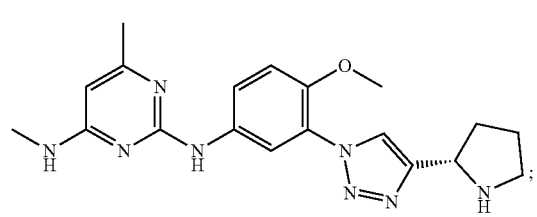
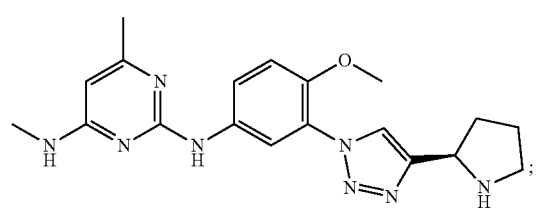
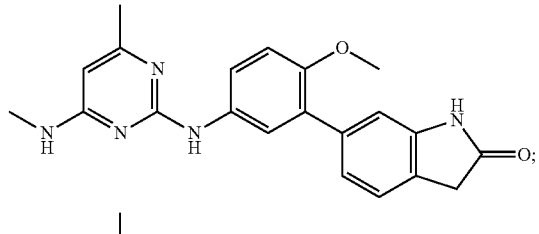
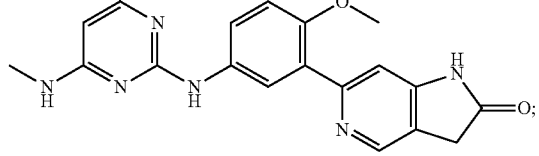
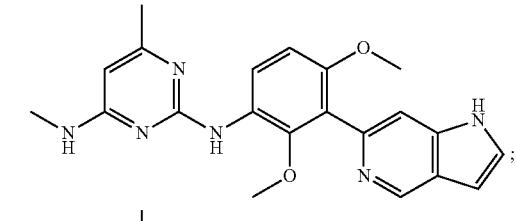
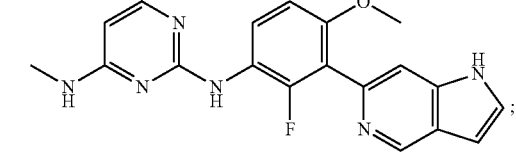
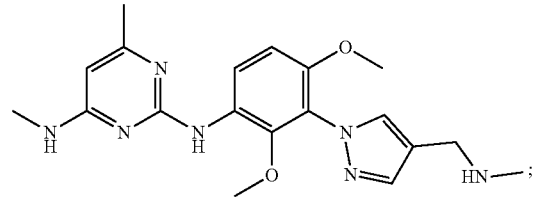

643
-continued
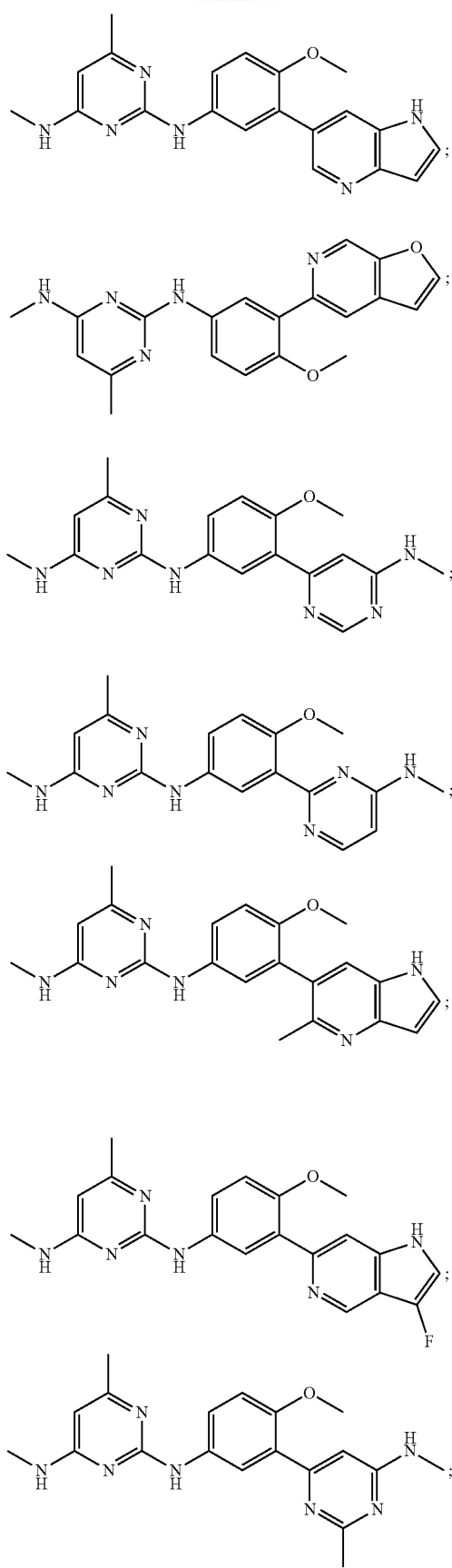
644
-continued
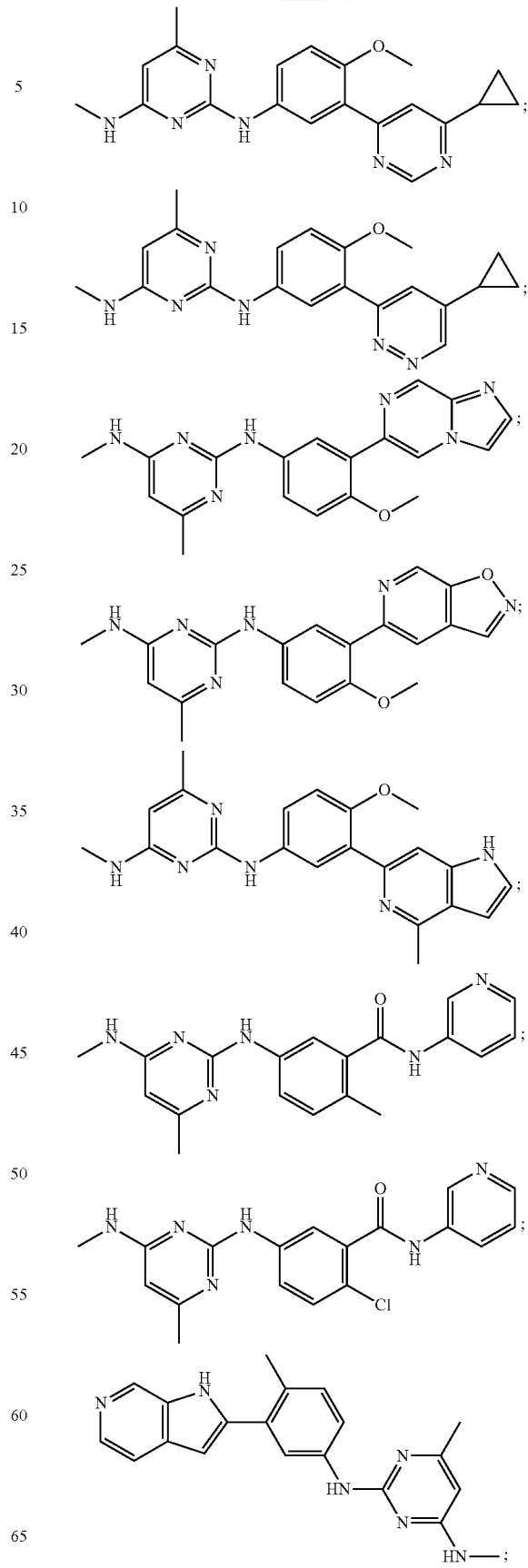

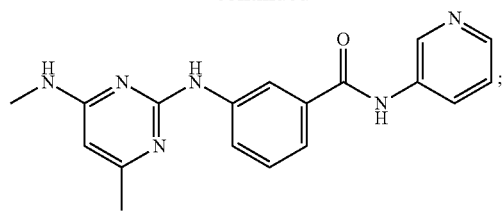
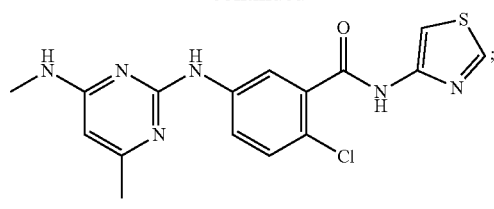
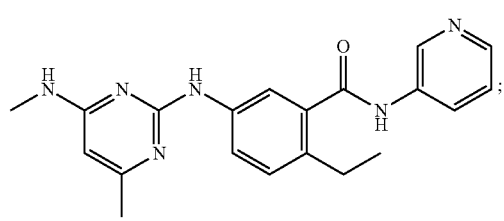
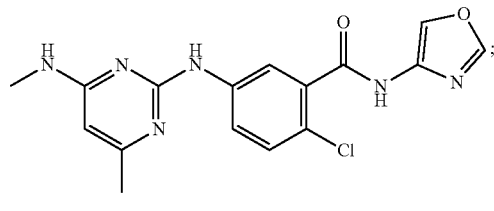
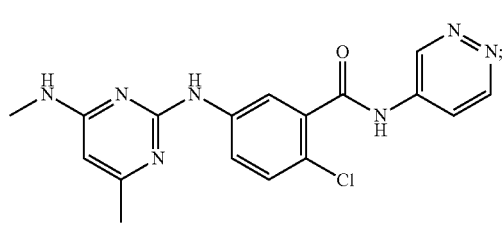
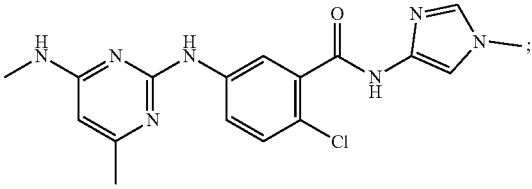
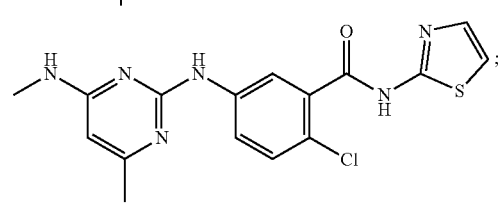
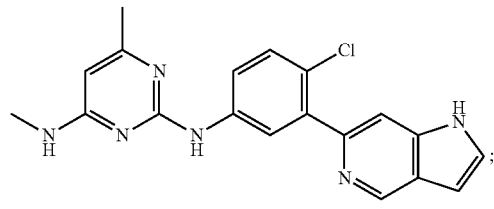
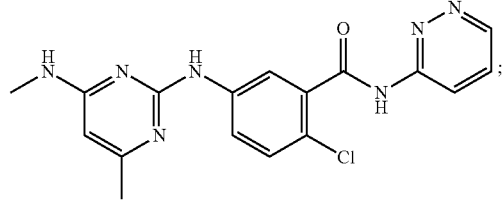
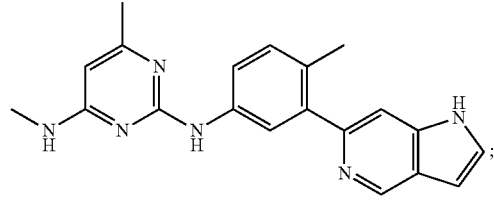
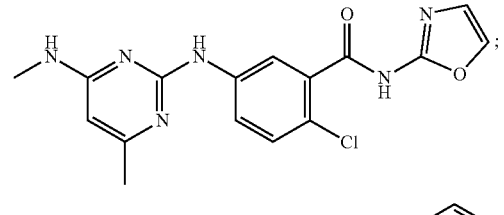
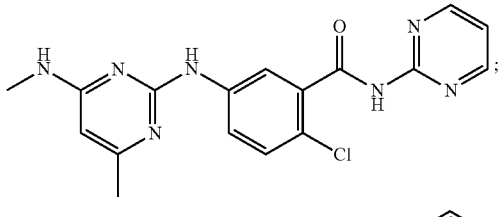
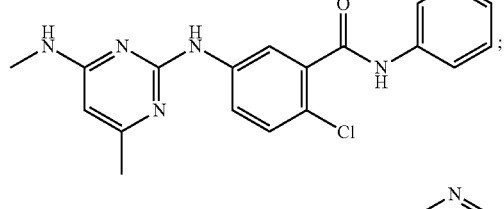
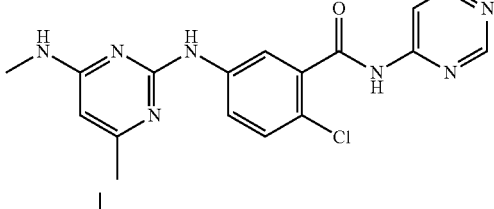
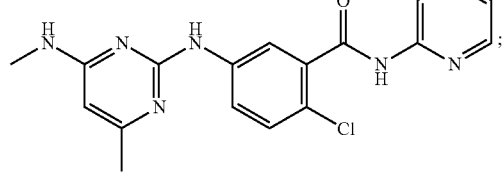
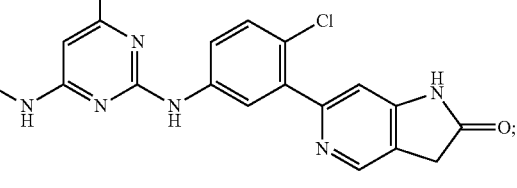

647
-continued
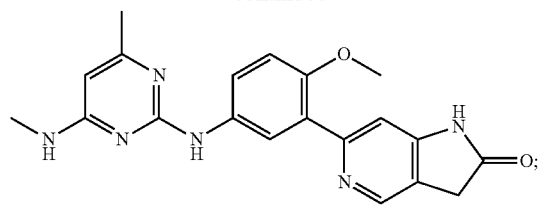
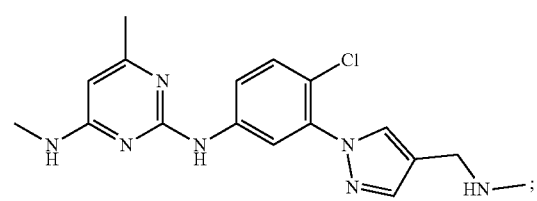
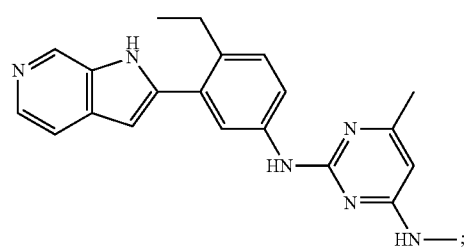
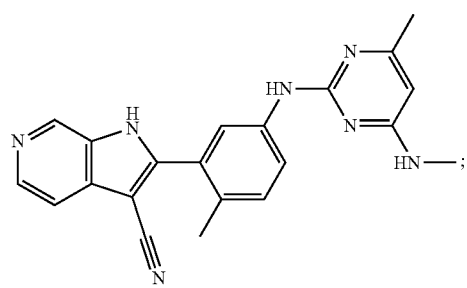
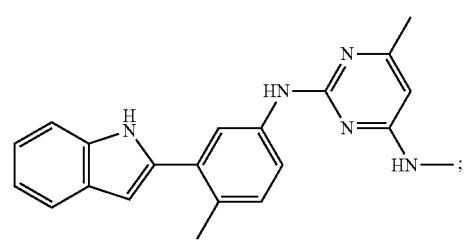
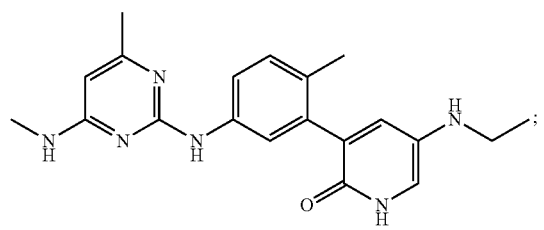
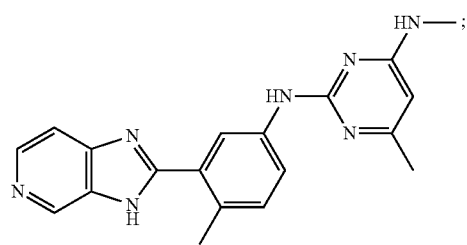
648
-continued
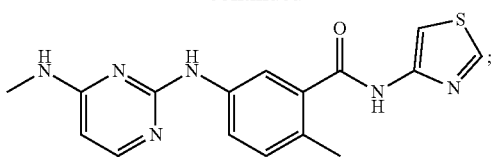
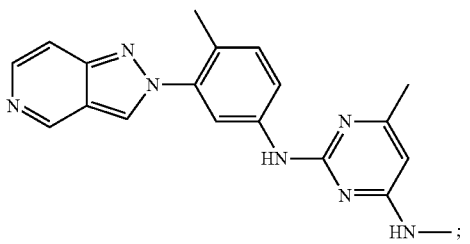
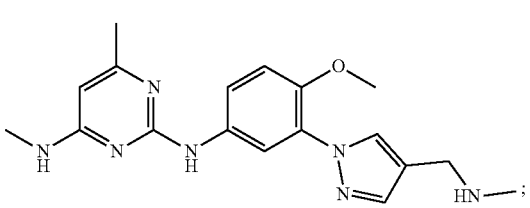
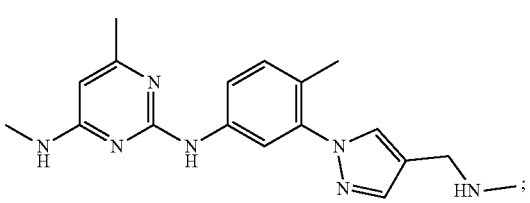
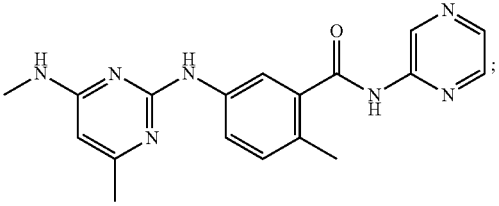
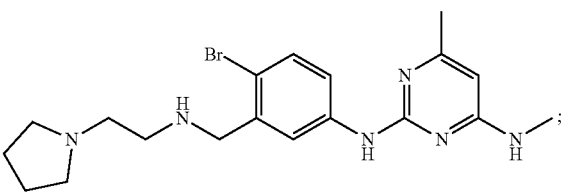
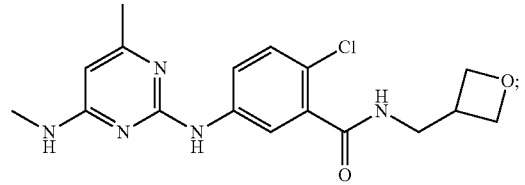
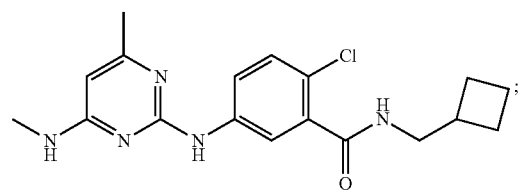

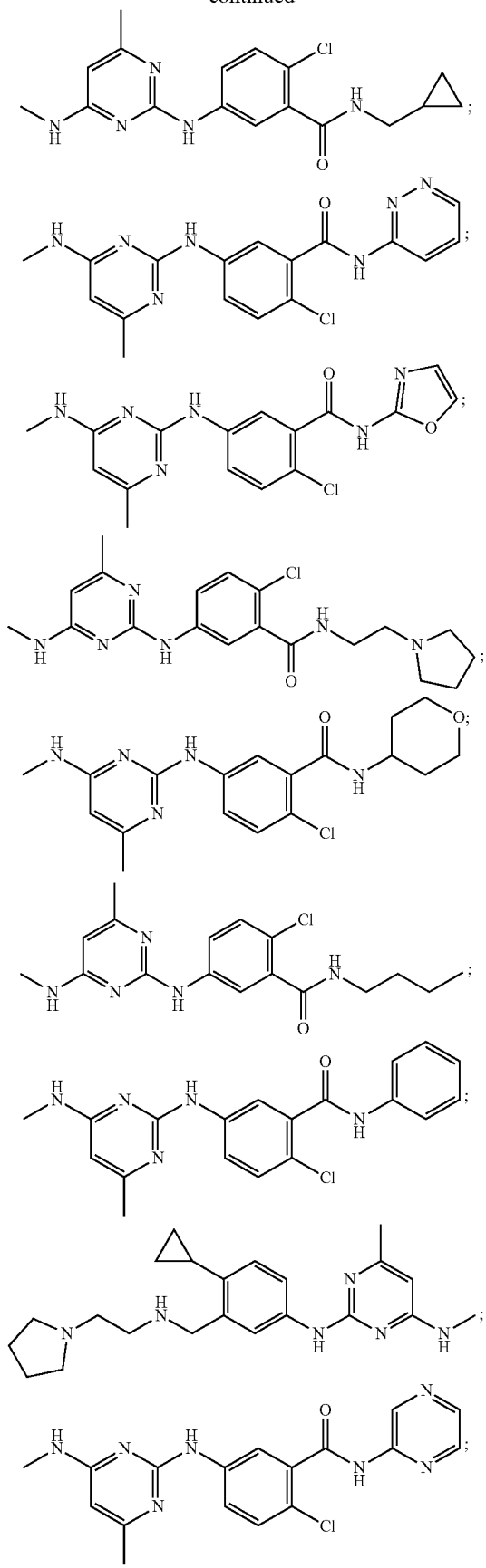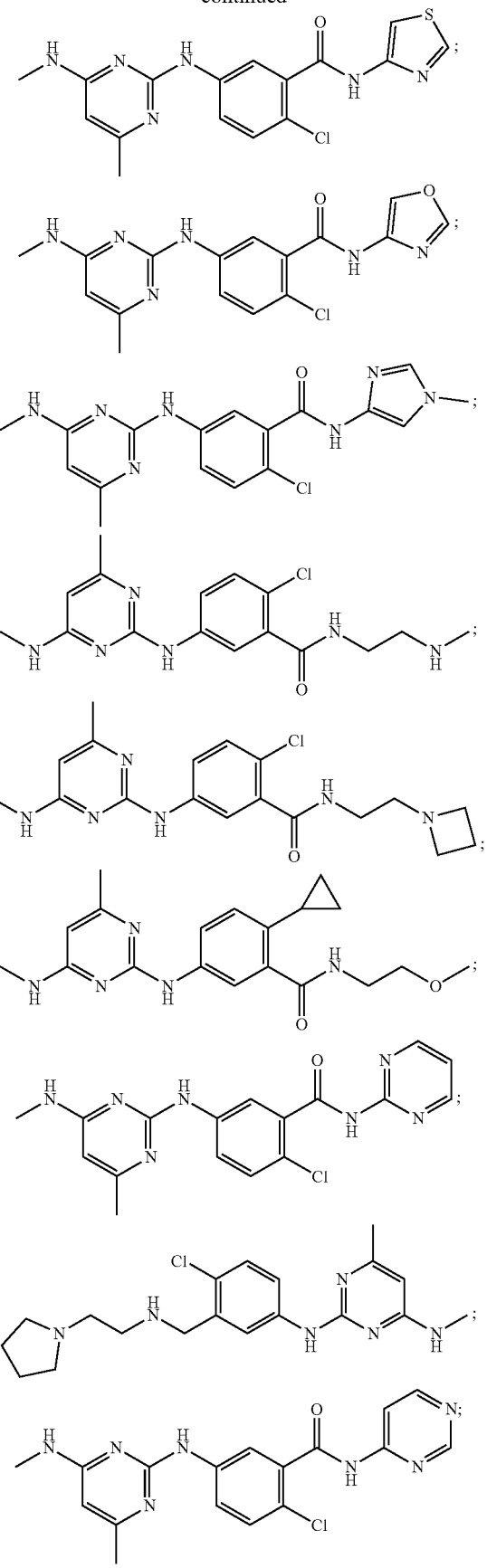

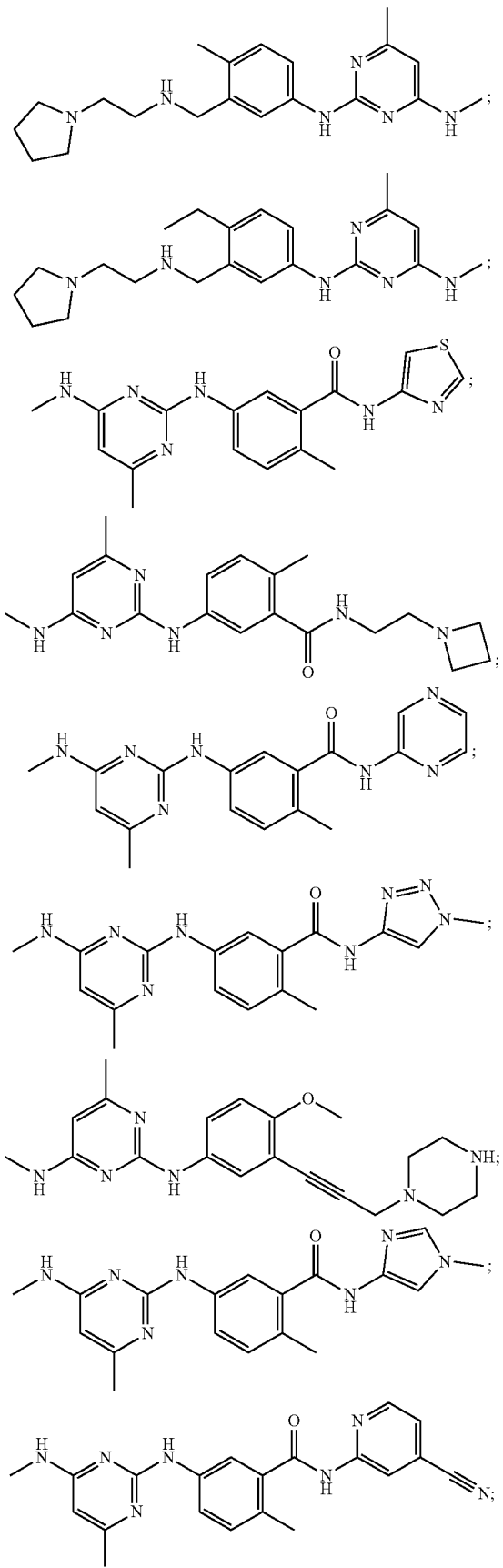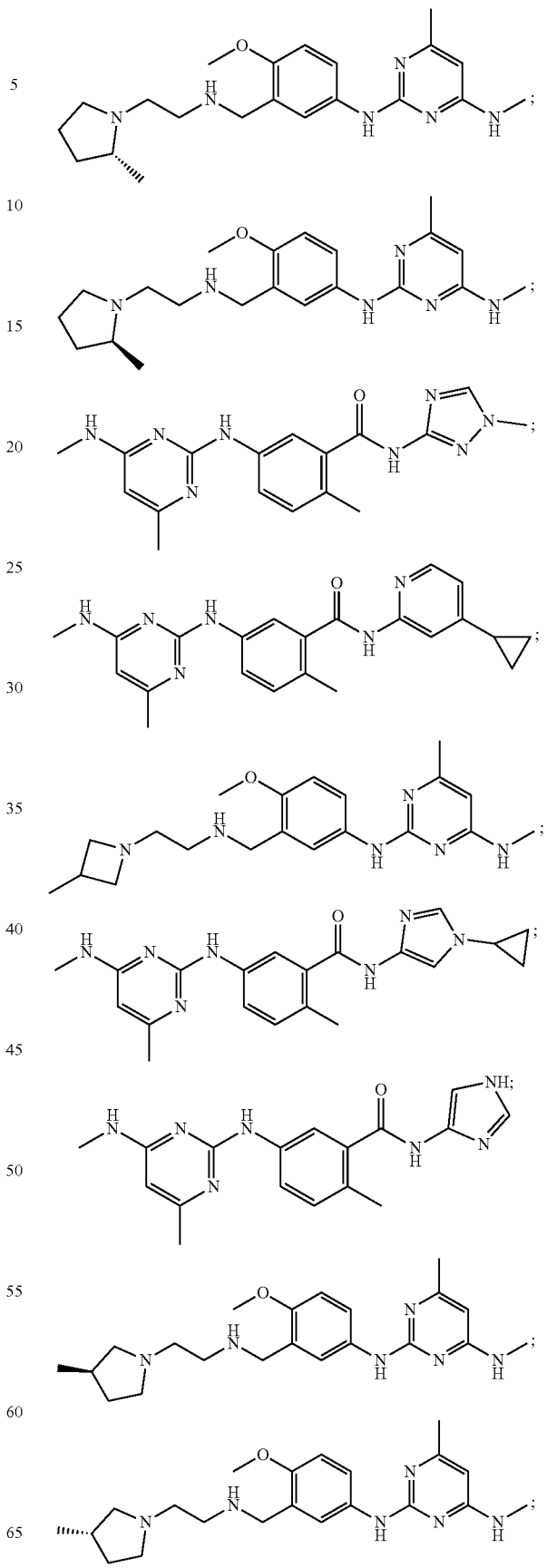

653
-continued
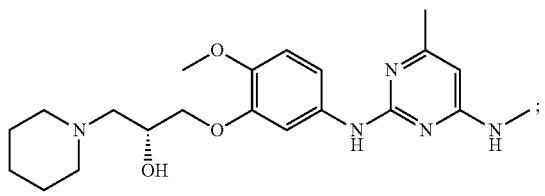
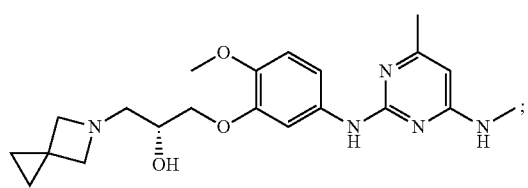
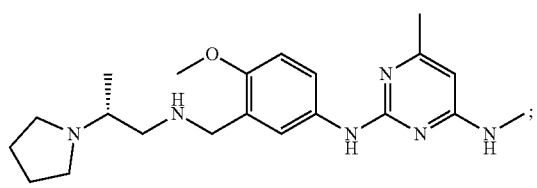
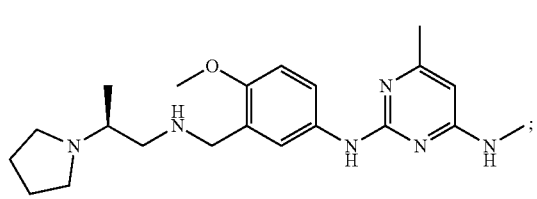
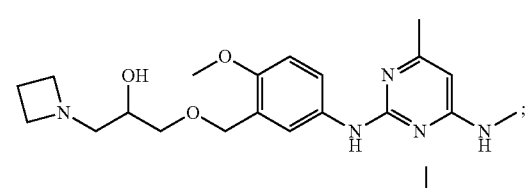
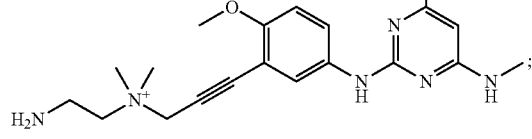
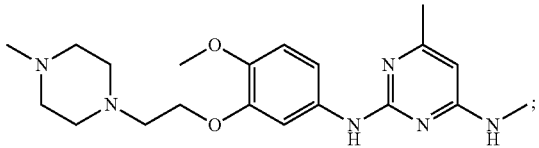
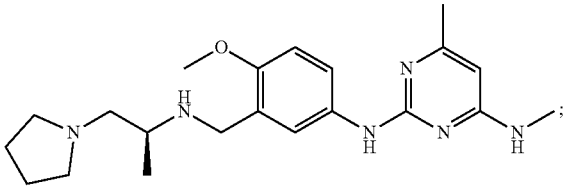
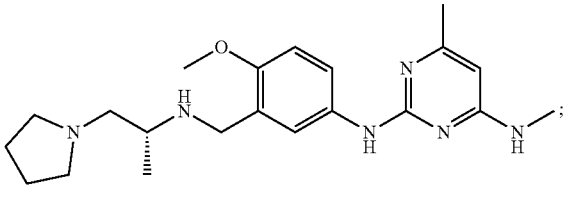
654
-continued
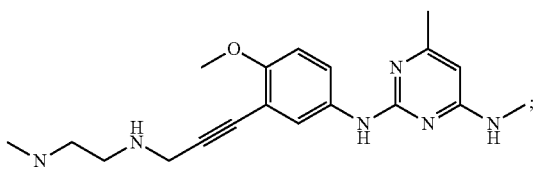
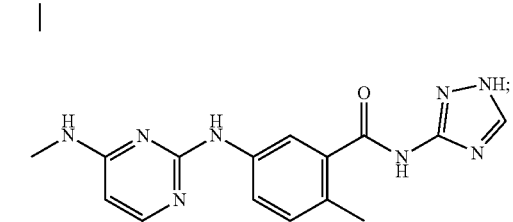
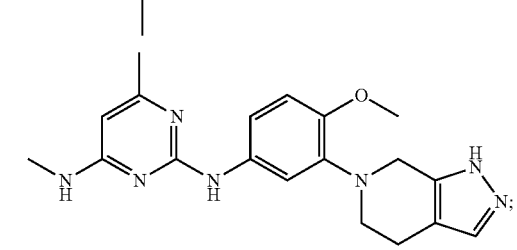
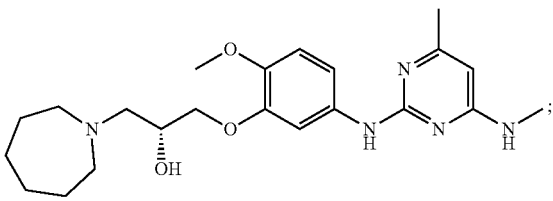
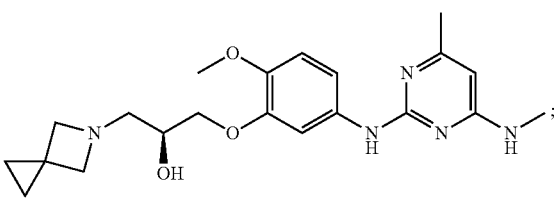
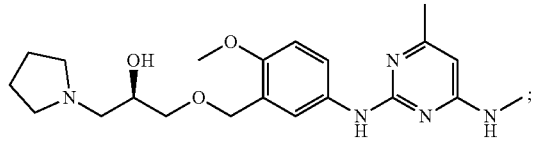
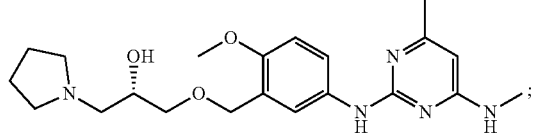
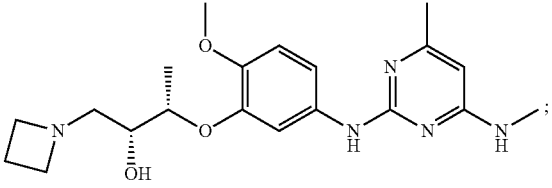
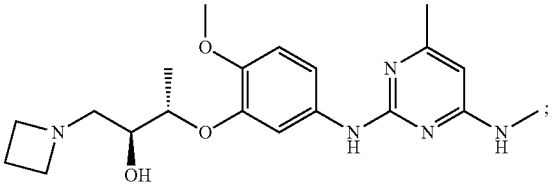

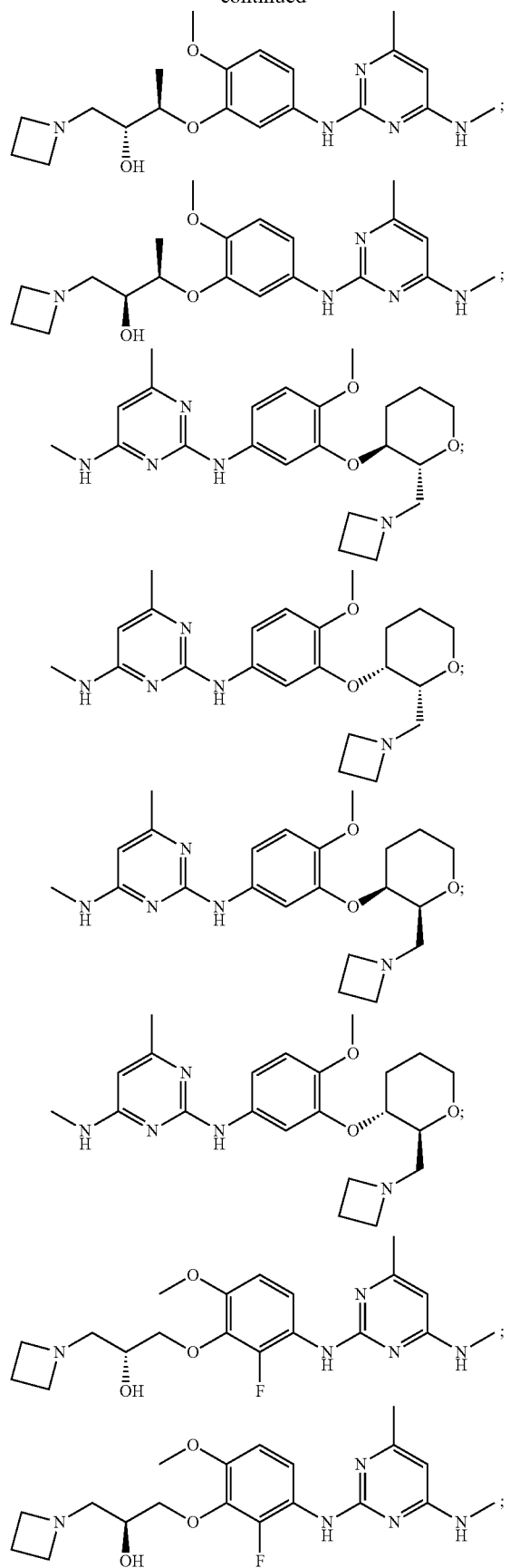
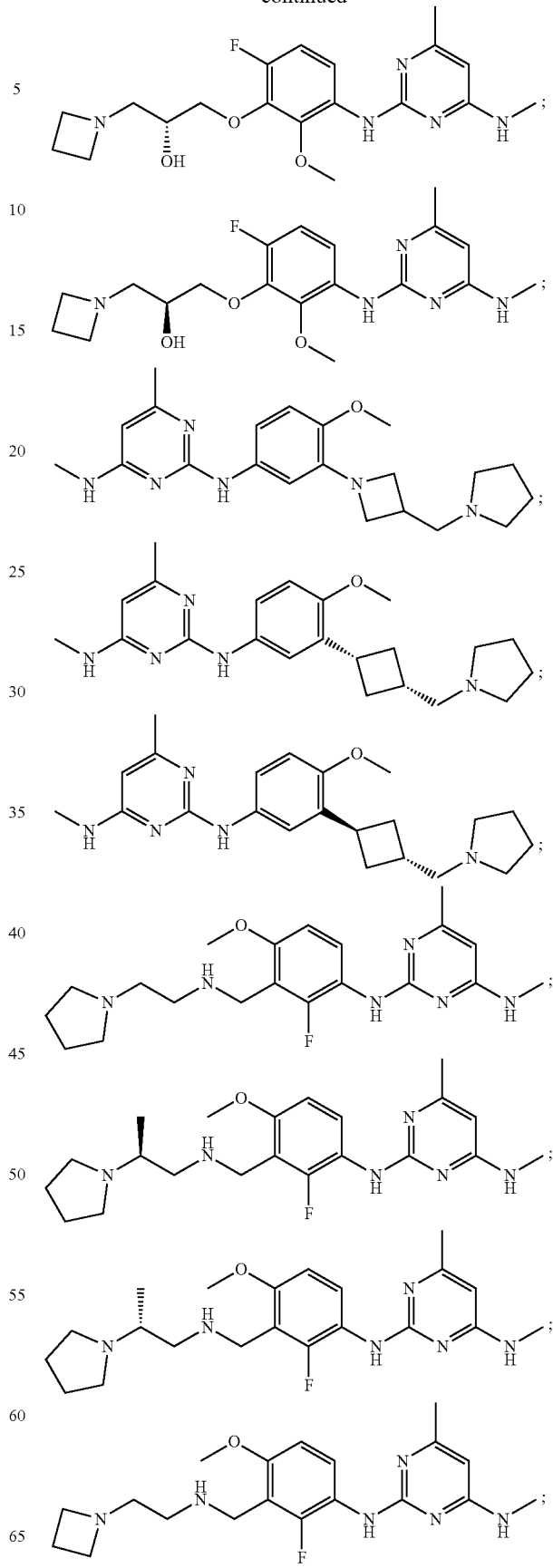

657
-continued
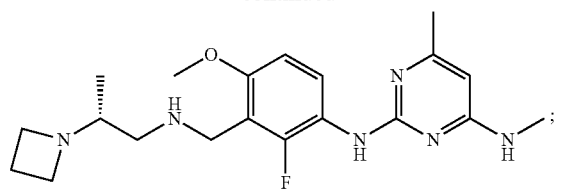
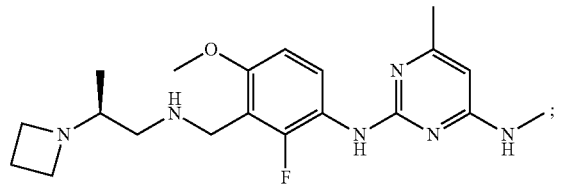
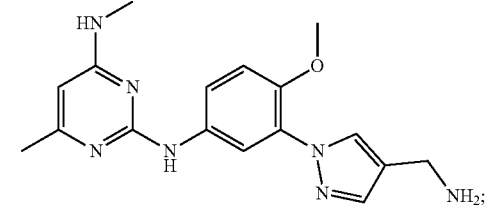
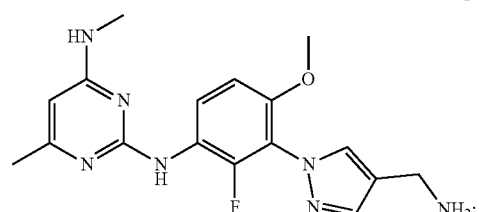
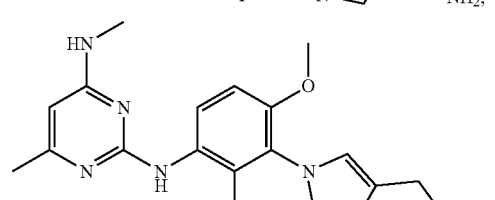
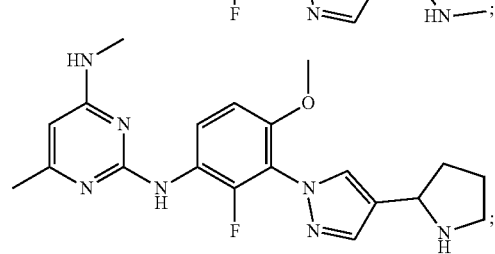
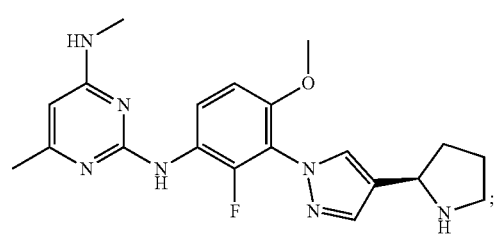
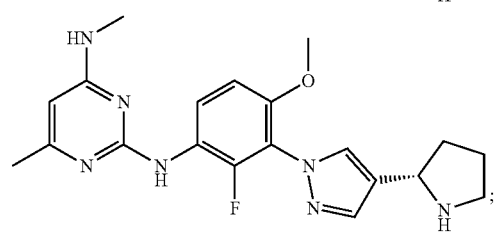
658
-continued
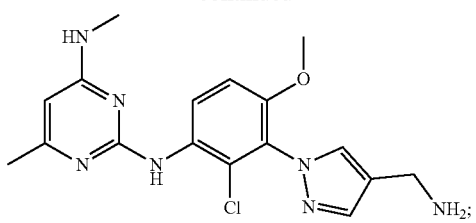
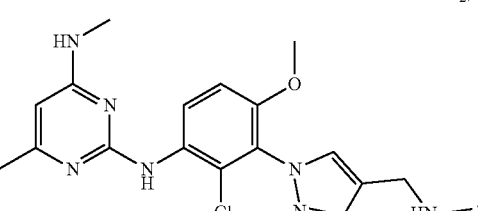
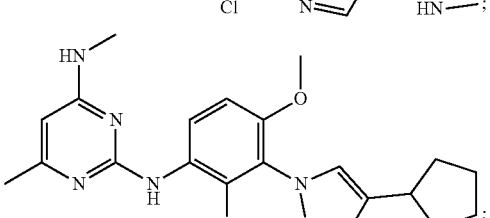
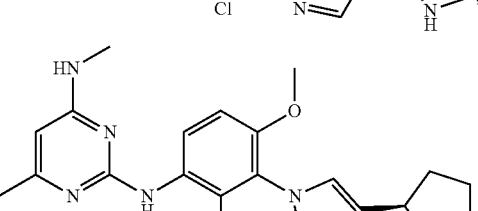
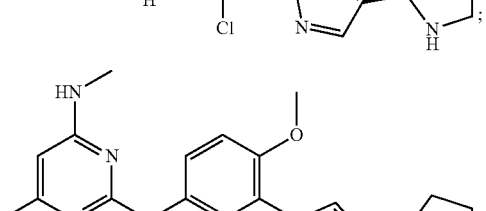
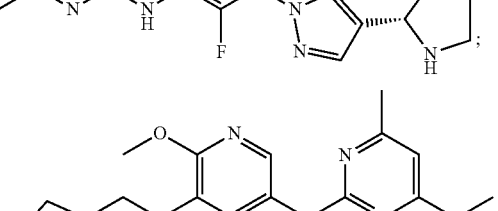
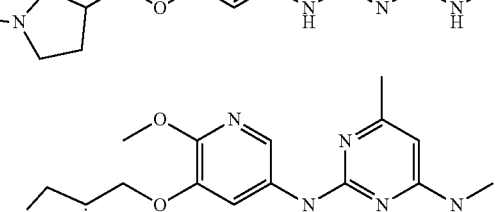
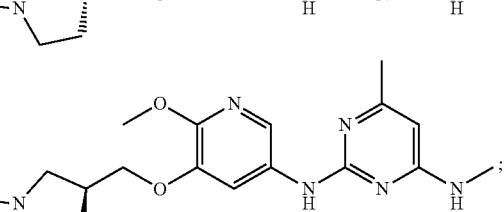

-continued

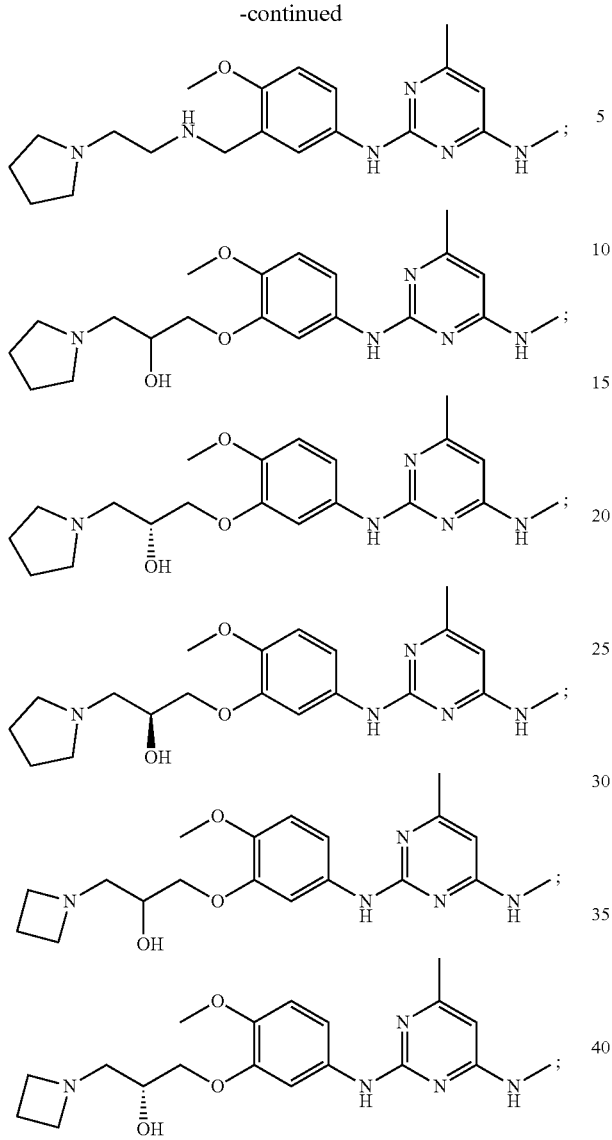

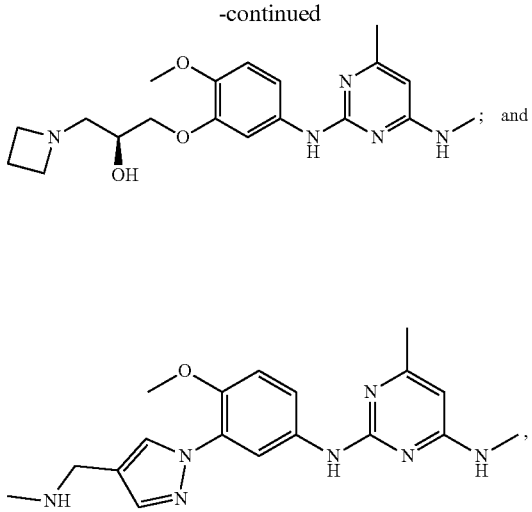

or a pharmaceutically acceptable salt thereof,
and one or more additional therapeutic agent selected from a PI3K inhibitor, a MTOR inhibitor, an AKT inhibitor, a BRAF inhibitor, a MEK1 inhibitor, a MEK2 inhibitor, an ERK inhibitor, an EGFR inhibitor, a DNMT inhibitor, a cKIT inhibitor, and a CDK4/6 inhibitor, or any combination thereof.

2. The method of claim 1, wherein the compound and the one or more additional therapeutic agent are administered simultaneously, sequentially, or in alteration.

3. The method of claim 1, wherein the one or more additional therapeutic agent is BKM120, GDC-0068, sorafenib, BVD-523, erlotinib, trametinib, selumetinib, pictilisib, MK-2206, everolimus, decitabine, palbociclib, or imatinib, a pharmaceutically acceptable salt thereof, or any combination thereof.

4. A method of inhibiting or decreasing growth, viability, survival, or proliferation of an acute myeloid leukemia (AML), acute lymphocytic leukemia (ALL), or melanoma cell comprising (1) contacting the cell with (a) a compound selected from:

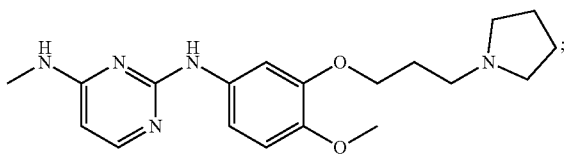

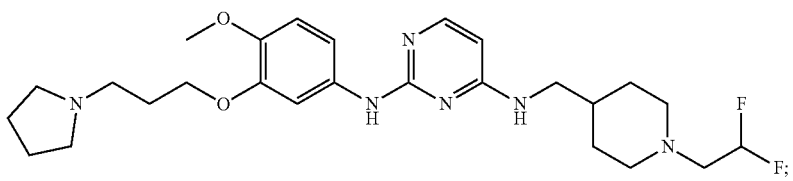

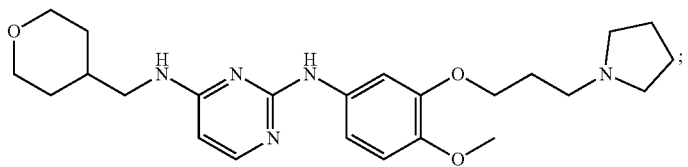

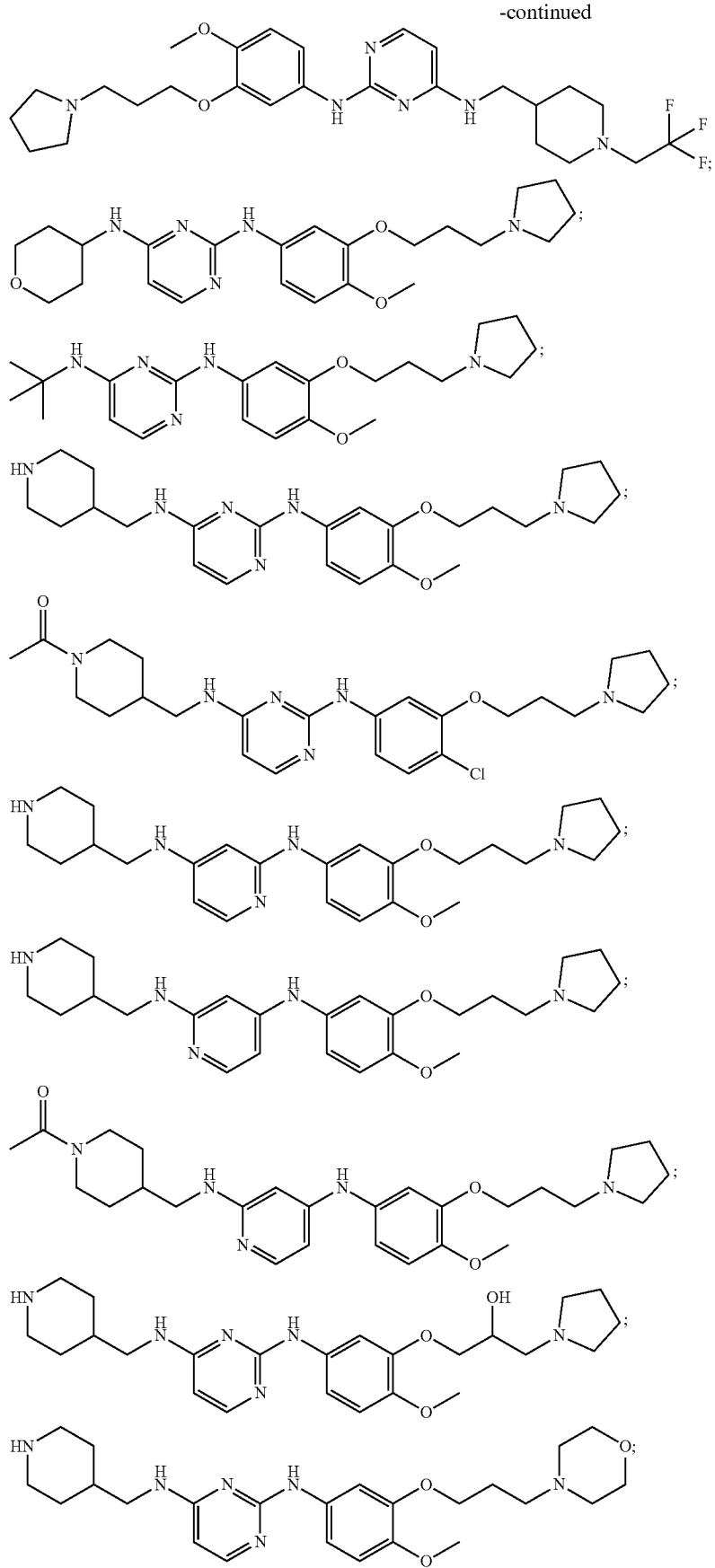

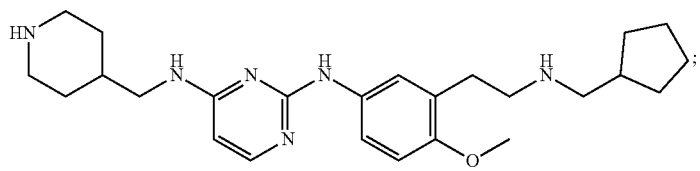
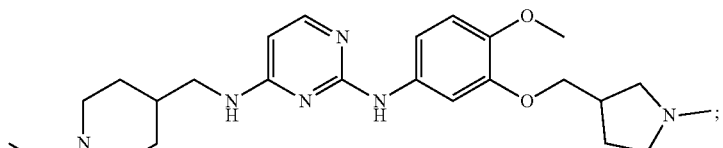
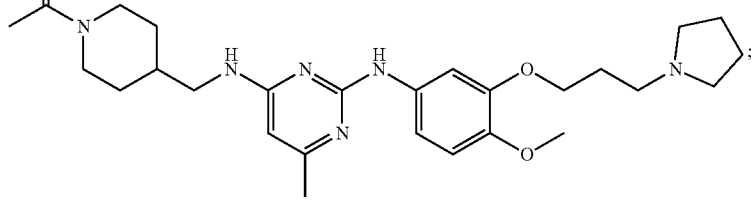
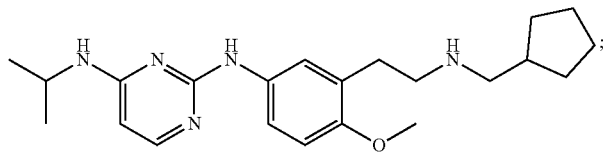
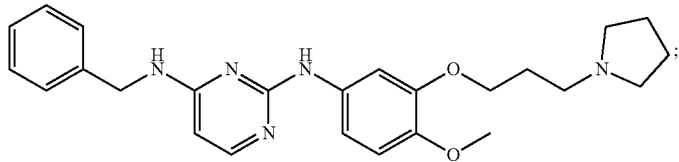
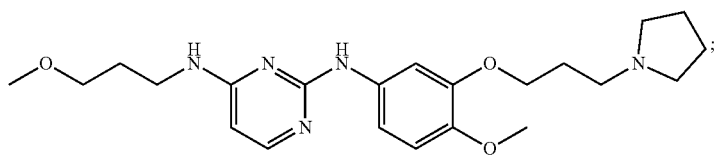
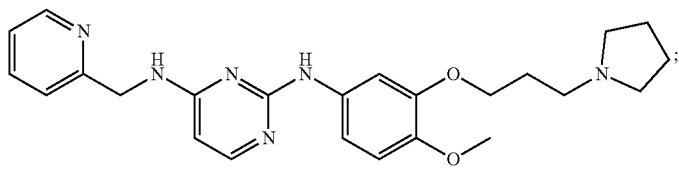
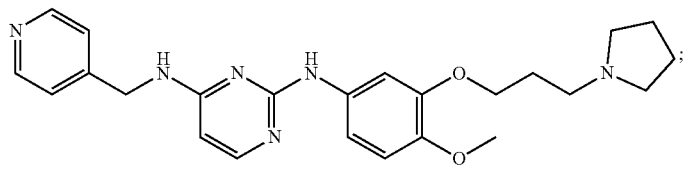
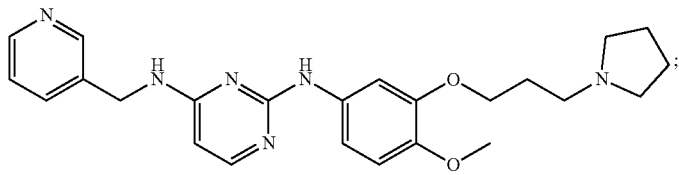

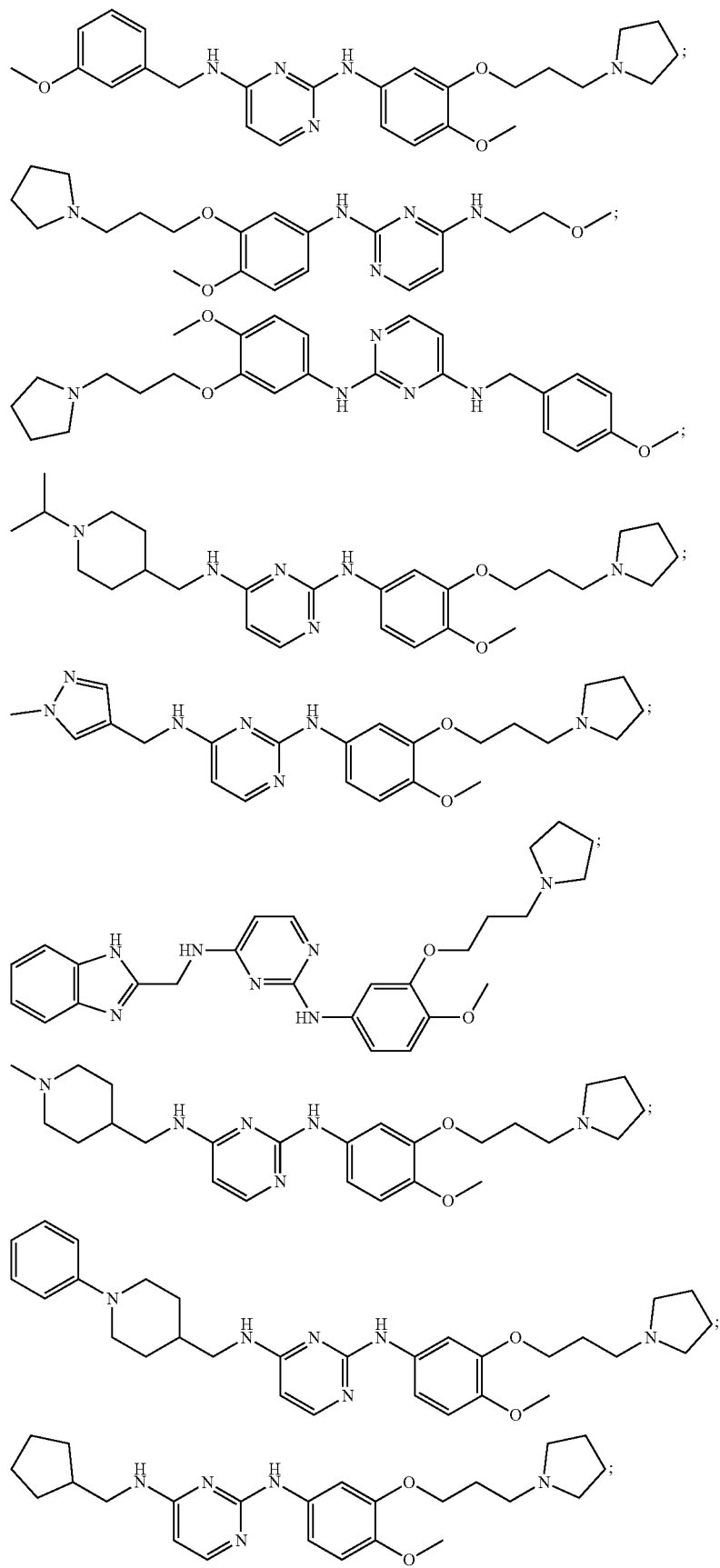

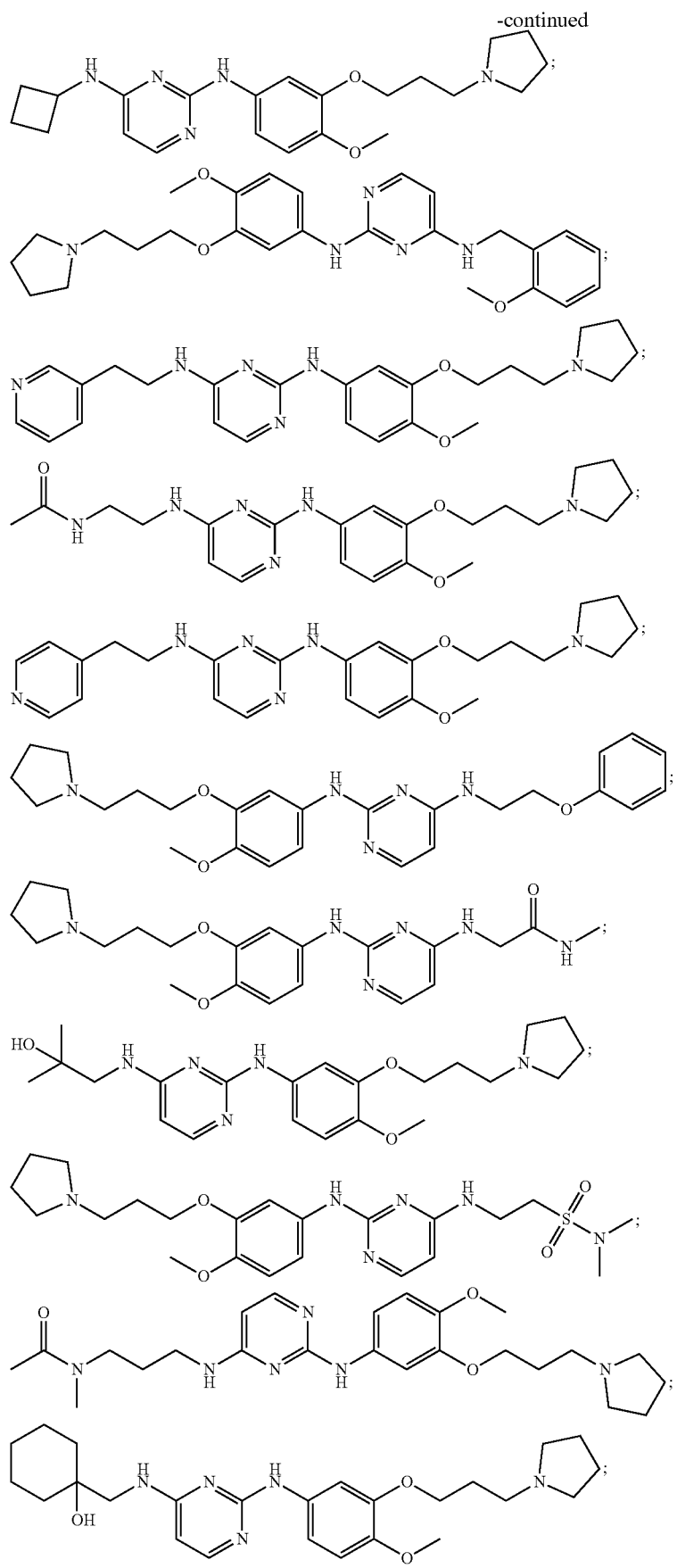

-continued
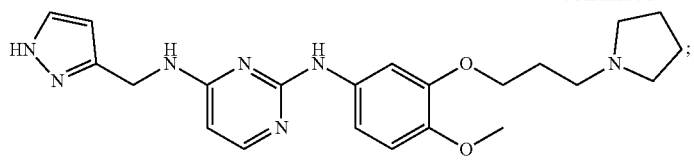
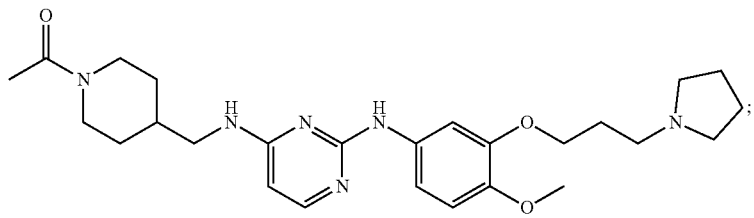
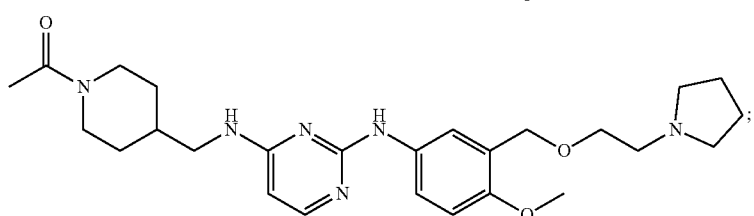
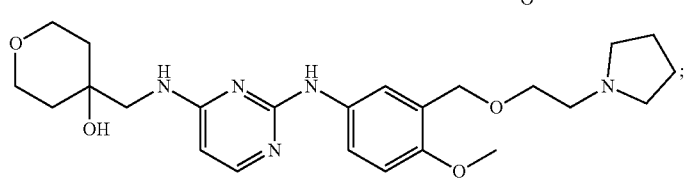
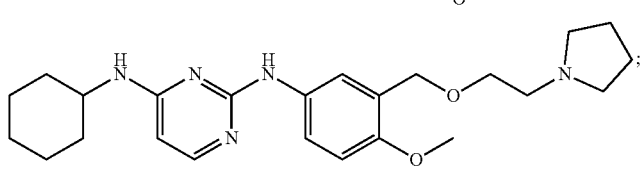
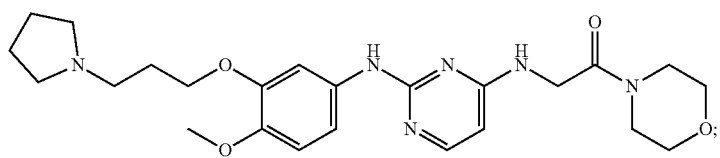
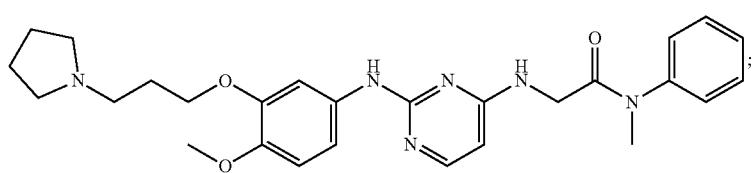
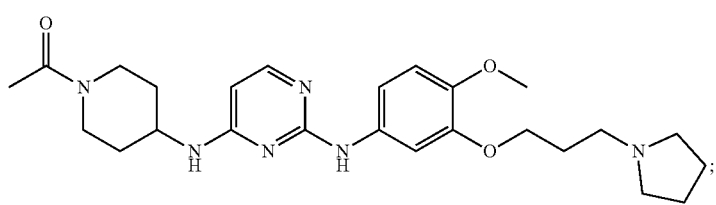
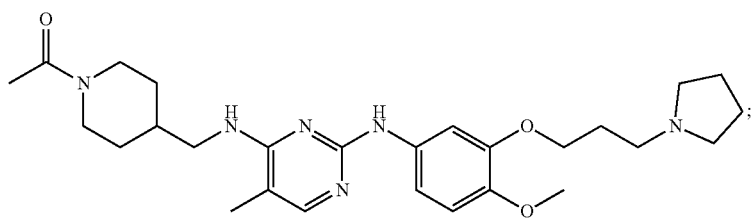

-continued
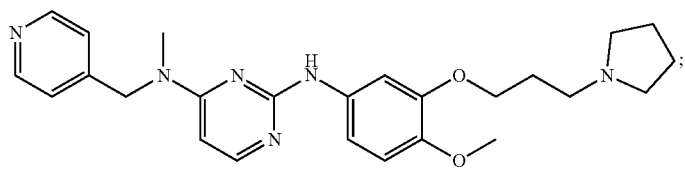
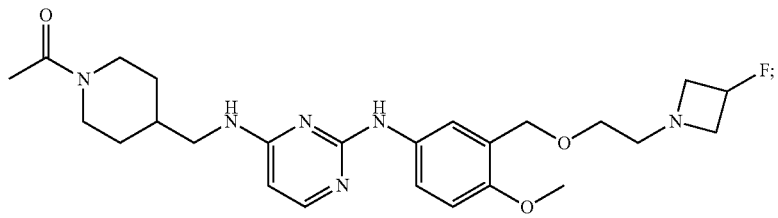
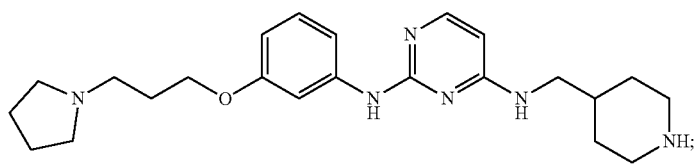
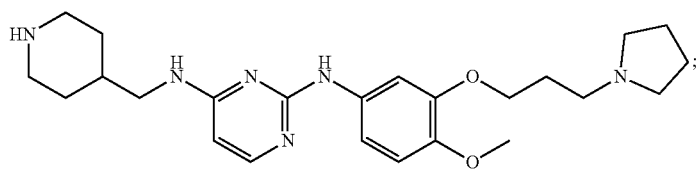
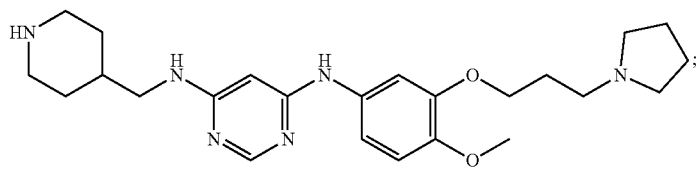
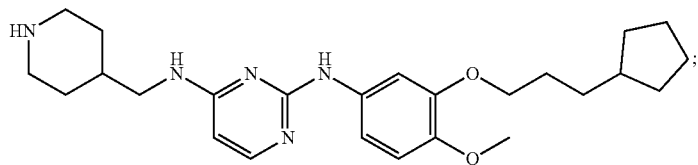
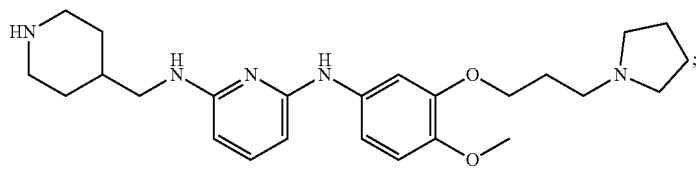
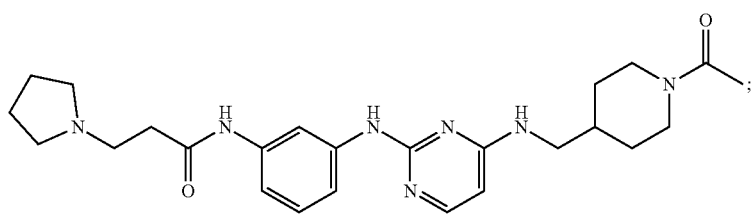
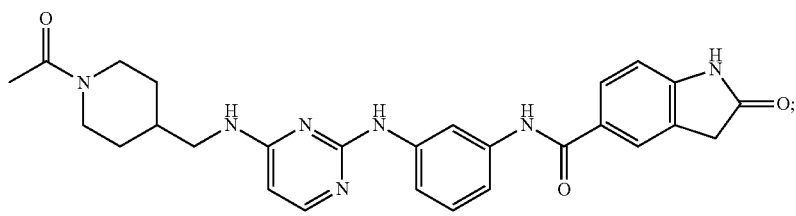

-continued
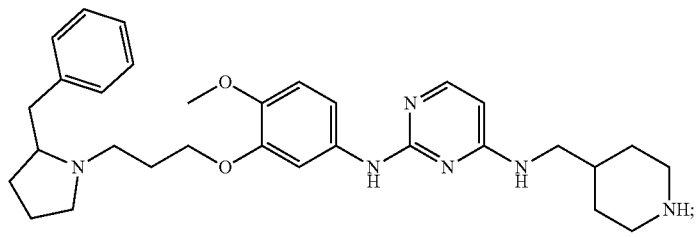
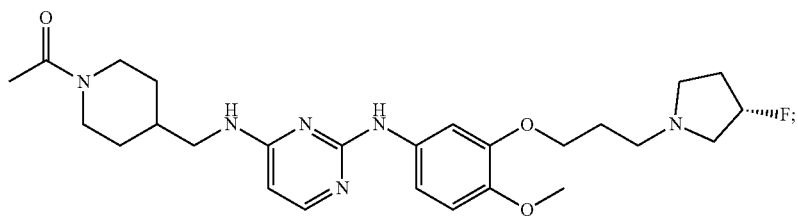
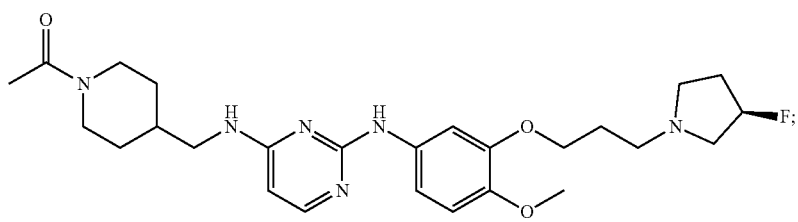
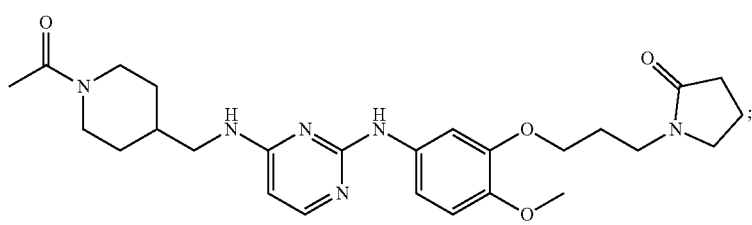
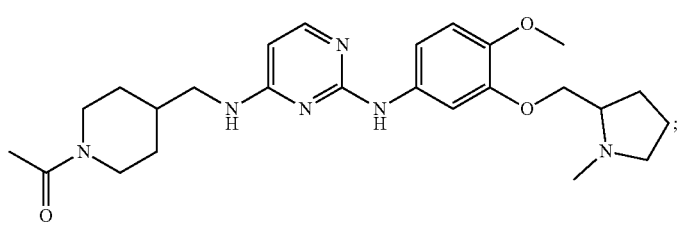
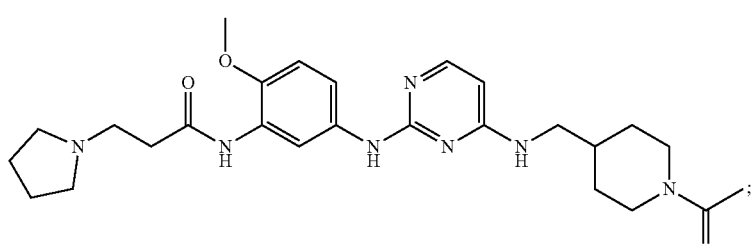

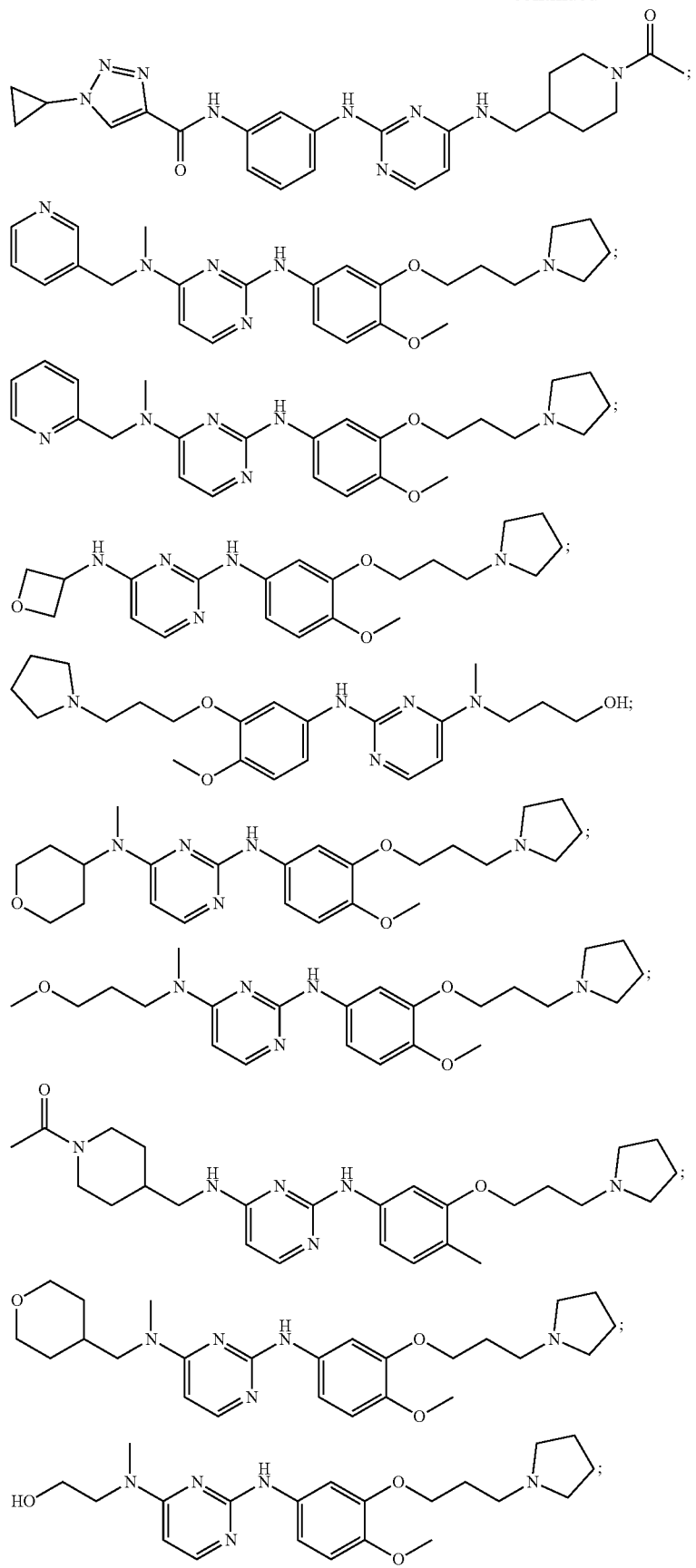

-continued
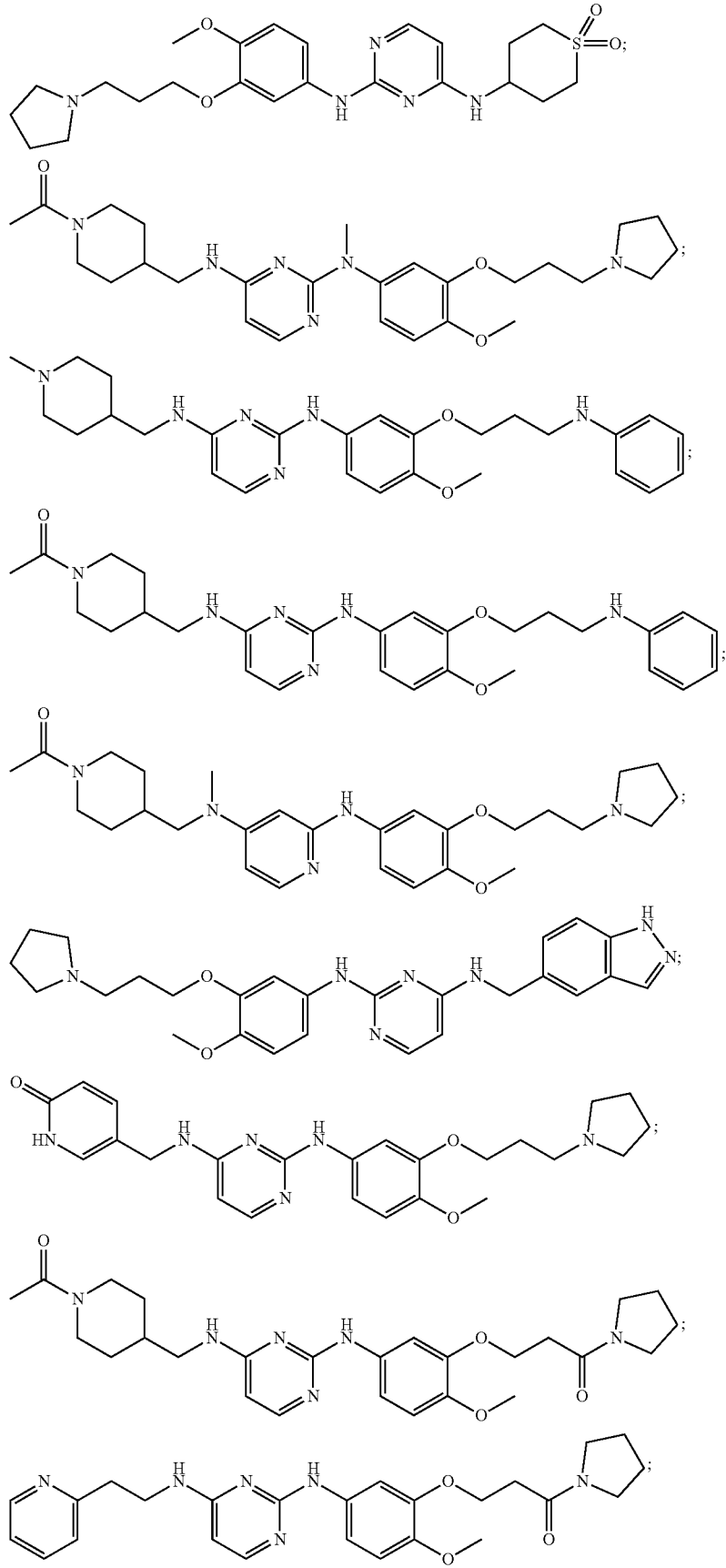

-continued
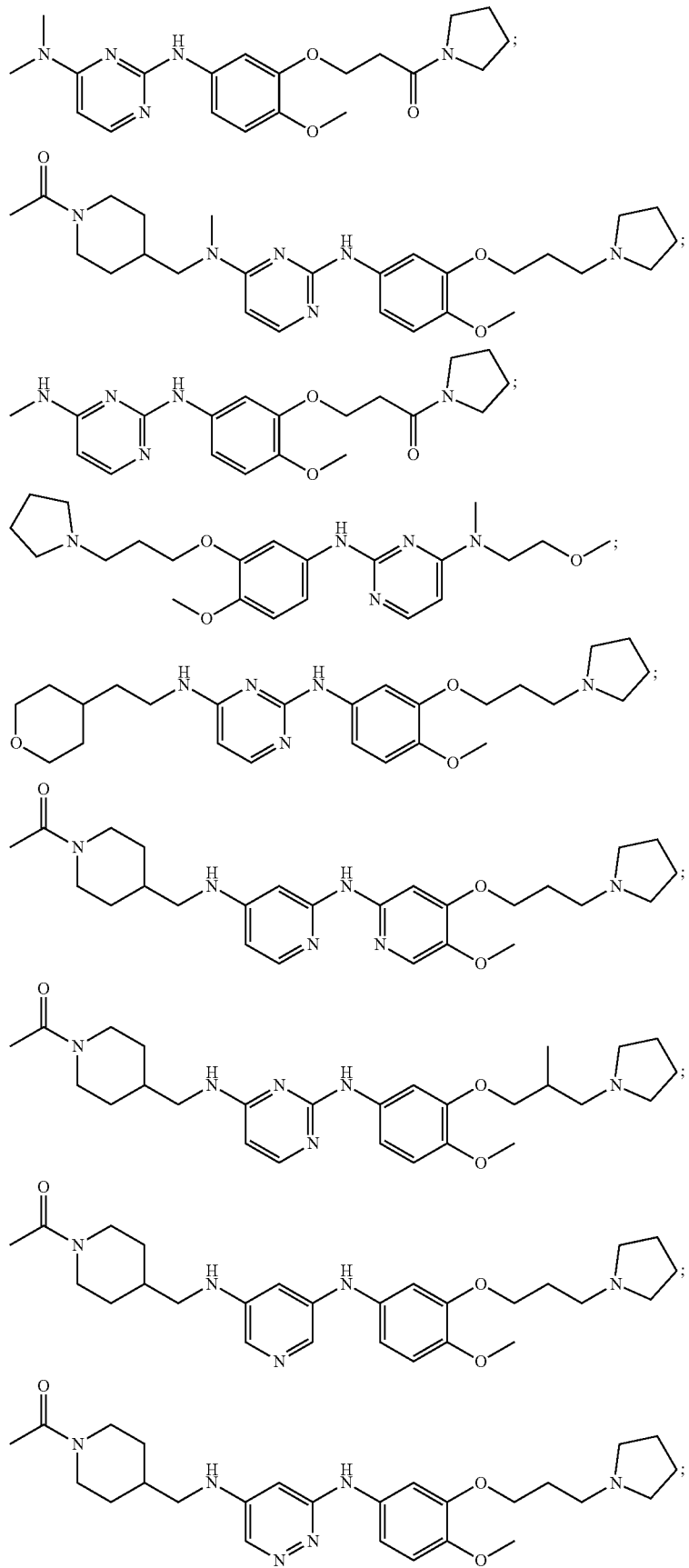

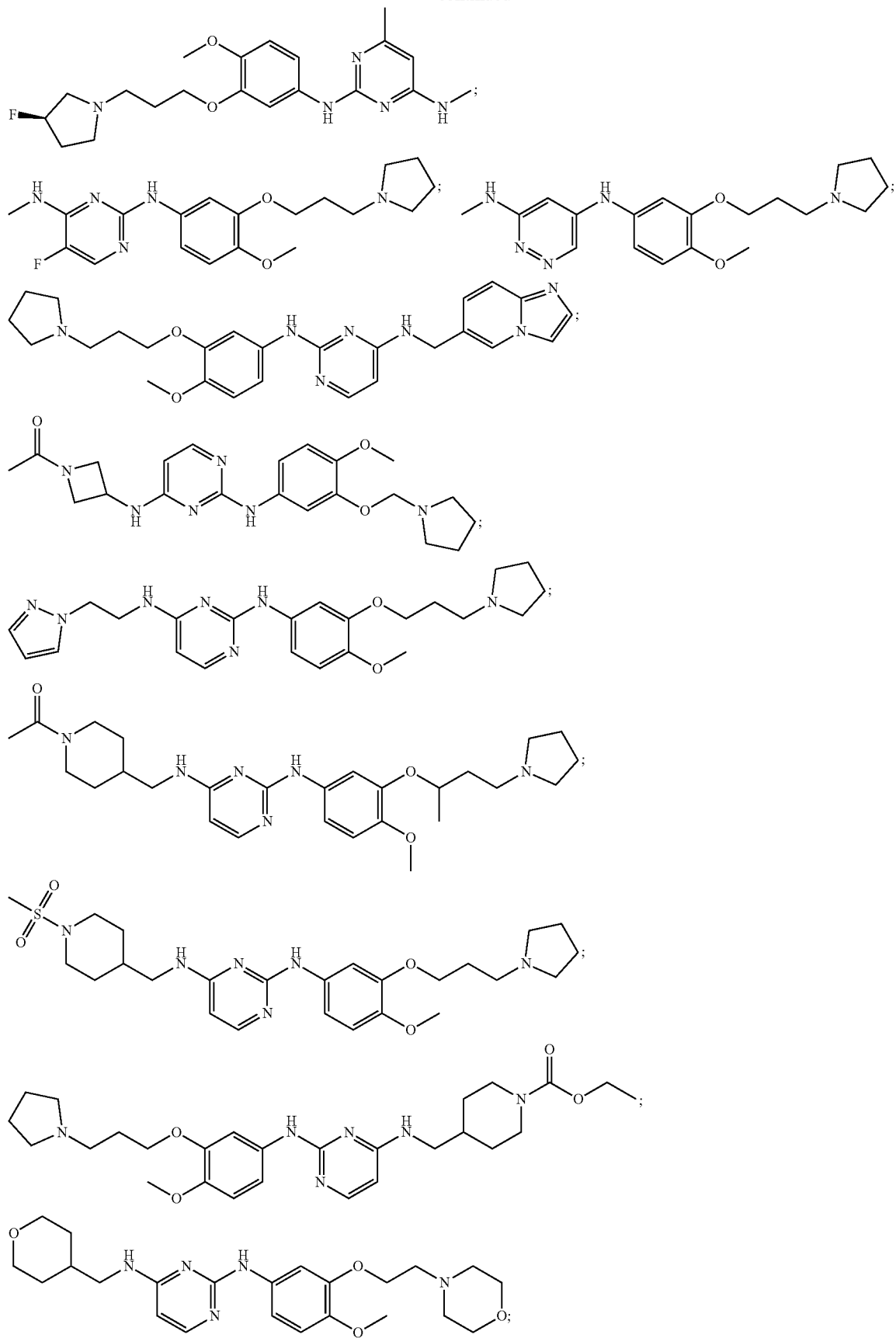

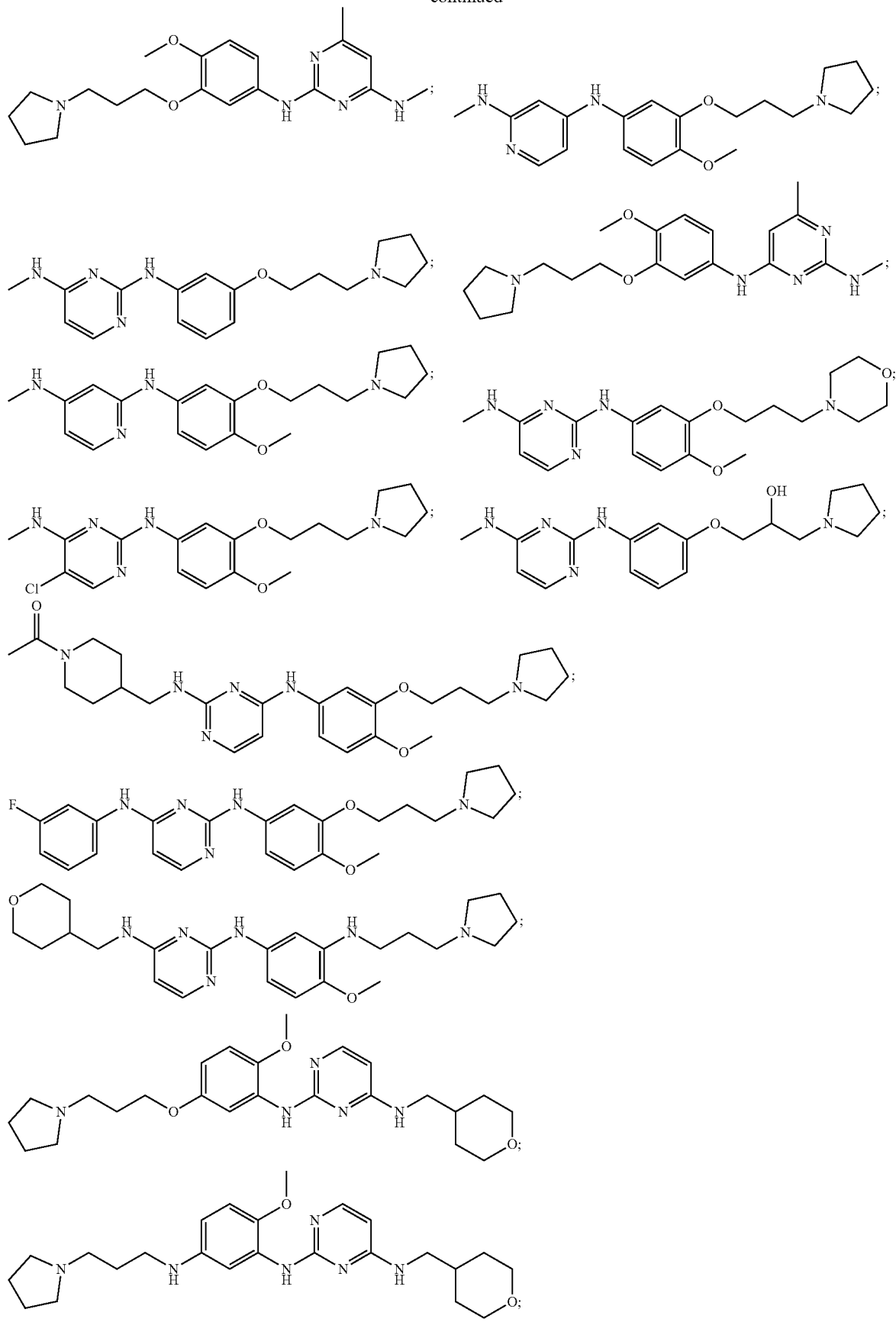

685 686
-continued
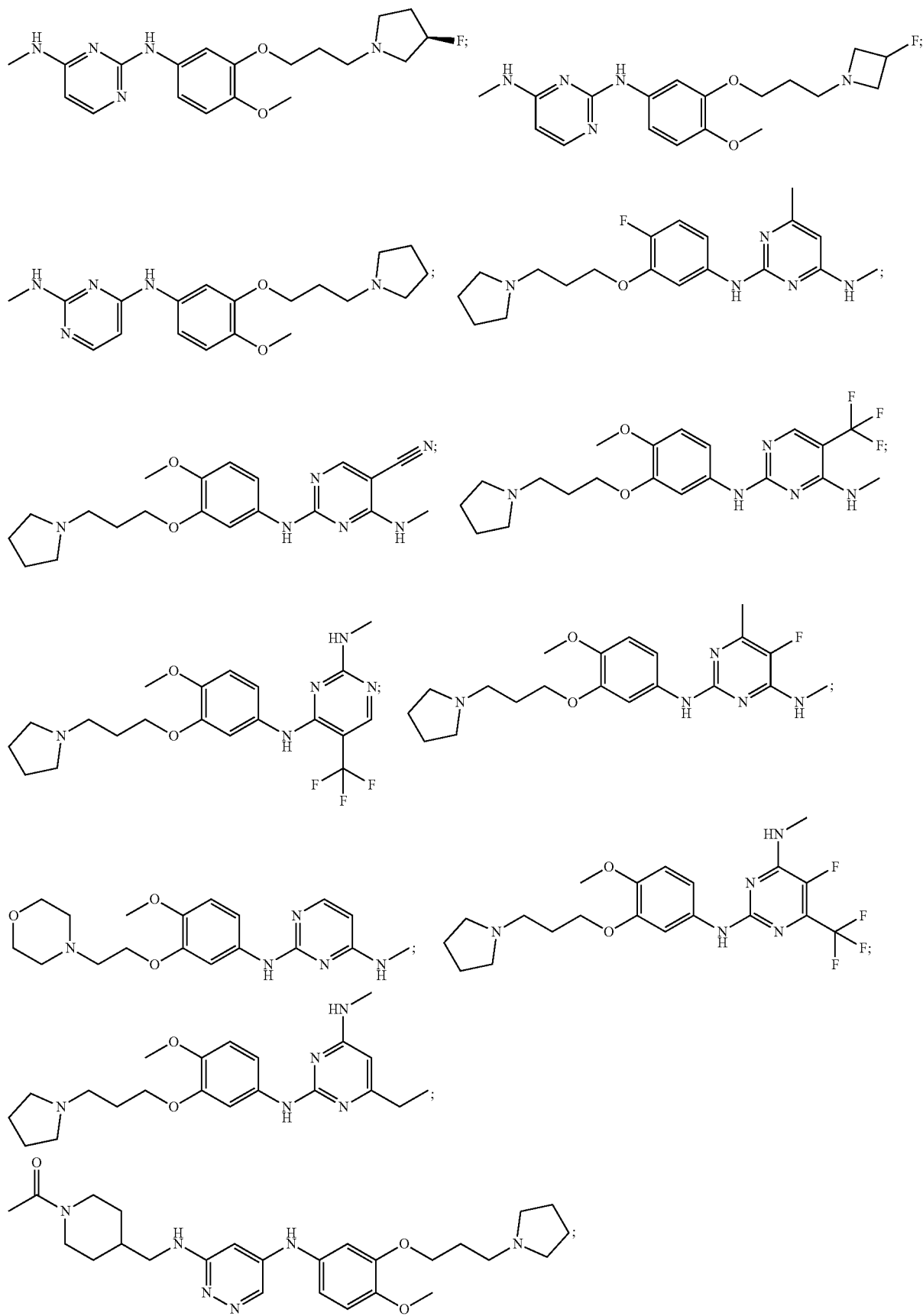

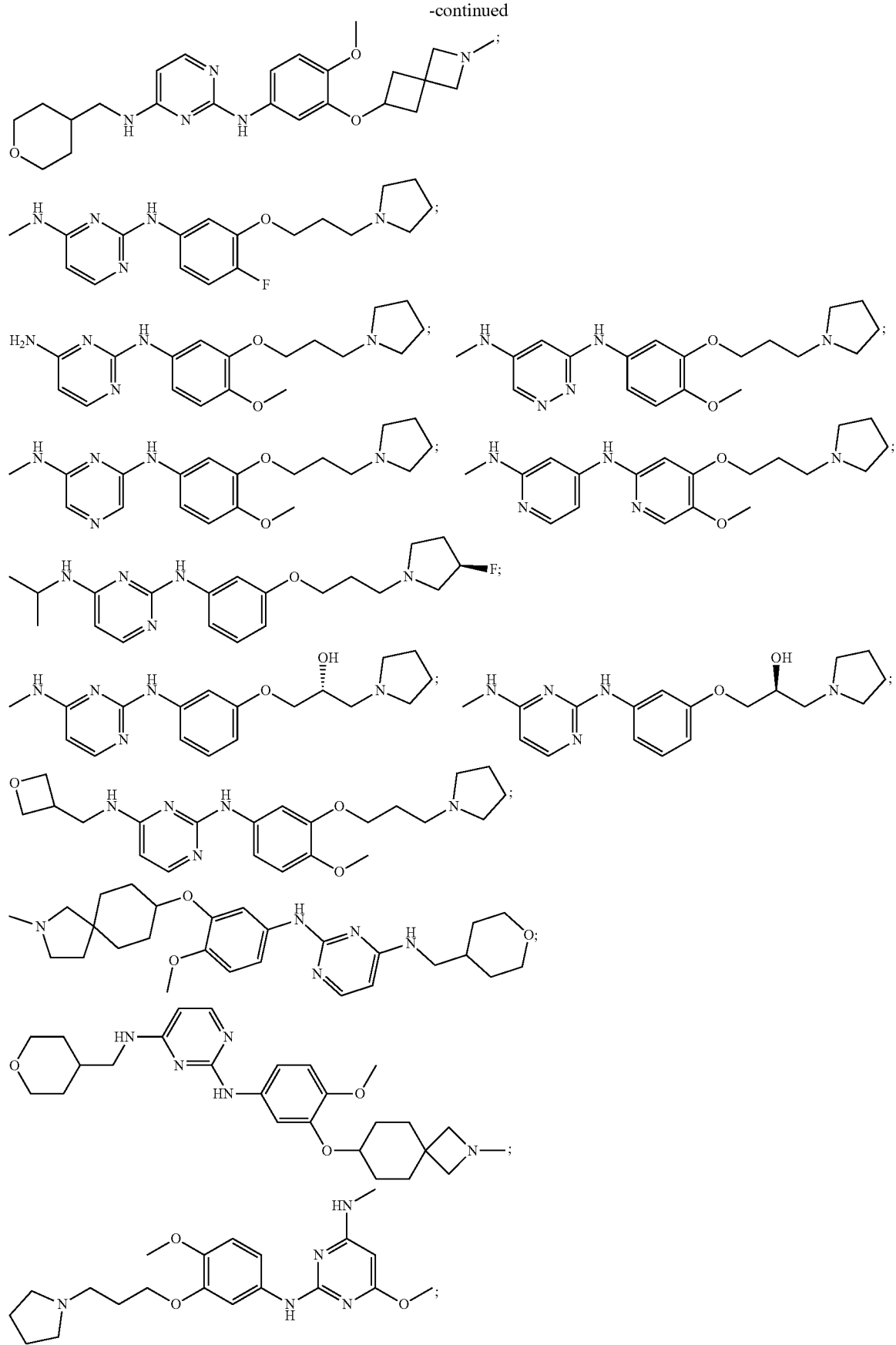

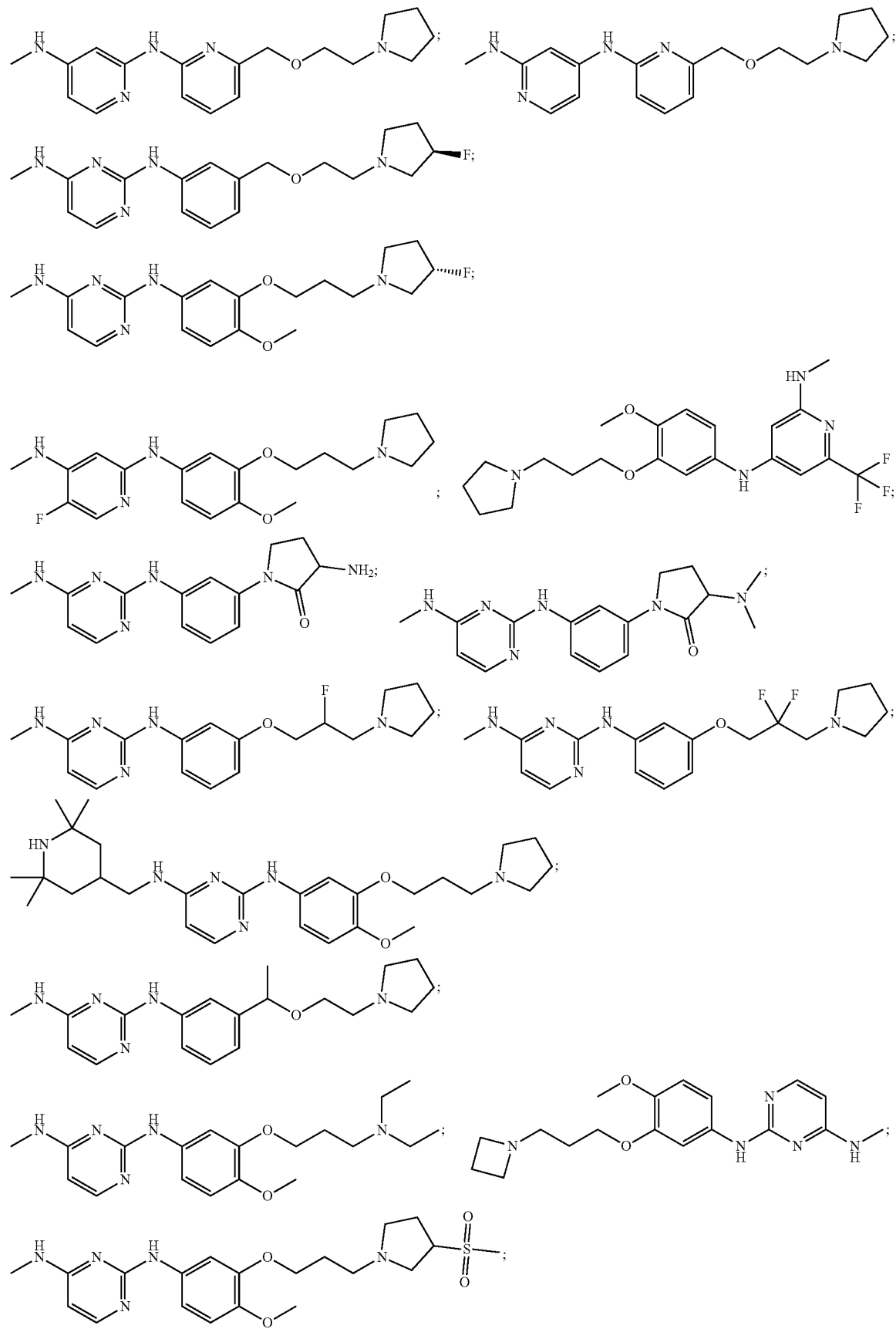

691
-continued
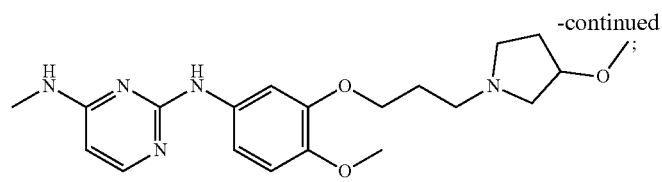
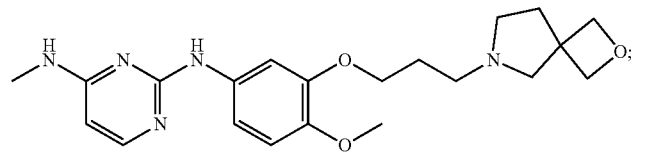
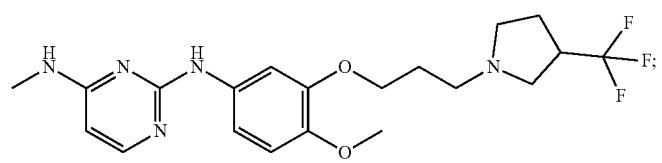
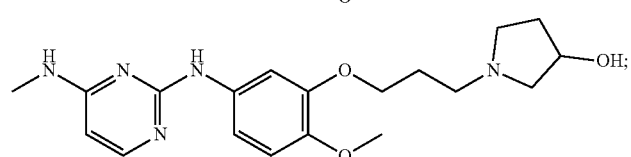
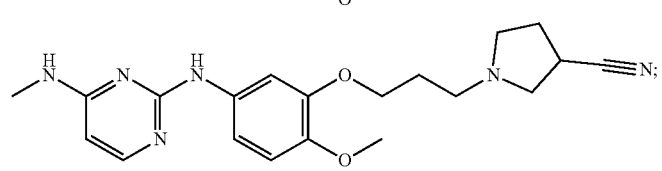
692
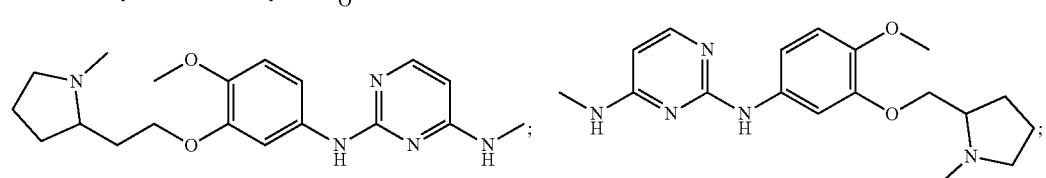
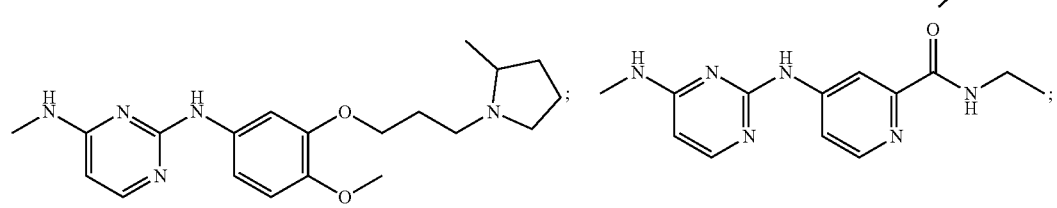
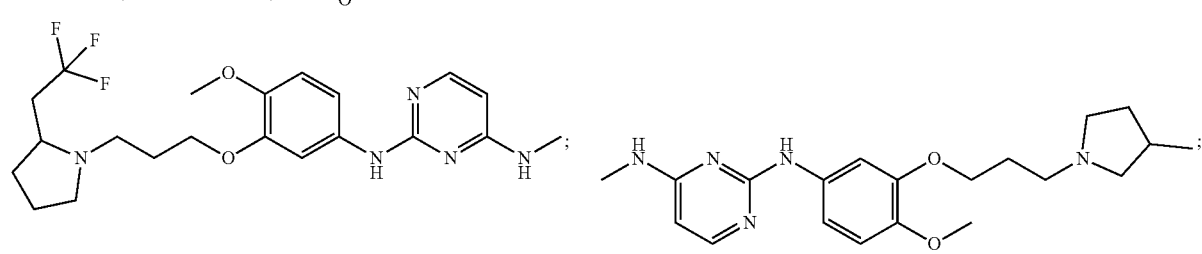
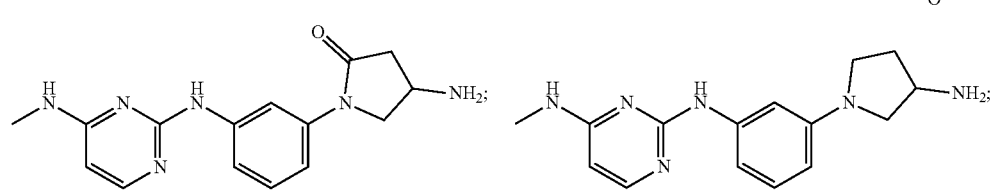

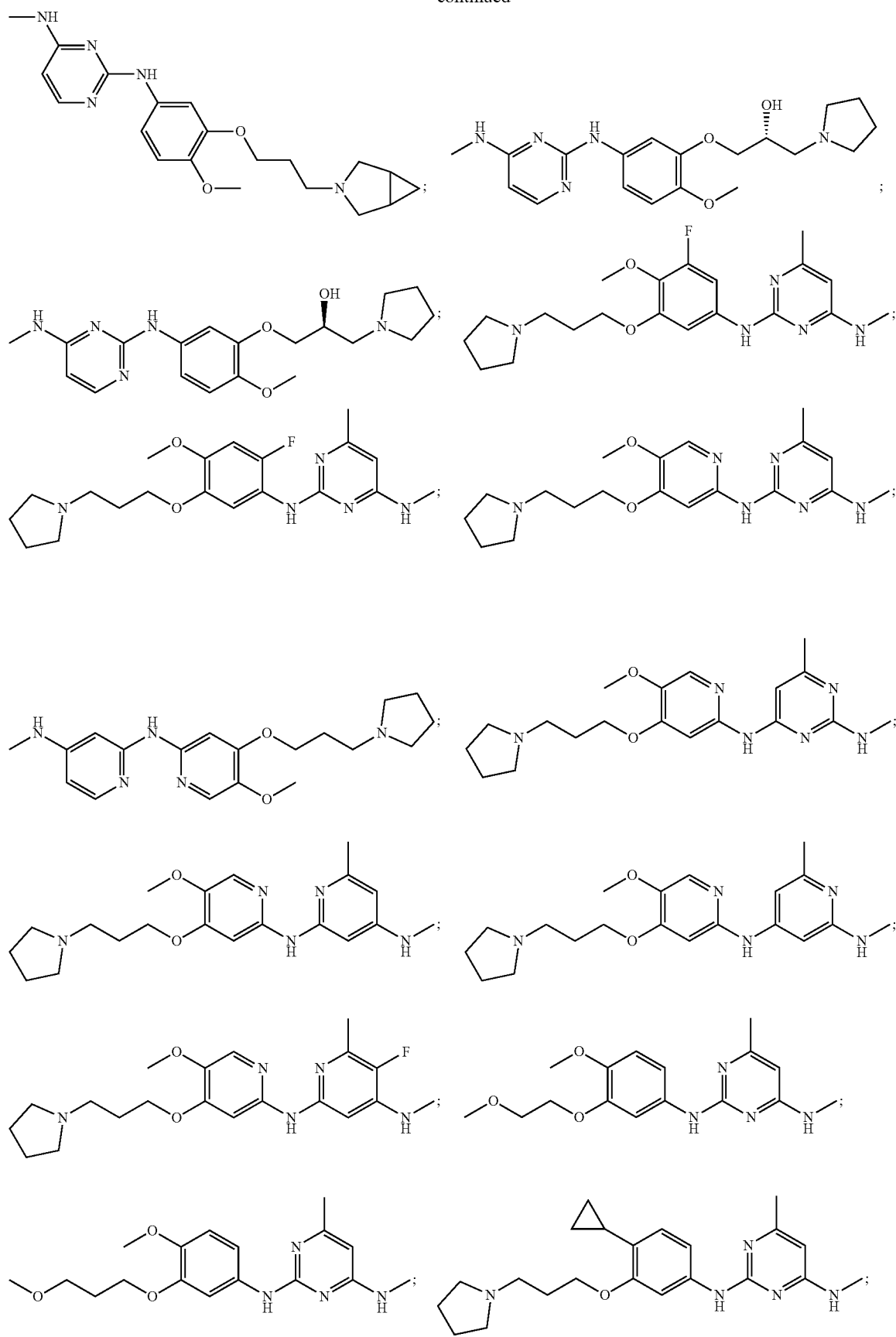

695 696
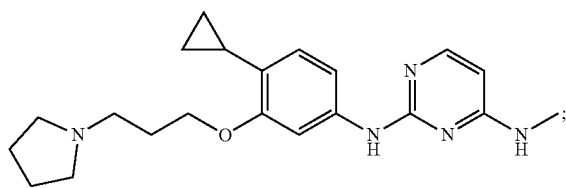
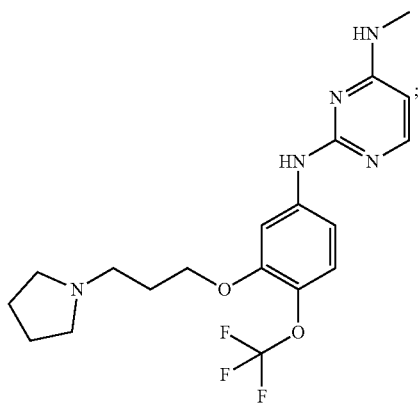
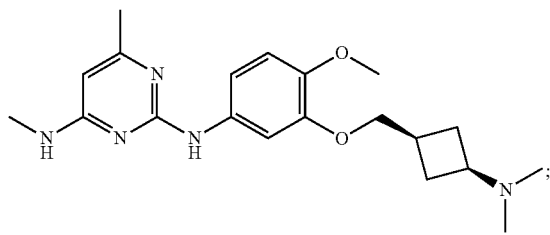
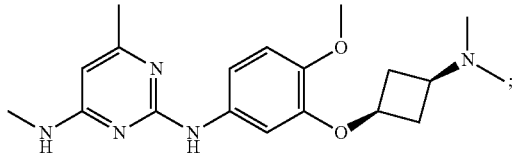
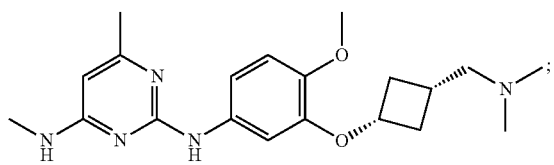
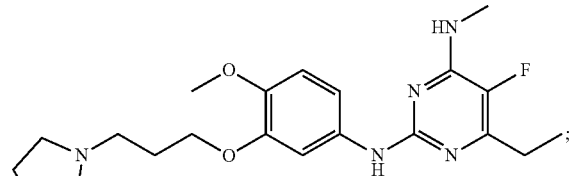
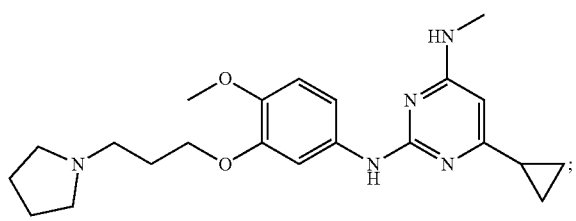
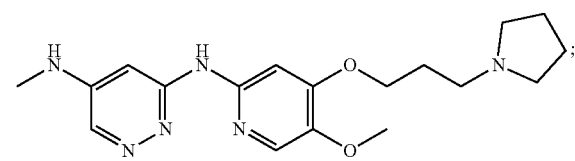
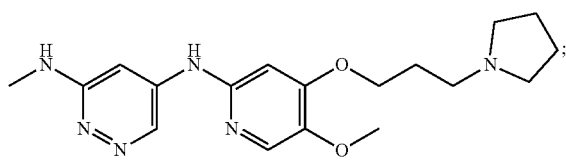
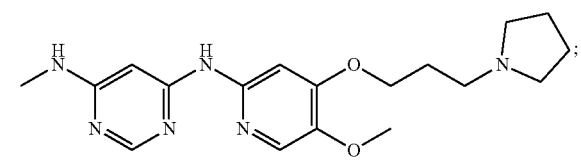
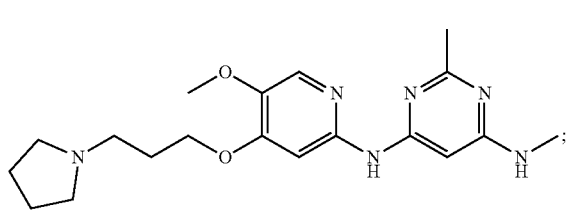
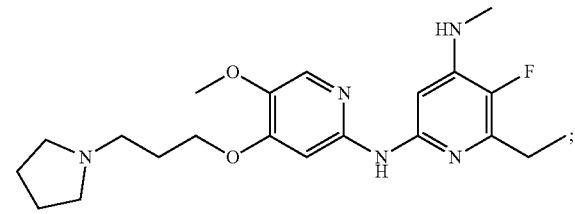

697 698
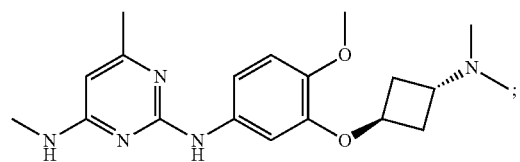 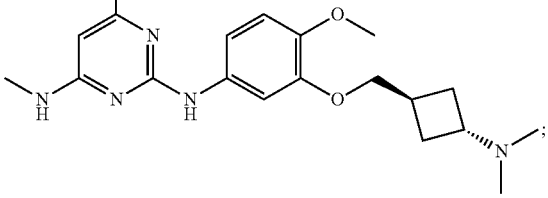
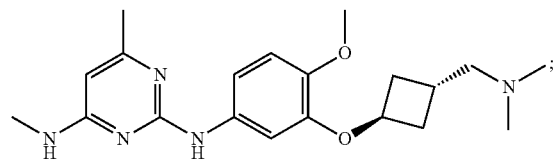 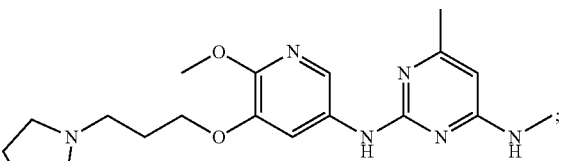
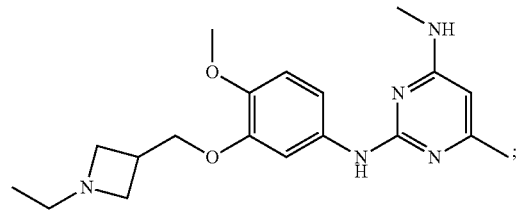 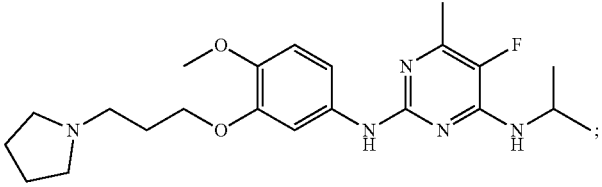
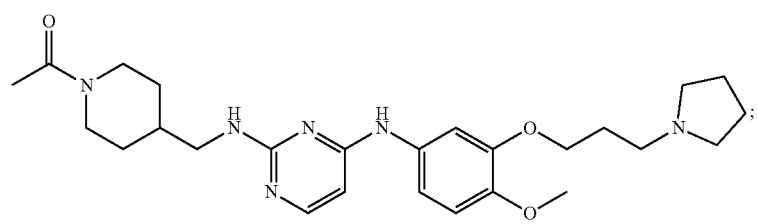
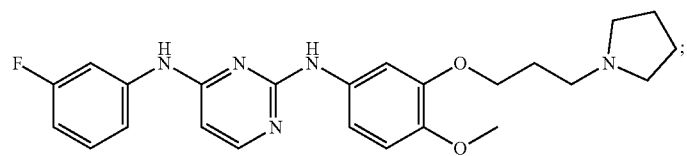
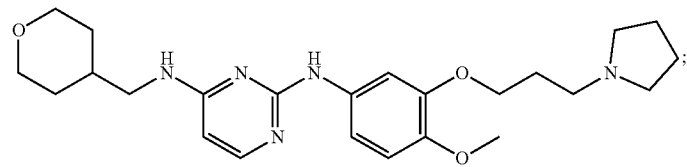
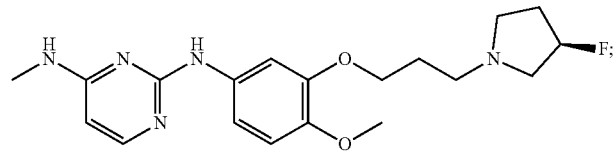
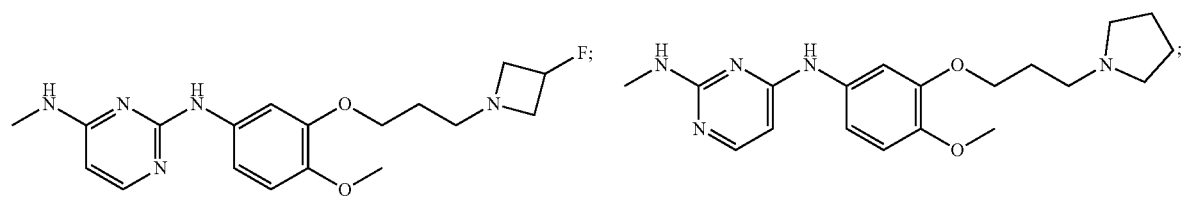

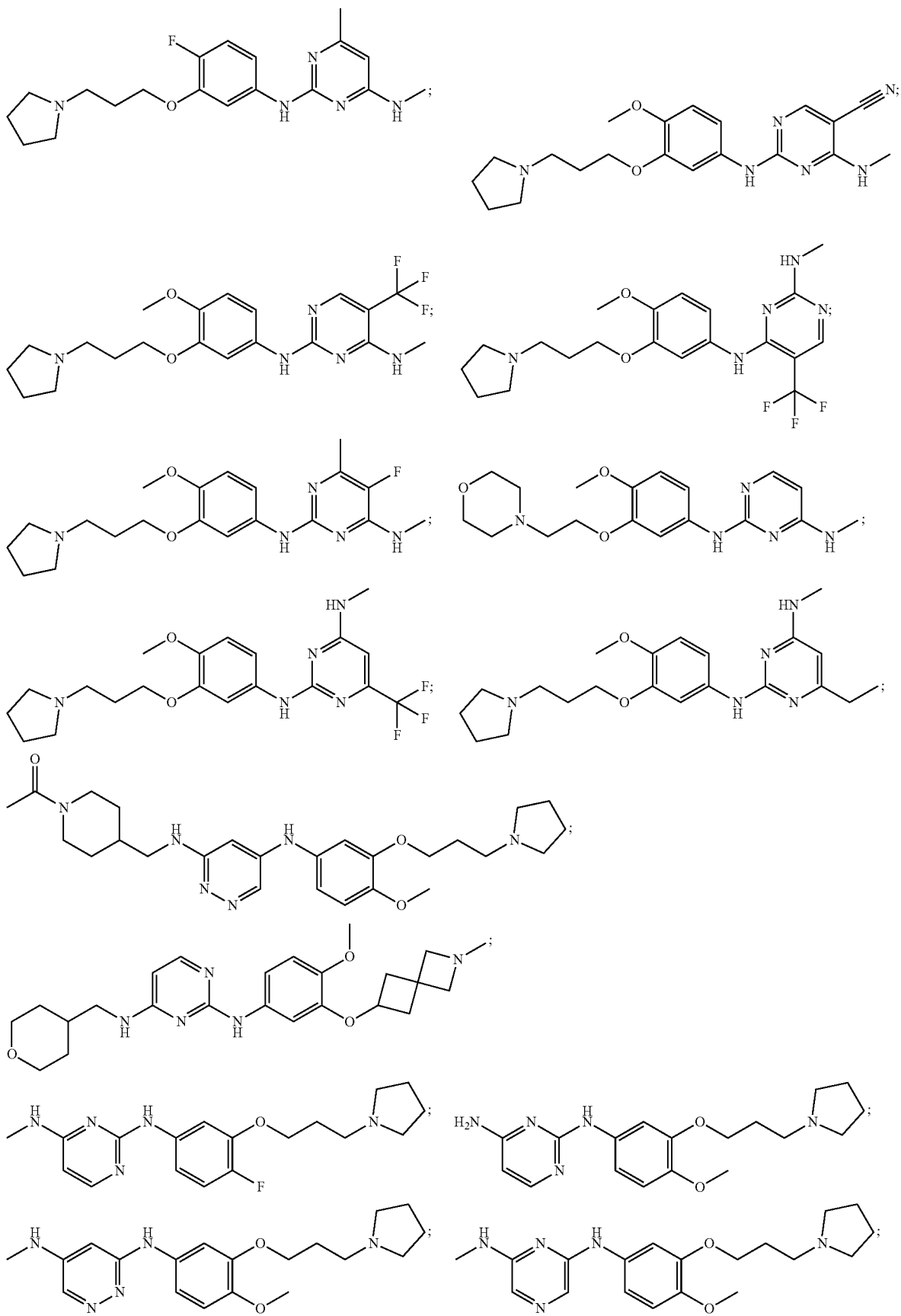

701 702
-continued
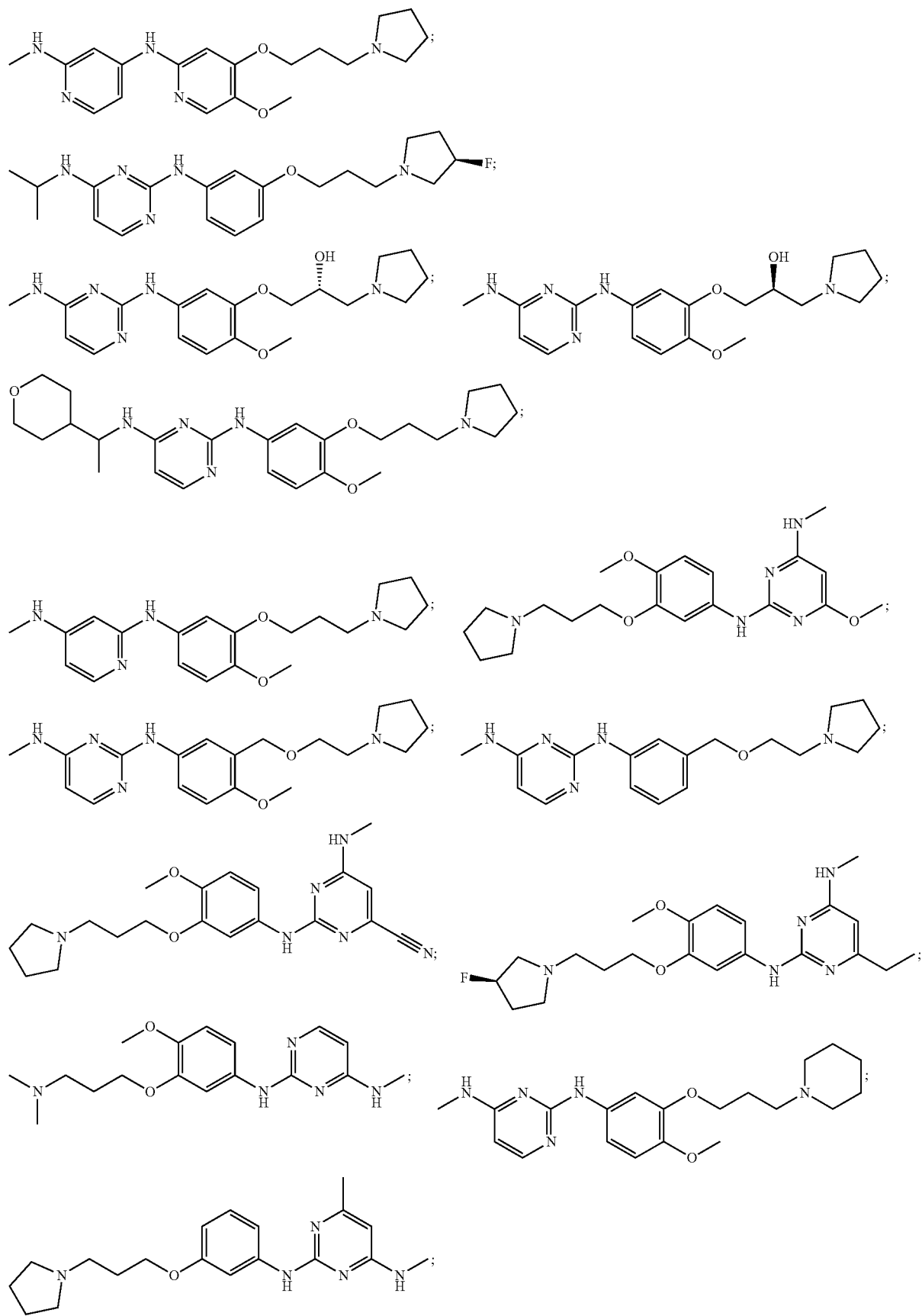

703  704
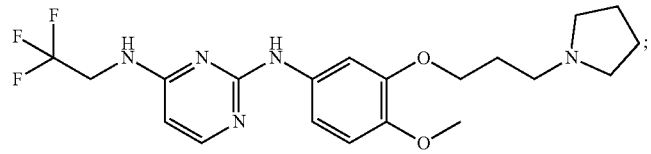
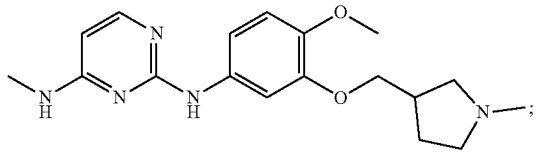
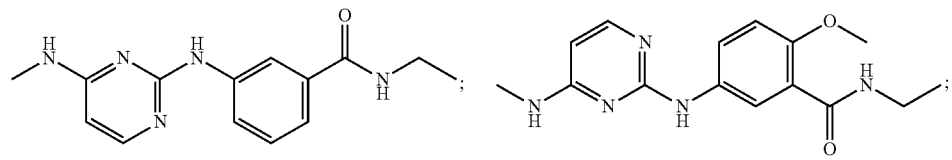
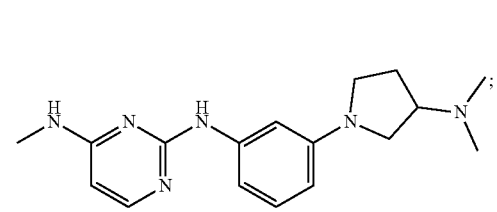
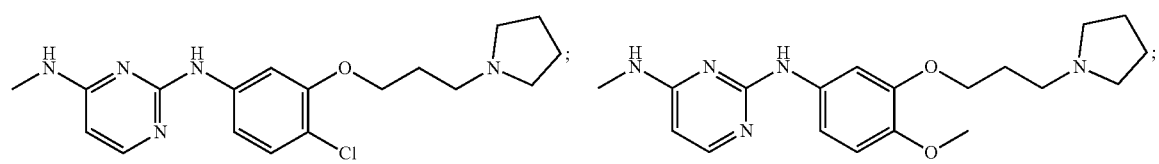
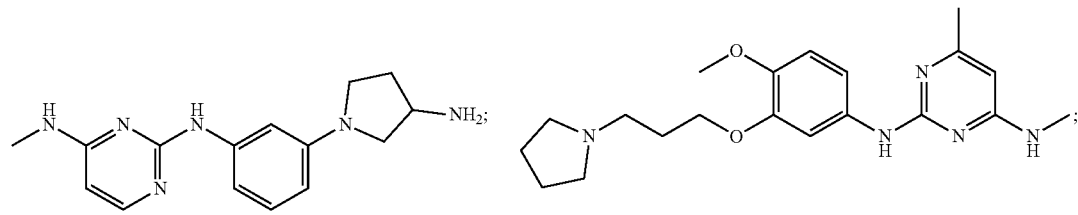
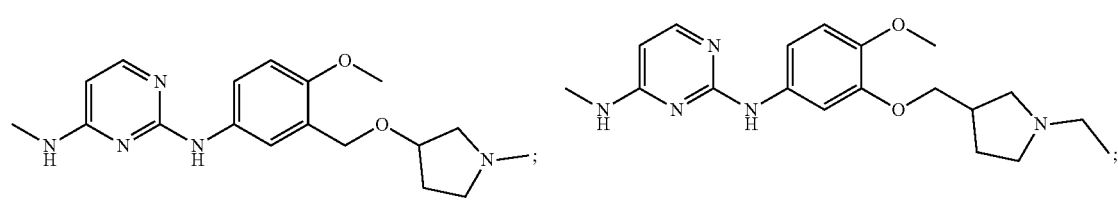
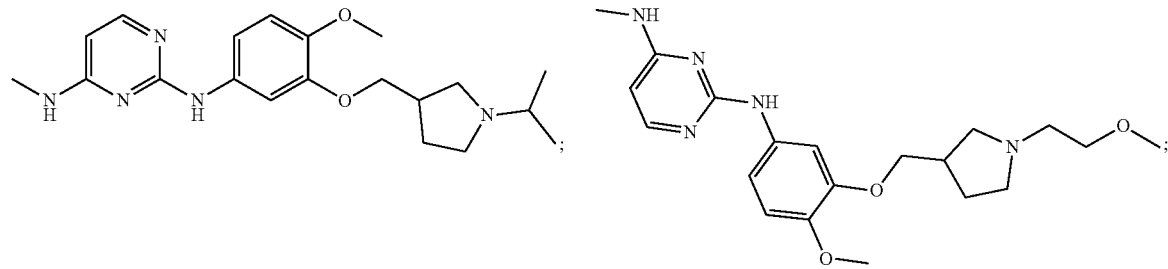
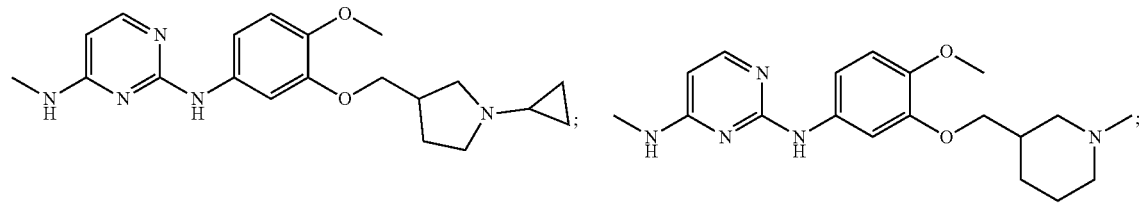

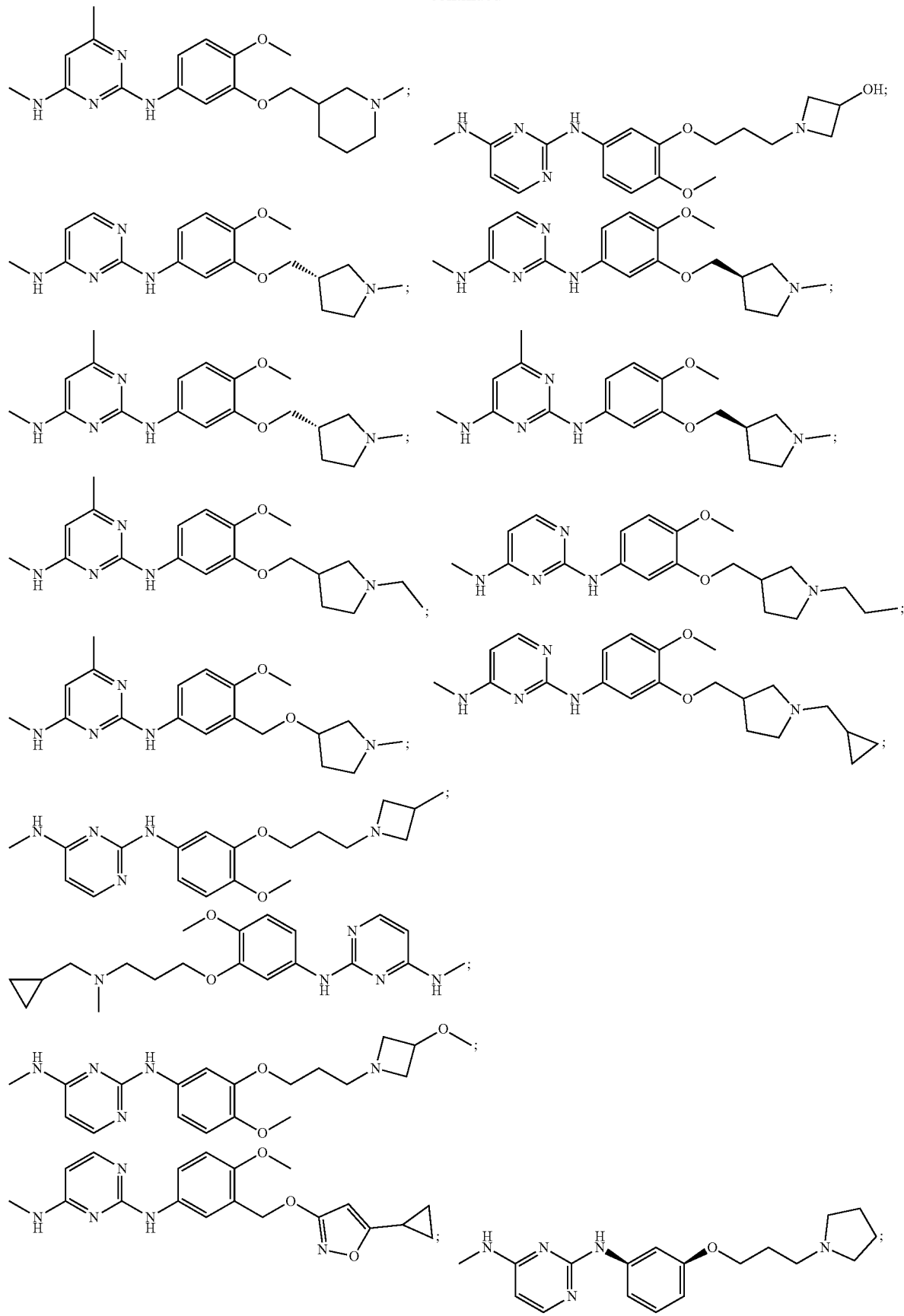

707                                          708
-continued
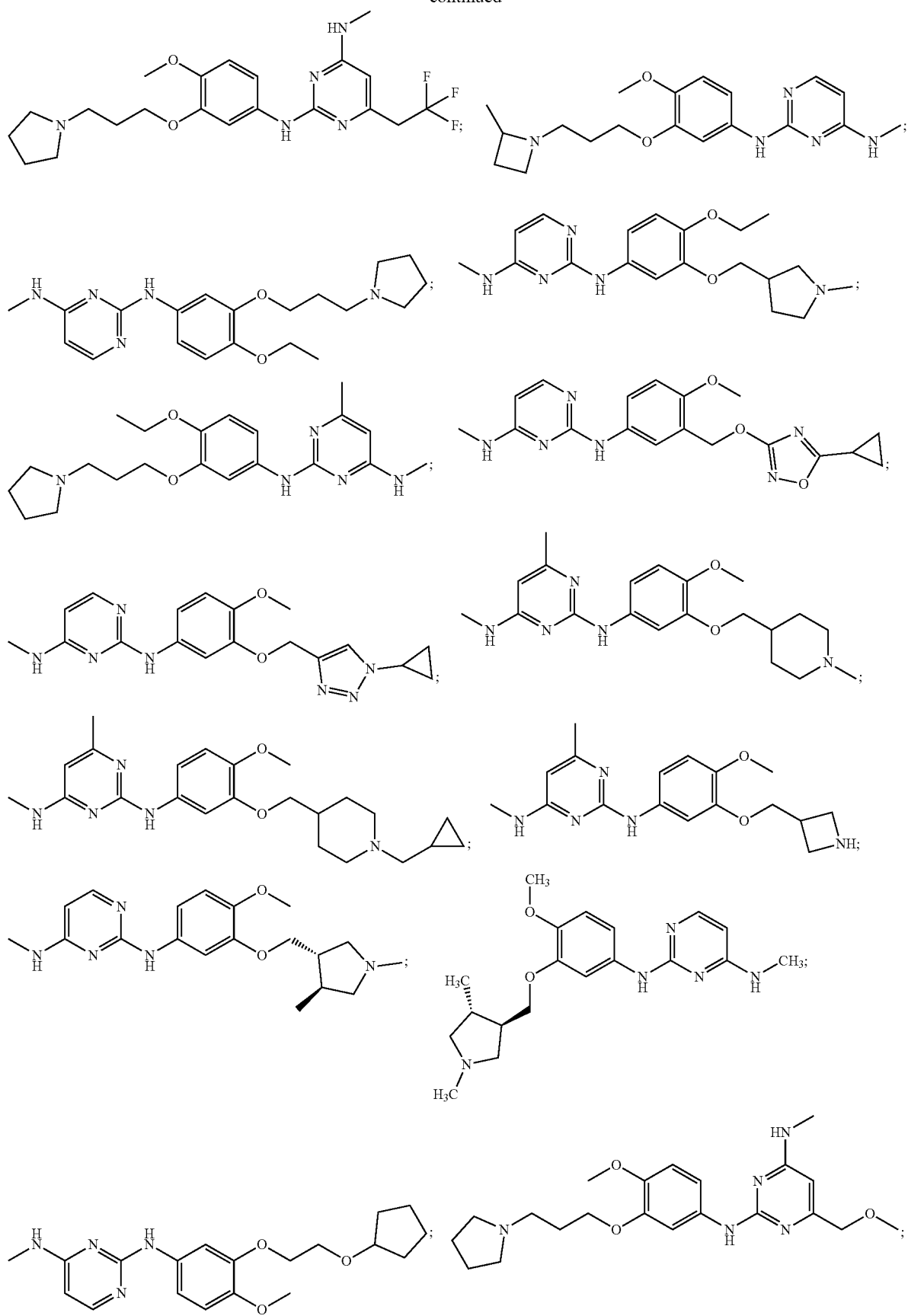

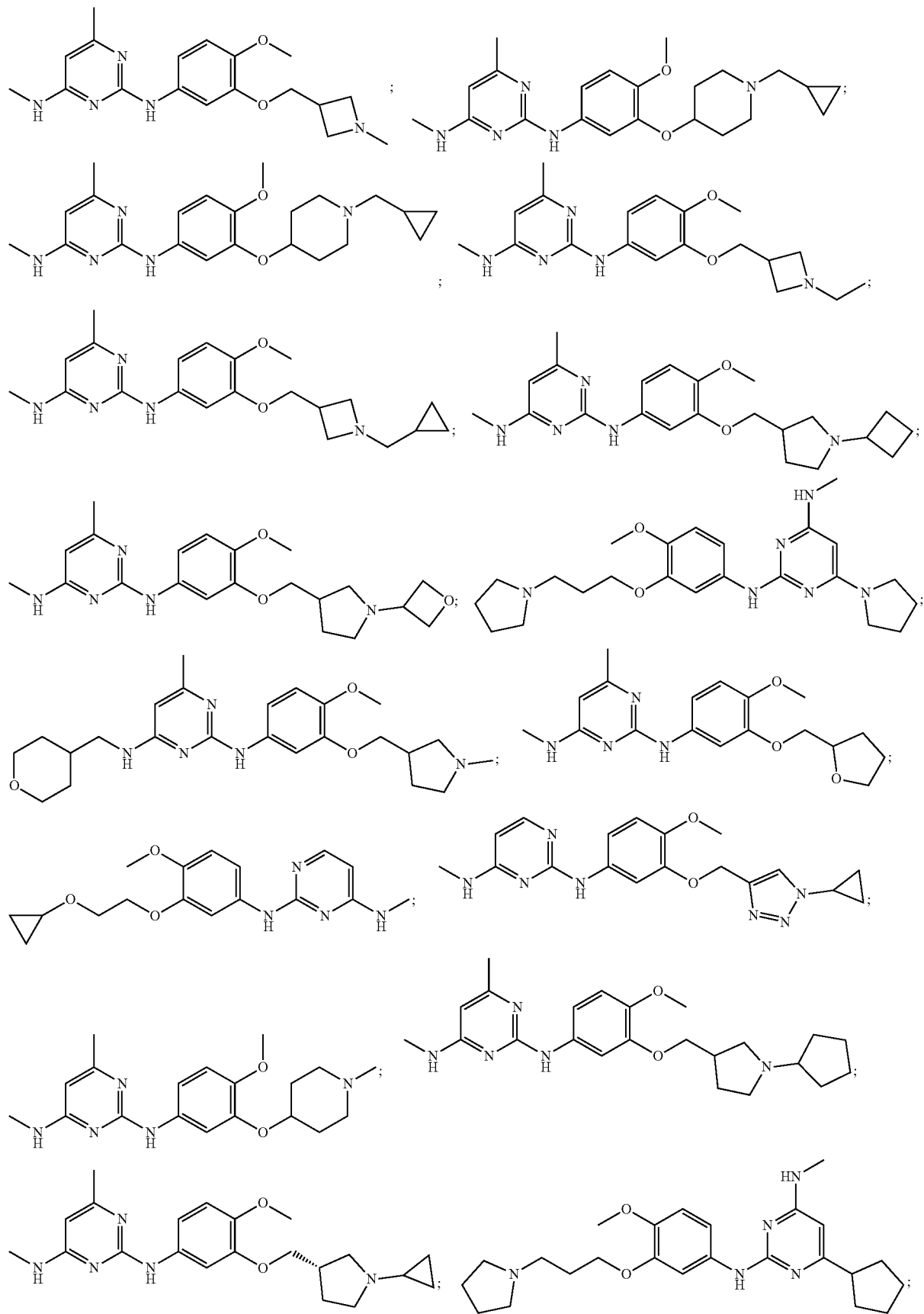

711
-continued
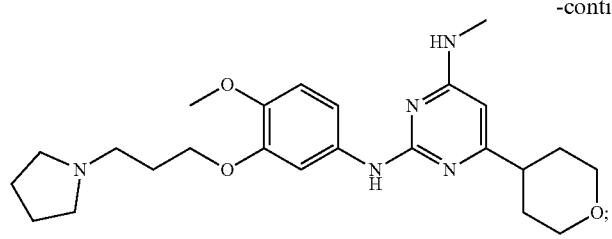
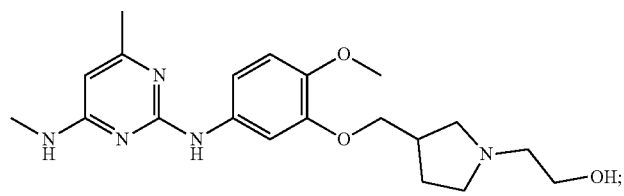
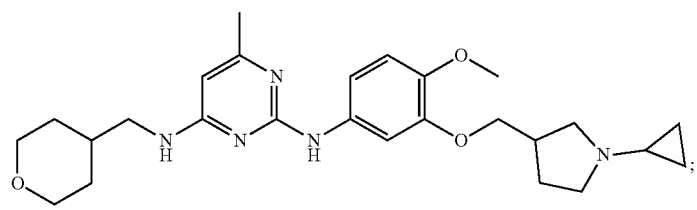
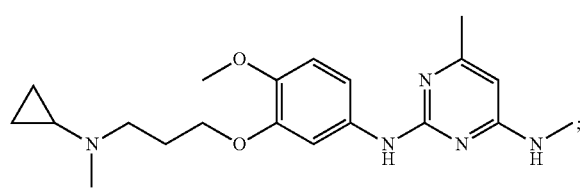
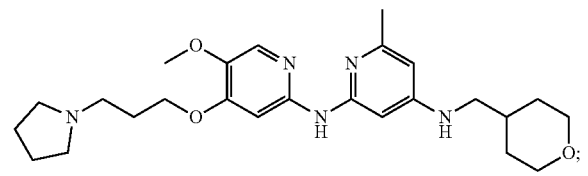
712
-continued
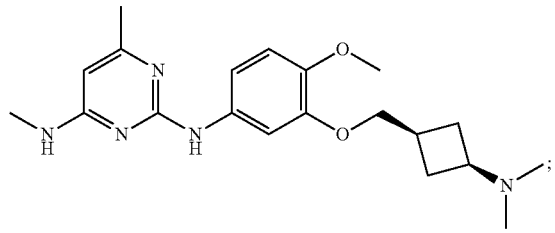
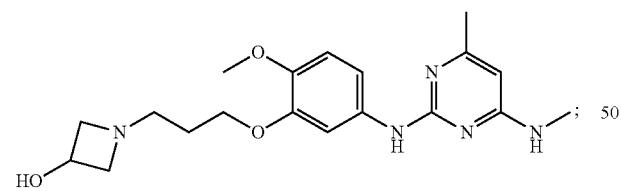
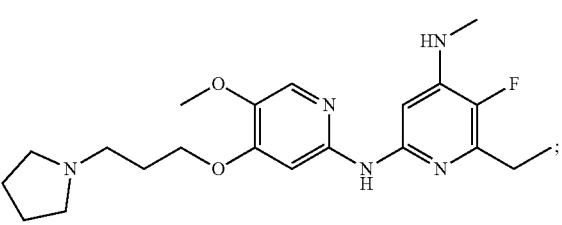
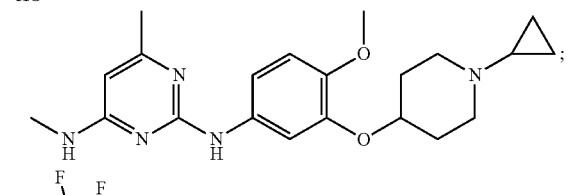
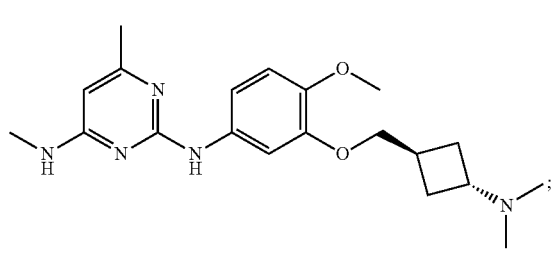
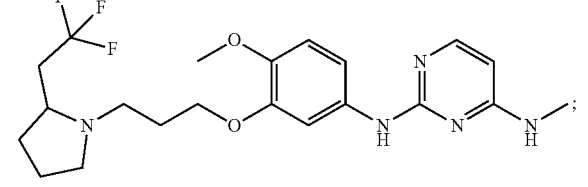

713
-continued
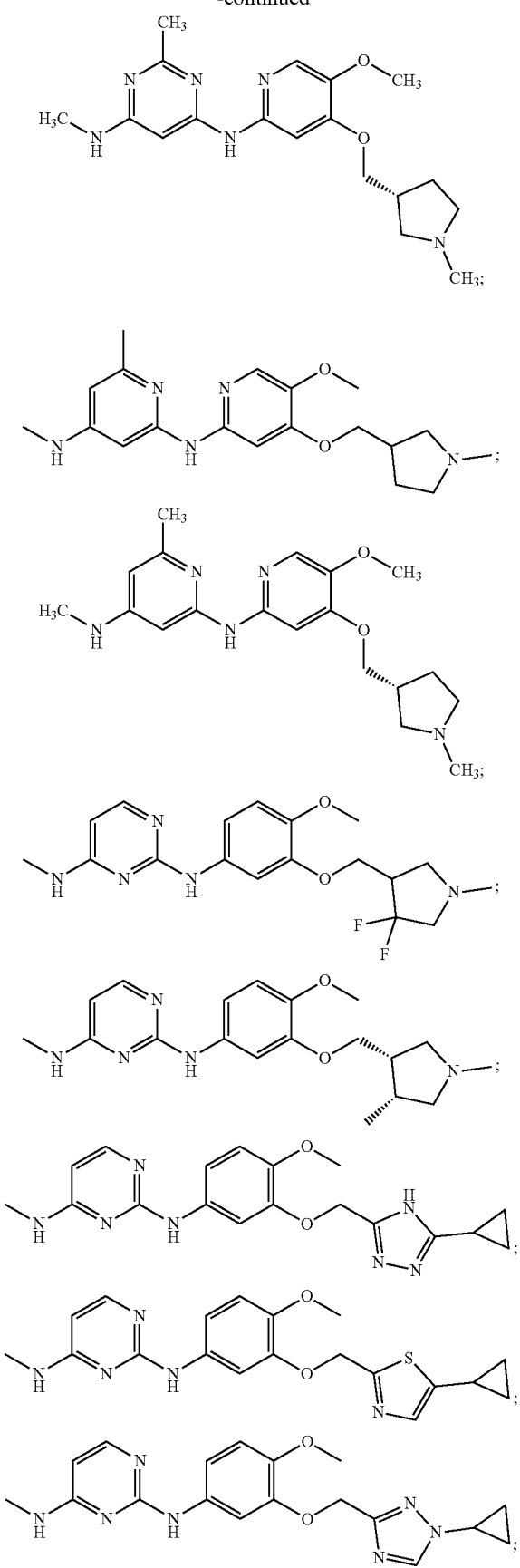
714
-continued
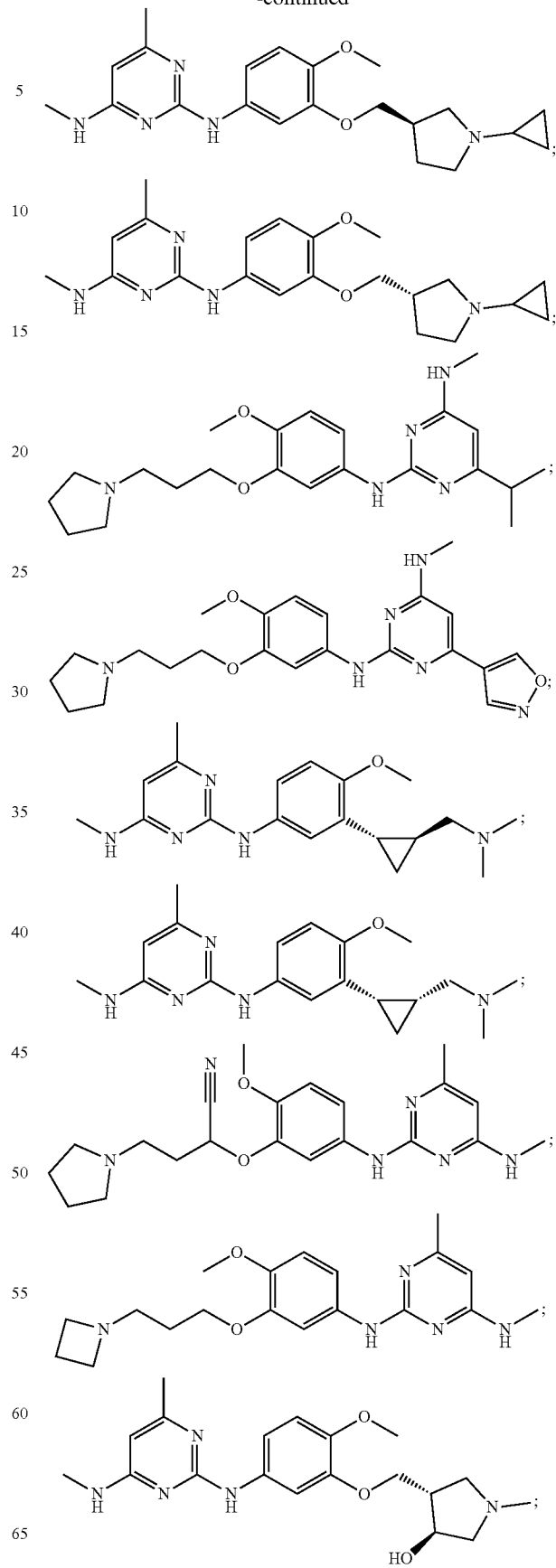

715
-continued
716
-continued
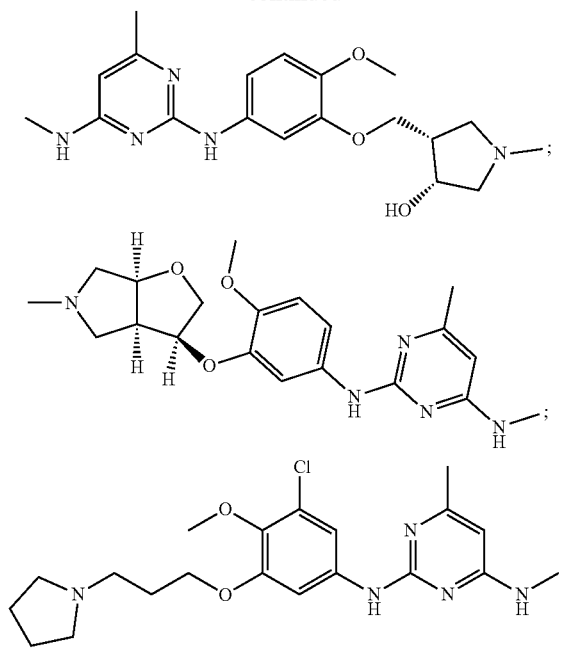
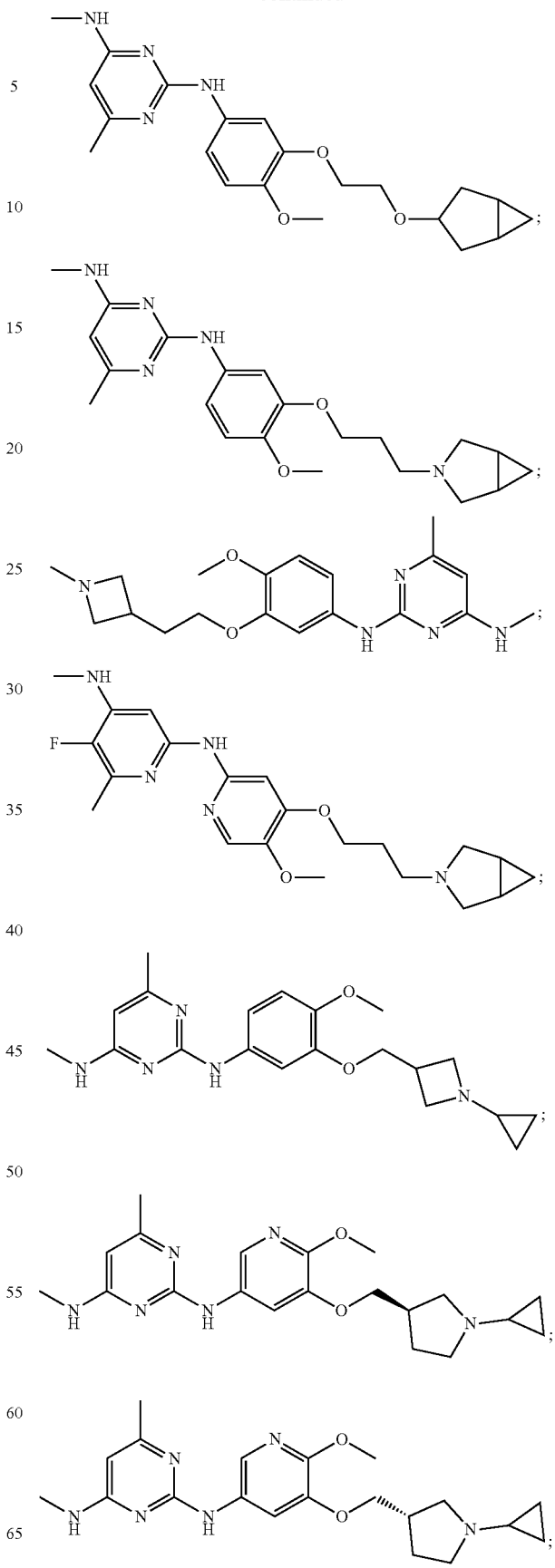

717
-continued
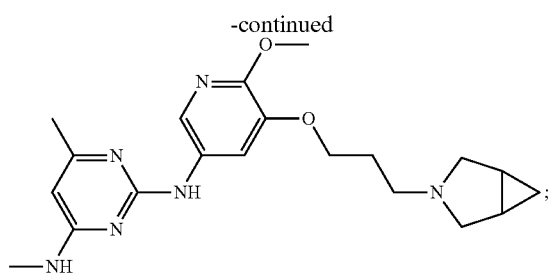
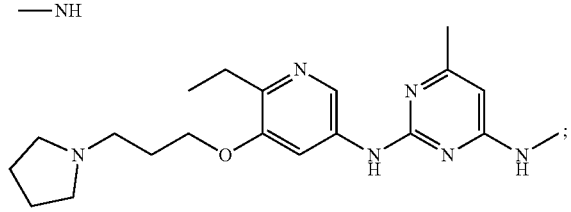
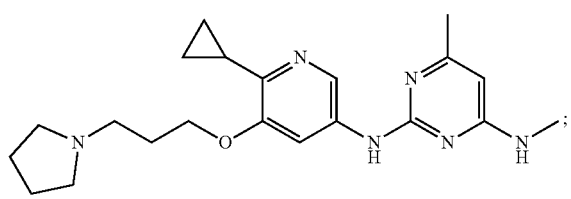
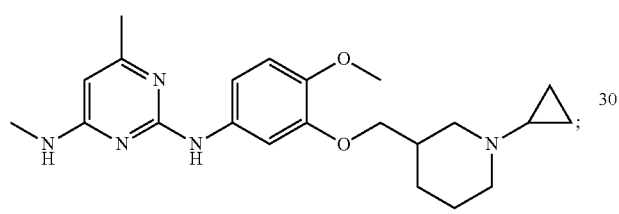
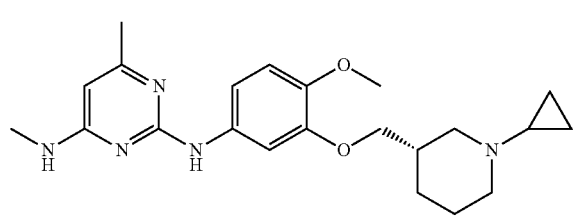
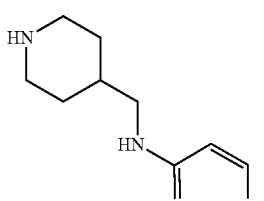
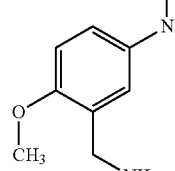
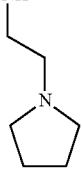
718
-continued
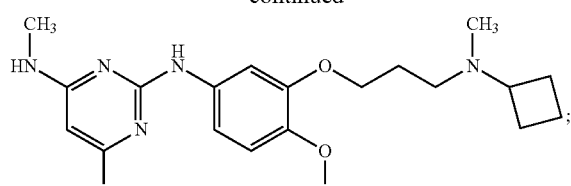
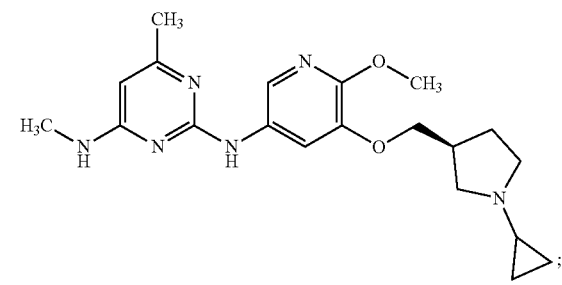
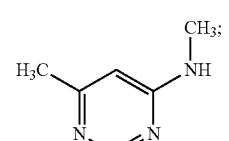
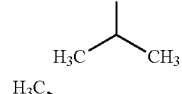
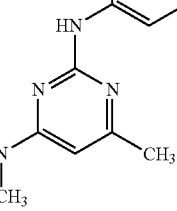
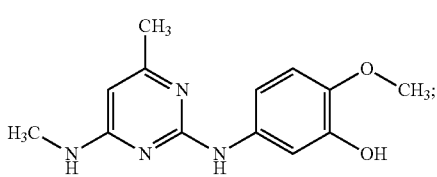

719
-continued
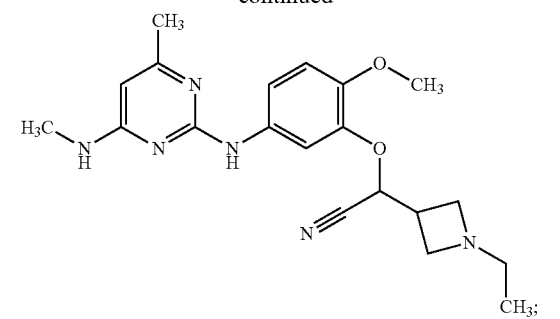
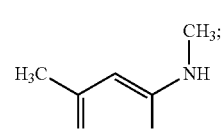
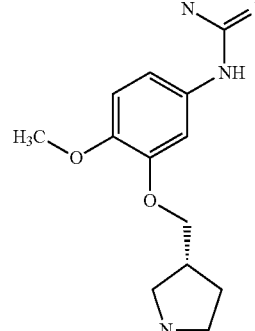
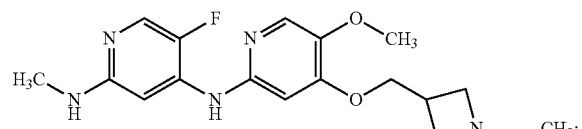
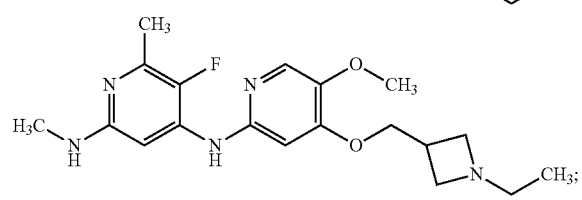
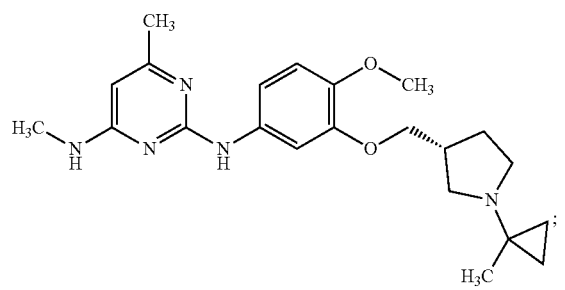
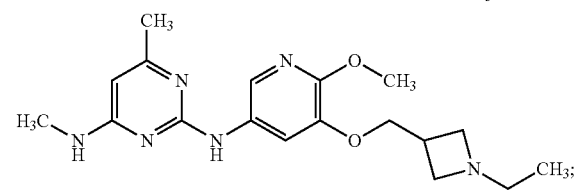
720
-continued
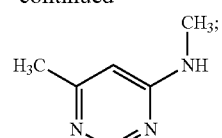
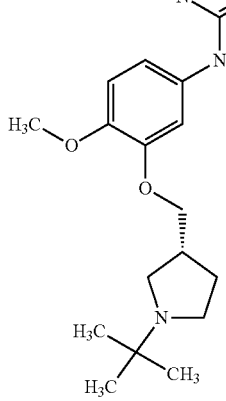
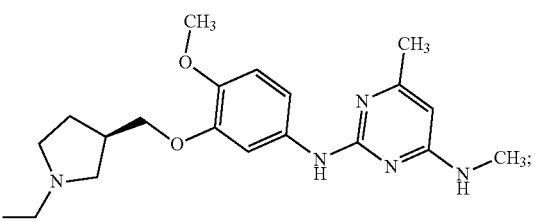
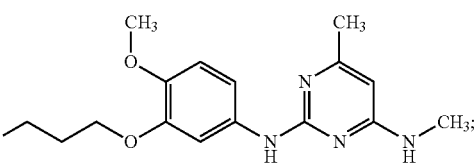
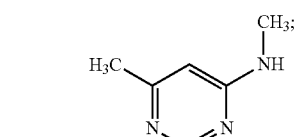
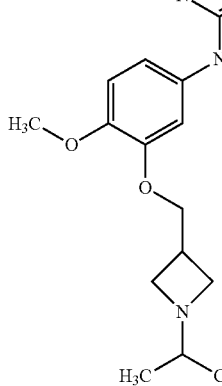

721
-continued
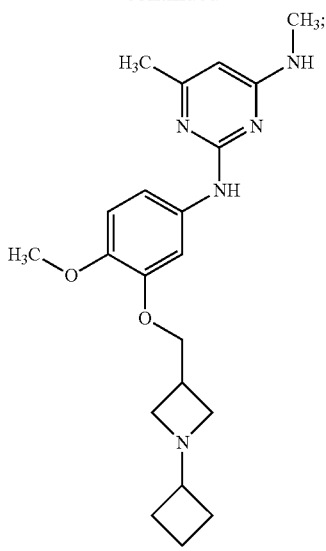
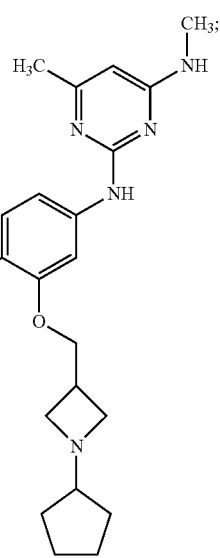
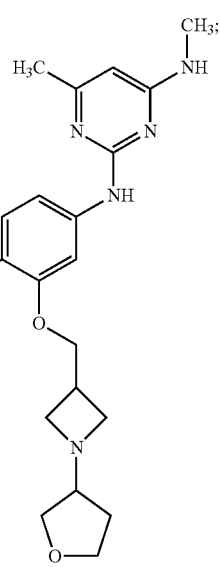
722
-continued
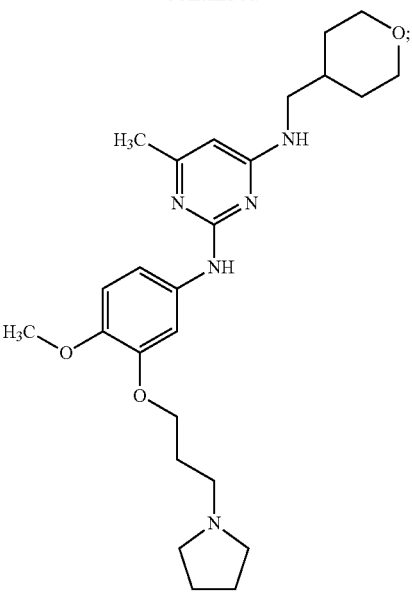
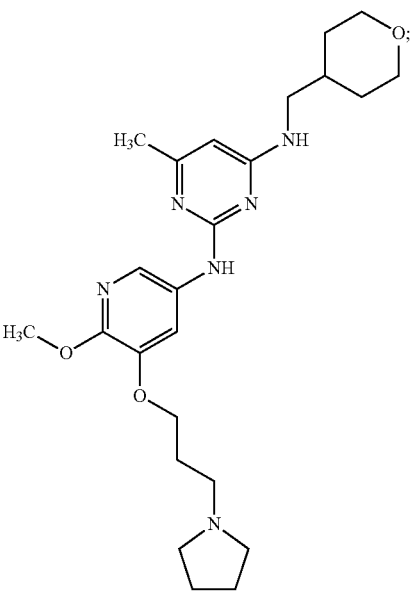

723
-continued
724
-continued
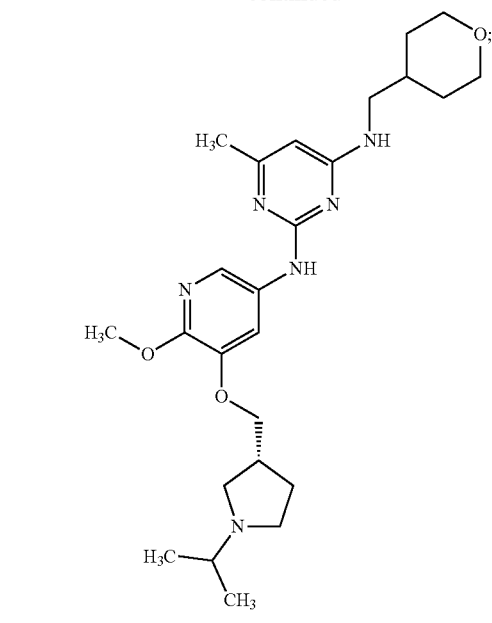
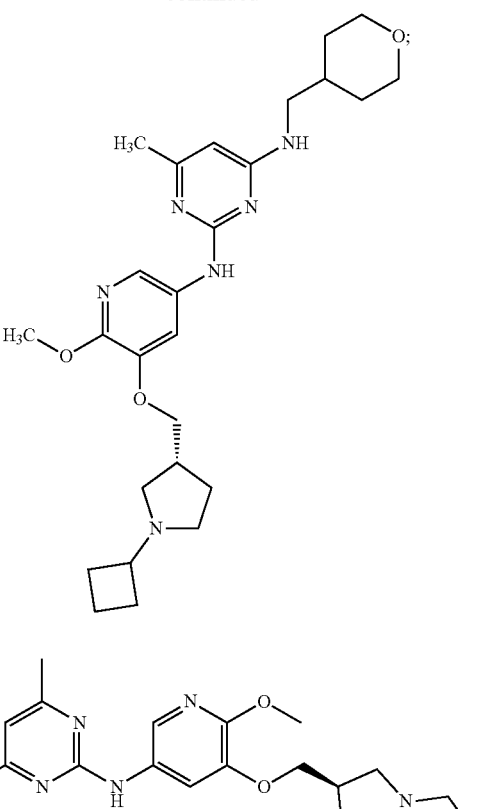
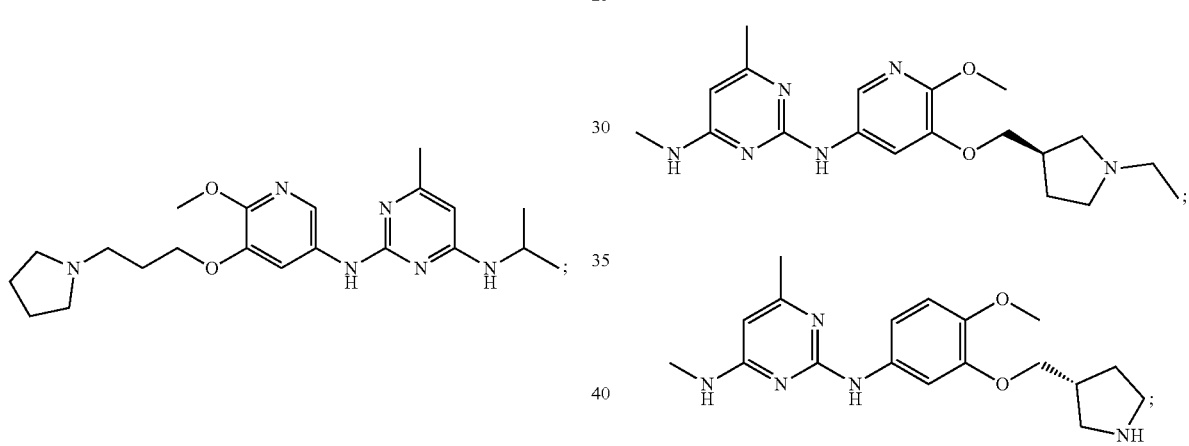
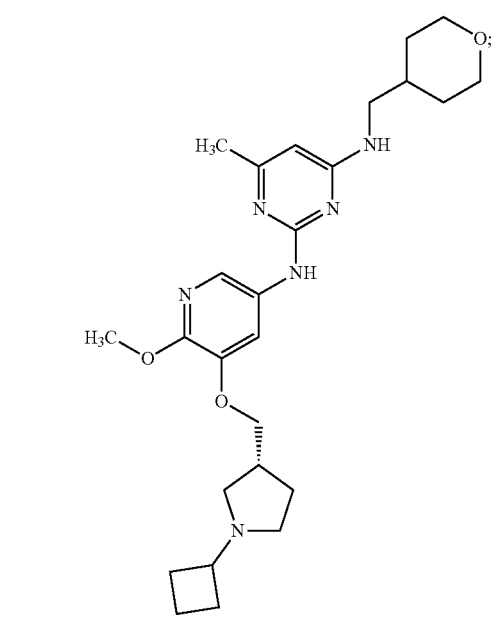
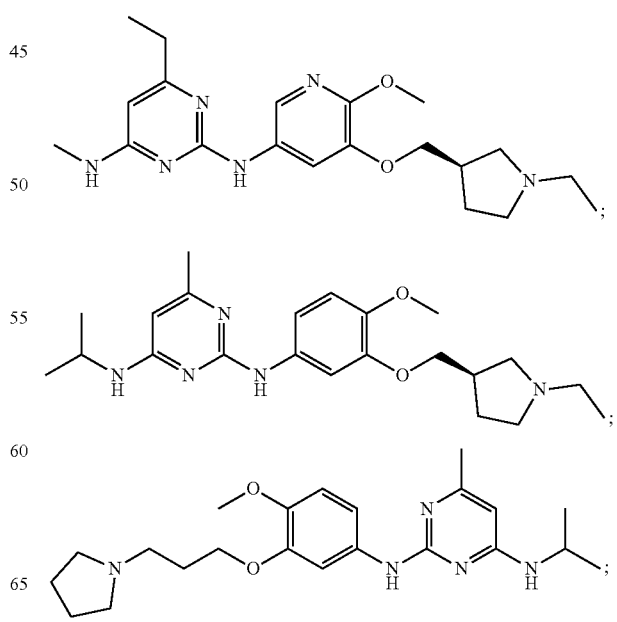

725
-continued
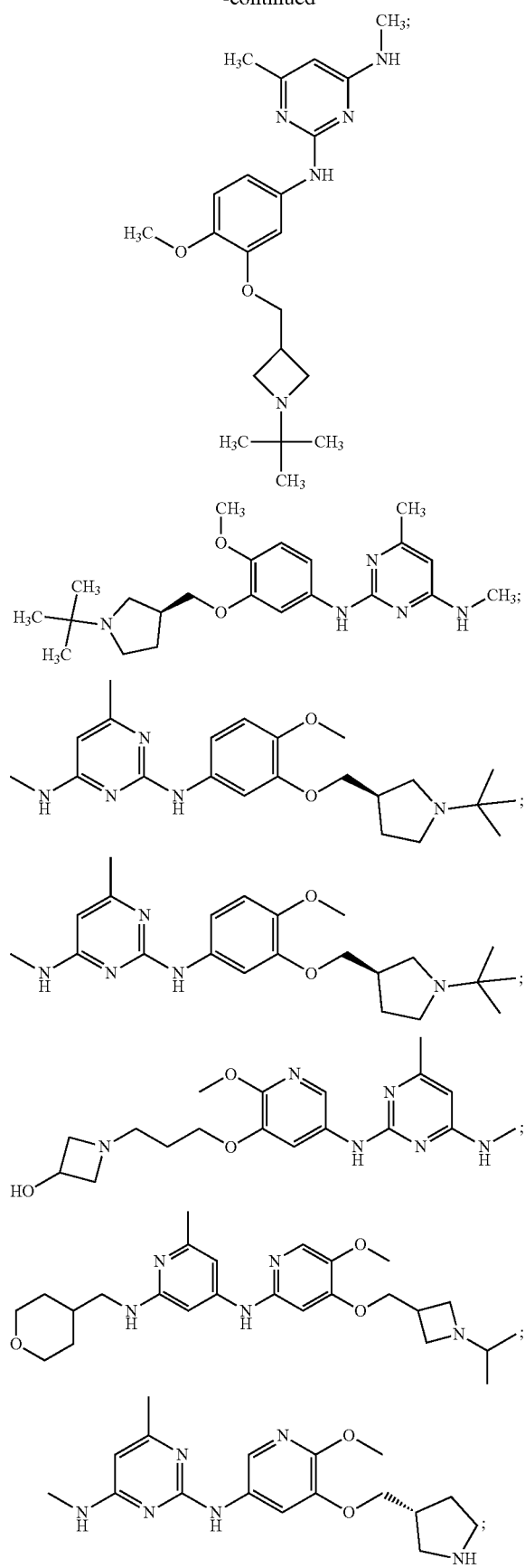
726
-continued
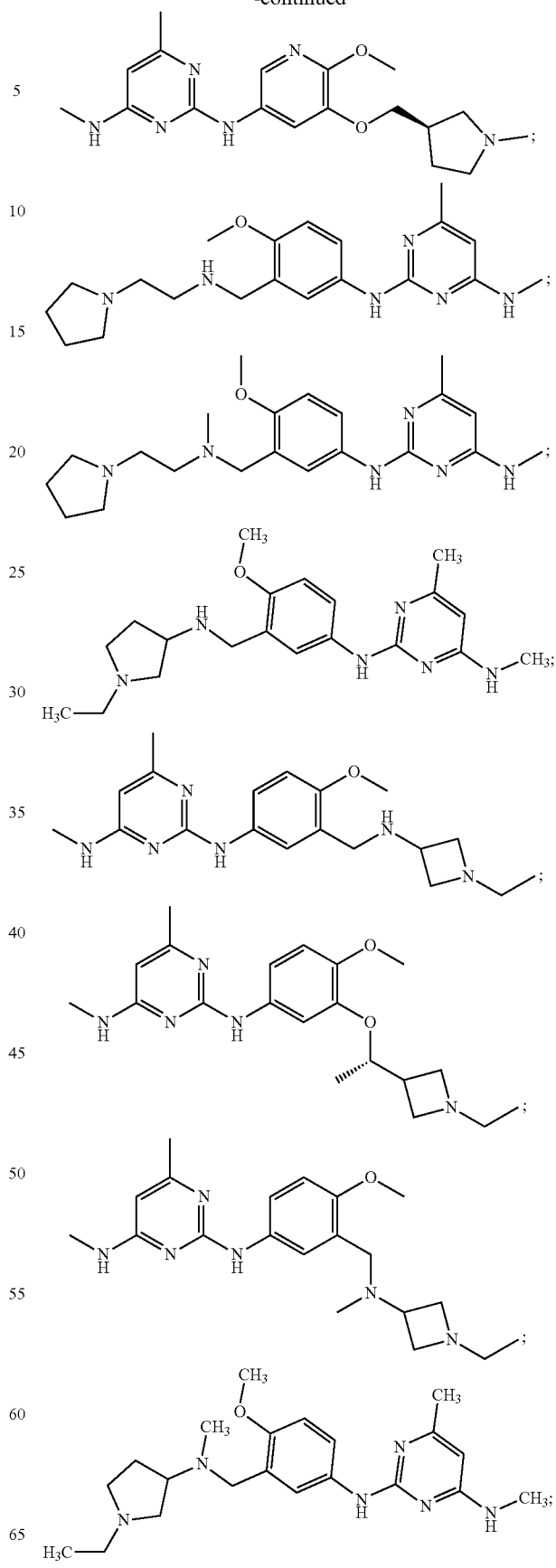

727
-continued
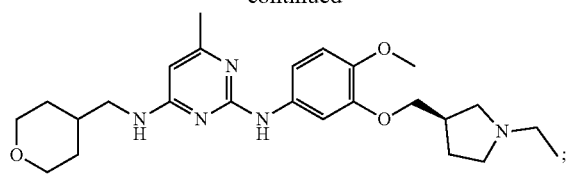
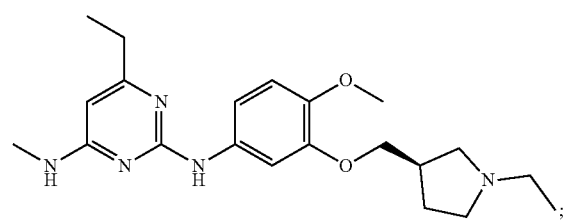
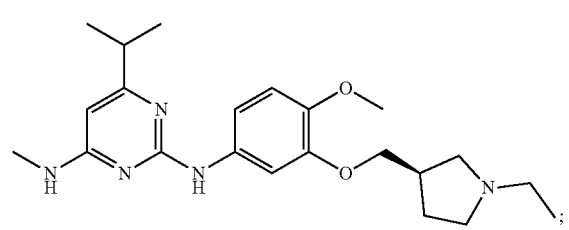
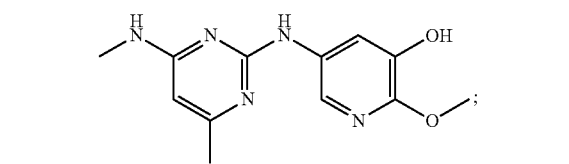
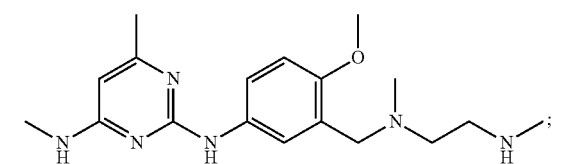
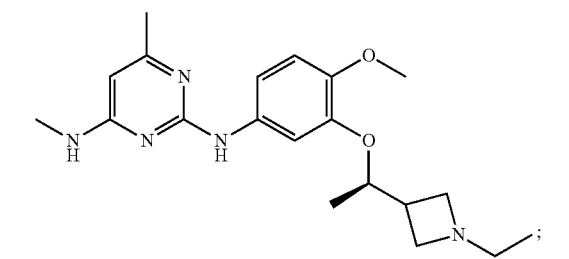
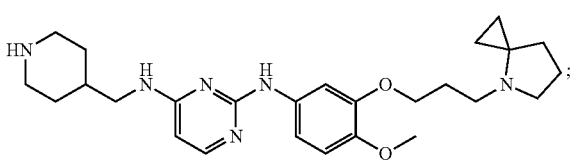
728
-continued
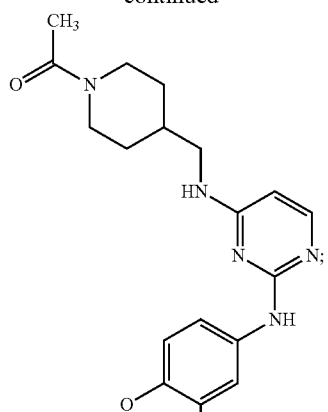
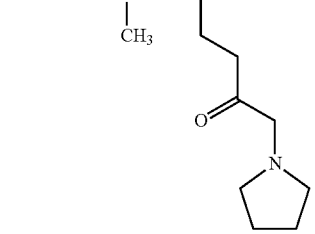
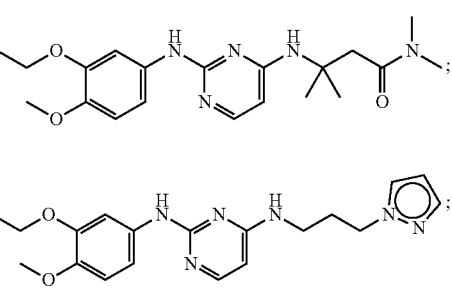
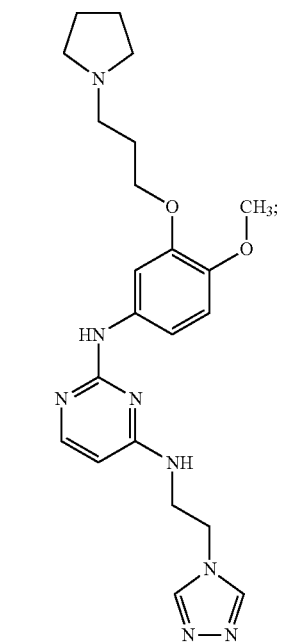

729
-continued
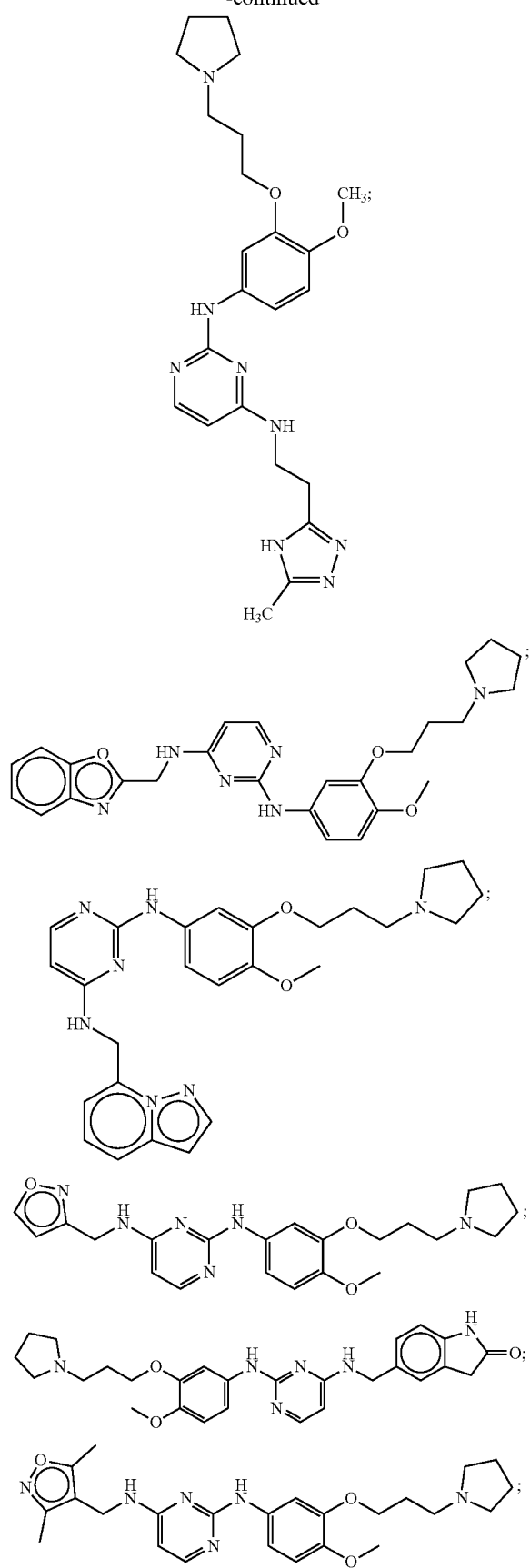
730
-continued
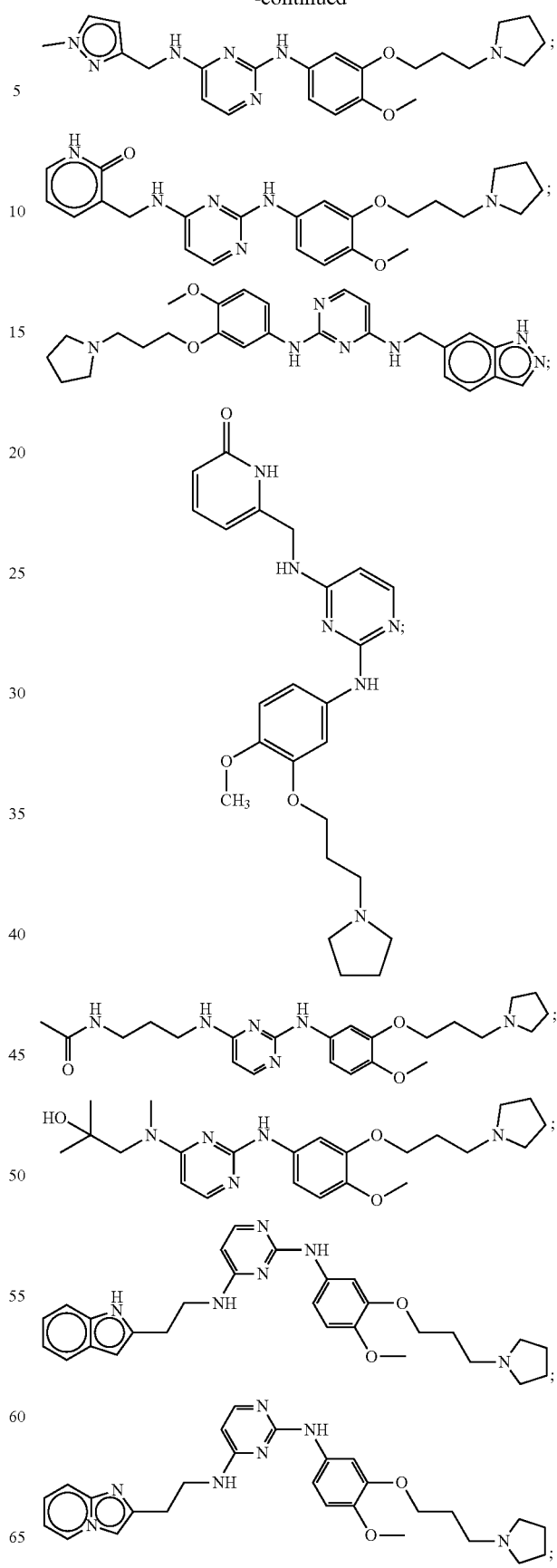

731
-continued
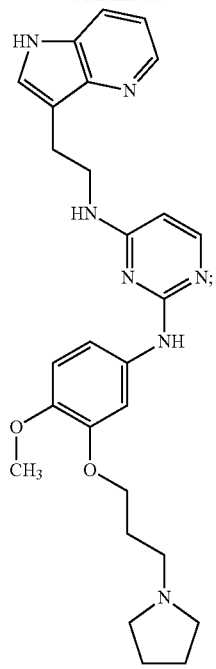
732
-continued
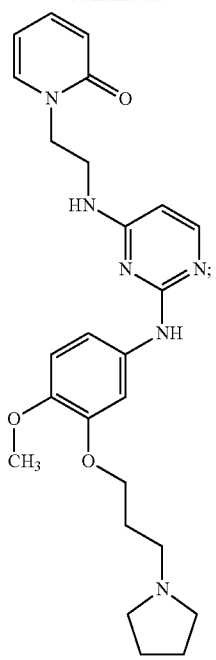
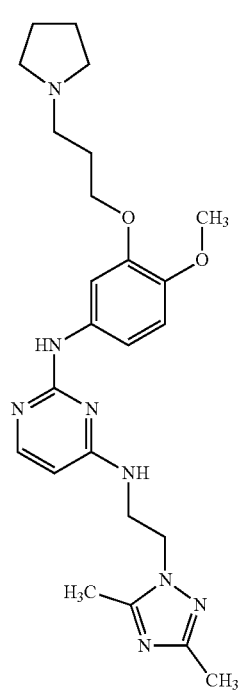
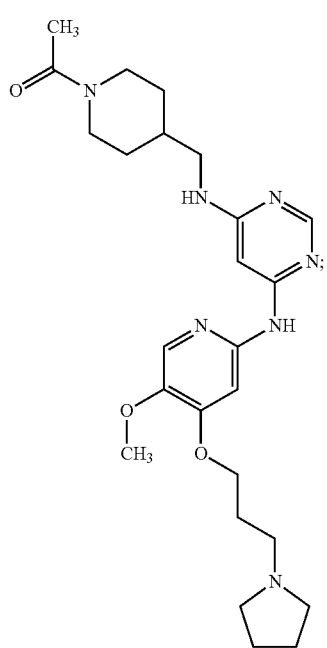

733
-continued
734
-continued
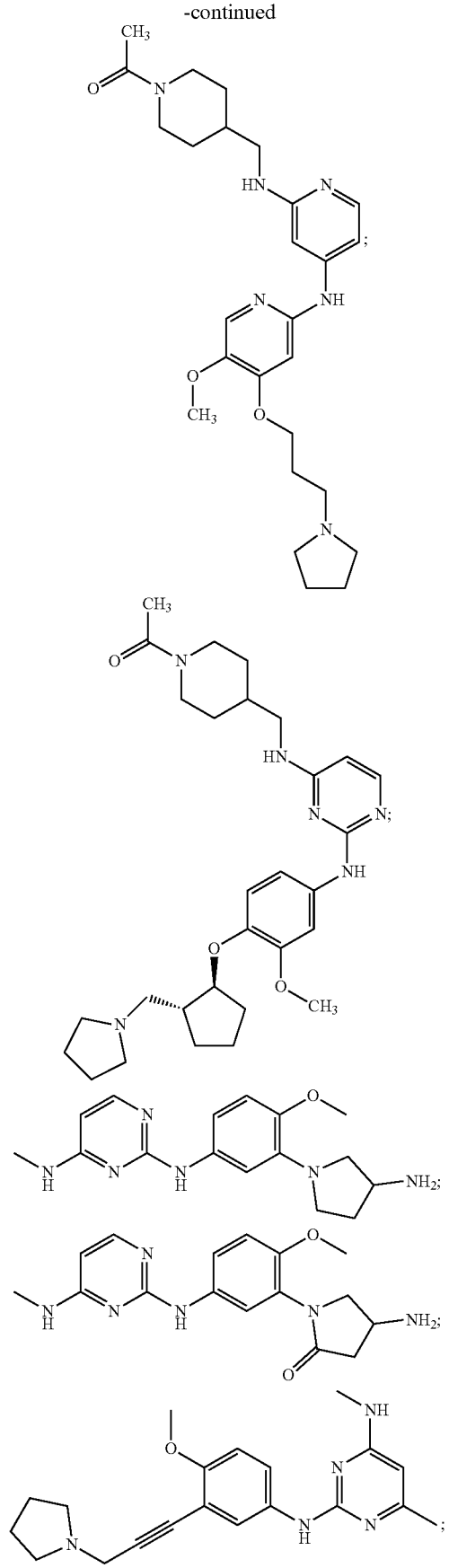
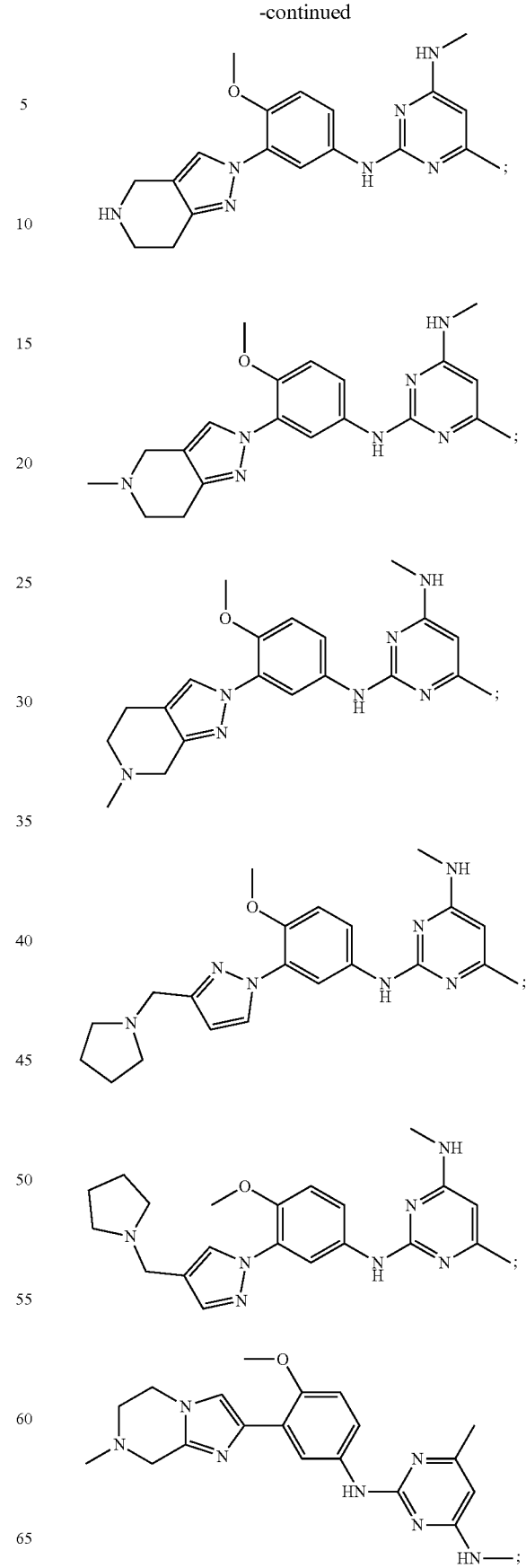

-continued

737
-continued
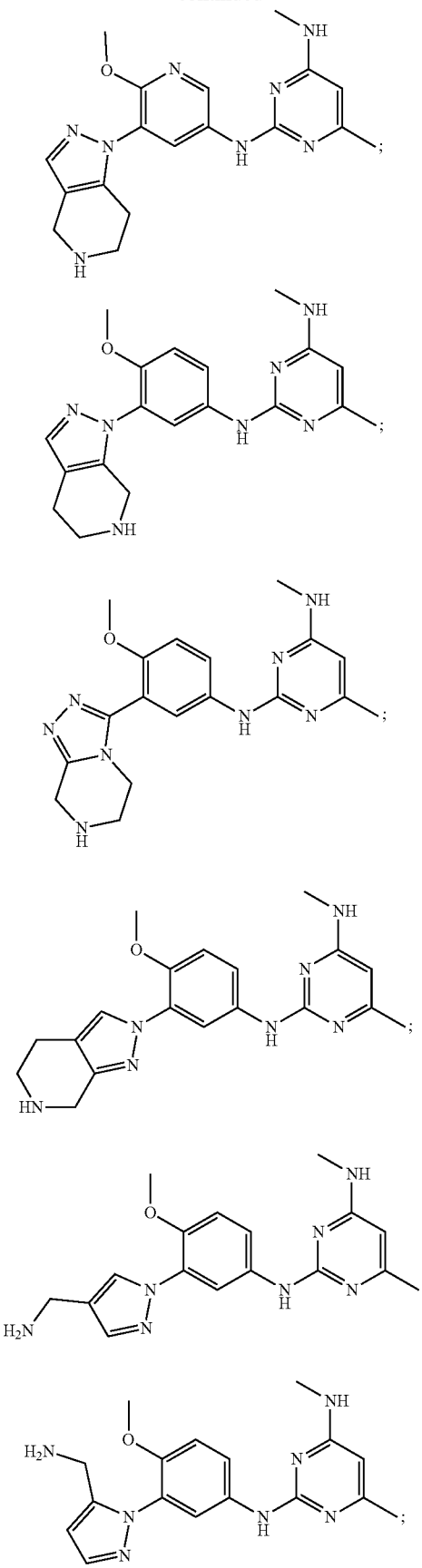
738
-continued
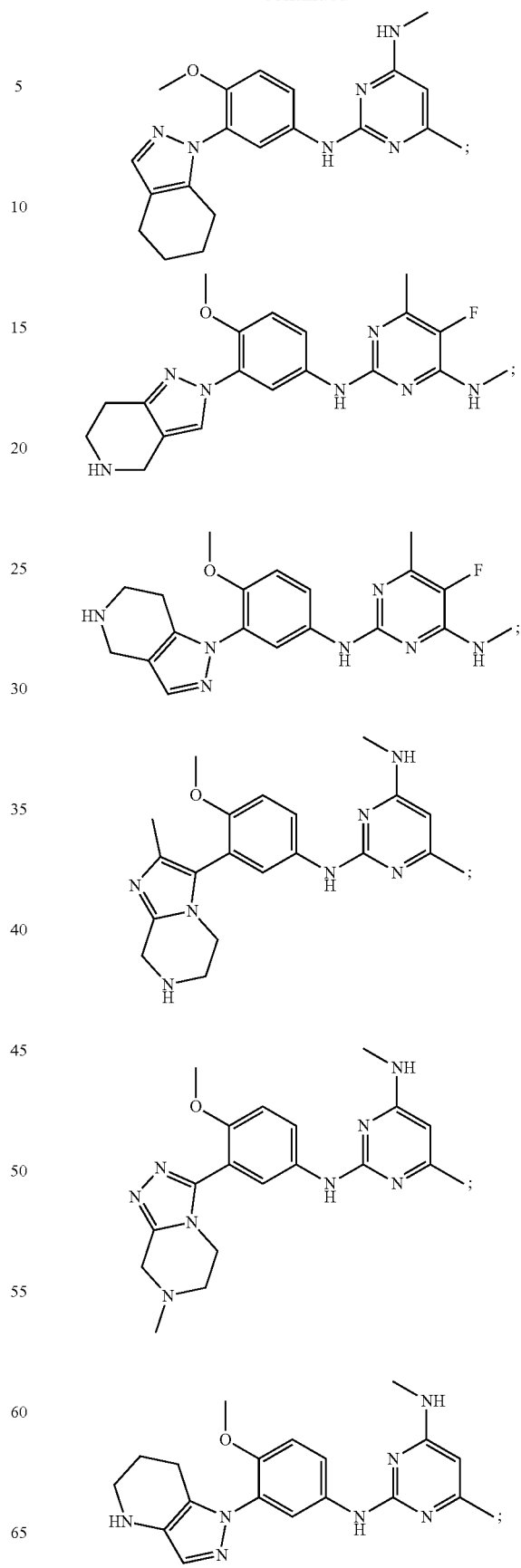

739
-continued
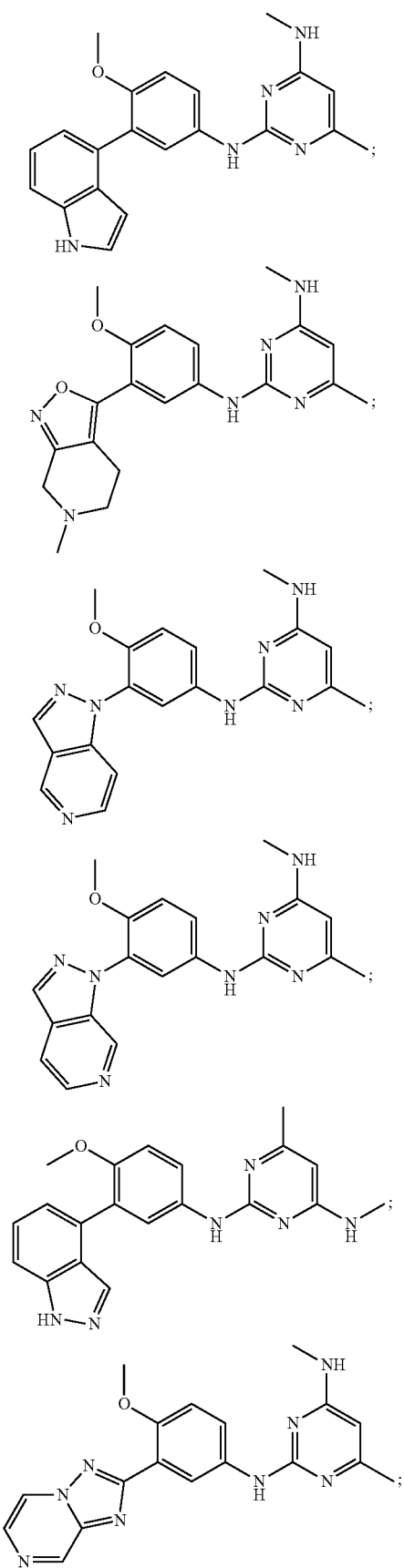
740
-continued
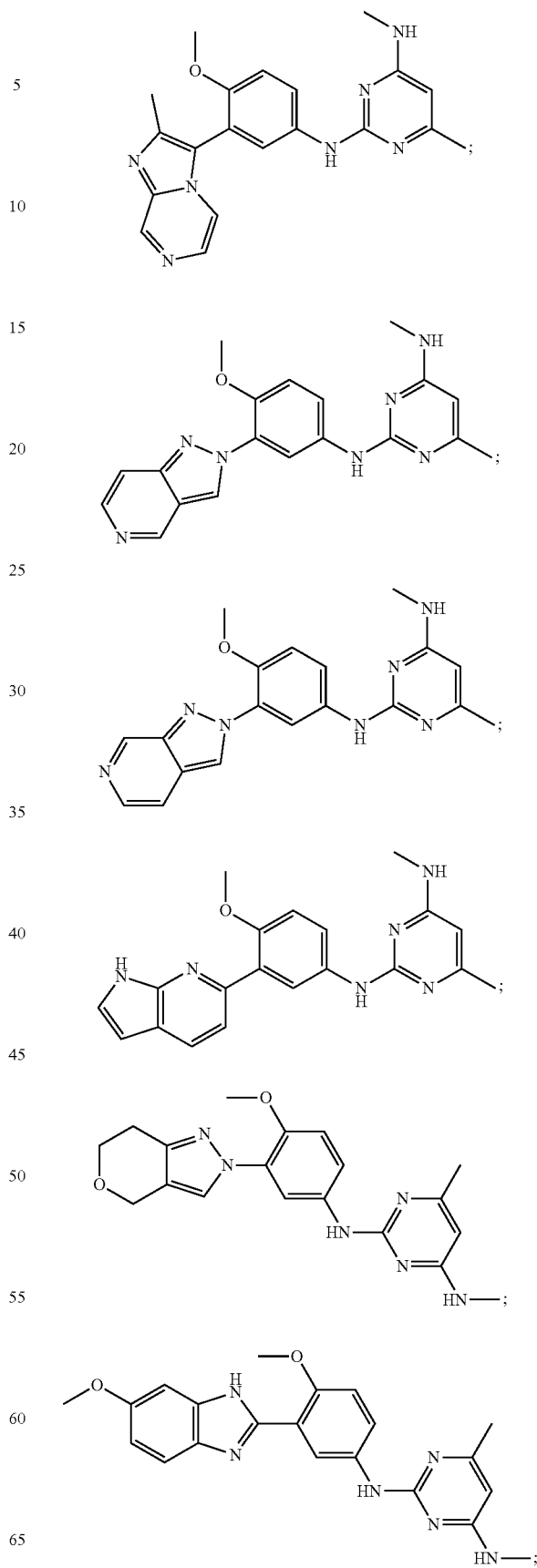

-continued
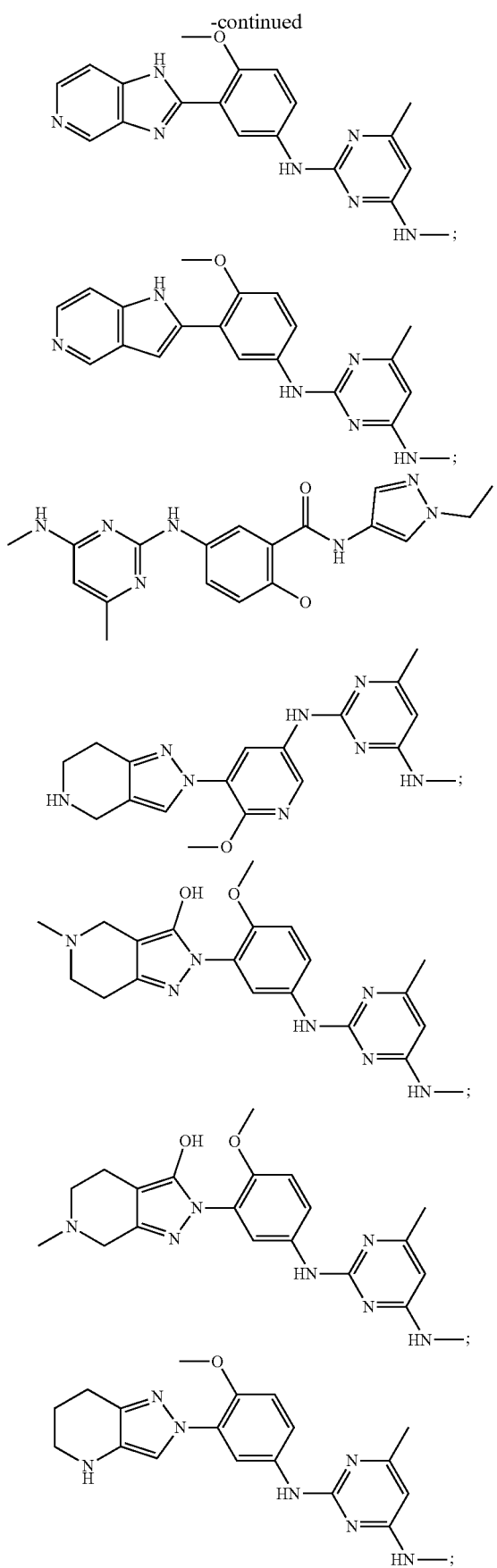
-continued
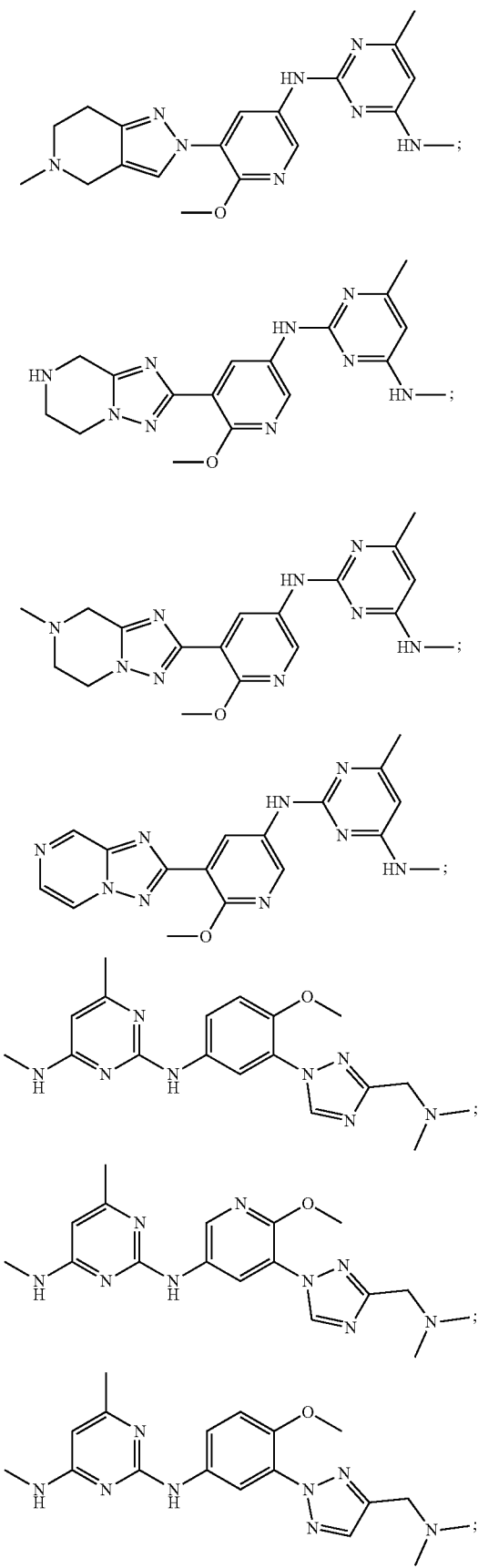

743
-continued
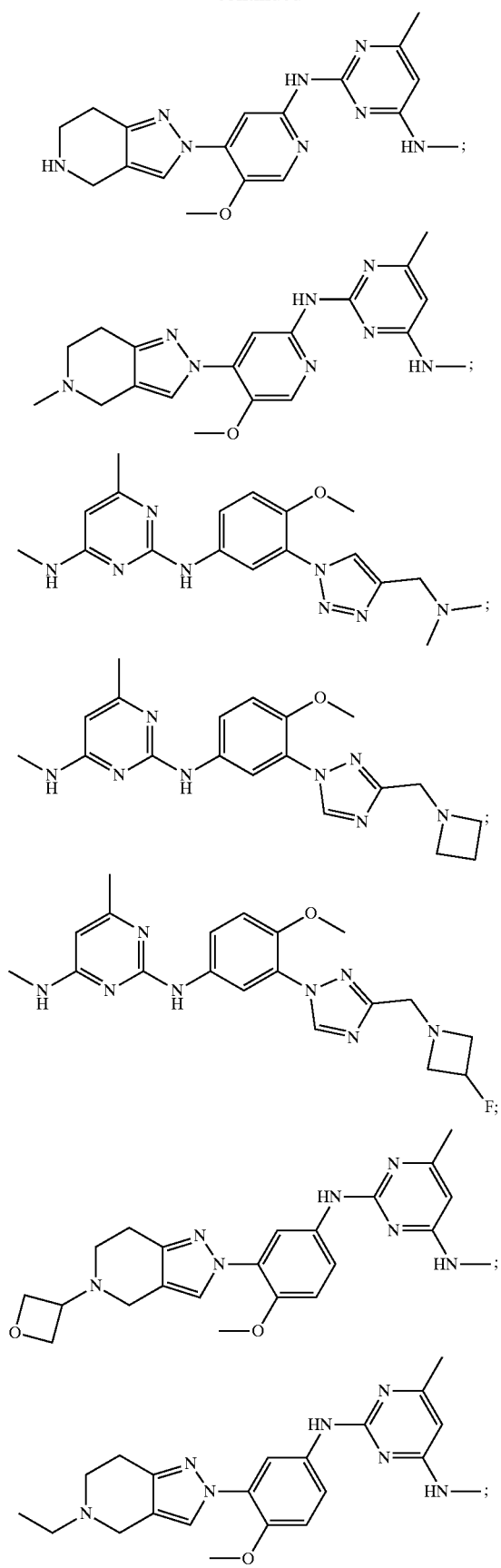
744
-continued

745
-continued
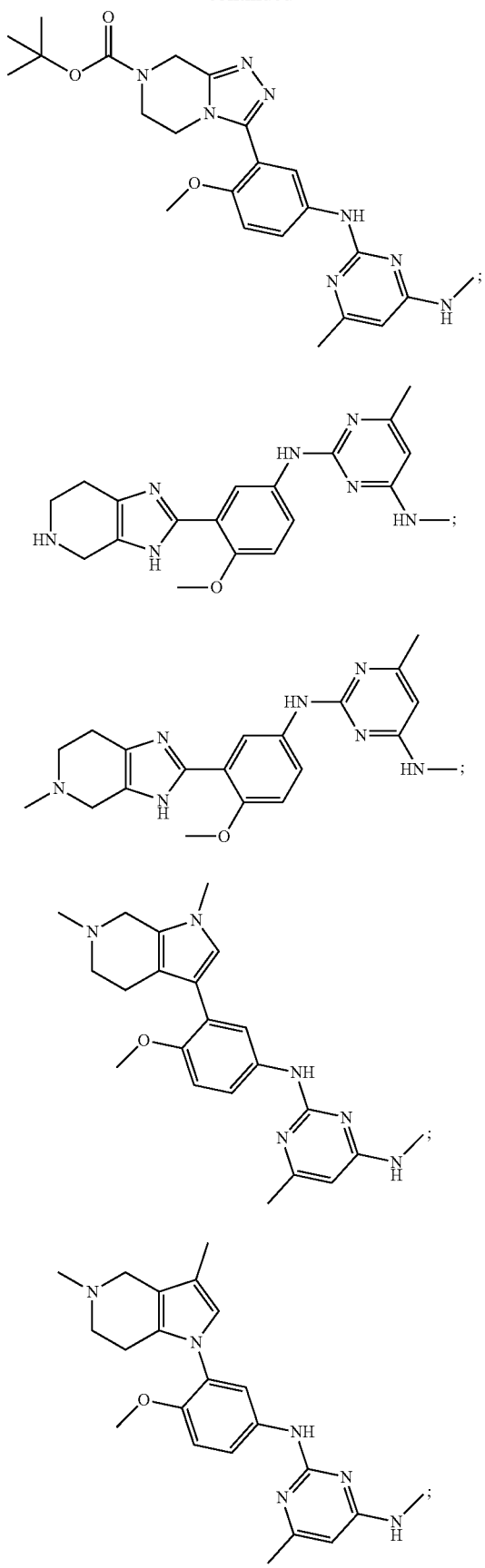
746
-continued
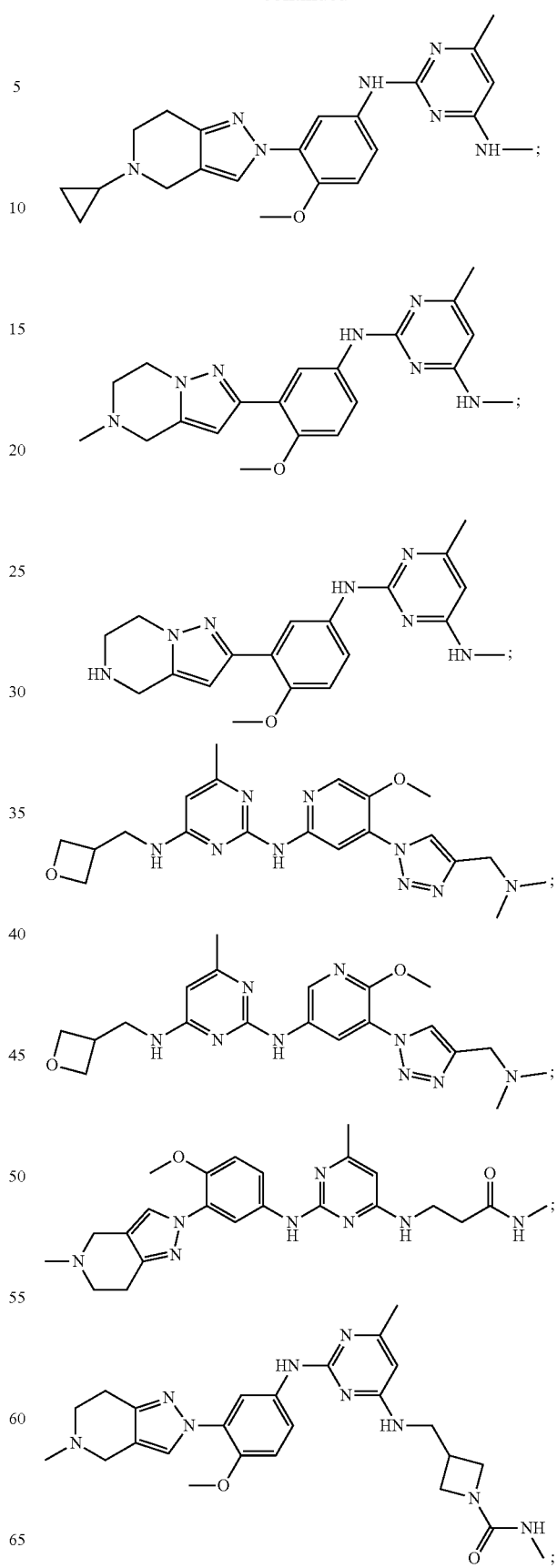

747
-continued
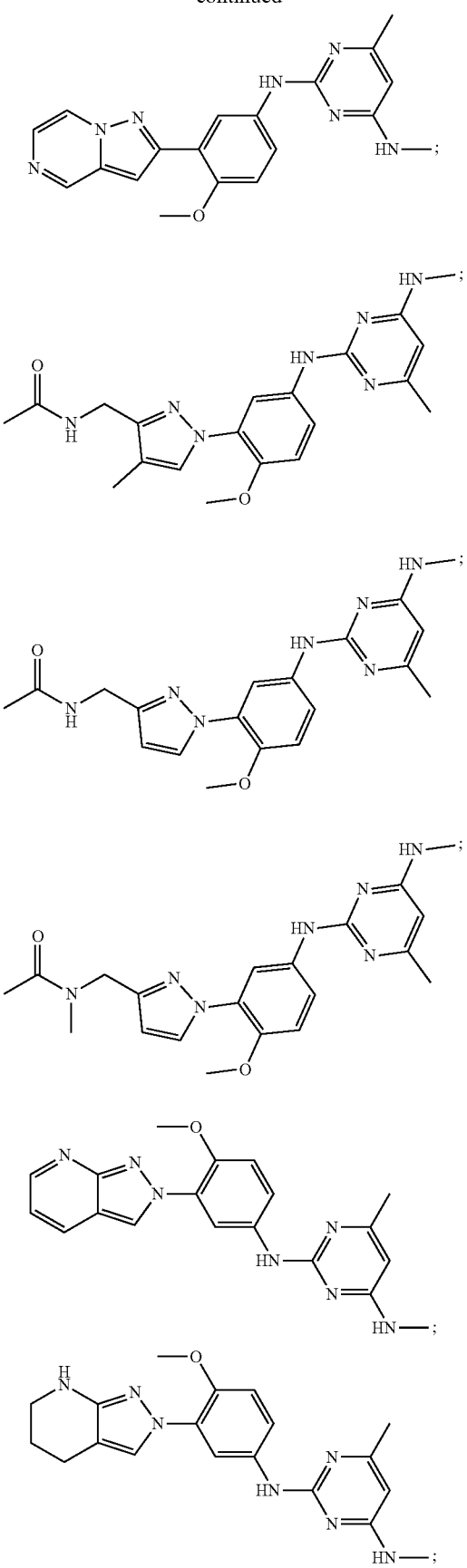
748
-continued
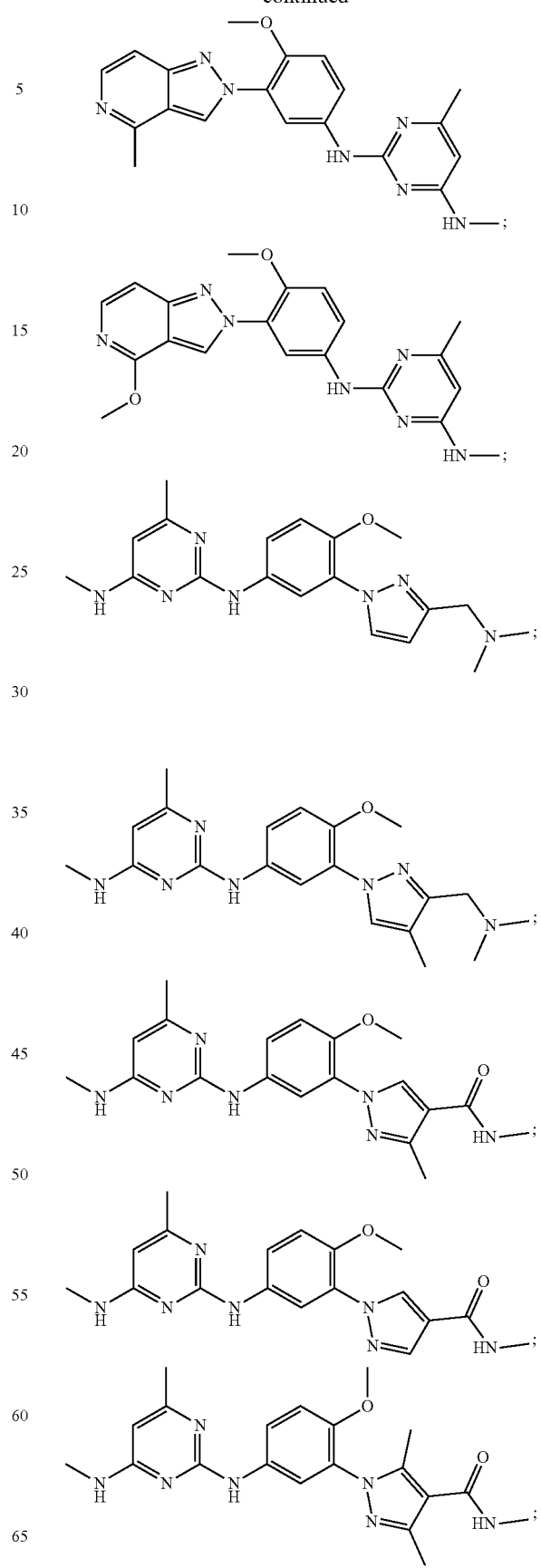

749
-continued
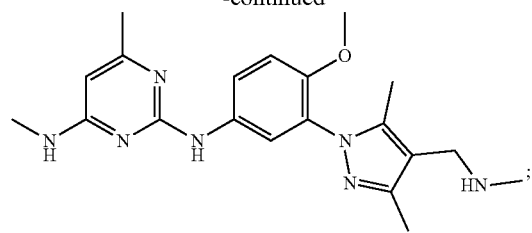
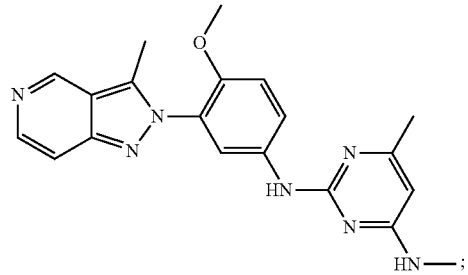
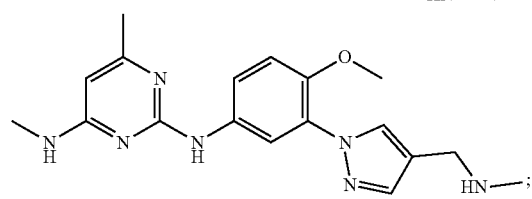
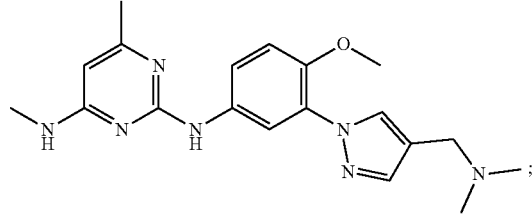
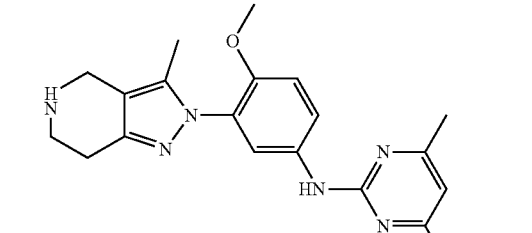
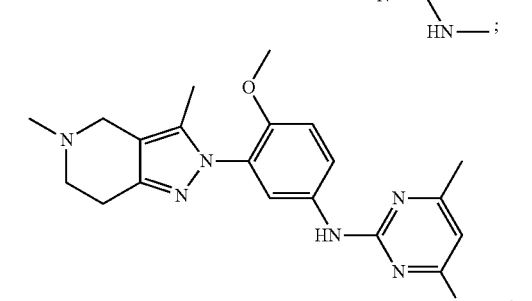
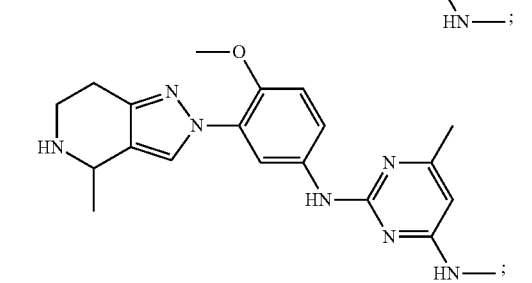
750
-continued
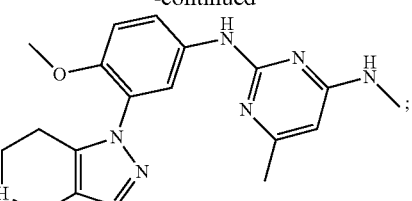
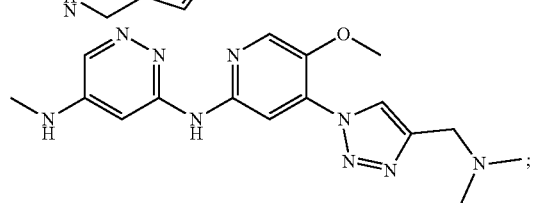
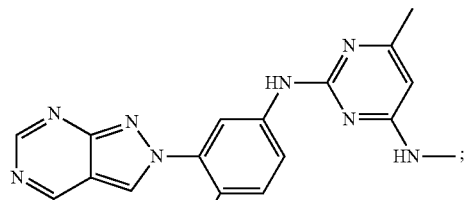
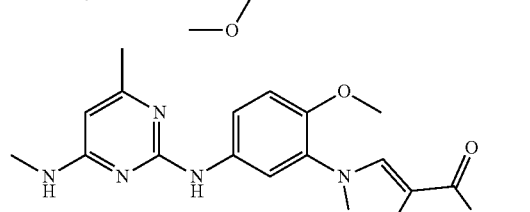
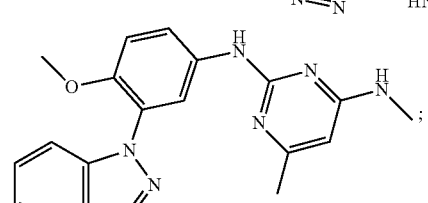
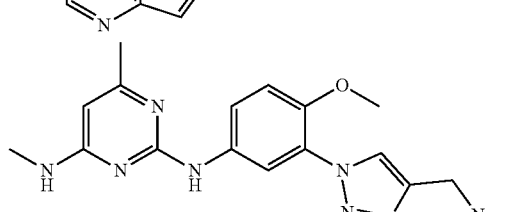
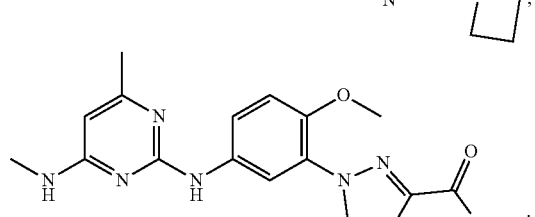
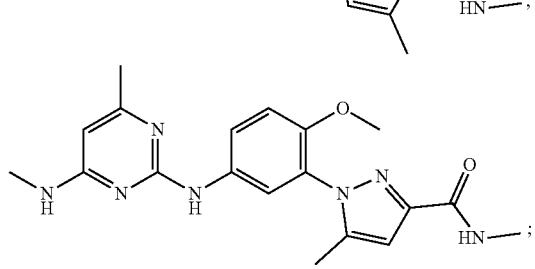

-continued
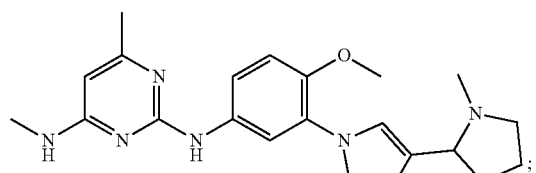
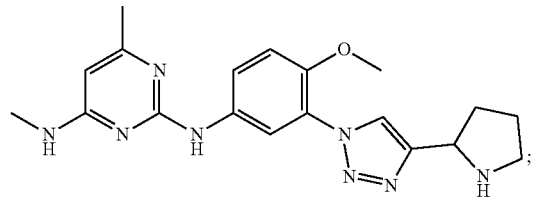
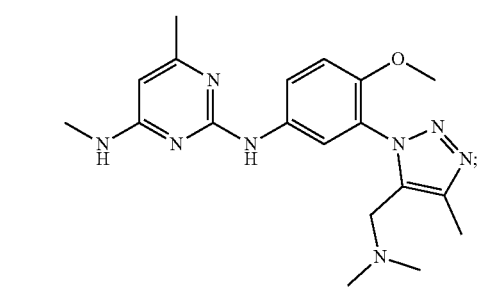
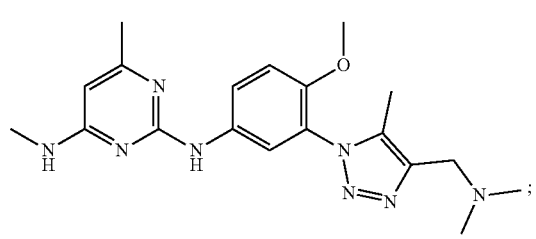
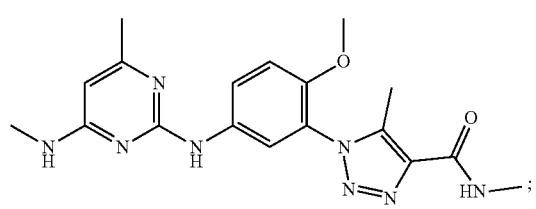
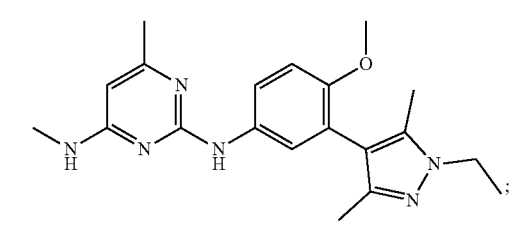
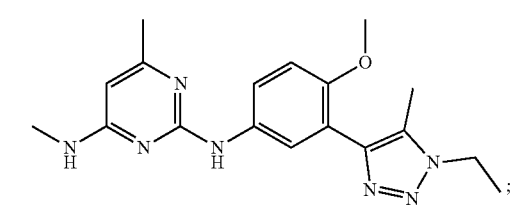
-continued
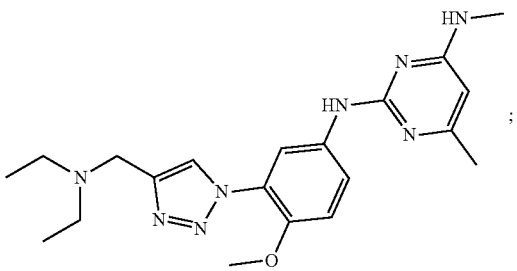
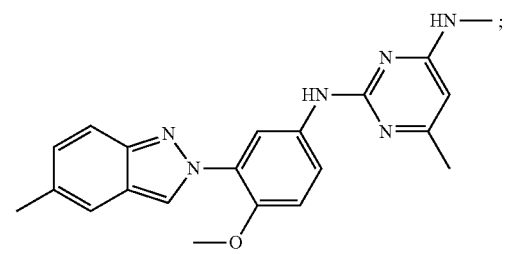
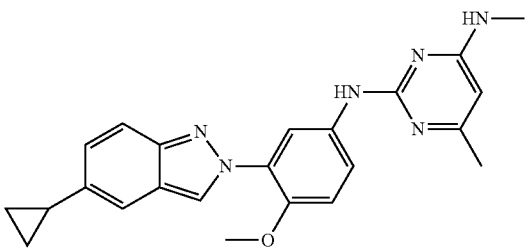
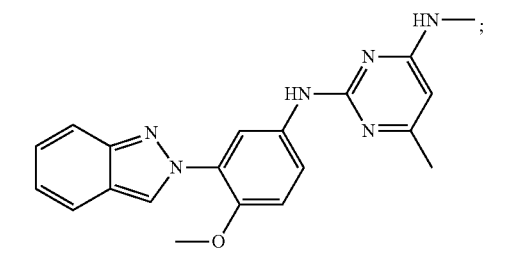
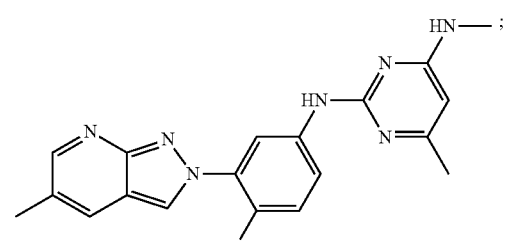
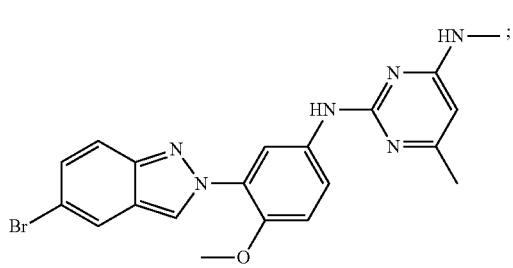

753
-continued
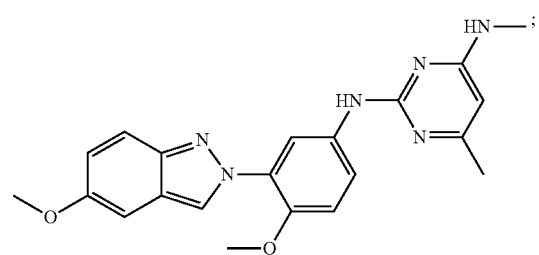
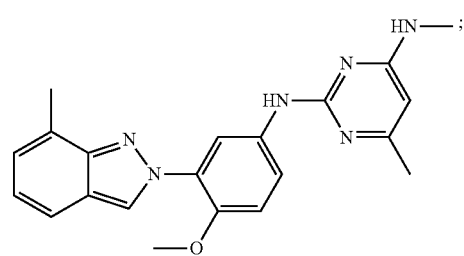
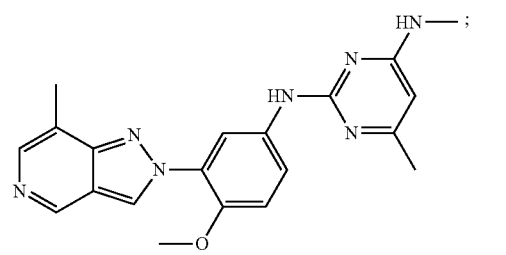
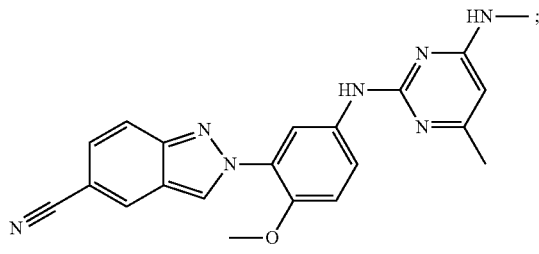
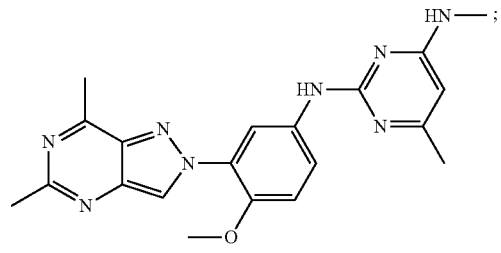
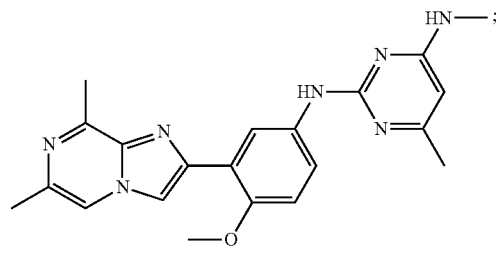
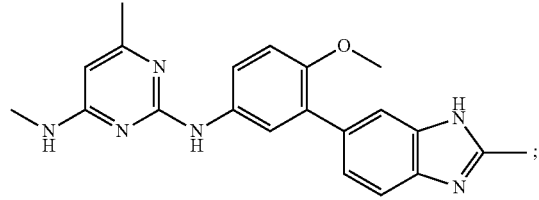
754
-continued
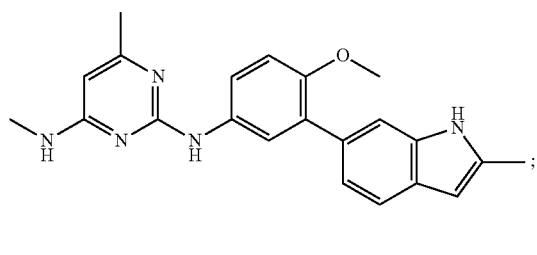
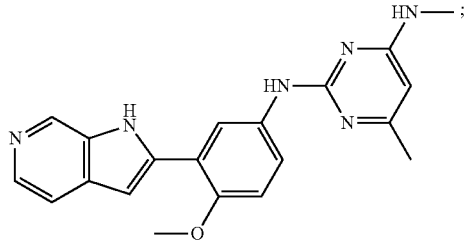
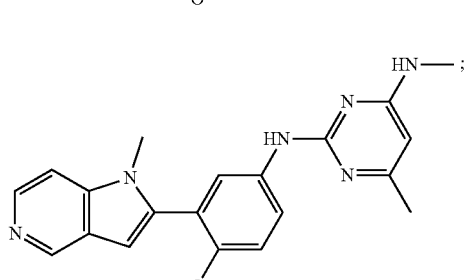
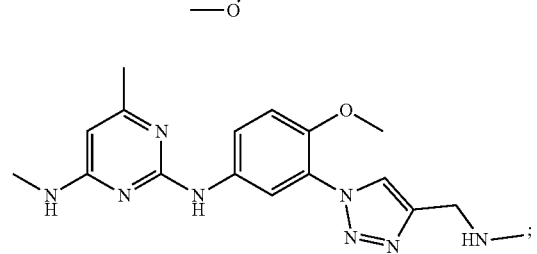
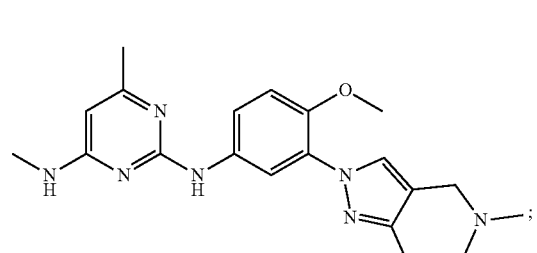
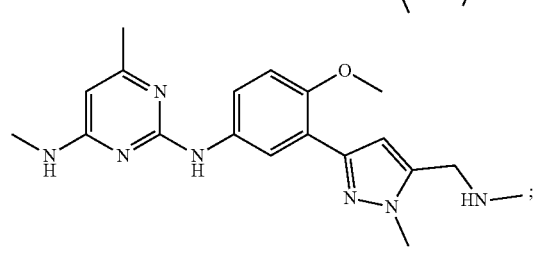
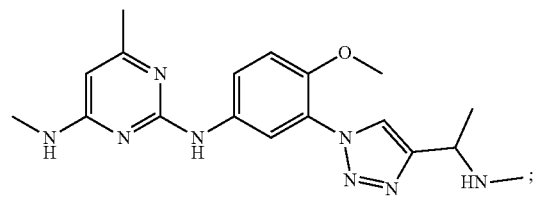

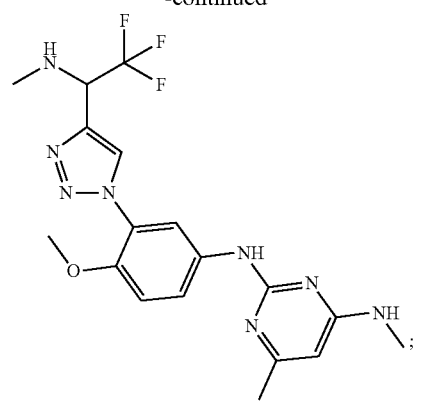
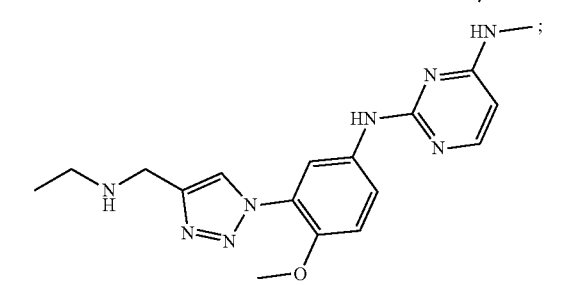
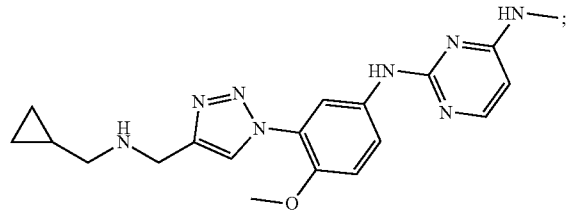
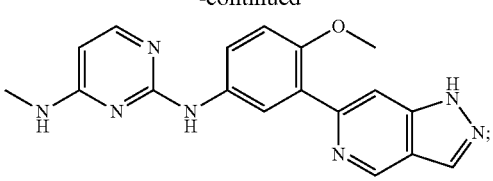
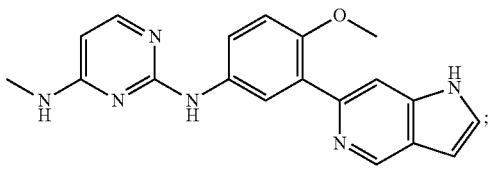
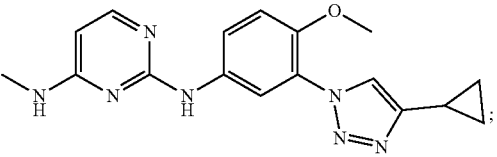
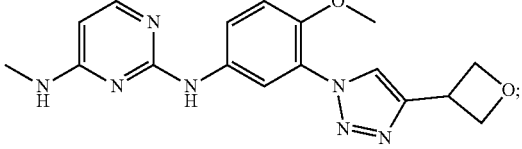
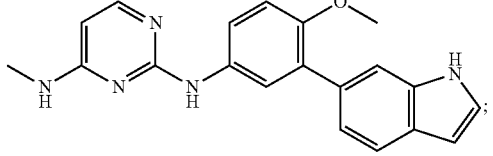
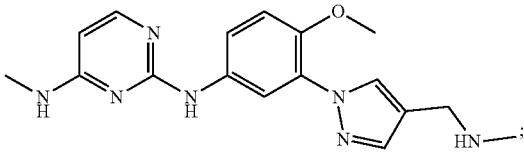
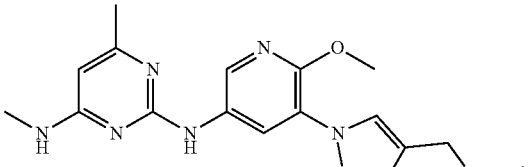
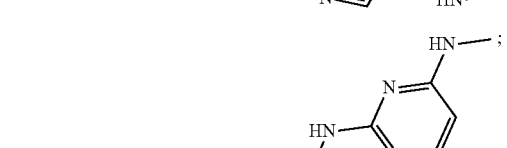
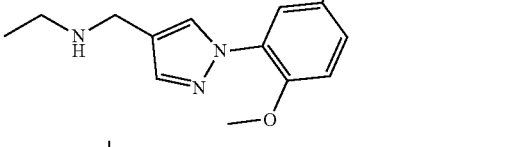
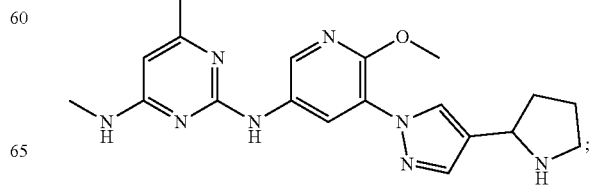

757
-continued
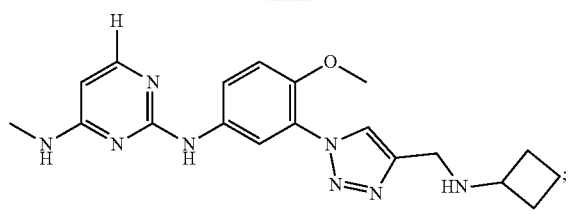
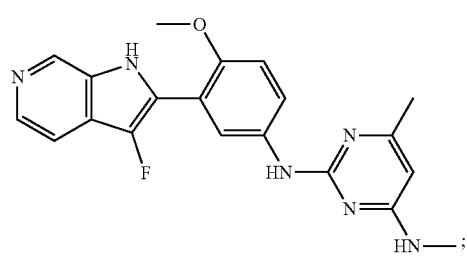
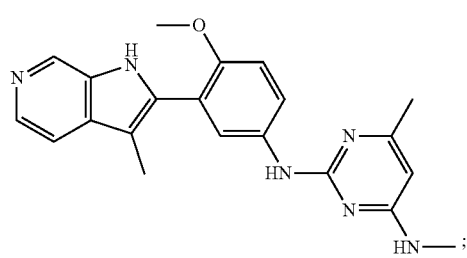
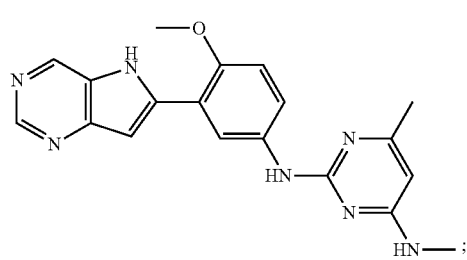
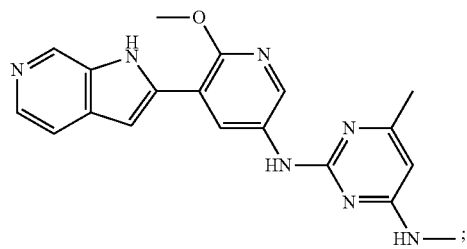
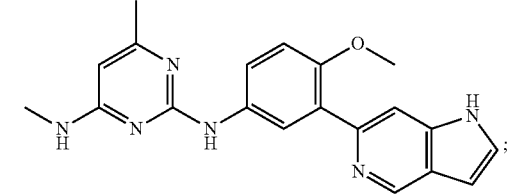
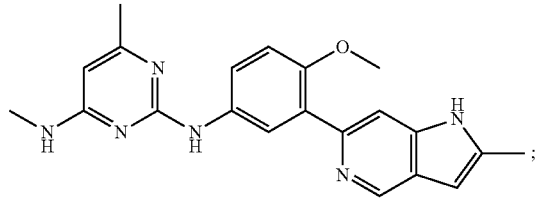
758
-continued
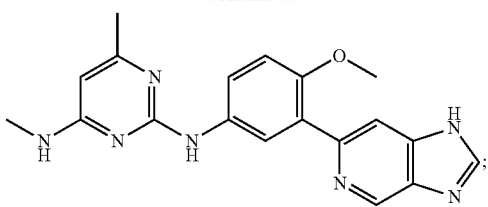
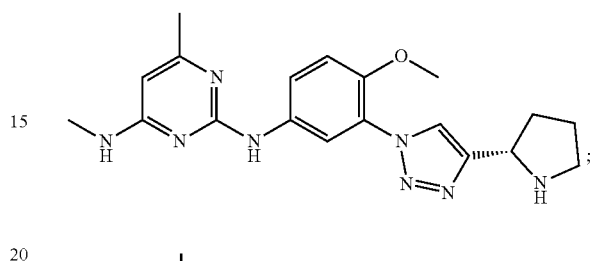
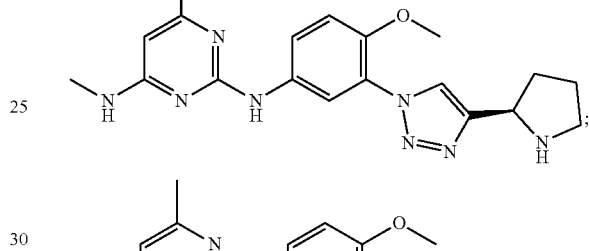
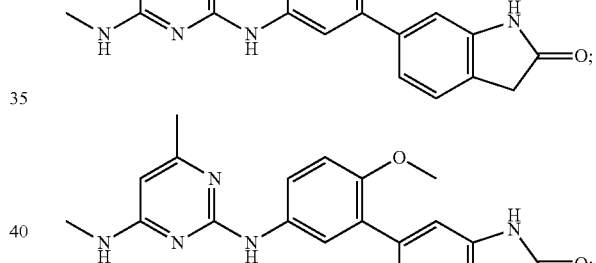
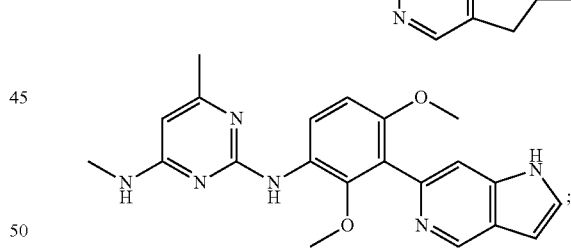
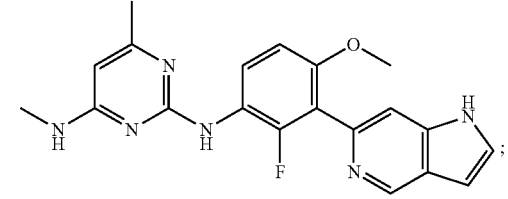
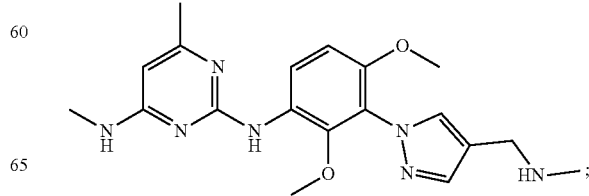

759
-continued
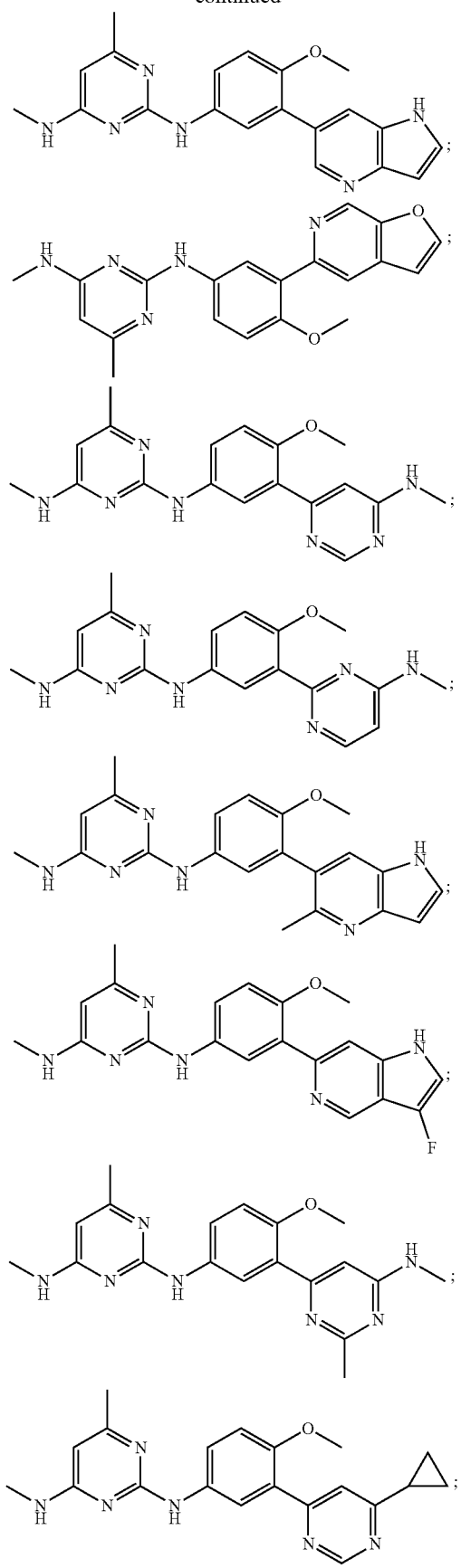
760
-continued
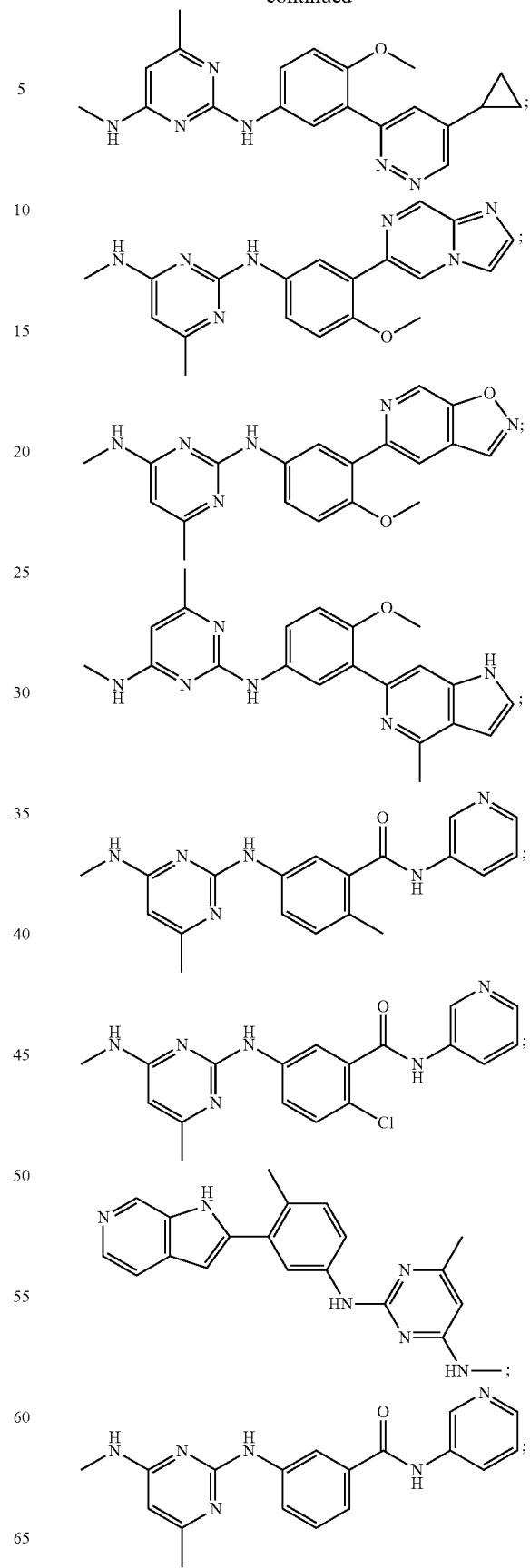

761
-continued
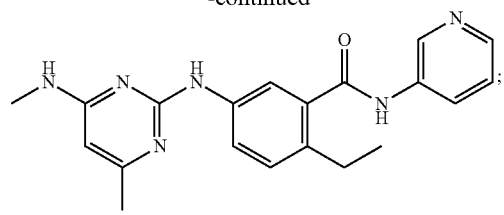
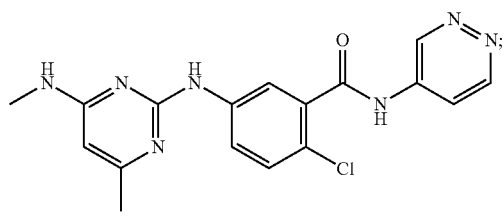
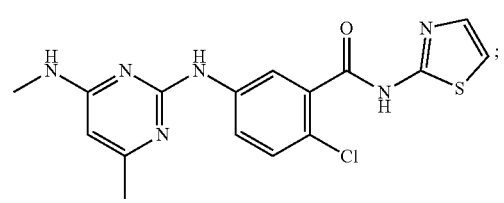
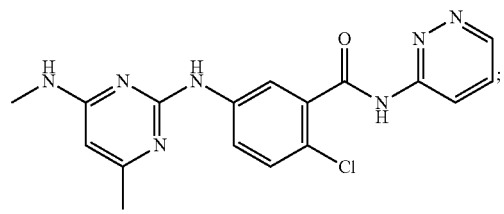
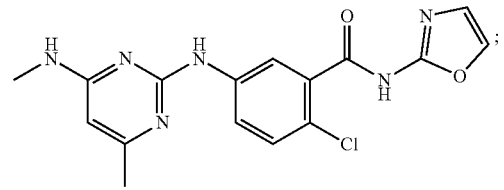
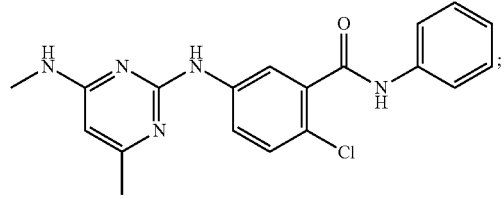
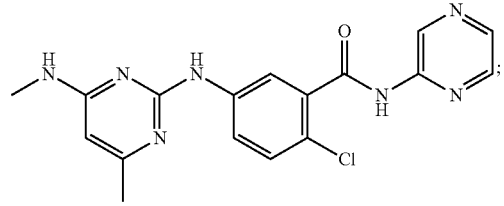
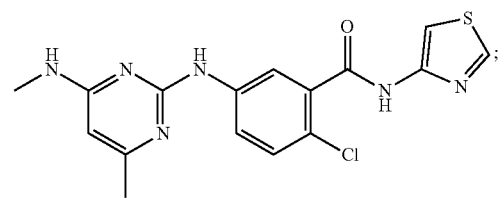
762
-continued
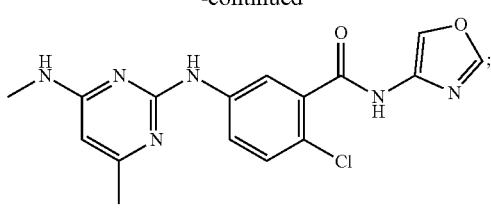
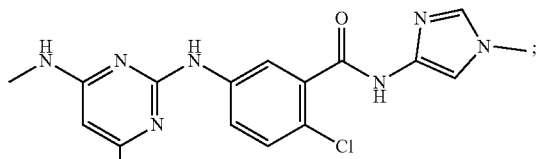
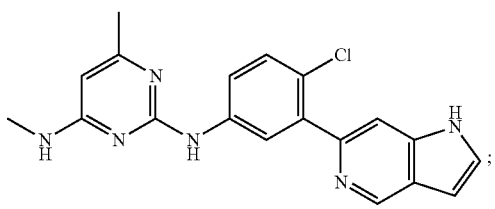
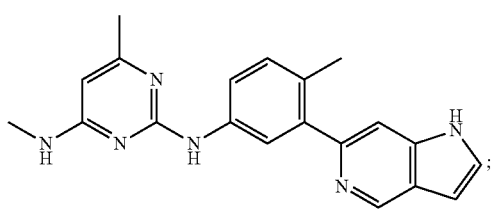
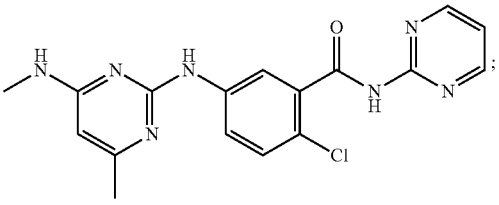
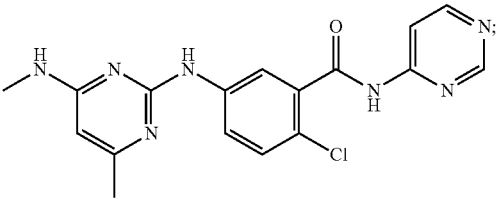
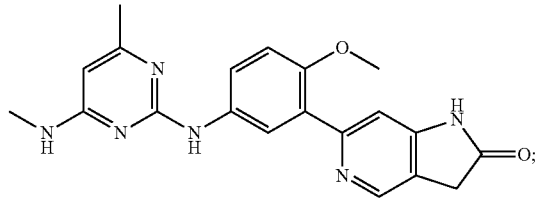

763
-continued
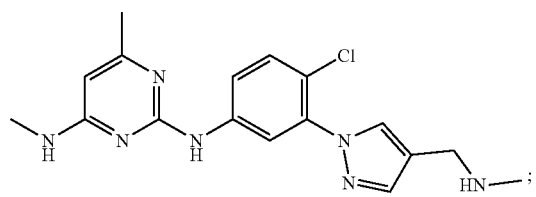
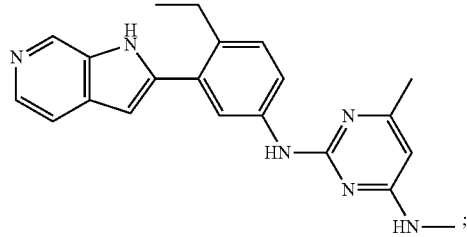
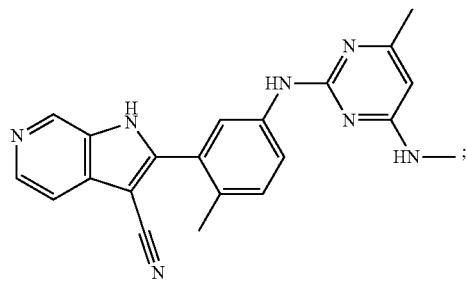
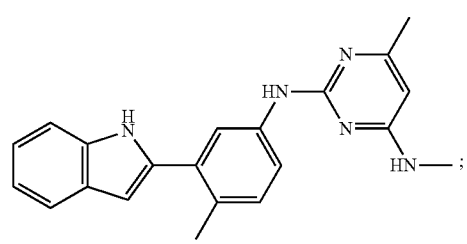
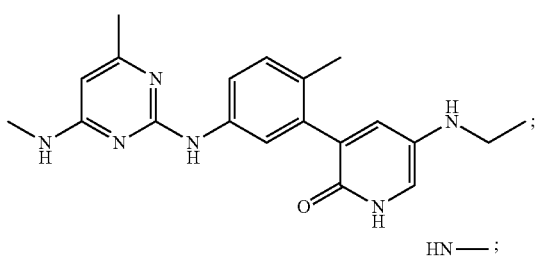
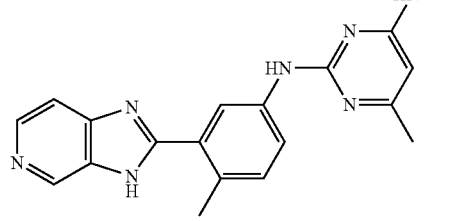
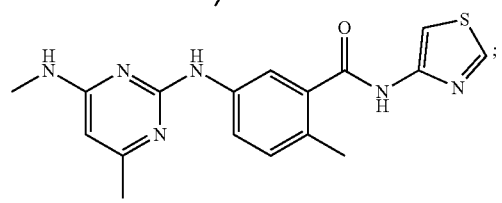
764
-continued
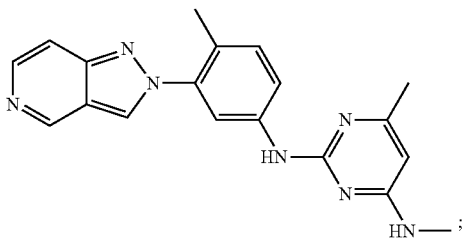
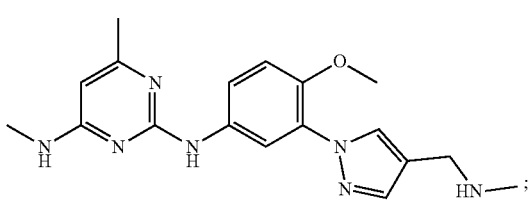
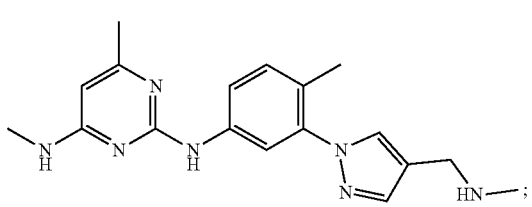
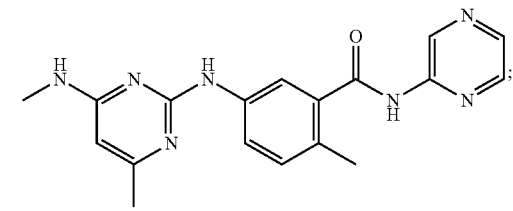
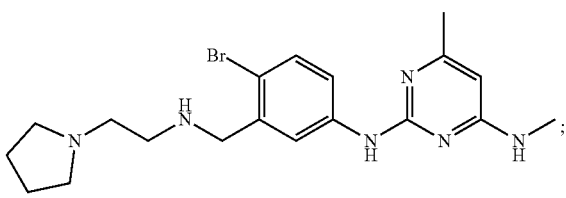
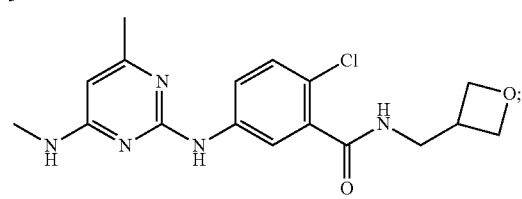
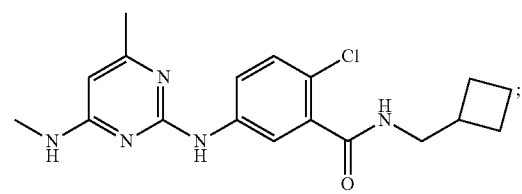
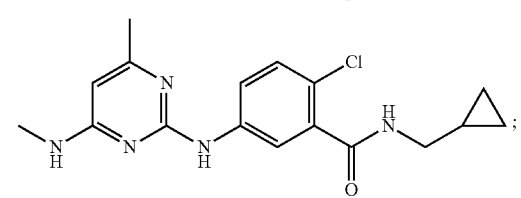

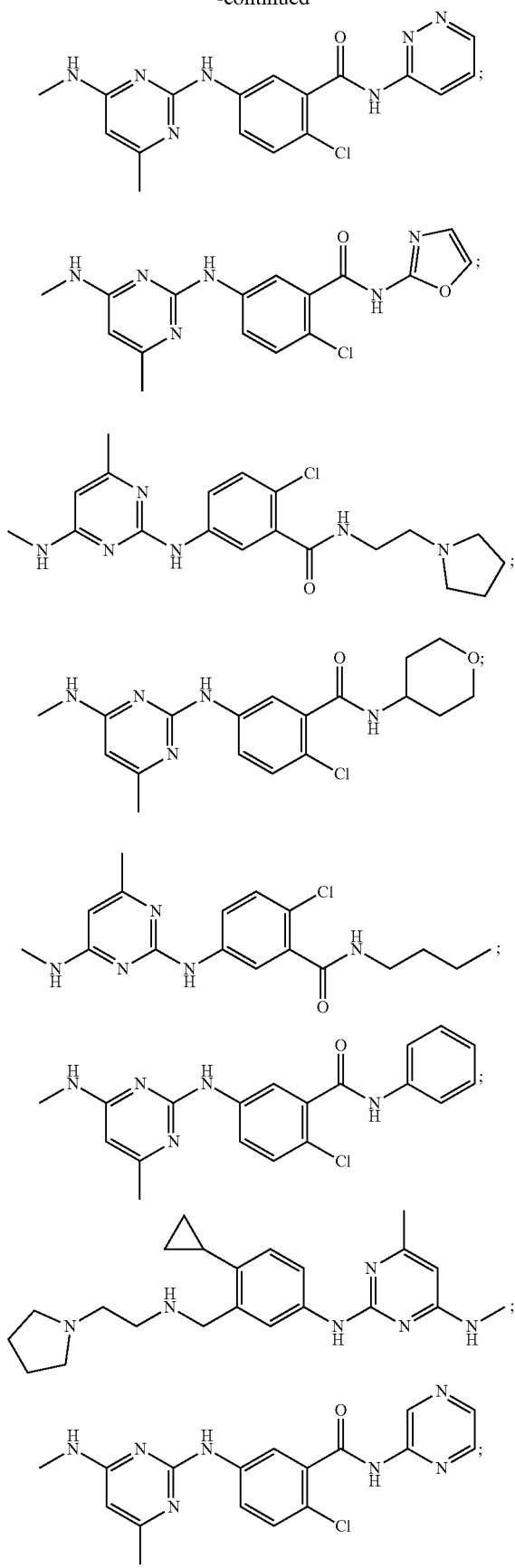
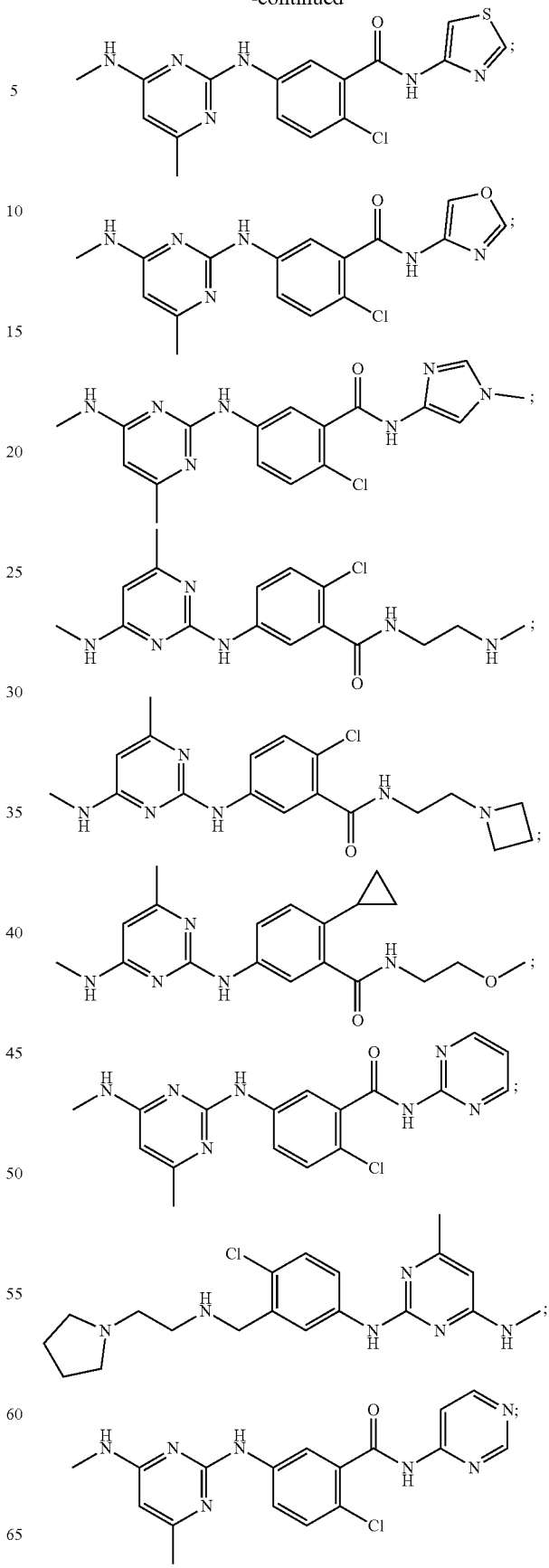

-continued
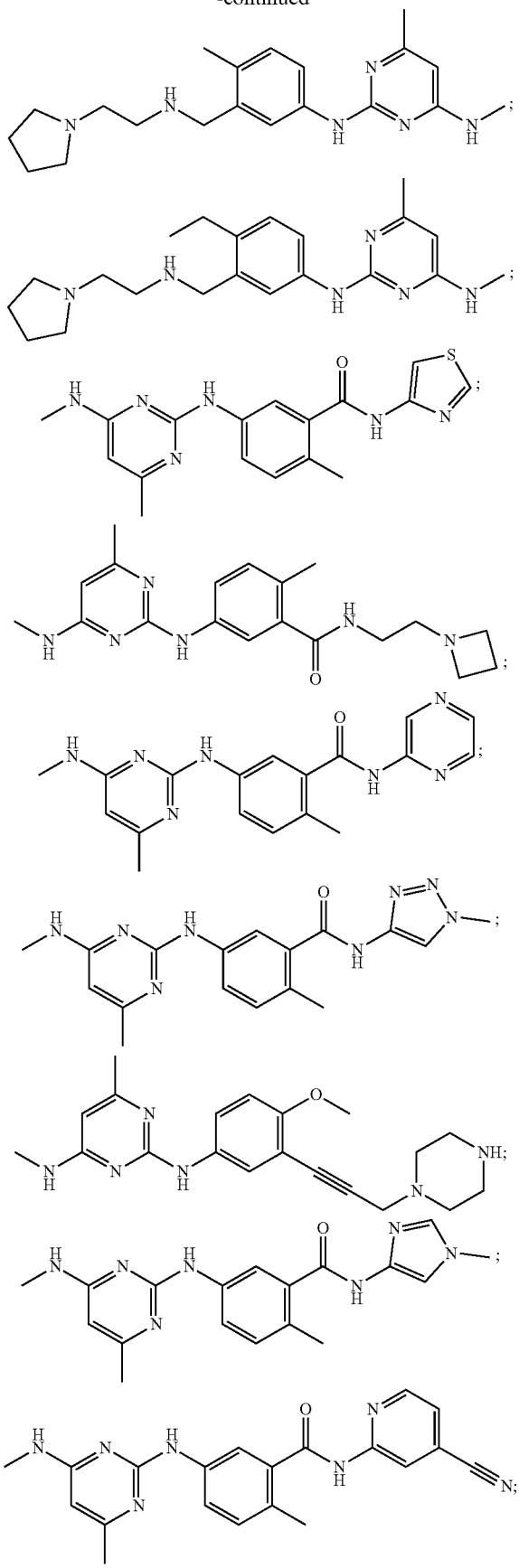
-continued
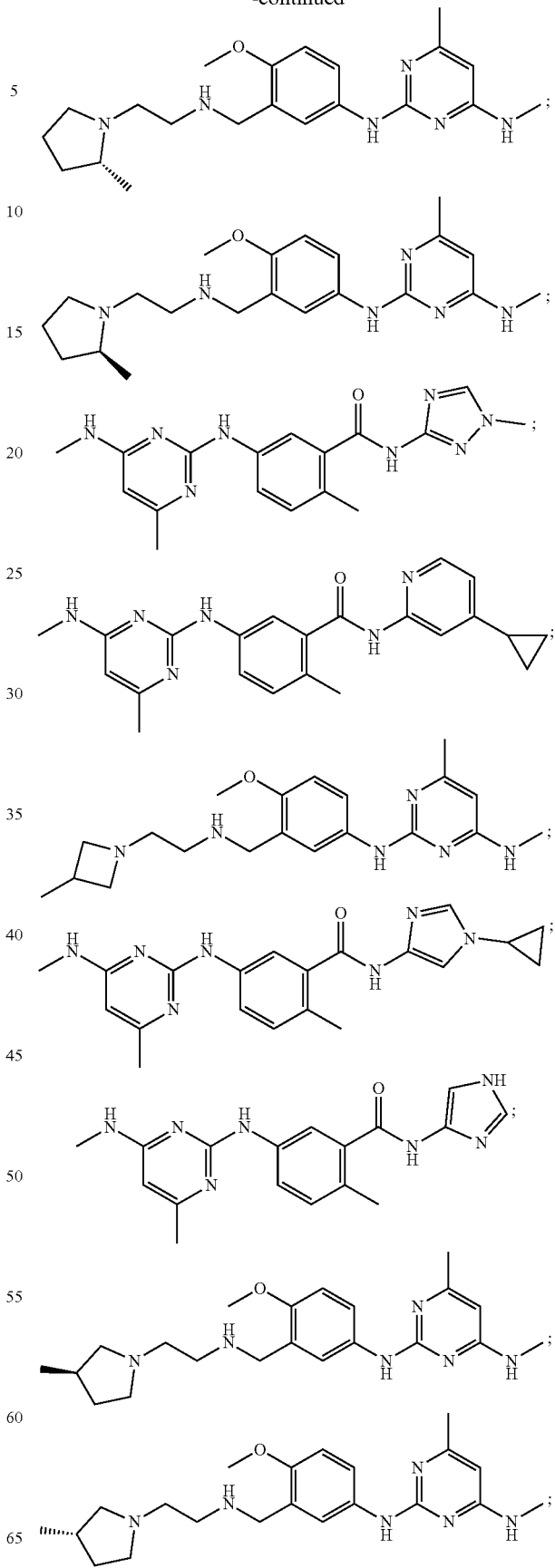

769
-continued
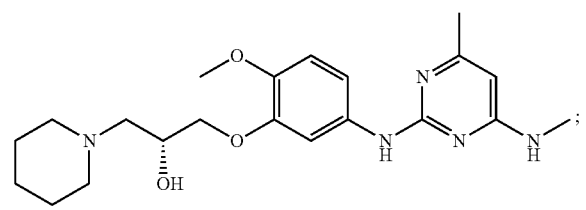
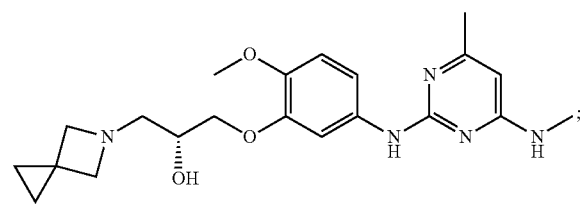
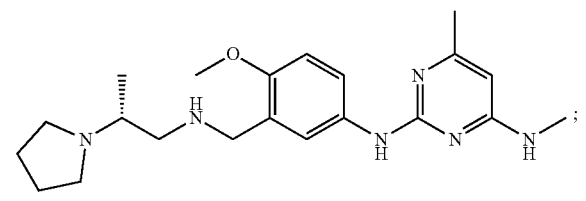
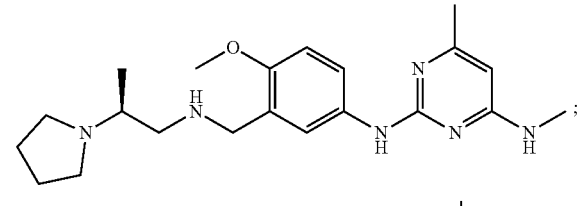
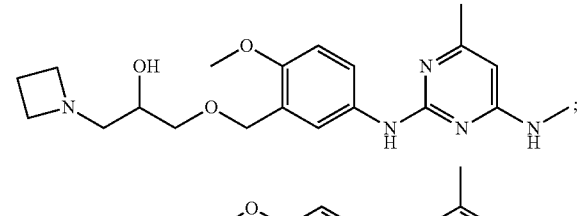
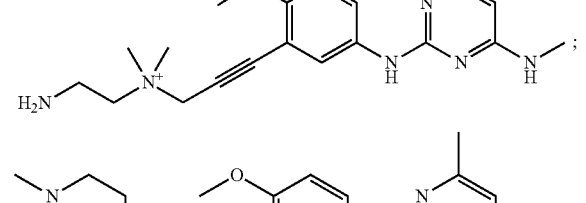
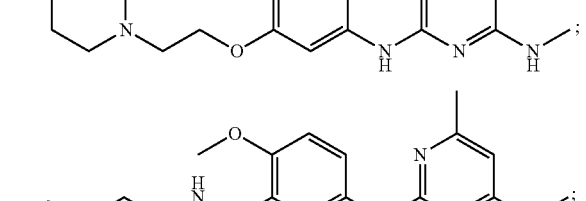
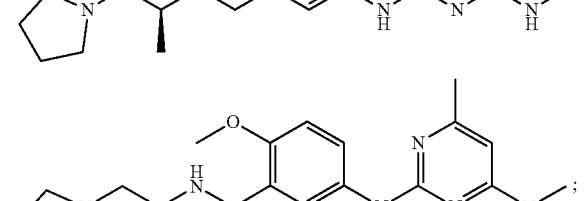
770
-continued
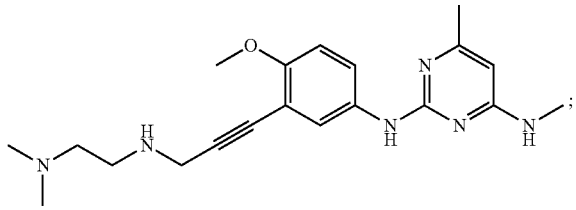
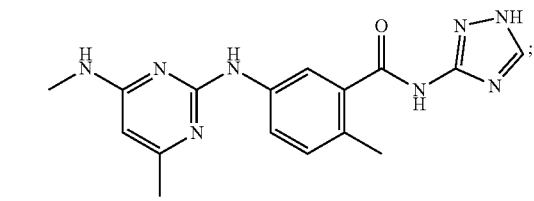
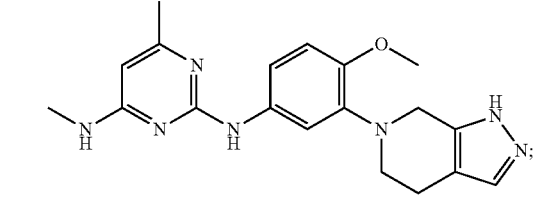
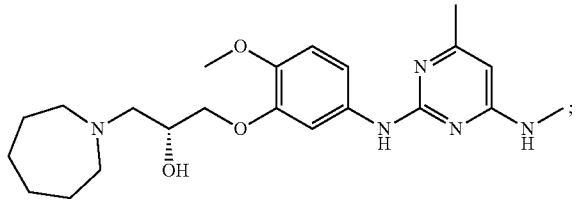
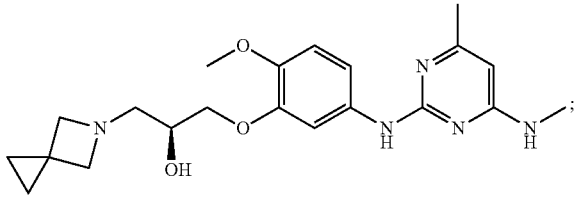
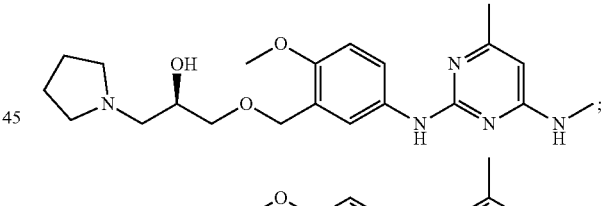
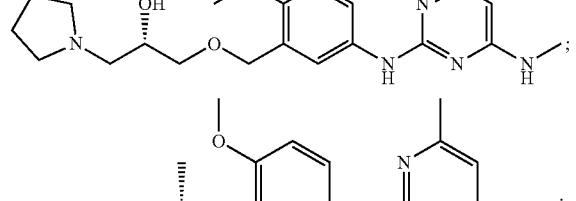
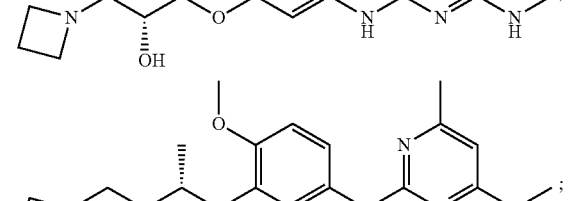

-continued
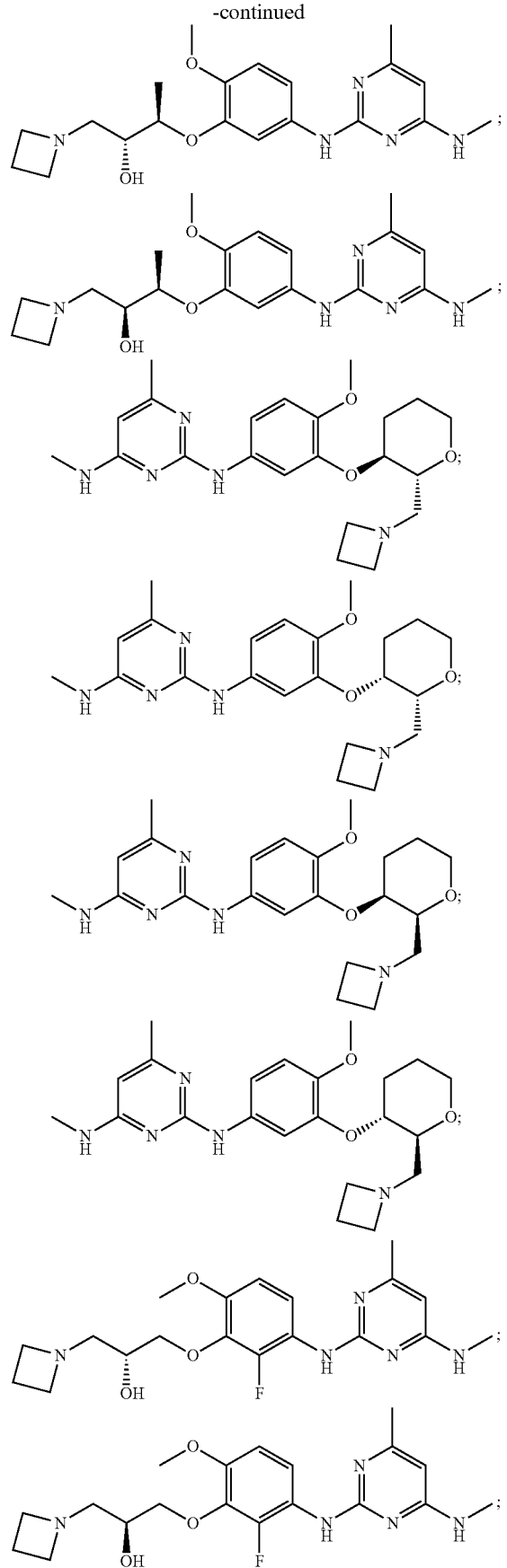
-continued
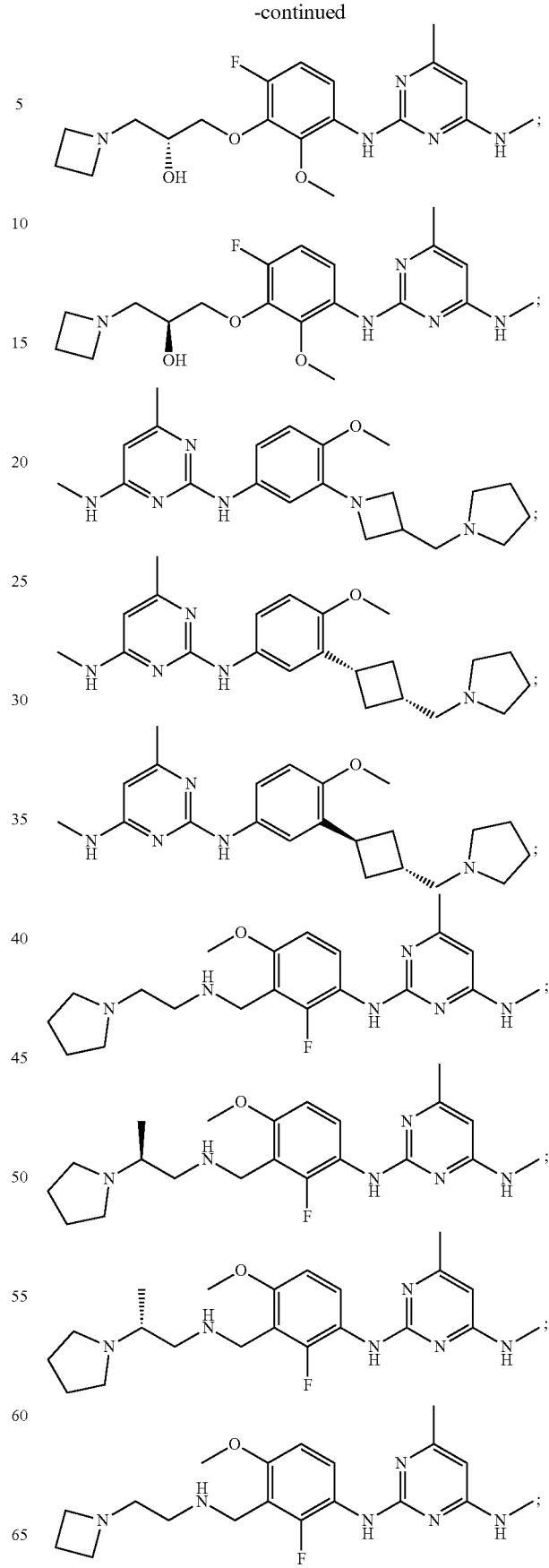

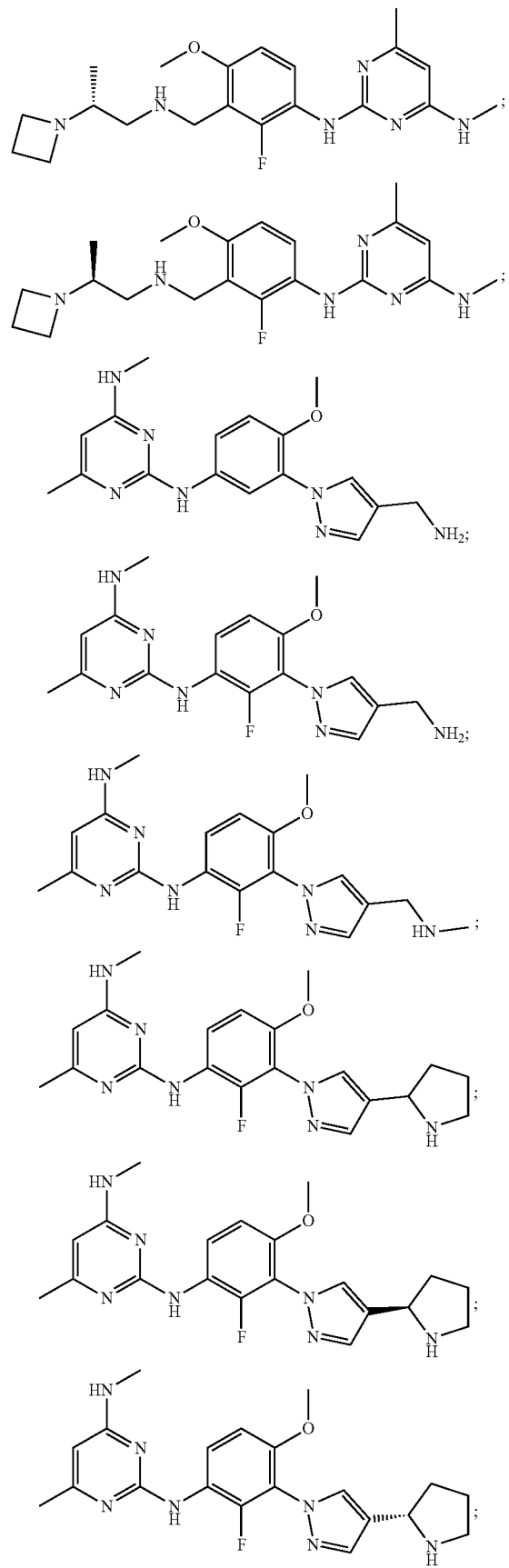
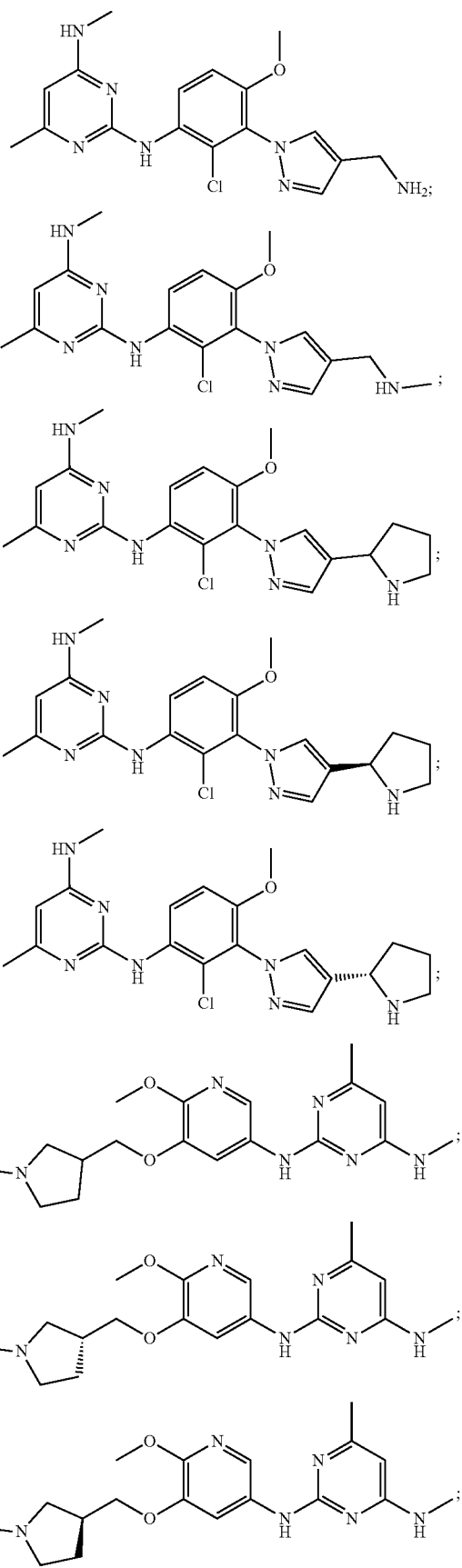

-continued

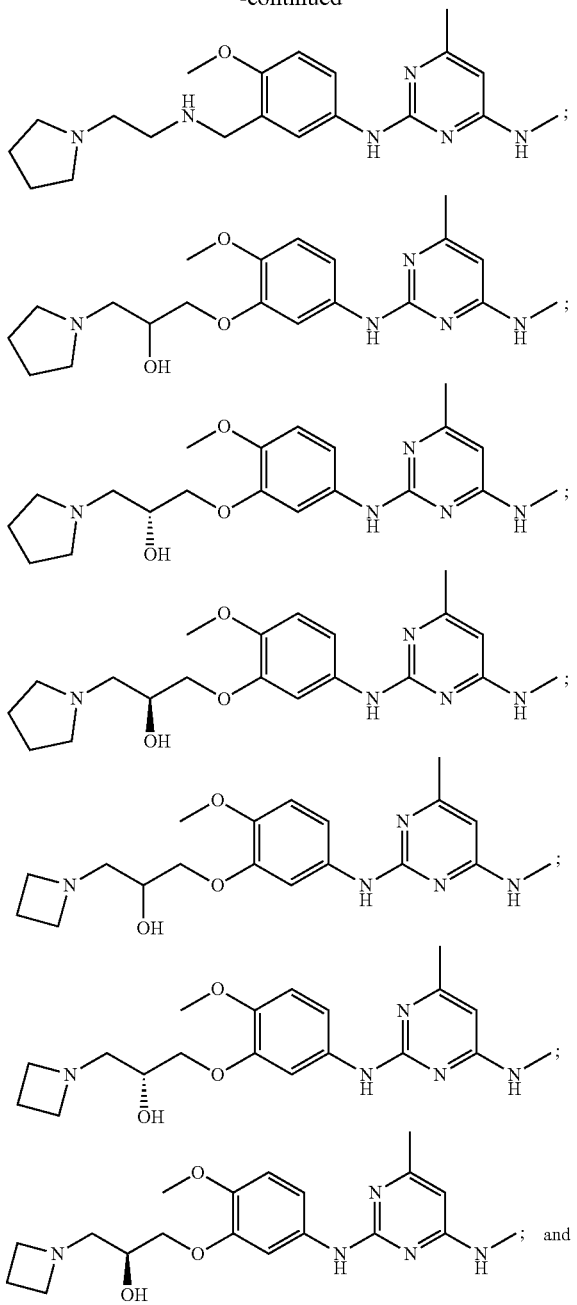

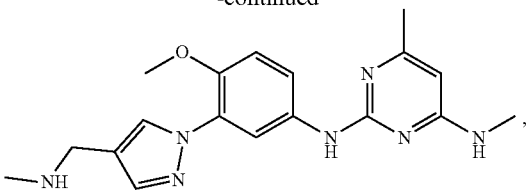

or a pharmaceutically acceptable salt thereof, and (b) one or more additional therapeutic agent selected from a PI3K inhibitor, a MTOR inhibitor, an AKT inhibitor, a BRAF inhibitor, a MEK1 inhibitor, a MEK2 inhibitor, an ERK inhibitor, an EGFR inhibitor, a DNMT inhibitor, a cKIT inhibitor, and a CDK4/6 inhibitor, or any combination thereof.

5. The method of claim 1, wherein the compound is a selective inhibitor of EHMT2.

6. The method of claim 1, wherein the one or more additional therapeutic agent is a PI3K inhibitor.

7. The method of claim 1, wherein the one or more additional therapeutic agent is a MTOR inhibitor.

8. The method of claim 1, wherein the one or more additional therapeutic agent is an AKT inhibitor.

9. The method of claim 1, wherein the one or more additional therapeutic agent is a BRAF inhibitor.

10. The method of claim 1, wherein the one or more additional therapeutic agent is a MEK1 inhibitor or a MEK2 inhibitor.

11. The method of claim 1, wherein the one or more additional therapeutic agent is an ERK inhibitor.

12. The method of claim 1, wherein the one or more additional therapeutic agent is an EGFR inhibitor.

13. The method of claim 1, wherein the one or more additional therapeutic agent is a DNMT inhibitor.

14. The method of claim 1, wherein the one or more additional therapeutic agent is a cKIT inhibitor.

15. The method of claim 1, wherein the one or more additional therapeutic agent is a CDK4/6 inhibitor.

16. The method of claim 1, wherein the one or more additional therapeutic agent is decitabine.

17. The method of claim 1, wherein the one or more additional therapeutic agent is azacitidine.

18. The method of claim 1, wherein the one or more additional therapeutic agent is venetoclax.

19. The method of claim 1, wherein the one or more additional therapeutic agent is ATRA.

20. The method of claim 1, wherein the one or more additional therapeutic agent is everolimus.

\* \* \* \* \*